US011505558B1

(12) United States Patent
Szymaniak et al.

(10) Patent No.: US 11,505,558 B1
(45) Date of Patent: Nov. 22, 2022

(54) ANTIVIRAL HETEROCYCLIC COMPOUNDS

(71) Applicant: Enanta Pharmaceuticals, Inc., Watertown, MA (US)

(72) Inventors: Adam Szymaniak, Boston, MA (US); Kevin McGrath, Brighton, MA (US); Jianming Yu, Plainsboro, NJ (US); Tyler Mann, Brighton, MA (US); Long Nguyen, Boston, MA (US); Kaicheng Zhu, Belmont, MA (US); In Jong Kim, Lexington, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 17/220,300

(22) Filed: Apr. 1, 2021

Related U.S. Application Data

(63) Continuation-in-part of application No. 16/930,622, filed on Jul. 16, 2020.

(60) Provisional application No. 62/910,712, filed on Oct. 4, 2019, provisional application No. 62/959,230, filed on Jan. 10, 2020, provisional application No. 63/038,234, filed on Jun. 12, 2020.

(51) Int. Cl.
| | |
|---|---|
| *C07D 471/04* | (2006.01) |
| *C07D 491/044* | (2006.01) |
| *C07D 491/048* | (2006.01) |
| *C07D 491/052* | (2006.01) |

(52) U.S. Cl.
CPC ....... *C07D 491/052* (2013.01); *C07D 471/04* (2013.01); *C07D 491/044* (2013.01); *C07D 491/048* (2013.01)

(58) Field of Classification Search
CPC .............. C07D 471/04; C07D 491/044; C07D 491/048; C07D 491/052
See application file for complete search history.

(56) References Cited

U.S. PATENT DOCUMENTS

| | | | |
|---|---|---|---|
| 4,010,153 A | 3/1977 | Kajfez et al. | |
| 4,511,510 A | 4/1985 | Mauri | |
| 4,988,692 A | 1/1991 | Gasc et al. | |
| 5,571,809 A | 11/1996 | Hargrave et al. | |
| 5,637,697 A | 6/1997 | Finch et al. | |
| 5,646,140 A | 7/1997 | Sugg et al. | |
| 5,681,833 A | 10/1997 | Castro et al. | |
| 7,582,624 B2 | 9/2009 | Carter et al. | |
| 8,999,969 B2 | 4/2015 | Mackman et al. | |
| 9,732,098 B2 | 8/2017 | Hunt et al. | |
| 9,957,281 B2 | 5/2018 | Shook et al. | |
| 10,358,441 B2 | 7/2019 | Kim et al. | |
| 10,398,706 B2 | 9/2019 | Shook et al. | |
| 10,865,215 B2 | 12/2020 | Shook et al. | |
| 2006/0040923 A1 | 2/2006 | Carter et al. | |
| 2006/0083741 A1 | 4/2006 | Hoffman et al. | |
| 2007/0142403 A1 | 6/2007 | Powell et al. | |
| 2007/0185094 A1 | 8/2007 | Lattmann et al. | |
| 2007/0185096 A1 | 8/2007 | Powell et al. | |
| 2007/0293482 A1 | 12/2007 | Dowdell et al. | |
| 2008/0139536 A1 | 6/2008 | Dowdell et al. | |
| 2009/0274655 A1 | 11/2009 | Grimes et al. | |
| 2010/0015063 A1 | 1/2010 | Carter et al. | |
| 2010/0168384 A1 | 7/2010 | Mdcaniel et al. | |

(Continued)

FOREIGN PATENT DOCUMENTS

| | | |
|---|---|---|
| CN | 109966244 A | 7/2019 |
| EP | 0167919 A2 | 1/1986 |

(Continued)

OTHER PUBLICATIONS

"'N-[(2R)-2-[(3S)-3-Amino-7-(3-chloro-4-A fluorophenyl)-3-methyl-2H-furo[2,3-c]pyridin-5-yl]-3,3,3-trifluoro-2-hydroxypropyl]-4-ethoxy-3-methoxybenzamide'", Pubchem Compound Record for CID 117923975, U.S. National Library of Medicine, Feb. 23, 2016 (Feb. 23, 2016), pp. 1-9 (https:I/pubchem.ncbi.nlm.nih.gov/compound/117923975); p. 2.

(Continued)

*Primary Examiner* — Laura L Stockton
(74) *Attorney, Agent, or Firm* — Edgar W. Harlan; Carolyn S. Elmore; Elmore Patent Law Group, P.C.

(57) ABSTRACT

The present invention discloses compounds of Formula (I), or pharmaceutically acceptable salts, esters, or prodrugs thereof:

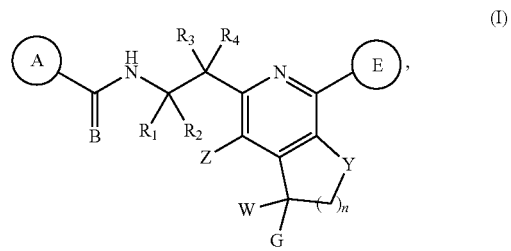

which inhibit Human Respiratory Syncytial Virus (HRSV) or Human Metapneumovirus (HMPV) inhibitors. The present invention further relates to pharmaceutical compositions comprising the aforementioned compounds for administration to a subject suffering from HRSV or HMPV infection. The invention also relates to methods of treating an HRSV or HMPV infection in a subject by administering a pharmaceutical composition comprising the compounds of the present invention.

21 Claims, No Drawings

(56) References Cited

U.S. PATENT DOCUMENTS

| | | | |
|---|---|---|---|
| 2011/0274654 A1* | 11/2011 | Bahadoor | A61K 31/454 424/85.4 |
| 2012/0196846 A1 | 8/2012 | Mackman et al. | |
| 2014/0038947 A1 | 2/2014 | Glick et al. | |
| 2014/0100365 A1 | 4/2014 | Gavai et al. | |
| 2014/0148573 A1 | 5/2014 | Ku et al. | |
| 2014/0328796 A1 | 11/2014 | Phadke et al. | |
| 2015/0038514 A1 | 2/2015 | Grunenberg et al. | |
| 2015/0065504 A1 | 3/2015 | Wang et al. | |
| 2015/0299210 A1 | 10/2015 | Bailey et al. | |
| 2016/0244460 A1 | 8/2016 | Wang et al. | |
| 2017/0022221 A1 | 1/2017 | Blaisdell et al. | |
| 2017/0226127 A1 | 8/2017 | Estrada et al. | |
| 2017/0226129 A1 | 8/2017 | Yu et al. | |
| 2017/0305935 A1 | 10/2017 | Hunt et al. | |
| 2017/0355717 A1 | 12/2017 | Hunt et al. | |
| 2018/0065932 A1 | 3/2018 | Wang et al. | |
| 2018/0193352 A1 | 7/2018 | Shook et al. | |
| 2018/0237425 A1 | 8/2018 | Kim et al. | |
| 2018/0258102 A1 | 9/2018 | Shook et al. | |
| 2018/0354912 A1 | 12/2018 | Or et al. | |
| 2019/0002478 A1 | 1/2019 | Kim et al. | |
| 2019/0002479 A1 | 1/2019 | Kim et al. | |
| 2019/0023692 A1 | 1/2019 | Tahri et al. | |
| 2019/0040084 A1 | 2/2019 | Yu et al. | |
| 2019/0092791 A1 | 3/2019 | Hunt et al. | |
| 2019/0152968 A1 | 5/2019 | Blaisdell et al. | |
| 2019/0177283 A1 | 6/2019 | Hague | |
| 2019/0192535 A1 | 6/2019 | Shook et al. | |
| 2019/0202841 A1 | 7/2019 | Hunt et al. | |
| 2019/0315766 A1 | 10/2019 | Yu et al. | |
| 2021/0238188 A1 | 8/2021 | He et al. | |

FOREIGN PATENT DOCUMENTS

| | | |
|---|---|---|
| EP | 0703222 A1 | 3/1996 |
| JP | 2004043456 A | 2/2004 |
| WO | 9308175 A1 | 4/1993 |
| WO | 9426718 A1 | 11/1994 |
| WO | 2004026843 A1 | 4/2004 |
| WO | 2004106310 A1 | 12/2004 |
| WO | 2005042530 A1 | 5/2005 |
| WO | 2005089769 A1 | 9/2005 |
| WO | 2005090319 A1 | 9/2005 |
| WO | 2006081389 A1 | 8/2006 |
| WO | 2010103306 A1 | 9/2010 |
| WO | 2011005842 A1 | 1/2011 |
| WO | 2011151651 A1 | 12/2011 |
| WO | 2012068622 A1 | 5/2012 |
| WO | 2012080446 A1 | 6/2012 |
| WO | 2012080447 A1 | 6/2012 |
| WO | 2012080449 A1 | 6/2012 |
| WO | 2012080450 A1 | 6/2012 |
| WO | 2012080451 A1 | 6/2012 |
| WO | 2013096681 A1 | 6/2013 |
| WO | 2013186332 A1 | 12/2013 |
| WO | 2013186334 A1 | 12/2013 |
| WO | 2014031784 A1 | 2/2014 |
| WO | 2014047369 A1 | 3/2014 |
| WO | 2014060411 A1 | 4/2014 |
| WO | 2014125444 A1 | 8/2014 |
| WO | 2014184350 A1 | 11/2014 |
| WO | 2014186035 A1 | 11/2014 |
| WO | 2015026792 A1 | 2/2015 |
| WO | 2015110446 A1 | 7/2015 |
| WO | 2016022464 A1 | 2/2016 |
| WO | 2016055791 A1 | 4/2016 |
| WO | 2016055792 A1 | 4/2016 |
| WO | 2016097761 A1 | 6/2016 |
| WO | 2016138158 A1 | 9/2016 |
| WO | 2016166546 A1 | 10/2016 |
| WO | 2017015449 A1 | 1/2017 |
| WO | 2017123884 A1 | 7/2017 |
| WO | 2017175000 A1 | 10/2017 |
| WO | 2019067864 A1 | 4/2019 |
| WO | 2021066922 A1 | 4/2021 |
| WO | 2021198981 A1 | 10/2021 |

OTHER PUBLICATIONS

"'N-[2-[8-[4-Fluoro-3-(1-fluoroethyl)phenyl]-4-iodo-4-methyl-2,3-dihydropyrano[2,3-]pyridin-6-yl]-2-oxoethyl]-3-methoxy-4-[2-[(4-methoxyphenyl)methoxy]ethoxy]benzamide'", Pubchem Compound Record for CID 117924454, U.S. National library of Medicine, Feb. 23, 2016 (Feb. 23, 2016), pp. 1-8 <https:I/pubchem.ncbi.nlm.nih.gov/compound/117924454); p. 2.

U.S. Appl. No. 16/930,622, filed Jul. 16, 2020.

Kozlova, A. et al., "Current State on Tryptophan 2,3-Dioxygenase Inhibitors: a Patent Review", Expert Opinion on Therapeutic Patents, vol. 29, Iss. 1, 2019, 1-32.

PUBCHEM-CID: 10595203, p. 3, Fig, Oct. 25, 2006, 1-9.

"4-(2-Hydroxyethoxy)-3-methoxy-N-[3,3,3-1-22 trifluoro-2-[7-(4-fluorophenyl)-3-[2-methylamino )ethyl]-2,3-dihydrofuro[2,3-c]pyridin-5-yl]-2-methylpropyl]benzamide", Pubmed Compound Record for CID 139332032, U.S. National Library of Medicine, Nov. 2, 2019, https:I/pubchem.ncbi.nlm.nih.gov/compound/139332032).

"N-[(2R)-2-[3-(Aminomethyl)-7-(4-fluorophenyl)-1-22 3-methyl-2H-furo[2,3-c]pyridin-5-yl]-3,3,3-trifluoro-2-hydroxypropyl]-4-(2-hydroxyethoxy)-3-methoxybenzamide", Pubmed Compound Record for CID 117924934, U.S. National Library of Medicine, Feb. 23, 2016, https://pubchem.ncbi.nlm.nih.gov/compound/117924934.

Bond, S. et al., "1,2,3,9b-Tetrahydro-5H-imidazo[2,1-a]isoindol-5-ones as a new class of respiratory syncytial virus (RSV) fusion inhibitors. Part 2: Identification of BTA9881 as a preclinical candidate", Bioorg & Med Chem Lett, 25, 2015, 976-981.

Carter, M. C. et al., "1,4-Benzodiazepines as Inhibitors of Respiratory Syncytial Virus", Journal of Medicinal Chemistry, vol. 49, Mar. 9, 2006, 2311-2319.

Chapman, J. et al., "RSV604, a Novel Inhibitor of Respiratory Syncytial Virus Replication", Antimicrobial Agents and Chemotherapy, vol. 51, No. 9, 2007, 3346-3353.

Contreras-Romo, M. et al., "Exploring the Ligand Recognition Properties of the Human Vasopressin V1a Receptor Using QSAR and Molecular Modeling Studies", Chem. Biol. Drug. Des., vol. 83, 2014, 207-223.

Fordyce, et al., "Discovery of novel benzothienoazepine derivatives as potent inhibitors of respiratory syncytial virus", Bioorganic & Medicinal Chemistry Letters, 27, 2017, 2201-2206.

Henderson, E. A. et al., "1,4-Benzodiazepines as Inhibitors of Respiratory Syncytial Virus. The Identification of a Clinical Candidate", Journal of Medicinal Chemistry, vol. 50, Mar. 7, 2007, 1685-1692.

Mackman, R. L. et al., "Discovery of an Oral Respiratory Syncytial Virus (RSV) Fusion Inhibitor (GS-5806) and Clinical Proof of Concept in a Human RSV Challenge Study", J. Med. Chem., 58, 2015, 1630-1643.

Mayo Clinic Staff, Respiratory syncytial virus (RSV) [online], retrieved from from internet on Jun. 25, 2017.; URL http://www.mayoclinic.org/diseases-condiitons/respiratory-syncytial-virus/basics/prevention.

Perron, M. et al., "GS-5806 Inhibits a Broad Range of Respiratory Syncytial Virus Clinical Isolates by Blocking the Virus-Cell Fusion Process", Antimicrobial Agents and Chemotherapy, 60(3), 2016, 1264-1273.

Sudo, K. et al., "YM-53403, a unique anti-respiratory syncytial virus agent with a novel mechanism of action", Antiviral Research, 2005, vol. 65, 2005, 125-131.

Wang, G. et al., "Discovery of 4'-Chloromethyl-2'-deoxy-3',5'-di-O-isobutyryl-2'-fluorocytidine (ALS-8176), A First-in-Class RSV Polymerase Inhibitor for Treatment of Human Respiratory Syncytial Virus Infection", J. Med. Chem., 58, 2015, 1862-1878.

Xiong, H. "Discovery of a Potent Respiratory Syncytial Virus RNA Polymerase Inhibitor", Bioorganic & Medicinal Chemistry Letters, 23, 2013, 6789-6793.

* cited by examiner

ANTIVIRAL HETEROCYCLIC COMPOUNDS

RELATED APPLICATIONS

This application is a continuation-in-part of U.S. application Ser. No. 16/930,622, filed Jul. 16, 2020, which claims the benefit of U.S. Provisional Application No. 62/910,712, filed Oct. 4, 2019, U.S. Provisional Application No. 62/959,230, filed Jan. 10, 2020, and U.S. Provisional Application No. 63/038,234, filed Jun. 12, 2020. The entire teachings of the above applications are incorporated herein by reference.

TECHNICAL FIELD

The present invention relates generally to compounds and pharmaceutical compositions useful as Respiratory Syncytial Virus (RSV) inhibitors and Human Metapneumovirus (HMPV) inhibitors.

BACKGROUND OF THE INVENTION

Human respiratory syncytial virus (HRSV) is a negative sense virus, containing a non-segmented, single-stranded linear RNA genome. As a Paramyxovirus of two serotypes in the genus Pneumoviridae, HRSV contains 10 genes that encode for 11 proteins. The nucleocapsid protein (N), the RNA polymerase protein (L), the phosphoprotein (P) and the transcription anti-termination factor (M2-1) along with the RNA genome make up the ribonucleoprotein (RNP) complex. Several small-molecule compounds have been shown to target the RNP complex. Additionally, the fusion protein (F), paramount for viral attachment to the host, has been extensively studied. High resolution structures of the F protein interacting with inhibitors have been attained, while structural studies with the N protein are earlier in development. A direct result of the HRSV protein studies and research, the F protein, L protein and N protein have been the major focus of drug discovery efforts.

The increased effort in HRSV drug discovery is a result of HRSV being the leading cause of acute lower respiratory infections (ALRI) in patients of all ages. In addition to respiratory infections, patient populations at high risk during HRSV infections include the elderly, immunocompromised, children up to the age of two and patients with chronic obstructive pulmonary disorder (COPD) or chronic heart failure (CHF). HRSV was found over four years to cause 177,500 hospital admissions and 14,000 deaths in the U.S. elderly population. It is well-known that almost all children will be infected with HRSV in the first 3 years after birth and HRSV infection is more severe in premature infants. In fact, HRSV is the most common cause of bronchiolitis and pneumonia in infants under the age of one in the U.S. It is estimated that approximately 3.2 million hospitalizations and 66,000 deaths worldwide in children less than 5 years old are due to HRSV. HRSV has been associated with more deaths of infants below one year old and more infant hospitalizations than influenza.

HRSV infection can also affect healthy individuals and repeated HRSV infections even over the course of two months can occur. Symptoms are similar to colds in healthy individuals, however fever, wheezing, rapid and difficult breathing, and cyanosis occur in more severe cases. Currently, the treatment options for HRSV infection are quite limited and there is no vaccine due to unsuccessful attempts to date. Palivizumab is a monoclonal antibody that is approved for prophylactic use, but its use is limited due to its high price. Palivizumab is generally only used for high risk infants, such as premature infants or those with cardiac/lung disease, but has been only 60% effective in reducing hospitalizations. Ribavirin is approved as an inhalation treatment option, but its effectiveness is limited and there are safety concerns associated with it. Taking into account the treatment options, and the consistent seasonality of the HRSV epidemic, the development of new therapeutic agents for the treatment of HRSV is desirable.

There have been several RSV fusion inhibitors that have been disclosed in the following publications: WO2010/103306, WO2012/068622, WO2013/096681, WO2014/060411, WO2013/186995, WO2013/186334, WO 2013/186332, WO 2012 080451, WO 2012/080450, WO2012/080449, WO 2012/080447, WO 2012/080446, WO 2015/110446, WO 2017/009316, *J. Med Chem.* 2015, 58, 1630-1643, *Bioorg. Med Chem. Lett.*, 2015, 25, 976-981 and *Nat. Commun.*, 2017, 8, 167. Examples of other N-protein inhibitors for treatment of HRSV have been disclosed in the following publications: WO 2004/026843, *J. Med Chem.* 2006, 49, 2311-2319, and *J. Med Chem.* 2007, 50, 1685-1692. Examples of L-protein inhibitors for HRSV have been disclosed in the following publications: WO 2011/005842, WO 2005/042530, *Antiviral Res.* 2005, 65, 125-131, and *Bioorg. Med Chem. Lett.* 2013, 23, 6789-6793. Examples of nucleosides/polymerase inhibitors have been disclosed in the following publications: WO 2011/005842, WO 2013/242525, WO 2014/031784, WO 2015/026792, WO 2016/0055791, WO 2016/138158 and *J. Med. Chem.* 2015, 58, 1862-1878.

Likewise, human metapneumovirus (HMPV), a negative-sense, single-stranded RNA enveloped virus, that belongs to the Pneumoviridae family and Metapneumovirus genus discovered by van Den Hoogen in 2001, is also a common cause of acute lower respiratory tract infections (ALRTIs). Although often mild, this virus can be serious and life-threatening in high-risk groups, such as children under the age of 5 years, elderly adults over the age of 65 years, and adults with underlying disease (e.g., Chronic Obstructive Pulmonary Disease (COPD), asthma, congestive heart failure, or diabetes). In healthy adults over the age of 65 years, the annual incidence rate of HMPV infection is 1.2/1,000, and 38% of disease (e.g., COPD), and individuals are twice as likely to have symptomatic disease and requirement for medical care. In immunocompromised individuals, HMPV is responsible for 6% of total respiratory infections in lung transplants and 3% of lower respiratory infections associated with stem cell transplant. HMPV infection is also thought to be associated with acute graft rejection.

Like HRSV, infection is thought to attach to the target cell via the glycoprotein (G) protein interactions and followed by fusion via the F protein. HMPV L protein sequence is homologous to HRSV L protein.

HMPV infection is the second most common cause of lower respiratory tract infection in children (behind HRSV) and also problematic for the elderly population. There are 4 subtypes of HMPV found in clinical isolates (A1, A2, B1 and B2). Reinfection occurs throughout childhood following initial infection. No therapeutics are currently available for HMPV infection.

Taking into account the seasonality and predictability of the HRSV and HMPV epidemics, HRSV epidemics in elderly institutions, and the severity of infection in high risk infants, the need for a potent and effective treatment for HRSV and HMPV is clear. The present invention has identified compounds that are heterocyclic molecules that are potent against HRSV-A/B and HMPV. The invention includes methods to prepare these molecules, methods for the RSV cell-based assay, the HMPV-GFP cell-based assay and small-molecules that have potential to treat HRSV/HMPV infection.

SUMMARY OF THE INVENTION

The present invention provides compounds represented by Formula (I), and pharmaceutically acceptable salts, esters and prodrugs thereof that can be used to treat or prevent viral (particularly HRSV or HMPV) infection:

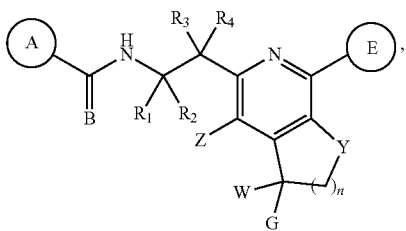

(I)

wherein:
A is selected from the group consisting of:
  1) optionally substituted aryl; and
  2) optionally substituted heteroaryl;
B is O or S;
$R_1$ and $R_2$ are each independently selected from the group consisting of:
  1) hydrogen;
  2) fluorine; and
  3) optionally substituted —$C_1$-$C_6$ alkyl;
alternatively, $R_1$ and $R_2$ are taken together with the carbon atom to which they are attached to form an optionally substituted 3- to 6-membered ring;
Z is selected from the group consisting of:
  1) hydrogen;
  2) halogen;
  3) hydroxy;
  4) cyano;
  5) nitro;
  6) optionally substituted —$C_1$-$C_6$ alkoxy; and
  7) optionally substituted —$C_1$-$C_6$ alkyl;
W is selected from the group consisting of:
  1) hydrogen;
  2) halogen;
  3) optionally substituted —$C_1$-$C_6$ alkoxy;
  4) optionally substituted —$C_1$-$C_6$ alkyl; and
  5) optionally substituted —$C_3$-$C_6$ cycloalkyl;
G is selected from the group consisting of:
  1) —C(O)O$R_{12}$;
  2) —C(O)N$R_{11}R_{12}$;
  3) optionally substituted —$C_1$-$C_6$ alkyl-CN;
  4) optionally substituted —$C_1$-$C_6$ alkyl-C(O)N$R_{11}R_{12}$;
  5) optionally substituted —$C_1$-$C_6$ alkyl-C(O)N$R_{11}$S(O)$_2R_{12}$;
  6) optionally substituted —$C_1$-$C_6$ alkyl-OC(O)N$R_{11}R_{12}$;
  7) optionally substituted —$C_1$-$C_6$ alkyl-NH$R_{13}$;
  8) optionally substituted —$C_1$-$C_6$ alkyl-NHC(O)$R_{13}$;
n is 1, 2 or 3; preferably n is 1 or 2;
Y is O, S, S(O)$_2$, or N$R_{14}$;
E is selected from the group consisting of:
  1) optionally substituted aryl;
  2) optionally substituted heteroaryl;
  3) optionally substituted 3- to 8-membered heterocyclic, and
  4) optionally substituted alkynyl;
$R_3$ is hydroxy or fluorine;
$R_4$ is selected from the group consisting of:
  1) hydrogen;
  2) optionally substituted —$C_1$-$C_6$ alkyl;
  3) optionally substituted —$C_3$-$C_8$ cycloalkyl; and
  4) optionally substituted 3- to 8-membered heterocyclic;
$R_{11}$ at each occurrence is independently selected from the group consisting of:
  1) hydrogen;
  2) optionally substituted —$C_1$-$C_8$-alkyl;
  3) optionally substituted —$C_3$-$C_8$-cycloalkyl;
  4) optionally substituted 4- to 8-membered heterocyclic;
  5) optionally substituted aryl;
  6) optionally substituted arylalkyl;
  7) optionally substituted heteroaryl; and
  8) optionally substituted heteroarylalkyl;
$R_{12}$ at each occurrence is independently selected from the group consisting of:
  1) hydrogen;
  2) optionally substituted —$C_1$-$C_8$-alkyl;
  3) optionally substituted —$C_3$-$C_8$-cycloalkyl;
  4) optionally substituted 4- to 8-membered heterocyclic;
  5) optionally substituted aryl;
  6) optionally substituted arylalkyl;
  7) optionally substituted heteroaryl; and
  8) optionally substituted heteroarylalkyl;
alternatively, $R_{11}$ and $R_{12}$ are taken together with the nitrogen atom to which they are attached to form a 3- to 12-membered heterocyclic ring, preferably the said 3- to 12-membered heterocyclic ring is, but not limited to morpholinyl, piperidinyl, piperazinyl, pyrrolidinyl, and, azetidine;
$R_{13}$ at each occurrence is independently selected from the group consisting of:
  1) Optionally substituted —$C_1$-$C_8$ alkyl;
  2) Optionally substituted —$C_3$-$C_8$ cycloalkyl;
  3) Optionally substituted 4- to 8-membered heterocyclic;
  4) Optionally substituted aryl;
  5) Optionally substituted arylalkyl;
  6) Optionally substituted heteroaryl; and
  7) Optionally substituted heteroarylalkyl; and
$R_{14}$ is selected from:
  1) hydrogen;
  2) optionally substituted —$C_1$-$C_8$-alkyl; and
  3) optionally substituted —$C_3$-$C_8$-cycloalkyl;
Each preferred group stated above can be taken in combination with one, any or all other preferred groups.

DETAILED DESCRIPTION OF THE INVENTION

In one embodiment of the present invention is a compound of Formula (I) as described above, or a pharmaceutically acceptable salt thereof.
In certain embodiments of the compounds of Formula (I), B is O.
In certain embodiments of the compounds of Formula (I), Y is O.
In certain embodiments of the compounds of Formula (I), B is O, Y is O, and n is 1 or 2.
In certain embodiments of the compounds of Formula (I), $R_1$ is hydrogen or F.
In certain embodiments of the compounds of Formula (I), $R_2$ is hydrogen or F.
In certain embodiments of the compounds of Formula (I), Z is hydrogen, Cl or F.

In certain embodiments of the compounds of Formula (I), $R_1$ is hydrogen, $R_2$ is hydrogen, and Z is hydrogen.

In certain embodiments of the compounds of Formula (I), W is optionally substituted methyl, optionally substituted ethyl, or optionally substituted cyclopropyl.

In certain embodiments of the compounds of Formula (I), W is —$CH_3$ or —$CF_3$.

In certain embodiments of the compounds of Formula (I), W is halogen, preferably chlorine or fluorine, and more preferably fluorine.

In certain embodiments of the compounds of Formula (I), $R_3$ is —OH.

In certain embodiments of the compounds of Formula (I), $R_4$ is optionally substituted methyl.

In certain embodiments of the compounds of Formula (I), $R_3$ is OH, and $R_4$ is $CF_3$.

In certain embodiments of the compounds of Formula (I), $R_1$ is hydrogen, $R_2$ is hydrogen, $R_3$ is OH, and $R_4$ is $CF_3$.

In certain embodiments of the compounds of Formula (I), G is optionally substituted —$C(O)NR_{11}R_{12}$.

In certain embodiments of the compounds of Formula (I), G is —$CH_2NHR_{13}$, —$CH_2C(O)NR_{11}R_{12}$, —$CH_2NHC(O)R_{13}$, —$CH_2OC(O)NR_{11}R_{12}$, —$CH_2CN$, or —$CH_2C(O)NR_{11}S(O)_2R_{12}$.

In certain embodiments of the compounds of Formula (I), A is selected from one of the following by removal of a hydrogen atom:

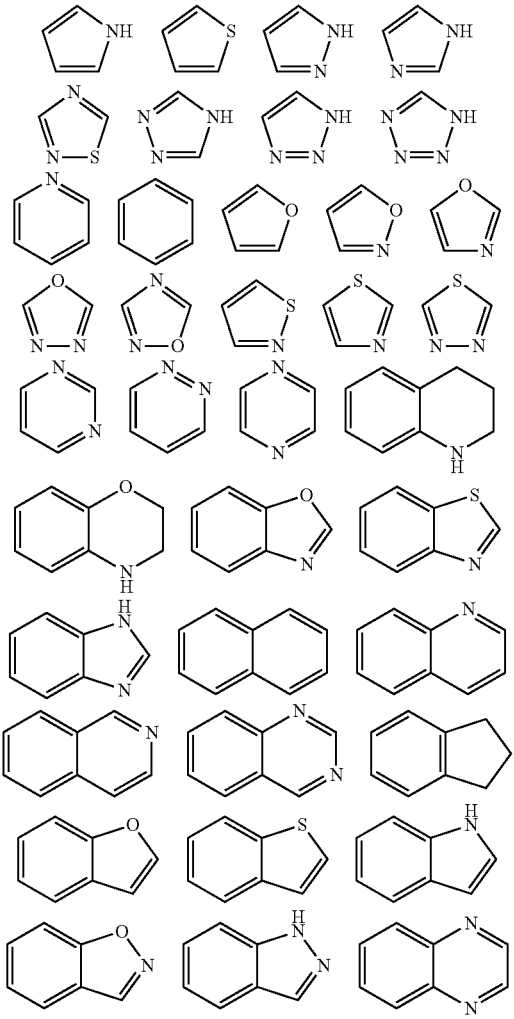

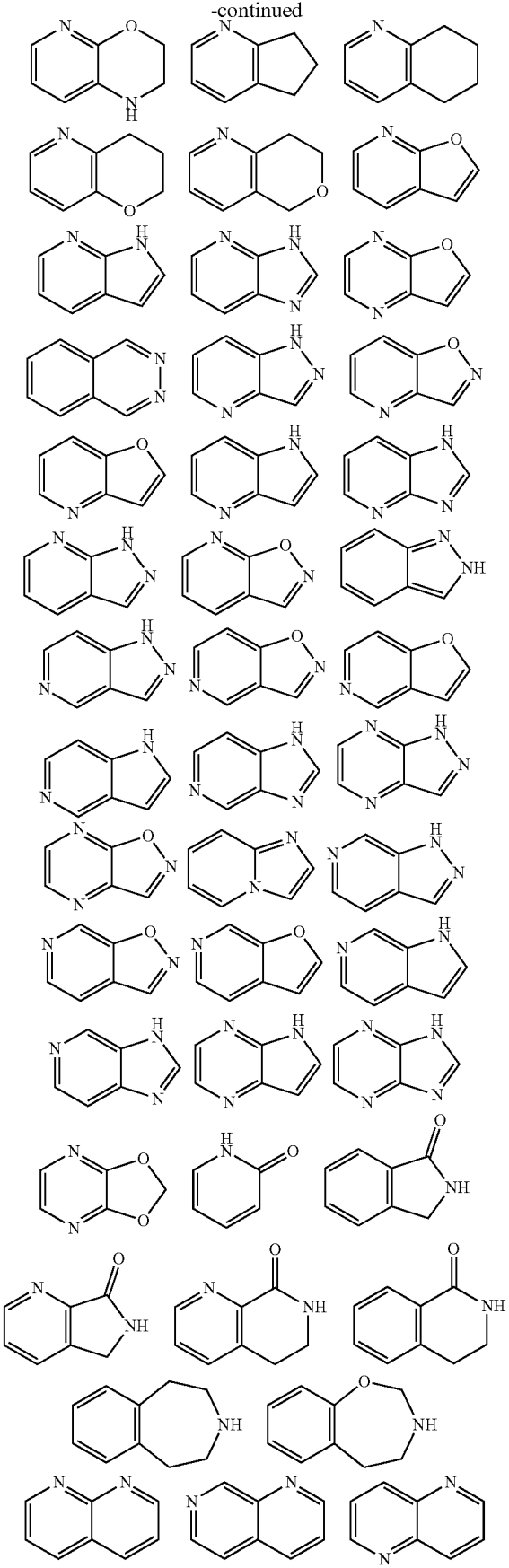

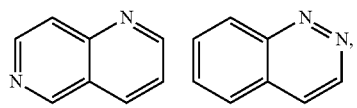
wherein each of these groups is optionally substituted.
In certain embodiments of the compounds of Formula (I), A is selected from the groups set forth below,
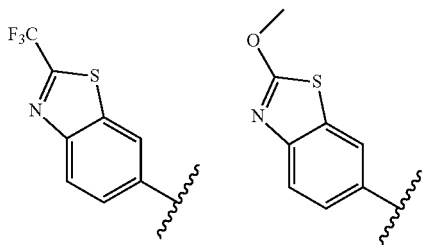
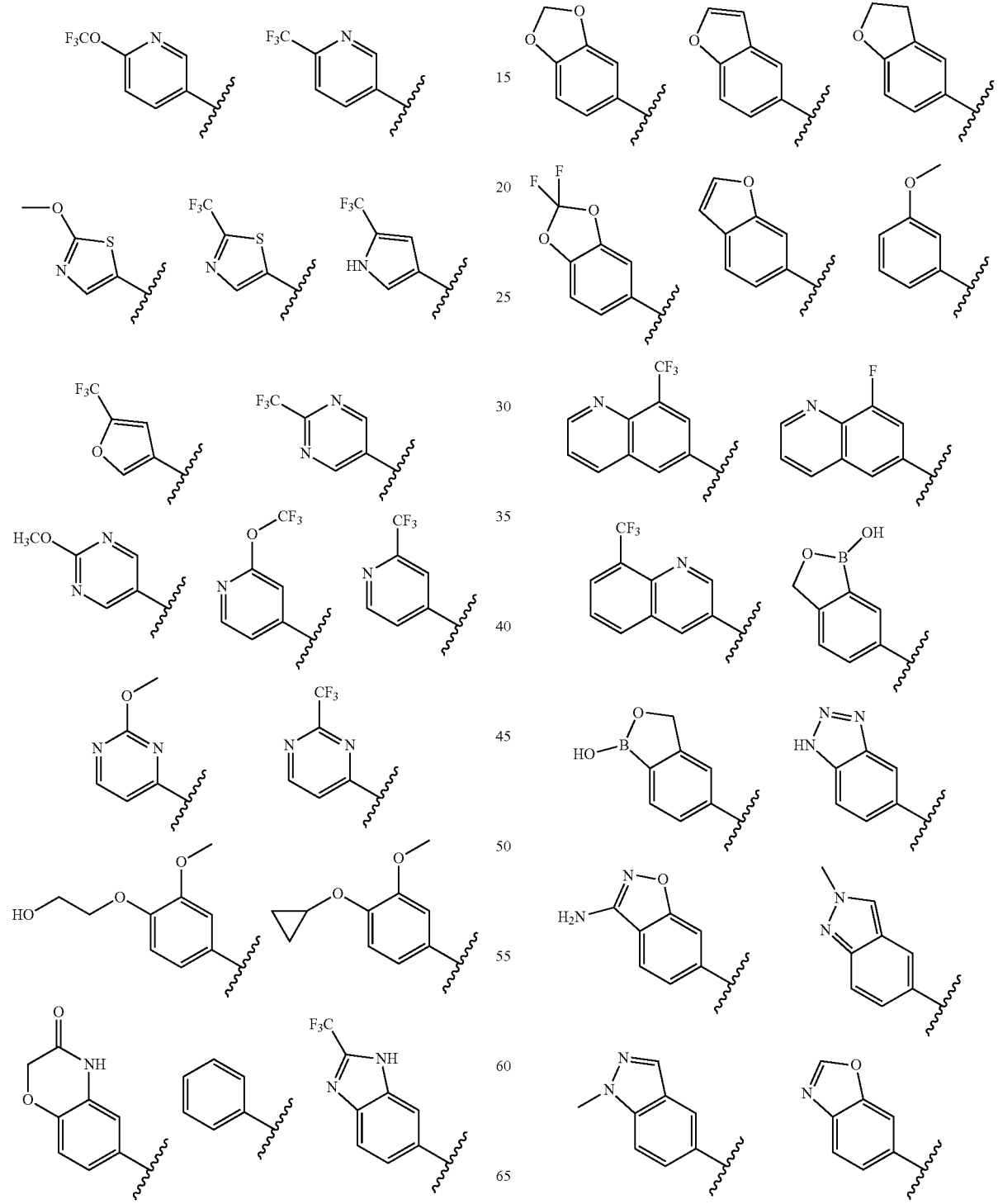

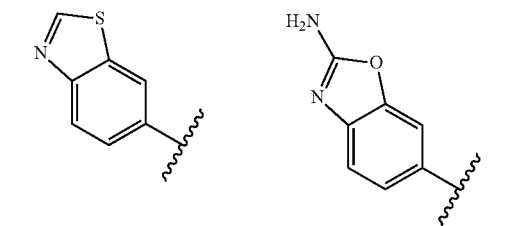
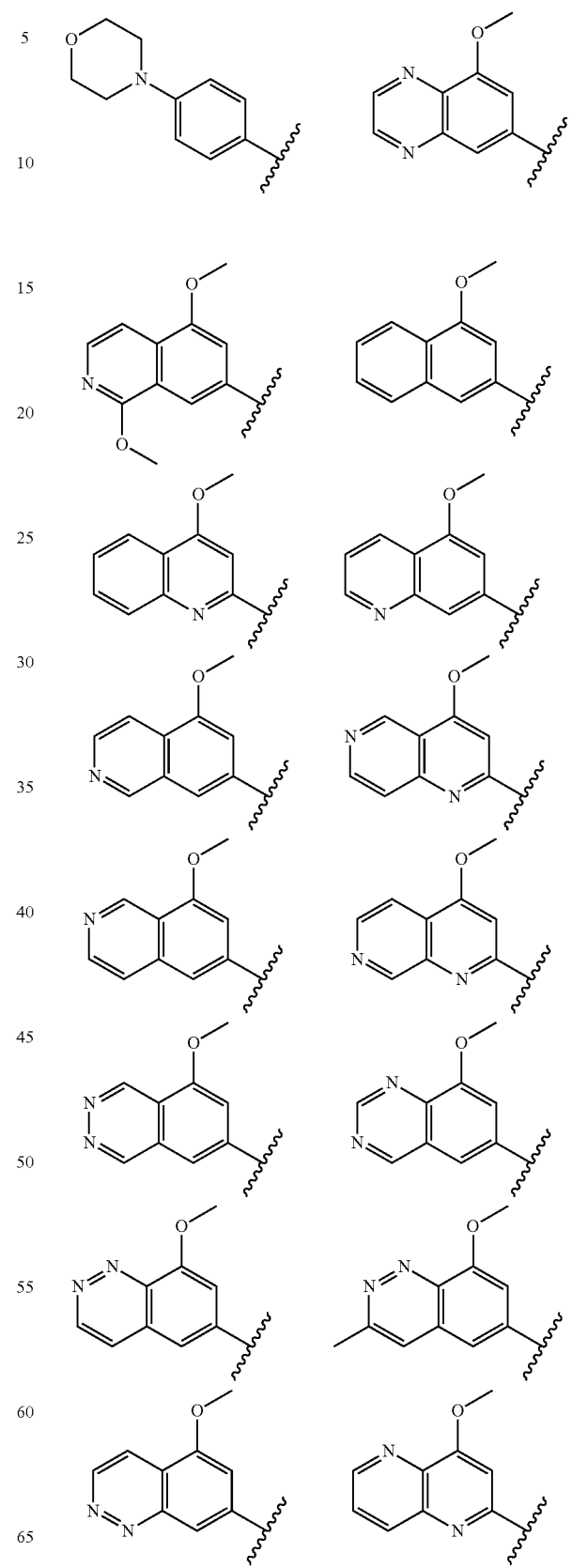

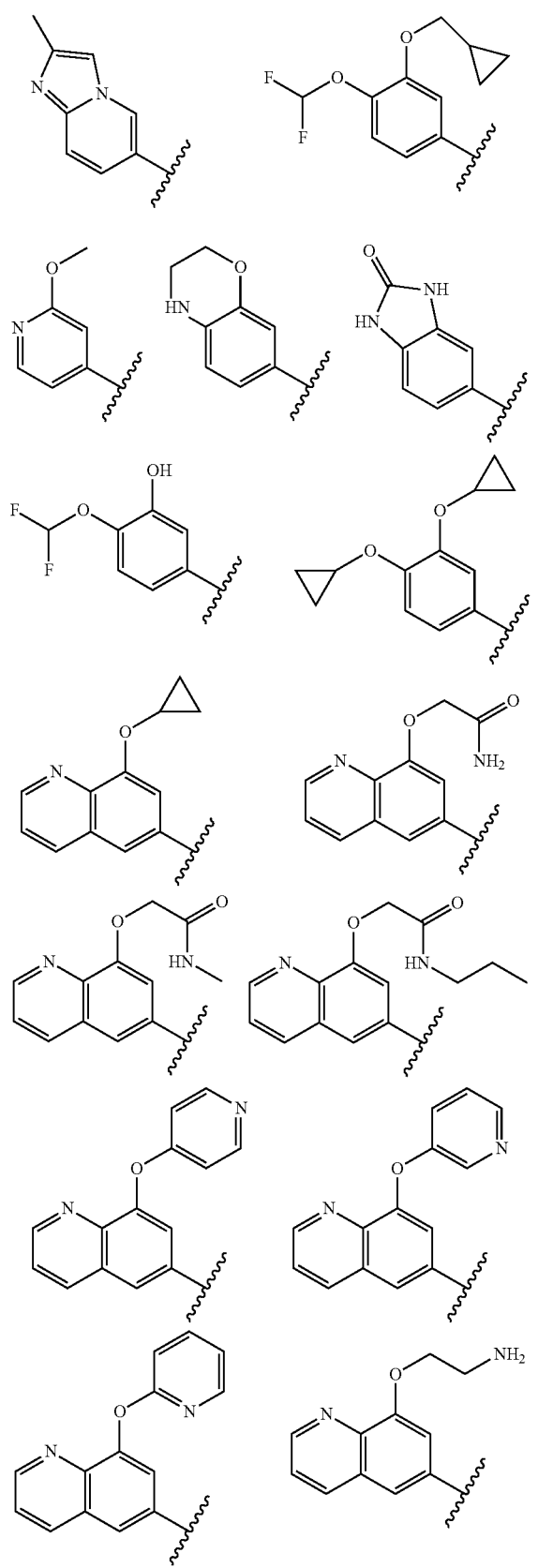
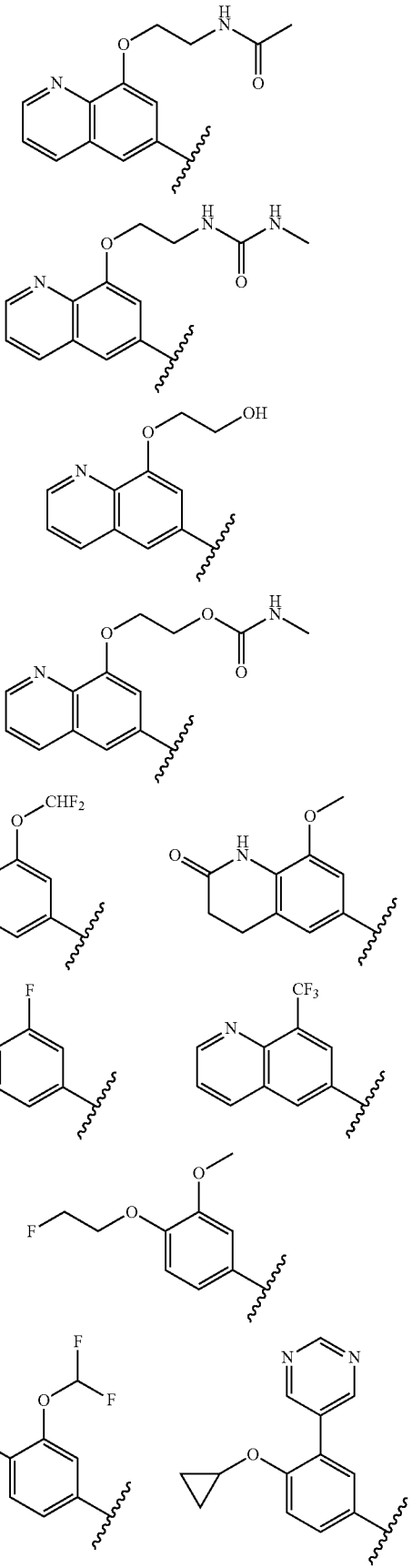

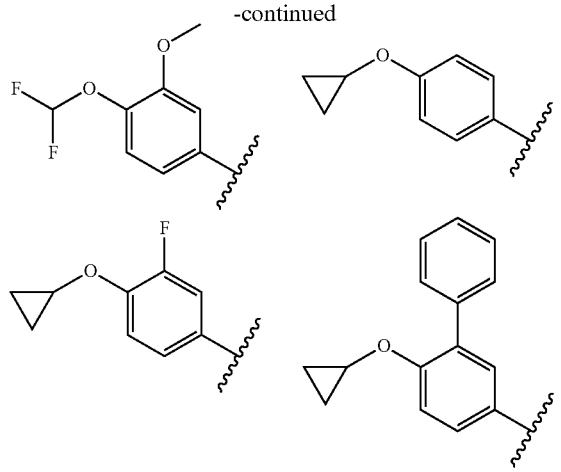

wherein each of these groups is optionally substituted.

In certain embodiments of the compounds of Formula (I), A is

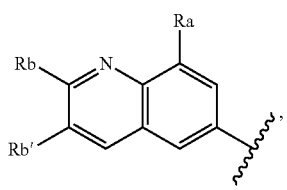

or

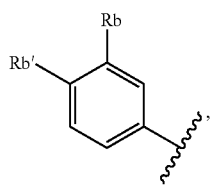

wherein Ra is hydrogen, halogen, —CN, —NO$_2$, —OR$_{11}$, —NR$_{11}$R$_{12}$, —NR$_{11}$C(O)R$_{12}$, —NR$_{11}$S(O)$_2$R$_2$, —S(O)$_2$R$_{12}$, —S(O)$_2$NR$_{11}$R$_{12}$, —NR$_{11}$C(O)NR$_{11}$R$_{12}$, —C(O)R$_{11}$, —C(O)OR$_{11}$, —C(O)NR$_{11}$R$_{12}$, optionally substituted —C$_1$-C$_6$ alkyl, optionally substituted —C$_3$-C$_8$-cycloalkyl, optionally substituted 3- to 8-membered heterocyclic, optionally substituted aryl, or optionally substituted heteroaryl; Rb and Rb' are each independently selected from hydrogen, halogen, —OR$_{11}$, —NR$_{11}$R$_{12}$, optionally substituted —C$_1$-C$_6$-alkyl, optionally substituted —C$_3$-C$_8$-cycloalkyl, optionally substituted 3- to 8-membered heterocyclic, optionally substituted aryl, and optionally substituted heteroaryl. Alternatively, Rb and Rb' are taken together with the carbon atoms to which they are attached to form a 4- to 7-membered ring fused with the phenyl ring.

In certain embodiments of the compounds of Formula (I), E is optionally substituted aryl, preferably optionally substituted phenyl.

In certain embodiments of the compounds of Formula (I), E is selected from one of the following by removal of a hydrogen atom:

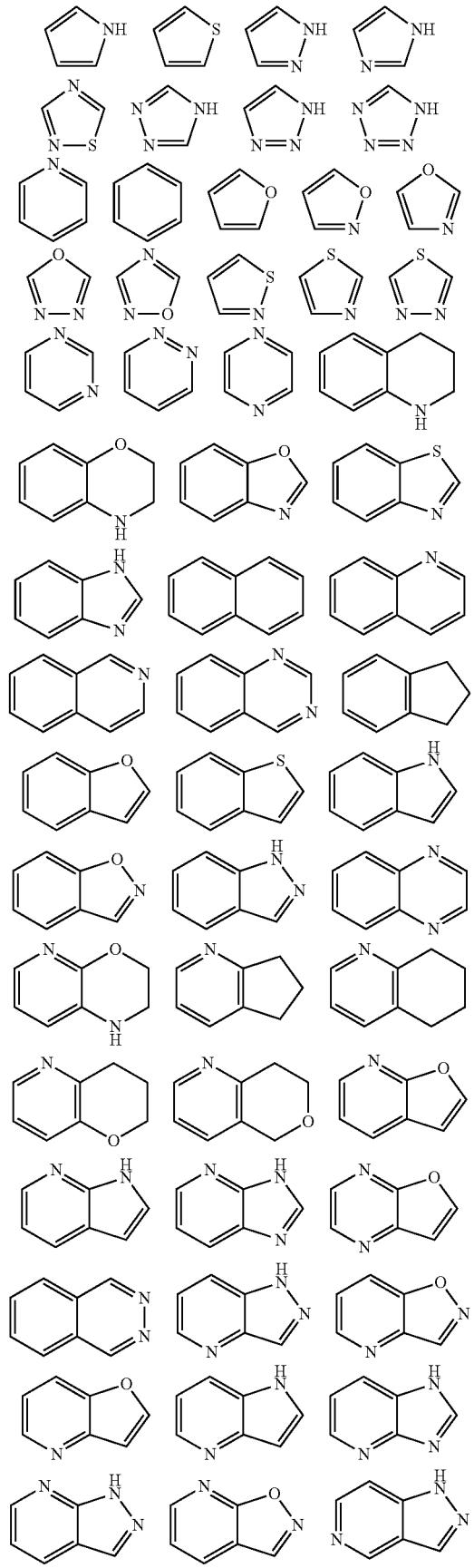

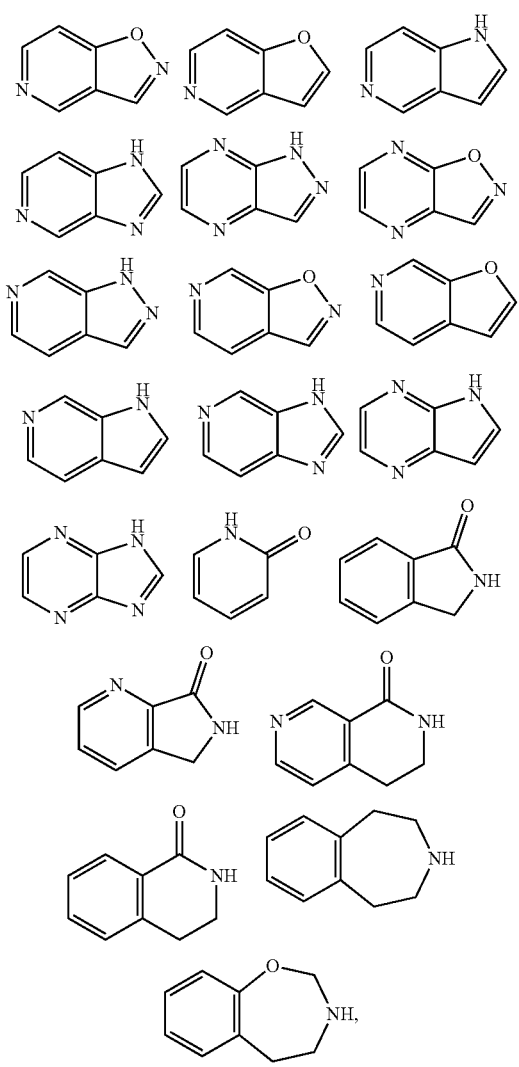

wherein each of these groups is optionally substituted.

In certain embodiments of the compounds of Formula (I), E is selected from the groups set forth below,

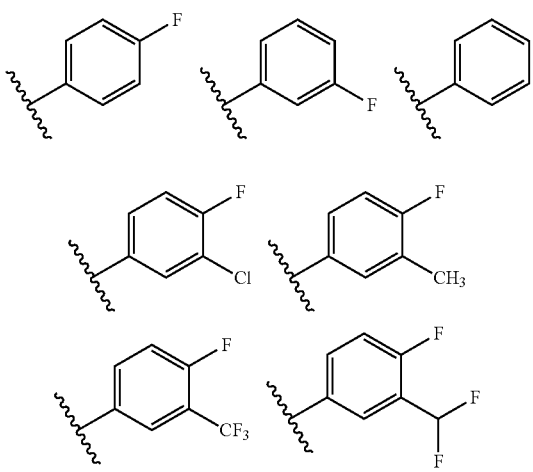

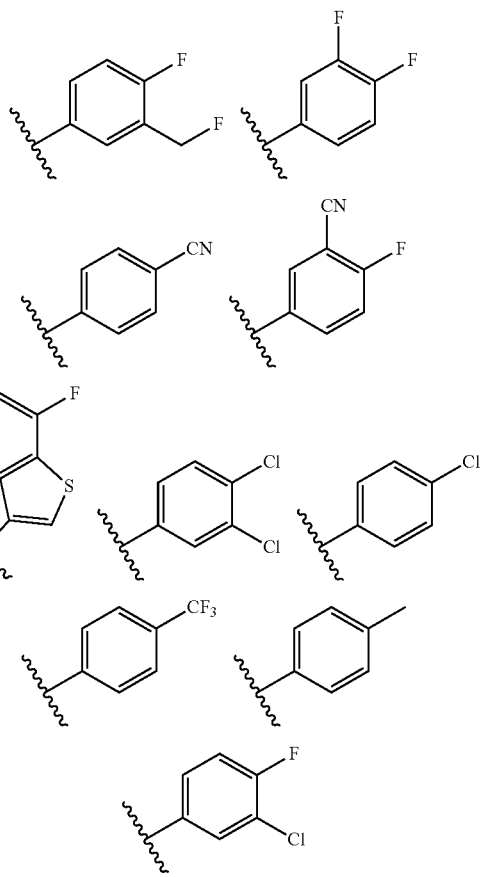

In one embodiment of the present invention, the compound of Formula (I) is represented by Formula (Ia) or Formula (Ib), or a pharmaceutically acceptable salt, ester or prodrug thereof:

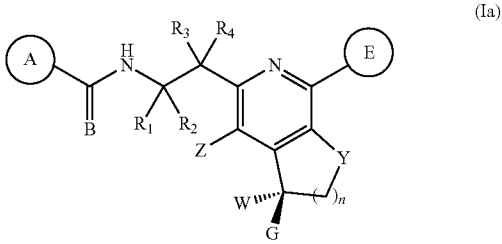

(Ia)

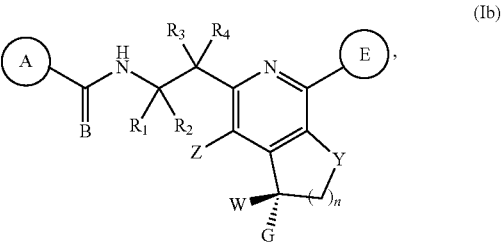

(Ib)

wherein A, B, $R_1$, $R_2$, Z, W, G, n, Y, E, $R_3$, and $R_4$ are as previously defined.

In a preferred embodiment, the compound of Formula (I) has the stereochemistry shown in Formula (Ib).

In one embodiment of the present invention, the compound of Formula (I) is represented by Formula (IIa) or Formula (IIb), or a pharmaceutically acceptable salt, ester or prodrug thereof:

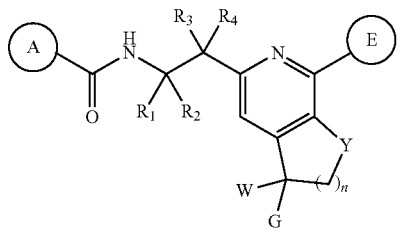
(IIa)

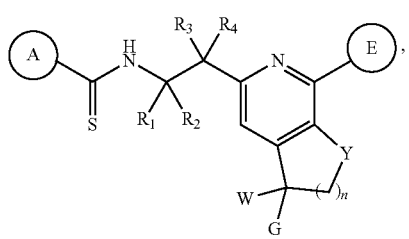
(IIb)

wherein A, $R_1$, $R_2$, W, G, n, Y, E, $R_3$, and $R_4$ are as previously defined.

In one embodiment of the present invention, the compound of Formula (I) is represented by Formula (IIIa) or Formula (IIIb), or a pharmaceutically acceptable salt, ester or prodrug thereof:

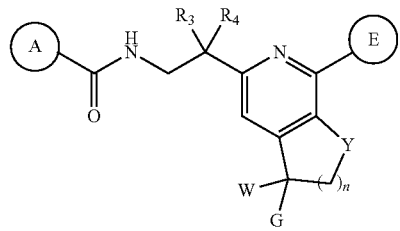
(IIIa)

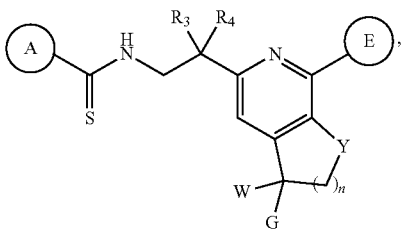
(IIIb)

wherein A, W, G, n, Y, E, n, $R_3$, and $R_4$ are as previously defined.

In one embodiment of the present invention, the compound of Formula (I) is represented by one of Formulae (IVa)~(IVd), or a pharmaceutically acceptable salt, ester or prodrug thereof:

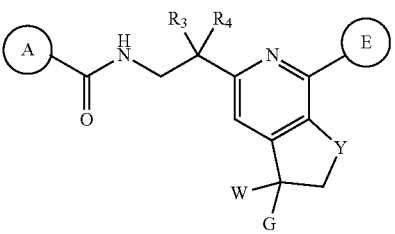
(IVa)

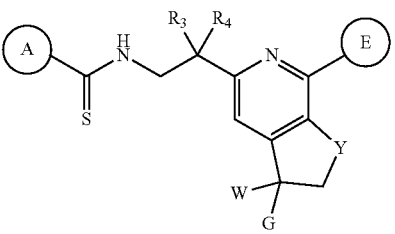
(IVb)

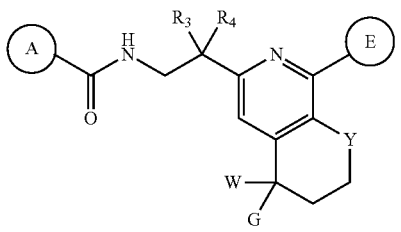
(IVc)

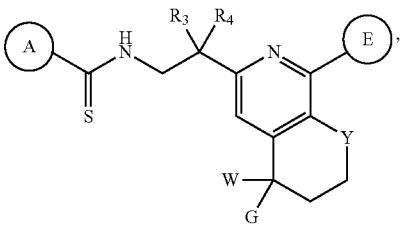
(IVd)

wherein A, W, G, Y, E, $R_3$, and $R_4$ are as previously defined.

In one embodiment of the present invention, the compound of Formula (I) is represented by one of Formulae (Va)~(Vd), or a pharmaceutically acceptable salt, ester or prodrug thereof:

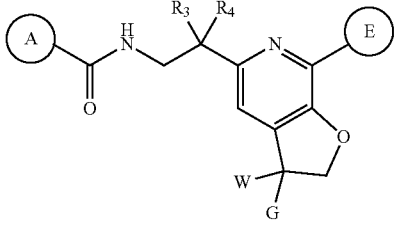
(Va)

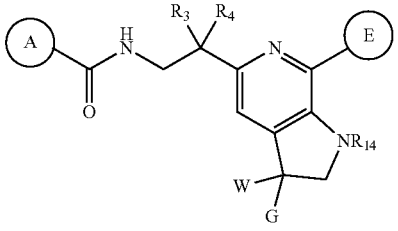
(Vb)

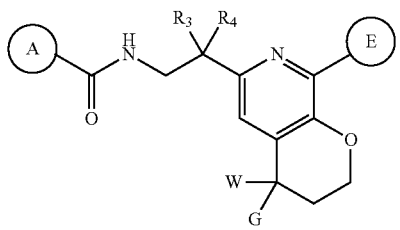
(Vc)

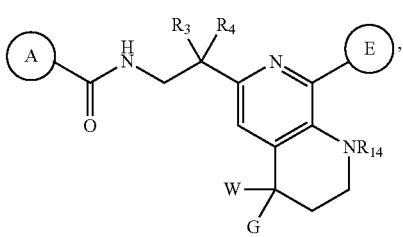
(Vd)

wherein A, W, G, E, $R_{14}$, $R_3$, and $R_4$ are as previously defined.

In one embodiment of the present invention, the compound of Formula (I) is represented by one of Formulae (VIa)~(VId), or a pharmaceutically acceptable salt, ester or prodrug thereof:

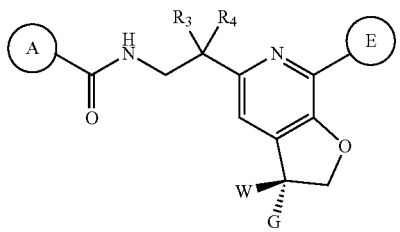
(VIa)

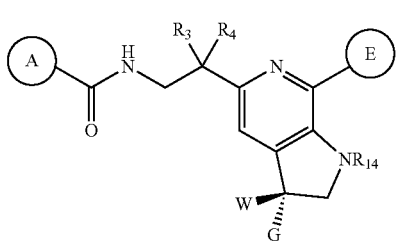
(VIb)

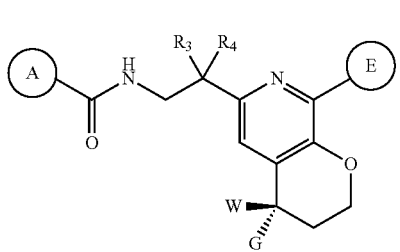
(VIc)

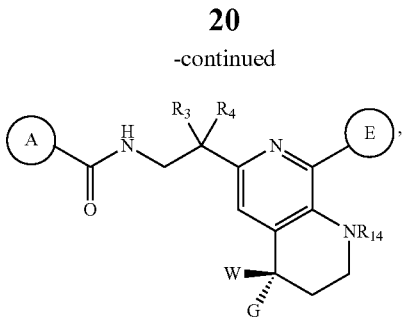
(VId)

wherein A, W, G, E, $R_{14}$, $R_3$, and $R_4$ are as previously defined. Preferably, W is optionally substituted methyl or halogen; more preferably, W is —$CH_3$, —$CF_3$ or fluorine.

In one embodiment of the present invention, the compound of Formula (I) is represented by one of Formulae (VII-1)~(VII-12), or a pharmaceutically acceptable salt, ester or prodrug thereof:

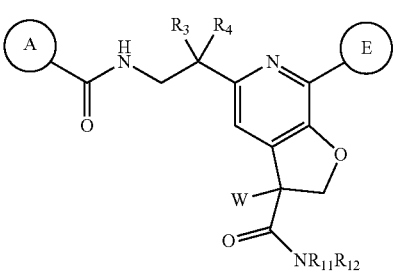
(VII-1)

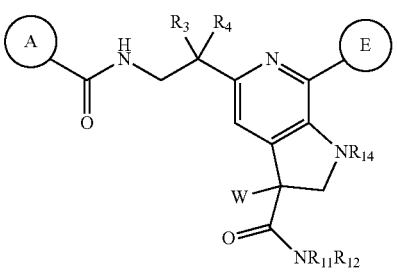
(VII-2)

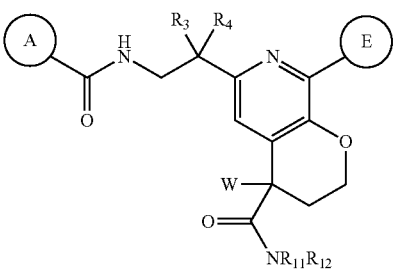
(VII-3)

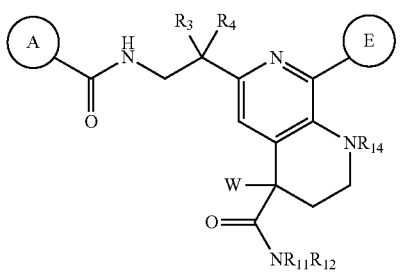
(VII-4)

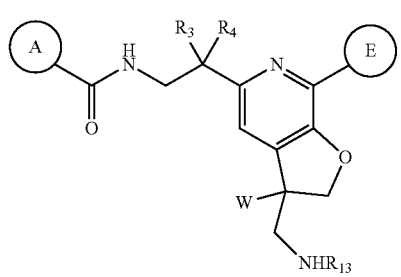

(VII-5)

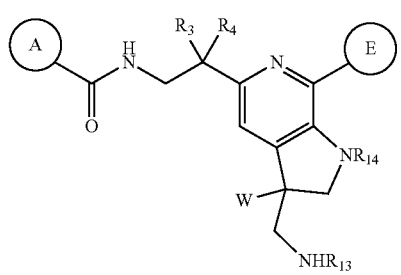

(VII-6)

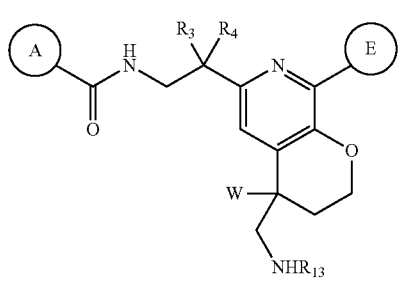

(VII-7)

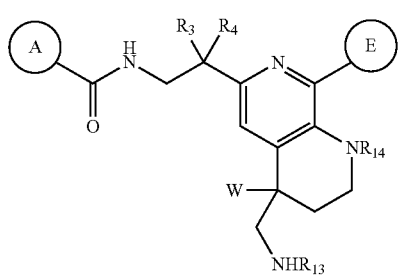

(VII-8)

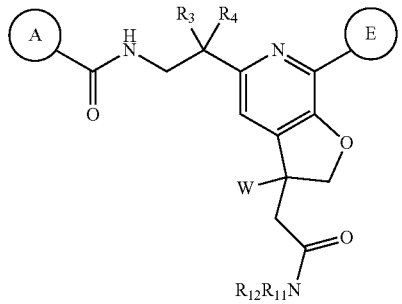

(VII-9)

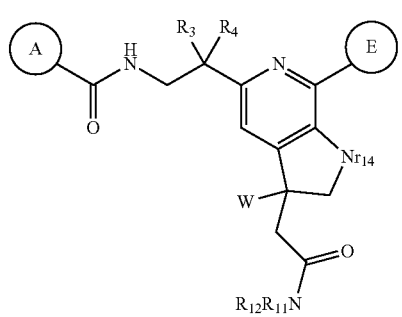

(VII-10)

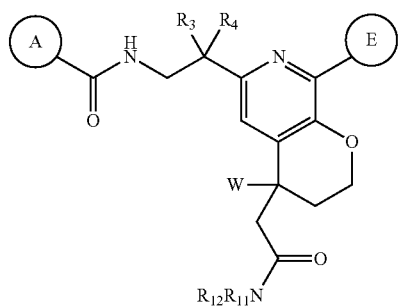

(VII-11)

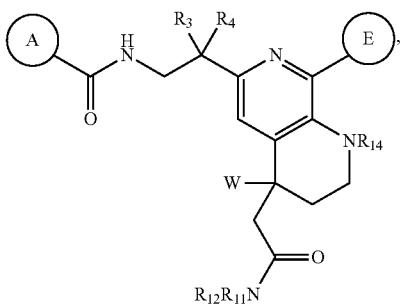

(VII-12)

wherein A, W, E, $R_{11}$, $R_{12}$, $R_{13}$, $R_{14}$, $R_3$, and $R_4$ are as previously defined. Preferably, W is optionally substituted methyl or halogen; more preferably, W is —$CH_3$, —$CF_3$ or fluorine.

In one embodiment of the present invention, the compound of Formula (I) is represented by one of Formulae (VII-1a)~(VII-12a), or a pharmaceutically acceptable salt, ester or prodrug thereof:

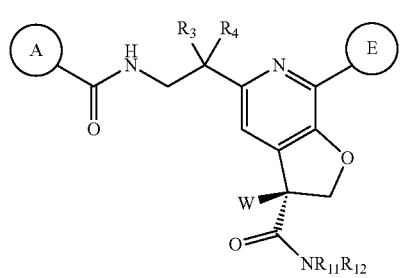

(VII-1a)

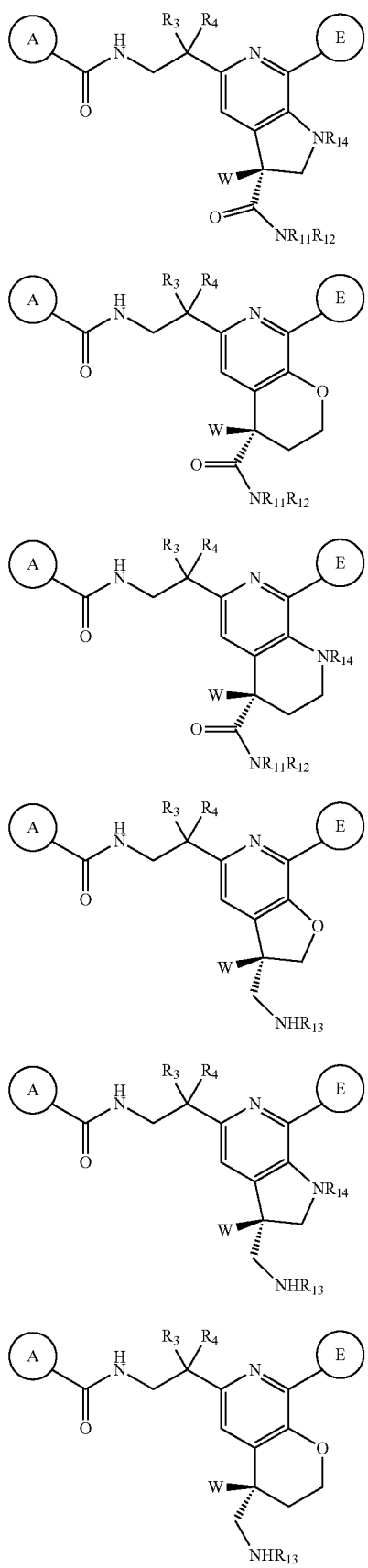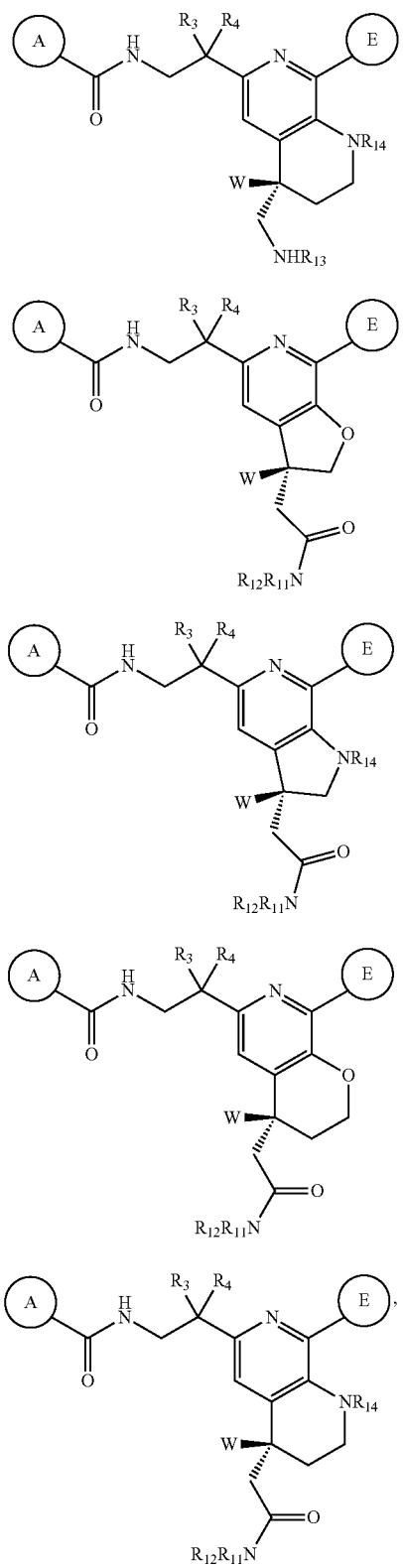
wherein A, W, E, $R_{11}$, $R_{12}$, $R_{13}$, $R_{14}$, $R_3$, and $R_4$ are as previously defined. Preferably, W is optionally substituted methyl or halogen; more preferably, W is —$CH_3$, —$CF_3$ or fluorine.

In one embodiment of the present invention, the compound of Formula (I) is represented by one of Formulae (VIIIa)~(VIIId), or a pharmaceutically acceptable salt, ester or prodrug thereof:

(VIIIa)
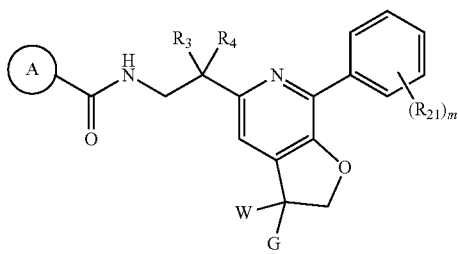

(VIIIb)
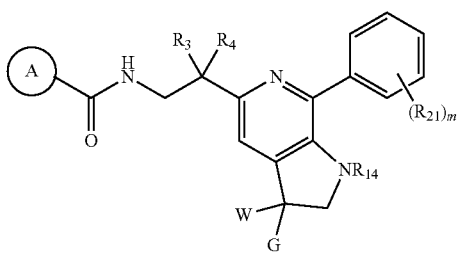

(VIIIc)
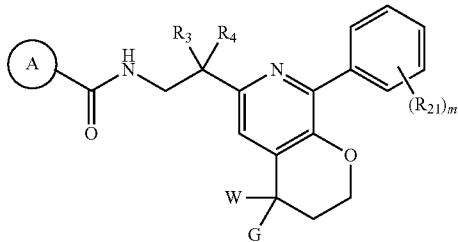

(VIIId)
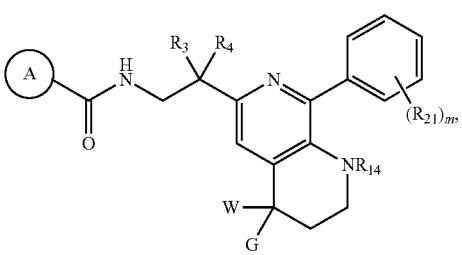

wherein each $R_{21}$ is independently optionally substituted methyl, halo, —CN, —$OR_{11}$, or —$NR_{11}R_{12}$; m is 0, 1, 2, 3, 4 or 5; A, W, G, $R_{11}$, $R_{12}$, $R_{14}$, $R_3$, and $R_4$ are as previously defined. Preferably, each $R_{21}$ is independently halo or optionally substituted methyl, and m is 1 or 2. More preferably, each $R_{21}$ is independently —F, —Cl, —CN, —$CF_3$, —$CH_2F$ or —$CHF_2$, and m is 1 or 2.

In one embodiment of the present invention, the compound of Formula (I) is represented by one of Formulae (VIIIe)~(VIIIh), or a pharmaceutically acceptable salt, ester, or prodrug thereof:

(VIIIe)
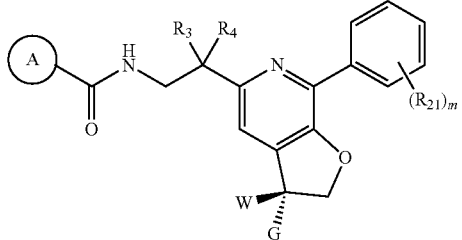

(VIIIf)
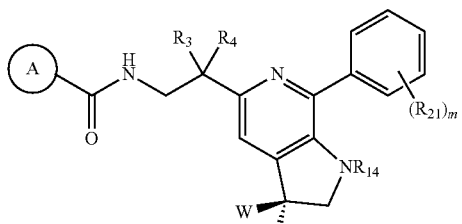

(VIIIg)
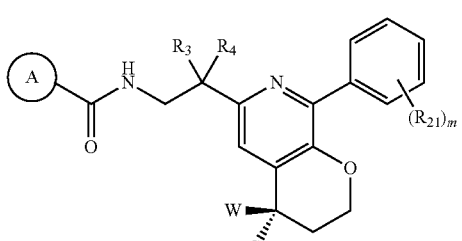

(VIIIh)
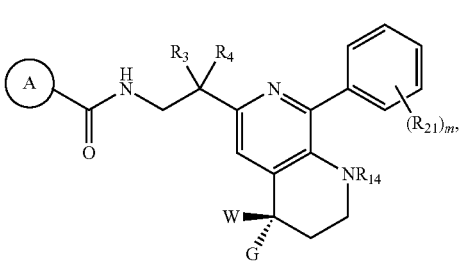

wherein $R_{21}$, m, A, W, G, $R_{14}$, $R_3$, and $R_4$ are as previously defined. Preferably, each $R_{21}$ is independently halo or optionally substituted methyl, and m is 1 or 2.

In one embodiment of the present invention, the compound of Formula (I) is represented by one of Formulae (IXa)~(IXd), or a pharmaceutically acceptable salt, ester, or prodrug thereof:

(IXa)
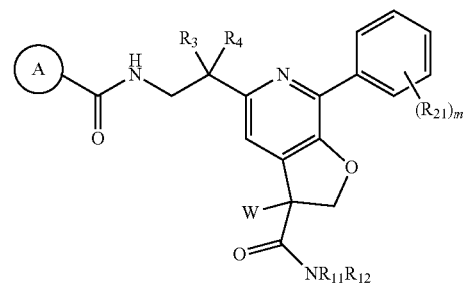

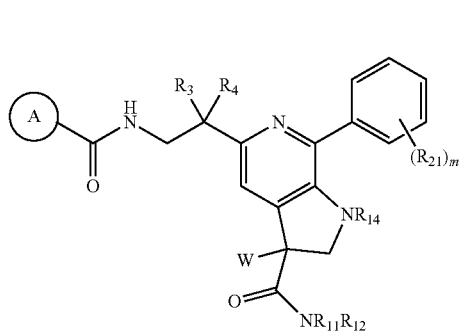

(IXb)

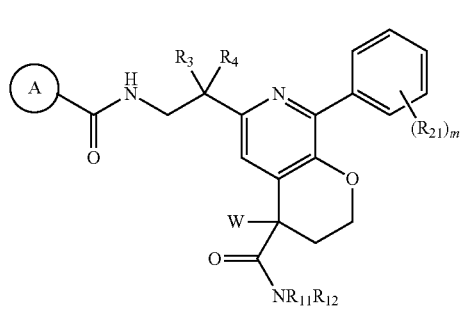

(IXc)

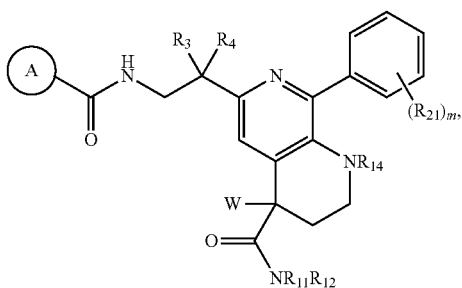

(IXd)


(IXf)

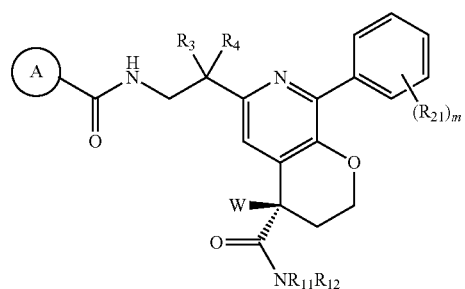

(IXg)

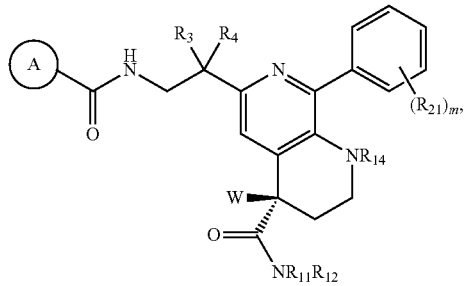

(IXh)

wherein $R_{21}$, m, $R_3$, $R_4$, A, W, $R_{11}$, $R_{12}$, and $R_{14}$ are as previously defined. Preferably, each $R_{21}$ is independently halo or optionally substituted methyl, and m is 1 or 2.

In one embodiment of the present invention, the compound of Formula (I) is represented by one of Formulae (IXe)~(IXh), or a pharmaceutically acceptable salt, ester or prodrug thereof:

wherein $R_{21}$, m, $R_3$, $R_4$, A, W, $R_{11}$, $R_{12}$, and $R_{14}$ are as previously defined. Preferably, $R_{21}$ is halo or optionally substituted methyl, and m is 1 or 2.

In one embodiment of the present invention, the compound of Formula (I) is represented by one of Formulae (X-1)~(X-6), or a pharmaceutically acceptable salt, ester or prodrug thereof:

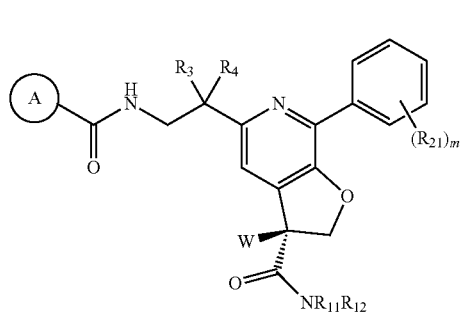

(IXe)

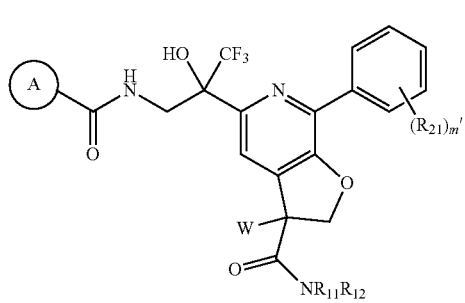

(X-1)

-continued
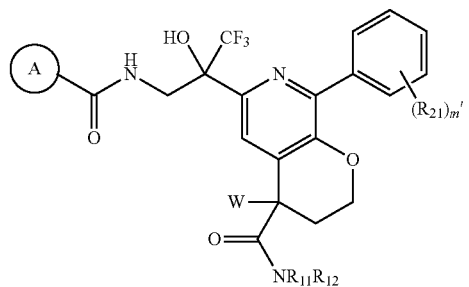
(X-2)
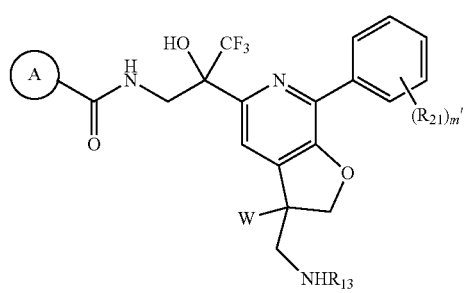
(X-3)
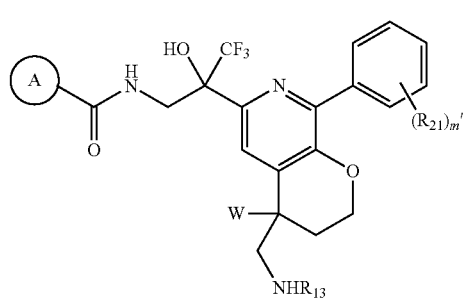
(X-4)
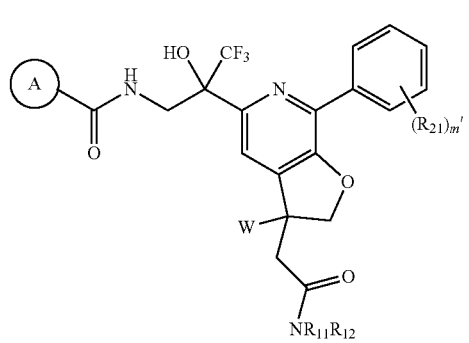
(X-5)
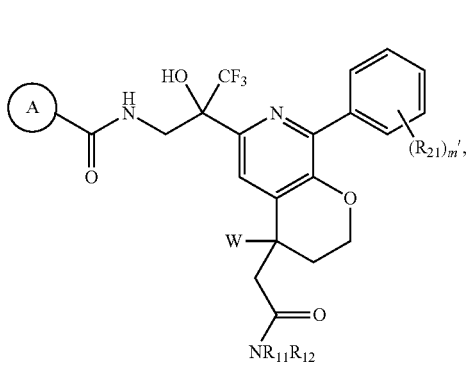
(X-6)
wherein m' is 0, 1 or 2; $R_{21}$, A, W, $R_{11}$, $R_{12}$, and $R_{13}$ are as previously defined. Preferably m' is 2.
In one embodiment of the present invention, the compound of Formula (I) is represented by one of Formulae (X-1a)~(X-6a), or a pharmaceutically acceptable salt, ester, or prodrug thereof:
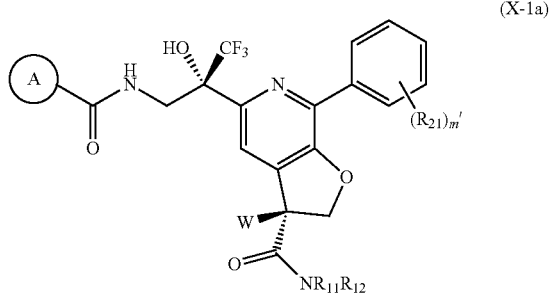
(X-1a)
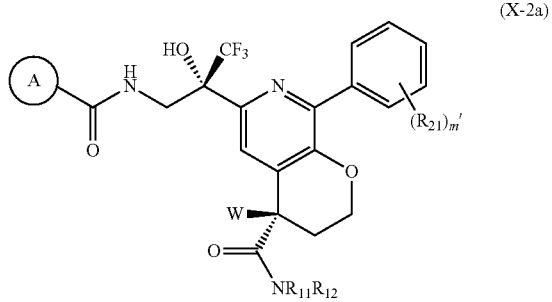
(X-2a)
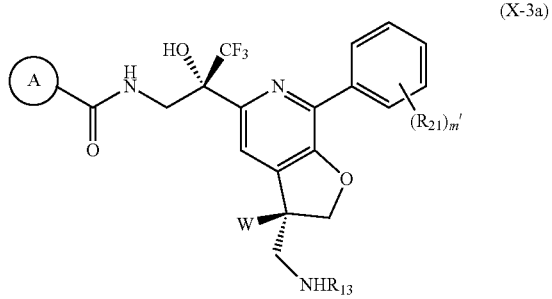
(X-3a)
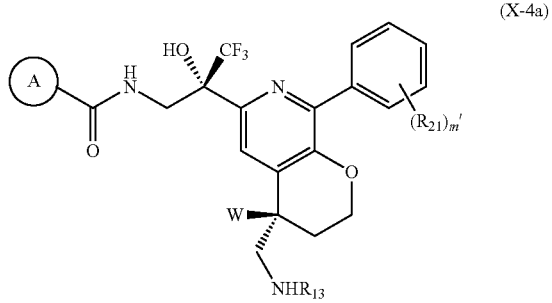
(X-4a)
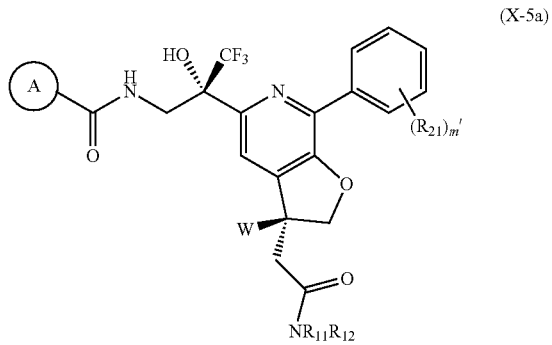
(X-5a)

(X-6a)
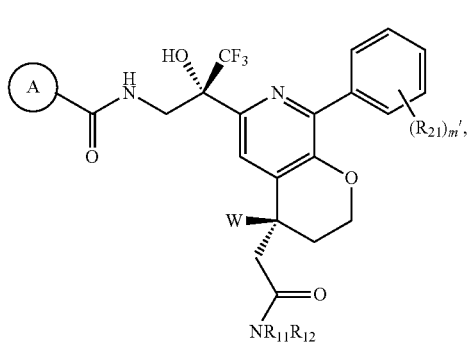
wherein $R_{21}$, m', A, W, $R_{11}$, $R_{12}$, and $R_{13}$ are as previously defined. Preferably m' is 2.
In one embodiment of the present invention, the compound of Formula (I) is represented by one of Formulae (XI-1)~(XI-12), or a pharmaceutically acceptable salt, ester, or prodrug thereof:
(XI-1)
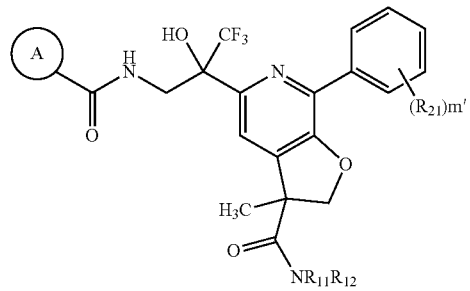
(XI-2)
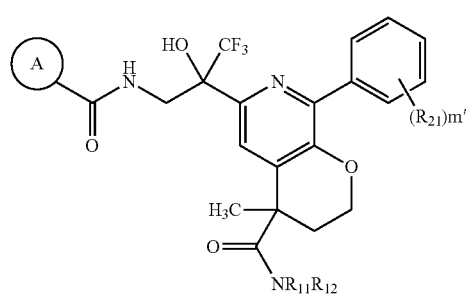
(XI-3)
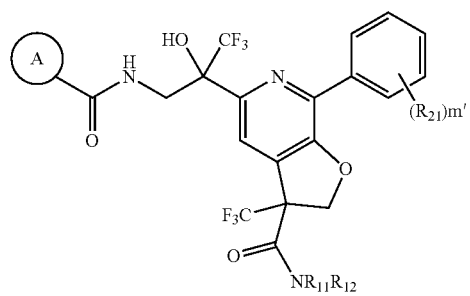
(XI-4)
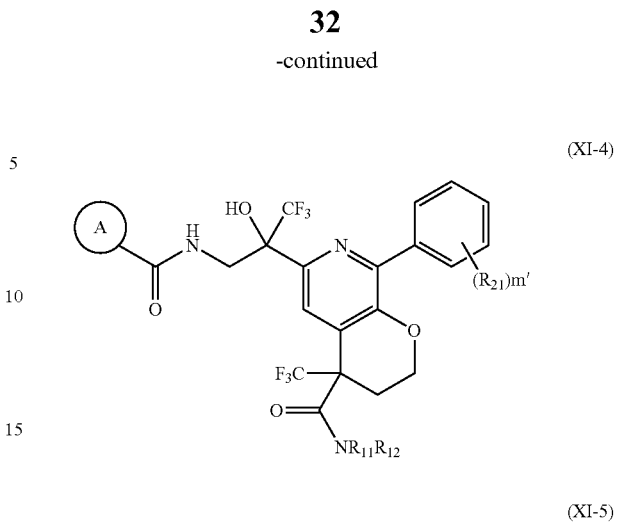
(XI-5)
(XI-6)
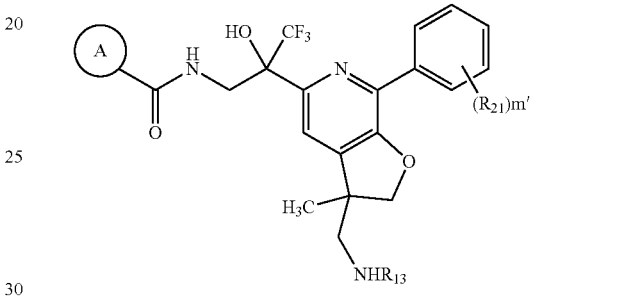
(XI-7)
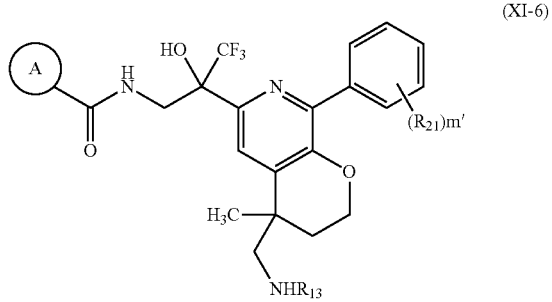
(XI-8)
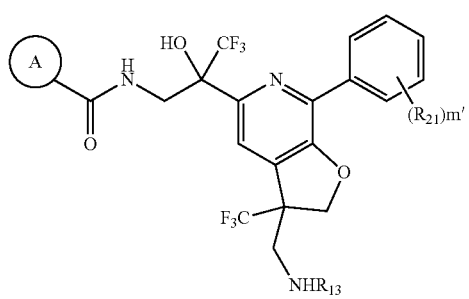
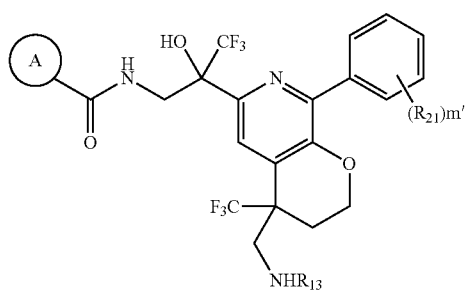

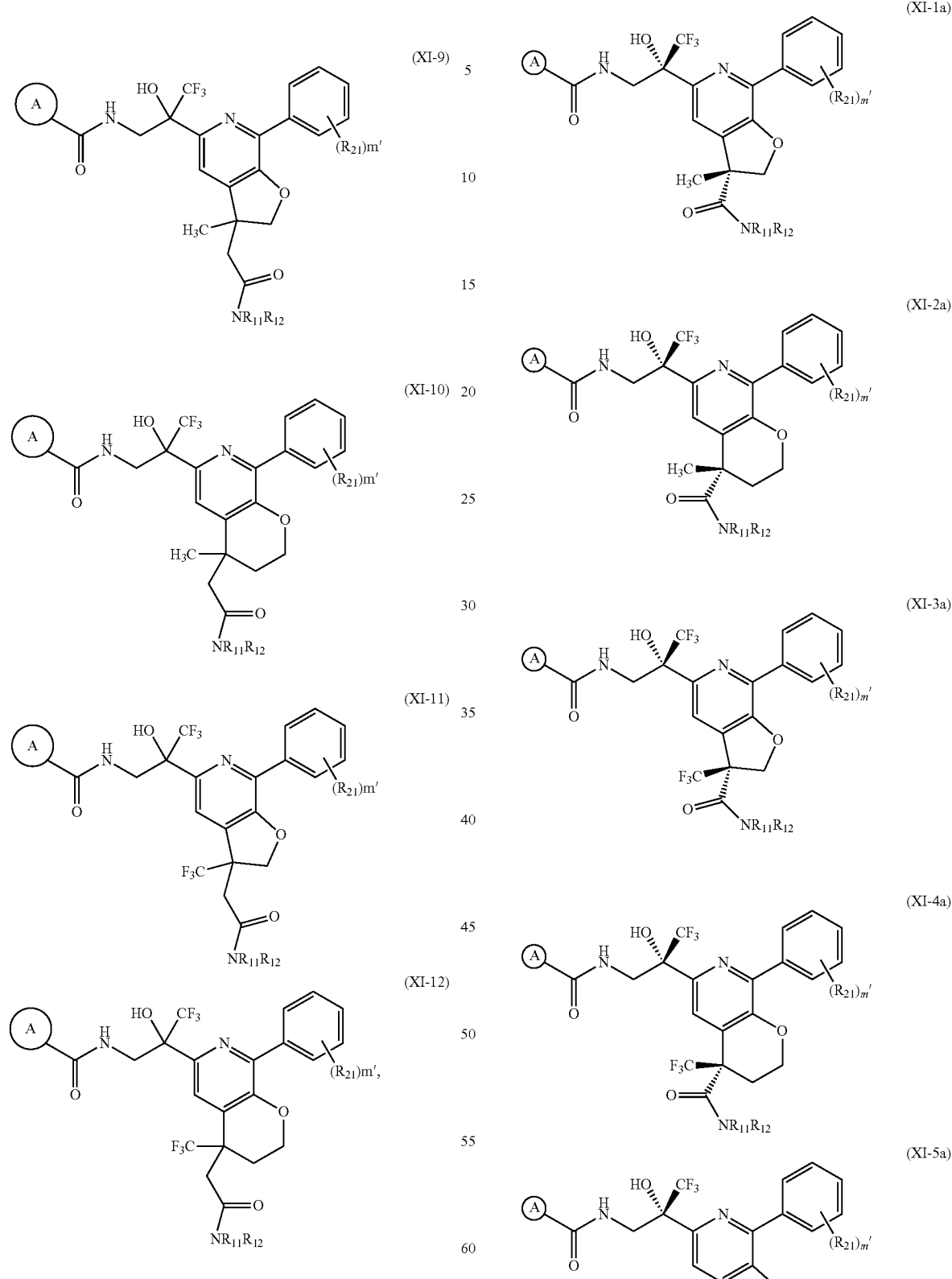
wherein $R_{21}$, m', A, $R_{11}$, $R_{12}$, and $R_{13}$ are as previously defined. Preferably m' is 2.
In one embodiment of the present invention, the compound of Formula (I) is represented by one of Formulae (XI-1a)~(XI-12a), or a pharmaceutically acceptable salt, ester or prodrug thereof:

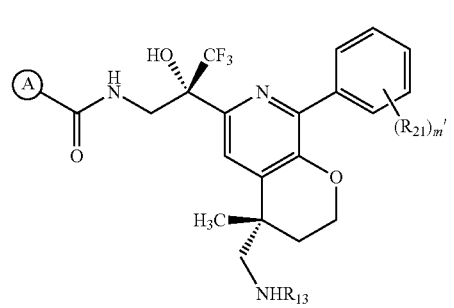 (XI-6a)
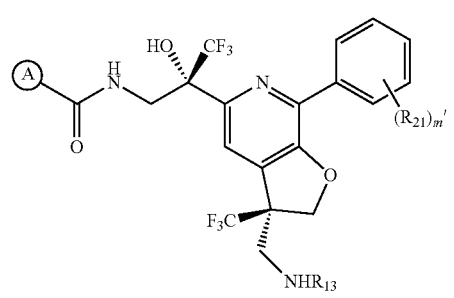 (XI-7a)
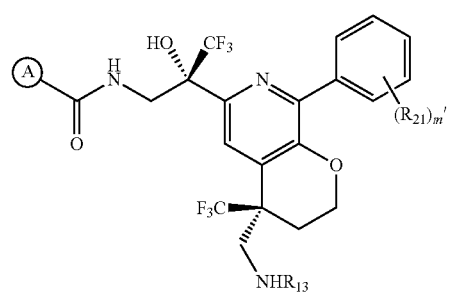 (XI-8a)
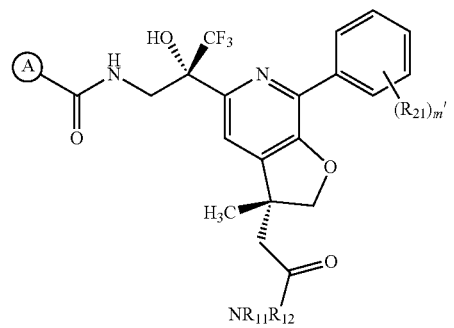 (XI-9a)
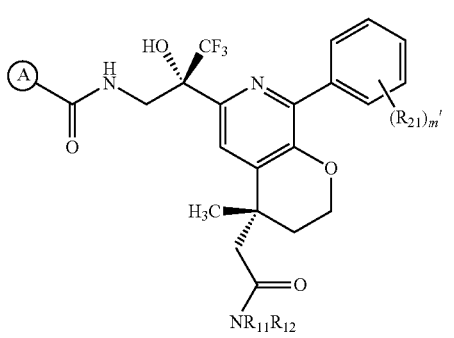 (XI-10a)
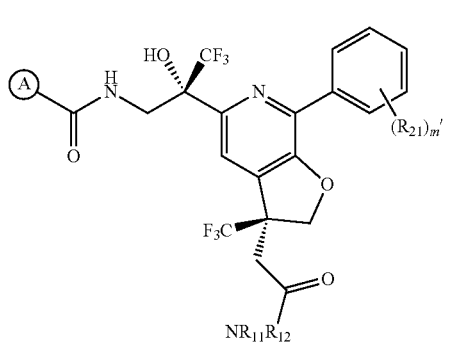 (XI-11a)
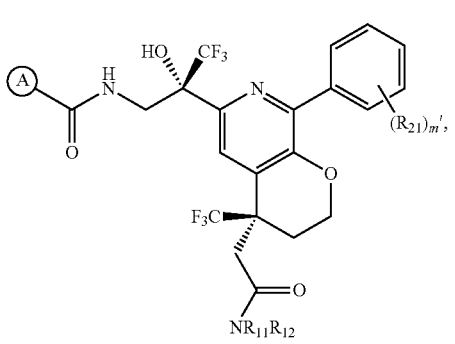 (XI-12a),
wherein $R_{21}$, m', A, $R_{11}$, $R_{12}$, and $R_{13}$ are as previously defined. Preferably m' is 2.
In one embodiment of the present invention, the compound of Formula (I) is represented by one of Formulae (XIVa)~(XIVd), or a pharmaceutically acceptable salt, ester or prodrug thereof:
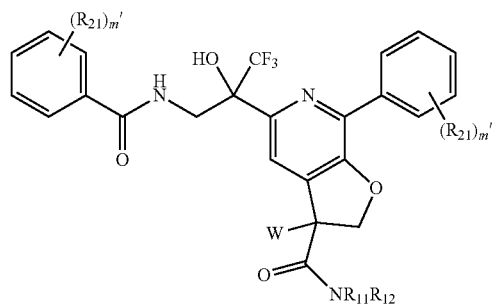 (XIVa)
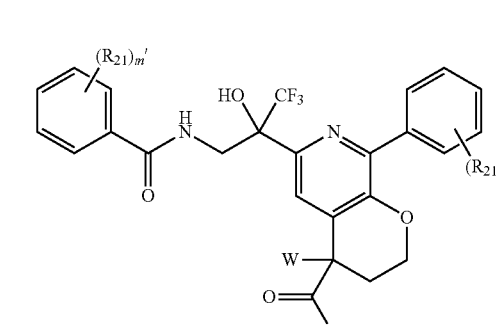 (XIVb)

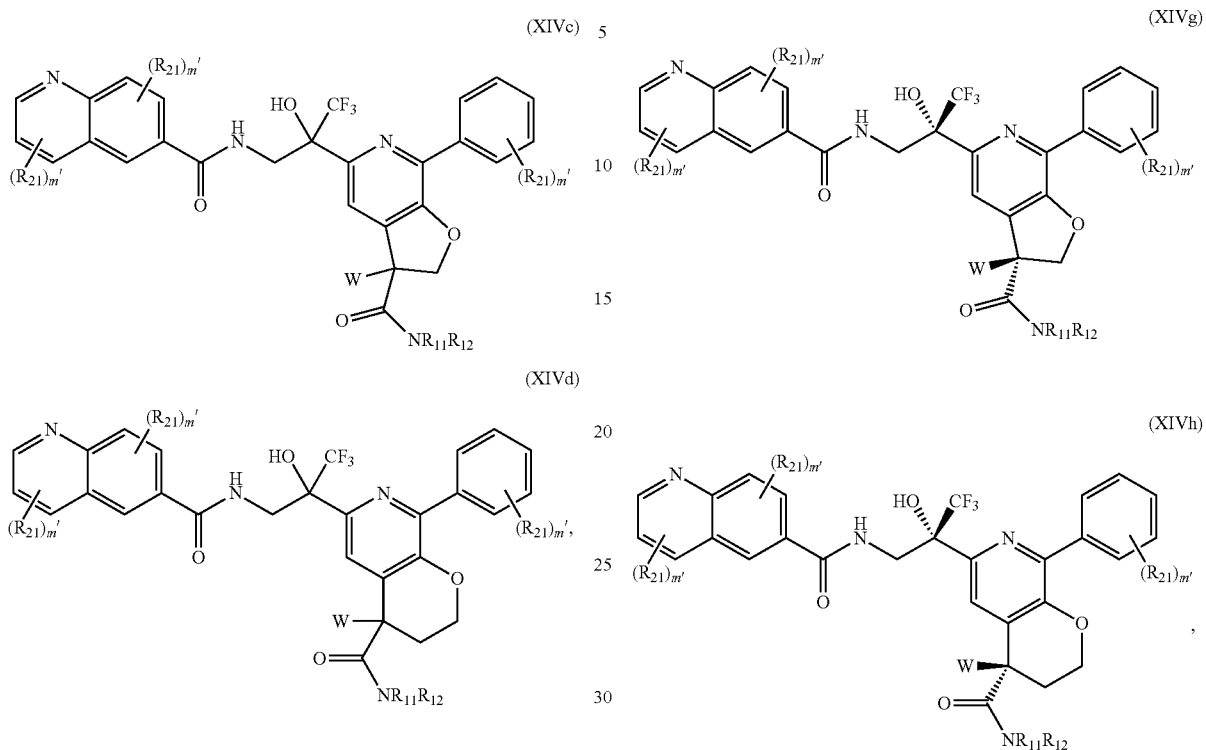

wherein W, $R_{21}$, m', $R_{11}$, and $R_{12}$ are as previously defined.

In one embodiment of the present invention, the compound of Formula (I) is represented by one of Formulae (XIVe)~(XIVh), or a pharmaceutically acceptable salt, ester or prodrug thereof:

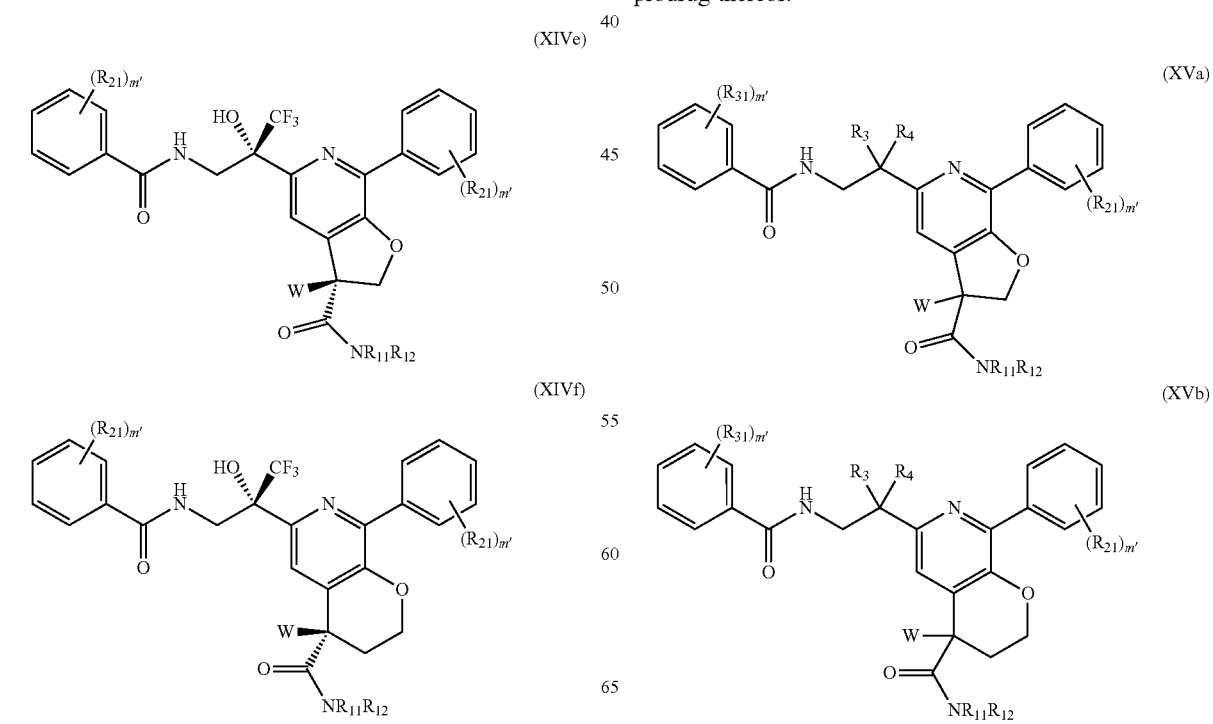

wherein W, $R_{21}$, m', $R_{11}$, and $R_{12}$ are as previously defined.

In one embodiment of the present invention, the compound of Formula (I) is represented by one of Formulae (XVa)~(XVd), or a pharmaceutically acceptable salt, ester or prodrug thereof:

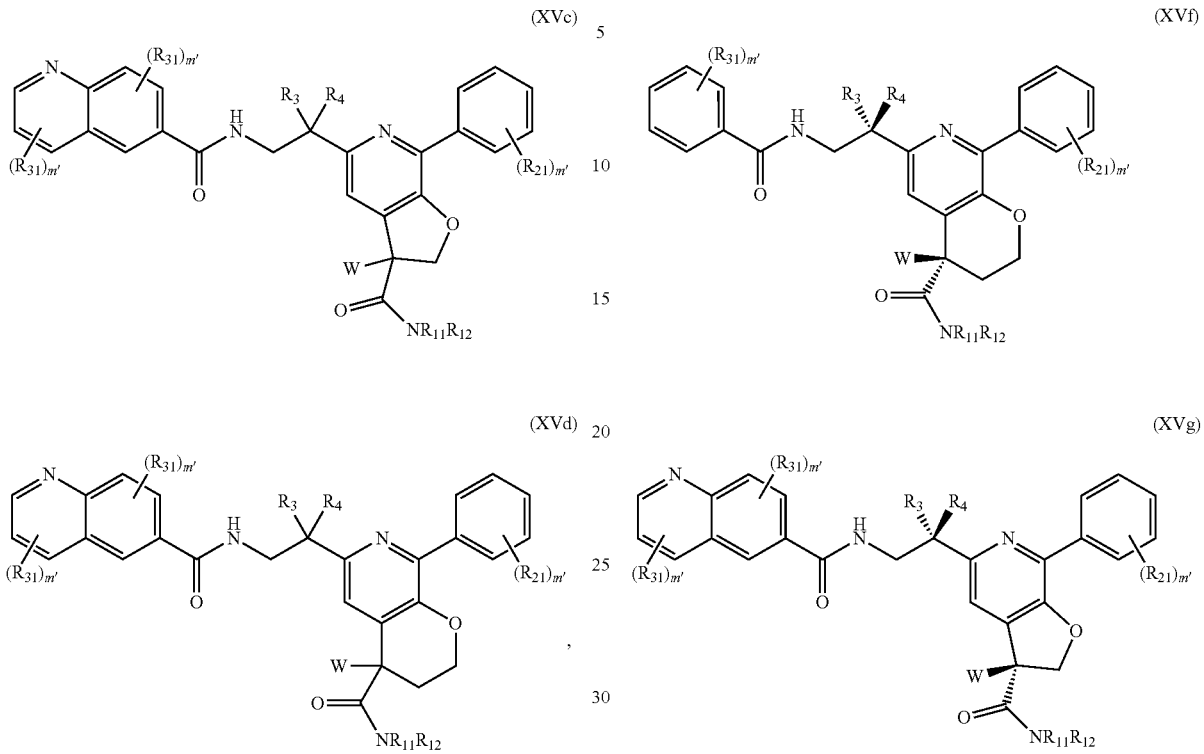

(XVc), (XVd), (XVf), (XVg), (XVh)

wherein each $R_{31}$ is independently halo; —CN; —NO$_2$, —OR$_{11}$; —NR$_{11}$R$_{12}$; —NR$_{11}$C(O)R$_{12}$; —NR$_{11}$S(O)$_2$R$_{12}$; —S(O)$_2$R$_{12}$; —S(O)$_2$NR$_{11}$R$_{12}$, —NR$_{11}$C(O)NR$_{11}$R$_{12}$; —C(O)R$_{11}$, —C(O)OR$_{11}$; —C(O)NR$_{11}$R$_{12}$; optionally substituted —C$_1$-C$_6$ alkyl; optionally substituted —C$_3$-C$_8$-cycloalkyl; optionally substituted 3- to 8-membered heterocyclic; optionally substituted aryl; or optionally substituted heteroaryl, and W, m', R$_3$, R$_4$, R$_{21}$, R$_{11}$, and R$_{12}$ are as previously defined. In certain embodiments, two adjacent R$_{31}$ groups are taken together with the carbon atoms to which they are attached to form a 4- to 12-membered carbocyclic or heterocyclic, and which said 4- to 12-membered carbocyclic or heterocyclic is fused with the phenyl or quinolinyl.

In one embodiment of the present invention, the compound of Formula (I) is represented by one of Formulae (XVe)~(XVh), or a pharmaceutically acceptable salt, ester or prodrug thereof:

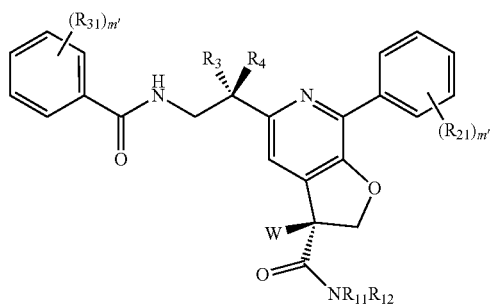

(XVe)

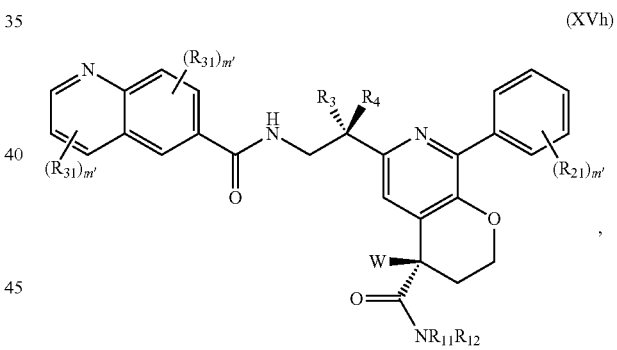

wherein W, m', R$_3$, R$_4$, R$_{21}$, R$_{31}$, R$_{11}$, and R$_{12}$ are as previously defined. In certain embodiment, two adjacent R$_{31}$ groups are taken together with the carbon atoms to which they are attached to form a 4- to 12-membered carbocyclic or heterocyclic ring, and which said 4- to 12-membered carbocyclic or heterocyclic is fused with the phenyl or quinolinyl.

In one embodiment of the present invention, the compound of Formula (I) is represented by one of Formulae (XVa)~(XVh), or a pharmaceutically acceptable salt, ester or prodrug thereof, R$_3$ is —OH, and R$_4$ is —CH$_3$, —CF$_3$, or cyclopropyl.

In one embodiment of the present invention, the compound of Formula (I) is represented by one of Formulae (XVa-1)~(XVb-1), Formulae (XVc-1)~(XVc-4), Formulae (XVd-1)~(XVd-4), or a pharmaceutically acceptable salt, ester or prodrug thereof:

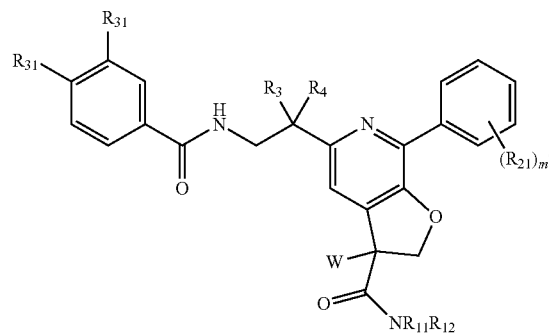
(XVa-1)
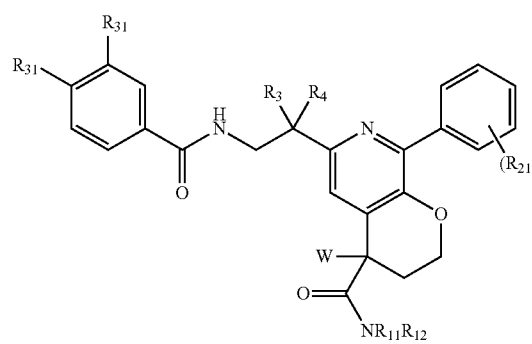
(XVb-1)
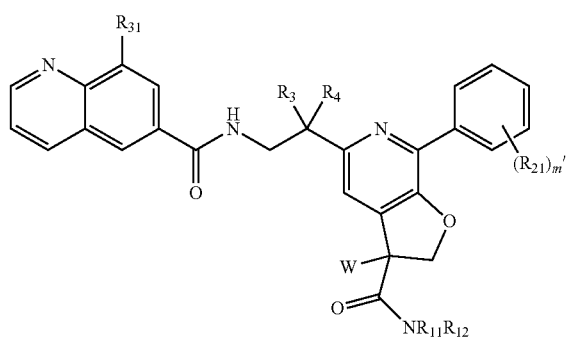
(XVc-1)
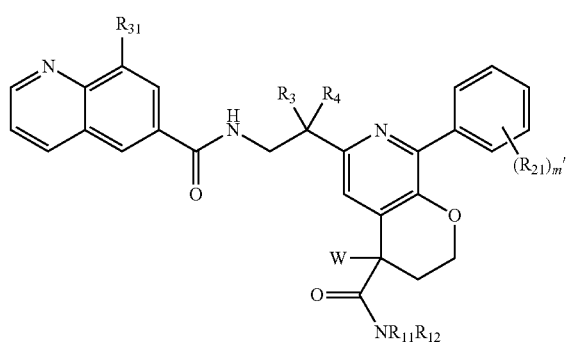
(XVd-1)
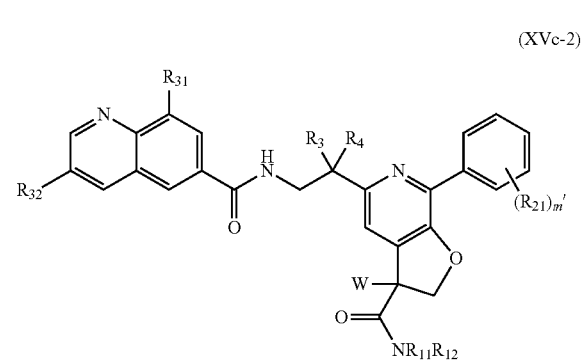
(XVc-2)
(XVd-2)
(XVc-3)
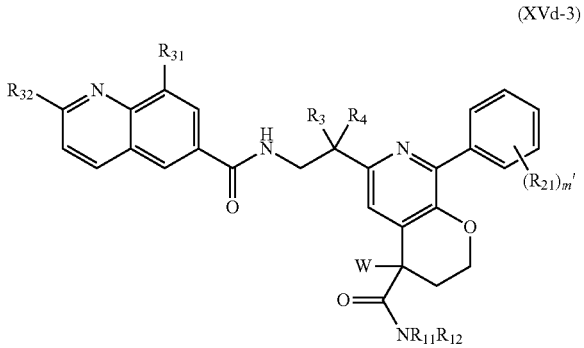
(XVd-3)

(XVc-4)

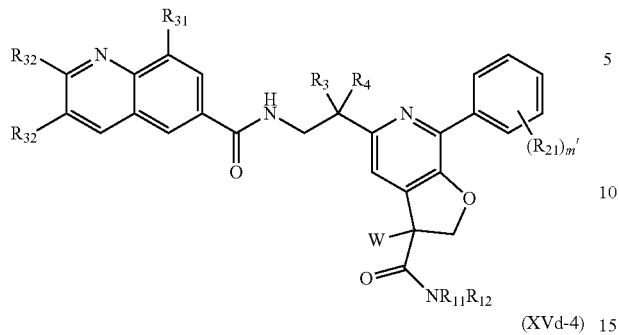

(XVd-4)

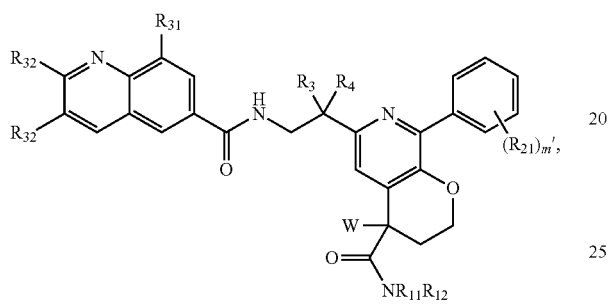

wherein each $R_{32}$ is independently halogen, —$OR_{11}$; —$NR_{11}R_{12}$, optionally substituted —$C_1$-$C_6$-alkyl; optionally substituted —$C_3$-$C_8$-cycloalkyl; optionally substituted 3- to 8-membered heterocyclic; optionally substituted aryl; or optionally substituted heteroaryl; W, m', $R_3$, $R_4$, $R_{21}$, $R_{31}$, $R_{11}$, and $R_{12}$ are as previously defined. In certain embodiment, two adjacent $R_{32}$ groups are taken together with the carbon atoms to which they are attached to form a 4- to 12-membered carbocyclic or heterocyclic ring, and which said 4- to 12-membered carbocyclic or heterocyclic is fused with the phenyl or quinolinyl.

In one embodiment of the present invention, the compound of Formula (I) is represented by one of Formulae (XVa-1)~(XVb-1), Formulae (XVc-1)~(XVc-4), Formulae (XVd-1)~(XVd-4), or a pharmaceutically acceptable salt, ester or prodrug thereof, $R_3$ is —OH, and $R_4$ is —$CH_3$, —$CF_3$, or cyclopropyl.

In one embodiment of the present invention, the compound of Formula (I) is represented by one of Formulae (XVe-1)~(XVf-1), Formulae (XVg-1)~(XVg-4), Formulae (XVh-1)~(XVh-4), or a pharmaceutically acceptable salt, ester or prodrug thereof:

(XVe-1)

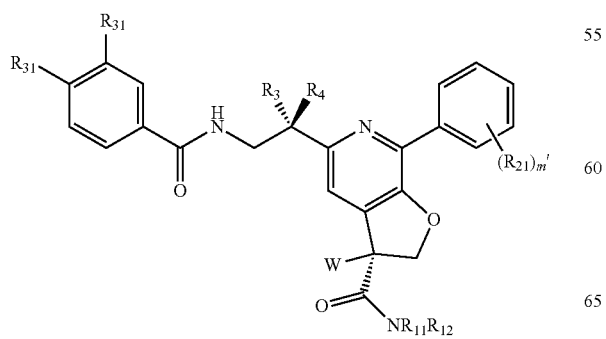

(XVf-1)

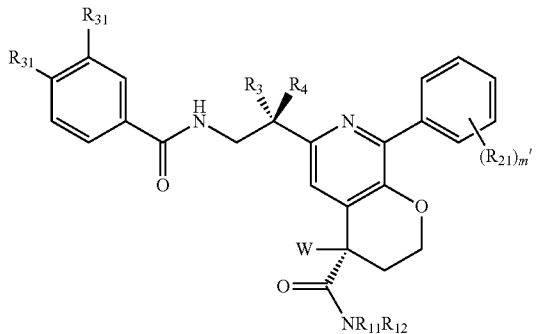

(XVg-1)

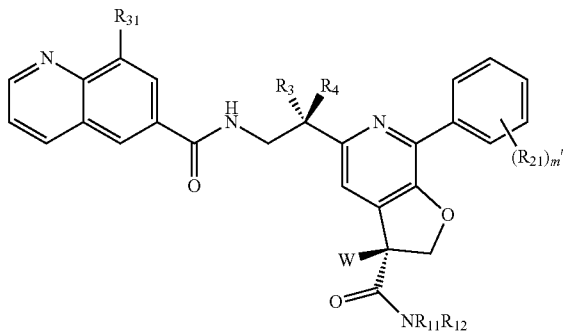

(XVh-1)

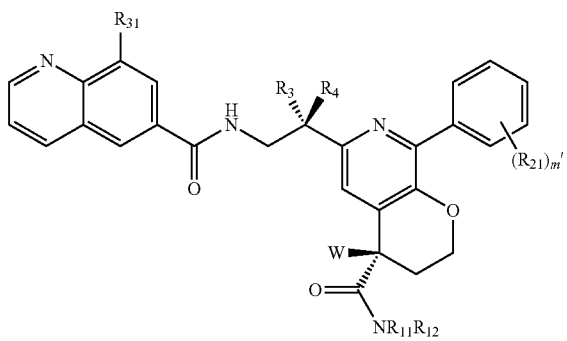

(XVg-2)

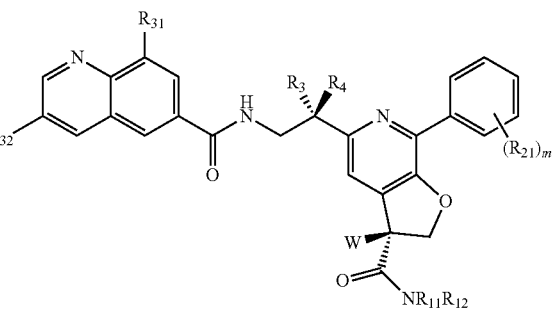

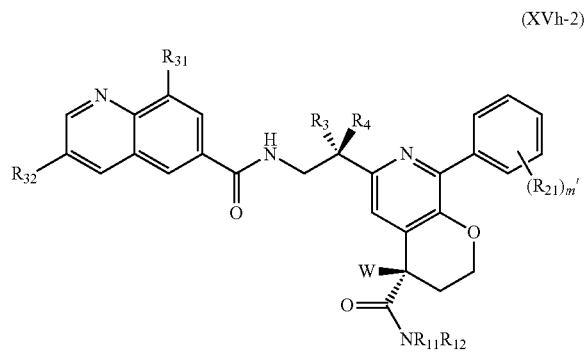

(XVh-2)

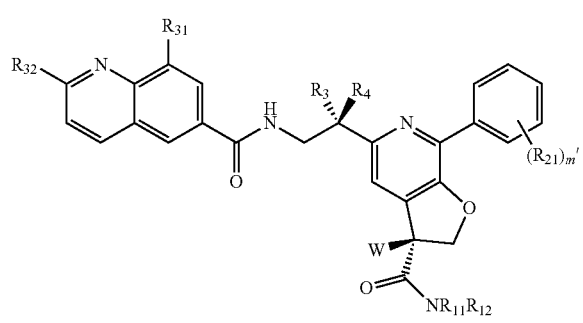

(XVg-3)

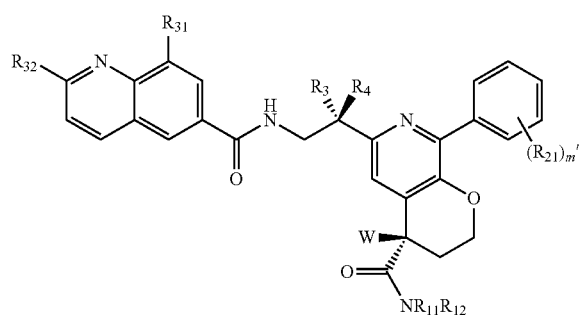

(XVh-3)

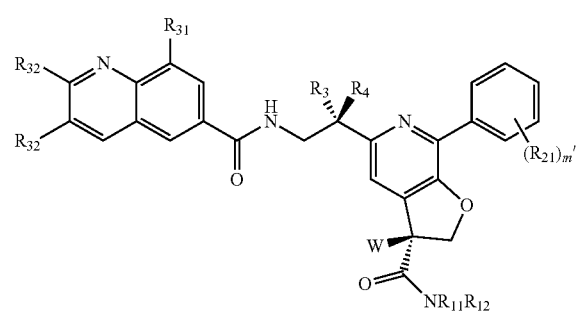

(XVg-4)

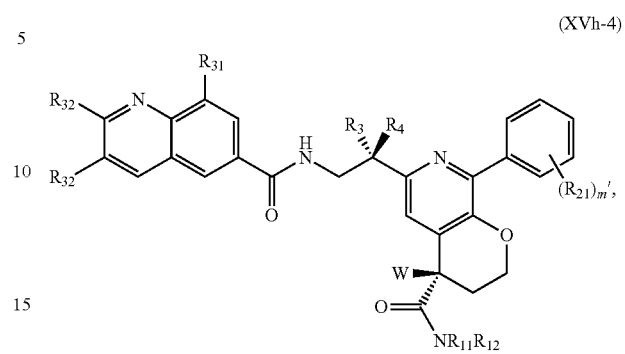

(XVh-4)

wherein W, m', $R_3$, $R_4$, $R_{21}$, $R_{31}$, $R_{32}$, $R_{11}$, and $R_{12}$ are as previously defined. In certain embodiments, two adjacent $R_{32}$ groups are taken together with the carbon atoms to which they are attached to form a 4- to 12-membered carbocyclic or heterocyclic ring, and which said 4- to 12-membered carbocyclic or heterocyclic is fused with the phenyl or quinolinyl.

In one embodiment of the present invention, the compound of Formula (I) is represented by one of Formulae (XVe-1)~(XVf-1), Formulae (XVg-1)~(XVg-4), Formulae (XVh-1)~(XVh-4), or a pharmaceutically acceptable salt, ester or prodrug thereof, $R_3$ is —OH, and $R_4$ is —CH$_3$, —CF$_3$, or cyclopropyl.

In one embodiment of the present invention, the compound of Formula (I) is represented by one of Formulae (XVIa)~(XVIh), or a pharmaceutically acceptable salt, ester or prodrug thereof:

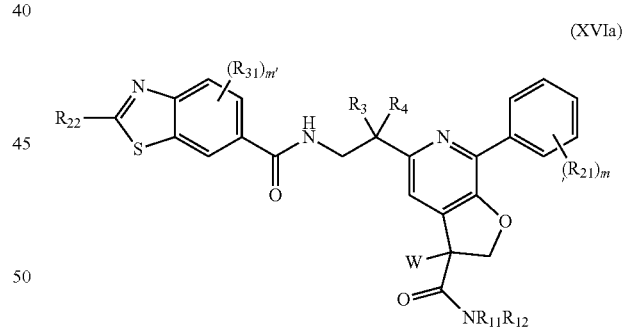

(XVIa)

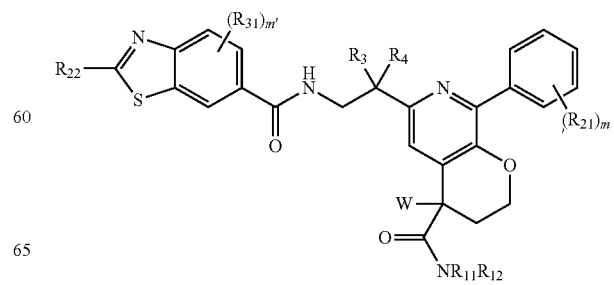

(XVIb)

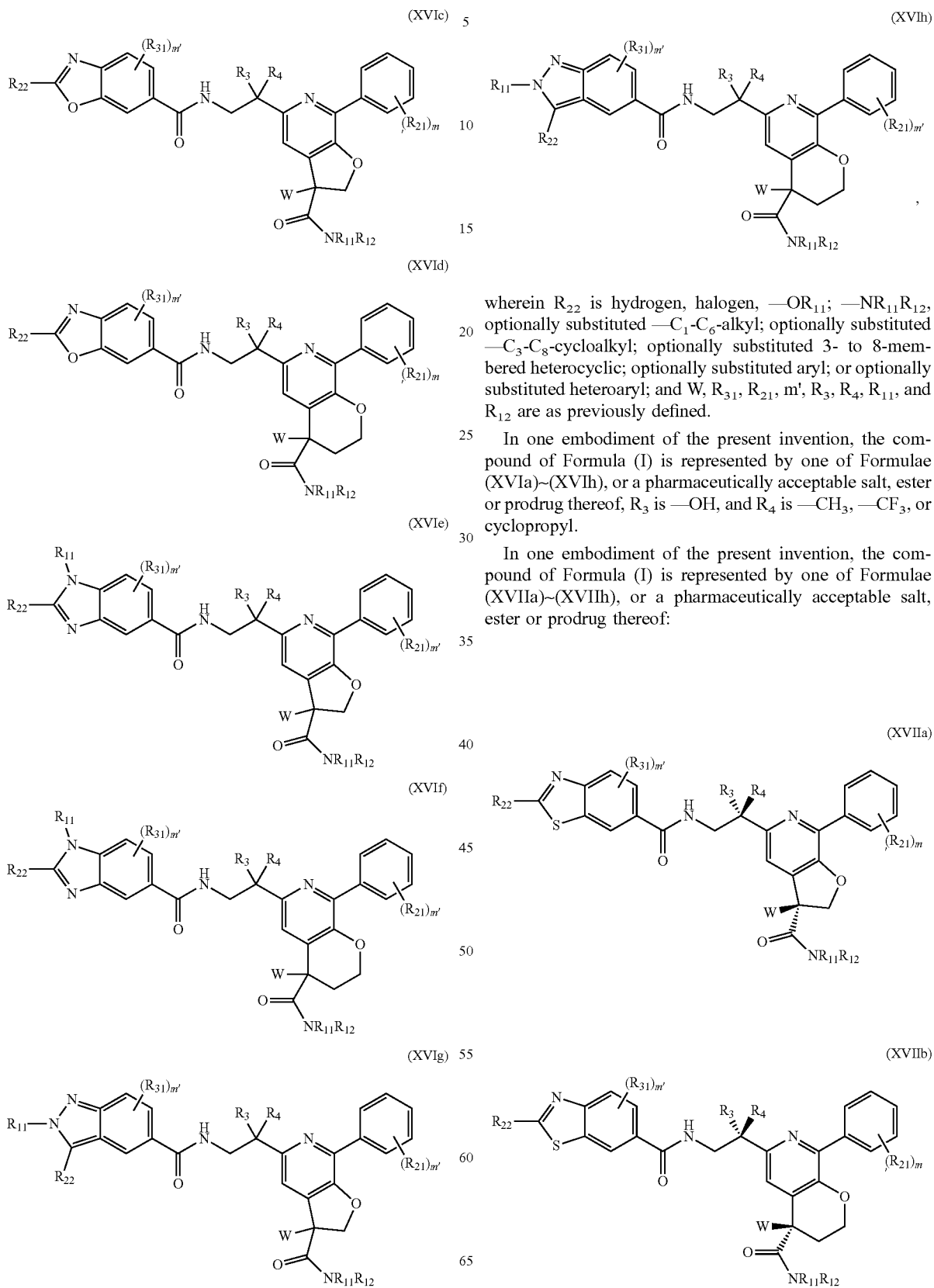

wherein $R_{22}$ is hydrogen, halogen, $-OR_{11}$; $-NR_{11}R_{12}$, optionally substituted $-C_1$-$C_6$-alkyl; optionally substituted $-C_3$-$C_8$-cycloalkyl; optionally substituted 3- to 8-membered heterocyclic; optionally substituted aryl; or optionally substituted heteroaryl; and W, $R_{31}$, $R_{21}$, m', $R_3$, $R_4$, $R_{11}$, and $R_{12}$ are as previously defined.

In one embodiment of the present invention, the compound of Formula (I) is represented by one of Formulae (XVIa)~(XVIh), or a pharmaceutically acceptable salt, ester or prodrug thereof, $R_3$ is $-OH$, and $R_4$ is $-CH_3$, $-CF_3$, or cyclopropyl.

In one embodiment of the present invention, the compound of Formula (I) is represented by one of Formulae (XVIIa)~(XVIIh), or a pharmaceutically acceptable salt, ester or prodrug thereof:

(XVIIc)

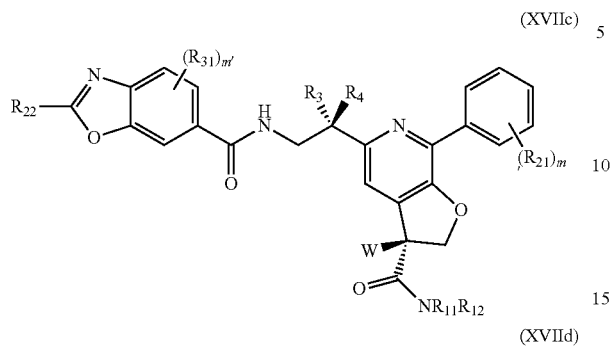

(XVIId)

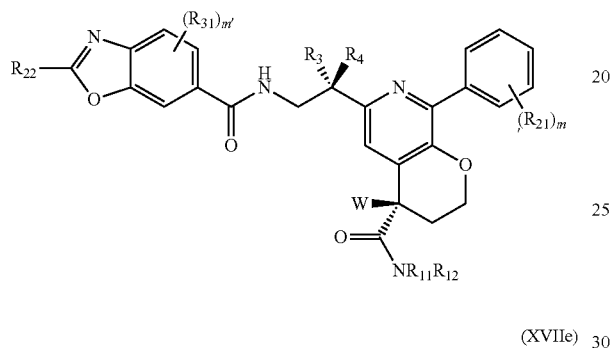

(XVIIe)

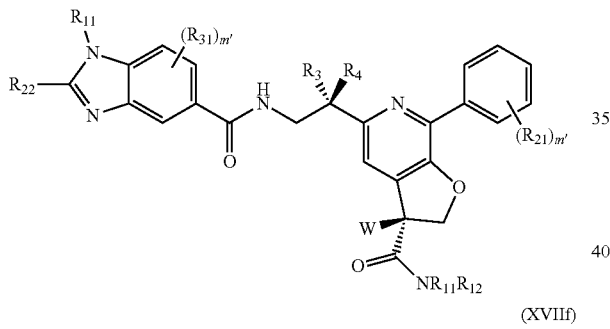

(XVIIf)

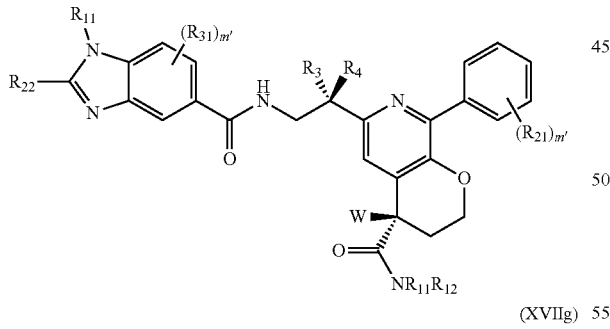

(XVIIg)

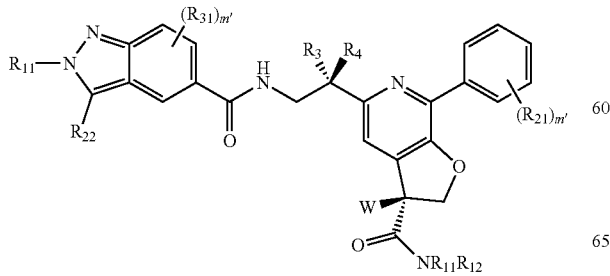

(XVIIh)

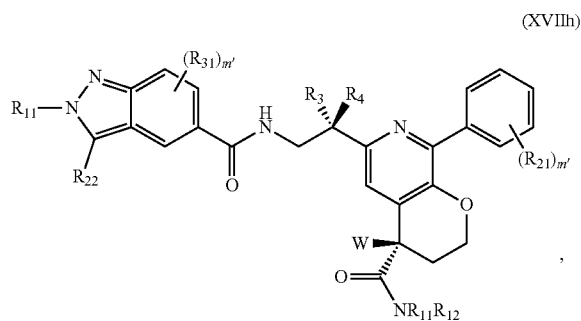

wherein W, $R_{21}$, $R_{22}$, $R_{31}$, m', $R_3$, $R_4$, $R_{11}$, and $R_{12}$ are as previously defined.

In one embodiment of the present invention, the compound of Formula (I) is represented by one of Formulae (XVIIa)~(XVIIh), or a pharmaceutically acceptable salt, ester or prodrug thereof, $R_3$ is —OH, and $R_4$ is —$CH_3$, —$CF_3$, or cyclopropyl.

In one embodiment of the present invention, the compound of Formula (I) is represented by one of Formulae (XVIIIa)~(XVIIId), or a pharmaceutically acceptable salt, ester or prodrug thereof:

(XVIIIa)

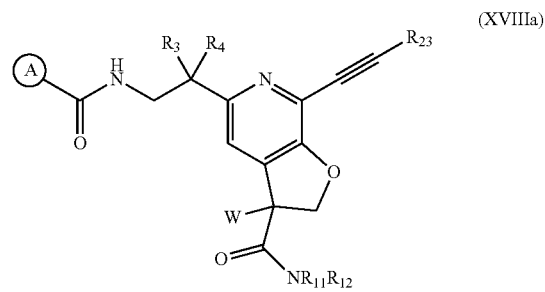

(XVIIIb)

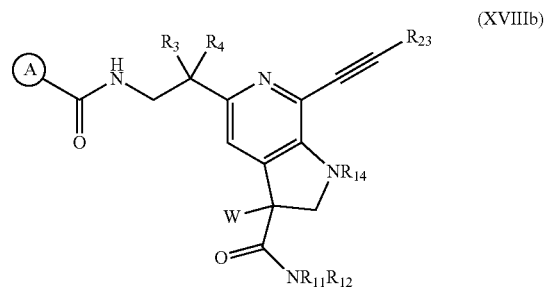

(XVIIIc)

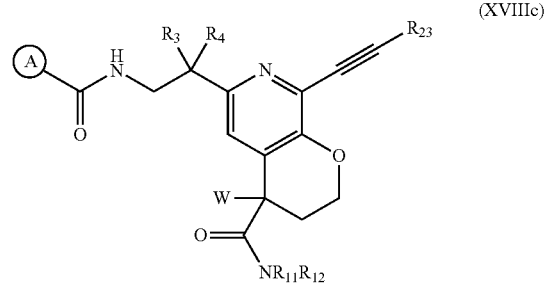

-continued

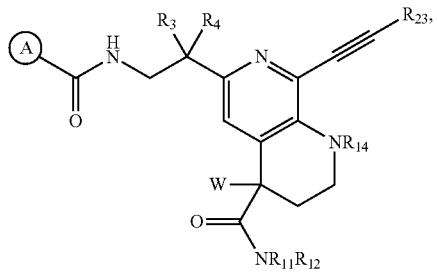

(XVIIId)

wherein $R_{23}$ is hydrogen, optionally substituted —$C_1$-$C_6$-alkyl; optionally substituted —$C_3$-$C_8$-cycloalkyl; optionally substituted 3- to 8-membered heterocyclic; optionally substituted aryl; or optionally substituted heteroaryl; $R_3$, $R_4$, A, W, $R_{11}$, $R_{12}$, and $R_{14}$ are as previously defined.

In one embodiment of the present invention, the compound of Formula (I) is represented by one of Formulae (XVIIIe)~(XVIIIh), or a pharmaceutically acceptable salt, ester or prodrug thereof:

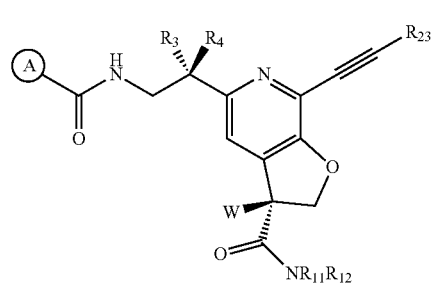

(XVIIIe)

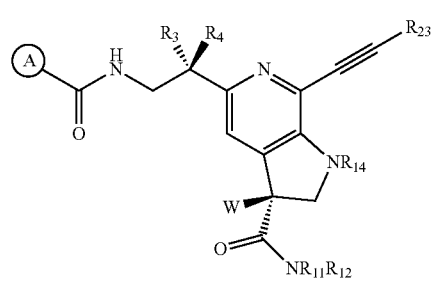

(XVIIIf)

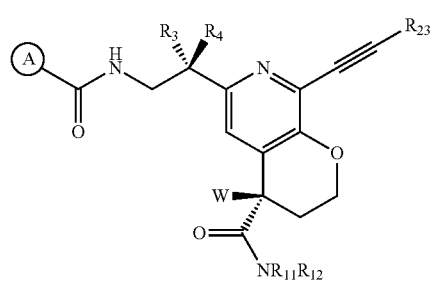

(XVIIIg)

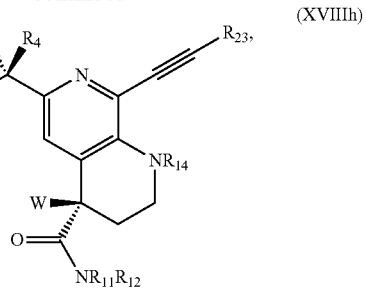

(XVIIIh)

wherein $R_{23}$, $R_3$, $R_4$, A, W, $R_{11}$, $R_{12}$, and $R_{14}$ are as previously defined.

In one embodiment of the present invention, the compound of Formula (I) is represented by one of Formulae (XVIIIa)~(XVIIIh), or a pharmaceutically acceptable salt, ester or prodrug thereof, $R_3$ is —OH, and $R_4$ is —$CH_3$, —$CF_3$, or cyclopropyl.

It will be appreciated that the description of the present invention herein should be construed in congruity with the laws and principles of chemical bonding. In some instances, it may be necessary to remove a hydrogen atom in order to accommodate a substituent at any given location.

It is intended that the definition of any substituent or variable (e.g., $R_1$, $R_2$, etc.) at a particular location in a molecule be independent of its definitions elsewhere in that molecule.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In certain embodiments, the present invention provides a method for the prevention or treatment of RSV activities and for treating RSV infection in a subject in need thereof. The method comprises administering to the subject a therapeutically effective amount of a compound of formula (I).

The present invention also provides the use of a compound of formula (I) for the preparation of a medicament for the prevention or treatment of RSV.

Thus, in one embodiment, a compound of formula (I), or pharmaceutically acceptable salt thereof, is combined with a steroid anti-inflammatory compound, for example budesonide or fluticasone. In a preferred embodiment, the steroid is administered in low doses to minimize immuno-suppressant effects. In another embodiment a compound of formula (I), or a pharmaceutically acceptable salt thereof, is combined with a non-steroid anti-inflammatory compound, for example leukotriene antagonists such as Singulair (Merck) or Accolate (Astra Zeneca), phosphodiesterase 4 inhibitors such as roflumilast (Altana), TNF alpha inhibitors such as Enbrel (Amgen), Remicade (Centocor), Humira (Abbott) or CDP870 (Celltech) or NSAIDS. In a further embodiment, a compound of formula (I) is combined with interleukin 8 or interleukin 9 inhibitors. The present invention thus also relates to a product containing a compound of formula (I), or a pharmaceutically acceptable salt thereof, and an anti-inflammatory compound for simultaneous, separate or sequential use in the treatment of RSV.

The present invention also relates to a combination of a compound of formula (I), or a pharmaceutically acceptable salt thereof, with an anti-influenza compound and the use of such a combination in the treatment of concomitant RSV and influenza infections. The present invention thus also relates to a product containing a compound of formula (I), or a pharmaceutically acceptable salt thereof, and an anti-influenza compound for simultaneous, separate or sequential use in the treatment of concomitant RSV and influenza infections. The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

In an embodiment, the compounds of the invention are administered by intranasal or intrabronchial administration. The present invention also provides an inhaler or nebulizer containing a medicament which comprises (a) a derivative of the formula (I), as defined above, or a pharmaceutically acceptable salt thereof, and (b) a pharmaceutically acceptable carrier or diluent.

The present invention also provides a pharmaceutical composition containing such a benzodiazepine derivative, or a pharmaceutically acceptable salt thereof, and a pharmaceutically acceptable carrier or diluent.

The compounds of the invention are typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, nontoxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The present invention also relates to the novel compounds, as defined above; or a pharmaceutically acceptable salt thereof, for use in a method of treating the human or animal body. The present invention also relates to a pharmaceutical composition comprising a novel compound as defined above and a pharmaceutically acceptable diluant or carrier. Preferably, the pharmaceutical composition comprises a pharmaceutically acceptable salt of a novel compound as defined above. A pharmaceutically acceptable salt is as defined above. The novel compounds of the invention are typically administered in the manner defined above and the compounds are typically formulated for administration in the manner defined above.

Preferably, the pharmaceutical compositions comprise optically active isomers of the novel compounds of the invention. Thus, for example, preferred novel compounds of the invention containing only one chiral center include an R enantiomer in substantially pure form, an S enantiomer in substantially pure form and enantiomeric mixtures which contain an excess of the R enantiomer or an excess of the S enantiomer. It is particularly preferred that pharmaceutical contains a compound of the invention which is a substantially pure optical isomer. For the avoidance of doubt, the novel compounds of the invention can, if desired, be used in the form of solvates.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono-, bi-, or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono-, bi-, or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_3$ alkyl," "$C_1$-$C_6$ alkyl," "$C_1$-$C_{10}$ alkyl" "$C_2$-$C_4$ alkyl," or "$C_3$-$C_6$ alkyl," refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_{10}$ alkenyl," "$C_2$-$C_8$ alkenyl," "$C_2$-$C_4$ alkenyl," or "$C_3$-$C_6$ alkenyl," refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. "$C_2$-$C_{10}$ alkynyl," "$C_2$-$C_8$ alkynyl," "$C_2$-$C_4$ alkynyl," or "$C_3$-$C_6$ alkynyl," refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), S(O)$_2$, C(O)O, C(O)NH, OC(O)O, OC(O)NH, OC(O)$NH_2$, S(O)$_2$NH, S(O)$_2$$NH_2$, NHC(O)$NH_2$, NHC(O)C(O)NH, NHS(O)$_2$NH, NHS(O)$_2$$NH_2$, C(O)NHS(O)$_2$, C(O)NHS(O)$_2$NH or C(O)NHS(O)$_2$$NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The term "carbocycle" or "carbocyclic" refers to a saturated, partially unsaturated or aromatic cyclic group in which each atom within the ring is carbon. Examples of cabocyclics include cycloalkyl, cycloalkenyl and aryl groups.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, —$C_1$-$C_{12}$-alkyl; —$C_2$-$C_{12}$-alkenyl, —$C_2$-$C_{12}$-alkynyl, —$C_3$-$C_{12}$-cycloalkyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —OCO$_2$—C$_3$-C$_{12}$-cycloalkyl, —OCO$_2$-aryl, —OCO$_2$-heteroaryl, —OCO$_2$-heterocycloalkyl, —CO$_2$—C$_1$-C$_{12}$ alkyl, —CO$_2$—C$_2$-C$_8$ alkenyl, —CO$_2$—C$_2$-C$_8$ alkynyl, CO$_2$—C$_3$-C$_{12}$-cycloalkyl, —CO$_2$-aryl, CO$_2$-heteroaryl, CO$_2$-heterocyloalkyl, —OCONH$_2$, —OCONH—C$_1$-C$_{12}$-alkyl, —OCONH—C$_2$-C$_8$-alkenyl, —OCONH—C$_2$-C$_8$-alkynyl, —OCONH—C$_3$-C$_{12}$-cycloalkyl, —OCONH-aryl, —OCONH-heteroaryl, —OCONH-heterocyclo-alkyl, —NHC(O)H, —NHC(O)—C$_1$-C$_{12}$-alkyl, —NHC(O)—C$_2$-C$_8$-alkenyl, —NHC(O)—C$_2$-C$_8$-alkynyl, —NHC(O)—C$_3$-C$_{12}$-cycloalkyl, —NHC(O)-aryl, —NHC(O)-heteroaryl, —NHC(O)-heterocyclo-alkyl, —NHCO$_2$—C$_1$-C$_{12}$-alkyl, —NHCO$_2$—C$_2$-C$_8$-alkenyl, —NHCO$_2$—C$_2$-C$_8$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_8$-alkenyl, —NHC(O)NH—C$_2$-C$_8$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_8$-alkenyl, —NHC(S)NH—C$_2$-C$_8$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_8$-alkenyl, —NHC(NH)NH—C$_2$-C$_8$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_8$-alkenyl, —NHC(NH)—C$_2$-C$_8$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_8$-alkenyl, —C(NH)NH—C$_2$-C$_8$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_8$-alkenyl, —S(O)—C$_2$-C$_8$-alkynyl, —S(O)—C$_3$-C$_{12}$-cycloalkyl, —S(O)-aryl, —S(O)-heteroaryl, —S(O)-heterocycloalkyl, —SO$_2$NH$_2$, —SO$_2$NH—C$_1$-C$_{12}$-alkyl, —SO$_2$NH—C$_2$-C$_8$-alkenyl, —SO$_2$NH—C$_2$-C$_8$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_8$-alkenyl, —NHSO$_2$—C$_2$-C$_8$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S-heteroaryl, —S-heterocycloalkyl, or methylthiomethyl. In certain embodiments, the substituents are independently selected from halo, preferably Cl and F; C$_1$-C$_4$-alkyl, preferably methyl and ethyl; halo-C$_1$-C$_4$-alkyl, such as fluoromethyl, difluoromethyl, and trifluoromethyl; C$_2$-C$_4$-alkenyl; halo-C$_2$-C$_4$-alkenyl; C$_3$-C$_6$-cycloalkyl, such as cyclopropyl; C$_1$-C$_4$-alkoxy, such as methoxy and ethoxy; halo-C$_1$-C$_4$-alkoxy, such as fluoromethoxy, difluoromethoxy, and trifluoromethoxy, —CN; —OH; NH$_2$; C$_1$-C$_4$-alkylamino; di(C$_1$-C$_4$-alkyl)amino; and NO$_2$. It is understood that the aryls, heteroaryls, alkyls, and the like can be further substituted. In some cases, each substituent in a substituted moiety is additionally optionally substituted when possible with one or more groups, each group being independently selected from C$_1$-C$_4$-alkyl; —CF$_3$, —OCH$_3$, —OCF$_3$, —F, —Cl, —Br, —I, —OH, —NO$_2$, —CN, and —NH$_2$.

In certain embodiments, a substituted alkyl, alkenyl or alkoxy group is substituted with one or more halogen atoms, preferably fluorine or chlorine atoms. Such substituted alkyl groups include fluoromethyl, difluoromethyl and trifluoromethyl. Such substituted alkoxy groups include fluoromethoxy, difluoromethoxy and trifluoromethoxy.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but are not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part-2*, (Biotechnology: Pharmaceutical Aspects), edited by V. J. Stella, et al, Springer and AAPSPress, 2007, pp 31-99.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enan-* tiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Pharmaceutically acceptable salts can also be prepared by deprotonation of the parent compound with a suitable base, thereby forming the anionic conjugate base of the parent compound. In such salts the counter ion is a cation. Suitable cations include ammonium and metal cations, such as alkali metal cations, including $Li^+$, $Na^+$, $K^+$ and $Cs^+$, and alkaline earth metal cations, such as $Mg^{2+}$ and $Ca^{2+}$.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

In certain embodiments, the invention provides pharmaceutically acceptable prodrugs of the compounds disclosed herein. The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed.). "Design and Application of Prodrugs, *Textbook of Drug Design and Development*, Chapter 5, 113-191 (1991); Bundgaard, et al., *Journal of Drug Deliver Reviews*, 8:1-38(1992); Bundgaard, *J. of Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

Additional types of prodrugs are also encompassed. For instance, free carboxyl groups can be derivatized as amides or alkyl esters. Free hydroxy groups may be derivatized using groups including but not limited to hemisuccinates, ethyl succinate, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities. In certain embodiments, a compound of the invention can incorporate two or more groups that are metabolically removed in vivo to yield the active parent compound.

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or nonstoichiometric amounts of solvent. Some compounds have a tendency to trap a fixed molar ratio of solvent molecules in the crystalline solid state, thus forming a solvate. If the solvent is water, the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1, 3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
ACN for acetonitrile;
AD-mix-β for (9S)-(9"S)-9,9"-[1,4-Phthalazinediylbis(oxy)]bis[10,11-dihydro-6'-methoxycinchonan];

Bn for benzyl;
BOP for (Benzotriazol-1-yloxy)tris(dimethylamino)phosphonium hexafluorophosphate;
BzCl for benzoyl chloride;
mCPBA for meta-chloroperbenzoic acid;
Cbz for benzyloxycarbonyl;
CDI for carbonyldiimidazole;
DAST for diethylaminosulfur trifluoride;
DBU for 1, 8-Diazabicycloundec-7-ene;
DCE for dichloroethane;
DCM for dichloromethane;
Dess-Martin periodinane for 1,1,1-tris(acetyloxy)-1,1-dihydro-1,2-benziodoxol-3-(1H)-one;
DIAD for diisopropyl azodicarboxylate;
DIBAL-H for diisobutylaluminum hydride;
DMAP for N,N-dimethylaminopyridine;
DME for 1,2-dimethoxyethane;
DMF for N,N-dimethyl formamide;
DMSO for dimethylsulfoxide;
DPPA for diphenylphosphoryl azide or diphenyl phosphorylazidate;
dppf for 1,1'-Bis(diphenylphosphino)ferrocene;
EDCI or EDC for 1-(3-diethylaminopropyl)-3-ethylcarbodiimide hydrochloride;
EtOAc for ethyl acetate;
Ghosez's reagent for 1-Chloro-N,N,2-trimethyl-1-propenylamine;
HATU for O (7-Azabenzotriazole-1-yl)-N,N,N',N'-tetramethyluronium hexafluorophosphate;
HCl for hydrochloric acid;
Hunig's base for diisopropylethylamine;
PyBOP for (Benzotriazol-1-yloxy)tripyrrolidinophosphonium hexafluorophosphate;
LDA for Lithium diisopropylamine;
Pd—C for palladium carbon;
Ph for phenyl;
RT for reverse transcription;
RT-PCR for reverse transcription-polymerase chain reaction;
TBME for tert-butyl methyl ether;
TEA for triethylamine;
Tf$_2$O for trifluoromethanesulfonic anhydride;
TFA for trifluoroacetic acid;
THF for tetrahydrofuran;
(TMS)$_2$NH for hexamethyldisilazane;
TBS for tert-Butyldimethylsilyl;
TBDPS for tert-Butyldiphenylsilyl;
TMS for trimethylsilyl;
TPAP tetrapropylammonium perruthenate;
TPP or PPh$_3$ for triphenylphosphine;
Ts or tosyl for p-CH$_3$C$_6$H$_4$SO$_2$—;
tBOC or Boc for tert-butyloxy carbonyl; and
Xantphos for 4,5-Bis-diphenylphosphanyl-9,9-dimethyl-9H-xanthene.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

Scheme 1 illustrates methods to prepare a compound of formula 11 from compounds 1 and 2, wherein n=1, 2 or 3; P is hydroxy protecting group; Ar is E; and E is as previously defined. Alkylation of the hydroxy pyridine 1 with hydroxy epoxide using Mitsunobu reaction conditions affords epoxide 4. Alternatively, hydroxy epoxide is converted to 3 which has a leaving group such as but not limited to, tosyl and methanlsulfonyl followed by alkylation in the presence of base such as but not limited to, K$_2$CO$_3$ and Cs$_2$CO$_3$, provides 4. Intramolecular epoxide opening mediated by base such as but not limited to, LDA, produces compound 5. Hydroxy group compound 5 is protected with proper protecting group such as but not limited to, TBDPS and TBS, affords compound 6. Trifluomethyl ketone 7 is obtained from iodine-magnesium exchange of compound 6 followed by addition of ester such as but not limited to, ethyl 2,2,2-trifluoroacetate. Trifluoromethyl ketone 7 in cross-coupled with various metal coupling partners 8, but not limited to, boronic acids, boronic esters, organotin reagents, organozinc reagents, organomagnesium reagents, organo silicon reagents or the like catalyzed by appropriate Pd, Ni, Cu or the like catalyst to afford compound 9. Nitromethane addition in the presence of base such as but not limited to, K$_2$CO$_3$ and Cs$_2$CO$_3$, to compound 9 affords compound 10. Reduction of nitro group with reducing reagents such as but not limited to, zinc and acetic acid, produces key intermediate 11.

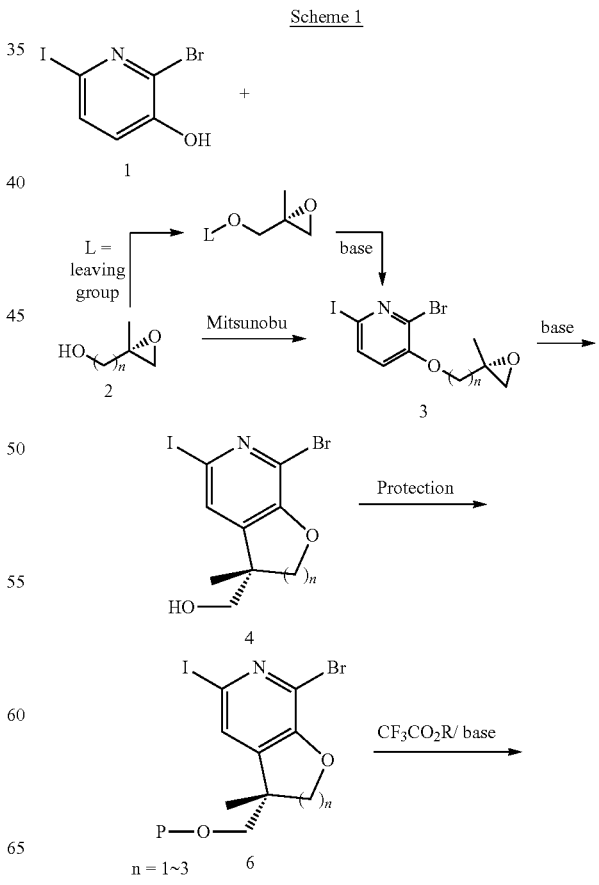

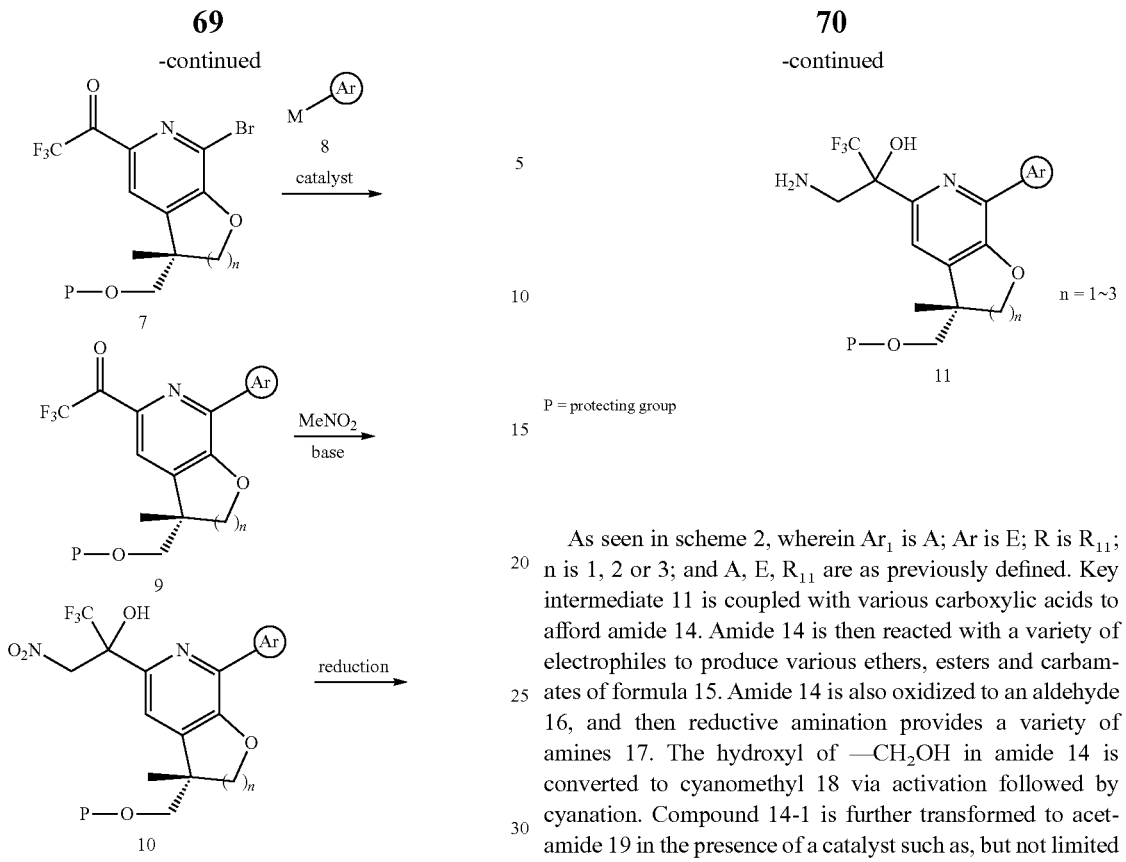

As seen in scheme 2, wherein $Ar_1$ is A; Ar is E; R is $R_{11}$; n is 1, 2 or 3; and A, E, $R_{11}$ are as previously defined. Key intermediate 11 is coupled with various carboxylic acids to afford amide 14. Amide 14 is then reacted with a variety of electrophiles to produce various ethers, esters and carbamates of formula 15. Amide 14 is also oxidized to an aldehyde 16, and then reductive amination provides a variety of amines 17. The hydroxyl of —$CH_2OH$ in amide 14 is converted to cyanomethyl 18 via activation followed by cyanation. Compound 14-1 is further transformed to acetamide 19 in the presence of a catalyst such as, but not limited to, Parkin's catalyst.

Scheme 2

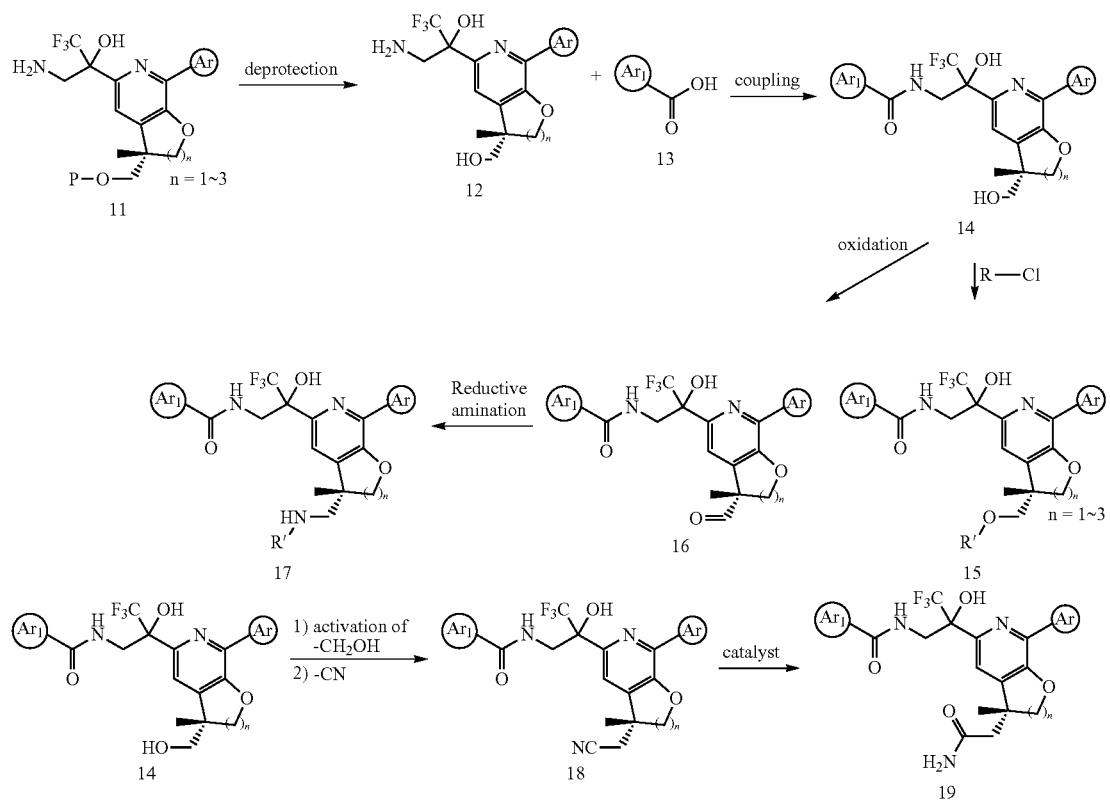

As seen in scheme 3, wherein $Ar_1$ is A; Ar is E; R is $R_{11}$; and A, E, $R_{11}$ are as previously defined. An aldehyde 16 is converted to the benzyl protected amine through reductive amination. Hydrogenolysis affords the free amine 20. Lastly, displacement with a variety of electrophiles gives N-substituted compounds 21.

Scheme 3

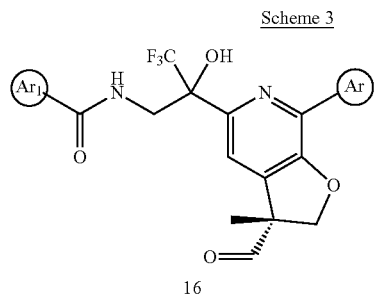

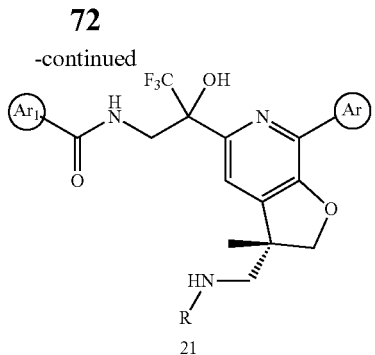

As seen in Scheme 4, wherein $Ar_1$ is A; Ar is E; R' is —$C_1$-$C_6$ alkyl, —$C_3$-$C_6$ cycloalkyl, aryl, or heteroaryl; n is 1, 2 or 3; and A and E are as previously defined. After oxidation of aldehyde 16 to acid 22, which is further converted to amides 23 and sulfonamides 24 using common methods such as but not limited to, HATU and DIPEA. From there diversification to a variety of esters and amides is conducted.

Scheme 4

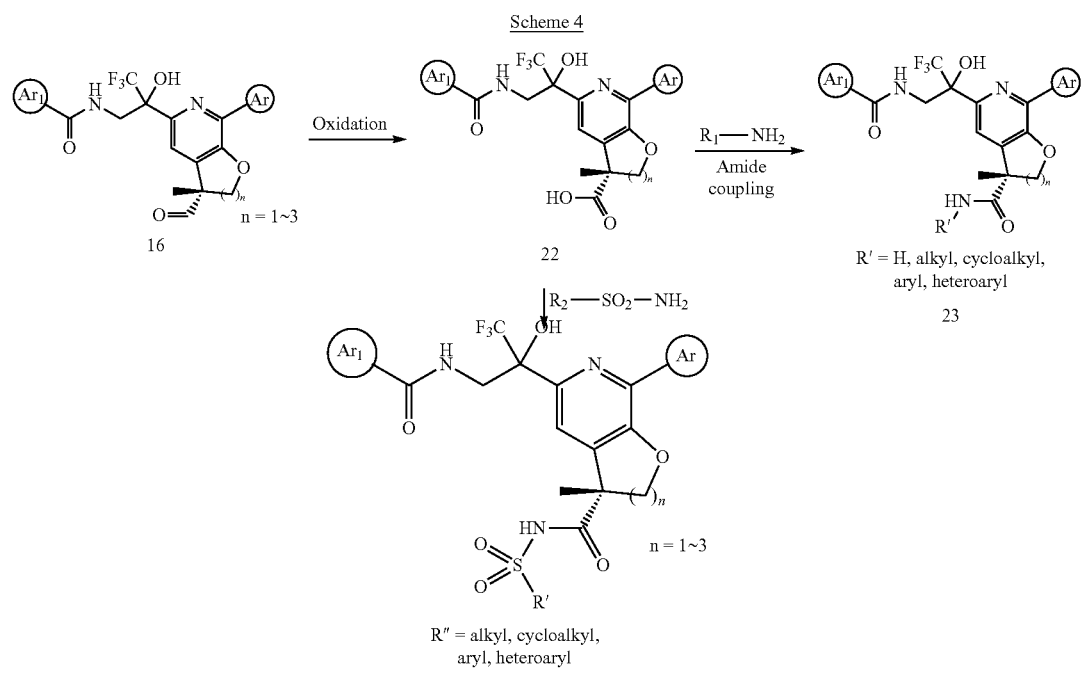

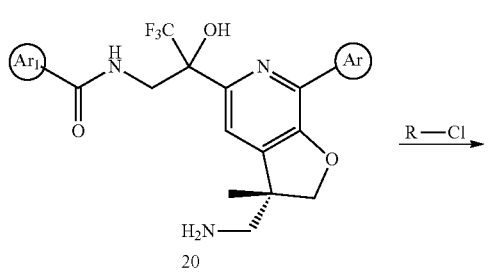

Scheme 5 illustrates another method to prepare a compound of formula 11, wherein Ar is E; P is a hydroxy protecting group; n is 1, 2 or 3; and E is as previously defined. Ketone 9 is converted to compound of formula 26 via olefination. Alternatively, 26 is obtained from; 1) 6 via cross-coupling with metal coupling partner 6-1, which can be, but is not limited to, a boronic acid, a boronic ester, an organotin reagent, an organozinc reagent, an organomagnesium reagent, an organosilicon reagent or the like catalyzed by appropriate Pd, Ni, Cu or the like catalyst to afford compound 25; 2) compound 25 is converted to compound 26 as previously described method in scheme 1. With 26 in hand, Compounds of formula 27 are prepared by dihydroxylation followed by epoxide formation. Epoxide opening of compound 27 with amine equivalent such as but not limited to, $NH_4OH$ and $NH_3$, provides compounds of formula 11.

Scheme 5

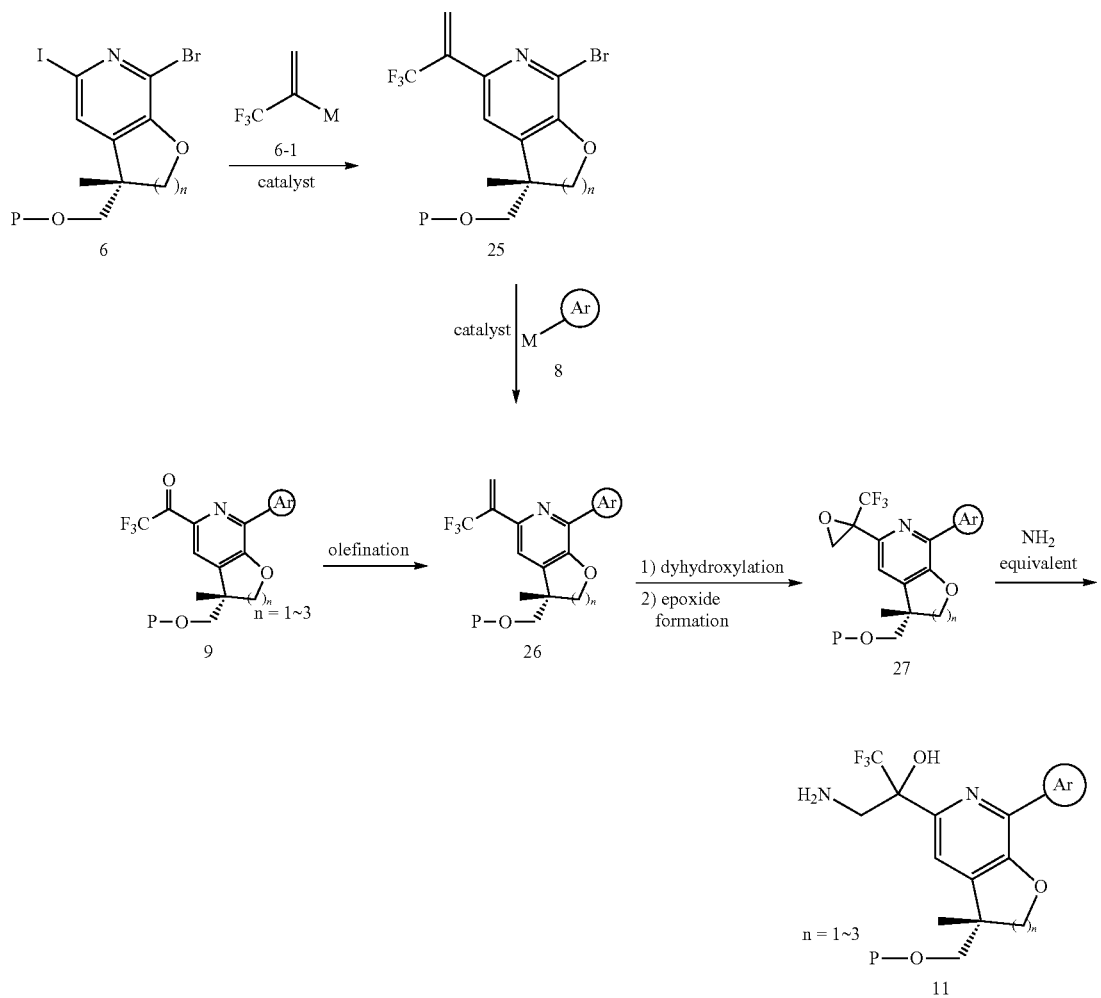

Scheme 6 illustrates another method to prepare a compound of formula 23, wherein Ar₁ is A; Ar is E; R' is —C₁-C₆ alkyl, —C₃-C₆ cycloalkyl, aryl, or heteroaryl; n is 1, 2 or 3; and A, and E are as previously defined. Amine 11 is protected with a protecting group such as but not limited to, Boc and Cbz. After deprotection of hydroxy protecting group, subsequent oxidations provide acid 30. Compound 30 is coupled with various amines to provide amide 31. Deprotection of amine protecting group followed by subsequent amide formation affords compounds of formula 23.

Scheme 6

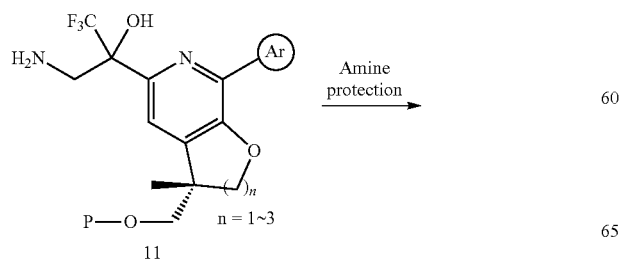

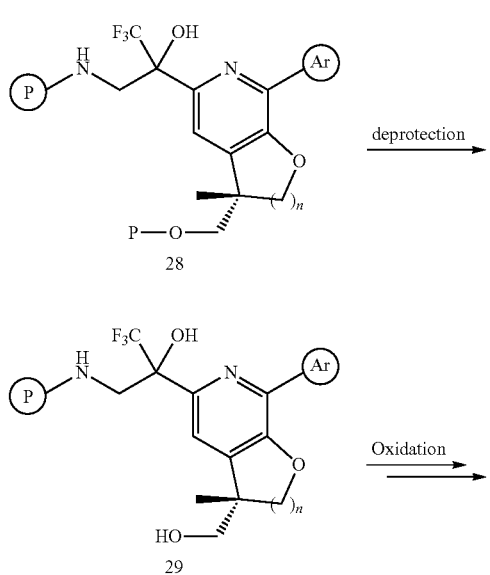

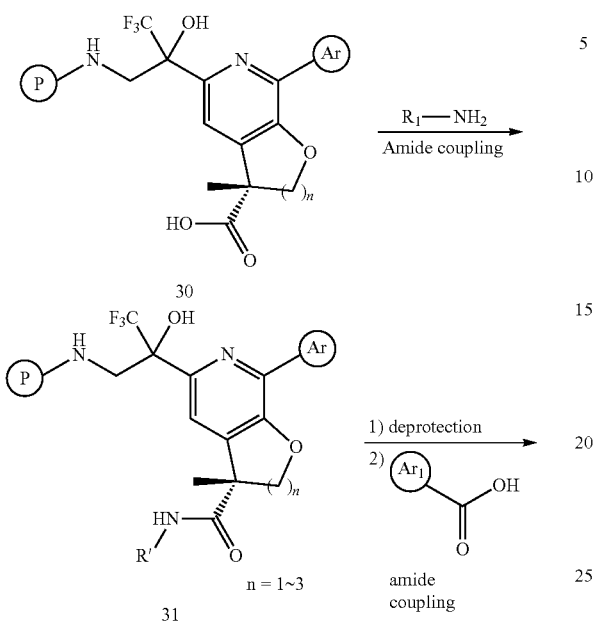

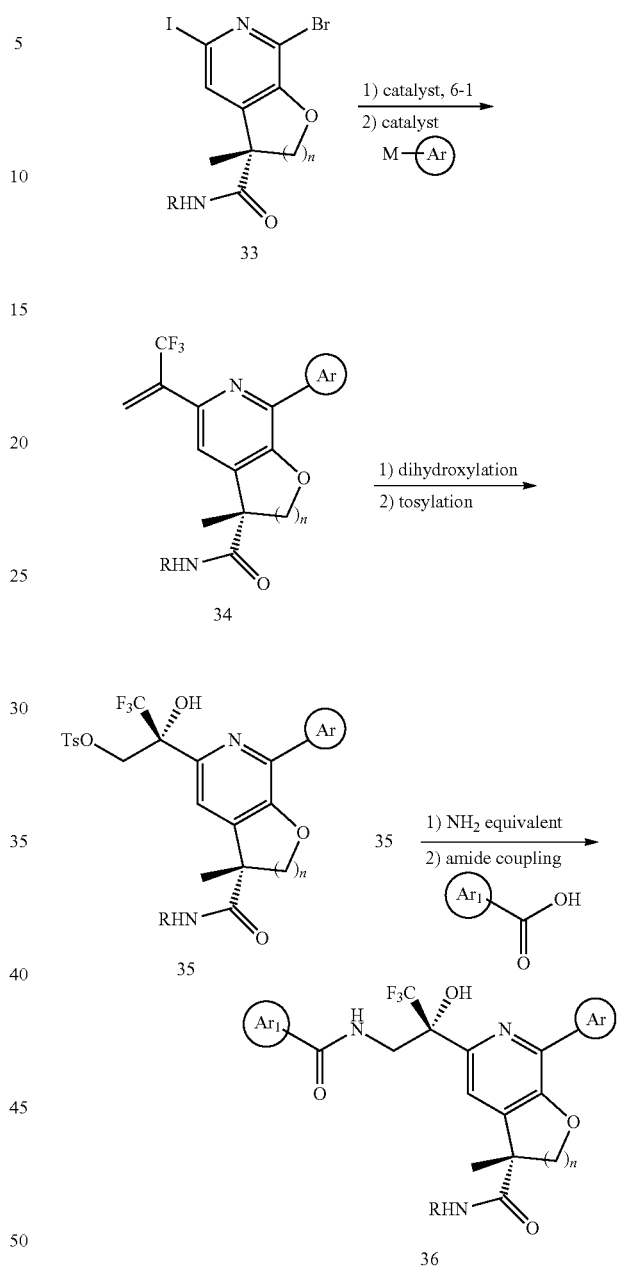

Scheme 7 illustrates an additional route for the synthesis of the desired compounds. The difference for this route is that it starts with oxidation and amide coupling to install the amide 33 at the beginning of the synthesis. Sequential vinylation and arylation afford the bis-coupled product 34. Asymmetric dihydroxylation followed by activation and substitution affords the amino alcohol precursor. Lastly, amide coupling with the respective aryl acid produces the desired compounds depicted by compound 36.

Scheme 7

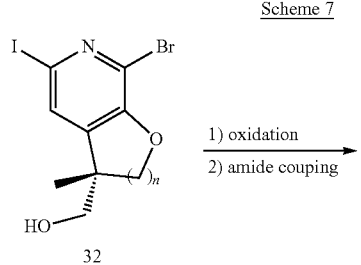

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art, and such changes and modifications including, without limitation, those relating to the chemical structures, substituents, derivatives, formulations and/or methods of the invention may be made without departing from the spirit of the invention and the scope of the appended claims.

Example 1

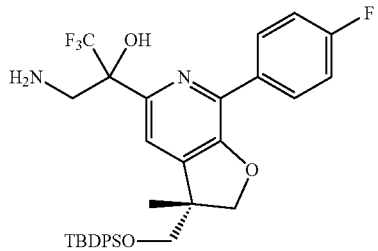

Example 1 Step a

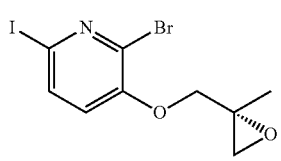

To a 500-mL round bottom flask equipped with a stir bar was added 2-bromo-6-iodopyridin-3-ol (14.21 g, 47.4 mmol) and 2-pyridyldiphenylphospine (13.3 g, 52.1 mmol). The flask was purged with nitrogen, and the solids dissolved in THF (95 mL, 0.5 M). At 0° C., (S)-(2-methyloxiran-2-yl)methanol (4.176 g, 47.4 mmol) was added followed by DIAD (10.14 ml, 52.1 mmol) slowly. The flask was warmed to room temperature and reaction monitored by LCMS (5 hrs). The reaction was diluted with EtOAc and quenched with water. An EtOAc extraction was carried out, the crude residue was purified by automated column chromatography (silica gel, $R_f$=0.75 in 50% ethyl acetate in hexanes) and dried under high vacuum to give the title compound as an off-white, foamy solid (11.77 g, 67%). ESI-MS m/z: 370.0/372.0 [M+H]$^+$.

Example 1 Step b

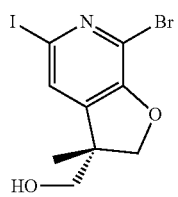

To a 500-mL round bottom flask equipped with a stir bar was added to the compound from step a (11.77 g, 31.8 mmol). The flask was purged with nitrogen, and the solid dissolved in THF (80 mL, 0.3 M). At 0° C., an LDA solution (35.0 mmol, 17.5 mL 2.0 M LDA in 26 mL THF) was slowly added (fast, dropwise pace) over 10 minutes. The reaction was stirred at 0° C. and monitored by LCMS (5- and 6-membered rings have different retention times). If not complete, the flask was warmed to room temperature until complete. The reaction mixture was diluted with EtOAc at 0° C., quenched with water and saturated ammonium chloride. An EtOAc extraction was carried out and the residue was dried on vacuum overnight to remove diisopropylamine to provide the title compound which was used for next reaction without purification. ESI-MS m/z: 370.0/372.0 [M+H]$^+$.

Example 1 Step c

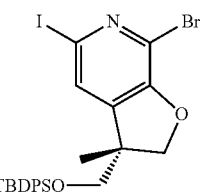

To a 500-mL round bottom flask containing the compound from step b (11.77 g, 31.8 mmol, mixture) was added a stir bar. The residue was dissolved in DMF (64 mL, 0.5 M), and imidazole (4.76 g, 70.0 mmol) was added. The flask was purged with nitrogen and tert-butylchlorodi-phenylsilane (9.10 ml, 35.0 mmol) was added at 0° C. The flask was warmed to room temperature and the reaction monitored by LMCS (3 hrs). The reaction was diluted with EtOAc and quenched with water. An EtOAc extraction was carried out, the crude residue purified by automated column chromatography (silica gel, $R_f$=0.78 in 25% ethyl acetate in hexanes) and dried under high vacuum to give the title compound as an off-white, foamy solid (7.87 g. 57%) over two-steps). ESI-MS m/z: 608.4/610.4 [M+H]$^+$.

Example 1 Step d

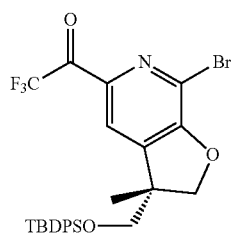

To a 250-mL round bottom flask containing the compound from step c (7.87 g, 12.94 mmol) was added a stir bar, and the flask purged with nitrogen. The flask was cooled to −40° C. and ethyl trifluoroacetate (2.317 ml, 19.40 mmol) was added. Isopropylmagnesium chloride (7.76 ml, 15.52 mmol) was then slowly added and the reaction stirred for 10 minutes. The flask was then warmed to 0° C. and monitored by LCMS. (1 hr: the reaction can be warmed to room temperature). The reaction was diluted with EtOAc at 0° C. and quenched with water and saturated ammonium chloride. An EtOAc extraction was carried out, the crude residue was purified by automated column chromatography (silica gel, 0-100% ethyl acetate in hexanes, multiple peaks due to hydrate formation) and dried under high vacuum to give the title compound as a clear, sticky residue (7.27 g, 97%, mixture of ketone and hydrate). ESI-MS m/z: 610.2/612.4 [M+H]$^+$ (MeOH adduct from LCMS in MeOH).

Example 1 Step e

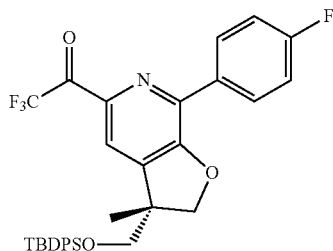

To a 250-mL round bottom flask containing the compound from step d (7.27 g, 12.57 mmol) was added a stir bar. The residue was dissolved in 1,4-dioxane (50 mL, 0.2 M), and potassium carbonate (3.91 g, 28.3 mmol) was added. $PdCl_2$ (dppf) (0.460 g, 0.628 mmol) and 2-(4-fluorophenyl)-4,4,5,5-tetramethyl-1,3,2-dioxaborolane (3.35 g, 15.08 mmol) were added and the flask purged with nitrogen. Water (12 mL, sparged with nitrogen for 15 minutes) was then added. The flask was then quickly equipped with a condenser and heated to 90° C. for 14 hrs under flow of nitrogen. Reaction conversion monitored by LCMS. The reaction was diluted with EtOAc and quenched with saturated ammonium chloride. An EtOAc extraction was carried out and the crude residue was purified by automated column chromatography (silica gel, 0-100% ethyl acetate in hexanes) to give a mixture of product and hydrate. The product was dissolved in 20 mL toluene, and $MgSO_4$ was added to form a suspension and stirred vigorously for 1.5 hr to dehydrate. Dehydration was monitored by HNMR aliquots. The $MgSO_4$ was filtered off and rinsed with DCM and concentrated. The solid was triturated with DCM to give the title compound as a white, foamy solid (6.33 g, 85%). ESI-MS m/z: 612.4 $[M+H]^+$ (water adduct on LCMS).

Example 1 Step f

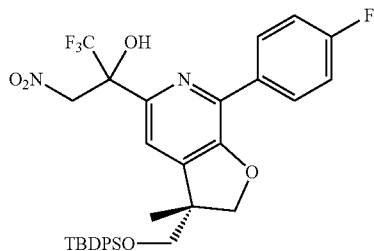

To a 250-mL round bottom flask containing the compound from step e (6.33 g, 10.02 mmol) was added a stir bar. Nitromethane (40 mL, 0.25 M) was added followed by potassium carbonate (4.16 g, 30.1 mmol). The flask was stirred at room temperature and the progress was monitored by LCMS (2.5 hrs). The reaction was diluted with EtOAc and quenched with water and saturated ammonium chloride. An EtOAc extraction was carried out, the crude residue purified by automated column chromatography (silica gel, $R_f$=0.70 in 25% ethyl acetate in hexanes) and dried over high vacuum to afford the title compound as a white, foamy solid (6.02 g, 92%, mixture of diastereomers). ESI-MS m/z: 655.4 $[M+H]^+$.

Example 1 Step g

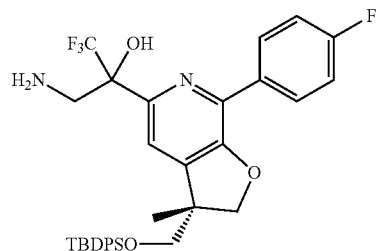

To a 250-mL round bottom flask containing the compound from step f (6.02 g, 9.19 mmol) was added a stir bar. The solid was dissolved in AcOH (28 mL, 0.33 M) and the flask cooled to 0° C. Zinc (6.01 g, 92 mmol) was added, the reaction warmed to room temperature and monitored by LCMS (2 hrs). The reaction was diluted with EtOAc and the zinc removed by filtering over a pad of celite. The celite was rinsed with EtOAc and MeOH. The combined organics were concentrated under reduced pressure to remove most of the acetic acid. The crude residue was dissolved in EtOAc and water was added. The pH was brought about 8-9 with saturated sodium bicarbonate and stirring. The aqueous was extracted with EtOAc (4 times) and concentrated under reduced pressure. The crude residue was purified by automated column chromatography (silica gel, 0-25% methanol in dichloromethane) to give the title compound as a white, foamy solid (4.40 g, 77%, mixture of diastereomers). ESI-MS m/z: 625.4 $[M+H]^+$.

Example 2

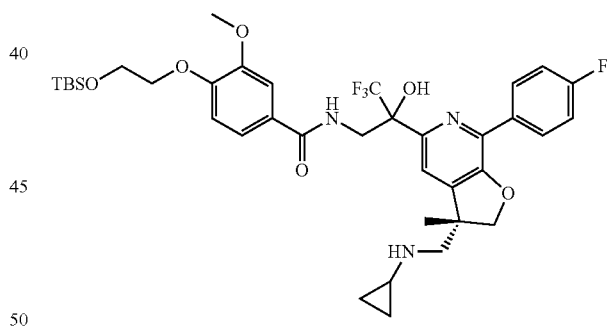

Example 2 Step a

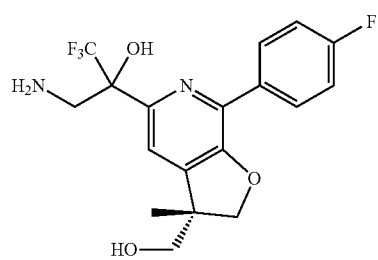 [SMILES: C[C@]1(CO)COc2c1cc(C(O)(CN)C(F)(F)F)nc2-c1ccc(F)cc1]

Method A

To a 40-mL flask equipped with a stir bar was added to the compound from Example 1, step g (1.00 g, 1.601 mmol). The flask was purged with nitrogen, and the solid dissolved in THF (5 mL, 0.33 M). At 0° C., TBAF (3.20 ml, 3.20 mmol) was slowly added. The reaction was stirred at room temperature and monitored by LCMS (3 hrs). Upon completion, the stir bar was removed, the reaction concentrated and directly purified by automated column chromatography (silica gel, ethyl acetate in hexanes to 25% methanol in dichloromethane). The residue was dissolved in EtOAc, and washed 3× with water to remove ammonium salts to afford the title compound as a white, fluffy solid (489 mg, 79%, mixture of diastereomers). ESI-MS m/z: 387.4 [M+H]⁺.

Example 2, Step b

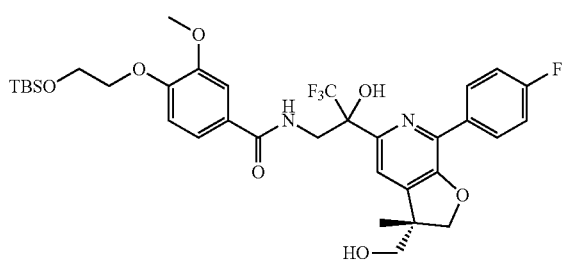 [SMILES: COc1cc(C(=O)NCC(O)(c2cc3c(c(-c4ccc(F)cc4)n2)OC[C@]3(C)CO)C(F)(F)F)ccc1OCCO[Si](C)(C)C(C)(C)C]

To a 20-mL vial equipped with a stir bar was added to the compound from step a (489 mg, 1.266 mmol) and 4-(2-((tert-butyldimethylsilyl)oxy)ethoxy)-3-methoxybenzoic acid (413 mg, 1.266 mmol). The solids were dissolved in DMF (3.84 mL, 0.33 M) and Hunig's base (442 µl, 2.53 mmol) was added. HATU (578 mg, 1.519 mmol) was added in one portion, the vial purged with nitrogen, and the reaction stirred at room temperature until completion (LCMS, 4 hrs). The mixture was diluted with EtOAc and quenched with water and saturated ammonium chloride.

An EtOAc extraction was carried out with a phase separator cartridge and the crude residue purified by automated column chromatography (silica gel, R$_f$=0.80 in ethyl acetate) to afford the title compound as a white, foamy solid (625 mg, 71%, mixture of diastereomers). ESI-MS m/z: 695.4 [M+H]⁺.

Example 2 Step c

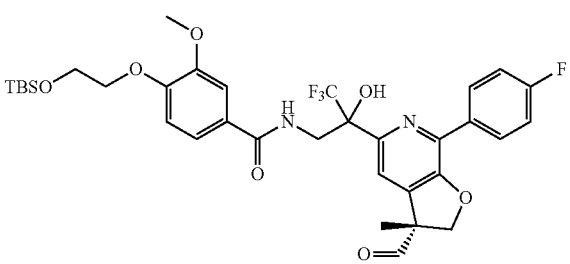 [SMILES: COc1cc(C(=O)NCC(O)(c2cc3c(c(-c4ccc(F)cc4)n2)OC[C@]3(C)C=O)C(F)(F)F)ccc1OCCO[Si](C)(C)C(C)(C)C]

Method B

To a 20-mL vial equipped with a stir bar was added to the compound from step b (575 mg, 0.828 mmol). The solid was dissolved in DCM (2.5 mL, 0.33 M) and the vial cooled to 0° C. Dess-Martin Periodinane (386 mg, 0.91 mmol) was added, the vial purged with nitrogen and stirred for 10 minutes. The reaction was warmed to room temperature and monitored by LCMS (30 minutes-1 hr). Upon completion, the reaction was diluted with DCM and quenched with a 1:1 solution of saturated sodium bicarbonate: saturated sodium thiosulfate. The mixture was stirred vigorously for around 20 minutes until the solution became clear. A DCM extraction was carried out with a phase separator cartridge and the crude residue purified by automated column chromatography (silica gel, 0-100% ethyl acetate in hexanes) to give the title compound as a white, foamy solid (518 mg, 90%, mixture of diastereomers). ESI-MS m/z: 693.2 [M+H]⁺.

Example 2 Step d

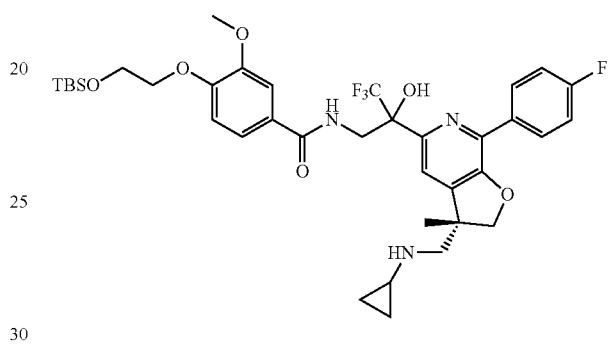

Method C

To a 2-dram vial equipped with a stir bar was added to the compound from step c (40 mg, 0.058 mmol). The solid was dissolved in DCE (0.2 mL, 0.33 M) and cyclopropylamine was added (solution of DCE, 3.3 mg, 0.058 mmol). Sodium triacetoxyborohydride (18.36 mg, 0.087 mmol) was added in one portion, the vial purged with nitrogen and stirred at room temperature. The reaction was monitored by LCMS (4 hrs), diluted with DCM and quenched with water. The aqueous was brought to pH around 8-9 with saturated sodium bicarbonate. A DCM extraction was carried out with a phase separator cartridge, residue concentrated. The crude residue was carried forward to the TBS deprotection seen below in Method D. ESI-MS m/z: 734.6 [M+H]⁺.

Example 3

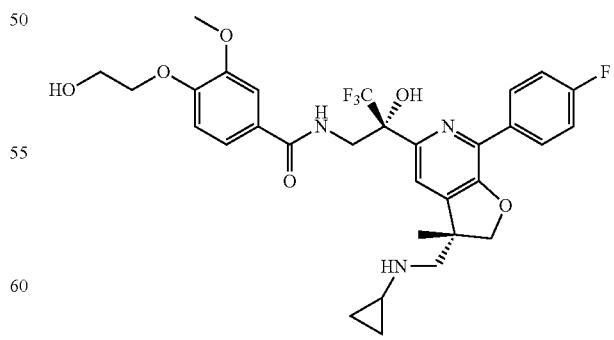

Method D

To a 20-mL vial containing the compound from example 2, step d (42.4 mg, 0.058 mmol) was added a stir bar, and the solid dissolved in DCM (0.39 mL, 0.15 M). HCl in dioxane (4M, 0.19 mL, 0.74 mmol) was added and the reaction stirred at room temperature. Upon completion by LCMS (2 hrs), the reaction was diluted with DCM and quenched with saturated sodium bicarbonate until pH about 8-9. A DCM extraction was carried out with a phase separator cartridge and the organics concentrated. The mixture of diastereomers was analyzed on HPLC to check separation. The mixture was purified by prep-HPLC (20-90%, 25 min) and lyophilized to give the title compound as a white, fluffy solid (5.1 mg, 14%). ESI-MS m/z: 620.4 [M+H]$^+$.

Example 4

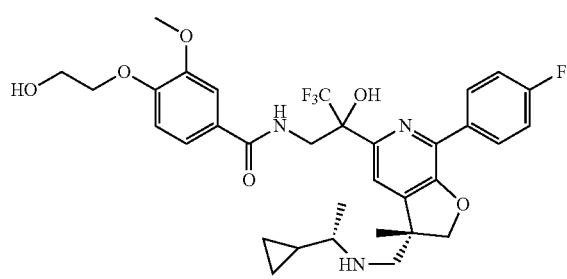 [SMILES: COc1cc(C(=O)NCC(O)(c2cc3c(c(-c4ccc(F)cc4)n2)OC[C@]3(C)CN[C@@H](C)C2CC2)C(F)(F)F)ccc1OCCO]

The title compound was synthesized in an analogous sequence to Methods C and D using 40 mg of the compound from example 2, step c and (S)-1-cyclopropylethyl amine. ESI-MS m/z: 762.4 [M+H]$^+$ (TBS alcohol). The mixture of diastereomers did not separate well on HPLC. The mixture was purified by automated column chromatography (silica gel, R$_f$=0.65 in 5% methanol in dichloromethane, purified in EtOAc/hexanes then MeOH/DCM) and lyophilized to afford the title compound as a white, fluffy solid (23 mg, 63%, mixture of diastereomers). ESI-MS m/z: 648.4 [M+H]$^+$.

Example 5

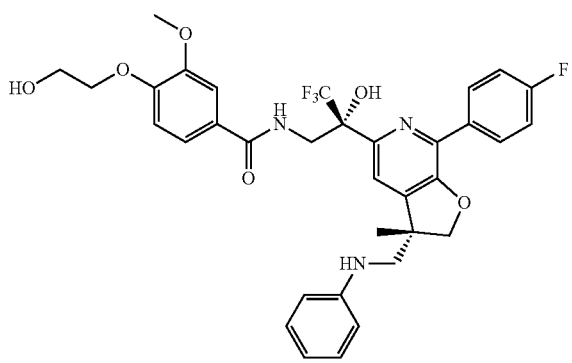 [SMILES: COc1cc(C(=O)NC[C@](O)(c2cc3c(c(-c4ccc(F)cc4)n2)OC[C@]3(C)CNc2ccccc2)C(F)(F)F)ccc1OCCO]

The title compound was synthesized in an analogous sequence to Methods C and D using 40 mg of the compound from example 2, step c and aniline. ESI-MS m/z: 770.3 [M+H]$^+$ (TBS alcohol). The mixture of diastereomers was analyzed on HPLC to check separation. The mixture was purified by prep-HPLC (20-90%, 25 min) and lyophilized to give the title compound as a white, fluffy solid (9 mg, 23%). ESI-MS m/z: 656.4 [M+H]$^+$.

Example 6

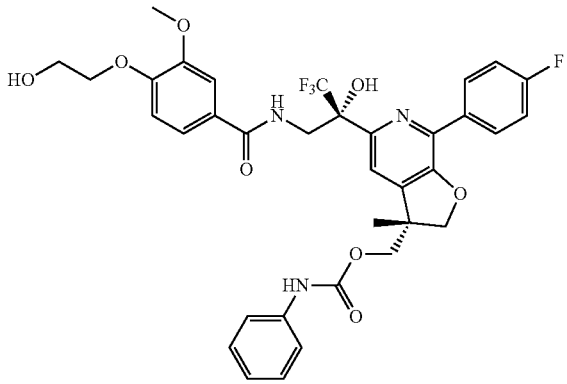 [SMILES: COc1cc(C(=O)NC[C@](O)(c2cc3c(c(-c4ccc(F)cc4)n2)OC[C@]3(C)COC(=O)Nc2ccccc2)C(F)(F)F)ccc1OCCO]

To a 2-dram vial equipped with a stir was added to the compound from example 2, step b (32.3 mg, 0.046 mmol). The vial was purged with nitrogen and the solid dissolved in DCM (0.23 mL, 0.2 M). Hunig's base (20.30 µl, 0.116 mmol) was added, followed by phenyl isocyanate (6.10 µl, 0.056 mmol). The reaction was monitored by LCMS (1 hr). The reaction mixture was diluted with DCM and quenched with saturated sodium bicarbonate. A DCM extraction was carried out with a phase separator cartridge. ESI-MS m/z: 814.4 [M+H]$^+$ (TBS alcohol). The crude residue was carried forward to the TBS deprotection as explained in Method D. The mixture of diastereomers was analyzed on HPLC to check separation. The mixture was purified by prep-HPLC (20-90%, 25 min) and lyophilized to give the title compound as a white, fluffy solid (7 mg, 29%) ESI-MS m/z: 700.5 [M+H]$^+$.

Example 7

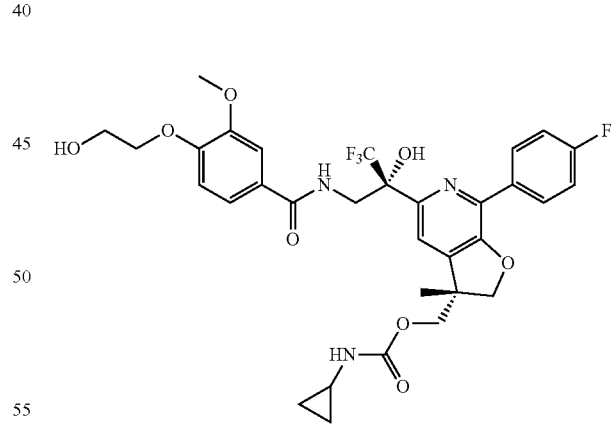

The title compound was synthesized similarly to the phenyl carbamate formation above (Example 6) using 30 mg of the compound from example 2, step b, however using cyclopropyl isocyanate (CAUTION, volatile). ESI-MS m/z: 778.5 [M+H]$^+$ (TBS alcohol). The TBS group was deprotected as explained in Method D. The mixture of diastereomers was analyzed on HPLC to check separation. The mixture was purified by prep-HPLC (20-90%, 25 min) and lyophilized to give the title compound as a white, fluffy solid (4 mg, 15%) ESI-MS m/z: 664.5 [M+H]$^+$.

Example 8

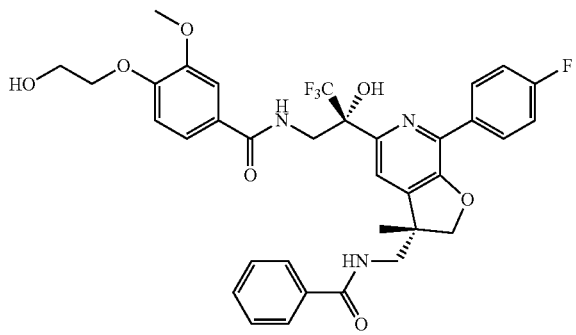 [SMILES: COc1cc(C(=O)NC[C@](O)(c2cc3c(c(-c4ccc(F)cc4)n2)OC[C@]3(C)CNC(=O)c2ccccc2)C(F)(F)F)ccc1OCCO]

Example 8 Step a

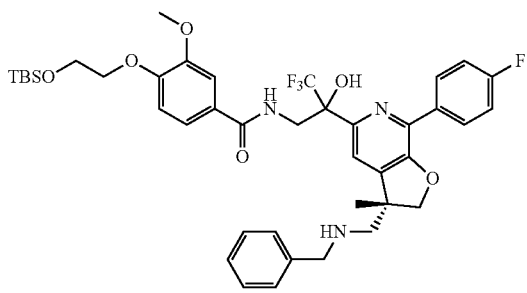 [SMILES: COc1cc(C(=O)NCC(O)(c2cc3c(c(-c4ccc(F)cc4)n2)OC[C@]3(C)CNCc2ccccc2)C(F)(F)F)ccc1OCCO[Si](C)(C)C(C)(C)C]

The title compound was synthesized according to Method C utilizing 137 mg of the compound from example 2, step c, benzyl amine (30.0 μl, 0.27 mmol, 1.7 equiv.) and 1.7 equiv. of sodium triacetoxyborohydride. The compound was purified by automated column chromatography (silica gel, R$_f$=0.50 in 50% ethyl acetate in hexanes) to afford the title compound as a white, foamy solid (112 mg, 72%, mixture of diastereomers ESI-MS m/z: 664.5 [M+H]$^+$.

Example 8 Step b

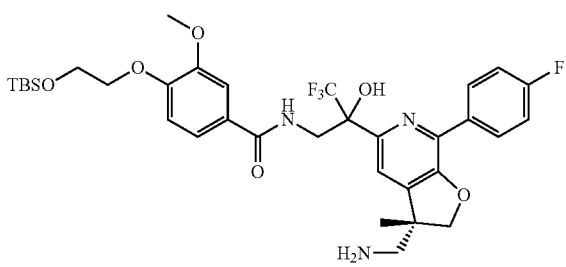 [SMILES: COc1cc(C(=O)NCC(O)(c2cc3c(c(-c4ccc(F)cc4)n2)OC[C@]3(C)CN)C(F)(F)F)ccc1OCCO[Si](C)(C)C(C)(C)C]

To a 20-mL vial containing the compound from step a (100 mg, 0.128 mmol) was added a stir bar. The solid was dissolved in anhydrous MeOH (0.85 mL, 0.15 M) and Pd—C (33.9 mg, 0.032 mmol) was added. The vial was purged with a balloon of H$_2$ and the reaction was kept under a balloon of H$_2$. The reaction was monitored by LCMS (2 hrs). The balloon was removed, and the mixture filtered over a pad of celite with EtOAc. The organics were concentrated triturated with DCM to afford the title compound as a white, foamy solid (75 mg, 84%, mixture of diastereomers). ESI-MS m/z: 694.4 [M+H]$^+$.

Example 8 Step c

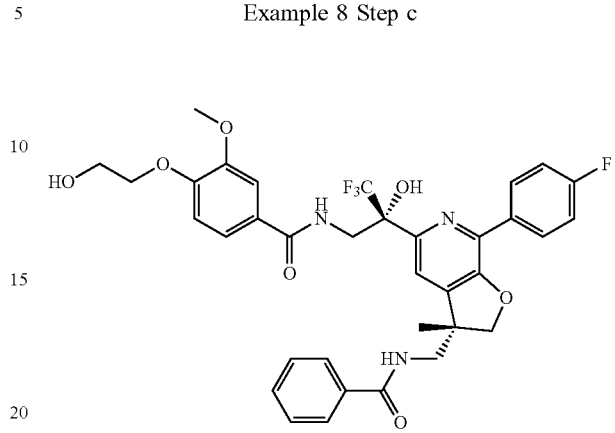

Method E

To a 2-dram vial equipped with a stir bar was added the compound from step b (28.65 mg, 0.041 mmol). The vial was purged with nitrogen and the solid dissolved in DCM (0.21 mL, 0.20 M). Hunig's base (15.87 μl, 0.091 mmol) was added, followed by benzoyl chloride (5.75 μl, 0.050 mmol). The reaction was stirred at room temperature and monitored by LCMS (1 hr). The reaction was diluted with DCM and quenched with saturated sodium bicarbonate. A DCM extraction was carried out with a phase separator cartridge. The crude residue was analyzed by HNMR to observed shifting of the primary amine alpha-protons. ESI-MS m/z: 798.3 [M+H]$^+$ (TBS alcohol).

The crude residue was carried forward to the TBS deprotection as explained in Method D. The mixture of diastereomers was analyzed on HPLC to check separation. The mixture was purified by prep-HPLC (20-90%, 25 min) and lyophilized to give the title compound as a white, fluffy solid (4.9 mg, 16%). ESI-MS m/z: 684.4 [M+H]$^+$.

Example 9

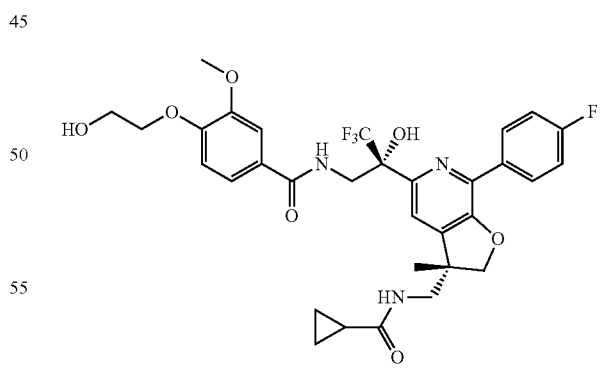

The title compound was synthesized according to Method E using 30 mg of the compound from example 8, step b and cyclopropanecarbonyl chloride. The crude residue was analyzed by HNMR to observed shifting of the primary amine alpha-protons.

The crude residue was carried forward to the TBS deprotection as described in Method D. The mixture of diastereomers was analyzed on HPLC to check separation. The mixture was purified by prep-HPLC (20-90%, 25 min) and lyophilized to give the title compound as a white, fluffy solid (6.1 mg, 19%). ESI-MS m/z: 648.4 [M+H]+.

Example 10

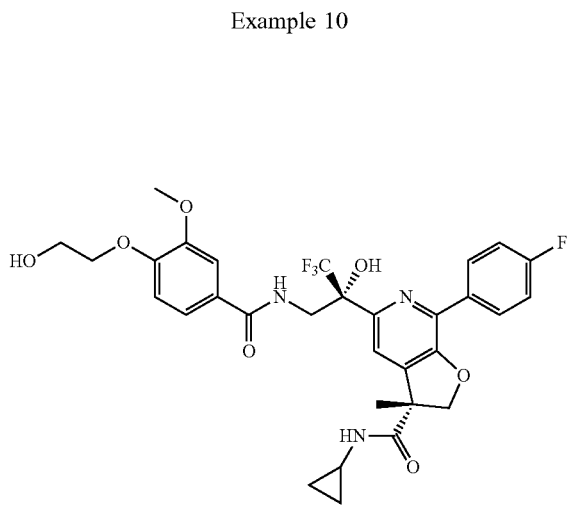

Example 10 Step a

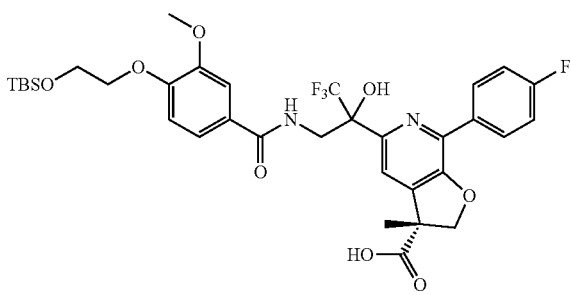 [SMILES: COc1cc(C(=O)NCC(O)(c2cc3c(c(-c4ccc(F)cc4)n2)OC[C@]3(C)C(=O)O)C(F)(F)F)ccc1OCCO[Si](C)(C)C(C)(C)C]

Method F

To a 20-mL vial equipped with a stir was added the compound from example 2, step c (300 mg, 0.433 mmol). The solid was dissolved in tert-BuOH (5.8 mL, 0.05 M), and 2-methyl-2-butene (1.0 M in THF, 6 mL, 12.0 mmol) was added. Sodium chlorite (490 mg, 4.33 mmol) and sodium phosphate monobasic (520 mg, 4.33 mmol) were dissolved in Water (2.9 mL), and the solution was added dropwise to the reaction vial. The vial was quickly purged with nitrogen and monitored by LCMS (30 minutes). The stir bar was removed, and the volatiles concentrated under reduced pressure. The mixture was diluted with EtOAc and water, and the pH checked to ensure acidic (about pH=4). An EtOAc extraction was carried out, and the residue purified by automated column chromatography (silica gel, $R_f$=0.20 in 5% methanol in dichloromethane) to afford the title compound as a white, foamy solid (252 mg, 82%, mixture of diastereomers). ESI-MS m/z: 709.4 [M+H]+.

Example 10 Step b

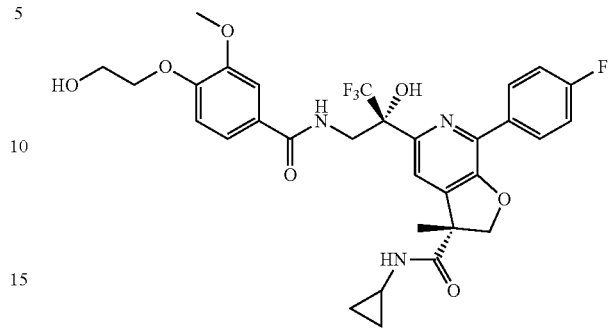

Method G

In a 2-dram vial equipped with a stir bar was added the compound from step a (52 mg, 0.073 mmol). The solid was dissolved in DMF (0.37 mL, 0.20 M), and cyclopropylamine (7.76 μl, 0.110 mmol) was added. Hunig's base (32.0 μl, 0.183 mmol) was added followed by HATU (33.5 mg, 0.088 mmol) in one portion. The reaction was purged with nitrogen and monitored by LCMS until complete (2.5 hrs). The reaction was diluted with EtOAc and quenched with water. Extracted with EtOAc using a phase separator cartridge. ESI-MS m/z: 748.3 [M+H]+ (TBS alcohol).

The crude residue was carried forward to the TBS deprotection as explained in Method D. The mixture of diastereomers was analyzed on HPLC to check separation. The mixture was purified by prep-HPLC (20-90%, 25 min) and lyophilized to give the title compound as a white, fluffy solid (4 mg, 5%). ESI-MS m/z: 634.4 [M+H]+.

Example 11

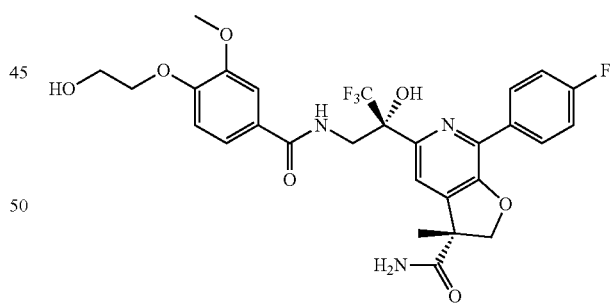

The title compound was synthesized according to Method G using 50 mg of the compound from Example 10, step a, ammonium chloride (15 mg, 0.28 mmol, 4.0 equiv.) and 6.0 equiv of Hunig's base. ESI-MS m/z: 708.4 [M+H]+ (TBS alcohol).

The crude residue was carried forward to the TBS deprotection as explained in Method D. The mixture of diastereomers was analyzed on HPLC to check separation. The mixture was purified by prep-HPLC (20-90%, 25 min) and lyophilized to give the title compound as a white, fluffy solid (4 mg, 10%). ESI-MS m/z: 594.1 [M+H]+.

Example 12

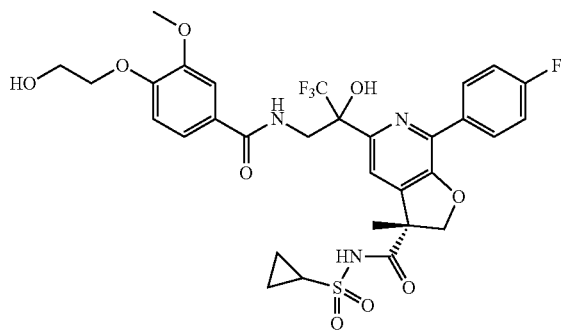 [SMILES: COc1cc(C(=O)NCC(O)(c2cc3c(c(-c4ccc(F)cc4)n2)OC[C@]3(C)C(=O)NS(=O)(=O)C2CC2)C(F)(F)F)ccc1OCCO]

The title compound was synthesized according to Method G using 50 mg of the compound from Example 10, step a, cyclopropylsulfonamide (26 mg, 0.212 mmol, 3.0 equiv.), 3.0 equiv Hunig's base and 1.5 equiv HATU. ESI-MS m/z: 812.4 [M+H]+ (TBS alcohol).

The crude residue was carried forward to the TBS deprotection as explained in Method D. The mixture of diastereomers was analyzed on HPLC to check separation. The mixture was purified by prep-HPLC (20-90%, 25 min) and lyophilized to give the title compound as a white, fluffy solid (6 mg, 12%, mixture of diastereomers). ESI-MS m/z: 698.1 [M+H]+.

Example 13

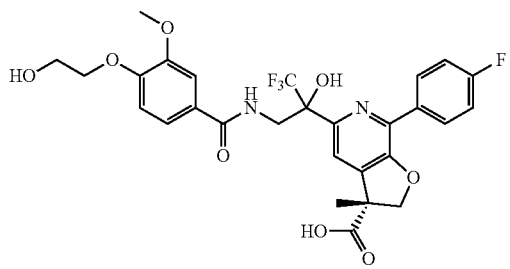 [SMILES: COc1cc(C(=O)NCC(O)(c2cc3c(c(-c4ccc(F)cc4)n2)OC[C@]3(C)C(=O)O)C(F)(F)F)ccc1OCCO]

44 mg of the compound from Example 10, step a, was carried forward to the TBS deprotection as explained in Method D. The mixture of diastereomers was analyzed on HPLC to check separation. The mixture was purified by automated column chromatography (silica gel, R$_f$=0.20 in 10% methanol in dichloromethane) and lyophilized overnight to give the title compound as a white, fluffy solid (23 mg, 62%, mixture of diastereomers). ESI-MS m/z: 595.1 [M+H]+.

Example 14

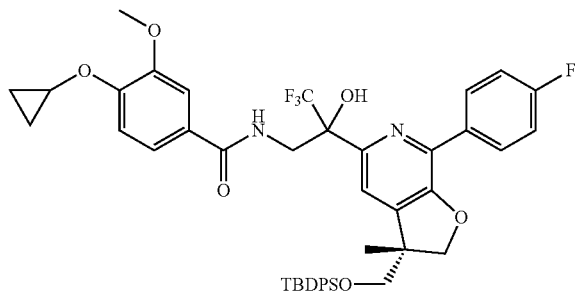

Method H

To a 40 mL vial equipped with a stir bar was added 4-cyclopropoxy-3-methoxybenzoic acid (100 mg, 0.480 mmol), and the vial was purged with nitrogen. DCM (3.20 mL, 0.15 M) was added, and then Ghosez's reagent (127 μl, 0.960 mmol) was slowly added. The reaction was allowed to stir at room temperature for 1.3 hours.

The stir bar was removed, and reaction concentrated. Place on high vacuum for about 45 minutes to remove any Ghosez's reagent. A stir bar was added to the acid chloride, the vial purged with nitrogen and DCM (2 mL) was added. Amino alcohol from Example 1, step g (300 mg, 0.480 mmol) was then added as a solution of DCM (1.2 mL) and pyridine (252 μl, 3.12 mmol). The reaction was stirred at room temperature and monitored by LCMS (1 hr). The reaction was quenched with MeOH and then water. Diluted with DCM and sat. sodium bicarbonate added to pH about 9. Extracted with DCM using a phase separator cartridge. Concentrated and then placed on high vacuum to remove pyridine. The solid was purified by automated column chromatography (silica gel, R$_f$=0.21 in 20% ethyl acetate in hexanes) to afford the title compound as a white, foamy solid (343 mg, 88%, mixture of diastereomers). ESI-MS m/z: 815.2 [M+H]+.

Example 15

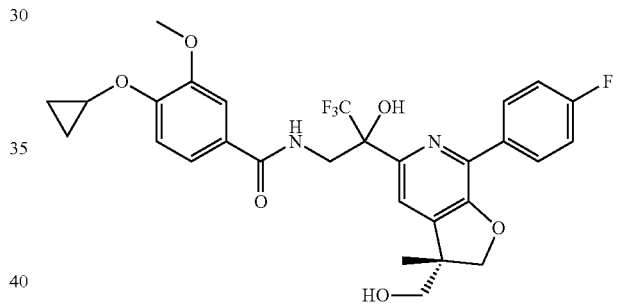

The title compound was synthesized according to Method A using 343 mg of the compound from Example 14 and purified by automated column chromatography (silica gel, R$_f$=0.2, 0.30 in 50% ethyl acetate in hexanes) to give the title compound as a white, foamy solid (195 mg, 80%, mixture of diastereomers). ESI-MS m/z: 577.4 [M+H]+.

Example 16

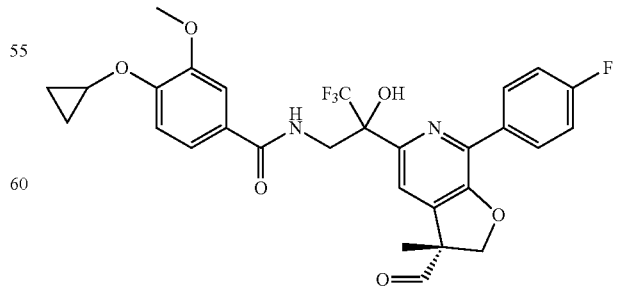

The title compound was synthesized according to Method B using 195 mg of the compound from Example 15 and purified by automated column chromatography (silica gel, 0-100% ethyl acetate in hexanes) to give a the title compound as white, foamy solid (155 mg, 80%, mixture of diastereomers). ESI-MS m/z: 593.4 [M+H]+ (water adduct on LCMS).

Example 17

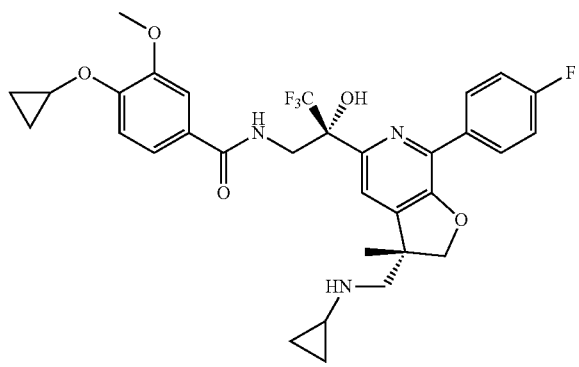 [SMILES: COc1cc(C(=O)NC[C@](O)(c2cc3c(c(-c4ccc(F)cc4)n2)OC[C@]3(C)CNC2CC2)C(F)(F)F)ccc1OC1CC1]

The title compound was synthesized according to Method C using 50 mg of the compound from Example 16. The mixture of diastereomers was analyzed on HPLC and by TLC to check separation. The mixture was purified by automated column chromatography (silica gel, $R_f$=0.20 in 40% ethyl acetate in hexanes) and lyophilized to give the title compound as a white, fluffy solid (21.3 mg, 39%). ESI-MS m/z: 616.4 [M+H]+.

Example 18

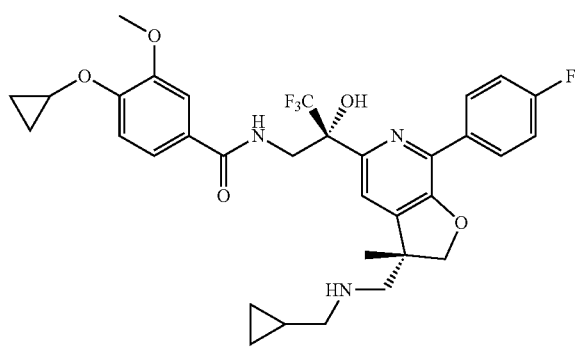 [SMILES: COc1cc(C(=O)NC[C@](O)(c2cc3c(c(-c4ccc(F)cc4)n2)OC[C@]3(C)CNCC2CC2)C(F)(F)F)ccc1OC1CC1]

The title compound was synthesized according to Method C using 50 mg of the compound from Example 16 and cyclopropylmethylamine. The mixture of diastereomers was analyzed on HPLC and by TLC to check separation. The mixture was purified by prep-HPLC (20-90%, 25 min) and lyophilized to the give the title compound as a white, fluffy solid (13 mg, 29%). ESI-MS m/z: 630.4 [M+H]+.

Example 19

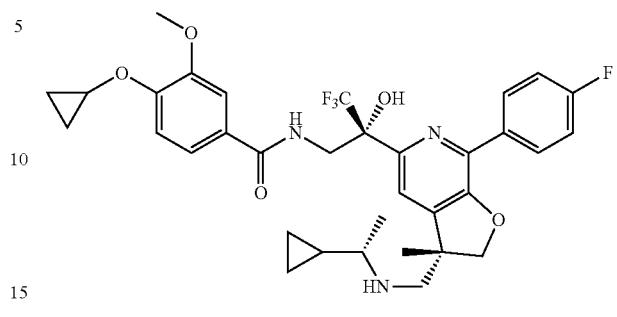

The title compound was synthesized according to Method C using 50 mg of the compound from Example 16 and (S)-1-cyclopropylethylamine. The mixture of diastereomers was analyzed on HPLC and by TLC to check separation. The mixture was purified by automated column chromatography (silica gel, $R_f$=0.40 in 75% ethyl acetate in hexanes) and lyophilized to give the title compound as a white, fluffy solid (18 mg, 27%). ESI-MS m/z: 644.4 [M+H]+.

Example 20

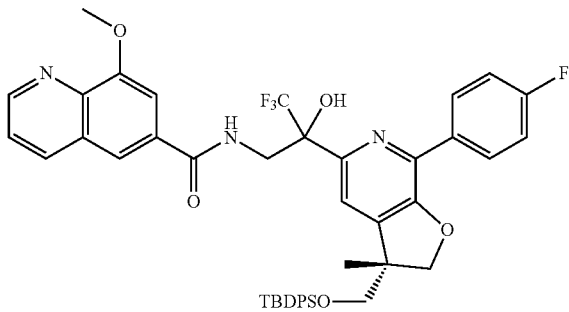

The title compound was synthesized according to Method H using 500 mg of the compound from Example 1, step g and 163 mg of respective acid, and purified by automated column chromatography (silica gel, $R_f$=0.35 in 70% ethyl acetate in hexanes) to give the title compound as a white, foamy solid (428 mg, 66%, mixture of diastereomers). ESI-MS m/z: 810.3 [M+H]+.

Example 21

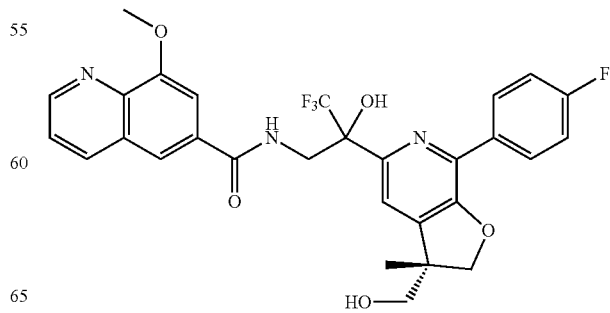

The title compound was synthesized according to Method A using 428 mg of the compound from example 20 and purified by automated column chromatography (silica gel, $R_f$=0.33 in 5% methanol in dichloromethane) to give the title compound as a white, foamy solid (282 mg, 79%, mixture of diastereomers). ESI-MS m/z: 572.2 [M+H]+.

Example 22

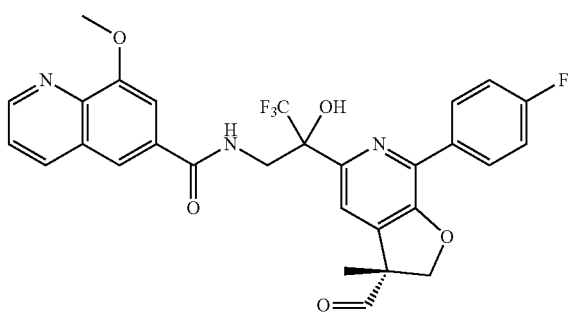 [SMILES: COc1cc(C(=O)NCC(O)(c2cc3c(c(-c4ccc(F)cc4)n2)OC[C@]3(C)C=O)C(F)(F)F)cc2cccnc12]

The title compound was synthesized according to Method B using 282 mg of the compound from example 21 and purified by automated column chromatography (silica gel, 0-100% ethyl acetate in hexanes, then 0-25% methanol in dichloromethane) to give a the title compound as a white, foamy solid (260 mg, 93%, mixture of diastereomers). ESI-MS m/z: 570.2 [M+H]+.

Example 23

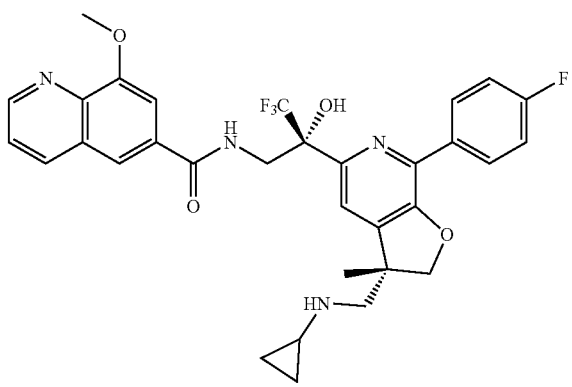 [SMILES: COc1cc(C(=O)NC[C@](O)(c2cc3c(c(-c4ccc(F)cc4)n2)OC[C@]3(C)CNC2CC2)C(F)(F)F)cc2cccnc12]

The title compound was synthesized according to Method C using 50 mg of the compound from example 22. 1.50 equiv. of each amine and borohydride were used, and the reaction stirred overnight. The mixture of diastereomers was analyzed on HPLC and by TLC to check separation. The mixture was purified by prep-HPLC (20-90%, 25 min) and lyophilized to give the title compound as a white, fluffy solid (11.7 mg, 21%). ESI-MS m/z: 611.2 [M+H]+.

Example 24

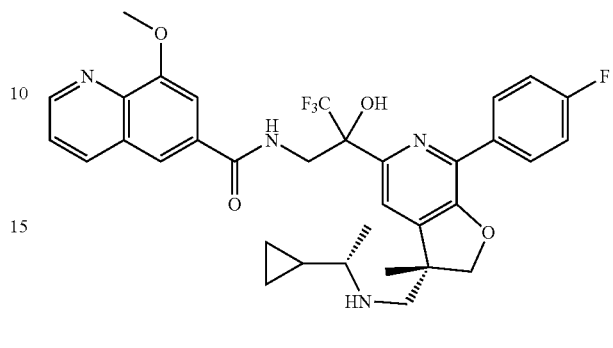

The title compound was synthesized according to Method C using 50 mg of the compound from example 22. 1.50 equiv. of each (S)-1-cyclopropylethylamine and sodium triacetoxyborohydride were used, and the reaction stirred overnight. The mixture of diastereomers was analyzed on HPLC and by TLC to check separation. The mixture was purified by automated column chromatography (silica gel, 0-100% ethyl acetate in hexanes) and lyophilized to give a white, fluffy solid (40 mg, 72%, mixture of diastereomers). ESI-MS m/z: 639.6 [M+H]+.

Example 25

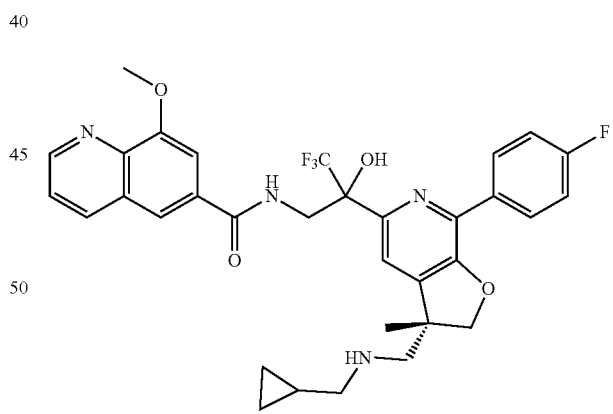

The title compound was synthesized according to Method C using 50 mg of the compound from example 22. 1.50 equiv. of each cyclopropylmethylamine and sodium triacethoxyborohydride were used, and the reaction stirred overnight. The mixture of diastereomers was analyzed on HPLC and by TLC to check separation. The mixture was purified by prep-HPLC (20-90%, 25 min, 0.01% TFA), washed with saturated sodium bicarbonate, and lyophilized to give a white, fluffy solid (31.4 mg, 64%, mixture of diastereomers). ESI-MS m/z: 625.2 [M+H]+.

Example 26

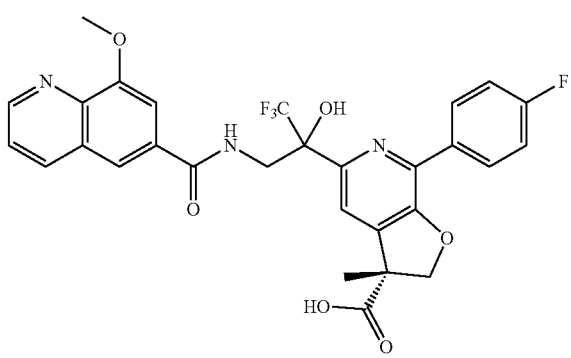 [SMILES: COc1cc(C(=O)NCC(O)(c2cc3c(c(-c4ccc(F)cc4)n2)OC[C@]3(C)C(=O)O)C(F)(F)F)cc2cccnc12]

The title compound was synthesized according to Method F using 100 mg of the compound from example 22, dried on high vacuum overnight, and carried forward crude to the next step. White solid (100 mg, 97%).

Example 27

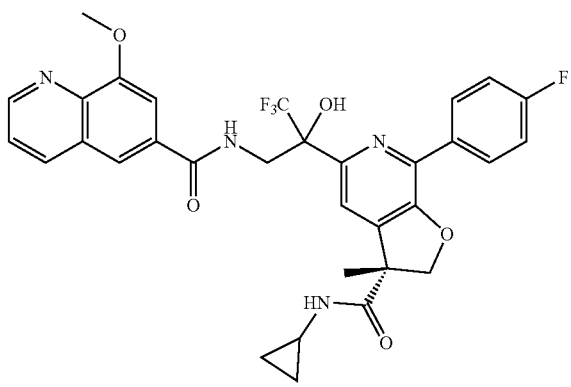 [SMILES: COc1cc(C(=O)NCC(O)(c2cc3c(c(-c4ccc(F)cc4)n2)OC[C@]3(C)C(=O)NC2CC2)C(F)(F)F)cc2cccnc12]

The title compound was synthesized according to Method G using 50 mg of the compound from example 26. The mixture of diastereomers was analyzed on HPLC and by TLC to check separation. The mixture was purified by prep-HPLC (20-90%, 25 min, 0.01% TFA), washed with saturated sodium bicarbonate, and lyophilized to give the title compound as a white, fluffy solid (15 mg, 28%, mixture of diastereomers). ESI-MS m/z: 625.1 [M+H]⁺.

Example 28

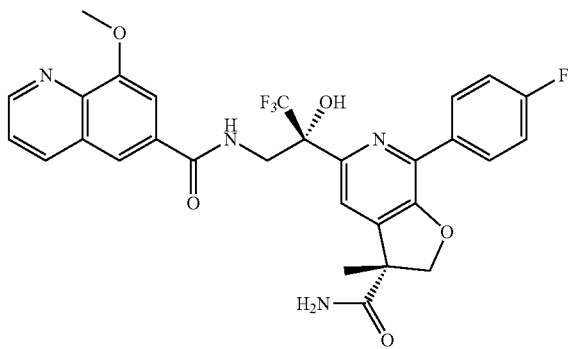 [SMILES: COc1cc(C(=O)NC[C@](O)(c2cc3c(c(-c4ccc(F)cc4)n2)OC[C@]3(C)C(N)=O)C(F)(F)F)cc2cccnc12]

The title compound was synthesized according to Method G using 56 mg of the compound from example 26, ammonium chloride (20.46 mg, 0.383 mmol, 4.0 equiv), 5.0 equiv Hunig's base and BOP (50.8 mg, 0.115 mmol, 1.2 equiv.) as the coupling agent. The mixture was purified by automated column chromatography (silica gel, R$_f$=0.31 in 5% methanol in dichloromethane) and lyophilized to give the title compound as a white, fluffy solid (7 mg, 13%). ESI-MS m/z: 585.2 [M+H]⁺.

Example 29 Step a

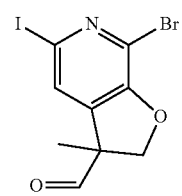

The title compound was synthesized according to procedure Method B using 1.0 g of the compound from Example 1, step b and purified by column chromatography (silica gel, R$_f$=0.52 in 50% ethyl acetate in hexanes) to give the title compound as a white and foamy solid (501 mg, 50%). ESI-MS m/z: 384/385.8 [M+H]⁺.

Example 29 Step b

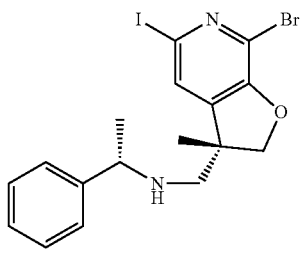

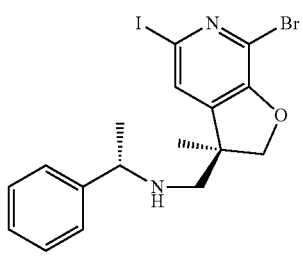

The title compounds were synthesized according to Method C using 501 mg of the compound from example 29, step a and (S)-1-phenylethan-1-amine (176 µl, 1.362 mmol). The residue was purified by column chromatography (silica gel, R$_f$=0.25 in 25% ethyl acetate in hexanes) to give the title compound as a white solid as single diastereomers (172 mg peak 1=P1, 184 mg P2, 55%). P1: ESI-MS m/z: 473.4/475.4 [M+H]⁺; P2: ESI-MS m/z: 473.4/475.4 [M+H]⁺.

Example 29 Step c

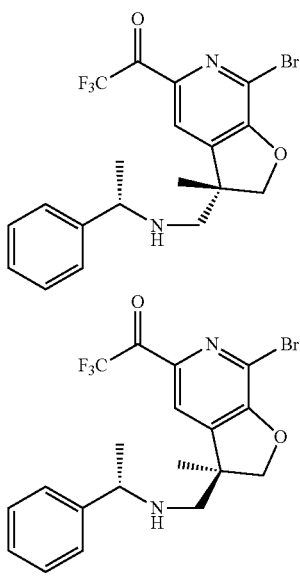

The title compounds were synthesized according the procedure in Example 1, step d using 2.6 equiv of Grignard reagent, and example 29, step b (172 mg P1 and 184 mg P2 from step b, respectively). The residue was purified by column chromatography (silica gel, 0-100% ethyl acetate in hexanes) to give the title compounds as a white solid as single diastereomers. (P1: 132 mg, 82%, P2: 141 mg, 82%, respectively) P1: ESI-MS m/z: 443.0/445.0 [M+H]$^+$; P2:ESI-MS m/z: 443.2/445.4 [M+H]$^+$.

Example 29 Step d

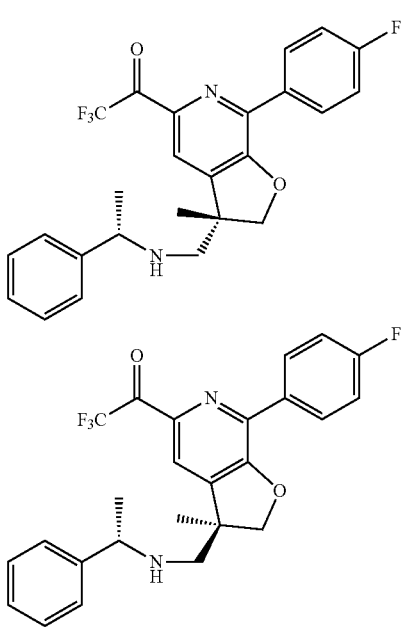

The title compounds were synthesized according the procedure in Example 1, step e using of the compounds from step c (P1: 132 mg, and P2: 144 mg, respectively). The residue was purified using automated column chromatography (silica gel, 0-100% ethyl acetate in hexanes) to give sticky residues as single diastereomers. The residues were dehydrated by azeotroping/triturating 3× with 2 mL of toluene (P1: 101 mg, 73%, P2: 141 mg, 80%, respectively). P1: ESI-MS m/z: 477.4 [M+H]$^+$ (water adduct); P2: ESI-MS m/z: 477.2 [M+H]$^+$ (water adduct).

Example 29 Step e

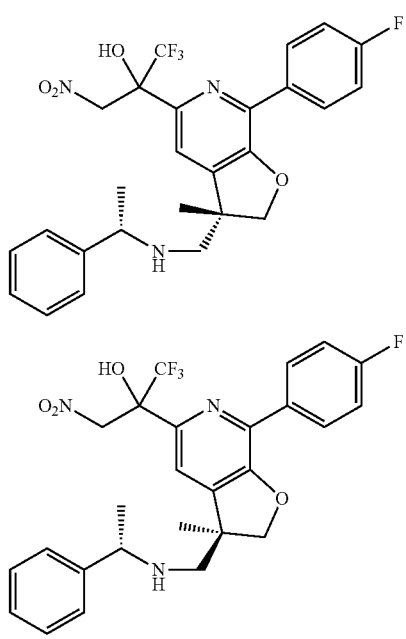

The title compounds were synthesized according the procedure in Example 1, step f using of the compound from step d (P1: 101 mg and P2:141 mg, respectively). The crude residues were dried on high vacuum to give the title compounds as white solids (P1: 97 mg, 84%, P2: 113 mg, 85%). The crude material was carried forward to the next step without further purification. P1: ESI-MS m/z: 520.5 [M+H]$^+$; P2: ESI-MS m/z: 520.3 [M+H]$^+$.

Example 29 Step f

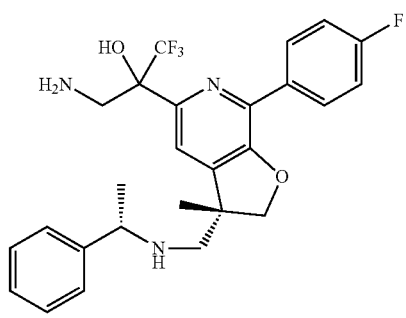

-continued

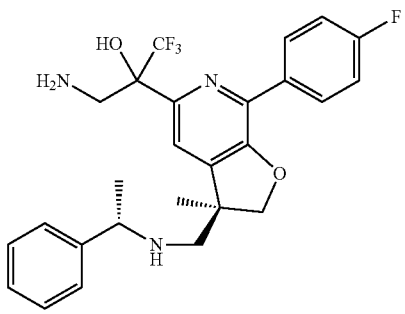

The title compounds were synthesized according the procedure in Example 1, step g using of the compounds from step e (P1: 97 mg, and P2: 113 mg, respectively). The crude residues were dried on high vacuum to give white, foamy solids (P1: 90 mg, 98%, P2: 103 mg, 94%). The crude material was carried forward to the next step. P1: ESI-MS m/z: 490.3 [M+H]$^+$; P2: ESI-MS m/z: 490.4 [M+H]$^+$.

Example 30a and 30b

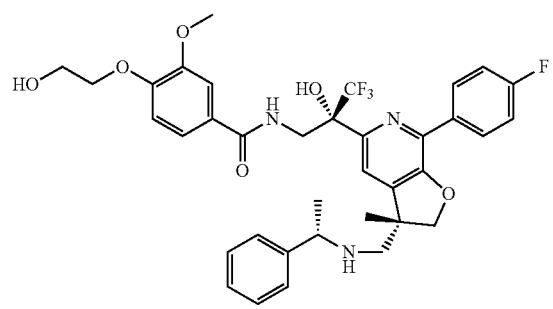

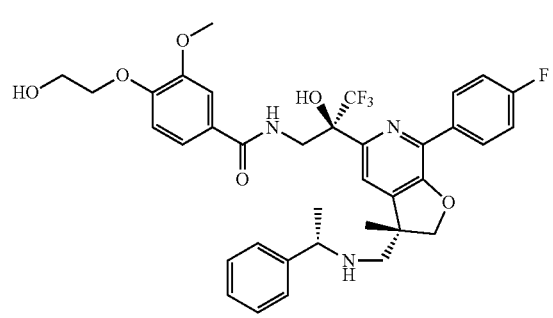

The title compounds were synthesized according to Method G using 90 mg P1 from example 29, step f and 39 mg of the respective acid. The crude residue was purified by automated column chromatography (silica gel, 0-100% ethyl acetate in hexanes), and prep-HPLC (20-90%, 25 min) to get pure samples of the two diastereomers (10 mg P1-A, 11 mg P1-B, 18%) P1-A: ESI-MS m/z: 684.5 [M+H]$^+$; P1-B: ESI-MS m/z: 684.4 [M+H]$^+$.

Example 31

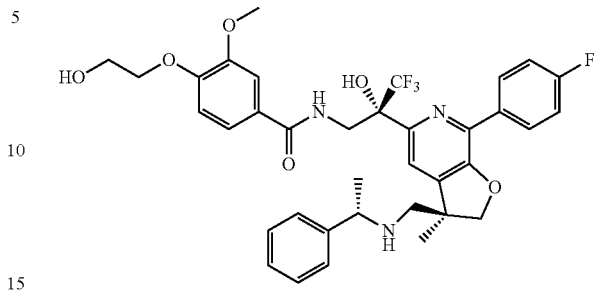

The title compounds were synthesized according to Method G using 103 mg of P2 from example 29, step f and 45 mg of the respective acid. The crude residue was purified by automated column chromatography (silica gel, 0-100% ethyl acetate in hexanes), and prep-HPLC (20-90%, 25 min) to get pure samples of the two diastereomers (18 mg P2-A, 14 mg P2-B, 22%) P2-A: ESI-MS m/z: 684.5 [M+H]$^+$; P2-B: ESI-MS m/z: 684.4 [M+H]$^+$.

Example 32, Step a

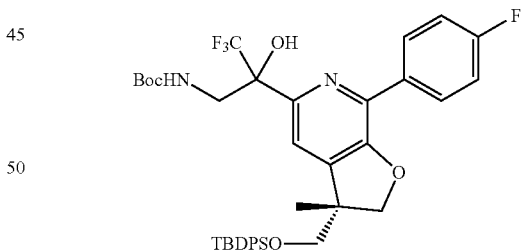

To a 50 round bottom flask containing the compound from Example 1, step g (2.164 g, 3.46 mmol) was added a stir bar. The flask was purged with nitrogen, and DCM (17 mL, 0.2 M) was added. Triethylamine (0.724 ml, 5.20 mmol) was added, the flask cooled to 0° C., and Boc-anhydride (3.81 ml, 3.81 mmol) was added. The reaction was stirred at room temperature and monitored by LCMS (5 hrs). The stir bar was removed, and the mixture directly concentrated. The crude residue was purified by automated column chromatography (silica gel, R$_f$=0.72 in 20% ethyl acetate in hexanes) to afford the title compound as a white, foamy solid (2.30 g, 93%). ESI-MS m/z: 724.9 [M+H]$^+$.

Example 32, Step b

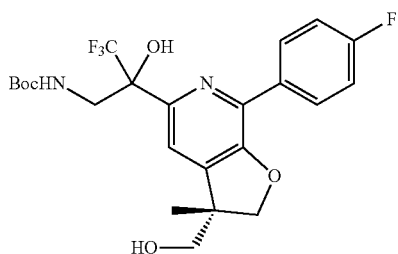 [SMILES: CC(C)(C)OC(=O)NCC(O)(c1cc2c(c(-c3ccc(F)cc3)n1)OC[C@]2(C)CO)C(F)(F)F]

To a 40 mL vial containing the compound from step a (2.515 g, 3.47 mmol) was added a stir bar. The vial was purged with nitrogen, and THF (17 mL, 0.2 M) was added. The vial was cooled to 0° C. and TBAF (6.94 ml, 6.94 mmol) was added. The reaction was stirred for 10 minutes, warmed to room temperature and monitored by LCMS (1.5 hrs, and then 3.0 equiv more of TBAF was added over an additional 2 hrs). The stir bar was removed, and the reaction directly concentrated. The crude residue was purified by automated column chromatography (silica gel, $R_f$=0.29 in 33% ethyl acetate in hexanes) to afford the title compound as a white, foamy solid (525 mg non-polar peak P1, 600 mg polar peak P2, 67%). P1: ESI-MS m/z: 487.2 [M+H]$^+$; P2: ESI-MS m/z: 487.2 [M+H]$^+$.

Example 33

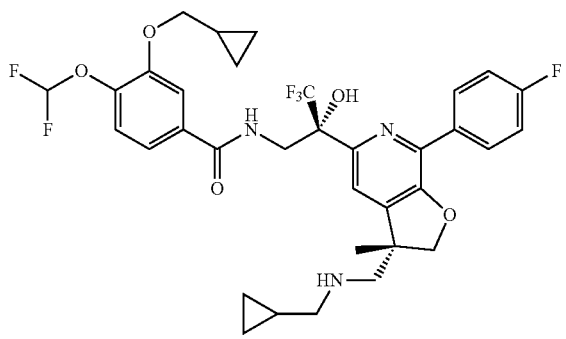 [SMILES: C[C@]1(CNCC2CC2)COc2c1cc([C@@](O)(CNC(=O)c1ccc(OC(F)F)c(OCC3CC3)c1)C(F)(F)F)nc2-c1ccc(F)cc1]

Example 33 Step a

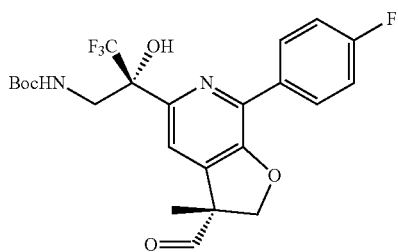 [SMILES: CC(C)(C)OC(=O)NC[C@](O)(c1cc2c(c(-c3ccc(F)cc3)n1)OC[C@]2(C)C=O)C(F)(F)F]

The title compound was synthesized according to Method B using 472 mg of the compound (P1) from example 32, step b. The crude residue was purified using automated column chromatography (silica gel, 0-100% ethyl acetate in hexanes) to afford the title compound as a white, foamy solid (387 mg, 82%, single diastereomer). ESI-MS m/z: 485.0 [M+H]$^+$.

Example 33 Step b

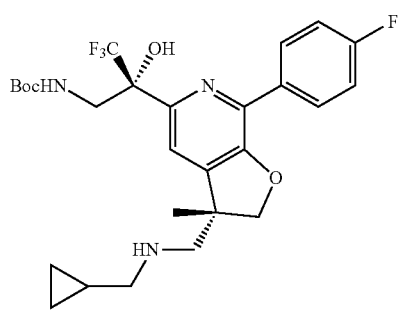 [SMILES: CC(C)(C)OC(=O)NC[C@](O)(c1cc2c(c(-c3ccc(F)cc3)n1)OC[C@]2(C)CNCC1CC1)C(F)(F)F]

The title compound was synthesized according to Method C using 200 mg of the compound from step a, but with 5.0 equiv of cyclopropylmethylamine and 5.0 equiv hydride for 14 hours. The crude residue was purified using automated column chromatography (silica gel, 0-100% ethyl acetate in hexanes) to afford the title compound as a white, foamy solid (163 mg, 73%). ESI-MS m/z: 540.2 [M+H]$^+$.

Example 33 Step c

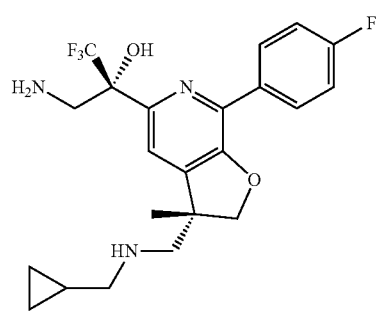 [SMILES: C[C@]1(CNCC2CC2)COc2c1cc([C@@](O)(CN)C(F)(F)F)nc2-c1ccc(F)cc1]

To a 20 mL scintillation vial containing the compound from step b (193 mg, 0.358 mmol) was added a stir bar. DCM (1.40 mL) was added followed by MeOH (0.35 mL). The vial was cooled to 0° C., and HCl in dioxane (4.0 M, 894 µl, 3.58 mmol) was added. The reaction was stirred for 5 minutes, warmed to room temperature and monitored by LCMS (1.5 hr). The reaction was diluted with EtOAc and quenched with water. The pH was brought to pH 8-9 with sat. sodium bicarbonate. An ethyl acetate extraction was performed, and the sticky residue lyophilized to afford a clear, sticky solid (141 mg, 90%). ESI-MS m/z: 440.2 [M+H]$^+$.

Example 33 Step d

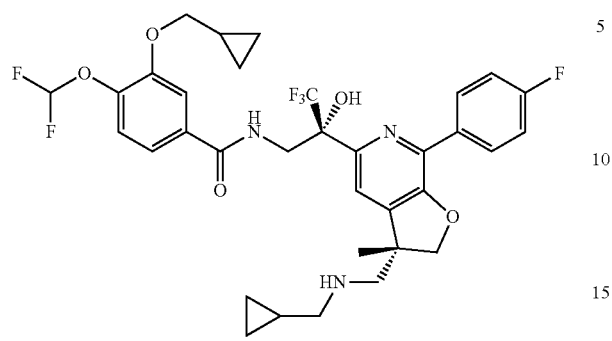

The title compound was synthesized according to Method G using 15 mg of the compound from step c and 1.0 equiv of the respective acid for 2 hrs. The crude residue was purified by automated column chromatography (silica gel, 0-100% ethyl acetate in hexanes) and lyophilized to afford the title compound as white, fluffy solid (12.8 mg, 55%). ESI-MS m/z: 680.2 [M+H]$^+$.

Example 34

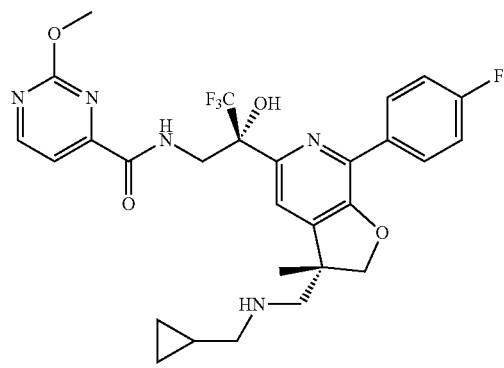 [SMILES: COc1nccc(C(=O)NC[C@](O)(c2cc3c(c(-c4ccc(F)cc4)n2)OC[C@]3(C)CNCC2CC2)C(F)(F)F)n1]

The title compound was synthesized according to Method G using 15 mg of the compound from step c and 1.0 equiv of the respective acid for 2 hrs. The crude residue was purified by prep-HPLC (20-90%, 25 min) and lyophilized to afford a white, fluffy solid (5 mg, 26%). ESI-MS m/z: 576.2 [M+H]$^+$.

The title compound was synthesized according to Method G using 15 mg of the compound from step c and 1.0 equiv of the respective acid for 2 hrs. The crude residue was purified by automated column chromatography (silica gel, 0-100% ethyl acetate in hexanes) and lyophilized to afford a white, fluffy solid (10.2 mg, 43%). ESI-MS m/z: 614.2 [M+H]$^+$.

Example 35

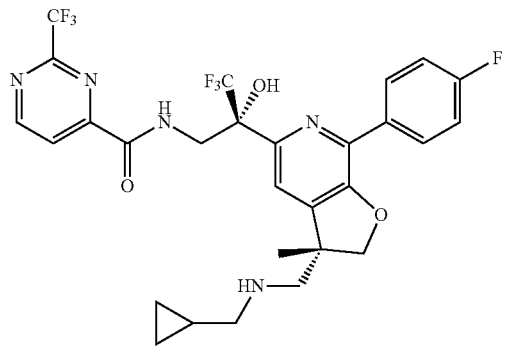 [SMILES: C[C@]1(CNCC2CC2)COc2c1cc([C@@](O)(CNC(=O)c1ccnc(C(F)(F)F)n1)C(F)(F)F)nc2-c1ccc(F)cc1]

Example 36

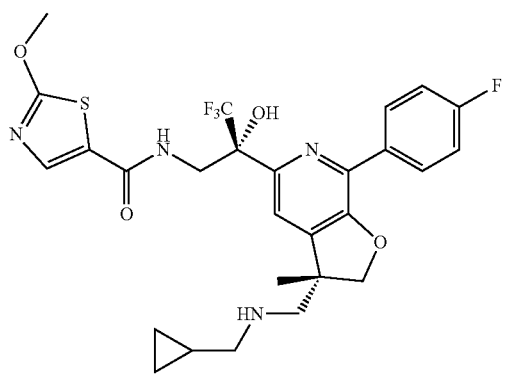 [SMILES: COc1ncc(C(=O)NC[C@](O)(c2cc3c(c(-c4ccc(F)cc4)n2)OC[C@]3(C)CNCC2CC2)C(F)(F)F)s1]

The title compound was synthesized according to Method G using 15 mg of the compound from step c, 1.0 equiv of the respective acid and PyBOP (21 mg, 1.2 equiv) as the coupling agent for 2 hrs. The crude residue was purified by automated column chromatography (silica gel, 0-100% ethyl acetate in hexanes) and lyophilized to afford a white, fluffy solid (9 mg, 42%). ESI-MS m/z: 581.2 [M+H]+.

Example 37

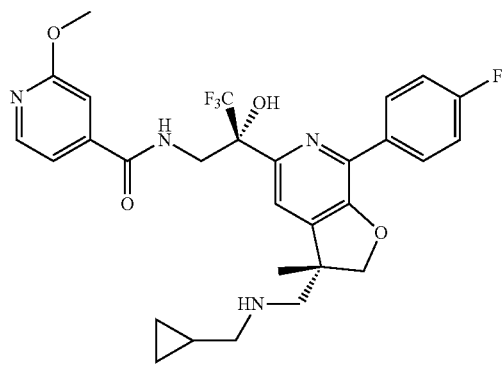 [SMILES: COc1cc(C(=O)NC[C@](O)(c2cc3c(c(-c4ccc(F)cc4)n2)OC[C@]3(C)CNCC2CC2)C(F)(F)F)ccn1]

The title compound was synthesized according to Method G using 15 mg of the compound from step c, 1.0 equiv of the respective acid and PyBOP (21 mg, 1.2 equiv) as the coupling agent for 2 hrs. The crude residue was purified by automated column chromatography (silica gel, 0-100% ethyl acetate in hexanes) and lyophilized to afford a white, fluffy solid (14.1 mg, 72%). ESI-MS m/z: 575.2 [M+H]+.

Example 38

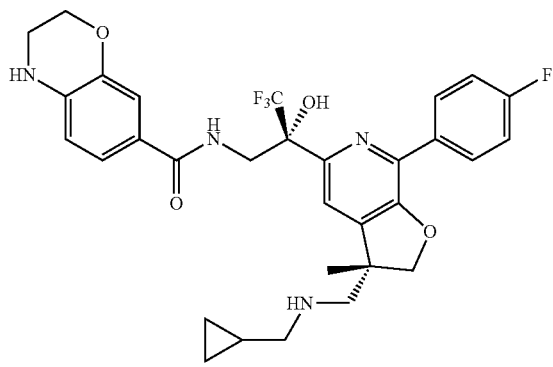 [SMILES: C[C@]1(CNCC2CC2)COc2c1cc([C@@](O)(CNC(=O)c1ccc3c(c1)OCCN3)C(F)(F)F)nc2-c1ccc(F)cc1]

The title compound was synthesized according to Method G using 15 mg of the compound from step c, 1.0 equiv of the respective acid and PyBOP (21 mg, 1.2 equiv) as the coupling agent for 2 hrs. The crude residue was purified by automated column chromatography (silica gel, 0-50% ethyl acetate in hexanes to 0-20% methanol in dichloromethane) and lyophilized to afford a white, fluffy solid (16.2 mg, 79%). ESI-MS m/z: 601.2 [M+H]+.

Example 39

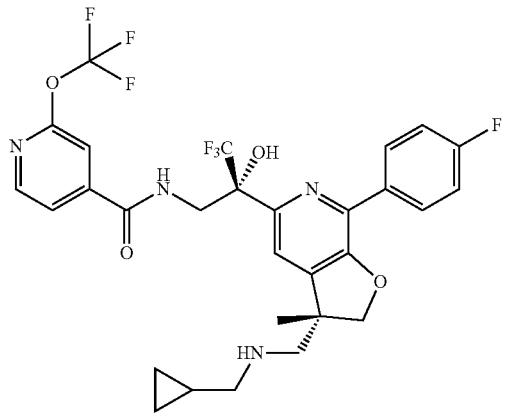 [SMILES: C[C@]1(CNCC2CC2)COc2c1cc([C@@](O)(CNC(=O)c1ccnc(OC(F)(F)F)c1)C(F)(F)F)nc2-c1ccc(F)cc1]

The title compound was synthesized according to Method G using 15 mg of the compound from step c, 1.0 equiv of the respective acid and PyBOP (21 mg, 1.2 equiv) as the coupling agent for 2 hrs. The crude residue was purified by automated column chromatography (silica gel, 0-100% ethyl acetate in hexanes) and lyophilized to afford a white, fluffy solid (8 mg, 37%). ESI-MS m/z: 619.1 [M+H]+.

Example 40

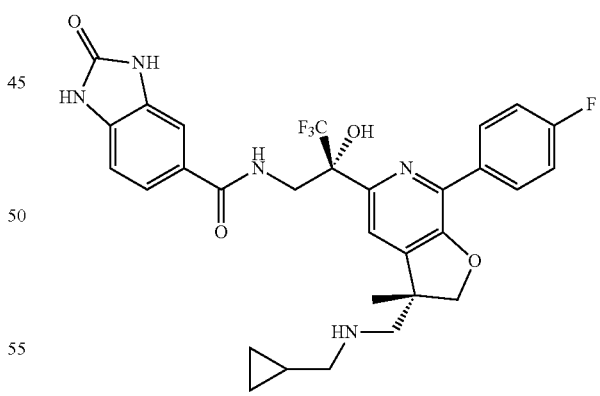

The title compound was synthesized according to Method G using 15 mg of the compound from step c, 1.0 equiv of the respective acid and PyBOP (21 mg, 1.2 equiv) as the coupling agent for 2 hrs. The crude residue was purified by automated column chromatography (silica gel, 0-50% ethyl acetate in hexanes to 0-20% methanol in dichloromethane) and lyophilized to afford a white, fluffy solid (12 mg, 59%). ESI-MS m/z: 600.2 [M+H]+.

Example 41

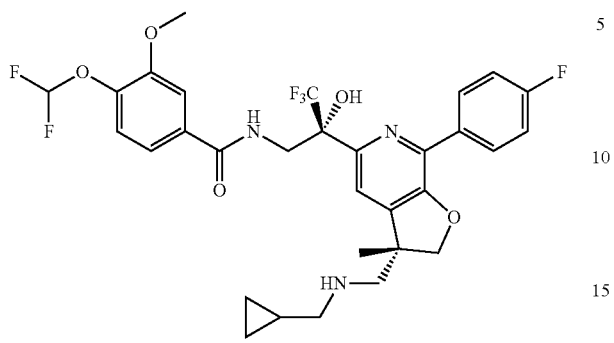

The title compound was synthesized according to Method G using 16 mg of example 33, step c, 1.0 equiv of the respective acid and PyBOP (23 mg, 1.2 equiv) as the coupling agent for 2 hrs. The crude residue was purified by automated column chromatography (silica gel, 0-100% ethyl acetate in hexanes) and lyophilized to afford a white, fluffy solid (16.6 mg, 71%). ESI-MS m/z: 640.2 [M+H]+.

Example 42

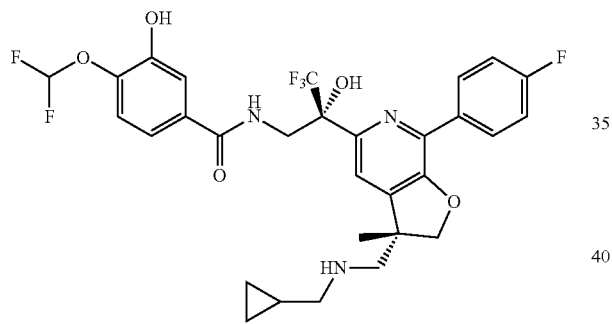

The title compound was synthesized according to Method G using 16 mg of example 33, step c, 1.0 equiv of the respective acid and PyBOP (23 mg, 1.2 equiv) as the coupling agent for 2 hrs. The crude residue was purified by automated column chromatography (silica gel, 0-100% ethyl acetate in hexanes) and lyophilized to afford a white, fluffy solid (7.6 mg, 33%). ESI-MS m/z: 626.2 [M+H]+.

Example 43

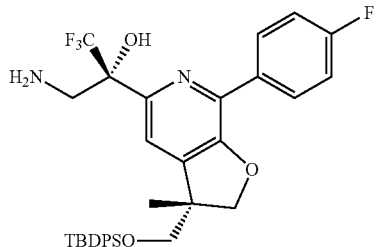

Example 43 Step a

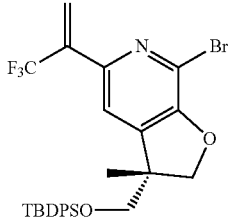

In a vial, the compound from Example 1, step d (1 g, 1.644 mmol), 4,4,6-trimethyl-2-(3,3,3-trifluoroprop-1-en-2-yl)-1,3,2-dioxaborinane (438 mg, 1.972 mmol), Pd(dppf)Cl$_2$.DCM (81 mg, 0.099 mmol), and K$_2$CO$_3$ (681 mg, 4.93 mmol) were dissolved in 1,4-dioxane (7.40 ml) and water (0.822 ml). The reaction was sparged with N$_2$ and sealed. The reaction was heated at 90° C. for 2 hr and cooled to room temperature and water was added. The aqueous layer was washed with EtOAc. The combined organic layer was washed with water and brine before drying over MgSO$_4$ and concentrated in vacuo.

The residue was purified by silica gel column (0-20% hexanes/ethyl acetate) to yield the title compound (816 mg, 86%) as a clear viscous liquid. ESI-MS: 576/578 m/z [M+H]+.

Example 43 Step b

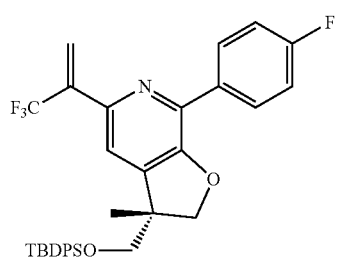

In a vial, the product from Example 43 step a (686 mg, 1.190 mmol), (4-fluorophenyl)boronic acid (200 mg, 1.428 mmol), PdCl$_2$(dppf) (43.5 mg, 0.059 mmol), and K$_2$CO$_3$ (370 mg, 2.68 mmol) were dissolved in dioxane (4.76 ml) and water (1.190 ml). The reaction was sparged with N$_2$ and sealed. The vial was heated at 90° C. for 2 hr. The reaction was monitored by LCMS. Vial cooled to RT and water added. Aqueous layer washed with EtOAc and combined organic layer washed with water and brine before drying over MgSO$_4$ and concentrated in vacuo. The residue was purified by silica gel column, 0-20% Hexanes/Ethyl acetate, to furnish the title compound (584 mg, 83%) as a clear viscous liquid. ESI-MS: 592.2 m/z [M+H]+.

Example 43 Step c

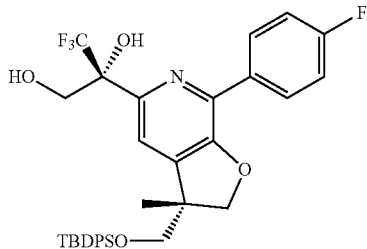

In a vial, the compound from step b (400 mg, 0.676 mmol) was dissolved in tert-BuOH (3.38 ml) followed by water (3.38 ml) (causes olefin to begin to crash out). The solution was cooled to 0° C. Methanesulfonamide (64.3 mg, 0.676 mmol) was added followed by AD-mix-β (1053 mg, 1.352 mmol). The reaction was allowed to warm to room temperature and stir overnight. Reaction diluted with EtOAc and quench with sat. aq. sodium thiosulfate. Aqueous layer washed with EtOAc and combined organic layer dried over MgSO$_4$ and concentrated. The residue purified by column chromatography (0-30% hexanes/EtOAc) to furnish the title compound (330 mg, 78%). ESI-MS: 626.34 m/z [M+H]$^+$.

Example 43 Step d

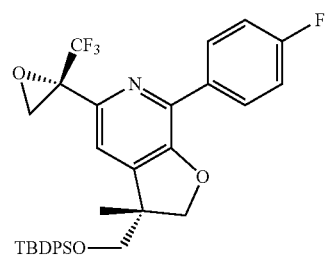

In a vial, the compound from step c (270 mg, 0.431 mmol) was dissolved in THF (4.31 ml). The vial was cooled to 0° C. and sodium hydride (43.1 mg, 1.079 mmol) was added. The reaction was allowed to stir at least 1 hr at 0° C. before tosyl chloride (99 mg, 0.518 mmol) was added. The reaction was allowed to stir 1 hr then warmed to room temperature. Water added to quench and aqueous layer washed with EtOAc. Combined organic layer dried over MgSO$_4$ and concentrated. The residues were purified by silica gel column (0-40% hexanes/EtOAc) to provide the title compound (216 mg, 82%). ESI-MS: 608.38 m/z [M+H]$^+$.

Example 43 Step e

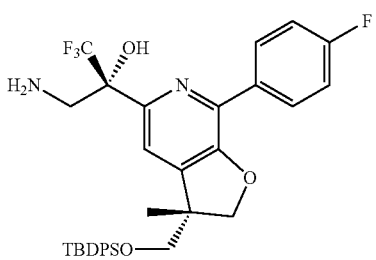

In a vial, the compound from step d (216 mg, 0.355 mmol) was dissolved in DMF (7.11 ml). Ammonium hydroxide (138 µl, 3.55 mmol) was added and the reaction was sealed and allowed to stir overnight. Water was added and the aqueous layer was washed with DCM. The combined organic layer was washed with H$_2$O and dried over MgSO$_4$ before concentrating to give a foaming solid. The crude reaction was used for next step without further purification. ESI-MS: 625.61 m/z [M+H]$^+$.

Example 43 is a key chiral intermediate in the synthesis of compounds of Formula (I), (Ia) or (Ib).

Example 44

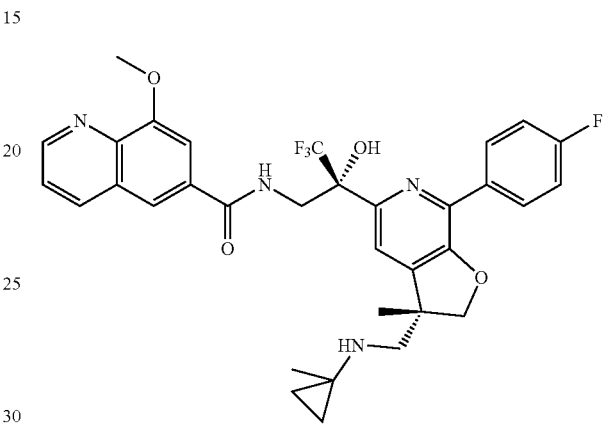

The title compound was synthesized according to Method C using 20 mg of the compound from example 22 (as a single diastereomer). 3.0 equiv. of amine HCl salt. 3.0 equiv borohydride, 4.0 equiv. TEA were used, and the reaction stirred overnight. The crude reaction was purified by prep-HPLC (20-90%, 25 min) and lyophilized to give the title compound as a white, fluffy solid (6.0 mg, 27%). ESI-MS m/z: 625.2 [M+H]$^+$.

Example 45

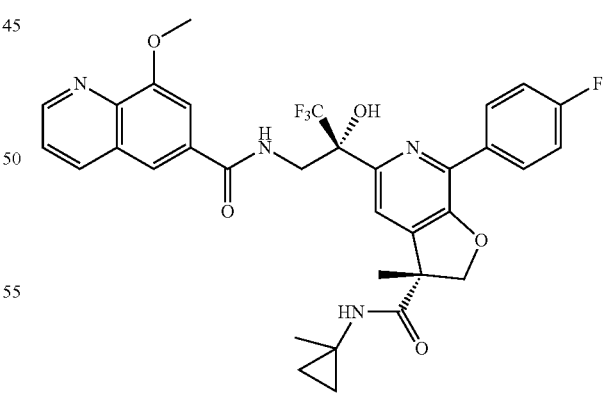

The title compound was synthesized according to Method G using 25 mg of the compound from example 26 (as a single diastereomer), 4.0 equiv of amine HCl salt, and 5.0 equiv. of DIPEA. The crude reaction was purified by prep-HPLC (20-90%, 25 min), and lyophilized to give the title compound as a white, fluffy solid (9.1 mg, 33%). ESI-MS m/z: 629.2 [M+H]$^+$.

Example 46

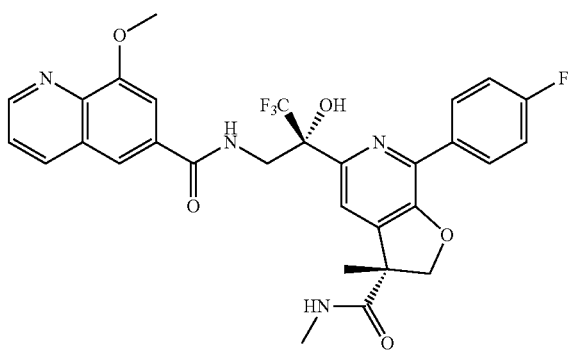 [SMILES: CNC(=O)[C@@]1(C)COc2c1cc([C@@](O)(CNC(=O)c1cc(OC)c3ncccc3c1)C(F)(F)F)nc2-c1ccc(F)cc1]

The title compound was synthesized according to Method G using 25 mg of the compound from example 26 (as a single diastereomer), 12.0 equiv of amine, and 5.0 equiv. of DIPEA for 48 hrs. The crude reaction was purified by automated column chromatography (silica gel, 0-10% methanol in dichloromethane), and lyophilized to give the title compound as a white, fluffy solid (16.1 mg, 63%). ESI-MS m/z: 599.2 [M+H]$^+$.

Example 47

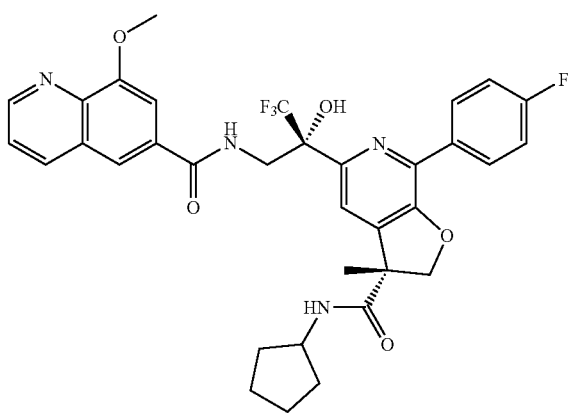 [SMILES: COc1cc(C(=O)NC[C@](O)(c2cc3c(c(-c4ccc(F)cc4)n2)OC[C@]3(C)C(=O)NC2CCCC2)C(F)(F)F)cc2cccnc12]

The title compound was synthesized according to Method G using 25 mg of the compound from example 26 (as a single diastereomer), 14.0 equiv of amine, and 4.0 equiv. of DIPEA. The crude reaction was purified by prep-HPLC (20-90%, 25 min), and lyophilized to give the title compound as a white, fluffy solid (4.5 mg, 16%). ESI-MS m/z: 653.3 [M+H]$^+$.

Example 48

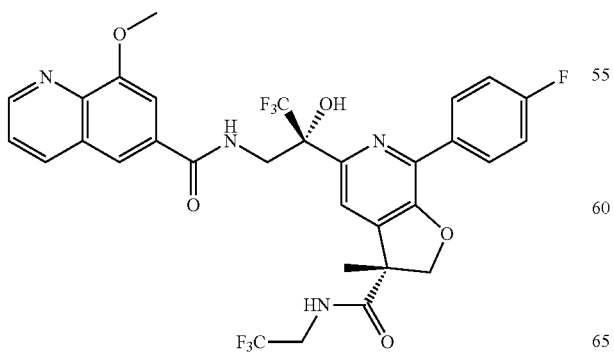

The title compound was synthesized according to Method G using 25 mg of the compound from example 26 (as a single diastereomer), 8.0 equiv of amine, 4.0 equiv. of DIPEA, and the adding 4.0 equiv more of HATU after 2 hrs. The crude reaction was purified by prep-HPLC (20-90%, 25 min), and lyophilized to give the title compound as a white, fluffy solid (5.3 mg, 19%). ESI-MS m/z: 667.1 [M+H]$^+$.

Example 49

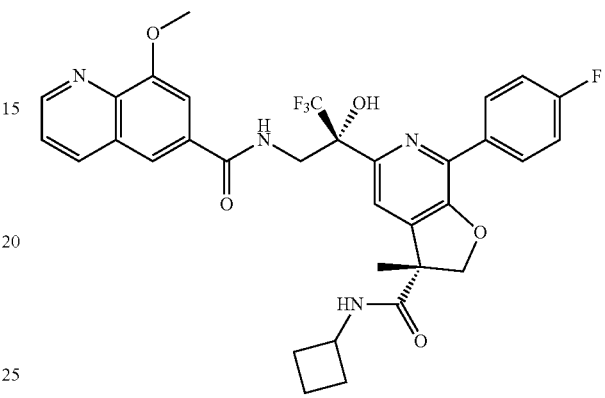

The title compound was synthesized according to Method G using 25 mg of the compound from example 26 (as a single diastereomer), 10.0 equiv of amine, 4.0 equiv. of DIPEA for 14 hrs. The crude reaction was purified by prep-HPLC (20-90%, 25 min), and lyophilized to give the title compound as a white, fluffy solid (6.0 mg, 22%). ESI-MS m/z: 629.2 [M+H]$^+$.

Example 50

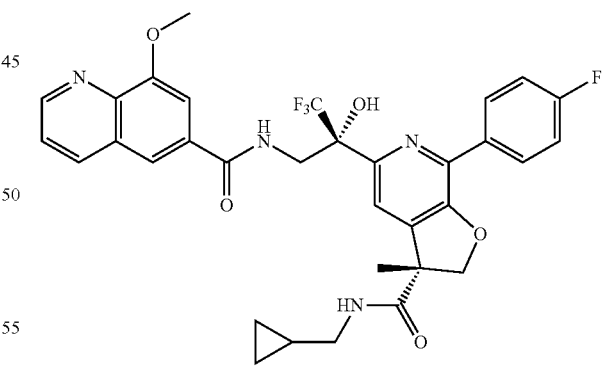

The title compound was synthesized according to Method G using 25 mg of the compound from example 26 (as a single diastereomer), 4.0 equiv of amine, 4.0 equiv. of DIPEA for 14 hrs, then 10 equiv. amine/DIPEA and 4.0 equiv HATU for 3 hrs. The crude reaction was purified by prep-HPLC (20-90%, 25 min), and lyophilized to give the title compound as a white, fluffy solid (6.0 mg, 22%). ESI-MS m/z: 639.2 [M+H]$^+$.

Example 51

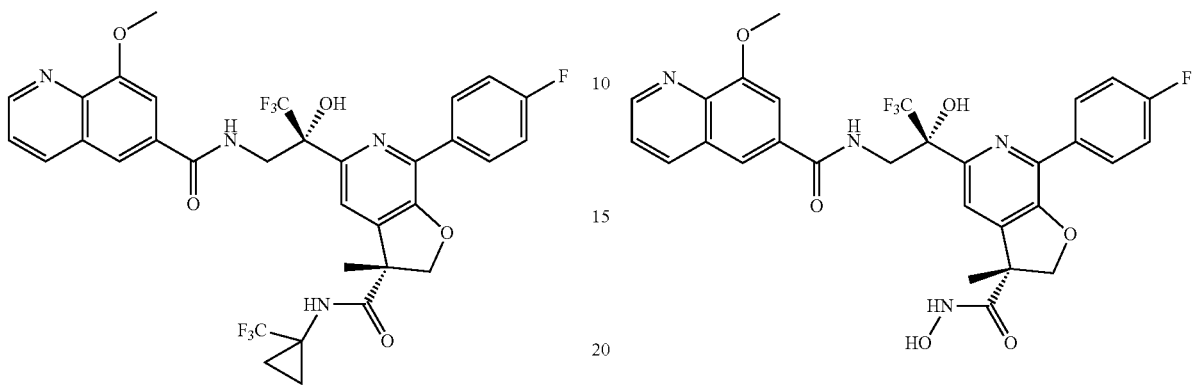

The title compound was synthesized according to Method G using 25 mg of the compound from example 26 (as a single diastereomer), 5.0 equiv of amine HCl salt, 6.0 equiv. of DIPEA for 3 hrs, then 5 equiv. amine/DIPEA and 4.0 equiv HATU for 2 hrs. The crude reaction was purified by prep-HPLC (20-90%, 25 min), and lyophilized to give the title compound as a white, fluffy solid (8.4 mg, 28%). ESI-MS m/z: 693.2 [M+H]$^+$.

Example 53

The title compound was synthesized according to Method G using 25 mg of the compound from example 26 (as a single diastereomer), 4.0 equiv of amine HCl salt, 5.0 equiv. of DIPEA for 4 hrs, then 10 equiv. amine/DIPEA and 4.0 equiv HATU for 18 hrs. The crude reaction was purified by prep-HPLC (20-90%, 25 min), and lyophilized to give the title compound as a white, fluffy solid (12.0 mg, 39%). ESI-MS m/z: 601.0 [M+H]$^+$.

Example 52

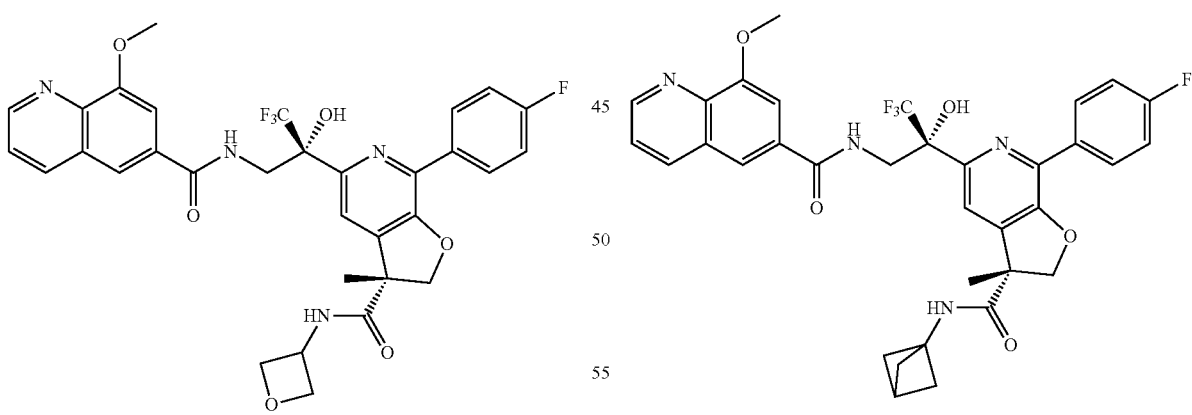

The title compound was synthesized according to Method G using 25 mg of the compound from example 26 (as a single diastereomer), 4.0 equiv of amine, 4.0 equiv. of DIPEA for 4 hrs, then 10 equiv. amine/DIPEA and 4.0 equiv HATU for 18 hrs. The crude reaction was purified by prep-HPLC (20-90%, 25 min), and lyophilized to give the title compound as a white, fluffy solid (11.5 mg, 42%). ESI-MS m/z: 641.2 [M+H]$^+$.

Example 54

The title compound was synthesized according to Method G using 25 mg of the compound from example 26 (as a single diastereomer), 4.0 equiv of amine HCl salt, 5.0 equiv. of DIPEA for 14 hrs. The crude reaction was purified by prep-HPLC (20-90%, 25 min), and lyophilized to give the title compound as a white, fluffy solid (8.6 mg, 31%). ESI-MS m/z: 651.2 [M+H]$^+$.

115

Example 55

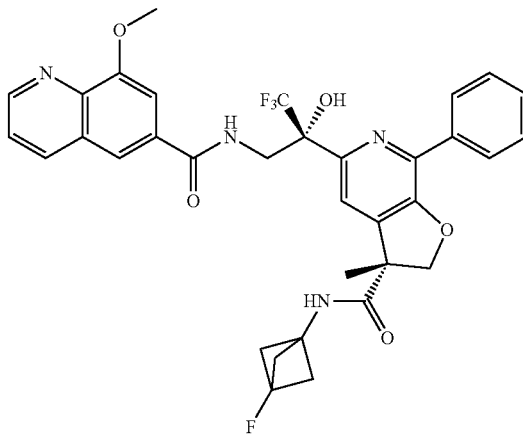

The title compound was synthesized according to Method G using 25 mg of the compound from example 26 (as a single diastereomer), 4.0 equiv of amine HCl salt, 5.0 equiv. of DIPEA for 14 hrs. The crude reaction was purified by prep-HPLC (20-90%, 25 min), and lyophilized to give the title compound as a white, fluffy solid (12.0 mg, 42%). ESI-MS m/z: 669.2 [M+H]+.

Example 56

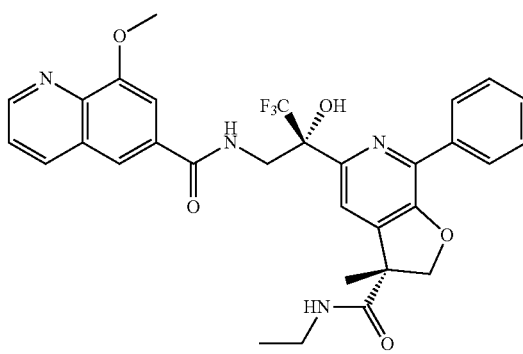

The title compound was synthesized according to Method G using 25 mg of the compound from example 26 (as a single diastereomer), 10.0 equiv of amine, 5.0 equiv. of DIPEA for 14 hrs. The crude reaction was purified by automated column chromatography (0-10% methanol in dichloromethane), and lyophilized to give the title compound as a white, fluffy solid (15.0 mg, 57%). ESI-MS m/z: 613.0 [M+H]+.

116

Example 57

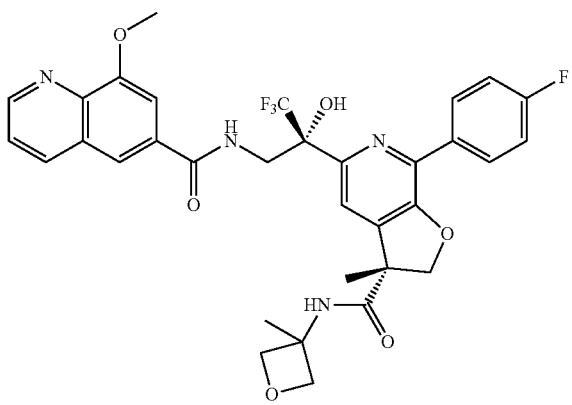 [SMILES: COc1cc(C(=O)NC[C@](O)(c2cc3c(c(-c4ccc(F)cc4)n2)OC[C@]3(C)C(=O)NC2(C)COC2)C(F)(F)F)cc2cccnc12]

The title compound was synthesized according to Method G using 25 mg of the compound from example 26 (as a single diastereomer), 4.0 equiv of amine HCl salt, 5.0 equiv. of DIPEA for 14 hrs. The crude reaction was purified by prep-HPLC (20-90%, 25 min), and lyophilized to give the title compound as a white, fluffy solid (8.0 mg, 29%). ESI-MS m/z: 655.0 [M+H]+.

Example 58

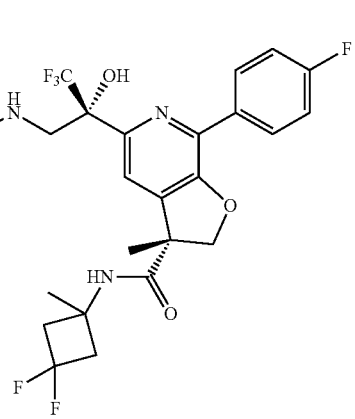

The title compound was synthesized according to Method G using 25 mg of the compound from example 26 (as a single diastereomer), 4.0 equiv of amine HCl salt, 5.0 equiv. of DIPEA for 14 hrs. The crude reaction was purified by prep-HPLC (20-90%, 25 min), and lyophilized to give the title compound as a white, fluffy solid (10.9 mg, 37%). ESI-MS m/z: 689.0 [M+H]+.

Example 59

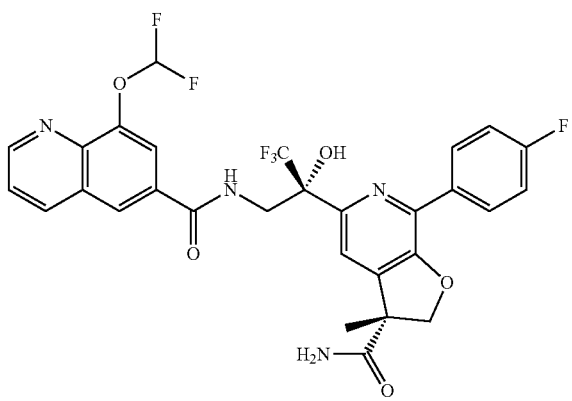 [SMILES: C[C@]1(C(N)=O)COc2c1cc([C@@](O)(CNC(=O)c1cc(OC(F)F)c3ncccc3c1)C(F)(F)F)nc2-c1ccc(F)cc1]

Example 59 Step a

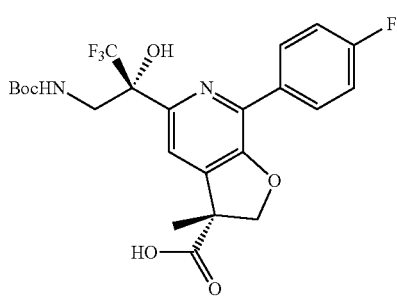 [SMILES: CC(C)(C)OC(=O)NC[C@](O)(c1cc2c(c(-c3ccc(F)cc3)n1)OC[C@]2(C)C(=O)O)C(F)(F)F]

The title compound was synthesized according to Method F using 380 mg of the aldehyde (as a single diastereomer). The crude residue was purified using automated column chromatography (silica gel, 0-100% ethyl acetate in hexanes) to afford the title compound as a light yellow solid (354 mg, 90%, ESI-MS m/z: 444.9 [M+H]$^+$.

Example 59 Step b

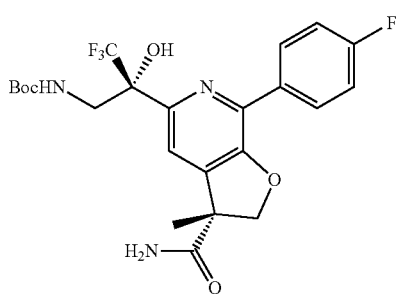 [SMILES: CC(C)(C)OC(=O)NC[C@](O)(c1cc2c(c(-c3ccc(F)cc3)n1)OC[C@]2(C)C(N)=O)C(F)(F)F]

The title compound was synthesized according to Method G using 354 mg of the acid from step a. The crude residue was purified using automated column chromatography (silica gel, 0-100% ethyl acetate in hexanes) to afford the title compound as a light yellow solid (266 mg, 57%), ESI-MS m/z: 443.9 [M+H]$^+$.

Example 59 Step c

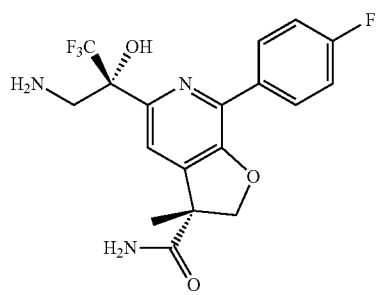 [SMILES: C[C@]1(C(N)=O)COc2c1cc([C@@](O)(CN)C(F)(F)F)nc2-c1ccc(F)cc1]

The title compound was synthesized according to the deprotection procedure in example 33, step c, using 120 mg of the amide from step b. The crude residue was triturated with dichloromethane/hexanes, to afford a light yellow solid (95 mg, 99%), ESI-MS m/z: 400.0 [M+H]$^+$.

Example 59 Step d

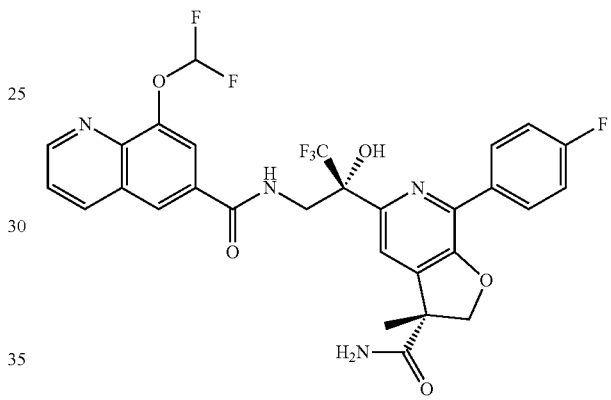

The title compound was synthesized according to Method G using 20 mg of the compound from example 59 step c above, (1.0 equiv) and 1.0 equiv. of respective acid for 1.5 hrs. The crude reaction was purified by automated column chromatography (silica gel, 0-10% methanol in dichloromethane) and lyophilized to give the title compound as a white, fluffy solid (6.7 mg, 24%). ESI-MS m/z: 621.1 [M+H]$^+$.

Example 60

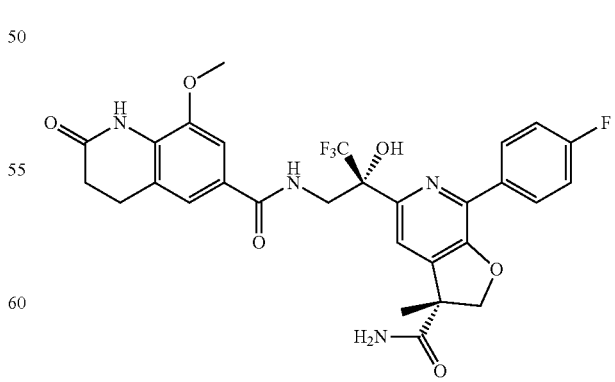

The title compound was synthesized according to Method G using 20 mg of the compound from example 59 step c above, (1.0 equiv) and 1.0 equiv. of respective acid for 1.5 hrs. The crude reaction was purified by automated column chromatography (silica gel, 0-10% methanol in dichloromethane) and lyophilized to give the title compound as a white, fluffy solid (19.6 mg, 72%). ESI-MS m/z: 603.1 [M+H]⁺.

Example 61

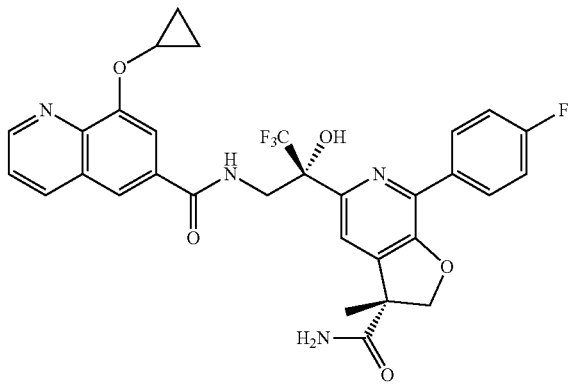

The title compound was synthesized according to Method G using 20 mg of the compound from example 59 step c above, (1.0 equiv) and 1.0 equiv. of respective acid for 1.5 hrs. The crude reaction was purified by automated column chromatography (silica gel, 0-20% methanol in dichloromethane) and lyophilized to give the title compound as a white, fluffy solid (20.9 mg, 76%). ESI-MS m/z: 611.1 [M+H]⁺.

Example 62

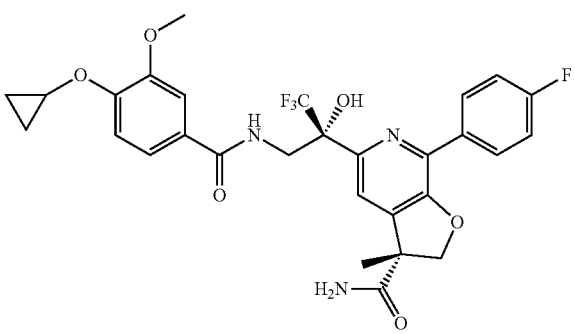 [SMILES: COc1cc(C(=O)NC[C@](O)(c2cc3c(c(-c4ccc(F)cc4)n2)OC[C@]3(C)C(N)=O)C(F)(F)F)ccc1OC1CC1]

The title compound was synthesized according to Method G using 23 mg of the compound from example 59 step c above, (1.0 equiv) and 1.0 equiv. of respective acid for 1.5 hrs. The crude reaction was purified by automated column chromatography (silica gel, 0-100% ethyl acetate in hexanes) and lyophilized to give the title compound as a white, fluffy solid (16.0 mg, 52%). ESI-MS m/z: 590.0 [M+H]⁺.

Example 63

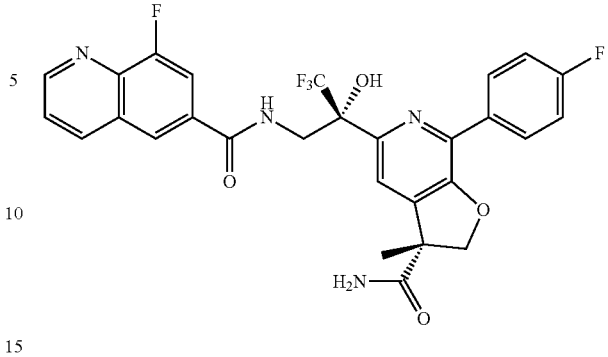

The title compound was synthesized according to Method G using 20 mg of the compound from example 59 step c above, (1.0 equiv) and 1.0 equiv of respective acid for 1.5 hrs. The crude reaction was purified by automated column chromatography (silica gel, 0-10% methanol in dichloromethane) and lyophilized to give the title compound as a white, fluffy solid (10.5 mg, 41%). ESI-MS m/z: 572.9 [M+H]⁺.

Example 64

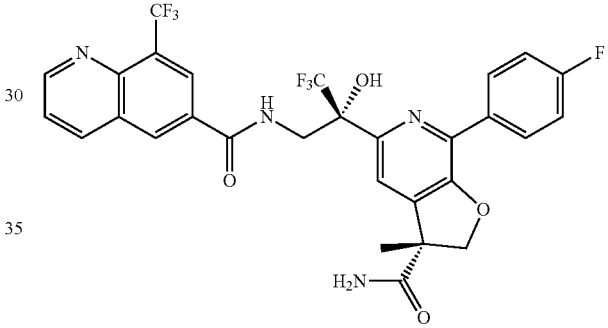

The title compound was synthesized according to Method G using 20 mg of the compound from example 59 step c above, (1.0 equiv) and 1.0 equiv of respective acid for 1.5 hrs. The crude reaction was purified by prep-HPLC (20-90% MeCN/H₂O, 25 min) and lyophilized to give the title compound as a white, fluffy solid (6.3 mg, 22%). ESI-MS m/z: 622.9 [M+H]⁺.

Example 65

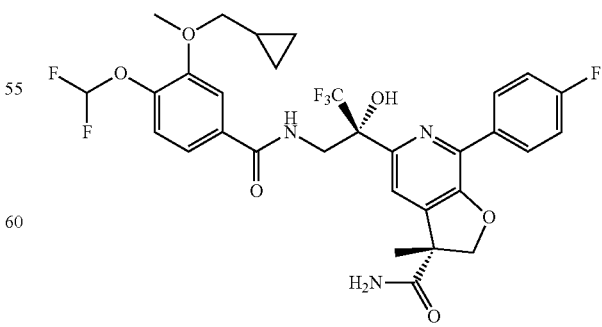

The title compound was synthesized according to Method G using 20 mg of the compound from example 59 step c above, (1.0 equiv) and 1.0 equiv of respective acid for 1.5 hrs. The crude reaction was purified by prep-HPLC (20-90% MeCN/H₂O, 25 min) and lyophilized to give the title compound as a white, fluffy solid (10.9 mg, 38%). ESI-MS m/z: 640.0 [M+H]⁺.

Example 66

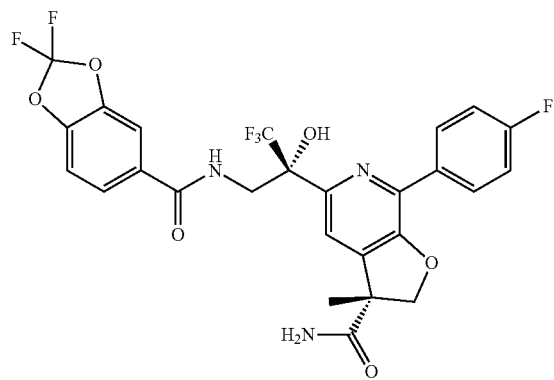 [SMILES: C[C@]1(C(N)=O)COc2c1cc([C@@](O)(CNC(=O)c1ccc3c(c1)OC(F)(F)O3)C(F)(F)F)nc2-c1ccc(F)cc1]

The title compound was synthesized according to Method G using 20 mg of the compound from example 59 step c above, (1.0 equiv) and 1.0 equiv. of respective acid for 1.5 hrs. The crude reaction was purified by prep-HPLC (20-90% MeCN/H₂O, 25 min) and lyophilized to give the title compound as a white, fluffy solid (9.3 mg, 35%). ESI-MS m/z: 583.9 [M+H]⁺.

Example 67

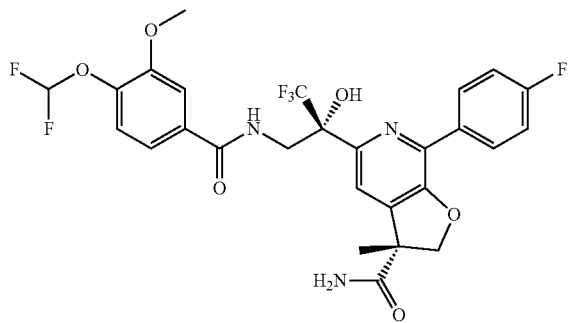 [SMILES: COc1cc(C(=O)NC[C@](O)(c2cc3c(c(-c4ccc(F)cc4)n2)OC[C@]3(C)C(N)=O)C(F)(F)F)ccc1OC(F)F]

The title compound was synthesized according to Method G using 20 mg of the compound from example 59 step c above, (1.0 equiv) and 1.0 equiv. of respective acid for 1.5 hrs. The crude reaction was purified by prep-HPLC (20-90% MeCN/H₂O, 25 min) and lyophilized to give the title compound as a white, fluffy solid (11.3 mg, 34%). ESI-MS m/z: 600.0 [M+H]⁺.

Example 68

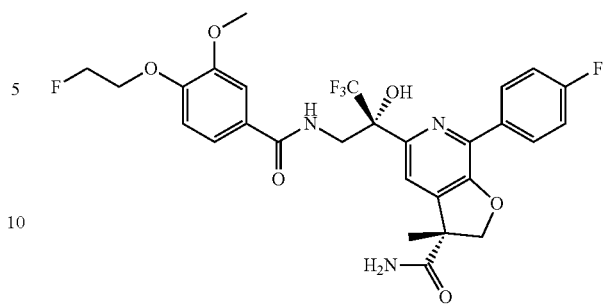

The title compound was synthesized according to Method G using 25 mg of the compound from example 59 step c above, (1.0 equiv) and 1.0 equiv. of respective acid for 1.5 hrs. The crude reaction was purified by prep-HPLC (20-90% MeCN/H₂O, 25 min) and lyophilized to give the title compound as a white, fluffy solid (10.4 mg, 31%). ESI-MS m/z: 596.0 [M+H]⁺.

Example 69

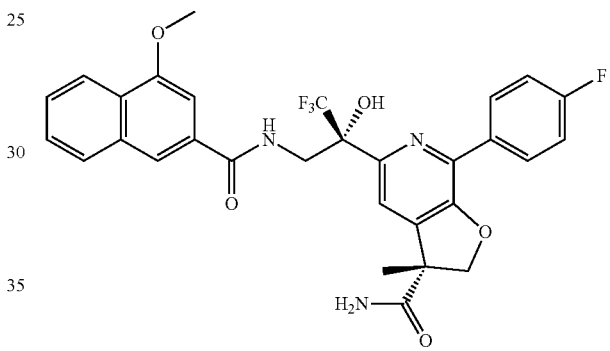

The title compound was synthesized according to Method G using 25 mg of the compound from example 59 step c above, (1.0 equiv) and 1.0 equiv. of respective acid for 1.5 hrs. The crude reaction was purified by prep-HPLC (20-90% MeCN/H₂O, 25 min) and lyophilized to give the title compound as a white, fluffy solid (10.0 mg, 31%). ESI-MS m/z: 584.1 [M+H]⁺.

Example 70

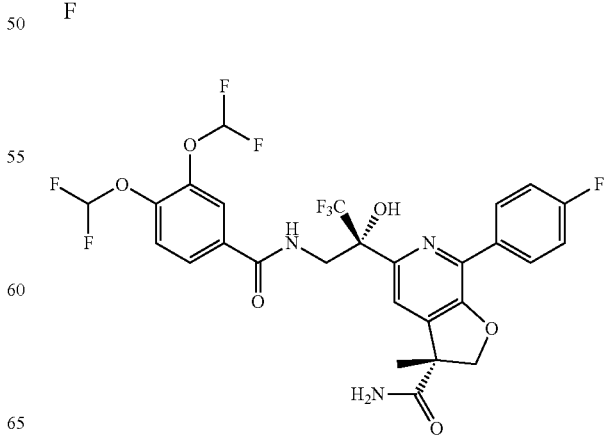

The title compound was synthesized according to Method G using 20 mg of the compound from example 59 step c above, (1.0 equiv) and 1.0 equiv. of respective acid for 1.5 hrs. The crude reaction was purified by automated column chromatography (silica gel) and lyophilized to give the title compound as a white, fluffy solid (10.5 mg, 31%). ESI-MS m/z: 636.2 [M+H]⁺.

Example 71

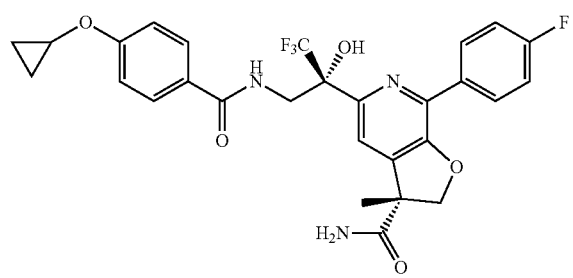 [SMILES: C[C@]1(C(N)=O)COc2c1cc([C@@](O)(CNC(=O)c1ccc(OC3CC3)cc1)C(F)(F)F)nc2-c1ccc(F)cc1]

The title compound was synthesized according to Method G using 20 mg of the compound from example 59 step c above, (1.0 equiv) and 1.0 equiv. of respective acid for 1.5 hrs. The crude reaction was purified by automated column chromatography (silica gel) and lyophilized to give the title compound as a white, fluffy solid (10.1 mg, 37%). ESI-MS m/z: 560.3 [M+H]⁺.

Example 72

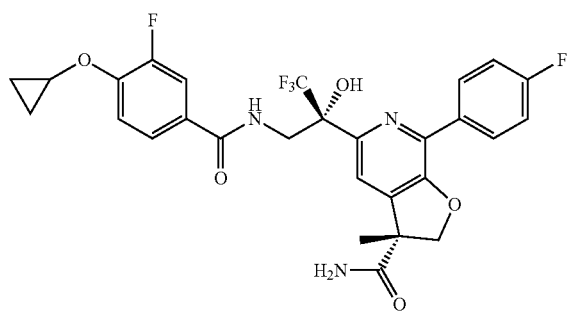 [SMILES: C[C@]1(C(N)=O)COc2c1cc([C@@](O)(CNC(=O)c1ccc(OC3CC3)c(F)c1)C(F)(F)F)nc2-c1ccc(F)cc1]

The title compound was synthesized according to Method G using 20 mg of the compound from example 59 step c above, (1.0 equiv) and 1.0 equiv. of respective acid for 1.5 hrs. The crude reaction was purified by automated column chromatography (silica gel) and lyophilized to give the title compound as a white, fluffy solid (9.8 mg, 29%). ESI-MS m/z: 578.3 [M+H]⁺.

Example 73

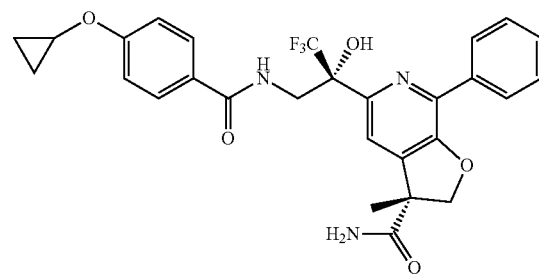

The title compound was synthesized according to Method G using 20 mg of the compound from example 59 step c above, (1.0 equiv) and 1.0 equiv. of respective acid for 1.5 hrs. The crude reaction was purified by automated column chromatography and lyophilized to give the title compound as a white, fluffy solid (8.6 mg, 25%). ESI-MS m/z: 615.2 [M+H]⁺.

Example 74

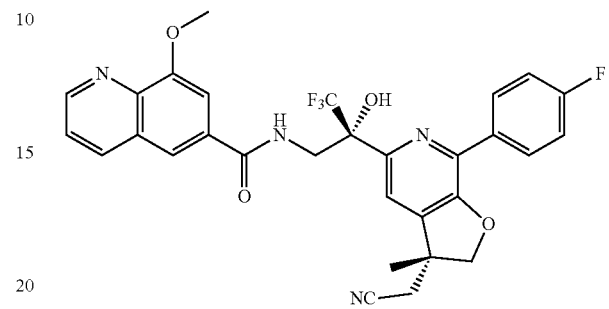

Example 74 Step a

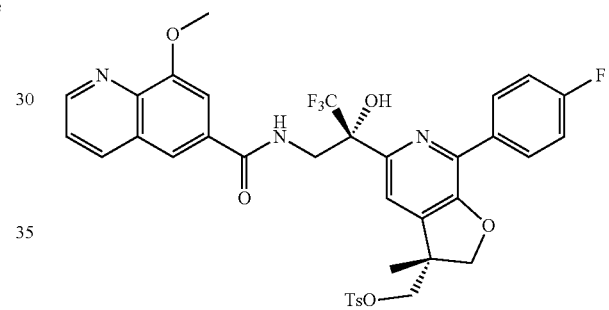

To a round flask was charged example 21 (as a single diastereomer) (200 mg, 0.35 mmol) in DMF (4 mL), then 4-methylbenzenesulfonyl chloride (70.0 mg, 0.37 mmol), N,N-dimethylpyridin-4-amine (42.8 mg, 0.35 mmol) and triethylamine (0.15 mL, 1.05 mmol) were slowly added. After the resulting mixture was stirred at room temperature for 20 hrs, it was diluted with DCM (50 mL). The mixture was washed with brine, dried and purified by automated column chromatography (silica gel, 0-3% methanol in dichloromethane) to afford the title compound (87 mg, 34%). ESI-MS m/z: 726.1 [M+H]⁺.

Example 74 Step b

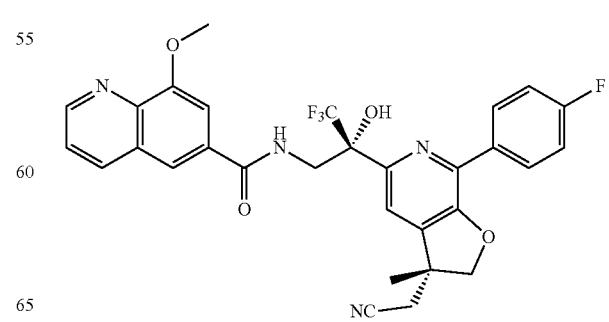

A solution of compound from Example 74 step a (80 mg, 0.11 mmol) and cyanosodium (10.80 mg, 0.22 mmol) in DMSO (2 mL) was heated in a sealed vessel at 100° C. for 12 hrs. The reaction mixture was diluted with DCM (150 mL), washed with brine (50 mL×3), dried and purified by automated column chromatography (silica gel, 0-2% methanol in dichloromethane) to afford the title compound (24 mg, 37.5%). ESI-MS m/z: 581.0 [M+H]⁺.

Example 75

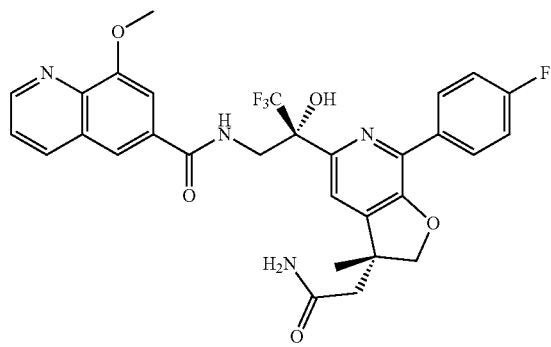 [SMILES: COc1cc(C(=O)NC[C@](O)(c2cc3c(c(-c4ccc(F)cc4)n2)OC[C@]3(C)CC(N)=O)C(F)(F)F)cc2cccnc12]

A solution of compound from Example 74 step b (20 mg, 0.034 mmol) and Ghaffar-Parkins catalyst hydrido(dimethylphosphinous acid-kP)[hydrogen bis(dimethylphosphinito-kP)]platinum(II) (2.95 mg, 6.89 µmol) in EtOH/H₂O (4:1, 1.75 mL) was heated in a sealed vessel at 85° C. for 2 hrs. After evaporating the solvents, the residue was purified by automated column chromatography (silica gel, 04% methanol in dichloromethane to afford the title compound (11 mg, 53.3%). ESI-MS m/z: 599.0 [M+H]⁺.

Example 76

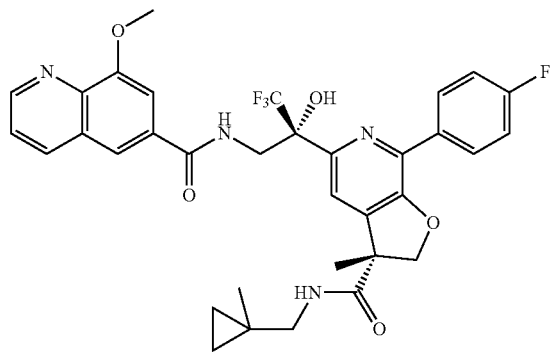 [SMILES: COc1cc(C(=O)NC[C@](O)(c2cc3c(c(-c4ccc(F)cc4)n2)OC[C@]3(C)C(=O)NCC2(C)CC2)C(F)(F)F)cc2cccnc12]

The title compound was synthesized according to Method G using 25 mg of the compound from example 26 (as a single diastereomer), 8.0 equiv of amine HCl salt, 8.0 equiv. of DIPEA for 4 hrs, then 10 equiv amine HCl salt/DIPEA and 4.0 equiv HATU for 2 hrs. The crude reaction was purified by prep-HPLC (20-90%, 25 min), and lyophilized to give the title compound as a white, fluffy solid (6.2 mg, 22%). ESI-MS m/z: 653.2 [M+H]⁺.

Example 77

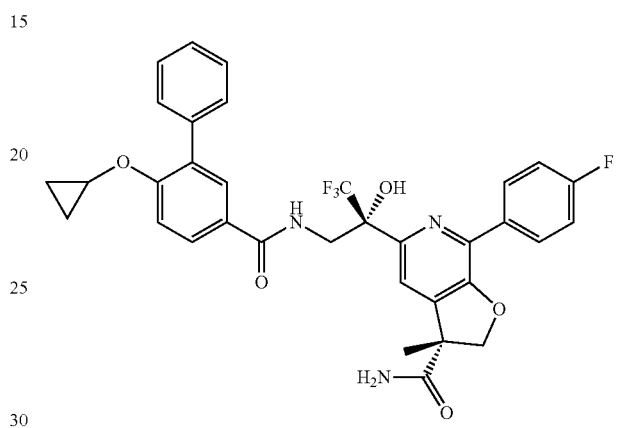

Example 77 was prepared using a procedure similar to that used to prepare example 59 from the corresponding acid in step d. ESI-MS m/z: 636.2 [M+H]⁺.

Example 78

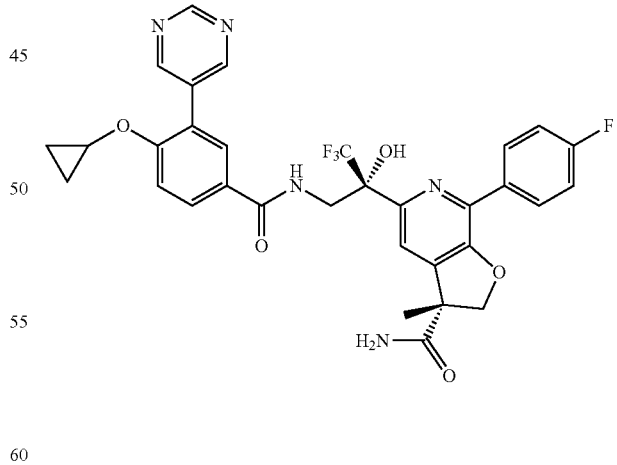

Example 78 was prepared using a procedure similar to that used to prepare example 59 from the corresponding acid in step d. ESI-MS m/z: 638.2 [M+H]⁺.

The following examples in Table 1 were made in an analogous fashion to Example 59 with the corresponding intermediates.

TABLE 1
| Example | Structure | MS+ m/z |
|---|---|---|
| 79 | 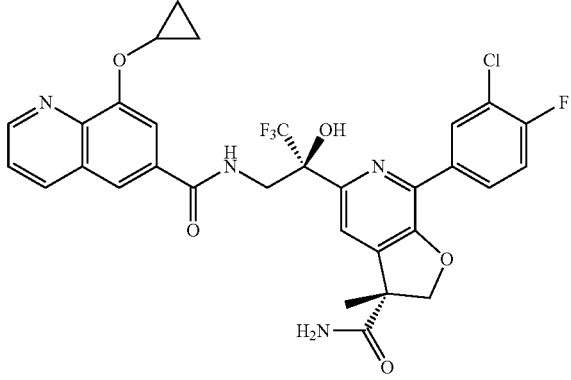 [SMILES: C[C@]1(C(N)=O)COc2c1cc([C@](O)(CNC(=O)c1cc(OC3CC3)c3ncccc3c1)C(F)(F)F)nc2-c1ccc(F)c(Cl)c1] | 645.10 |
| 80 | 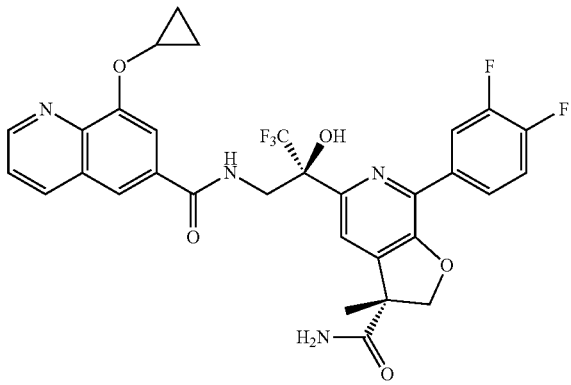 [SMILES: C[C@]1(C(N)=O)COc2c1cc([C@](O)(CNC(=O)c1cc(OC3CC3)c3ncccc3c1)C(F)(F)F)nc2-c1ccc(F)c(F)c1] | 629.10 |
| 81 | 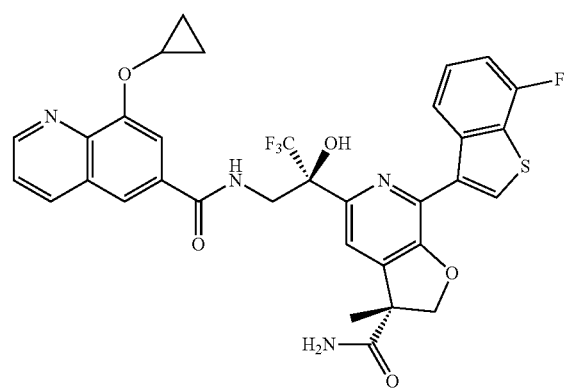 [SMILES: C[C@]1(C(N)=O)COc2c1cc([C@](O)(CNC(=O)c1cc(OC3CC3)c3ncccc3c1)C(F)(F)F)nc2-c1csc2c(F)cccc12] | 667.10 |
| 82 | 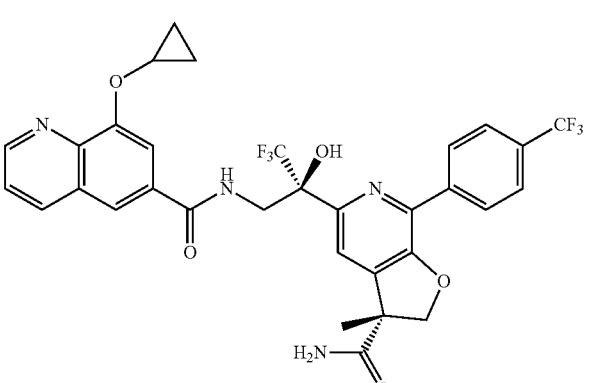 | 661.15 |

TABLE 1-continued
| Example | Structure | MS+ m/z |
|---|---|---|
| 83 | 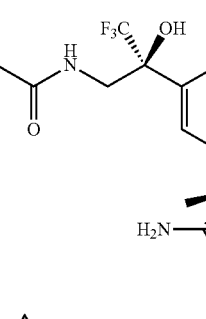 | 618.15 |
| 84 | 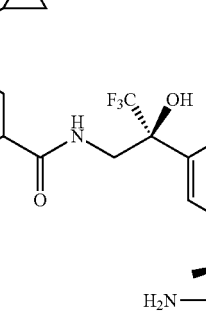 | 636.10 |
| 85 | 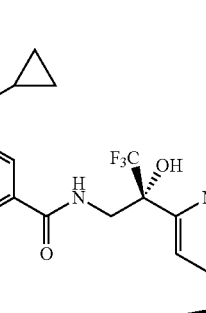 | 679.05 |
| 86 | 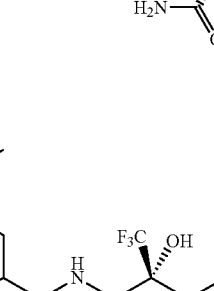 | 619.05 |

TABLE 1-continued

| Example | Structure | MS+ m/z |
|---|---|---|
| 87 | 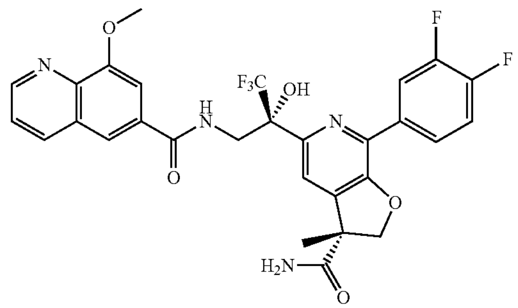 [SMILES: COc1cc(C(=O)NC[C@](O)(c2cc3c(c(-c4ccc(F)c(F)c4)n2)OC[C@]3(C)C(N)=O)C(F)(F)F)cc2cccnc12] | 603.10 |
| 88 | 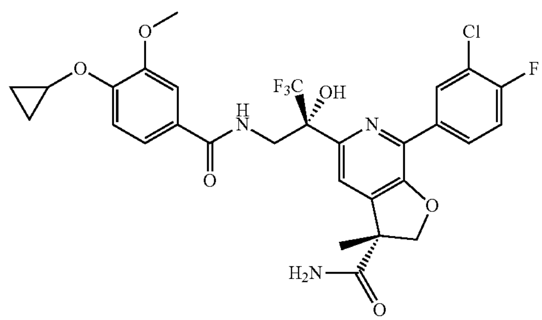 [SMILES: COc1cc(C(=O)NC[C@](O)(c2cc3c(c(-c4ccc(F)c(Cl)c4)n2)OC[C@]3(C)C(N)=O)C(F)(F)F)ccc1OC1CC1] | 624.05 |
| 89 | 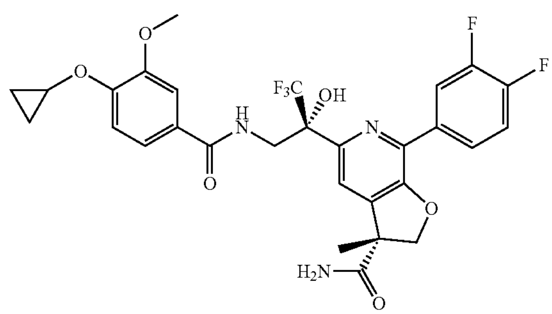 [SMILES: COc1cc(C(=O)NC[C@](O)(c2cc3c(c(-c4ccc(F)c(F)c4)n2)OC[C@]3(C)C(N)=O)C(F)(F)F)ccc1OC1CC1] | 608.10 |
| 90 | 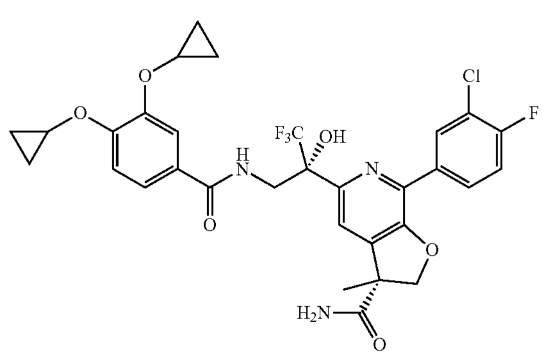 [SMILES: C[C@]1(C(N)=O)COc2c1cc([C@@](O)(CNC(=O)c1ccc(OC3CC3)c(OC3CC3)c1)C(F)(F)F)nc2-c1ccc(F)c(Cl)c1] | 650.20 |

TABLE 1-continued
| Example | Structure | MS+ m/z |
|---|---|---|
| 91 | 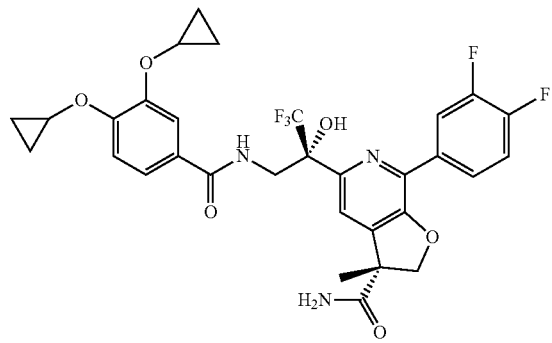 [SMILES: C[C@]1(C(N)=O)COc2c1cc([C@@](O)(CNC(=O)c1ccc(OC3CC3)c(OC3CC3)c1)C(F)(F)F)nc2-c1ccc(F)c(F)c1] | 634.20 |
| 92 | 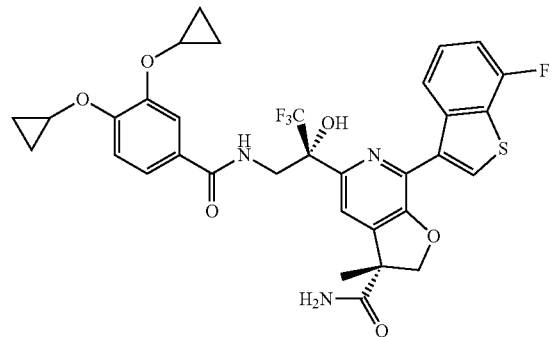 [SMILES: C[C@]1(C(N)=O)COc2c1cc([C@@](O)(CNC(=O)c1ccc(OC3CC3)c(OC3CC3)c1)C(F)(F)F)nc2-c1csc2c(F)cccc12] | 672.15 |
| 93 | 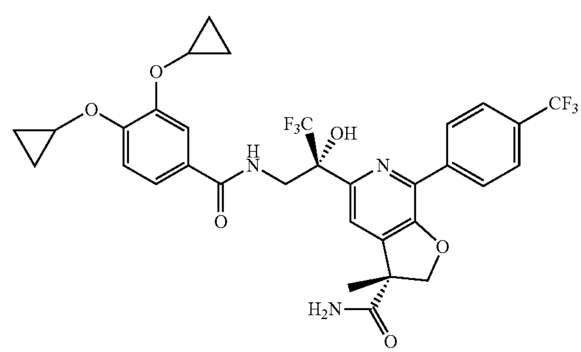 [SMILES: C[C@]1(C(N)=O)COc2c1cc([C@@](O)(CNC(=O)c1ccc(OC3CC3)c(OC3CC3)c1)C(F)(F)F)nc2-c1ccc(C(F)(F)F)cc1] | 666.20 |
| 94 | 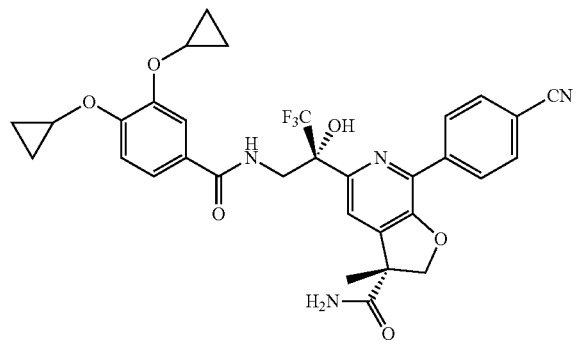 [SMILES: C[C@]1(C(N)=O)COc2c1cc([C@@](O)(CNC(=O)c1ccc(OC3CC3)c(OC3CC3)c1)C(F)(F)F)nc2-c1ccc(C#N)cc1] | 623.15 |

TABLE 1-continued
| Example | Structure | MS+ m/z |
|---|---|---|
| 95 | 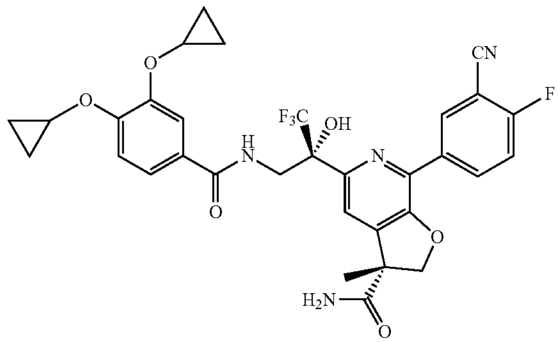 [SMILES: C[C@]1(C(N)=O)COc2c1cc([C@@](O)(CNC(=O)c1ccc(OC3CC3)c(OC3CC3)c1)C(F)(F)F)nc2-c1ccc(F)c(C#N)c1] | 641.10 |
| 96 | 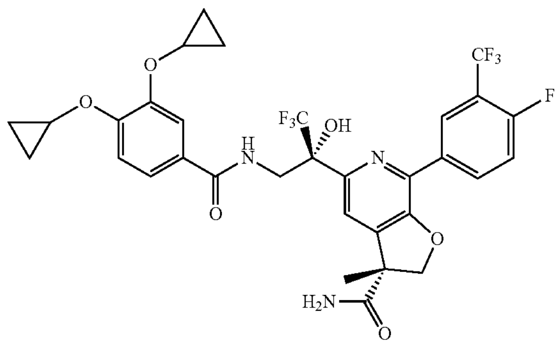 [SMILES: C[C@]1(C(N)=O)COc2c1cc([C@@](O)(CNC(=O)c1ccc(OC3CC3)c(OC3CC3)c1)C(F)(F)F)nc2-c1ccc(F)c(C(F)(F)F)c1] | 684.10 |
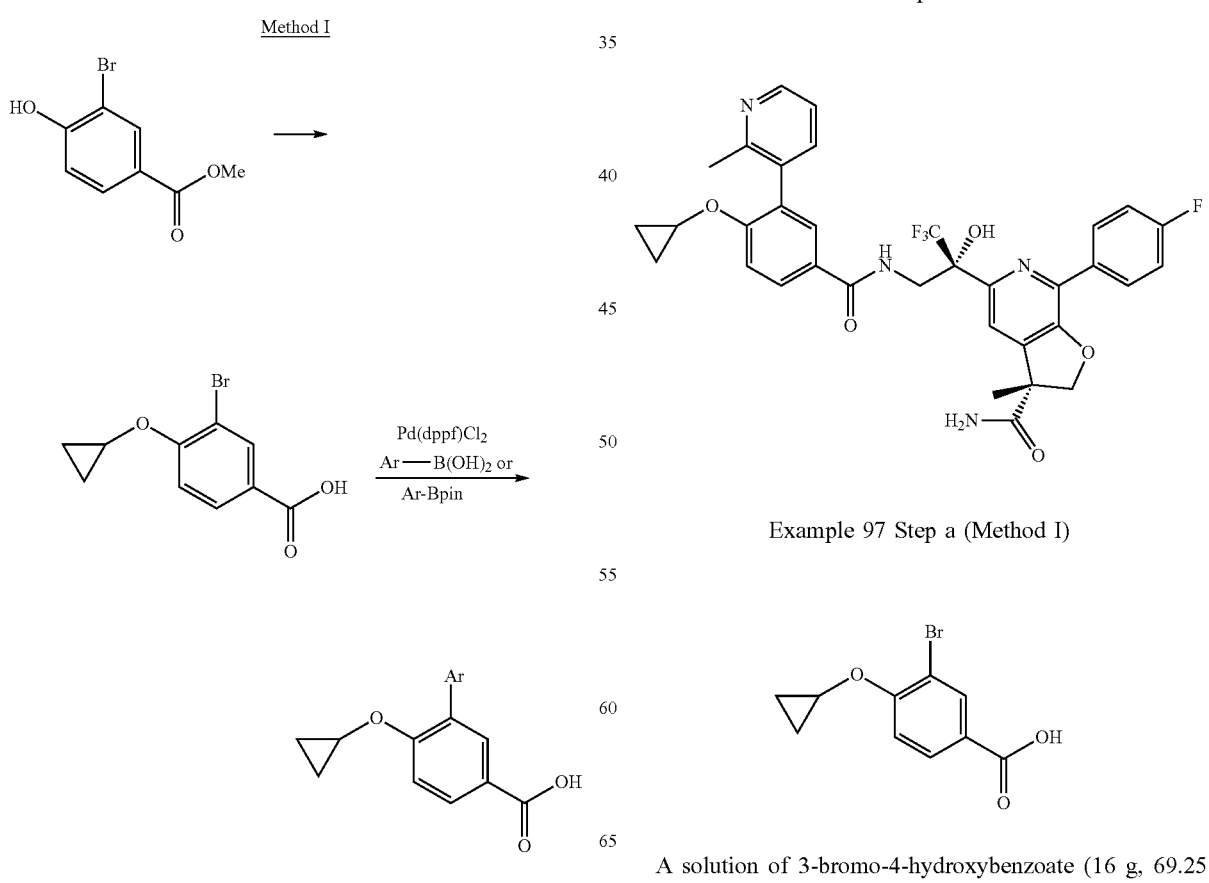
Example 97
Example 97 Step a (Method I)
A solution of 3-bromo-4-hydroxybenzoate (16 g, 69.25 mmol), $Cs_2CO_3$ (68 g, 207.75 mmol), KI (46 g, 277.00 mmol) and bromocyclopropane (21 g, 173.12 mmol) in NMP (30 mL) was stirred for 16 hours at 180° C. in a Parr reactor. The resulting solution was diluted with water and extracted with EtOAC. The combined organics were dried and concentrated. The resulting solution was purified by reverse phase C18 column chromatography (CH₃CN/H₂O) to afford desired product as a yellow solid (3 g, 22%). ESI-MS m/z: 257.05 [M+H]⁺. (Methyl ester product was also isolated and used)

Example 97 Step b (Method I)

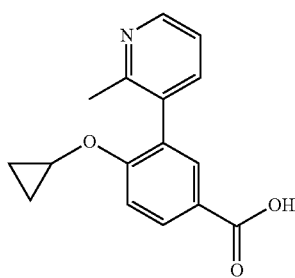 [SMILES: Cc1ncccc1-c1cc(C(=O)O)ccc1OC1CC1]

A solution of the compound from step a (250 mg, 0.98 mmol), Pd(dppf)Cl₂ (142 mg, 0.19 mmol), 2-methyl-3-(4,4,5,5-tetramethyl-1,3,2-dioxaborolan-2-yl)pyridine (425 mg, 1.94 mmol), H₂O (0.1 mL) and Cs₂CO₃ (950 mg, 2.91 mmol) in dioxane (3 mL) was stirred for 2 hours at 90° C. under N₂ atmosphere. The resulting solution was purified by reverse phase C18 column chromatography (MeOH/0.1% FA in H₂O) to afford the desired product as a white solid (180 mg, 68%). ESI-MS m/z: 270.15 [M+H]⁺.

Example 97 Step c (Method J)

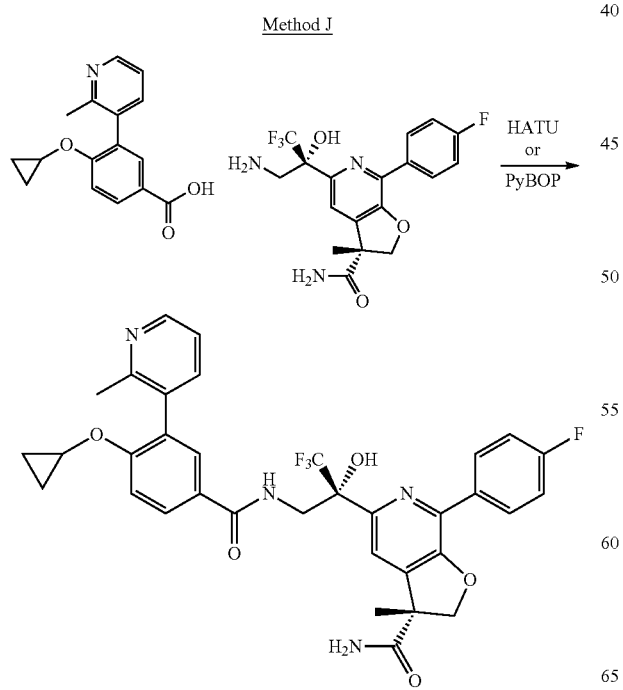

To a 2-dram vial equipped with a stir bar was added amine (30 mg, 0.075 mmol), acid (19.18 mg, 0.075 mmol), and the material was dissolved in DMF (0.2 M). Hunig's base (0.053 mL, 0.30 mmol) was added and the vial was cooled to 0° C. HATU (43 mg, 0.113 mmol) was added, the reaction stirred for 10 minutes, warmed to room temperature and monitored by LCMS (1 hr). The reaction was diluted with EtOAc and quenched with water. The aqueous was extracted with EtOAc and DCM/MeOH with a phase separator cartridge and concentrated. The material was purified by prep-HPLC 20-90%, MeCN/Water, 25 min to afford the title compound as a white solid (23.6 mg, 48%). ESI-MS m/z: 651.25 [M+H]⁺.

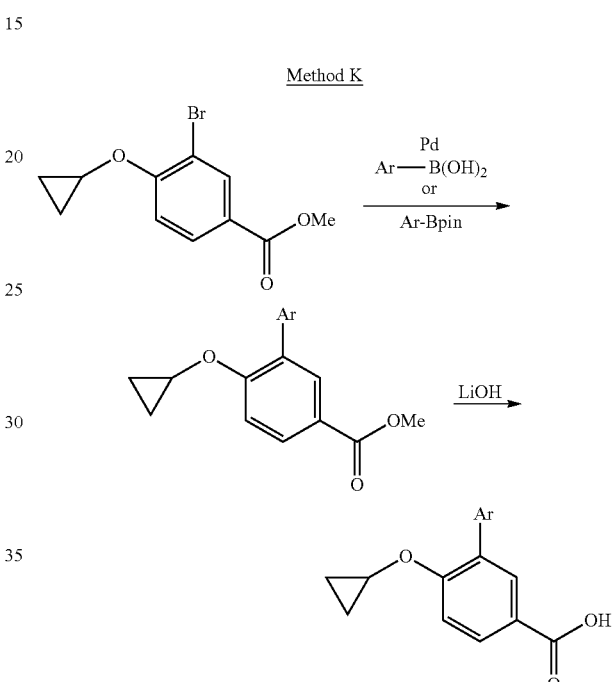

Example 98 Step a (Method K)

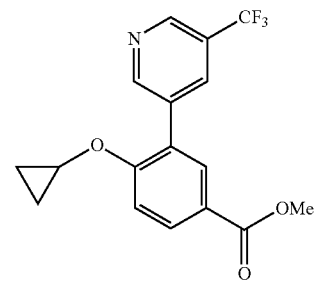 [SMILES: COC(=O)c1ccc(OC2CC2)c(-c2cncc(C(F)(F)F)c2)c1]

The following example was made in analogous fashion to Method I step a with 3-(4,4,5,5-tetramethyl-1,3,2-dioxaborolan-2-yl)-5-(trifluoromethyl)pyridine and methyl 3-bromo-4-cyclopropoxybenzoate. The material was purified by automated column chromatography (silica gel, 0-100% EtOAc in hexanes) to afford the title compound. ESI-MS m/z: 338.10 [M+H]⁺.

Example 98 Step b (Method K)

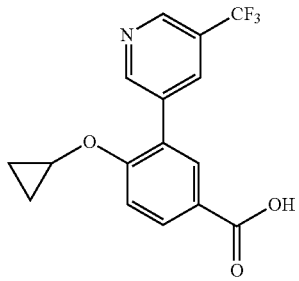 [SMILES: O=C(O)c1ccc(OC2CC2)c(-c2cncc(C(F)(F)F)c2)c1]

A solution of the compound from step a (crude), LiOH (300 mg, 12.52 mmol) and H₂O (1 mL) in MeOH (3 mL) was stirred for 16 hours at room temperature. The resulting solution was purified by reverse phase C18 column chromatography (MeOH/0.10% FA in H2O) to afford desired product as a white solid (228 mg). ESI-MS m/z: 256.10 [M+H]⁺.

Method L

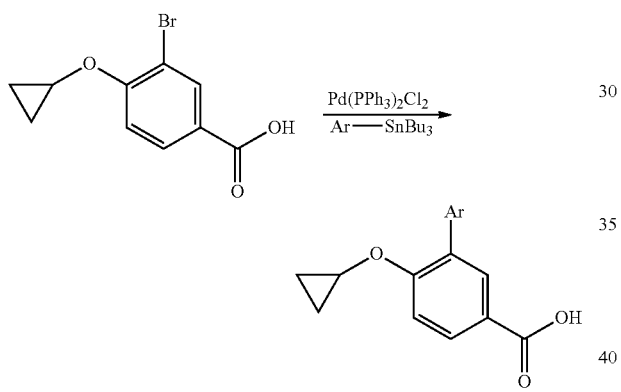

Example 99 (Method L)

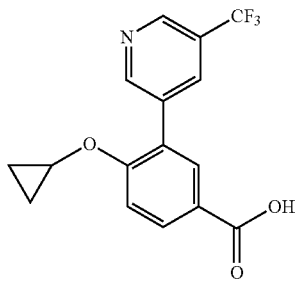 [SMILES: O=C(O)c1ccc(OC2CC2)c(-c2cncc(C(F)(F)F)c2)c1]

A solution of the compound from example 97 step a bromide (250 mg, 0.98 mmol), 2-(tributylstannyl)pyridine (537 mg, 1.46 mmol) and Pd(PPh₃)₂Cl₂ (68 mg, 0.09 mmol) in DMF (3 mL) was stirred for 2 hours at 90° C. under N₂ atmosphere. The resulting solution was purified by reverse phase C18 column chromatography (MeOH/0.1% FA in H2O) to afford desired product as a white solid (90.6 mg, 37%). ESI-MS m/z: 256.15 [M+H]⁺.

Method M

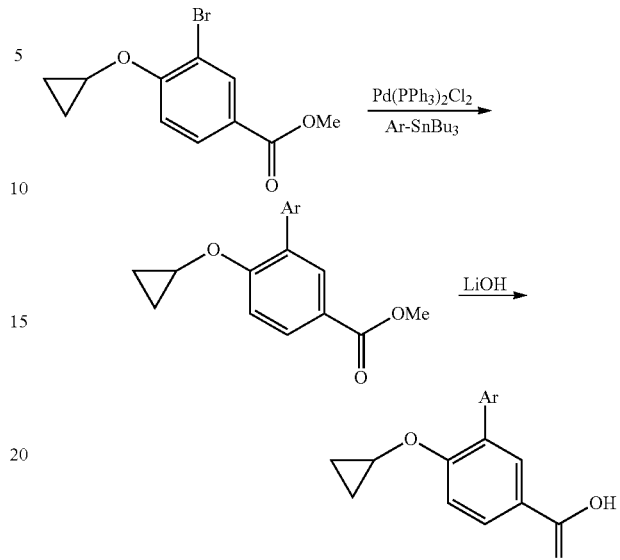

Example 100 Steps a and b (Method M)

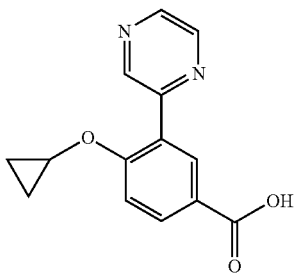 [SMILES: O=C(O)c1ccc(OC2CC2)c(-c2cnccn2)c1]

A solution of the methyl 3-bromo-4-cyclopropoxybenzoate (300 mg, 1.11 mmol), 2-(tributylstannyl)pyrazine (615 mg, 1.66 mmol) and Pd(PPh₃)₂Cl₂ (68 mg, 0.09 mmol) in DMF (3 mL) was stirred for 2 hours at 90° C. under N₂ atmosphere. The resulting solution was purified by silica gel column chromatography (EtOAc in hexanes) to afford desired product as a white solid. ESI-MS m/z: 271.00 [M+H]⁺.

The methyl ester was hydrolyzed in an analogous fashion to Method K, and the crude solution was purified by reverse phase C18 column chromatography (MeOH/0.1% FA in H2O) to afford desired product as a white solid (100 mg, 35%) ESI-MS m/z: 257.05 [M+H]⁺.

Method N

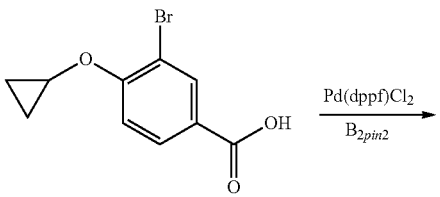

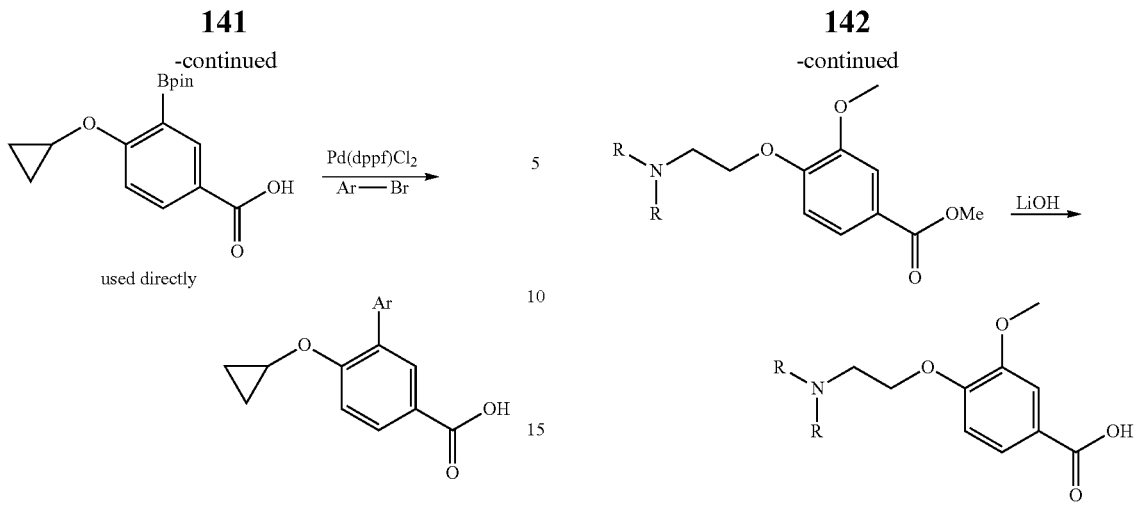

Example 101 Steps a and b (Method N)

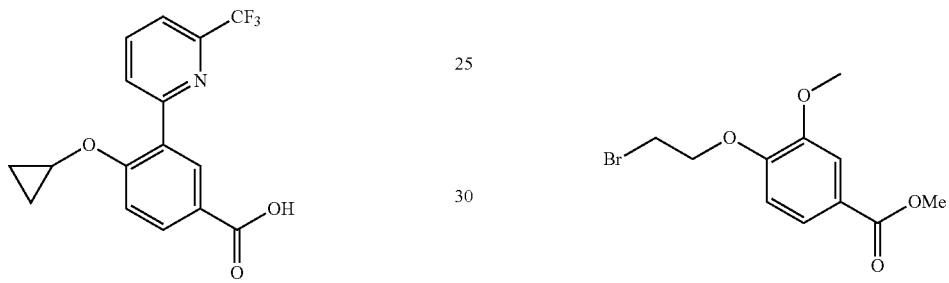

A solution of the 3-bromo-4-cyclopropoxybenzoic acid (1 g, 3.9 mmol), bis(pinacolato)diboron (2 g, 7.78 mmol), KOAc (1.2 g, 11.67 mmol) and Pd(dppf)Cl$_2$(DCM) (635 mg, 0.78 mmol) in dioxane (6 mL) was stirred for 2 hours at 90° C. ESI-MS m/z: 223.05 [M+H]$^+$. A solution of the compound from step a (2 mL), 2-bromo-6-(trifluoromethyl) pyridine (611 mg, 2.70 mmol), Cs$_2$CO$_3$ (1.3 g, 4.05 mmol), H$_2$O (0.1 mL) and Pd(dppf)Cl$_2$ (221 mg, 0.27 mmol) in dioxane (3 mL) was stirred for 2 hours at 90° C. under N$_2$ atmosphere. The resulting solution was purified by reverse phase C18 column chromatography (MeOH/0.10% FA in H2O) to afford desired product as a white solid (130 mg). ESI-MS m/z: 256.10 [M+H]$^+$.

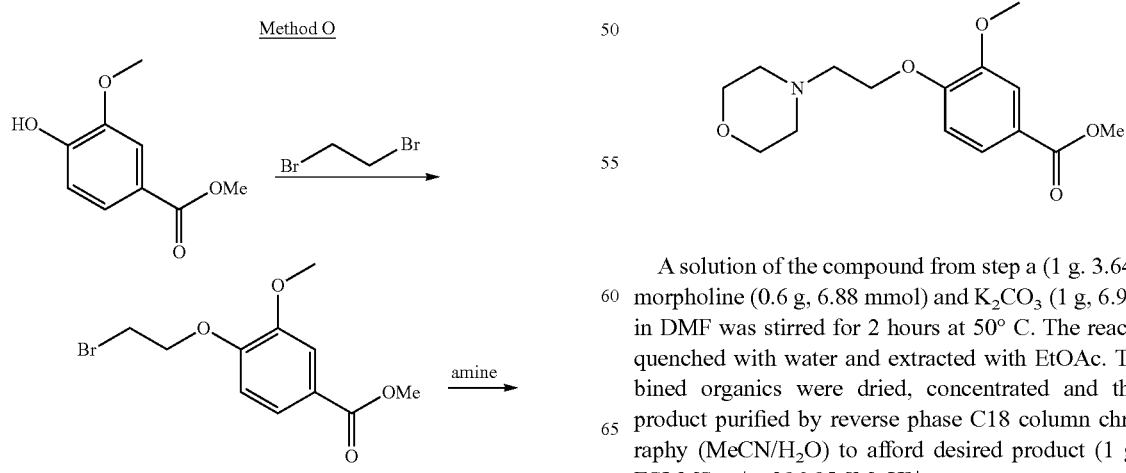

Example 102 Step a (Method O)

A solution of methyl 4-hydroxy-3-methoxybenzoate (3 g, 16.47 mmol), K$_2$CO$_3$ (6.8 g, 49.57 mmol), 1,2-dibromoethane (15.5 g, 82.34 mmol) in DMF (30 mL) was stirred for 2 hours at 45° C. The resulting solution was quenched with water and extracted with EtOAc. The combined organics were dried, concentrated and purified by reverse phase C18 column chromatography (MeCN/H$_2$O) to afford desired product as a light-yellow solid (3 g, 61%).

Example 102 Step b (Method O)

A solution of the compound from step a (1 g. 3.64 mmol), morpholine (0.6 g, 6.88 mmol) and K$_2$CO$_3$ (1 g, 6.95 mmol) in DMF was stirred for 2 hours at 50° C. The reaction was quenched with water and extracted with EtOAc. The combined organics were dried, concentrated and the crude product purified by reverse phase C18 column chromatography (MeCN/H$_2$O) to afford desired product (1 g, 93%). ESI-MS m/z: 296.05 [M+H]$^+$.

Example 102 Step c (Method O)

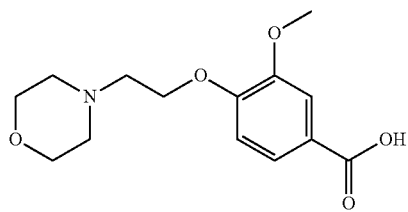 [SMILES: COc1cc(C(=O)O)ccc1OCCN1CCOCC1]

A solution of the compound from step b (1 g, 3.55 mmol) and LiOH (0.8 g, 33.76 mmol) in MeOH:H$_2$O (2:1, 60 mL) was stirred for 2 hours at room temperature. The pH of the resulting solution was adjusted to pH=6 with HCl(aq) and extracted with EtOAc. The combined organics were dried, concentrated and the crude product was purified by reverse phase C18 column chromatography (MeCN/H$_2$O, 100 FA) to afford desired product as a white solid (1 g, 990%). ESM-MS m/z: 282.05 [M+H]$^+$.

The following examples in Table 2 were made in an analogous fashion to Method J with the corresponding acid intermediates, and the compounds were purified by prep-HPLC. The corresponding acid precursors were synthesized by the previously described methods (Method I, Methods K-O).

TABLE 2

| Example | Structure | MS$^+$ m/z |
|---|---|---|
| 103 | 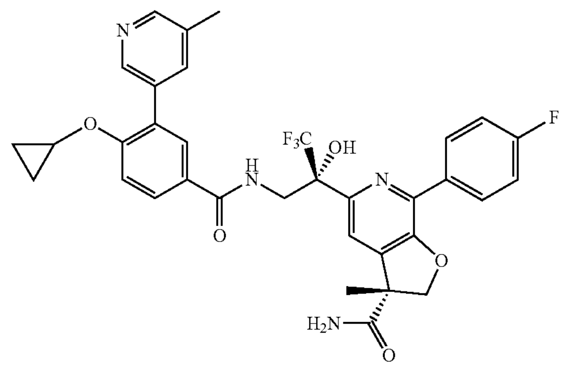 [SMILES: Cc1cncc(-c2cc(C(=O)NC[C@](O)(c3cc4c(c(-c5ccc(F)cc5)n3)OC[C@]4(C)C(N)=O)C(F)(F)F)ccc2OC2CC2)c1] | 651.25 |
| 104 | 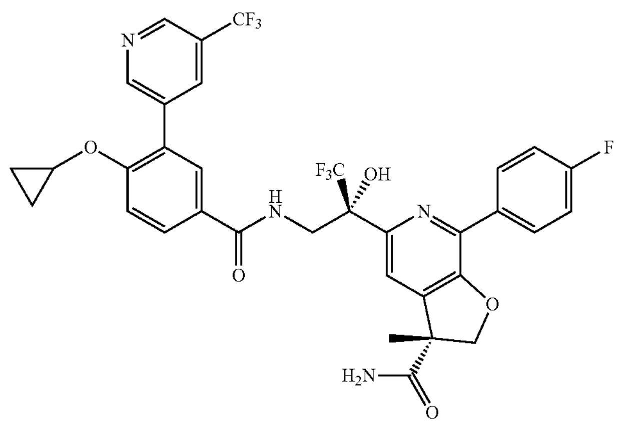 [SMILES: C[C@]1(C(N)=O)COc2c1cc([C@@](O)(CNC(=O)c1ccc(OC3CC3)c(-c3cncc(C(F)(F)F)c3)c1)C(F)(F)F)nc2-c1ccc(F)cc1] | 705.20 |
| 105 | 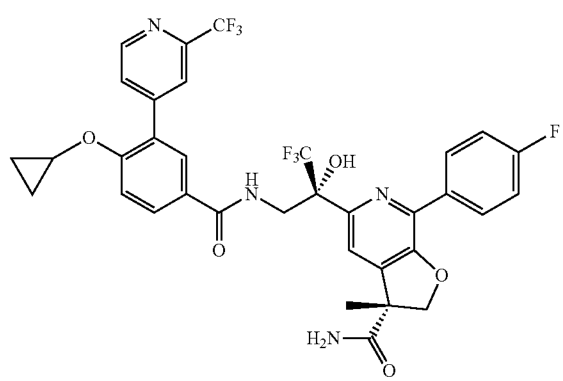 [SMILES: C[C@]1(C(N)=O)COc2c1cc([C@@](O)(CNC(=O)c1ccc(OC3CC3)c(-c3ccnc(C(F)(F)F)c3)c1)C(F)(F)F)nc2-c1ccc(F)cc1] | 705.20 |

TABLE 2-continued

| Example | Structure | MS+ m/z |
|---------|-----------|---------|
| 106 | 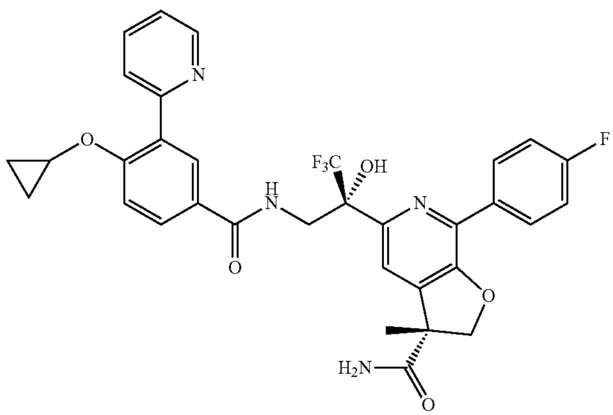 | 637.20 |
| 107 | 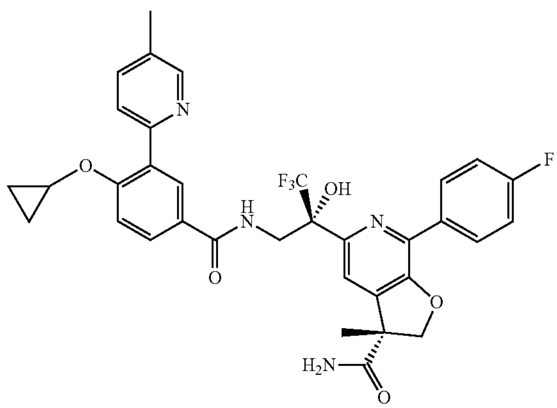 [SMILES: Cc1ccc(-c2cc(C(=O)NC[C@](O)(c3cc4c(c(-c5ccc(F)cc5)n3)OC[C@]4(C)C(N)=O)C(F)(F)F)ccc2OC2CC2)nc1] | 651.20 |
| 108 | 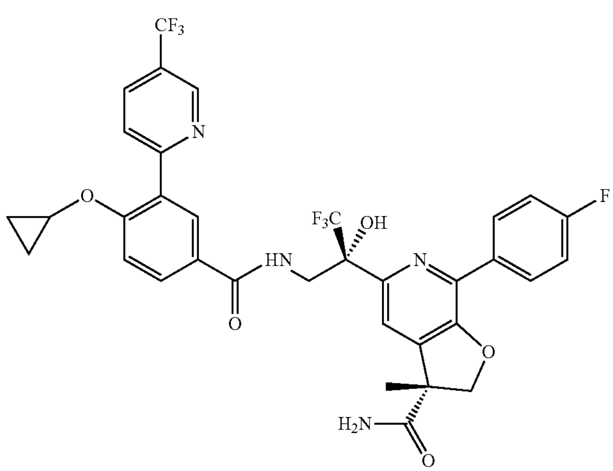 [SMILES: C[C@]1(C(N)=O)COc2c1cc([C@@](O)(CNC(=O)c1ccc(OC3CC3)c(-c3ccc(C(F)(F)F)cn3)c1)C(F)(F)F)nc2-c1ccc(F)cc1] | 705.20 |

TABLE 2-continued

| Example | Structure | MS+ m/z |
|---|---|---|
| 109 | 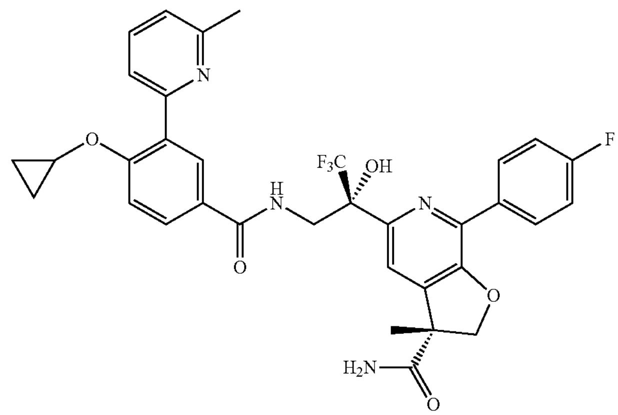 [SMILES: Cc1cccc(-c2cc(C(=O)NC[C@](O)(c3cc4c(c(-c5ccc(F)cc5)n3)OC[C@]4(C)C(N)=O)C(F)(F)F)ccc2OC2CC2)n1] | 651.20 |
| 110 | 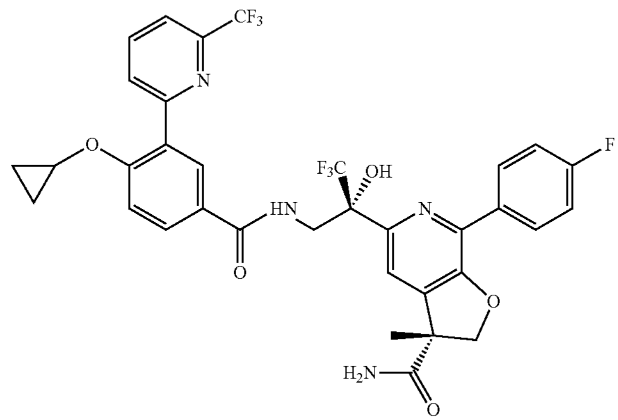 [SMILES: C[C@]1(C(N)=O)COc2c1cc([C@@](O)(CNC(=O)c1ccc(OC3CC3)c(-c3cccc(C(F)(F)F)n3)c1)C(F)(F)F)nc2-c1ccc(F)cc1] | 705.20 |
| 111 | 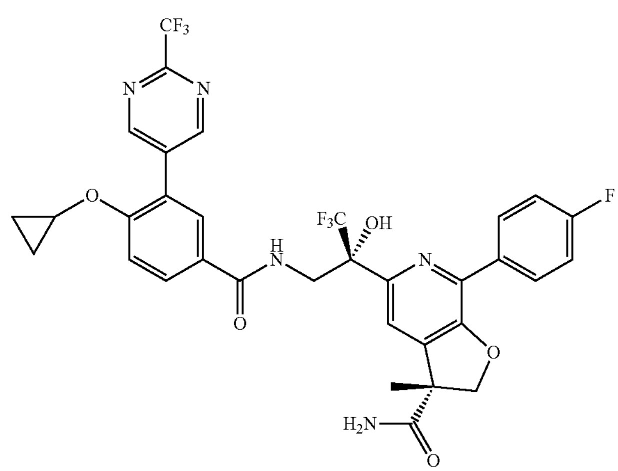 [SMILES: C[C@]1(C(N)=O)COc2c1cc([C@@](O)(CNC(=O)c1ccc(OC3CC3)c(-c3cnc(C(F)(F)F)nc3)c1)C(F)(F)F)nc2-c1ccc(F)cc1] | 706.20 |

TABLE 2-continued
| Example | Structure | MS+ m/z |
|---------|-----------|---------|
| 112 | 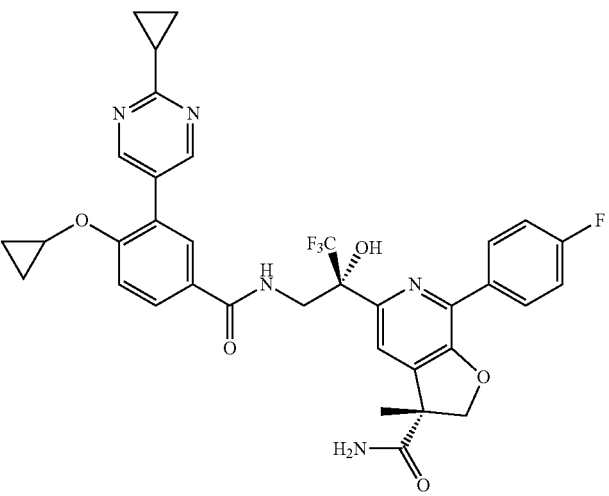 [SMILES: C[C@]1(C(N)=O)COc2c1cc([C@@](O)(CNC(=O)c1ccc(OC3CC3)c(-c3cnc(C4CC4)nc3)c1)C(F)(F)F)nc2-c1ccc(F)cc1] | 678.20 |
| 113 | 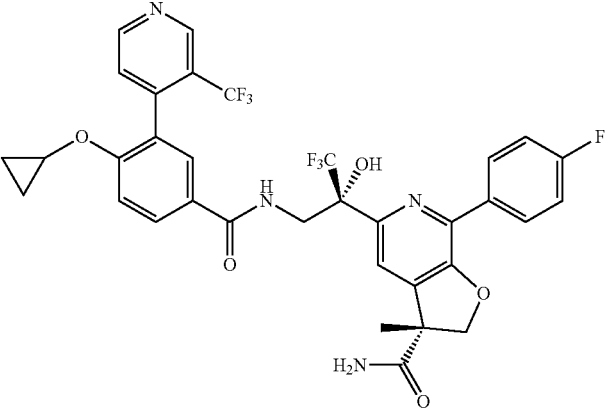 [SMILES: C[C@]1(C(N)=O)COc2c1cc([C@@](O)(CNC(=O)c1ccc(OC3CC3)c(-c3ccncc3C(F)(F)F)c1)C(F)(F)F)nc2-c1ccc(F)cc1] | 705.35 |
| 114 | 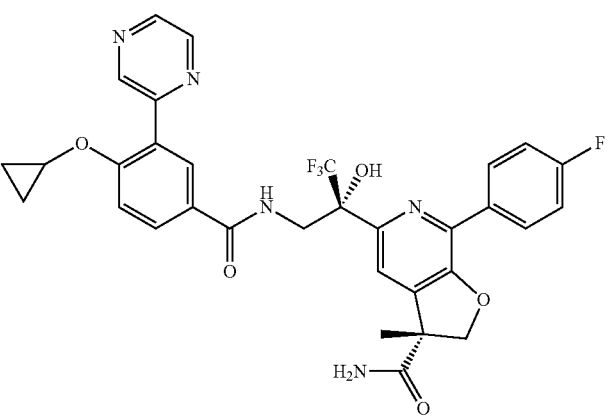 | 638.40 |

TABLE 2-continued

| Example | Structure | MS+ m/z |
|---------|-----------|---------|
| 115 | 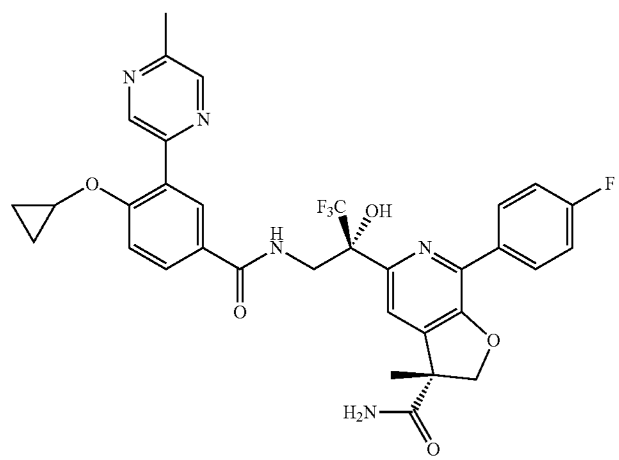 [SMILES: Cc1cnc(-c2cc(C(=O)NC[C@](O)(c3cc4c(c(-c5ccc(F)cc5)n3)OC[C@]4(C)C(N)=O)C(F)(F)F)ccc2OC2CC2)cn1] | 652.40 |
| 116 | 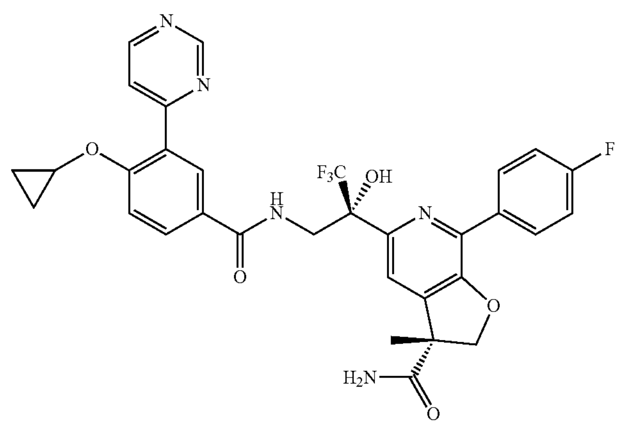 [SMILES: C[C@]1(C(N)=O)COc2c1cc([C@@](O)(CNC(=O)c1ccc(OC3CC3)c(-c3ccncn3)c1)C(F)(F)F)nc2-c1ccc(F)cc1] | 638.40 |
| 117 | 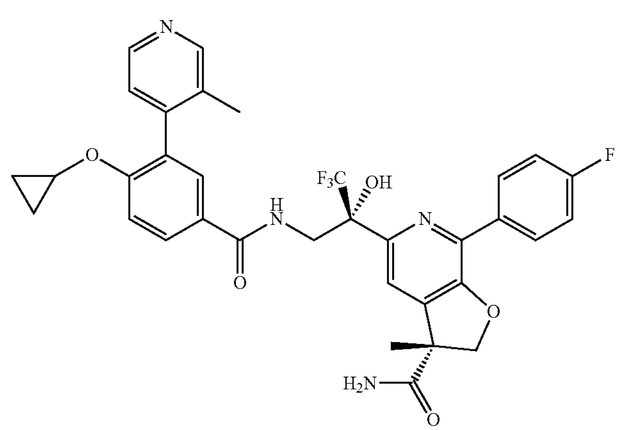 [SMILES: Cc1cnccc1-c1cc(C(=O)NC[C@](O)(c2cc3c(c(-c4ccc(F)cc4)n2)OC[C@]3(C)C(N)=O)C(F)(F)F)ccc1OC1CC1] | 651.37 |

TABLE 2-continued
| Example | Structure | MS+ m/z |
|---------|-----------|---------|
| 118 | 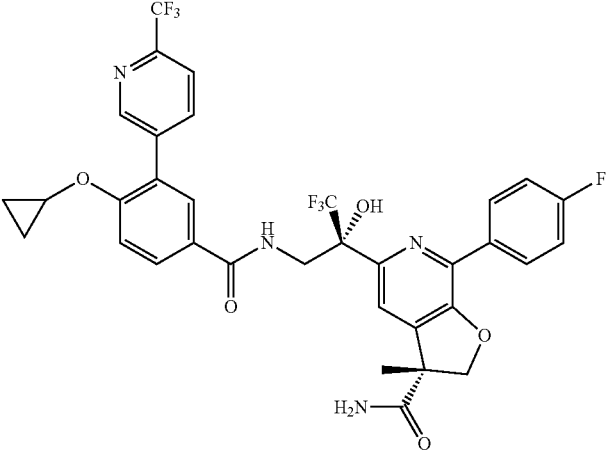 [SMILES: C[C@]1(C(N)=O)COc2c1cc([C@@](O)(CNC(=O)c1ccc(OC3CC3)c(-c3ccc(C(F)(F)F)nc3)c1)C(F)(F)F)nc2-c1ccc(F)cc1] | 705.35 |
| 119 | 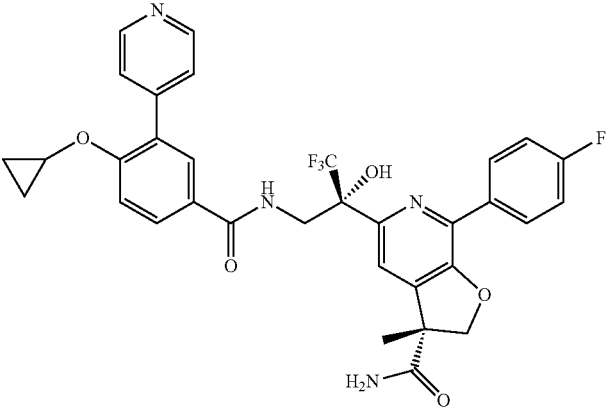 [SMILES: C[C@]1(C(N)=O)COc2c1cc([C@@](O)(CNC(=O)c1ccc(OC3CC3)c(-c3ccncc3)c1)C(F)(F)F)nc2-c1ccc(F)cc1] | 637.40 |
| 120 | 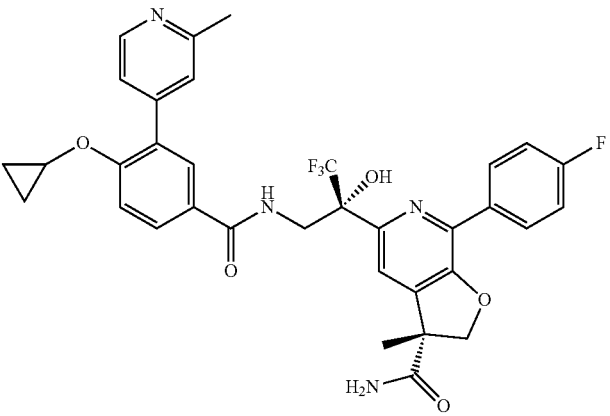 [SMILES: Cc1cc(-c2cc(C(=O)NC[C@](O)(c3cc4c(c(-c5ccc(F)cc5)n3)OC[C@]4(C)C(N)=O)C(F)(F)F)ccc2OC2CC2)ccn1] | 651.45 |

TABLE 2-continued

| Example | Structure | MS+ m/z |
|---|---|---|
| 121 | 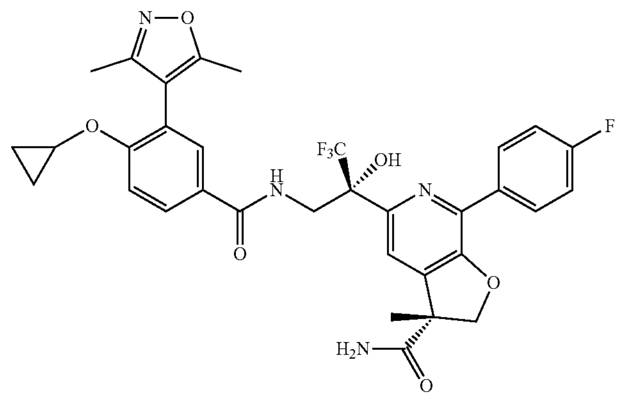 [SMILES: Cc1noc(C)c1-c1cc(C(=O)NC[C@](O)(c2cc3c(c(-c4ccc(F)cc4)n2)OC[C@]3(C)C(N)=O)C(F)(F)F)ccc1OC1CC1] | 655.15 |
| 122 | 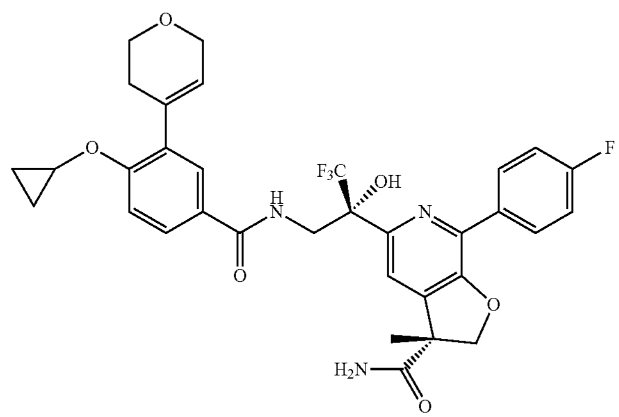 [SMILES: C[C@]1(C(N)=O)COc2c1cc([C@@](O)(CNC(=O)c1ccc(OC3CC3)c(C3=CCOCC3)c1)C(F)(F)F)nc2-c1ccc(F)cc1] | 642.20 |
| 123 | 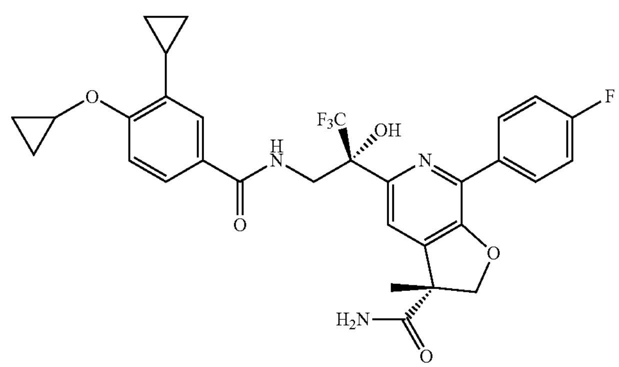 [SMILES: C[C@]1(C(N)=O)COc2c1cc([C@@](O)(CNC(=O)c1ccc(OC3CC3)c(C3CC3)c1)C(F)(F)F)nc2-c1ccc(F)cc1] | 600.20 |
| 124 | 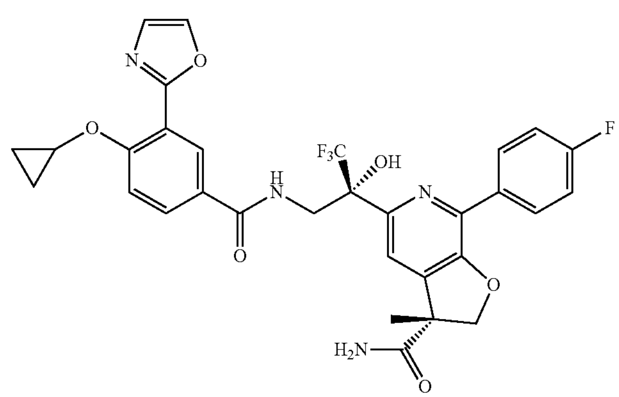 [SMILES: C[C@]1(C(N)=O)COc2c1cc([C@@](O)(CNC(=O)c1ccc(OC3CC3)c(-c3ncco3)c1)C(F)(F)F)nc2-c1ccc(F)cc1] | 627.35 |

TABLE 2-continued

| Example | Structure | MS⁺ m/z |
|---|---|---|
| 125 | 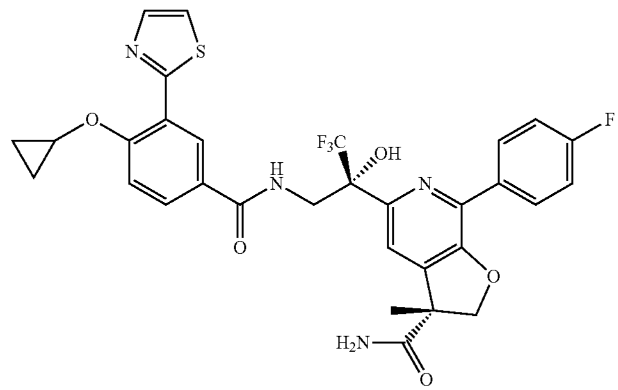 [SMILES: C[C@]1(C(N)=O)COc2c1cc([C@@](O)(CNC(=O)c1ccc(OC3CC3)c(-c3nccs3)c1)C(F)(F)F)nc2-c1ccc(F)cc1] | 643.35 |
| 126 | 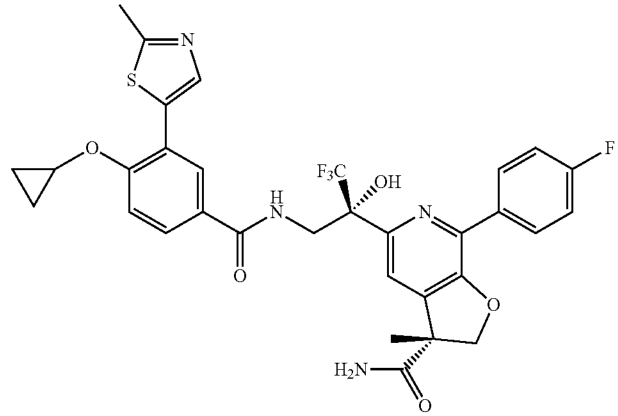 [SMILES: Cc1ncc(-c2cc(C(=O)NC[C@](O)(c3cc4c(c(-c5ccc(F)cc5)n3)OC[C@]4(C)C(N)=O)C(F)(F)F)ccc2OC2CC2)s1] | 657.35 |
| 127 | 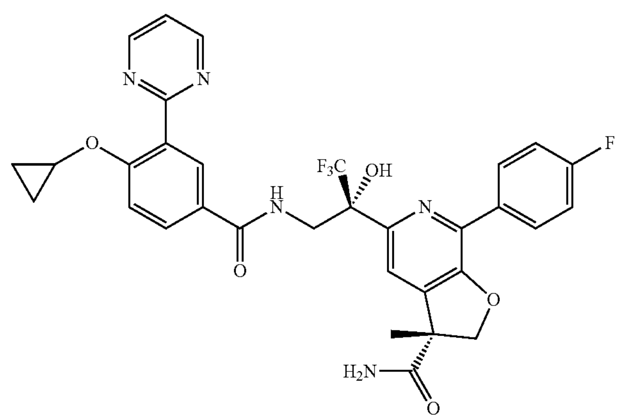 [SMILES: C[C@]1(C(N)=O)COc2c1cc([C@@](O)(CNC(=O)c1ccc(OC3CC3)c(-c3ncccn3)c1)C(F)(F)F)nc2-c1ccc(F)cc1] | 638.40 |
| 128 | 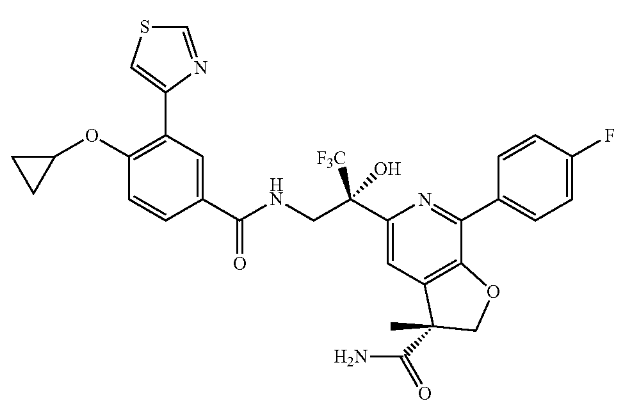 [SMILES: C[C@]1(C(N)=O)COc2c1cc([C@@](O)(CNC(=O)c1ccc(OC3CC3)c(-c3cscn3)c1)C(F)(F)F)nc2-c1ccc(F)cc1] | 643.35 |

TABLE 2-continued

| Example | Structure | MS+ m/z |
|---------|-----------|---------|
| 129 | 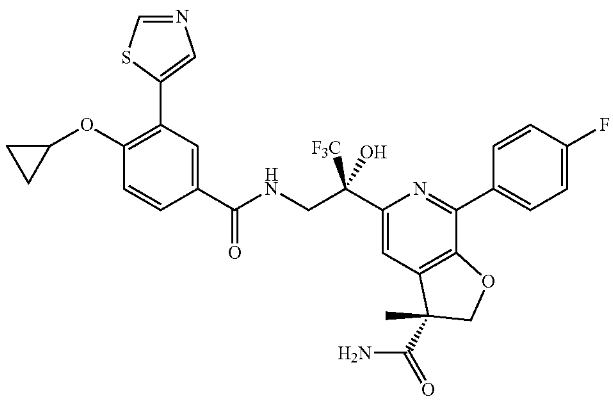 [SMILES: C[C@]1(C(N)=O)COc2c1cc([C@@](O)(CNC(=O)c1ccc(OC3CC3)c(-c3cncs3)c1)C(F)(F)F)nc2-c1ccc(F)cc1] | 643.35 |
| 130 | 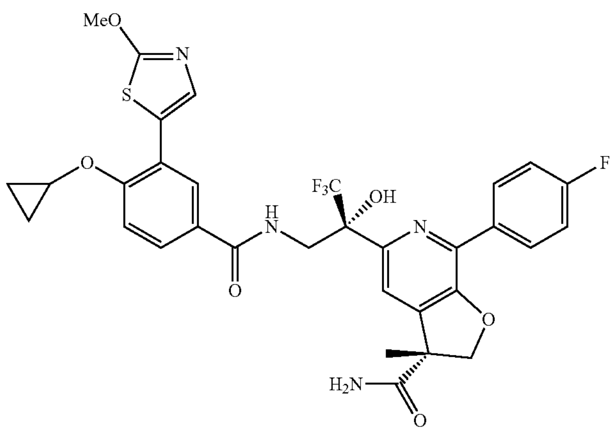 [SMILES: COc1ncc(-c2cc(C(=O)NC[C@](O)(c3cc4c(c(-c5ccc(F)cc5)n3)OC[C@]4(C)C(N)=O)C(F)(F)F)ccc2OC2CC2)s1] | 673.35 |
| 131 | 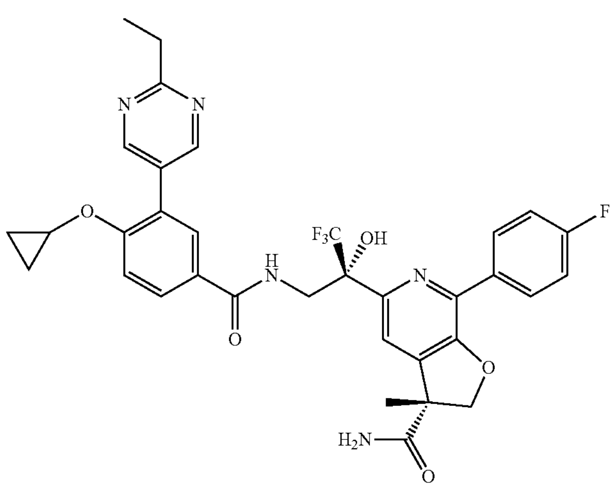 [SMILES: CCc1ncc(-c2cc(C(=O)NC[C@](O)(c3cc4c(c(-c5ccc(F)cc5)n3)OC[C@]4(C)C(N)=O)C(F)(F)F)ccc2OC2CC2)cn1] | 666.15 |

TABLE 2-continued
| Example | Structure | MS+ m/z |
|---------|-----------|---------|
| 132 | 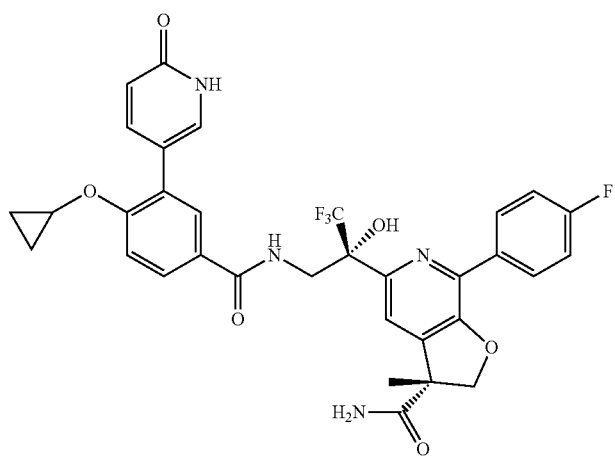 [SMILES: C[C@]1(C(N)=O)COc2c1cc([C@@](O)(CNC(=O)c1ccc(OC3CC3)c(-c3ccc(=O)[nH]c3)c1)C(F)(F)F)nc2-c1ccc(F)cc1] | 653.10 |
| 133 | 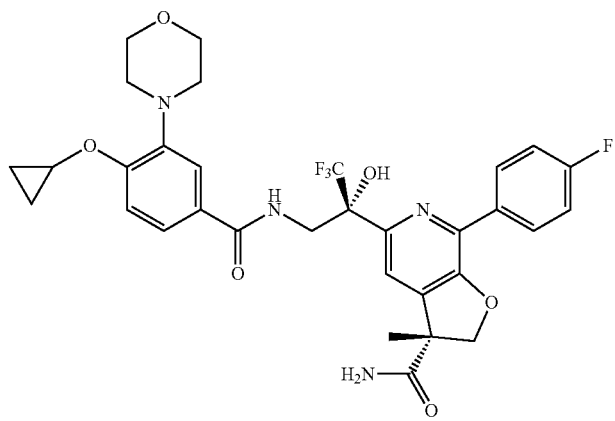 [SMILES: C[C@]1(C(N)=O)COc2c1cc([C@@](O)(CNC(=O)c1ccc(OC3CC3)c(N3CCOCC3)c1)C(F)(F)F)nc2-c1ccc(F)cc1] | 645.40 |
| 134 | 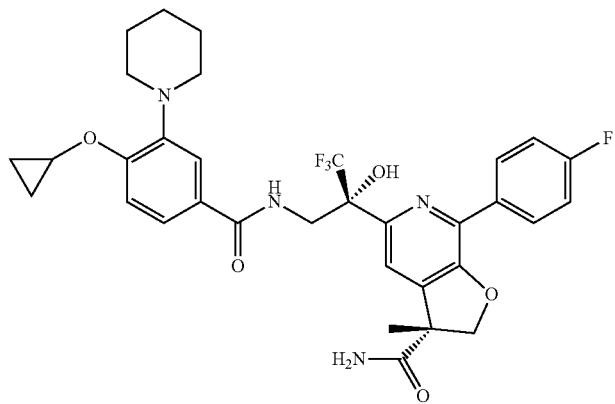 [SMILES: C[C@]1(C(N)=O)COc2c1cc([C@@](O)(CNC(=O)c1ccc(OC3CC3)c(N3CCCCC3)c1)C(F)(F)F)nc2-c1ccc(F)cc1] | 643.45 |

| Example | Structure | MS+ m/z |
|---|---|---|
| 135 | 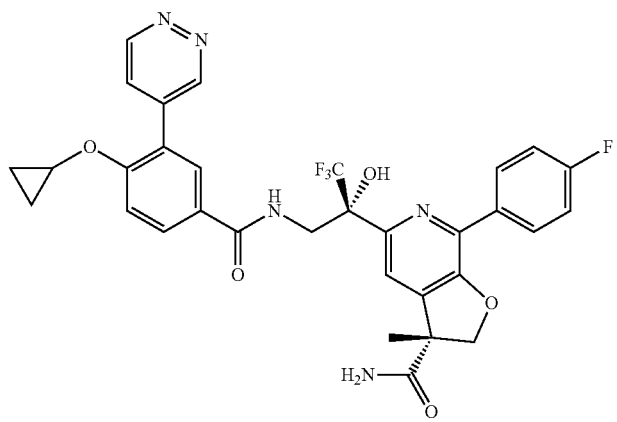 [SMILES: C[C@]1(C(N)=O)COc2c1cc([C@@](O)(CNC(=O)c1ccc(OC3CC3)c(-c3ccnnc3)c1)C(F)(F)F)nc2-c1ccc(F)cc1] | 638.40 |
| 136 | 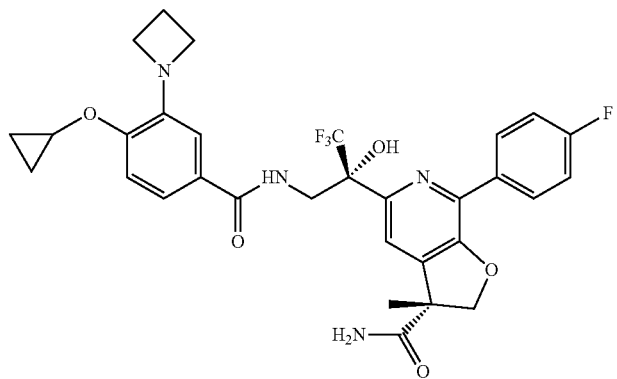 [SMILES: C[C@]1(C(N)=O)COc2c1cc([C@@](O)(CNC(=O)c1ccc(OC3CC3)c(N3CCC3)c1)C(F)(F)F)nc2-c1ccc(F)cc1] | 615.10 |
| 137 | 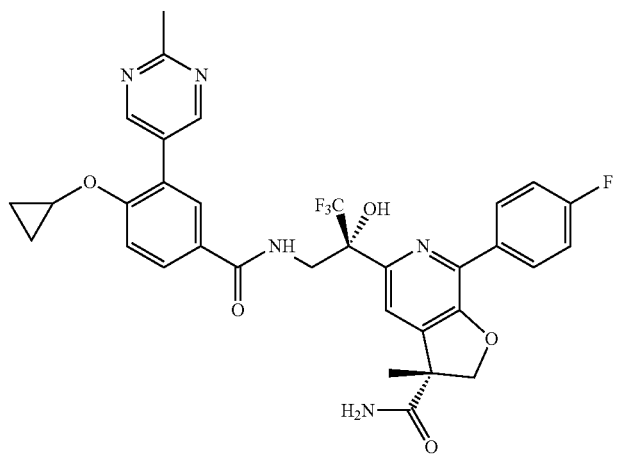 [SMILES: Cc1ncc(-c2cc(C(=O)NC[C@](O)(c3cc4c(c(-c5ccc(F)cc5)n3)OC[C@]4(C)C(N)=O)C(F)(F)F)ccc2OC2CC2)cn1] | 652.40 |

TABLE 2-continued

| Example | Structure | MS⁺ m/z |
|---|---|---|
| 138 | 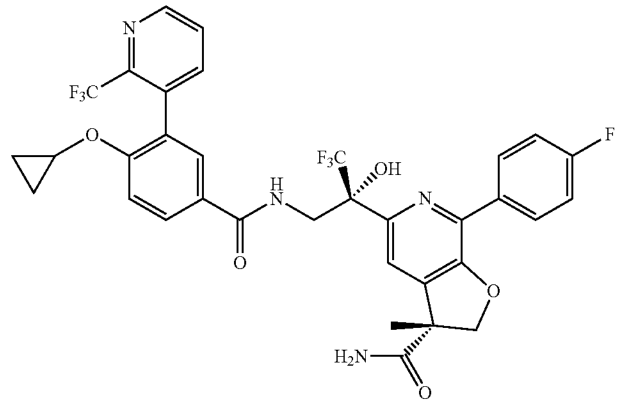 [SMILES: C[C@]1(C(N)=O)COc2c1cc([C@@](O)(CNC(=O)c1ccc(OC3CC3)c(-c3cccnc3C(F)(F)F)c1)C(F)(F)F)nc2-c1ccc(F)cc1] | 705.21 |
| 139 | 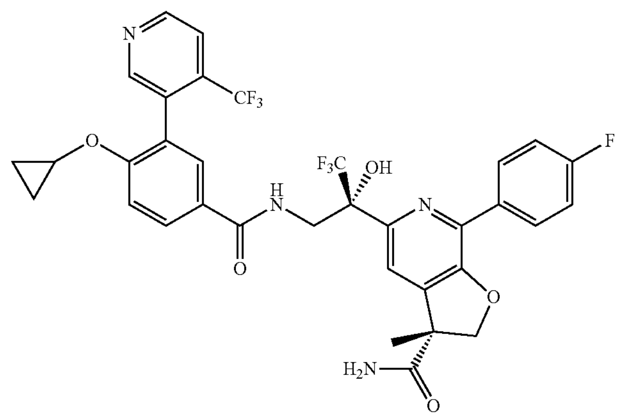 [SMILES: C[C@]1(C(N)=O)COc2c1cc([C@@](O)(CNC(=O)c1ccc(OC3CC3)c(-c3cnccc3C(F)(F)F)c1)C(F)(F)F)nc2-c1ccc(F)cc1] | 705.21 |
| 140 | 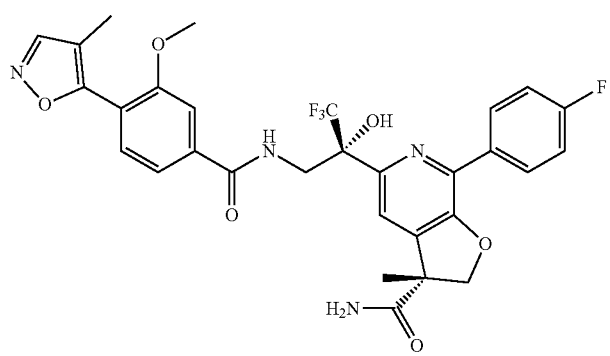 [SMILES: COc1cc(C(=O)NC[C@](O)(c2cc3c(c(-c4ccc(F)cc4)n2)OC[C@]3(C)C(N)=O)C(F)(F)F)ccc1-c1oncc1C] | 615.15 |
| 141 | 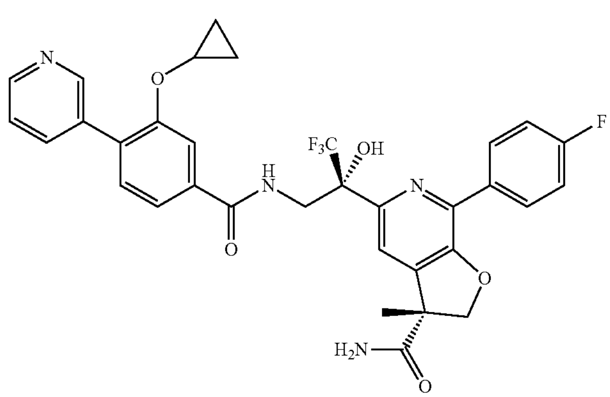 [SMILES: C[C@]1(C(N)=O)COc2c1cc([C@@](O)(CNC(=O)c1ccc(-c3cccnc3)c(OC3CC3)c1)C(F)(F)F)nc2-c1ccc(F)cc1] | 637.45 |

TABLE 2-continued

| Example | Structure | MS+ m/z |
|---|---|---|
| 142 | 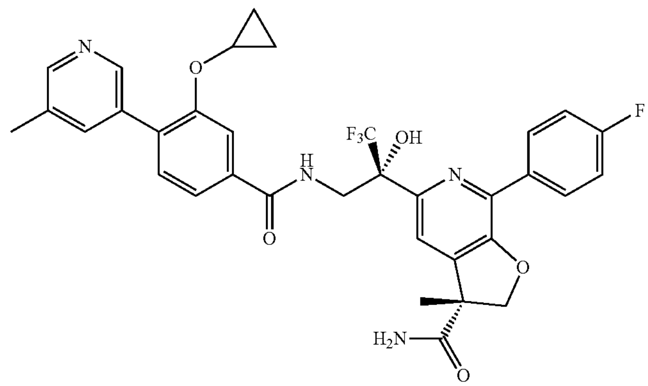 [SMILES: Cc1cncc(-c2ccc(C(=O)NC[C@](O)(c3cc4c(c(-c5ccc(F)cc5)n3)OC[C@]4(C)C(N)=O)C(F)(F)F)cc2OC2CC2)c1] | 651.15 |
| 143 | 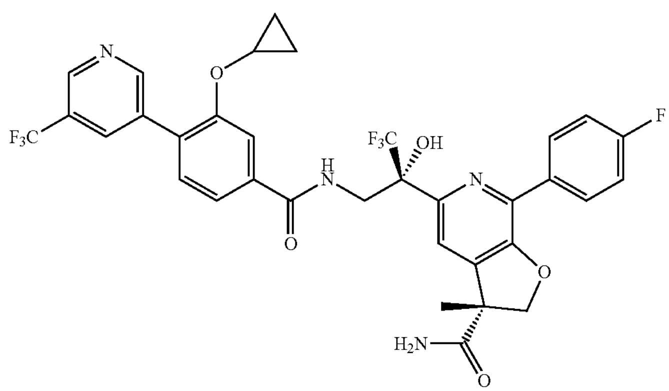 [SMILES: C[C@]1(C(N)=O)COc2c1cc([C@@](O)(CNC(=O)c1ccc(-c3cncc(C(F)(F)F)c3)c(OC3CC3)c1)C(F)(F)F)nc2-c1ccc(F)cc1] | 705.15 |
| 144 | 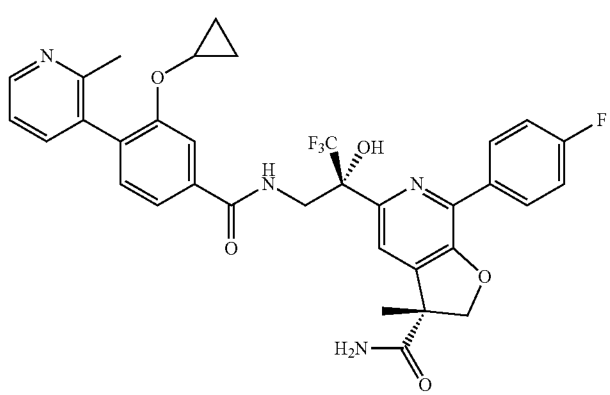 [SMILES: Cc1ncccc1-c1ccc(C(=O)NC[C@](O)(c2cc3c(c(-c4ccc(F)cc4)n2)OC[C@]3(C)C(N)=O)C(F)(F)F)cc1OC1CC1] | 651.40 |
| 145 | 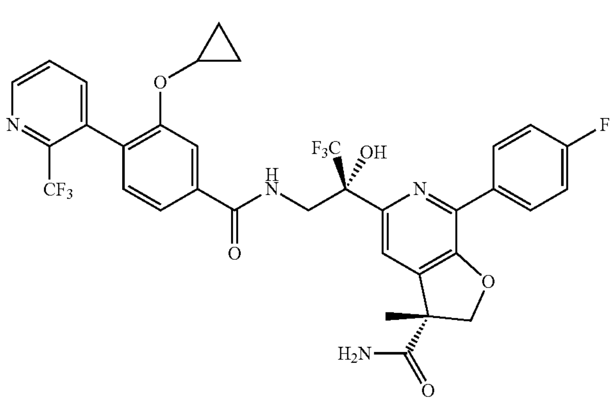 | 705.15 |

TABLE 2-continued

| Example | Structure | MS⁺ m/z |
|---|---|---|
| 146 | 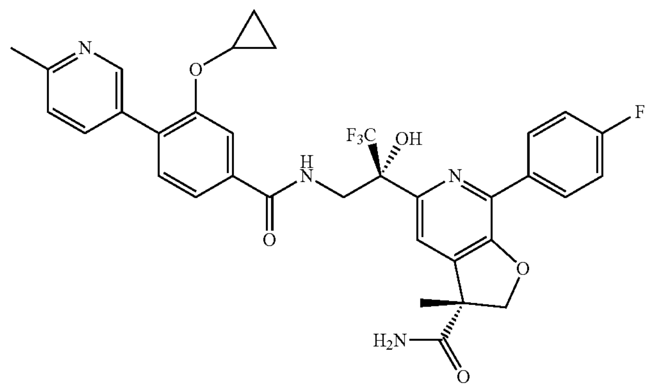 [SMILES: Cc1ccc(-c2ccc(C(=O)NC[C@](O)(c3cc4c(c(-c5ccc(F)cc5)n3)OC[C@]4(C)C(N)=O)C(F)(F)F)cc2OC2CC2)cn1] | 651.40 |
| 147 | 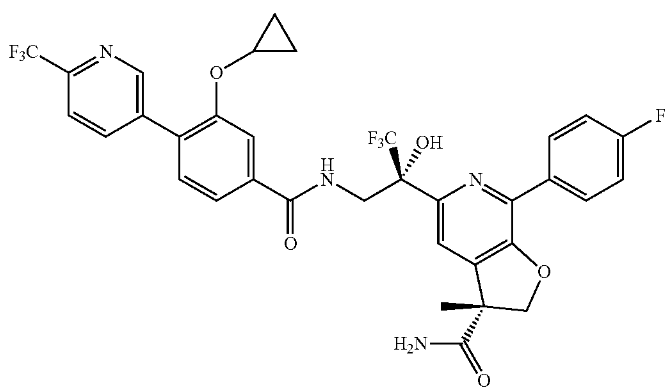 [SMILES: C[C@]1(C(N)=O)COc2c1cc([C@@](O)(CNC(=O)c1ccc(-c3ccc(C(F)(F)F)nc3)c(OC3CC3)c1)C(F)(F)F)nc2-c1ccc(F)cc1] | 705.40 |
| 148 | 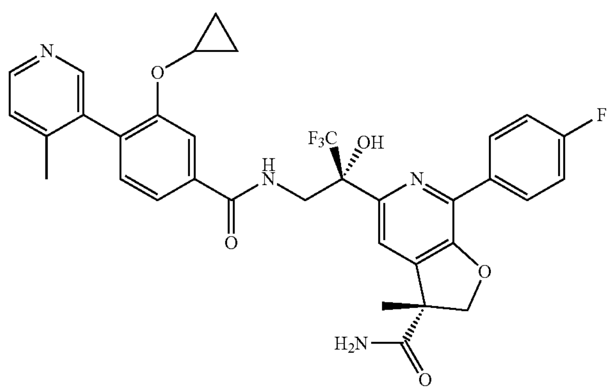 [SMILES: Cc1ccncc1-c1ccc(C(=O)NC[C@](O)(c2cc3c(c(-c4ccc(F)cc4)n2)OC[C@]3(C)C(N)=O)C(F)(F)F)cc1OC1CC1] | 651.15 |
| 149 | 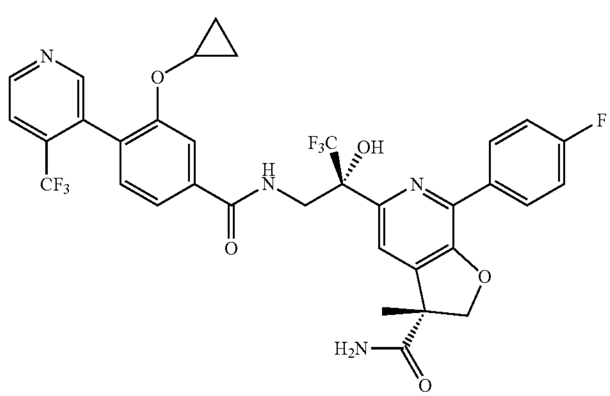 [SMILES: C[C@]1(C(N)=O)COc2c1cc([C@@](O)(CNC(=O)c1ccc(-c3cnccc3C(F)(F)F)c(OC3CC3)c1)C(F)(F)F)nc2-c1ccc(F)cc1] | 705.10 |

TABLE 2-continued
| Example | Structure | MS+ m/z |
|---|---|---|
| 150 | 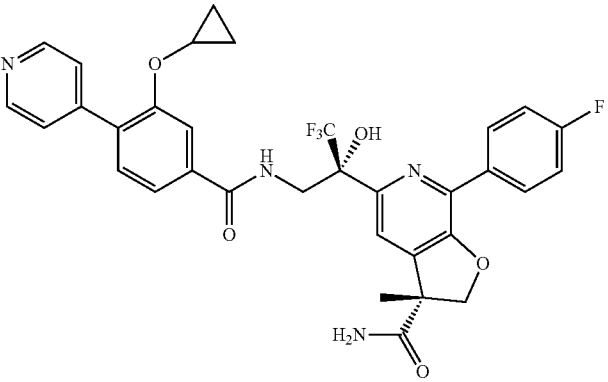 [SMILES: C[C@]1(C(N)=O)COc2c1cc([C@@](O)(CNC(=O)c1ccc(-c3ccncc3)c(OC3CC3)c1)C(F)(F)F)nc2-c1ccc(F)cc1] | 637.15 |
| 151 | 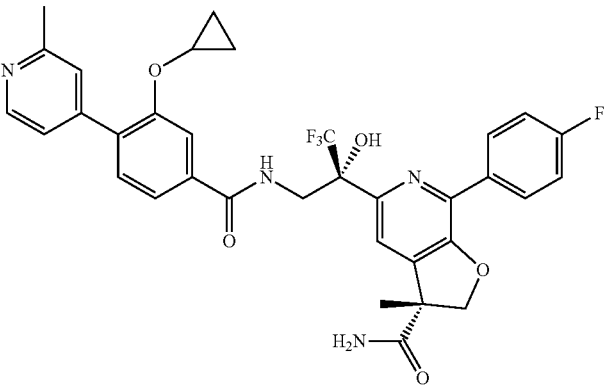 [SMILES: Cc1cc(-c2ccc(C(=O)NC[C@](O)(c3cc4c(c(-c5ccc(F)cc5)n3)OC[C@]4(C)C(N)=O)C(F)(F)F)cc2OC2CC2)ccn1] | 651.40 |
| 152 | 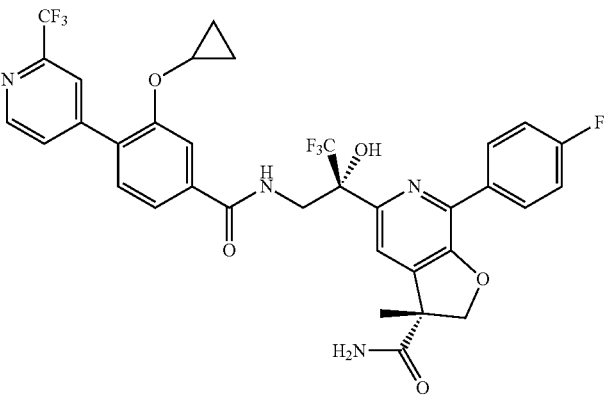 [SMILES: C[C@]1(C(N)=O)COc2c1cc([C@@](O)(CNC(=O)c1ccc(-c3ccnc(C(F)(F)F)c3)c(OC3CC3)c1)C(F)(F)F)nc2-c1ccc(F)cc1] | 705.10 |
| 153 | 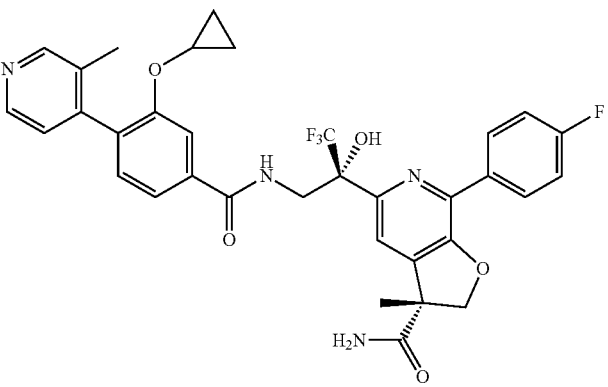 [SMILES: Cc1cnccc1-c1ccc(C(=O)NC[C@](O)(c2cc3c(c(-c4ccc(F)cc4)n2)OC[C@]3(C)C(N)=O)C(F)(F)F)cc1OC1CC1] | 651.40 |

TABLE 2-continued

| Example | Structure | MS+ m/z |
|---|---|---|
| 154 | 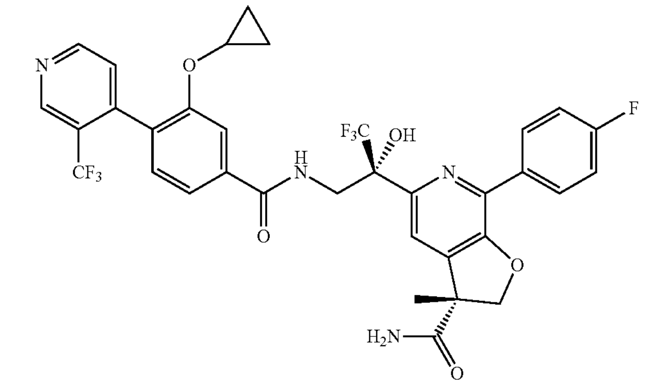 [SMILES: C[C@]1(C(N)=O)COc2c1cc([C@@](O)(CNC(=O)c1ccc(-c3ccncc3C(F)(F)F)c(OC3CC3)c1)C(F)(F)F)nc2-c1ccc(F)cc1] | 705.10 |
| 155 | 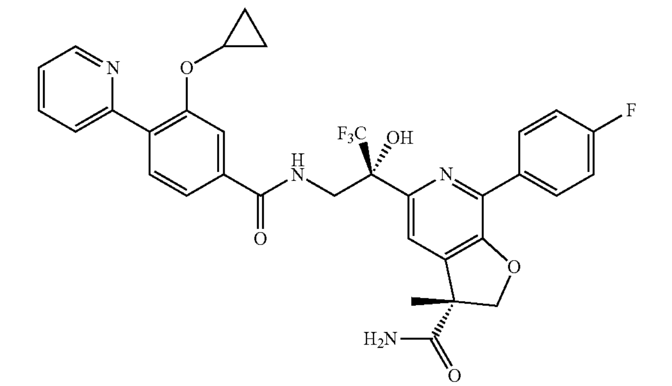 [SMILES: C[C@]1(C(N)=O)COc2c1cc([C@@](O)(CNC(=O)c1ccc(-c3ccccn3)c(OC3CC3)c1)C(F)(F)F)nc2-c1ccc(F)cc1] | 637.10 |
| 156 | 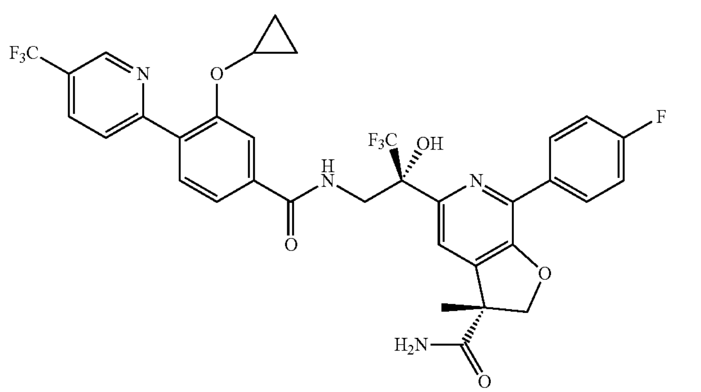 [SMILES: C[C@]1(C(N)=O)COc2c1cc([C@@](O)(CNC(=O)c1ccc(-c3ccc(C(F)(F)F)cn3)c(OC3CC3)c1)C(F)(F)F)nc2-c1ccc(F)cc1] | 705.40 |
| 157 | 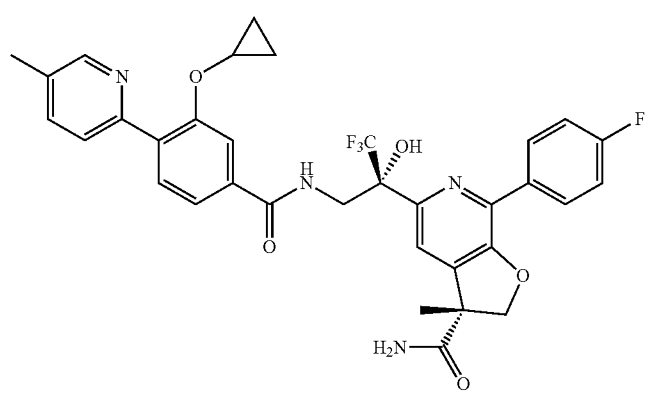 | 651.40 |

TABLE 2-continued

| Example | Structure | MS+ m/z |
|---|---|---|
| 158 | 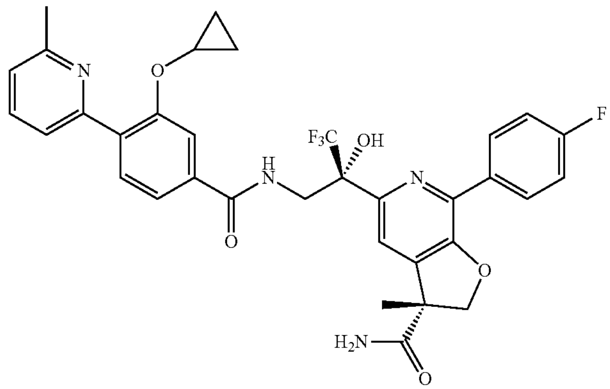 [SMILES: Cc1cccc(-c2ccc(C(=O)NC[C@](O)(c3cc4c(c(-c5ccc(F)cc5)n3)OC[C@]4(C)C(N)=O)C(F)(F)F)cc2OC2CC2)n1] | 651.40 |
| 159 | 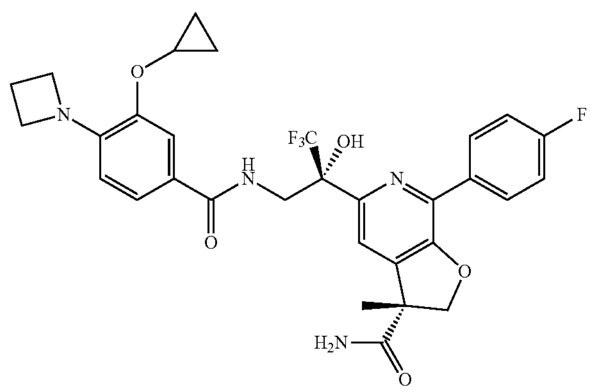 [SMILES: C[C@]1(C(N)=O)COc2c1cc([C@@](O)(CNC(=O)c1ccc(N3CCC3)c(OC3CC3)c1)C(F)(F)F)nc2-c1ccc(F)cc1] | 615.25 |
| 160 | 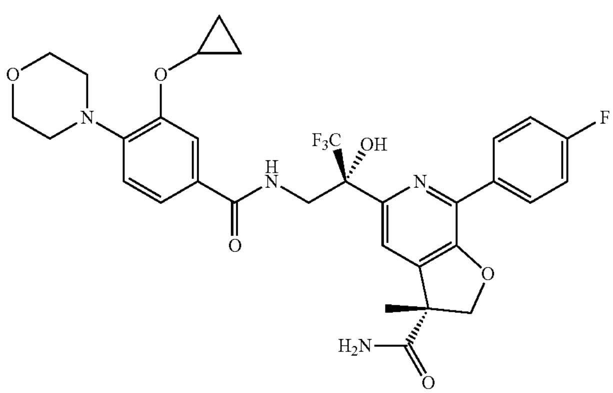 [SMILES: C[C@]1(C(N)=O)COc2c1cc([C@@](O)(CNC(=O)c1ccc(N3CCOCC3)c(OC3CC3)c1)C(F)(F)F)nc2-c1ccc(F)cc1] | 645.15 |
| 161 | 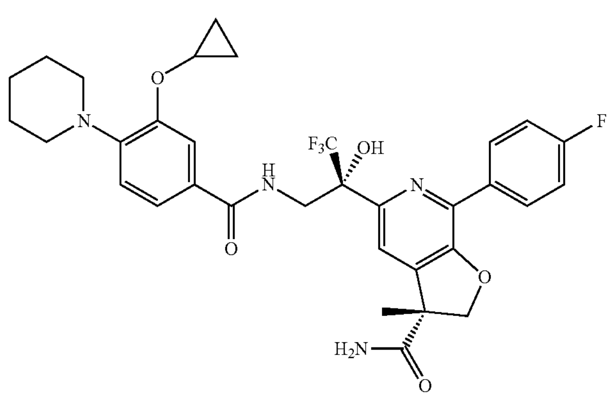 [SMILES: C[C@]1(C(N)=O)COc2c1cc([C@@](O)(CNC(=O)c1ccc(N3CCCCC3)c(OC3CC3)c1)C(F)(F)F)nc2-c1ccc(F)cc1] | 643.20 |

TABLE 2-continued

| Example | Structure | MS⁺ m/z |
|---|---|---|
| 162 | 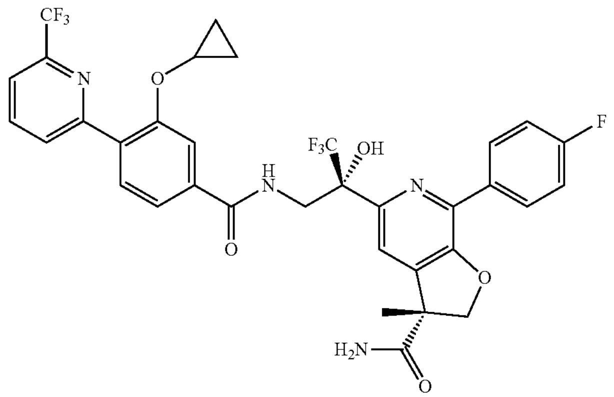 [SMILES: C[C@]1(C(N)=O)COc2c1cc([C@@](O)(CNC(=O)c1ccc(-c3cccc(C(F)(F)F)n3)c(OC3CC3)c1)C(F)(F)F)nc2-c1ccc(F)cc1] | 705.20 |
| 163 | 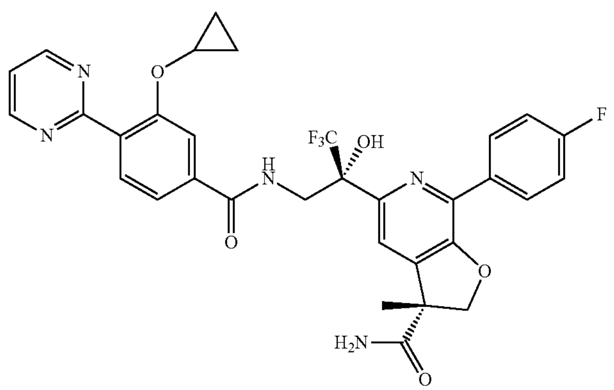 | 638.20 |
| 164 | 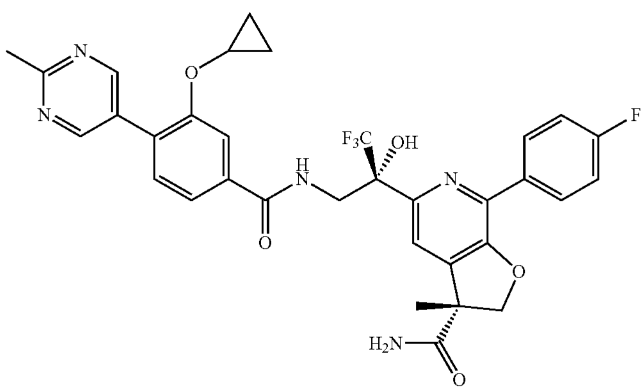 | 652.25 |
| 165 | 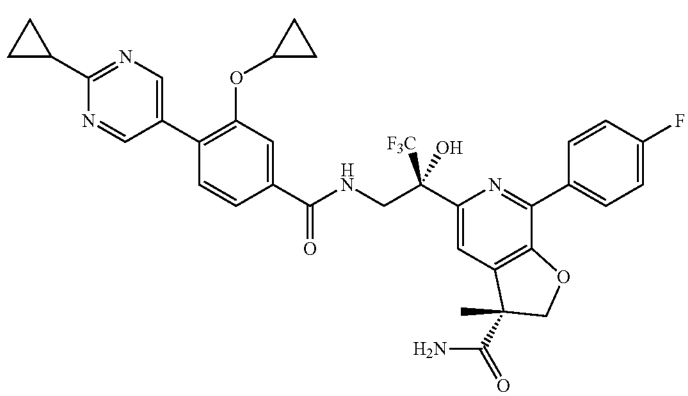 [SMILES: C[C@]1(C(N)=O)COc2c1cc([C@@](O)(CNC(=O)c1ccc(-c3cnc(C4CC4)nc3)c(OC3CC3)c1)C(F)(F)F)nc2-c1ccc(F)cc1] | 678.25 |

TABLE 2-continued

| Example | Structure | MS+ m/z |
|---------|-----------|---------|
| 166 | 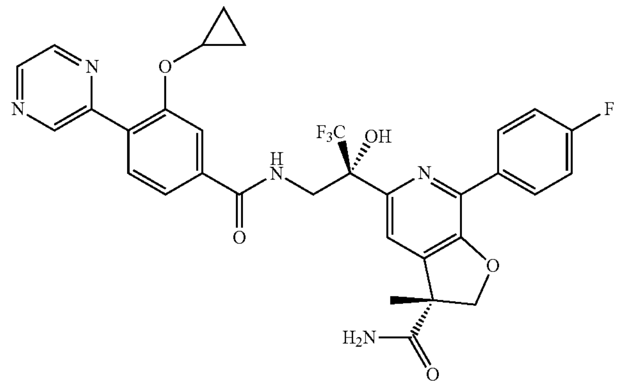 [SMILES: C[C@]1(C(N)=O)COc2c1cc([C@@](O)(CNC(=O)c1ccc(-c3cnccn3)c(OC3CC3)c1)C(F)(F)F)nc2-c1ccc(F)cc1] | 638.25 |
| 167 | 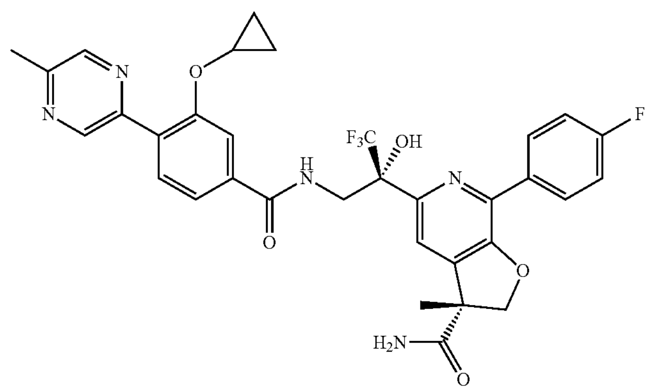 [SMILES: Cc1cnc(-c2ccc(C(=O)NC[C@](O)(c3cc4c(c(-c5ccc(F)cc5)n3)OC[C@]4(C)C(N)=O)C(F)(F)F)cc2OC2CC2)cn1] | 652.15 |
| 168 | 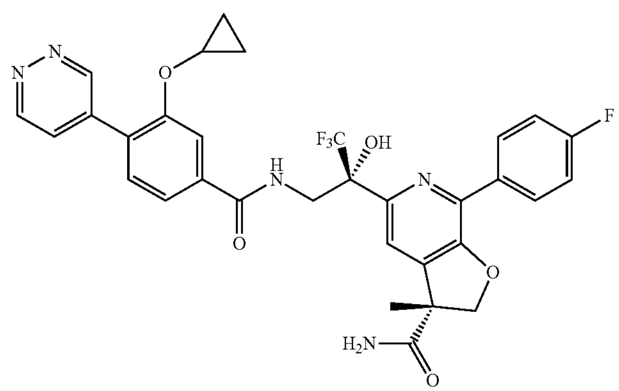 [SMILES: C[C@]1(C(N)=O)COc2c1cc([C@@](O)(CNC(=O)c1ccc(-c3ccnnc3)c(OC3CC3)c1)C(F)(F)F)nc2-c1ccc(F)cc1] | 638.20 |
| 169 | 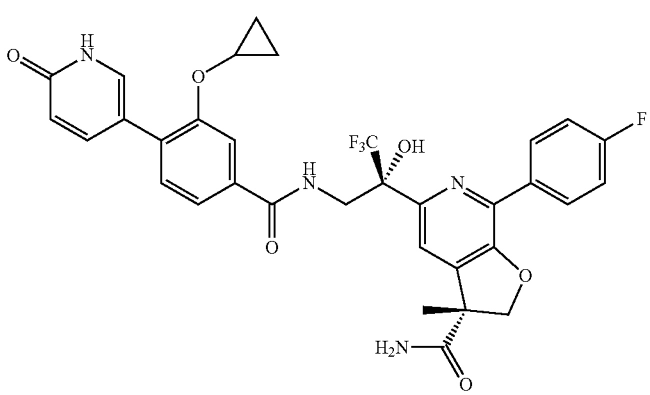 [SMILES: C[C@]1(C(N)=O)COc2c1cc([C@@](O)(CNC(=O)c1ccc(-c3ccc(=O)[nH]c3)c(OC3CC3)c1)C(F)(F)F)nc2-c1ccc(F)cc1] | 653.40 |

TABLE 2-continued
| Example | Structure | MS+ m/z |
|---|---|---|
| 170 | 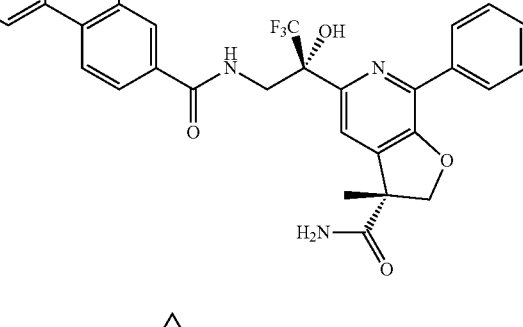 | 638.35 |
| 171 | 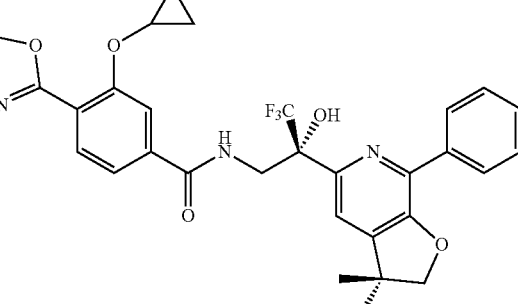 | 627.35 |
| 172 | 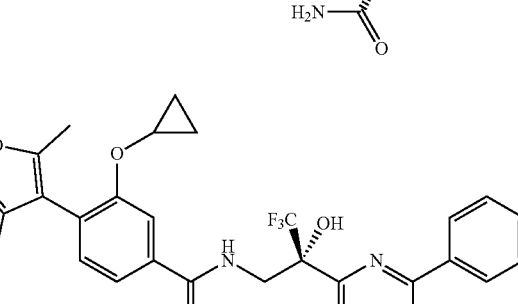 | 655.40 |
| 173 | 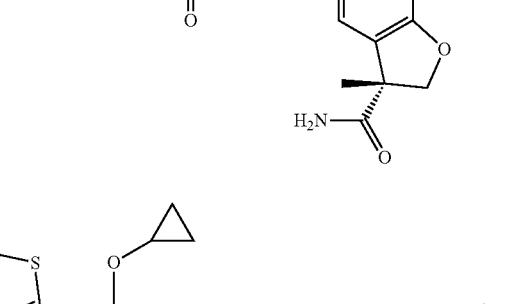 | 643.20 |

TABLE 2-continued

| Example | Structure | MS+ m/z |
|---|---|---|
| 174 | 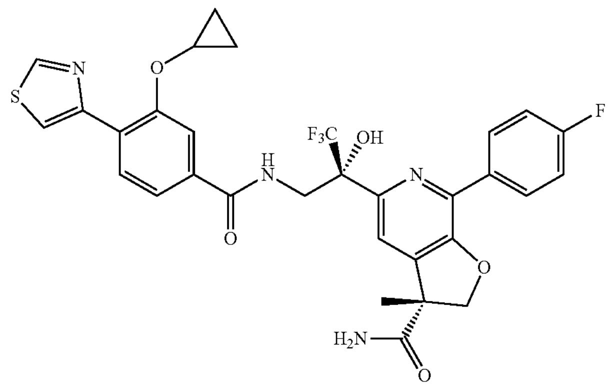 [SMILES: C[C@]1(C(N)=O)COc2c1cc([C@@](O)(CNC(=O)c1ccc(-c3cscn3)c(OC3CC3)c1)C(F)(F)F)nc2-c1ccc(F)cc1] | 643.10 |
| 175 | 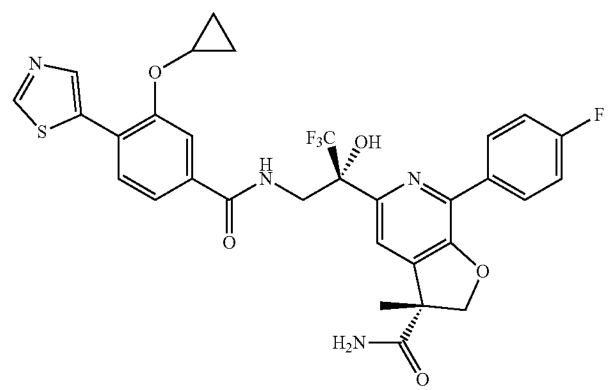 [SMILES: C[C@]1(C(N)=O)COc2c1cc([C@@](O)(CNC(=O)c1ccc(-c3cncs3)c(OC3CC3)c1)C(F)(F)F)nc2-c1ccc(F)cc1] | 643.10 |
| 176 | 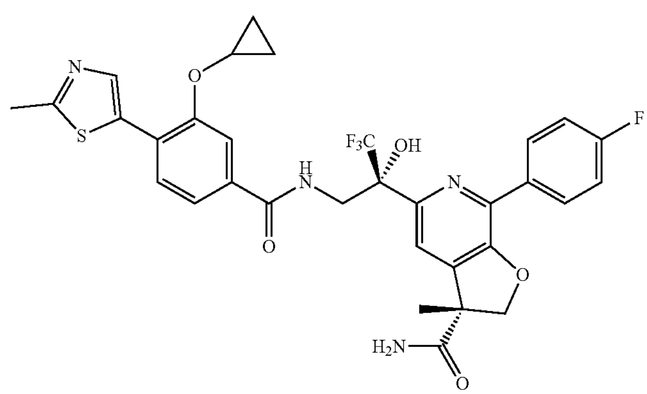 [SMILES: Cc1ncc(-c2ccc(C(=O)NC[C@](O)(c3cc4c(c(-c5ccc(F)cc5)n3)OC[C@]4(C)C(N)=O)C(F)(F)F)cc2OC2CC2)s1] | 657.10 |
| 177 | 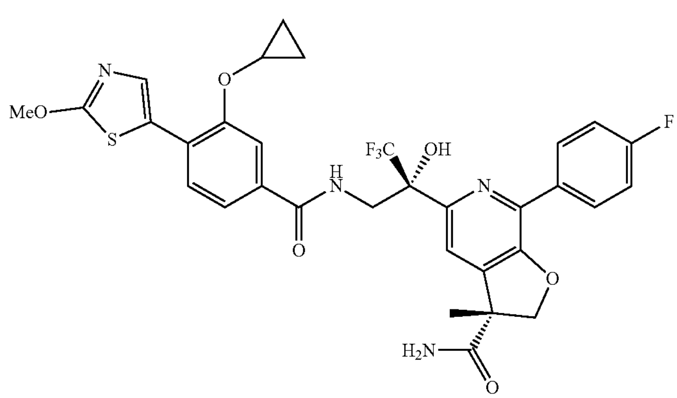 [SMILES: COc1ncc(-c2ccc(C(=O)NC[C@](O)(c3cc4c(c(-c5ccc(F)cc5)n3)OC[C@]4(C)C(N)=O)C(F)(F)F)cc2OC2CC2)s1] | 673.10 |

TABLE 2-continued

| Example | Structure | MS+ m/z |
|---------|-----------|---------|
| 178 | 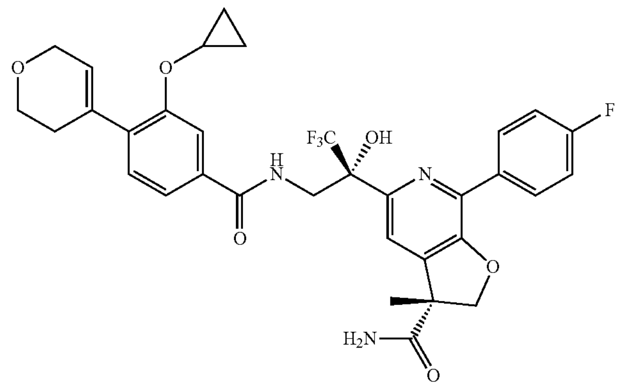 [SMILES: C[C@]1(C(N)=O)COc2c1cc([C@@](O)(CNC(=O)c1ccc(C3=CCOCC3)c(OC3CC3)c1)C(F)(F)F)nc2-c1ccc(F)cc1] | 642.15 |
| 179 | 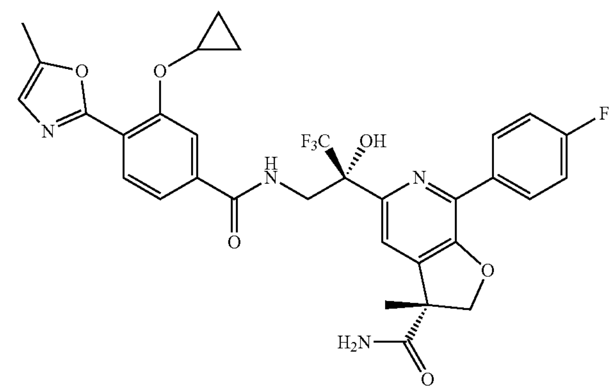 [SMILES: Cc1cnc(-c2ccc(C(=O)NC[C@](O)(c3cc4c(c(-c5ccc(F)cc5)n3)OC[C@]4(C)C(N)=O)C(F)(F)F)cc2OC2CC2)o1] | 641.10 |
| 180 | 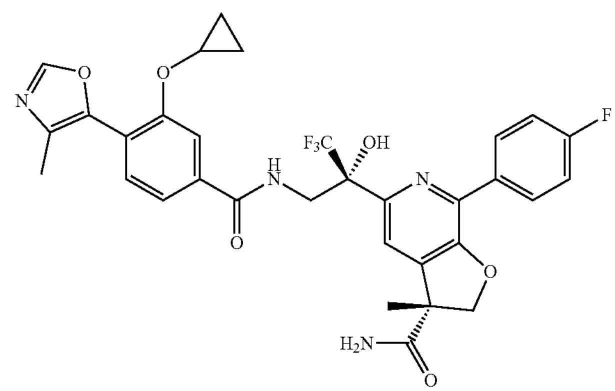 [SMILES: Cc1ncoc1-c1ccc(C(=O)NC[C@](O)(c2cc3c(c(-c4ccc(F)cc4)n2)OC[C@]3(C)C(N)=O)C(F)(F)F)cc1OC1CC1] | 641.19 |
| 181 | 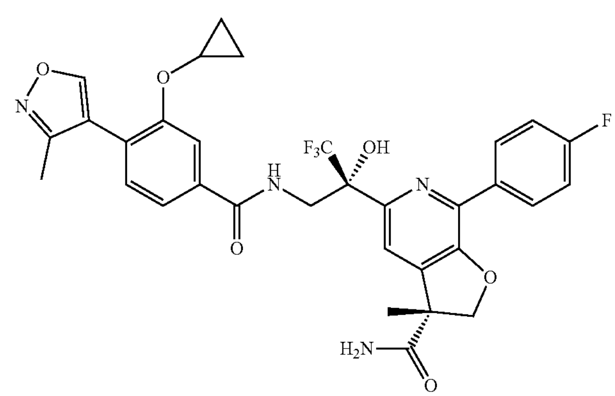 [SMILES: Cc1nocc1-c1ccc(C(=O)NC[C@](O)(c2cc3c(c(-c4ccc(F)cc4)n2)OC[C@]3(C)C(N)=O)C(F)(F)F)cc1OC1CC1] | 641.19 |

TABLE 2-continued

| Example | Structure | MS+ m/z |
| --- | --- | --- |
| 182 | 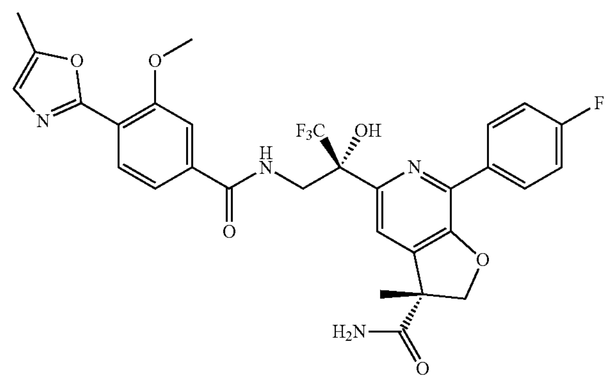 [SMILES: COc1cc(C(=O)NC[C@](O)(c2cc3c(c(-c4ccc(F)cc4)n2)OC[C@]3(C)C(N)=O)C(F)(F)F)ccc1-c1ncc(C)o1] | 615.10 |
| 183 | 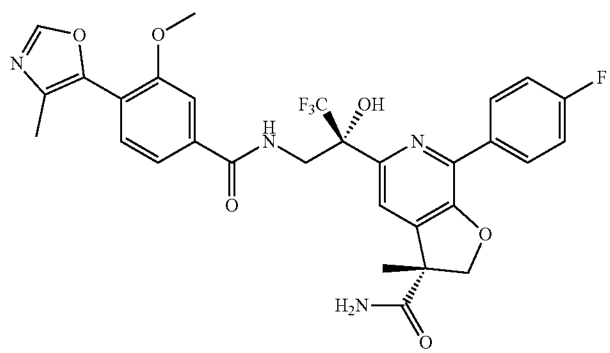 [SMILES: COc1cc(C(=O)NC[C@](O)(c2cc3c(c(-c4ccc(F)cc4)n2)OC[C@]3(C)C(N)=O)C(F)(F)F)ccc1-c1ocnc1C] | 615.18 |
| 184 | 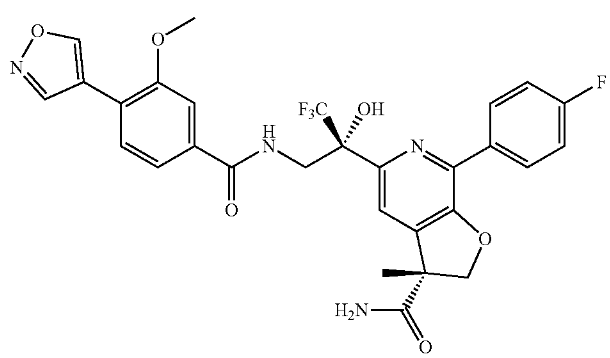 [SMILES: COc1cc(C(=O)NC[C@](O)(c2cc3c(c(-c4ccc(F)cc4)n2)OC[C@]3(C)C(N)=O)C(F)(F)F)ccc1-c1cnoc1] | 601.16 |
| 185 | 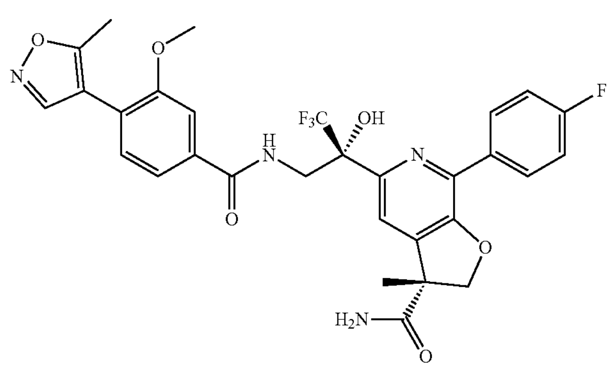 [SMILES: COc1cc(C(=O)NC[C@](O)(c2cc3c(c(-c4ccc(F)cc4)n2)OC[C@]3(C)C(N)=O)C(F)(F)F)ccc1-c1cnoc1C] | 615.18 |

TABLE 2-continued

| Example | Structure | MS+ m/z |
|---|---|---|
| 186 | 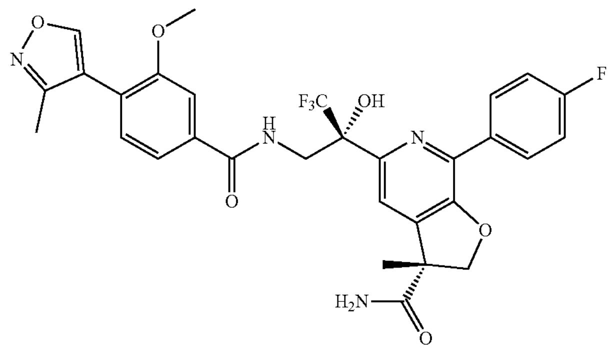 [SMILES: COc1cc(C(=O)NC[C@](O)(c2cc3c(c(-c4ccc(F)cc4)n2)OC[C@]3(C)C(N)=O)C(F)(F)F)ccc1-c1conc1C] | 615.18 |
| 187 | 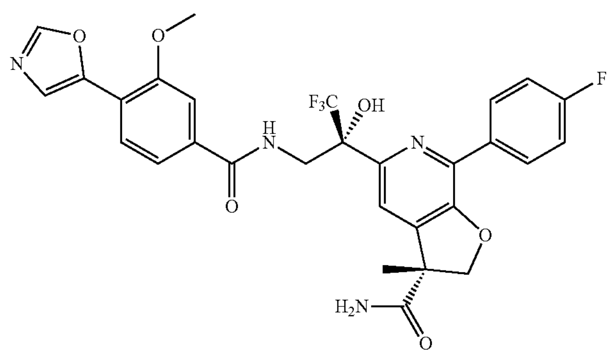 [SMILES: COc1cc(C(=O)NC[C@](O)(c2cc3c(c(-c4ccc(F)cc4)n2)OC[C@]3(C)C(N)=O)C(F)(F)F)ccc1-c1cnco1] | 601.05 |
| 188 | 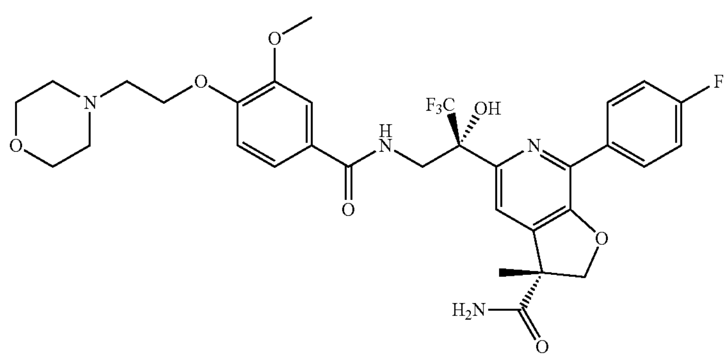 [SMILES: COc1cc(C(=O)NC[C@](O)(c2cc3c(c(-c4ccc(F)cc4)n2)OC[C@]3(C)C(N)=O)C(F)(F)F)ccc1OCCN1CCOCC1] | 663.20 |
| 189 | 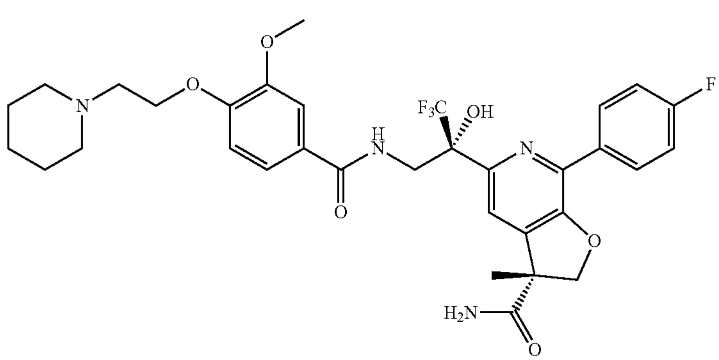 [SMILES: COc1cc(C(=O)NC[C@](O)(c2cc3c(c(-c4ccc(F)cc4)n2)OC[C@]3(C)C(N)=O)C(F)(F)F)ccc1OCCN1CCCCC1] | 661.20 |

TABLE 2-continued
| Example | Structure | MS+ m/z |
|---|---|---|
| 190 | 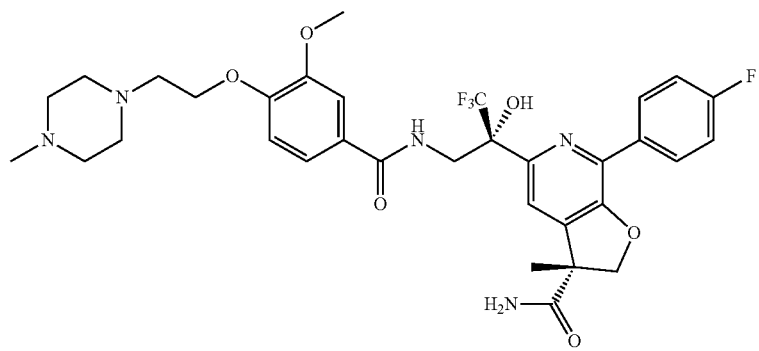 [SMILES: COc1cc(C(=O)NC[C@](O)(c2cc3c(c(-c4ccc(F)cc4)n2)OC[C@]3(C)C(N)=O)C(F)(F)F)ccc1OCCN1CCN(C)CC1] | 676.20 |
| 191 | 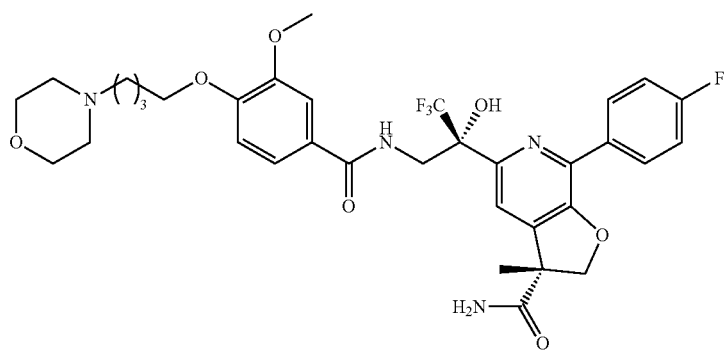 | 691.20 |
| 192 | 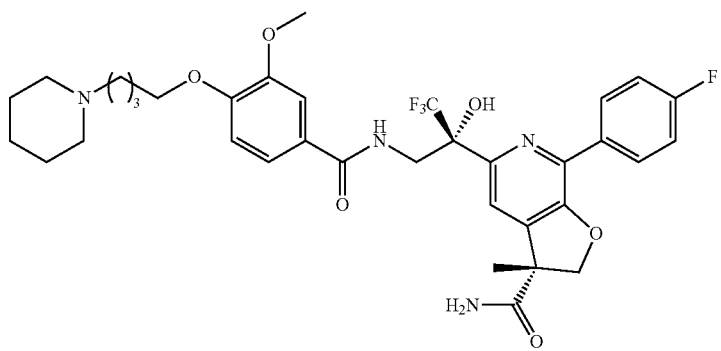 | 689.25 |
| 193 | 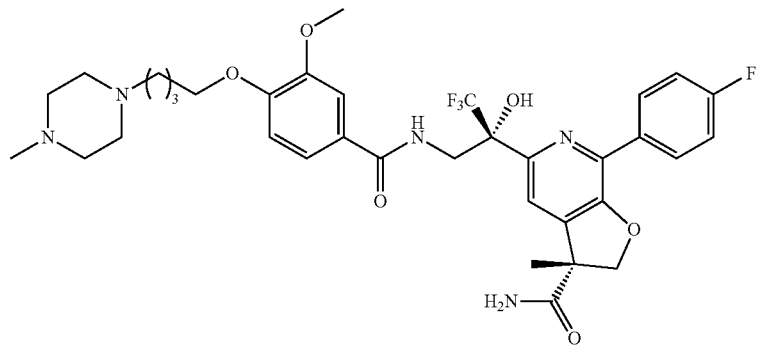 | 704.20 |

TABLE 2-continued

| Example | Structure | MS⁺ m/z |
|---|---|---|
| 194 | 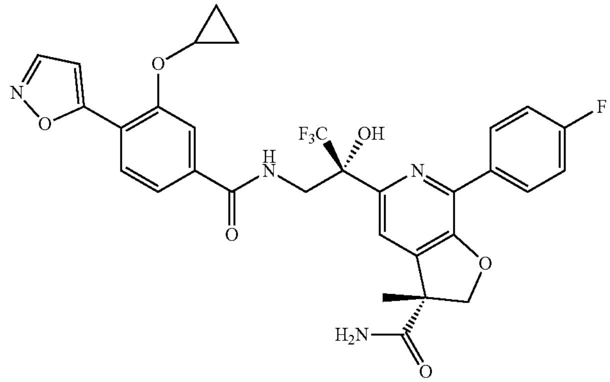 [SMILES: C[C@]1(C(N)=O)COc2c1cc([C@@](O)(CNC(=O)c1ccc(-c3ccno3)c(OC3CC3)c1)C(F)(F)F)nc2-c1ccc(F)cc1] | 627.10 |
| 195 | 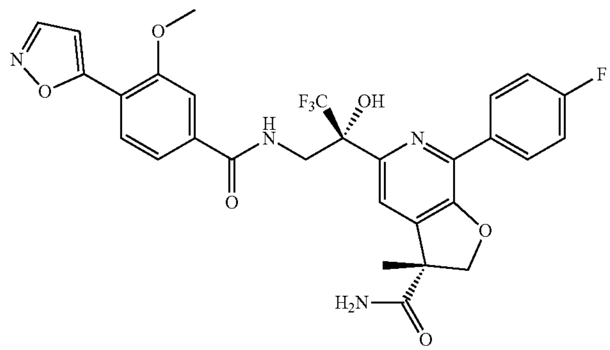 [SMILES: COc1cc(C(=O)NC[C@](O)(c2cc3c(c(-c4ccc(F)cc4)n2)OC[C@]3(C)C(N)=O)C(F)(F)F)ccc1-c1ccno1] | 601.10 |

Example 196

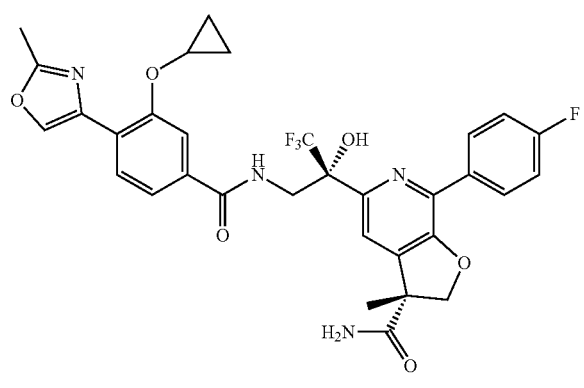 [SMILES: Cc1nc(-c2ccc(C(=O)NC[C@](O)(c3cc4c(c(-c5ccc(F)cc5)n3)OC[C@]4(C)C(N)=O)C(F)(F)F)cc2OC2CC2)co1]

Example 196 Step a

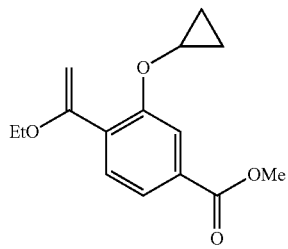 [SMILES: C=C(OCC)c1ccc(C(=O)OC)cc1OC1CC1]

Into a 40-mL vial were added methyl 4-bromo-3 cyclopropoxybenzoate (1 g, 3.69 mmol), tributyl(1-ethoxy-ethenyl)stannane (1.6 g, 4.426 mmol), Pd(dppf)Cl$_2$(DCM) (0.6 g, 0.74 mmol) and DMF (15 mL) at room temperature. The resulting mixture was stirred for 2 hr at 110° C. under nitrogen atmosphere and monitored by LCMS. The reaction was quenched with water, and the aqueous layer was extracted with DCM. The resulting mixture was concentrated and purified by automated column chromatography (0-25% EtOAc/hexanes) to afford the desired compound (450 mg, 47%). ESI-MS m/z: 263.12 [M+H]⁺.

Example 196 Step b

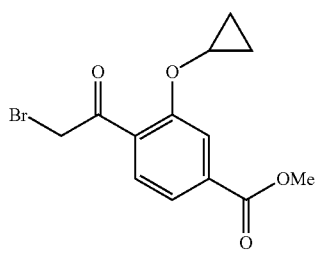 [SMILES: COC(=O)c1ccc(C(=O)CBr)c(OC2CC2)c1]

Into a 100 mL round-bottom flask were added the compound from step a (450 mg, 1.91 mmol), NBS (373 mg, 2.1 mmol), THF (10 mL) and H$_2$O (3 mL) at room temperature. The resulting mixture was stirred for 1 hr at room temperature under nitrogen atmosphere and monitored by LCMS. The resulting mixture was concentrated under reduced pressure. The residue was purified by reverse flash chromatography (C18 silica gel; 10-70%, 25 min. MeCN/H$_2$O) to afford the title compound (500 mg, 91%). ESI-MS m/z: 313.10 [M+H]$^+$.

Example 196 Steps c and d

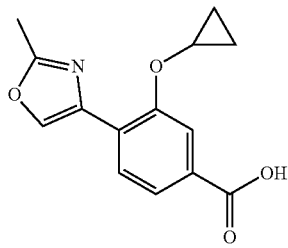 [SMILES: Cc1nc(-c2ccc(C(=O)O)cc2OC2CC2)co1]

Into a 20-mL vial were added the compound from step b (250 mg, 0.8 mmol), acetamide (236 mg, 4 mmol) and AcOH (5 mL) at room temperature. The resulting mixture was stirred at 120° C. for 16 hrs. The resulting mixture was concentrated under vacuum and purified by reverse phase chromatography (C18 silica gel; 10-70%, 25 min. MeCN/H$_2$O) to afford the title compound (45 mg, 20%). ESI-MS m/z: 274.10 [M+H]$^+$.

The methyl ester was hydrolyzed in a similar manner to Method O, and the material was purified by reverse phase chromatography (C18 silica gel; 10-70%, 25 min. MeCN/H$_2$O) to afford the title compound (45 mg, 99%). ESI-MS m/z: 260.08 [M+H]$^+$.

Example 196 Step e

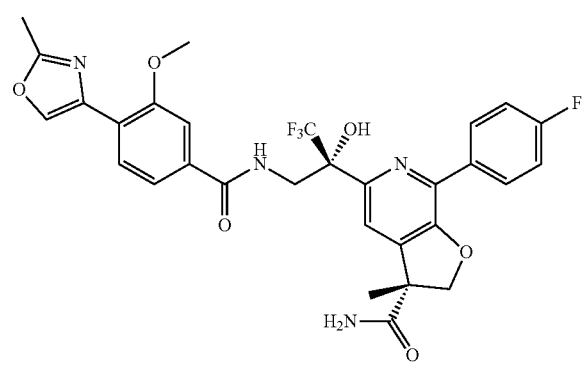 [SMILES: COc1cc(C(=O)NC[C@](O)(c2cc3c(c(-c4ccc(F)cc4)n2)OC[C@]3(C)C(N)=O)C(F)(F)F)ccc1-c1coc(C)n1]

The title compound was prepared in an analogous fashion to Method J with amine (30 mg, 0.075 mmol), and the material was purified by prep-HPLC (20-90%, MeCN/Water, 25 min) to afford the title compound (11 mg, 23%). ESI-MS m/z: 641.10 [M+H]$^+$.

Example 197

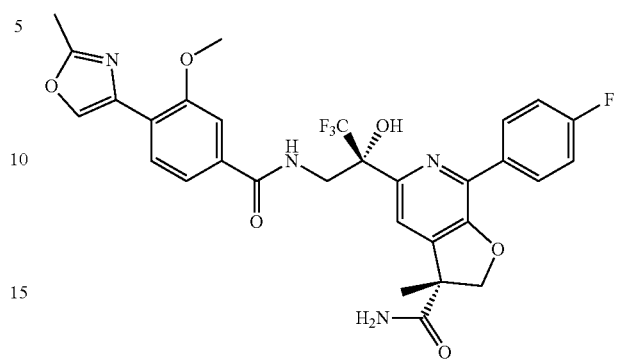

The title compound was prepared in an analogous fashion to Example 196 above with amine (30 mg, 0.075 mmol), and the material was purified by prep-HPLC (20-90%, MeCN/Water, 25 min) to afford the title compound (30.6 mg, 65%). ESI-MS m/z: 615.18 [M+H]$^+$.

Example 198

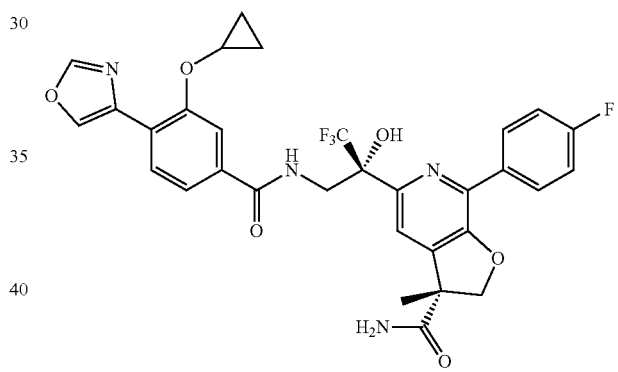

Example 198 Steps a and b

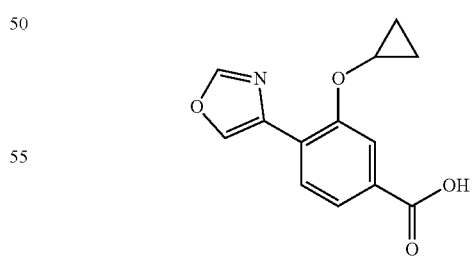

A solution of bromide from Example 196 step b (187 mg, 0.60 mmol), HCONH$_2$ (158 mg, 3.5 mmol) and formic acid (5 mL) was stirred at 100° C. under nitrogen atmosphere. The resulting mixture was concentrated under vacuum and by reverse phase chromatography (C18 silica gel; 10-70%, 25 min. MeCN/H$_2$O) to afford the title compound (60 mg, 33%). ESI-MS m/z: 260.08 [M+H]$^+$.

Example 198 Step c

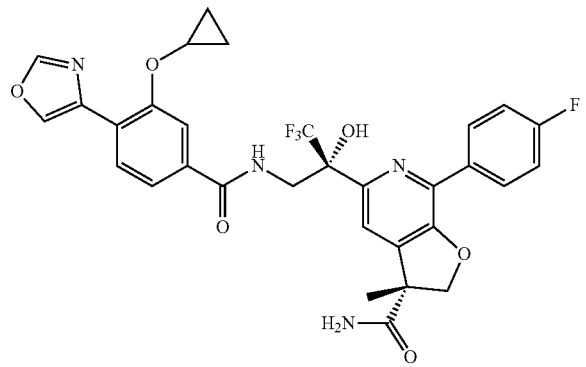 [SMILES: C[C@]1(C(N)=O)COc2c1cc([C@@](O)(CNC(=O)c1ccc(-c3cocn3)c(OC3CC3)c1)C(F)(F)F)nc2-c1ccc(F)cc1]

The title compound was prepared in an analogous fashion to Method J with amine (30 mg, 0.075 mmol), and the material was purified by prep-HPLC (20-90%, MeCN/Water, 25 min) to afford the title compound (36.7 mg, 74%). ESI-MS m/z: 627.25 [M+H]+.

Example 199

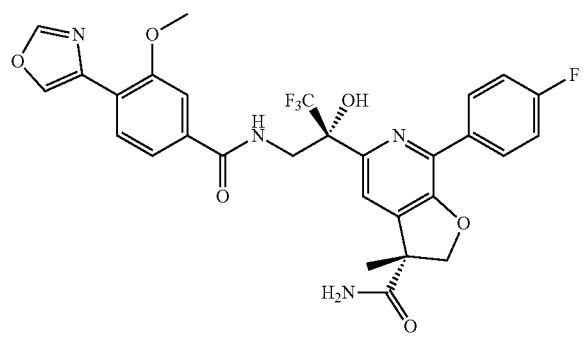 [SMILES: COc1cc(C(=O)NC[C@](O)(c2cc3c(c(-c4ccc(F)cc4)n2)OC[C@]3(C)C(N)=O)C(F)(F)F)ccc1-c1cocn1]

The title compound was prepared in an analogous sequence to Example 198 above with amine (30 mg, 0.075 mmol), and the material was purified by prep-HPLC (20-90%, MeCN/Water, 25 min) to afford the title compound (27.2 mg, 60%). ESI-MS m/z: 601.16 [M+H]+.

Example 200

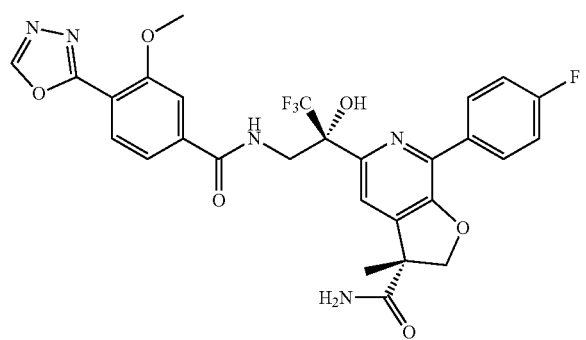 [SMILES: COc1cc(C(=O)NC[C@](O)(c2cc3c(c(-c4ccc(F)cc4)n2)OC[C@]3(C)C(N)=O)C(F)(F)F)ccc1-c1nnco1]

Example 200 Step a

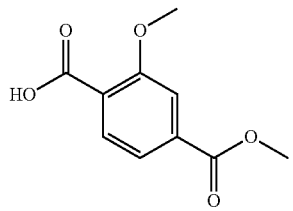

A solution of methyl 4-bromo-3-methoxybenzoate (4 g, 16.32 mmol), Pd(OAc)$_2$, (733 mg, 3.26 mmol) and dppp (1.3 g, 3.26 mmol) in DMF:H$_2$O:TEA (4:4:1, 20 mL) was stirred for 6 hours at 100° C. under CO atmosphere. The resulting solution was extracted with EtOAc, the organic layer dried and concentrated. The crude material was purified by reverse phase C18 column chromatography (MeCN/H$_2$O) to afford desired product (1.8 g, 52%). ESI-MS m/z: 211.10 [M+H]+.

Example 200 Steps b and c

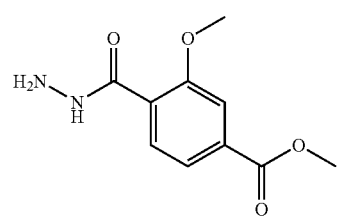 [SMILES: COC(=O)c1ccc(C(=O)NN)c(OC)c1]

A solution of the compound from step a (1.7 g, 8.08 mmol), HATU (4.6 g, 12.12 mmol), DIPEA (2 g, 16.17 mmol) and Boc-hydrazine (1.4 g, 12.12 mmol) in DMF (10 mL) was stirred for 2 hours at room temperature. The reaction was quenched with water, extracted with EtOAc, and combined organics were dried and concentrated. The crude material was purified by reverse phase C18 column chromatography (MeCN/H$_2$O) to afford desired product (2.1 g, 80%). ESI-MS m/z 269.10 [M+H-56]+.

A solution of the compound from step b (2 g, 6.17 mmol) in HCl in 1,4-dioxane (30 mL) was stirred for 0.5 hour at room temperature. The resulting solution was concentrated and purified by reverse phase C18 column chromatography (MeCN/H$_2$O) to afford desired product (1 g, 73%) as a yellow solid. ESI-MS m/z: 225.05 [M+H]+.

Example 200 Steps d and e

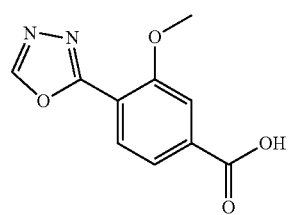 [SMILES: COc1cc(C(=O)O)ccc1-c1nnco1]

A solution of the compound from step c (250 mg, 1.11 mmol) and CH(OEt)₃ (355 mg, 3.34 mmol) in xylene (10 mL) was stirred for 3 hours at 100° C. The reaction was quenched with water, extracted with EtOAc, and combined organics were dried and concentrated. The crude material was purified by reverse phase C18 column chromatography (MeCN/H₂O) to afford desired product (130 mg, 49%) as a white solid. ESI-MS m/z: 235.10 [M+H]⁺.

The methyl ester hydrolysis was carried out in an analogous fashion to Method O, and the resulting solution was purified by reverse phase C18 column chromatography (MeOH/0.1% FA in H₂O) to afford desired product (56 mg, 46%). ESI-MS m/z: 221.00 [M+H]⁺.

Example 200 Step f

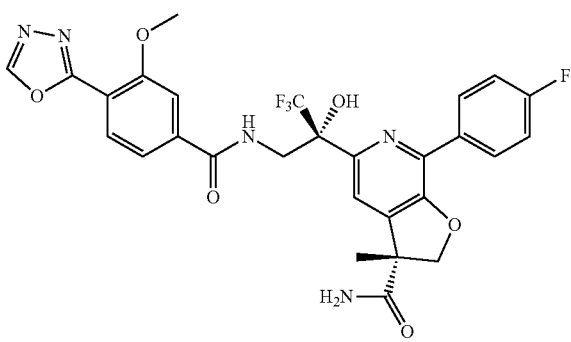 [SMILES: COc1cc(C(=O)NC[C@](O)(c2cc3c(c(-c4ccc(F)cc4)n2)OC[C@]3(C)C(N)=O)C(F)(F)F)ccc1-c1nnco1]

The title compound was prepared in an analogous fashion to Method J with amine (30 mg, 0.075 mmol), and the material was purified by prep-HPLC (20-90%, MeCN/Water, 25 min) to afford the title compound (36.5 mg, 74%). ESI-MS m/z: 602.05 [M+H]⁺.

Example 201

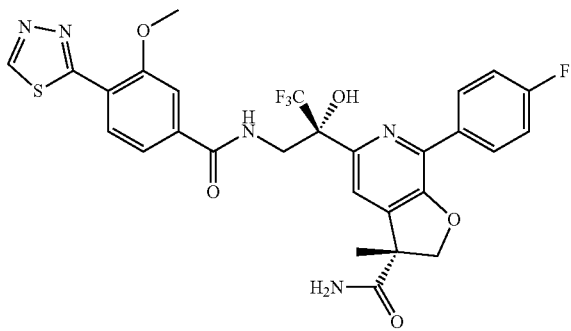 [SMILES: COc1cc(C(=O)NC[C@](O)(c2cc3c(c(-c4ccc(F)cc4)n2)OC[C@]3(C)C(N)=O)C(F)(F)F)ccc1-c1nncs1]

Example 201 Step a

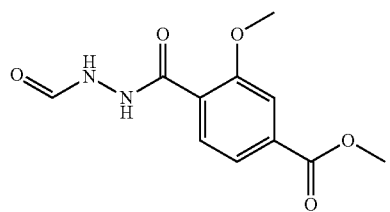 [SMILES: COC(=O)c1ccc(C(=O)NNC=O)c(OC)c1]

A solution of Example 200 step b (above) (300 mg, 1.34 mmol) and formic acid (924 mg, 20.07 mmol) in toluene (5 mL) was stirred for 4 hours at 120° C. The reaction was quenched with water, extracted with EtOAc, and combined organics were dried and concentrated. The crude material was purified by silica gel column chromatography to afford desired product (100 mg, 30%). ESI-MS m/z: 253.10 [M+H]⁺.

Example 201 Steps b and c

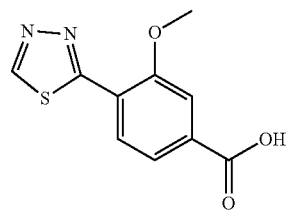 [SMILES: COc1cc(C(=O)O)ccc1-c1nncs1]

A solution of the compound from step a (80 mg, 0.32 mmol) and Lawesson's Reagent (385 mg, 0.95 mmol) in toluene (5 mL) was stirred for 30 min at 90° C. The reaction was quenched with water, extracted with EtOAc, and combined organics were dried and concentrated. The crude material was purified by silica gel column chromatography to afford desired product (60 mg, 76%). ESI-MS m/z: 251.10 [M+H]⁺.

The methyl ester hydrolysis was carried out in an analogous fashion to Method O, and the resulting solution was purified by reverse phase C18 column chromatography (MeOH/0.1% FA in H₂O) to afford desired product (60 mg, 99%). ESI-MS m/z: 236.95 [M+H]⁺.

Example 201 Step d

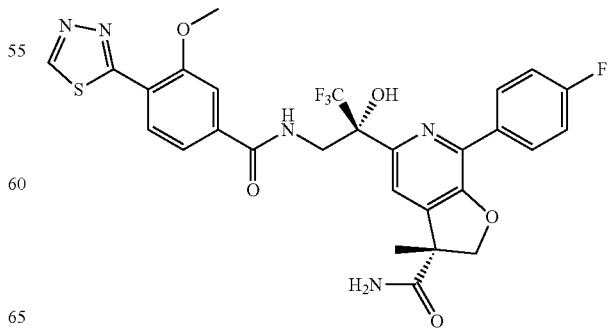

The title compound was prepared in an analogous fashion to Method J with amine (30 mg, 0.075 mmol), and the material was purified by prep-HPLC (20-90%, MeCN/Water, 25 min) to afford the title compound (24.9 mg, 53%). ESI-MS m/z: 618.05 [M+H]⁺.

Example 202

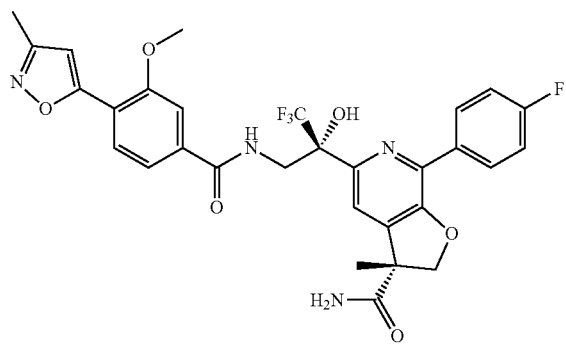 [SMILES: COc1cc(C(=O)NC[C@](O)(c2cc3c(c(-c4ccc(F)cc4)n2)OC[C@]3(C)C(N)=O)C(F)(F)F)ccc1-c1cc(C)no1]

Example 202 Step a

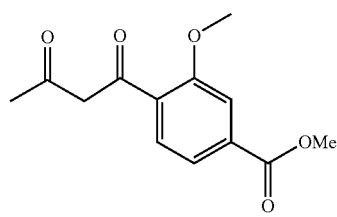 [SMILES: COC(=O)c1ccc(C(=O)CC(C)=O)c(OC)c1]

LDA was added to acetone (691 mg, 11.89 mmol) in THF (10 mL) at −78° C. The resulting solution was stirred for 0.5 hour at −78° C. A solution of 2-methoxy-4-(methoxycarbonyl)benzoic acid (500 mg, 2.38 mmol) and (1-chloro-2-methylprop-1-en-1-yl)dimethylamine (1.6 g, 12.03 mmol) in DCM (10 mL) was stirred for 0.5 hour at room temperature. The resulting mixture was concentrated under vacuum. The LDA reaction mixture was added and stirred for 30 minutes at room temperature. The reaction was quenched with water, extracted with EtOAc, and combined organics were dried and concentrated. The resulting solution was purified by reverse phase C18 column chromatography (MeCN/H₂O) to afford desired product (80 mg, 13%). ESI-MS m/z 251.15 [M+H]⁺.

Example 202 Steps b and c

A solution of the compound from step a (70 mg, 0.28 mmol) and NH₂OH.HCl (97 mg, 1.40 mmol) in EtOH:H₂O (1:1, 30 mL) was stirred for 2 hours at 80° C. The reaction was quenched with water, extracted with EtOAc, and combined organics were dried, concentrated. The material was purified by silica gel column chromatography (EtOAc: hexanes) to afford desired product (60 mg, 76%). ESI-MS m/z 248.10 [M+H]⁺.

The methyl ester hydrolysis was carried out in an analogous fashion to Method O, and the resulting solution was purified by reverse phase C18 column chromatography (MeOH/0.1% FA in H₂O) to afford desired product (60 mg) as a white solid. ESI-MS m/z: 234.10 [M+H]⁺.

Example 202 Step d

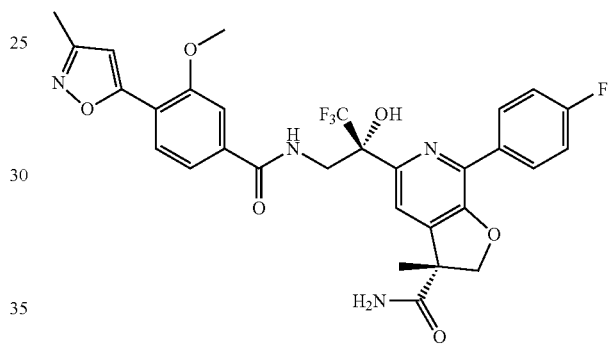

The title compound was prepared in an analogous fashion to Method J with amine (30 mg, 0.075 mmol), and the material was purified by prep-HPLC (20-90%, MeCN/Water, 25 min) to afford the title compound (30.8 mg, 67%). ESI-MS m/z: 615.15 [M+H]⁺.

Example 203

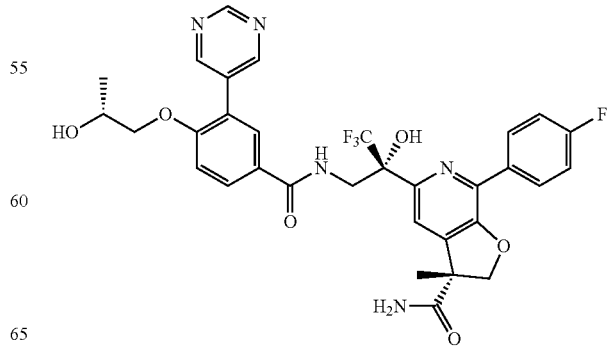

Example 203 Step a

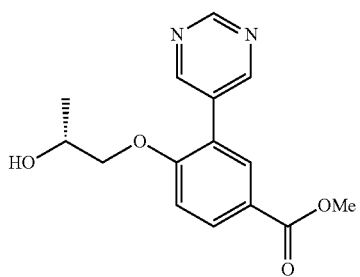 [SMILES: COC(=O)c1ccc(OC[C@@H](C)O)c(-c2cncnc2)c1]

In a vial, methyl (R)-3-bromo-4-(2-hydroxypropoxy)benzoate (100 mg, 0.346 mmol), PdCl$_2$(dppf) (25.3 mg, 0.035 mmol), K$_2$CO$_3$ (120 mg, 0.865 mmol), and pyrimidin-5-ylboronic acid (64.3 mg, 0.519 mmol) were dissolved in Dioxane (1.383 ml) and Water (0.346 ml). The reaction was heated to 85° C. overnight. The reaction was cooled to RT and water was added. The aqueous layer was washed with EtOAc and the combined organic layer was dried over MgSO$_4$. Crude reaction purified by silica gel chromatography 0-100% EtOAc/Hexanes to provide title compound (54 mg, 54%). ESI-MS m/z: 289.10 [M+H]$^+$.

Example 203 Step b

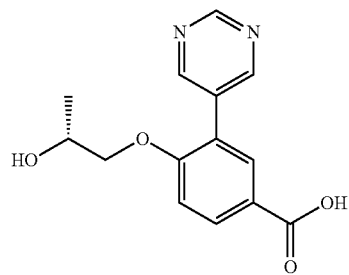 [SMILES: C[C@@H](O)COc1ccc(C(=O)O)cc1-c1cncnc1]

In a vial, methyl methyl (R)-4-(2-hydroxypropoxy)-3-(pyrimidin-5-yl)benzoate (54 mg, 0.187 mmol) and lithium hydroxide (22.43 mg, 0.937 mmol) were dissolved in THF (0.3 ml), MeOH (0.3 ml), and Water (0.3 ml). The reaction was allowed to stir overnight. Water was added and 1M aq. HCl was added to pH 2-3. White precipitate was filtered and dried under vacuum to give (R)-4-(2-hydroxypropoxy)-3-(pyrimidin-5-yl)benzoic acid (38 mg, 74%) as a white solid. ESI-MS m/z: 275.02 [M+H]$^+$

Example 203 Step c

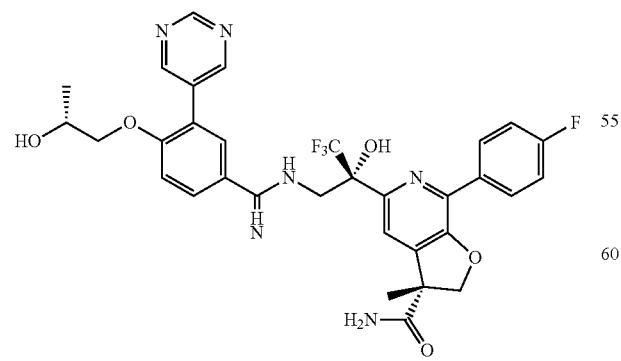

The title compound was prepared in an analogous fashion to Method J with amine (30 mg, 0.075 mmol), and the material was purified by prep-HPLC (20-90%, MeCN/Water, 25 min) to afford the title compound (35 mg, 66%). ESI-MS m/z: 656.24 [M+H]$^+$.

Example 204

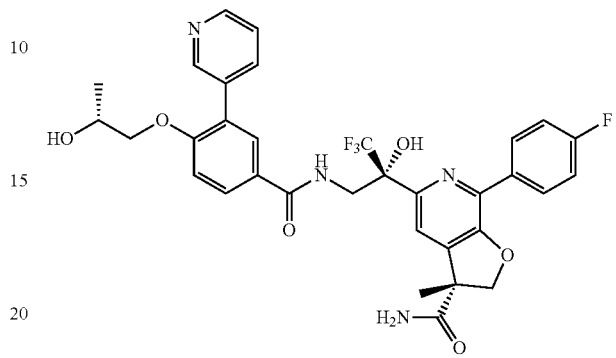

The title compound was prepared in an analogous fashion using Example 203 above and Method J with amine (30 mg, 0.075 mmol), and the material was purified by prep-HPLC (20-90%, MeCN/Water, 25 min) to afford the title compound (1.2 mg, 3%). ESI-MS m/z: 655.18 [M+H]$^+$.

Example 205

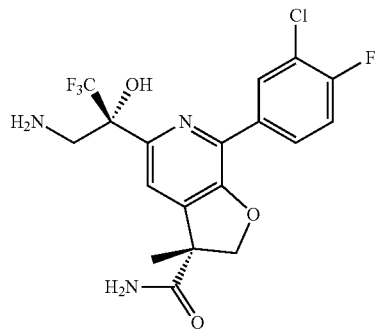

Example 205 Step a

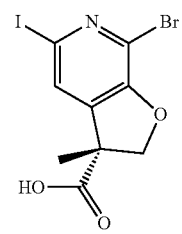

Into a 100 mL round-bottom flask were added Example 1, step b (3.80 g, 10.27 mmol), acetone (100 mL), the solution was cooled to 0° C., and then Jones reagent (1.9~2.2 M, 10 mL) was added dropwise (with internal temperature monitoring). The reaction was warmed to room temperature and monitored by LCMS (3 hr). The reaction was cooled to 0°

C., quenched with <sup>i</sup>PrOH and stirred for 15 minutes. The reaction was diluted with EtOAc and water. The aqueous was extracted, the combined organics were dried and concentrated under reduced pressure to get the crude product as a yellow solid (3.95 g, 99%). ESI-MS m/z: 383.80 [M+H]$^+$.

Example 205 Step b

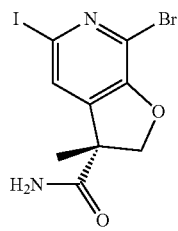

Into a 100 mL round-bottom flask were added the compound from step a (3.95 g, 10.28 mmol), NH$_4$Cl (1.10 g, 20.57 mmol) and the solids dissolved in DMF (20 mL). Hunig's base (5.27 mL, 30.84 mmol) was added, the reaction was cooled to 0° C., and HATU (7.82 g, 20.56 mmol) was added. The reaction was warmed to room temperature and monitored by LCMS (1 hr). The reaction was diluted with EtOAc and water. The aqueous was extracted, the combined organics were dried and concentrated. The material was purified by automated column chromatography (silica gel, 0-100% EtOAc in hexanes) to afford the title compound (3 g, 76%). ESI-MS m/z: 382.95 [M+H]$^+$.

Example 205 Step c

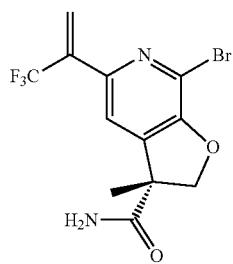 [SMILES: C=C(c1cc2c(c(Br)n1)OC[C@]2(C)C(N)=O)C(F)(F)F]

Into a 100 mL round-bottom flask were added the compound from step b (3.00 g, 7.83 mmol), 3,3,3-trifluoroprop-1-en-2-ylboronic acid (2.19 g, 15.65 mmol), Pd(dppf)Cl$_2$ (1.15 g, 1.56 mmol), and the material dissolved in dioxane (40 mL) and H$_2$O (5 mL). K$_2$CO$_3$ (3.25 g, 23.50 mmol) was then added and the resulting mixture was stirred for 1 h at 90° C. under nitrogen atmosphere. The mixture was cooled to room temperature, poured into water, extracted with EtOAc and the combined organics were concentrated under reduced pressure. The residue was purified by column chromatography (silica gel, 0-100% EtOAc in hexanes) to afford desired product as a brown oil (2.3 g, 83%). ESI-MS m/z: 350.90 [M+H]$^+$.

Example 205 Step d

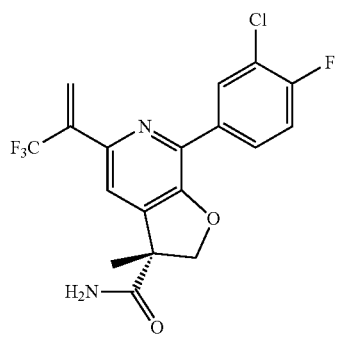 [SMILES: C=C(c1cc2c(c(-c3ccc(F)c(Cl)c3)n1)OC[C@]2(C)C(N)=O)C(F)(F)F]

To a stirred solution of step c (5.00 g, 14.24 mmol) and 3-chloro-4-fluorophenylboronic acid (3.72 g, 21.33 mmol) in THF (80 mL) were added Na$_2$CO$_3$ (3.32 g, 31.33 mmol), H$_2$O (20 mL) and Pd(PPh$_3$)$_2$Cl$_2$ (1.00 g, 1.42 mmol). The resulting mixture was stirred for 1 h at 70° C. under nitrogen atmosphere. The reaction was monitored by TLC and LCMS. The resulting mixture was extracted with EtOAc, and the combined organic layers were washed with brine, dried, and concentrated under reduced pressure. The residue was purified by automated column chromatography (silica gel, 0-75% EtOAc in hexanes) to afford the title compound as a yellow solid (5.8 g, 99%). ESI-MS m/z: 401.05 [M+H]$^+$.

Example 205 Step e

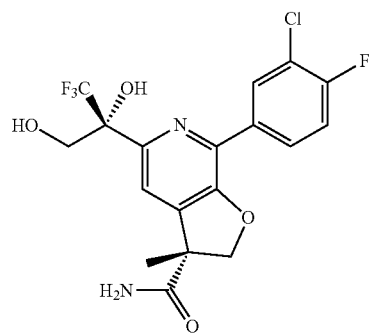 [SMILES: C[C@]1(C(N)=O)COc2c1cc([C@@](O)(CO)C(F)(F)F)nc2-c1ccc(F)c(Cl)c1]

To a 500 mL round-bottom flask equipped with a stir bar was added AD-mix-β (33.82 g, 43.41 mmol) and methanesulfonamide (1.38 g, 14.47 mmol). The solids were dissolved in tBuOH (60 mL) and H$_2$O (100 mL), and the flask cooled to 0° C. and the compound from step d (5.80 g, 14.47 mmol) was added slowly as a solution of tBuOH (40 mL). The reaction was allowed to warm to room temperature naturally and stirred for 16 hrs. The reaction was quenched with the addition of sodium sulfite (0.25 g per g AD-mix), diluted with water and EtOAc. The layers were separated, and the aqueous layer was extracted with EtOAc. The combined organics were washed with brine, dried over Na$_2$SO$_4$, filtered concentrated and purified by automated column chromatography (silica gel, 0-100% EtOAc in hexanes) to afford the title compound as a white solid (5.48 g, 87%). ESI-MS m/z: 435. [M+H]$^+$.

Example 205 Step f

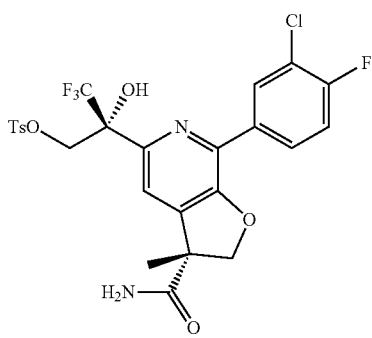 [SMILES: Cc1ccc(S(=O)(=O)OC[C@](O)(c2cc3c(c(-c4ccc(F)c(Cl)c4)n2)OC[C@]3(C)C(N)=O)C(F)(F)F)cc1]

Into a 250 mL round-bottom flask were added the compound from step e (4.70 g, 10.81 mmol) and DCM (80 mL) at room temperature. The solution was cooled to 0° C., and DMAP (264 mg, 2.16 mmol), TEA (3.28 g, 32.43 mmol and TsCl (2.47 g, 12.97 mmol) were then sequentially added. The resulting mixture was stirred for 1 h at 0° C. The mixture was acidified to pH 4 with 2 M HCl, and the aqueous extracted with DCM. The combined organic layers were dried over anhydrous $Na_2SO_4$ and concentrated under reduced pressure to afford the crude product as a light-yellow solid (6.2 g, 97%). ESI-MS m/z: 589.15 $[M+H]^+$.

Example 205 Step g

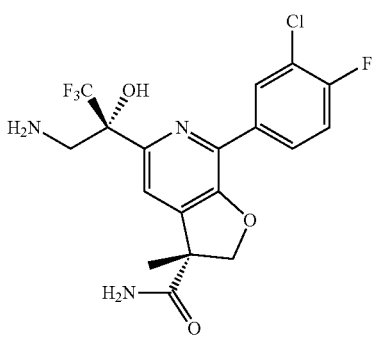

Into a 100 mL round-bottom flask was added $NH_3$ in MeOH (35 mL) at room temperature, and the compound from step g (6.20 g, 10.52 mmol) was slowly added. The resulting mixture was stirred at room temperature and monitored by LCMS (5 hr). The mixture was dissolved in EtOAc, washed with sat. sodium bicarbonate 3×, brine, dried, and concentrated to afford the title compound (2.93 g, 64%). ESI-MS m/z: 434.05 $[M+H]^+$.

Example 206

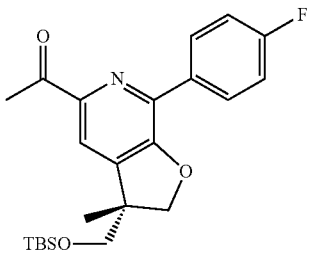 [SMILES: CC(=O)c1cc2c(c(-c3ccc(F)cc3)n1)OC[C@]2(C)CO[Si](C)(C)C(C)(C)C]

Example 206 Step a

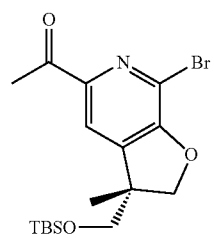 [SMILES: CC(=O)c1cc2c(c(Br)n1)OC[C@]2(C)CO[Si](C)(C)C(C)(C)C]

To a 100-mL round bottom flask containing the compound from (R)-7-bromo-3-(((tert-butyldimethylsilyl)oxy)methyl)-5-iodo-3-methyl-2,3-dihydrofuro[2,3-c]pyridine (4.32 g, 8.94 mmol) was added a stir bar, N-methoxy-N-methylacetamide (1.43 mL, 13.4 mmol) and THF (45 ml). The flask was purged with nitrogen, cooled to −40° C. and ethyl trifluoroacetate (2.317 ml, 19.40 mmol) was added. Isopropylmagnesium chloride (5.16 mL, 10.3 mmol) was then slowly added, the reaction was monitored by LCMS (stirred for 3 h between −40 and −20° C.). The reaction was quenched with 5 mL MeOH, and allowed to warm to room temperature. The mixture was diluted with water and EtOAc, the phases were separated and the aqueous layer washed with EtOAc, the combined organics were washed with brine, dried over $Na_2SO_4$, filtered, concentrated and purified by automated silica gel chromatography (0-5% EtOAc/hexanes) to afford the title compound as a clear, sticky residue (3.00 g, 84%.) ESI-MS m/z: 400.1/402.0 $[M+H]^+$.

Example 206 Step b

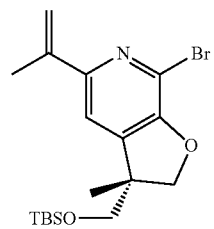 [SMILES: C=C(C)c1cc2c(c(Br)n1)OC[C@]2(C)CO[Si](C)(C)C(C)(C)C]

To a 250-mL round bottom flask containing methyltriphenylphosphonium bromide (5.34 g, 15.0 mmol), was added THF (42 mL), the mixture was cooled to 0° C. and potassium tert-butoxide (1.60 g, 14.2 mmol) was added slowly as a solution in THF (14 mL). The yellow suspension was stirred for 30 min at 0° C., then step a (4.327 g, 8.94 mmol) was added as a solution in THF (33 mL). The reaction was allowed to warm to room temperature and monitored by LCMS until complete (6.5 h.) The reaction was then quenched with 5 mL MeOH, and allowed to warm to room temperature. The mixture was diluted with water and EtOAc, the phases were separated and the aqueous layer washed with EtOAc, the combined organics were washed with brine, dried over Na₂SO₄, filtered, concentrated and purified by automated silica gel chromatography (0-5% EtOAc/hexanes,) to afford the title compound as a clear, sticky residue (2.88 g, 94%.) ESI-MS m/z: 398.2/400.1 [M+H]⁺.

Example 206 Step c

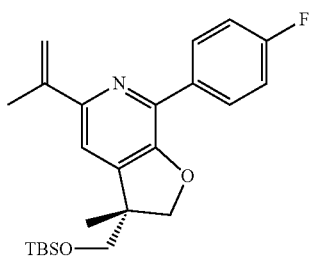 [SMILES: C=C(C)c1cc2c(c(-c3ccc(F)cc3)n1)OC[C@]2(C)CO[Si](C)(C)C(C)(C)C]

The title compound was synthesized according the procedure in Example 205, step d using 1.2 eq. of (4-fluorophenyl)boronic acid, and the compound from step b (2.13 g 5.36 mmol). The residue was purified by automated silica gel chromatography (0-5% EtOAc/hexanes) to give the title compound as a colorless oil. (2.19 g, 99%.) ESI-MS m/z: 414.8 [M+H]⁺.

Example 206 Step d

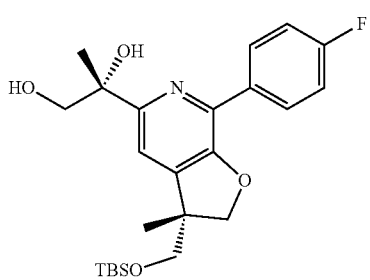 [SMILES: CC(C)(C)[Si](C)(C)OC[C@@]1(C)COc2c1cc([C@@](C)(O)CO)nc2-c1ccc(F)cc1]

A suspension of AD-mix-β (8.26 g, 10.6 mmol) and methanesulfonamide (0.504 g, 5.30 mmol) in water (26.5 mL) and tBuOH (2 mL) was cooled to 0° C. then was added the compound from step c (2.19 g, 5.30 mmol) as a solution in tBuOH (24.5 ml). The reaction was allowed to warm to room temperature with stirring for 16 h and was then quenched with the addition of sodium sulfite (2.00 g, 15.9 mmol), diluted with water and EtOAc. The layers were separated, and the aqueous layer was washed with EtOAc. The combined organics were washed with brine, dried over Na₂SO₄, filtered concentrated and purified by automated silica gel chromatography to afford the title compound (2.19 g, 89%) as a sticky, colorless oil. ESI-MS m/z: 448.7 [M+H]⁺.

Example 206 Step e

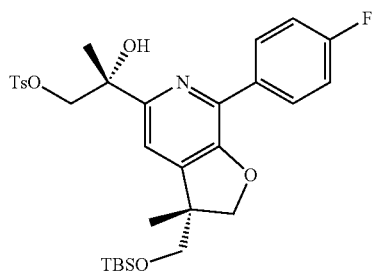 [SMILES: Cc1ccc(S(=O)(=O)OC[C@](C)(O)c2cc3c(c(-c4ccc(F)cc4)n2)OC[C@]3(C)CO[Si](C)(C)C(C)(C)C)cc1]

To a solution of the compound from step d (2.30 g, 5.13 mmol) was added triethylamine (2.1 mL, 15 mmol) and DMAP (627 mg, 5.13 mmol), the mixture was cooled in an ice bath, then TsCl (1.1 eq) was added slowly as a solid. The reaction was monitored by LCMS until complete (2 h), the reaction mixture was then concentrated and purified by automated silica gel chromatography (0-15% EtoAc/hexanes) to afford the title compound (2.97 g, 97%) as a white solid. ESI-MS m/z: 602.6 [M+H]⁺.

Example 206 Step f

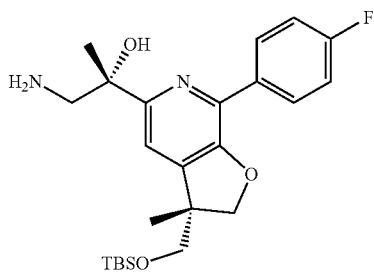

To a 250 mL flask, with stir bar was added ammonia in MeOH (116 mL, 7 M, 812 mmol) and the compound from step e (4.16 g, 6.92 mmol) was added as a solution in MeOH (10 mL). The reaction was monitored by LCMS until complete (62 h) and was then concentrated, placed under vacuum for 1 h and used in the next step directly. ESI-MS m/z: 447.6 [M+H]⁺.

Example 206 Step g

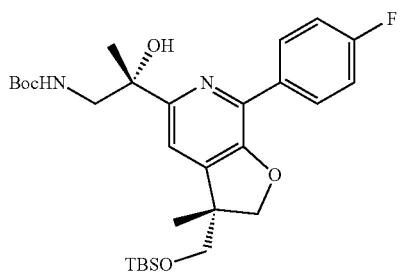 [SMILES: CC(C)(C)OC(=O)NC[C@](C)(O)c1cc2c(c(-c3ccc(F)cc3)n1)OC[C@]2(C)CO[Si](C)(C)C(C)(C)C]

The title compound was synthesized according to the procedure in Example 32, step a using the compound from step f (3.09 g, 6.92 mmol) and 1.1 equiv of Boc-anhydride.

The reaction mixture was purified by automated silica gel chromatography (0-15% EtOAc/hexanes) to afford the title compound (3.39 g, 90% over two steps) as a yellow oil. ESI-MS m/z: 547.7 [M+H]$^+$.

Example 206 Step h

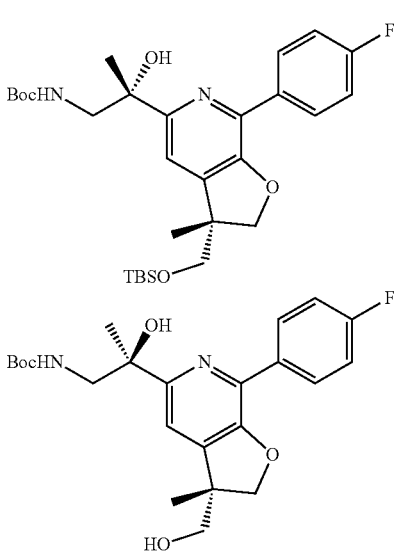

The title compound was prepared according to Method A using the compound from step g (3.39 g, 6.20 mmol) and 2.0 equiv TBAF. After aqueous workup the mixture was purified by automated silica gel chromatography (0-100% EtOAc/hexanes) to afford the title compounds as white solids as single diastereomers (2.19 g, 82% peak 1=P1, 192 mg, 7% peak 2=P2). Product 2 arises from imperfect selectivity in step d but was not apparent nor separable before this step. ESI-MS m/z: 433.5 [M+H]$^+$=P1, ESI-MS m/z: 433.5 [M+H]$^+$=P2.

Example 206 Step i

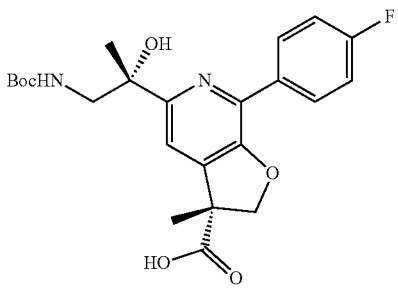 [SMILES: CC(C)(C)OC(=O)NC[C@](C)(O)c1cc2c(c(-c3ccc(F)cc3)n1)OC[C@]2(C)C(=O)O]

To a suspension of P1 from step h (220 mg, 0.508 mmol) in aqueous sodium hydroxide (1.2 mL, 5 wt %, 1.5 mmol), was added dropwise potassium permanganate (281 mg 0.778 mmol) as a solution in water (5.6 mL). The reaction was monitored by LCMS until complete (42 h), and was then cooled to 0° C., and quenched with the dropwise addition of sodium sulfite (640 mg, 5.08 mmol) as a solution in water (6.4 mL). The mixture was then acidified to pH 1-3 with the addition of 1 M HCl. The solids were collected on a frit and washed extensively with water to afford the title compound (137 mg, 60%) as a white solid. ESI-MS m/z: 447.3 [M+H]$^+$.

Example 206 Step j

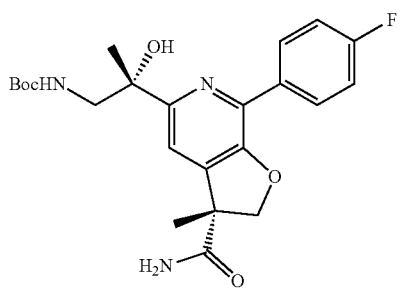 [SMILES: CC(C)(C)OC(=O)NC[C@](C)(O)c1cc2c(c(-c3ccc(F)cc3)n1)OC[C@]2(C)C(N)=O]

The title compound was synthesized according to Example 205 step b using 137 mg of the compound from step i and 10 equiv of NH$_4$Cl. The compound was purified by automated silica gel chromatography (0-100% EtOAc/hexanes) to afford the title compound (86 mg, 63%) as a white solid. ESI-MS m/z: 446.4 [M+H]$^+$.

Example 206 Step k

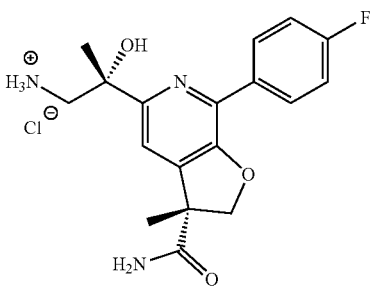 [SMILES: [Cl-] ; C[C@](O)(CN)c1cc2c(c(-c3ccc(F)cc3)n1)OC[C@]2(C)C(N)=O]

A suspension of the compound from step j (259 mg, 0.580 mmol) in DCM (7.3 mL) was cooled to 0° C. and HCl in water (1.5 mL, 4 N, 5.8 mmol) was added. The reaction was monitored by TLC and LCMS until complete (2 h,) at which time diethyl ether (20 mL) was added, and the mixture stirred for 1 h, as white solids precipitated. The solids were collected by filtration to afford the title compound (184 mg, 83%) as a white solid. ESI-MS m/z: 346.3 [M+H]$^+$.

Example 207

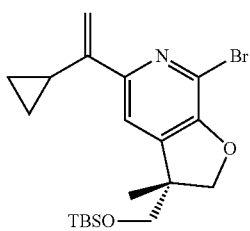 [SMILES: C=C(c1cc2c(c(Br)n1)OC[C@]2(C)CO[Si](C)(C)C(C)(C)C)C1CC1]

This intermediate was used for the synthesis of a wide variety of analogs in an analogous sequence to Examples 205 and 206.

This example was prepared in an analogous sequence to Example 206, instead using N-methoxy-N-methylcyclopropanecarboxamide. The residue was purified by silica gel column chromatography (10% EtOAc/hexanes) to afford the desired product as a yellow-green oil. ESI-MS m/z: 424.10 [M+H]$^+$.

Example 208 Step a

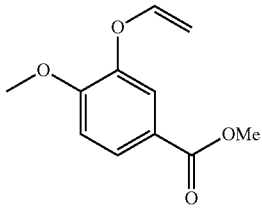

A solution of methyl 3-hydroxy-4-methoxybenzoate (20 g, 0.11 mol), vinyl acetate (19 g, 0.22 mol), [Ir(cod)Cl]$_2$ (62.4 mg, 0.11 mol) and NaHCO$_3$ (18.44 g, 0.22 mol) in toluene (500 mL) was stirred for 3 h at 110° C. under a N$_2$ atmosphere. The resulting mixture was concentrated under vacuum and the residue purified by silica gel column chromatography (20% EtOAc in hexanes, 30 min) to the desired compound as a yellow oil (10.4 g, 45%). ESI-MS m/z: 209.10 [M+H]$^+$.

Example 208 Steps b and c

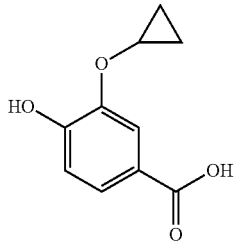 [SMILES: O=C(O)c1ccc(O)c(OC2CC2)c1]

To a stirred solution of the compound step a (10.4 g, 47.84 mmol) in DCE (200 mL) were added CH$_2$I$_2$ (25.65 g, 95.69 mmol) and Et$_2$Zn (1 M, 96 mL, 96 mmol) in portions at 0° C. under nitrogen atmosphere. The resulting mixture was stirred for 16 h at 0° C. under nitrogen atmosphere. The reaction was quenched by the addition of water DCM and the combined organics were washed with brine, dried and concentrated. The crude material was purified by reverse phase C18 column chromatography (MeCN/H$_2$O) to give the desired compound as a yellow solid (7.8 g, 70%). ESI-MS m/z: 223.10 [M+H]$^+$.

To a stirred solution of the compound from step b (7.8 g, 35.13 mmol) in DCM (100 mL) were added BBr$_3$ (22 g, 88 mmol) in portions at 0° C. under nitrogen atmosphere. The resulting mixture was stirred for 3 h at 0° C. and the reaction was quenched by the addition of NaHCO$_3$ (aq.). The resulting mixture was extracted with DCM and the combined organic was washed with brine, dried and concentrated. The crude material was purified by reverse phase C18 column chromatography (MeCN/H$_2$O) to give the desired compound as a yellow solid (4.6 g, 67%). ESI-MS m/z: 195.05 [M+H]$^+$.

Example 208 Step d

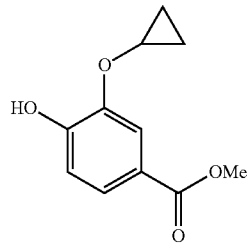 [SMILES: COC(=O)c1ccc(O)c(OC2CC2)c1]

A solution of the compound from step c (4.6 g, 23.59 mmol) in MeOH (40 mL) and H$_2$O (3 mL) was stirred for 3 hr at 80° C. under a nitrogen atmosphere. The resulting mixture was concentrated under vacuum and the residue was purified by silica gel column chromatography (20% EtOAc in hexanes, 30 min) to afford the desired compound as a yellow oil (4.7 g, 95.91%). ESI-MS m/z: 209.10 [M+H]$^+$.

Example 208 Steps e and f

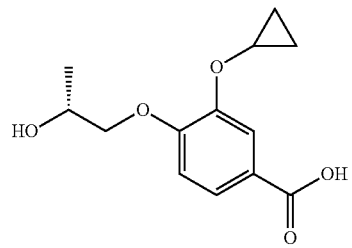 [SMILES: C[C@@H](O)COc1ccc(C(=O)O)cc1OC1CC1]

To a stirred solution of methyl 3-cyclopropoxy-4-hydroxybenzoate (4.0 g, 20 mmol) and (+)-propylene oxide (3.43 g, 60 mmol) in DMF (50 mL) were added K$_2$CO$_3$ (5.4 g, 40 mmol), and the resulting mixture was stirred for 16 hr at 80° C. The reaction was quenched with water at 0° C., and the resulting mixture was extracted with EtOAc. The combined organics were washed with brine, dried and concentrated. The crude material was purified by silica gel column chromatography (0-75% EtOAc in hexanes) to afford the product (3 g, 58%). ESI-MS m/z: 262.10 [M+H]$^+$.

The methyl ester was hydrolyzed in a similar manner to Method O, and the material was purified by reverse phase prep-HPLC (MeCN/H$_2$O) to give the desired compound as a yellow solid (1.95 g, 68%). ESI-MS m/z: 253.10 [M+H]$^+$.

Example 209

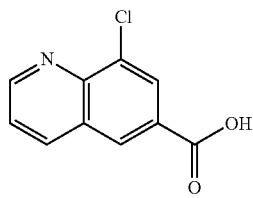

A solution of 8-chloroquinoline-6-carboxylic acid (5 g, 29.14 mmol) and acrolein (3.27 g, 58.28 mmol) in AcOH:

HCl (2:3, 20 mL) was stirred for 1 hour at 100° C. under N₂ atmosphere. The resulting solution was concentrated, and the crude material was purified by reverse phase C18 column chromatography (MeCN/H₂O) to afford desired product (1.088 g, 18%) as a white solid. ESI-MS m/z: 208.20 [M+H]⁺.

Example 210

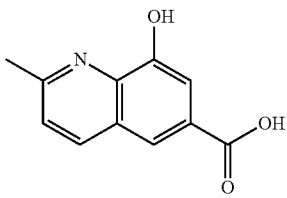

A solution of 4-amino-3-hydroxybenzoic acid (600 mg, 3.91 mmol) and crotonaldehyde (824 mg, 11.75 mmol) in AcOH:HCl (2:3, 10 mL) was stirred for 1 hour at 100° C. under N₂ atmosphere. The resulting solution was concentrated, and the crude material was purified by reverse phase C18 column chromatography (MeCN/H2O) to afford desired product (600 mg, 75%). ESI-MS m/z: 203.95 [M+H]⁺.

Example 211

Method P

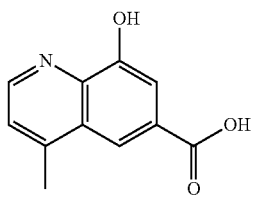

To a suspension of 4-amino-3-hydroxybenzoic acid (4.6348 g, 30.3 mmol) in a concentrated aqueous solution of hydrochloric acid (50.4 mL) was added but-3-en-2-one (4.88 ml, 60.5 mmol). The reaction mixture was stirred at 100° C. for 4 h. The mixture was cooled to room temperature and solids were collected by filtration to afford the desired product 8-hydroxy-4-methylquinoline-6-carboxylic acid (5.62 g, 91%) as a yellow solid. ESI-MS m/z: 203.9 [M+H]⁺.

Example 212

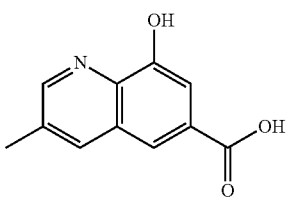

The title compound was synthesized according to Method P using 493 mg 4-amino-3-hydroxybenzoic acid and 533 µl methacrolein. Solids were collected by filtration to afford the title compound (195 mg, 30%) as a yellow solid. ESI-MS m/z: 203.9 [M+H]⁺.

Example 213

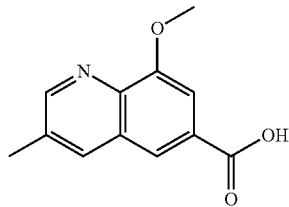 [SMILES: COc1cc(C(=O)O)cc2cc(C)cnc12]

The title compound was synthesized according to Method P using 5.00 g 4-amino-3-methoxybenzoic acid and 5.0 ml methacrolein. The aqueous layer was washed with EtOAc (4×20 mL), solids had then precipitated in the aqueous layer, these were collected by filtration to afford the title compound (1.23 g, 19%) as a yellow solid. ESI-MS m/z: 218.0 [M+H]⁺.

Example 214

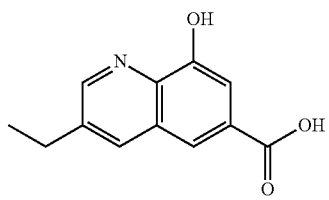 [SMILES: CCc1cnc2c(O)cc(C(=O)O)cc2c1]

The title compound was synthesized according to Method P using 2.00 g 4-amino-3-hydroxybenzoic acid and 1.82 g 2-methylenebutanal. The aqueous layer was washed with EtOAc (4×5 mL), solids had then precipitated in the aqueous layer, these were collected by filtration to afford the title compound (70 mg, 3%) as a yellow solid. ESI-MS m/z: 218.1 [M+H]⁺.

Example 215

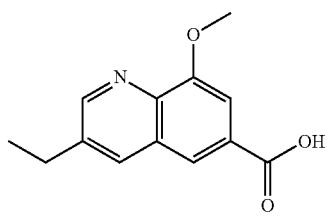 [SMILES: CCc1cnc2c(OC)cc(C(=O)O)cc2c1]

The title compound was synthesized according to Method P using 2.98 g 4-amino-3-methoxybenzoic acid and 3.00 g 2-methylenebutanal. The aqueous layer was washed with EtOAc (4×5 mL), solids had then precipitated in the aqueous layer, these were collected by filtration to afford the title compound (811 mg, 20%) as a yellow solid. ESI-MS m/z: 232.1 [M+H]⁺.

Example 216 Step a

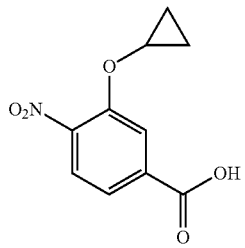

To a solution of methyl 3-fluoro-4-nitrobenzoate (5.66 g, 28.4 mmol) in DMF (56 mL) was added $Cs_2CO_3$ (13.89 g, 42.6 mmol) and cyclopropanol (2.7 ml, 42.6 mmol). The mixture was heated to 75° C. for 16 h, then cooled to room temperature and diluted with $H_2O$ (30 mL) and extracted with EtOAc (3×30 mL). The combined organic phase was washed with water (2×5 mL) then saturated aqueous NaCl (5 mL) and dried over $Na_2SO_4$. The crude material was carried forward to the next step directly. ESI-MS m/z: 237.7 $[M+H]^+$.

Example 216 Steps b and c

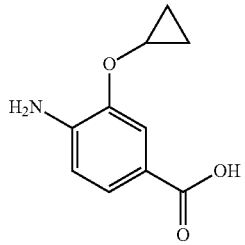 [SMILES: O=C(O)c1ccc([N+](=O)[O-])c(OC2CC2)c1]

To a solution of the compound from step a (6.74 g, 28.4 mmol) in EtOH (151 ml) and water (37.9 ml) was added iron (7.93 g, 142 mmol) and ammonium chloride (15.19 g, 284 mmol). The mixture was heated to 75° C. for 1 h, then cooled to room temperature and filtered through celite. The pH of the filtrate was adjusted to 9-11 using $NaHCO_3$, then diluted with EtOAc. The phases were separated and the aqueous layer was washed with EtOAc (4×50 mL), the combined organics were washed with saturated aqueous NaCl (20 mL), dried over $Na_2SO_4$ filtered, concentrated and purified by automated silica gel chromatography (0-20% EtOAc/hexanes) to afford the title compound as yellow oil (4.25 g, 72.2% yield over two steps). ESI-MS m/z: 208.0 $[M+H]^+$.

To solution of the compound from step b (6.74 g, 28.4 mmol) in THF (15 ml) was added potassium trimethylsilanolate (3.96 g, 28.6 mmol). The mixture was quenched with MeOH, then concentrated and used directly in the next step. ESI-MS m/z: 193.9 $[M+H]^+$.

Example 216 Step d

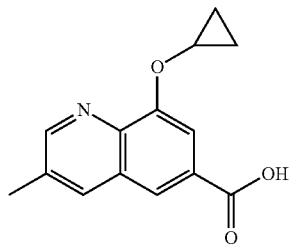 [SMILES: Cc1cnc2c(OC3CC3)cc(C(=O)O)cc2c1]

This example was prepared by Method P using the compound from step c and methacrolein.

After the reaction was complete the aqueous layer was washed with EtOAc (3×15 mL), the aqueous layer was then concentrated to dryness, the resulting solids were washed with MeOH (3 mL) and collected to afford desired product as yellow solids (160 mg, 14% over two steps). ESI-MS m/z: 244.0 $[M+H]^+$.

Example 217 Steps a and b

Method R

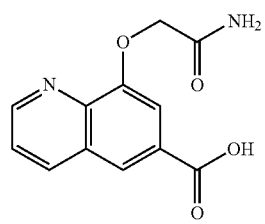

To a 50 mL round-bottom flask equipped with a stir bar was added methyl 8-hydroxyquinoline-6-carboxylate (500 mg, 2.461 mmol), 2-bromoacetamide (509 mg, 3.69 mmol) and potassium carbonate (850 mg, 6.15 mmol). The solids were dissolved in DMF (0.5 M), the reaction stirred at 40° C. and monitored by LCMS (3 hrs). The reaction was cooled to room temperature, diluted with EtOAc and quenched with water. Solid precipitated (quinoline products have solubility issues). Added DCM and hexanes to further precipitate. Stirred vigorously. Filtered and washed multiple times with DCM to afford the title compound as a light-brown solid (620 mg, 97%). ESI-MS m/z: 244.0 $[M+H]^+$.

To a 20-mL vial containing step a (400 mg, 1.537 mmol) was added a stir bar. The compound was dissolved in THF and MeOH, and Water (1:2:1, 0.33 M). Lithium hydroxide hydrate (129 mg, 3.07 mmol) was then added, the reaction stirred at room temperature and monitored by LCMS (30 min, acetamide can hydrolyze if too much LiOH). The reaction was cooled to 0° C., acidified with 2 M HCl, and the pH brought to around 4-5. The organics and aqueous was concentrated (product aqueous soluble). Place on high vacuum. The solid was suspended in minimal MeOH (white solid precipitated) and filtered to remove LiCl salts. The solid was rinsed with minimal MeOH, dried under high vacuum overnight to afford the title compound as a light brown/pink solid (240 mg, 63%). ESI-MS m/z: 246.994 $[M+H]^+$.

Example 218

Method 1

Example 218 Method 1 Step a

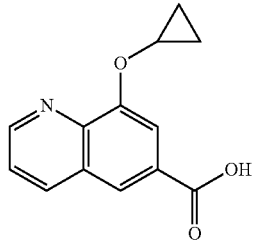 [SMILES: O=C(O)c1cc(OC2CC2)c2ncccc2c1]

The vinyl ether was synthesized in an analogous fashion to Example 208 step a utilizing methyl 8-hydroxyquinoline-6-carboxylate (5 g, 24.6 mmol). The material was purified by automated column chromatography to afford the title compound (1.97 g, 35%). ESI-MS m/z: 230.10 [M+H]⁺.

Example 218 Method 1 Steps b and c

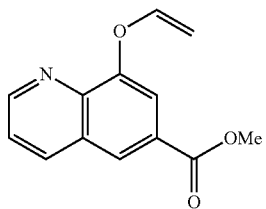 [SMILES: C=COc1cc(C(=O)OC)cc2cccnc12]

The cyclopropanation was carried out according to Example 208 step b using step a. The material was purified by automated column chromatography to afford the title compound (1.67 g, 80%). ESI-MS m/z: 243.08 [M+H]⁺.

The methyl ester was hydrolyzed in a similar manner to Method O, and the material was purified by reverse phase prep-HPLC (MeCN/H$_2$O) to give the desired compound as a white solid (1.50 g, 95%). ESI-MS m/z: 230.05 [M+H]⁺.

Method 2

Example 218 Method 2 Steps a, b, c

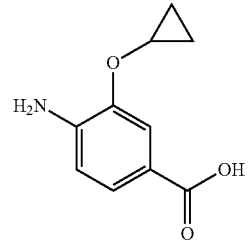

Cyclization precursor was synthesized in an analogous fashion to Example 216 steps a, b and c above. ESI-MS m/z: 194.0 [M+H]⁺.

Example 218 Method 2 Step d

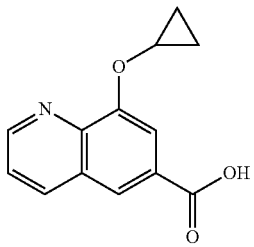 [SMILES: O=C(O)c1cc(OC2CC2)c2ncccc2c1]

The following example was prepared according to Method P using acrolein (1.5 eq) and step c to afford the title compound as a light, brown solid (5.2 g, 74%). ESI-MS m/z: 208.0 [M+H]⁺.

Method 3

Example 218 Method 3 Step a

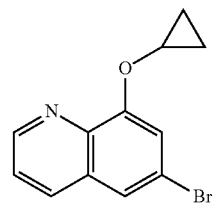 [SMILES: Brc1cc(OC2CC2)c2ncccc2c1]

To a 250-mL tank equipped with a stir bar was added to 6-bromoquinolin-8-ol (10 g, 44.64 mmol). The solid was dissolved in NMP (100 mL), then bromocyclopropane (10.8 g, 89.28 mmol), Cs$_2$CO$_3$ (43.52 g, 133.92 mmol) and KI (29.64 g, 178.56 mmol) were added. The sealed tank was stirred for 16 hr at 180° C. The resulting mixture was diluted with water and extracted with EtOAc. The residue was purified by silica gel column chromatography (0-20% EtOAc/hexanes) to give the desired product as a yellow oil (4.5 g, 38%). ESI-MS m/z: 263.90 [M+H]⁺.

Example 218 Method 3 Step b

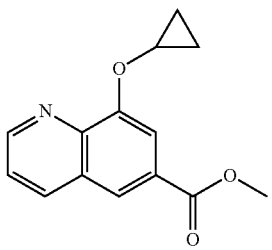 [SMILES: COC(=O)c1cc(OC2CC2)c2ncccc2c1]

To a stirred solution of step a (4.50 g, 17.03 mmol) in MeOH (50 mL) was added TEA (5.17 g, 51.11 mmol) and Pd(dppf)Cl$_2$ (1.25 g, 1.70 mmol). The resulting mixture was stirred for 4 hr at 100° C. under a CO atmosphere (10 atm). The reaction was monitored by LCMS. The resulting mixture was concentrated under reduced pressure. The residue was purified by silica gel column chromatography (0-20% EtOAc/hexanes) to afford the title compound (2.9 g, 70%) as a light-yellow solid. ESI-MS m/z: 244.05 [M+H]$^+$.

Example 218 Method 3 Step c

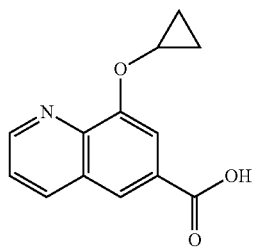 [SMILES: O=C(O)c1cc(OC2CC2)c2ncccc2c1]

The methyl ester was hydrolyzed in a similar manner to Method O, and the material was purified by reverse phase flash chromatography (MeCN/H$_2$O) to give the desired compound as a white solid (1.30 g, 48%). ESI-MS m/z: 230.15 [M+H]$^+$.

Method 4

Example 218 Method 4 Step a

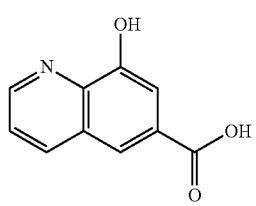 [SMILES: O=C(O)c1cc(O)c2ncccc2c1]

The following example was prepared according to Method P using acrolein (2.0 eq) to afford the title compound as a yellow solid (9.0 g, 36%). ESI-MS m/z: 208.0 [M+H]$^+$.

Example 218 Method 4 Step b

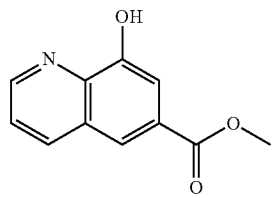

A solution of step a (9.00 g, 47.57 mmol) in 98% H$_2$SO$_4$ (8 mL) and MeOH (100 mL) was stirred for 2 h at 80° C. The resulting mixture was concentrated under reduced pressure. The crude material was diluted with EtOAc, washed with water and saturated NaHCO$_3$ and concentrated to afford the title compound (8.9 g, 91%) as a yellow solid. ESI-MS m/z: 204.05 [M+H]$^+$.

Example 218 Method 4 Steps c and d

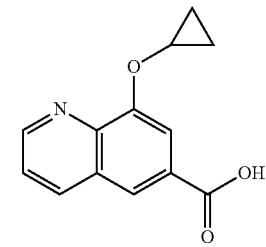 [SMILES: O=C(O)c1cc(OC2CC2)c2ncccc2c1]

The bromocyclopropane alkylation was carried out using step b in an analogous fashion to Example 218, Method 3 step a. The methyl ester hydrolysis was carried out in an analogous fashion to Example 218 Method 3 step c.

The following examples in Table 3 were prepared using the corresponding intermediates from Examples 205-207, or derivatives thereof. The target compounds were made according to Method J with PyBOP (and in some cases HATU) using either amine or amine HCl salt. The crude material was purified by Gilson prep-HPLC (20-90%, MeCN/Water, 25 min) in most cases. The aryl acid coupling partners were made according to Examples 208-218, and if not specifically listed, they were synthesized in an analogous manner.

TABLE 3

| Example | Structure | MS+ m/z |
|---|---|---|
| 219 | 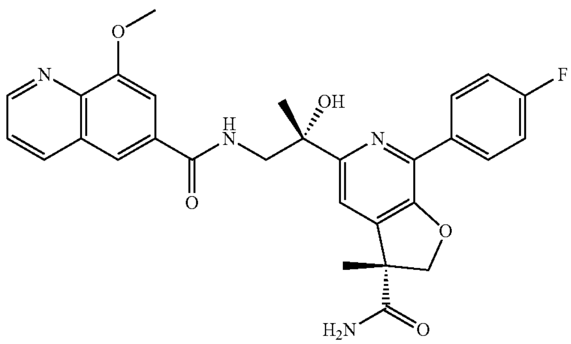 [SMILES: COc1cc(C(=O)NC[C@](C)(O)c2cc3c(c(-c4ccc(F)cc4)n2)OC[C@]3(C)C(N)=O)cc2cccnc12] | 531.20 |
| 220 | 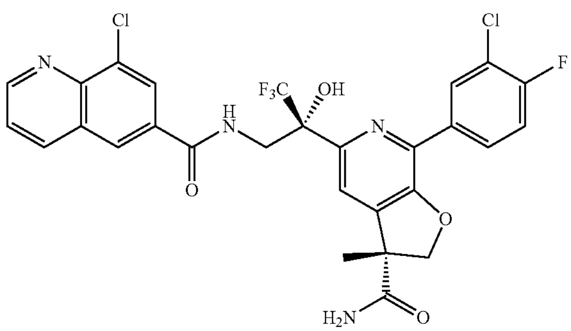 [SMILES: C[C@]1(C(N)=O)COc2c1cc([C@@](O)(CNC(=O)c1cc(Cl)c3ncccc3c1)C(F)(F)F)nc2-c1ccc(F)c(Cl)c1] | 623.09 |
| 221 | 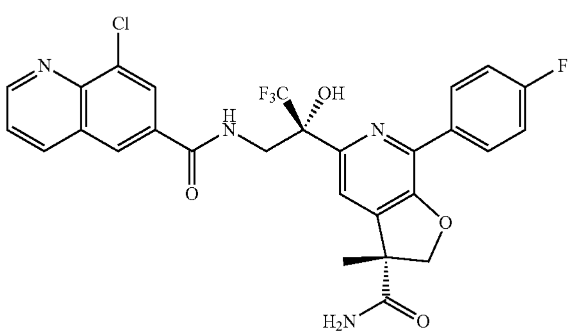 | 589.12 |
| 222 | 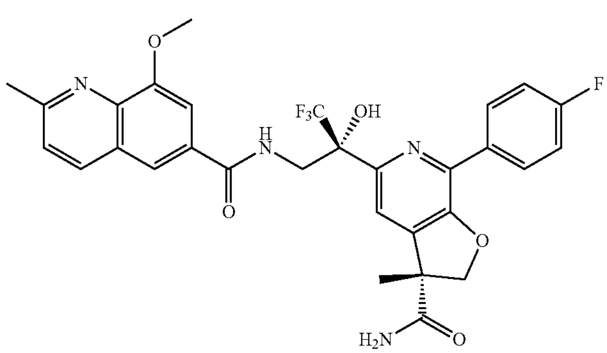 [SMILES: COc1cc(C(=O)NC[C@](O)(c2cc3c(c(-c4ccc(F)cc4)n2)OC[C@]3(C)C(N)=O)C(F)(F)F)cc2ccc(C)nc12] | 599.40 |

TABLE 3-continued

| Example | Structure | MS+ m/z |
|---|---|---|
| 223 | 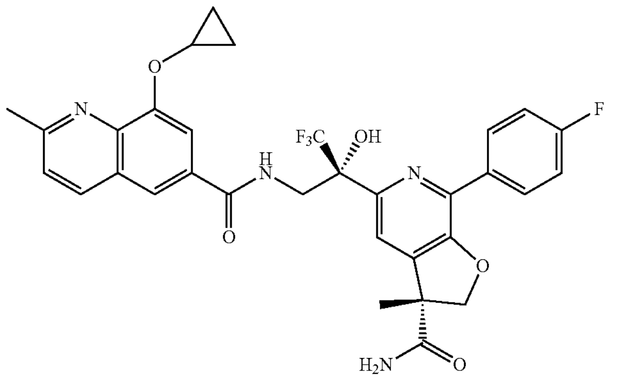 [SMILES: Cc1ccc2cc(C(=O)NC[C@](O)(c3cc4c(c(-c5ccc(F)cc5)n3)OC[C@]4(C)C(N)=O)C(F)(F)F)cc(OC3CC3)c2n1] | 625.40 |
| 224 | 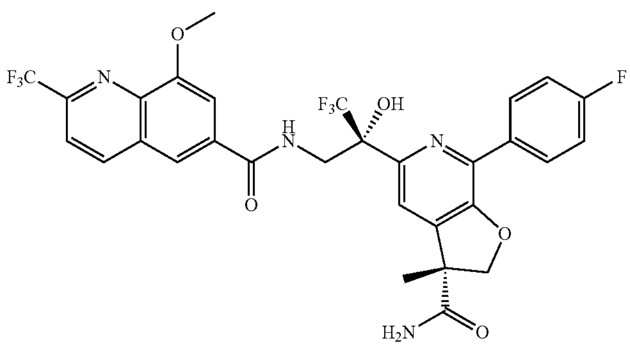 [SMILES: COc1cc(C(=O)NC[C@](O)(c2cc3c(c(-c4ccc(F)cc4)n2)OC[C@]3(C)C(N)=O)C(F)(F)F)cc2ccc(C(F)(F)F)nc12] | 653.40 |
| 225 | 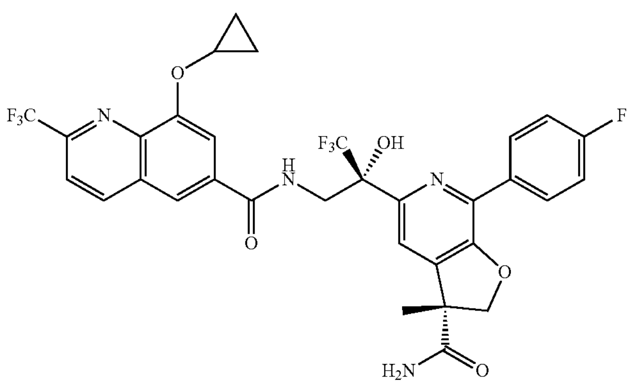 [SMILES: C[C@]1(C(N)=O)COc2c1cc([C@@](O)(CNC(=O)c1cc(OC3CC3)c3nc(C(F)(F)F)ccc3c1)C(F)(F)F)nc2-c1ccc(F)cc1] | 679.20 |
| 226 | 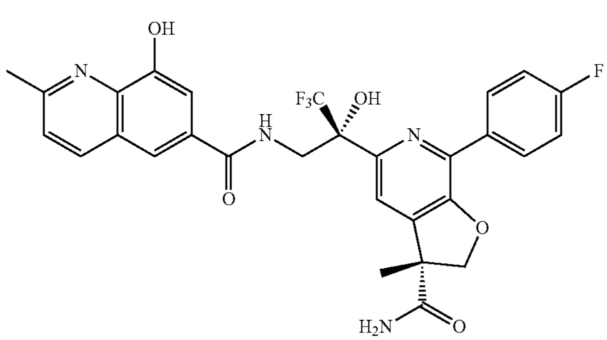 [SMILES: Cc1ccc2cc(C(=O)NC[C@](O)(c3cc4c(c(-c5ccc(F)cc5)n3)OC[C@]4(C)C(N)=O)C(F)(F)F)cc(O)c2n1] | 585.10 |

TABLE 3-continued

| Example | Structure | MS+ m/z |
|---|---|---|
| 227 | 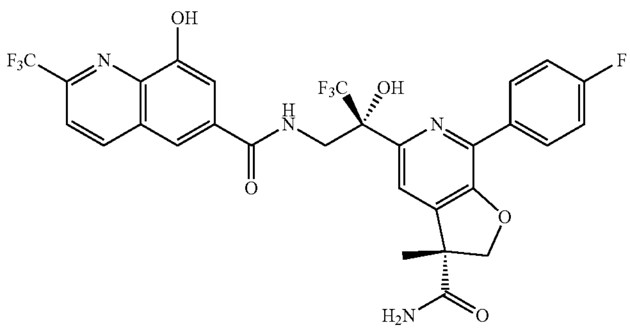 [SMILES: C[C@]1(C(N)=O)COc2c1cc([C@@](O)(CNC(=O)c1cc(O)c3nc(C(F)(F)F)ccc3c1)C(F)(F)F)nc2-c1ccc(F)cc1] | 639.15 |
| 228 | 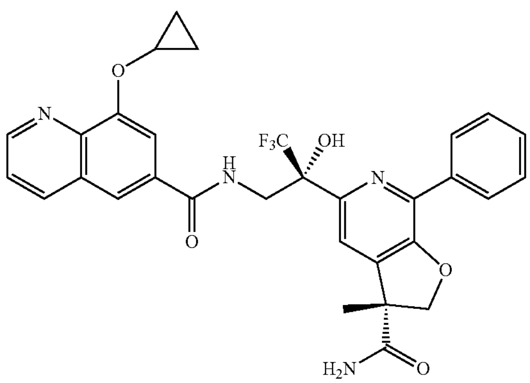 [SMILES: C[C@]1(C(N)=O)COc2c1cc([C@@](O)(CNC(=O)c1cc(OC3CC3)c3ncccc3c1)C(F)(F)F)nc2-c1ccccc1] | 593.20 |
| 229 | 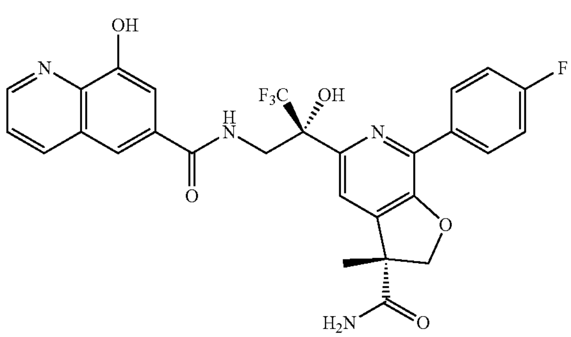 [SMILES: C[C@]1(C(N)=O)COc2c1cc([C@@](O)(CNC(=O)c1cc(O)c3ncccc3c1)C(F)(F)F)nc2-c1ccc(F)cc1] | 571.05 |
| 230 | 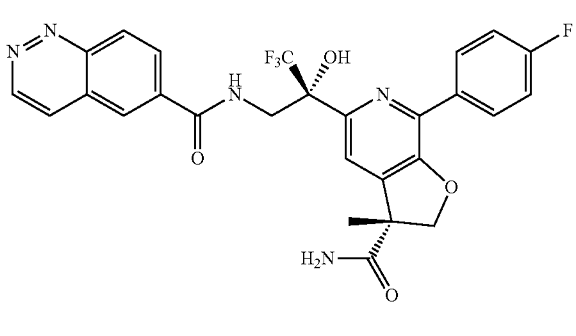 [SMILES: C[C@]1(C(N)=O)COc2c1cc([C@@](O)(CNC(=O)c1ccc3nnccc3c1)C(F)(F)F)nc2-c1ccc(F)cc1] | 556.14 |

TABLE 3-continued

| Example | Structure | MS+ m/z |
|---|---|---|
| 231 | 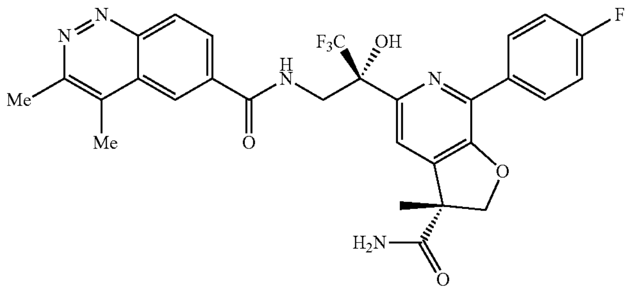 [SMILES: Cc1nnc2ccc(C(=O)NC[C@](O)(c3cc4c(c(-c5ccc(F)cc5)n3)OC[C@]4(C)C(N)=O)C(F)(F)F)cc2c1C] | 584.14 |
| 232 | 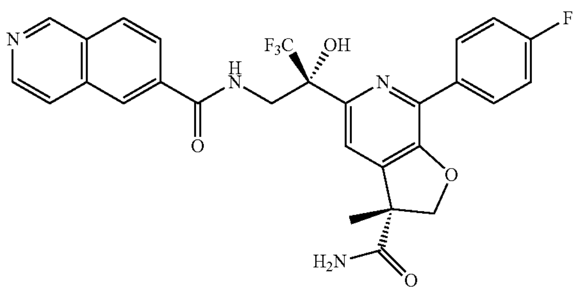 [SMILES: C[C@]1(C(N)=O)COc2c1cc([C@@](O)(CNC(=O)c1ccc3cnccc3c1)C(F)(F)F)nc2-c1ccc(F)cc1] | 555.41 |
| 233 | 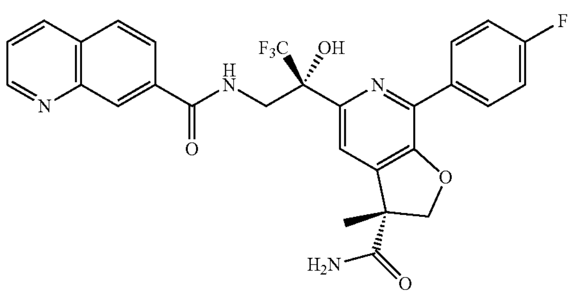 [SMILES: C[C@]1(C(N)=O)COc2c1cc([C@@](O)(CNC(=O)c1ccc3cccnc3c1)C(F)(F)F)nc2-c1ccc(F)cc1] | 555.41 |
| 234 | 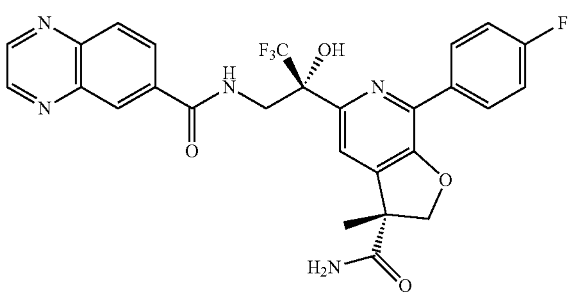 [SMILES: C[C@]1(C(N)=O)COc2c1cc([C@@](O)(CNC(=O)c1ccc3nccnc3c1)C(F)(F)F)nc2-c1ccc(F)cc1] | 556.20 |
| 235 | 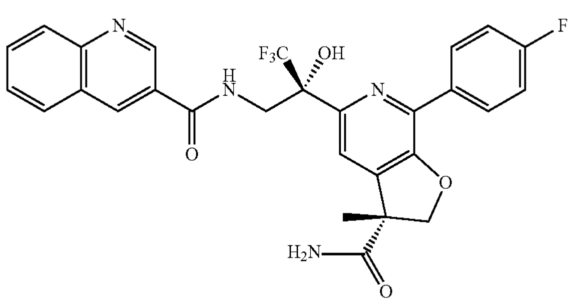 | 555.38 |

TABLE 3-continued

| Example | Structure | MS+ m/z |
|---|---|---|
| 236 | 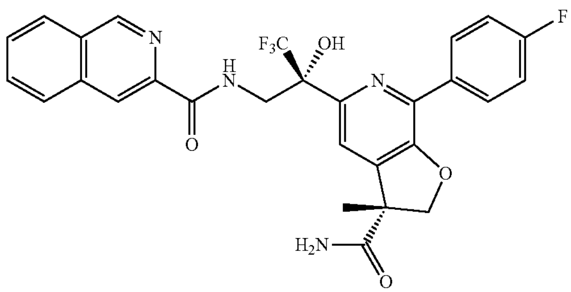 [SMILES: C[C@]1(C(N)=O)COc2c1cc([C@@](O)(CNC(=O)c1cc3ccccc3cn1)C(F)(F)F)nc2-c1ccc(F)cc1] | 555.26 |
| 237 | 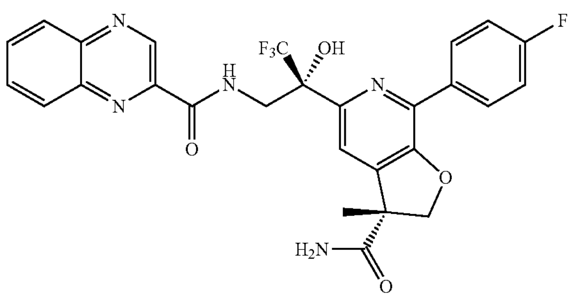 [SMILES: C[C@]1(C(N)=O)COc2c1cc([C@@](O)(CNC(=O)c1cnc3ccccc3n1)C(F)(F)F)nc2-c1ccc(F)cc1] | 556.21 |
| 238 | 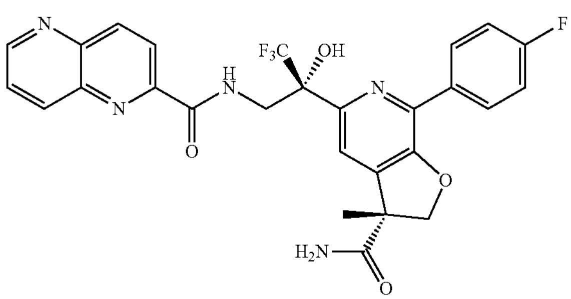 | 556.38 |
| 239 | 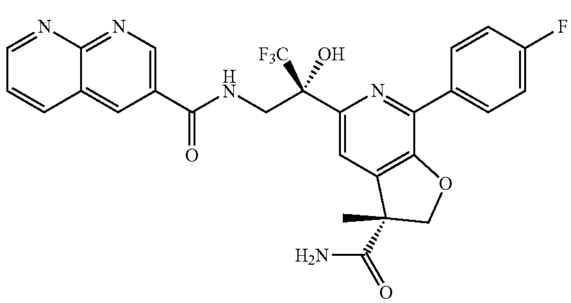 [SMILES: C[C@]1(C(N)=O)COc2c1cc([C@@](O)(CNC(=O)c1cnc3ncccc3c1)C(F)(F)F)nc2-c1ccc(F)cc1] | 556.26 |
| 240 | 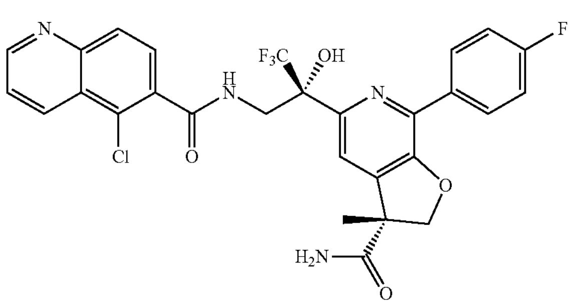 [SMILES: C[C@]1(C(N)=O)COc2c1cc([C@@](O)(CNC(=O)c1ccc3ncccc3c1Cl)C(F)(F)F)nc2-c1ccc(F)cc1] | 589.29 |

TABLE 3-continued

| Example | Structure | MS+ m/z |
|---|---|---|
| 241 | 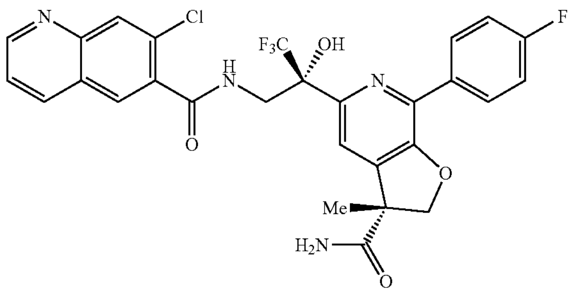 [SMILES: C[C@]1(C(N)=O)COc2c1cc([C@@](O)(CNC(=O)c1cc3cccnc3cc1Cl)C(F)(F)F)nc2-c1ccc(F)cc1] | 589.14 |
| 242 | 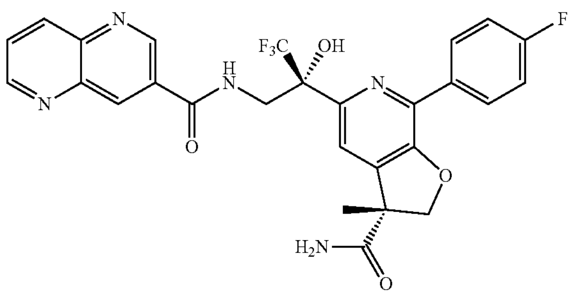 [SMILES: C[C@]1(C(N)=O)COc2c1cc([C@@](O)(CNC(=O)c1cnc3cccnc3c1)C(F)(F)F)nc2-c1ccc(F)cc1] | 556.21 |
| 243 | 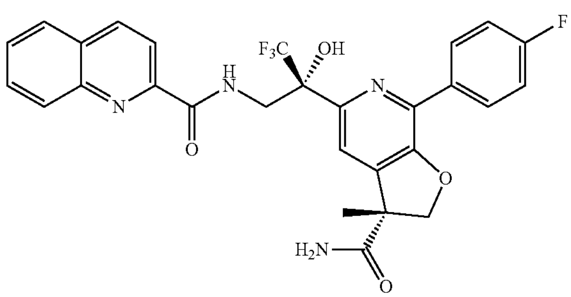 [SMILES: C[C@]1(C(N)=O)COc2c1cc([C@@](O)(CNC(=O)c1ccc3ccccc3n1)C(F)(F)F)nc2-c1ccc(F)cc1] | 555.31 |
| 244 | 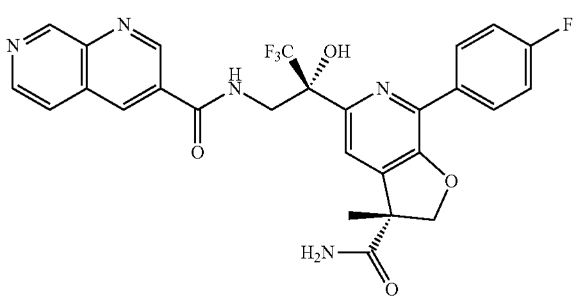 [SMILES: C[C@]1(C(N)=O)COc2c1cc([C@@](O)(CNC(=O)c1cnc3cnccc3c1)C(F)(F)F)nc2-c1ccc(F)cc1] | 556.14 |
| 245 | 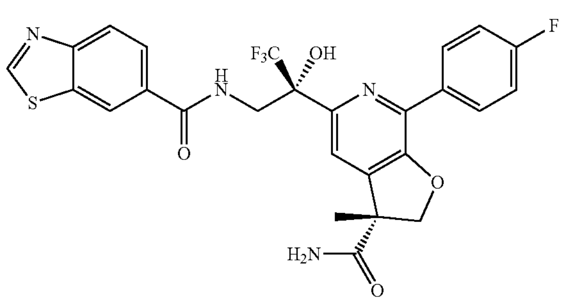 [SMILES: C[C@]1(C(N)=O)COc2c1cc([C@@](O)(CNC(=O)c1ccc3ncsc3c1)C(F)(F)F)nc2-c1ccc(F)cc1] | 561.12 |

TABLE 3-continued
| Example | Structure | MS+ m/z |
|---|---|---|
| 246 | 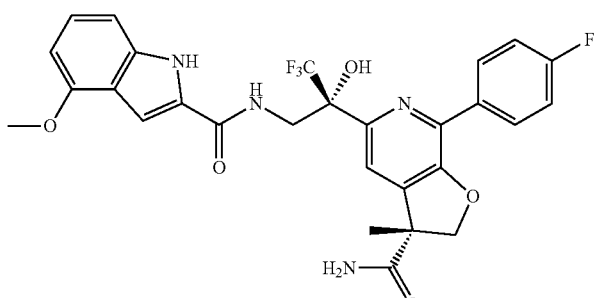 | 573.18 |
| 247 | 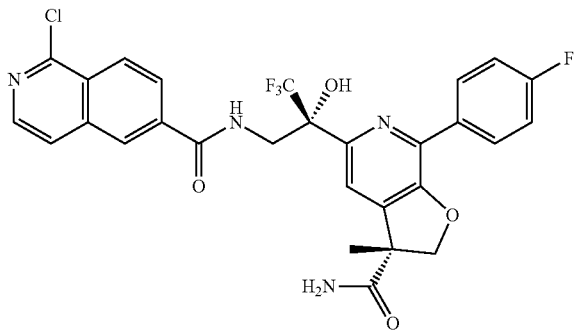 [SMILES: C[C@]1(C(N)=O)COc2c1cc([C@@](O)(CNC(=O)c1ccc3c(Cl)nccc3c1)C(F)(F)F)nc2-c1ccc(F)cc1] | 589.06 |
| 248 | 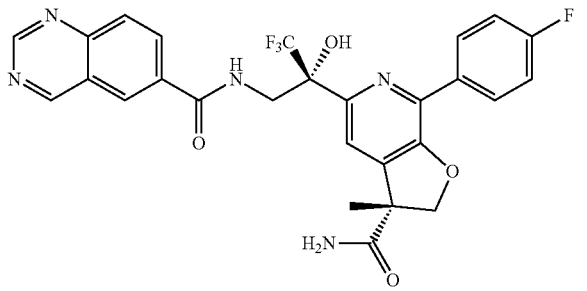 [SMILES: C[C@]1(C(N)=O)COc2c1cc([C@@](O)(CNC(=O)c1ccc3ncncc3c1)C(F)(F)F)nc2-c1ccc(F)cc1] | 556.12 |
| 249 | 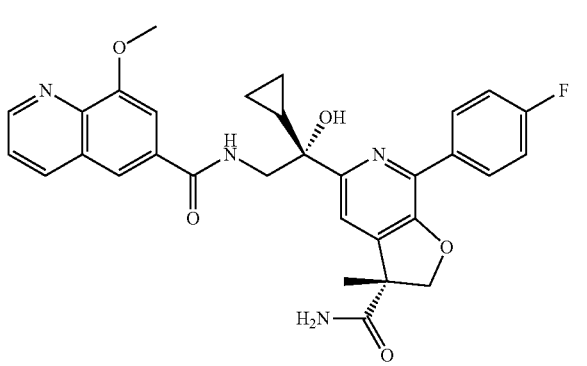 [SMILES: COc1cc(C(=O)NC[C@](O)(c2cc3c(c(-c4ccc(F)cc4)n2)OC[C@]3(C)C(N)=O)C2CC2)cc2cccnc12] | 557.17 |

TABLE 3-continued
| Example | Structure | MS+ m/z |
|---|---|---|
| 250 | 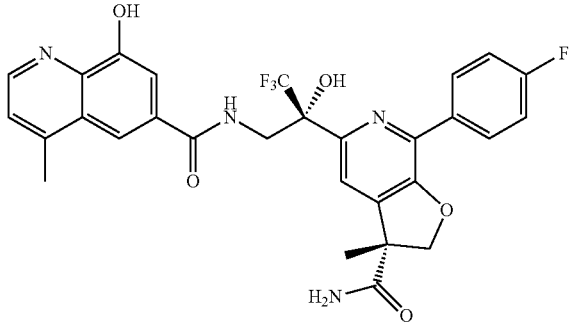 [SMILES: Cc1ccnc2c(O)cc(C(=O)NC[C@](O)(c3cc4c(c(-c5ccc(F)cc5)n3)OC[C@]4(C)C(N)=O)C(F)(F)F)cc12] | 585.19 |
| 251 | 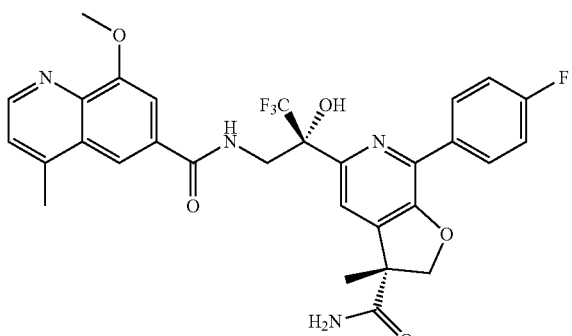 | 599.32 |
| 252 | 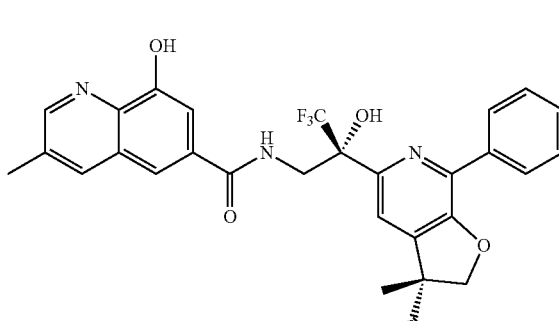 | 585.19 |
| 253 | 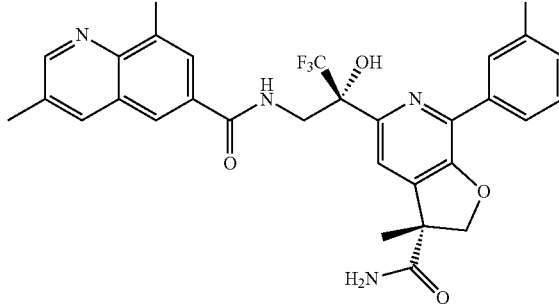 | 619.09 |

TABLE 3-continued

| Example | Structure | MS+ m/z |
|---|---|---|
| 254 | 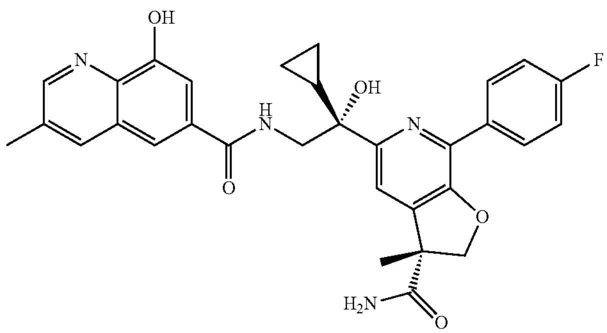 [SMILES: Cc1cnc2c(O)cc(C(=O)NC[C@](O)(c3cc4c(c(-c5ccc(F)cc5)n3)OC[C@]4(C)C(N)=O)C3CC3)cc2c1] | 557.45 |
| 255 | 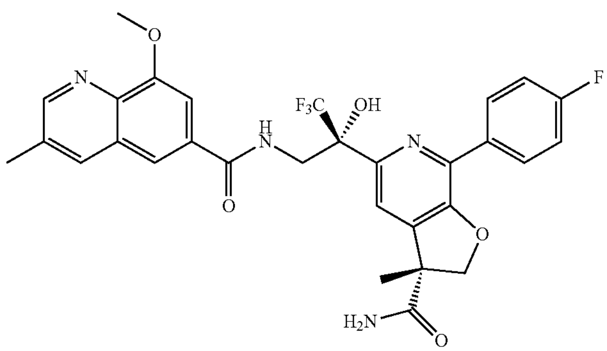 [SMILES: COc1cc(C(=O)NC[C@](O)(c2cc3c(c(-c4ccc(F)cc4)n2)OC[C@]3(C)C(N)=O)C(F)(F)F)cc2cc(C)cnc12] | 599.18 |
| 256 | 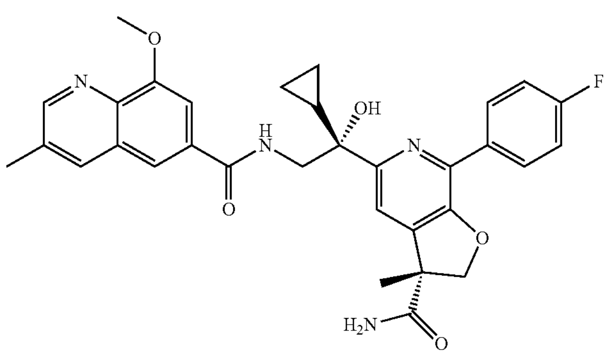 [SMILES: COc1cc(C(=O)NC[C@](O)(c2cc3c(c(-c4ccc(F)cc4)n2)OC[C@]3(C)C(N)=O)C2CC2)cc2cc(C)cnc12] | 571.35 |
| 257 | 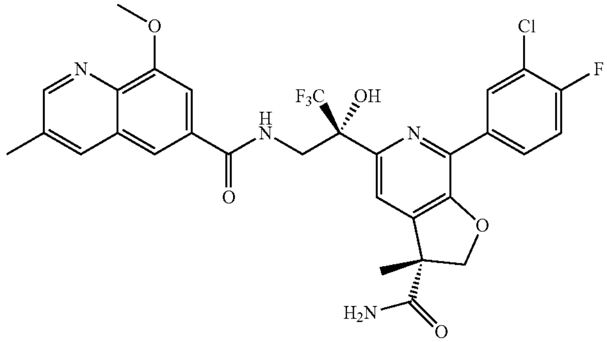 [SMILES: COc1cc(C(=O)NC[C@](O)(c2cc3c(c(-c4ccc(F)c(Cl)c4)n2)OC[C@]3(C)C(N)=O)C(F)(F)F)cc2cc(C)cnc12] | 633.31 |

TABLE 3-continued

| Example | Structure | MS+ m/z |
|---------|-----------|---------|
| 258 | 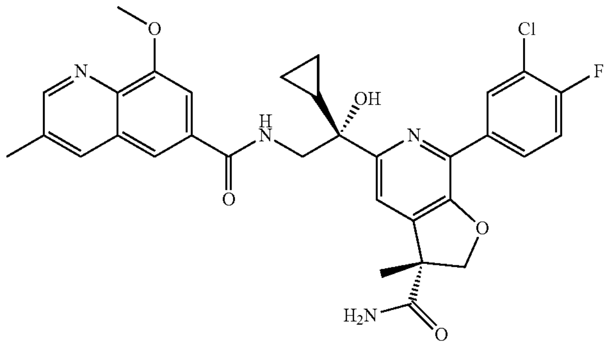 [SMILES: COc1cc(C(=O)NC[C@](O)(c2cc3c(c(-c4ccc(F)c(Cl)c4)n2)OC[C@]3(C)C(N)=O)C2CC2)cc2cc(C)cnc12] | 605.31 |
| 259 | 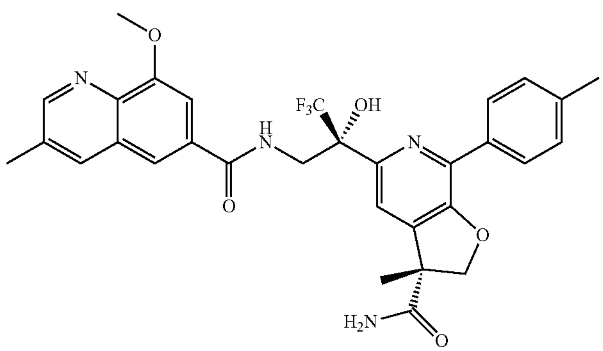 | 594.35 |
| 260 | 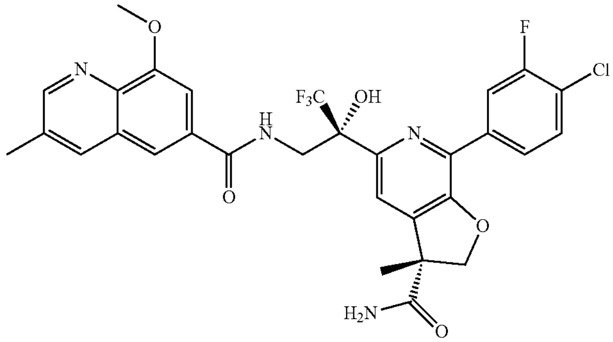 [SMILES: COc1cc(C(=O)NC[C@](O)(c2cc3c(c(-c4ccc(Cl)c(F)c4)n2)OC[C@]3(C)C(N)=O)C(F)(F)F)cc2cc(C)cnc12] | 633.33 |
| 261 | 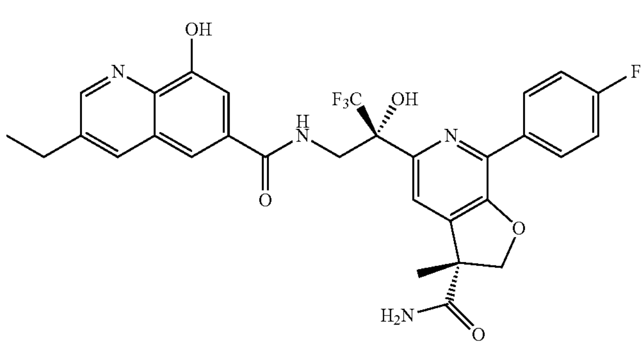 [SMILES: CCc1cnc2c(O)cc(C(=O)NC[C@](O)(c3cc4c(c(-c5ccc(F)cc5)n3)OC[C@]4(C)C(N)=O)C(F)(F)F)cc2c1] | 599.19 |

TABLE 3-continued

| Example | Structure | MS+ m/z |
|---------|-----------|---------|
| 262 | 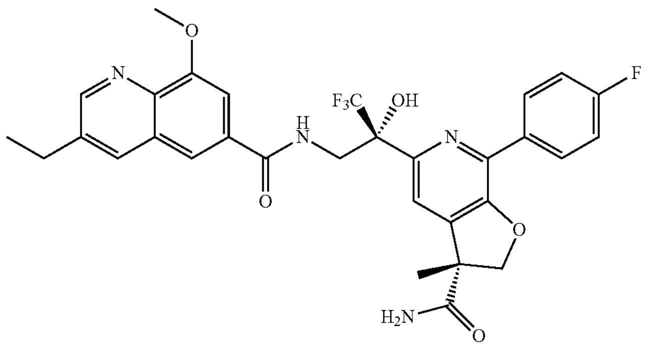 [SMILES: CCc1cnc2c(OC)cc(C(=O)NC[C@](O)(c3cc4c(c(-c5ccc(F)cc5)n3)OC[C@]4(C)C(N)=O)C(F)(F)F)cc2c1] | 613.40 |
| 263 | 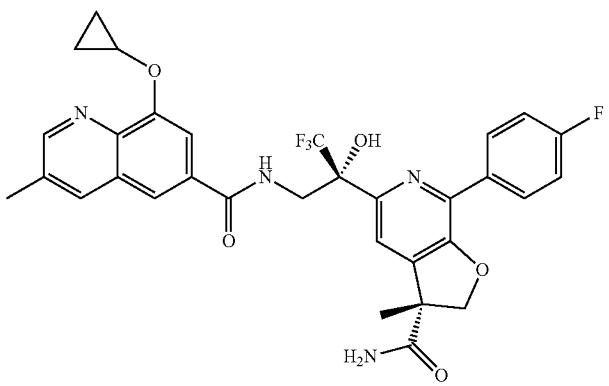 [SMILES: Cc1cnc2c(OC3CC3)cc(C(=O)NC[C@](O)(c3cc4c(c(-c5ccc(F)cc5)n3)OC[C@]4(C)C(N)=O)C(F)(F)F)cc2c1] | 625.39 |
| 264 | 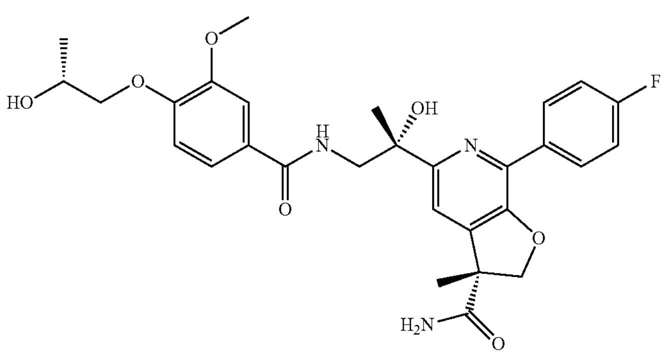 [SMILES: COc1cc(C(=O)NC[C@](C)(O)c2cc3c(c(-c4ccc(F)cc4)n2)OC[C@]3(C)C(N)=O)ccc1OC[C@@H](C)O] | 554.39 |
| 265 | 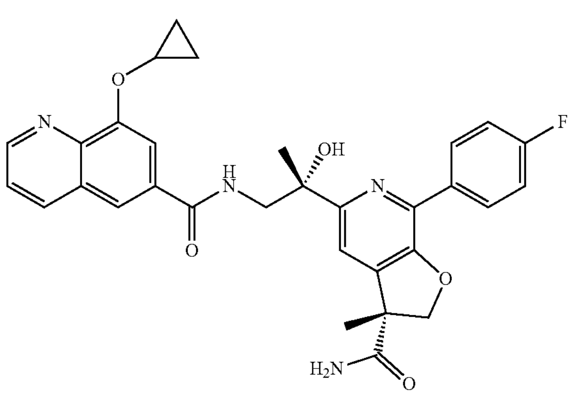 [SMILES: C[C@](O)(CNC(=O)c1cc(OC2CC2)c2ncccc2c1)c1cc2c(c(-c3ccc(F)cc3)n1)OC[C@]2(C)C(N)=O] | 557.39 |

TABLE 3-continued

| Example | Structure | MS+ m/z |
|---|---|---|
| 266 | 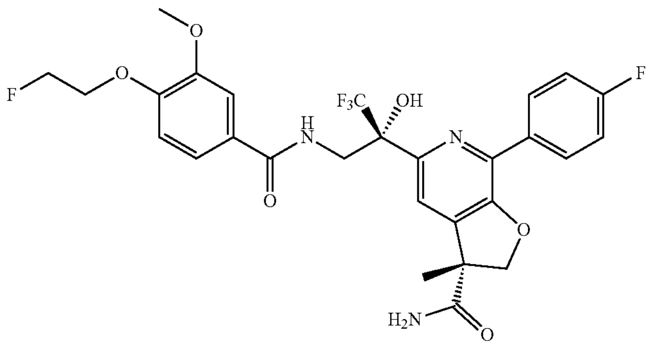 [SMILES: COc1cc(C(=O)NC[C@](O)(c2cc3c(c(-c4ccc(F)cc4)n2)OC[C@]3(C)C(N)=O)C(F)(F)F)ccc1OCCF] | 542.40 |
| 267 | 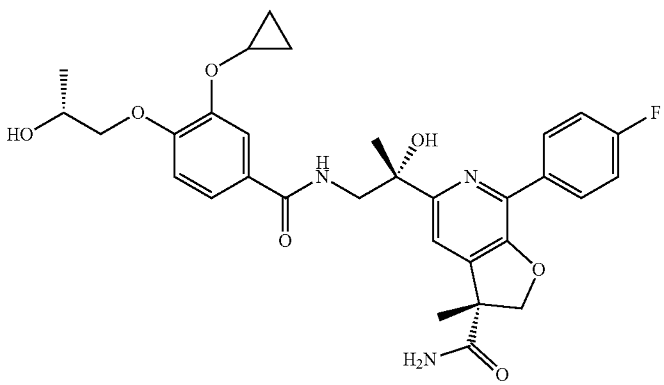 [SMILES: C[C@@H](O)COc1ccc(C(=O)NC[C@](C)(O)c2cc3c(c(-c4ccc(F)cc4)n2)OC[C@]3(C)C(N)=O)cc1OC1CC1] | 580.47 |
| 268 | 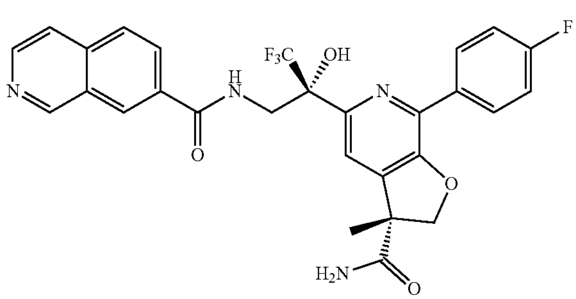 [SMILES: C[C@]1(C(N)=O)COc2c1cc([C@@](O)(CNC(=O)c1ccc3ccncc3c1)C(F)(F)F)nc2-c1ccc(F)cc1] | 555.39 |
| 269 | 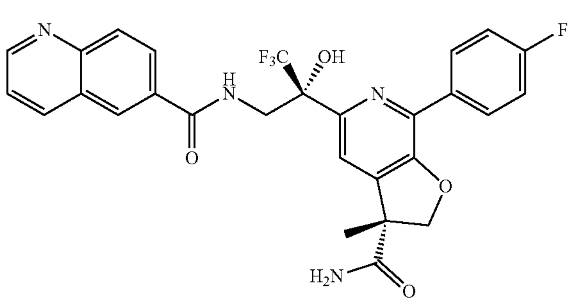 [SMILES: C[C@]1(C(N)=O)COc2c1cc([C@@](O)(CNC(=O)c1ccc3ncccc3c1)C(F)(F)F)nc2-c1ccc(F)cc1] | 555.20 |

TABLE 3-continued

| Example | Structure | MS+ m/z |
|---|---|---|
| 270 | 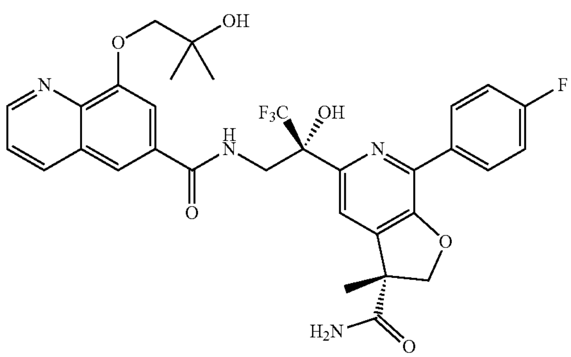 [SMILES: CC(C)(O)COc1cc(C(=O)NC[C@](O)(c2cc3c(c(-c4ccc(F)cc4)n2)OC[C@]3(C)C(N)=O)C(F)(F)F)cc2cccnc12] | 643.32 |
| 271 | 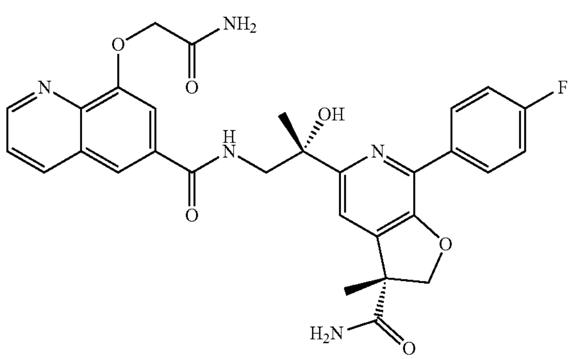 [SMILES: C[C@](O)(CNC(=O)c1cc(OCC(N)=O)c2ncccc2c1)c1cc2c(c(-c3ccc(F)cc3)n1)OC[C@]2(C)C(N)=O] | 575.29 |
| 272 | 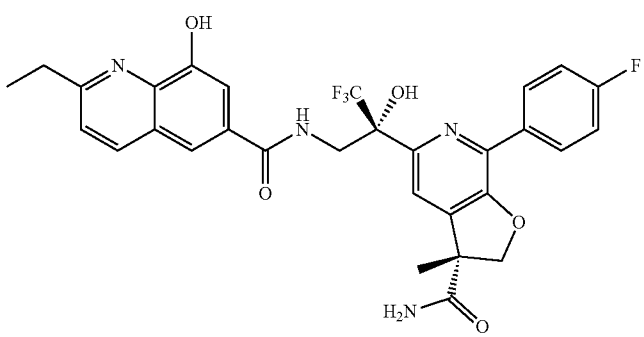 [SMILES: CCc1ccc2cc(C(=O)NC[C@](O)(c3cc4c(c(-c5ccc(F)cc5)n3)OC[C@]4(C)C(N)=O)C(F)(F)F)cc(O)c2n1] | 599.09 |
| 273 | 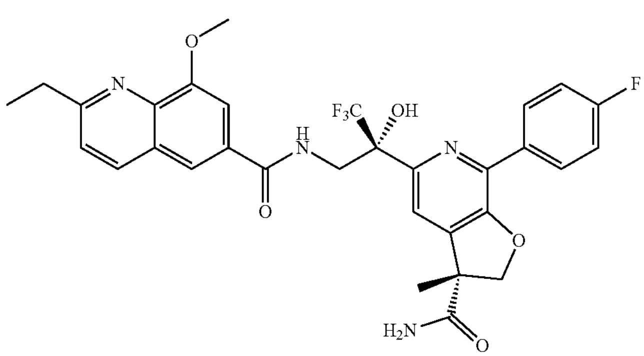 [SMILES: CCc1ccc2cc(C(=O)NC[C@](O)(c3cc4c(c(-c5ccc(F)cc5)n3)OC[C@]4(C)C(N)=O)C(F)(F)F)cc(OC)c2n1] | 613.33 |

TABLE 3-continued

| Example | Structure | MS+ m/z |
|---------|-----------|---------|
| 274 | 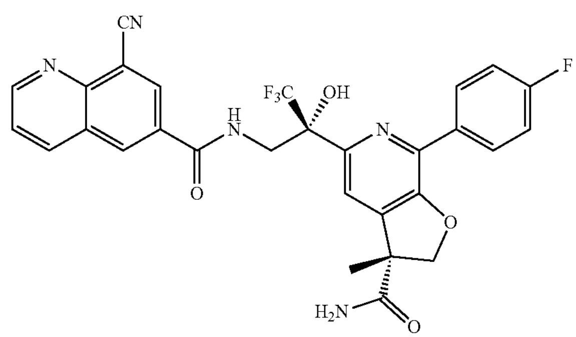 | 580.20 |
| 275 | 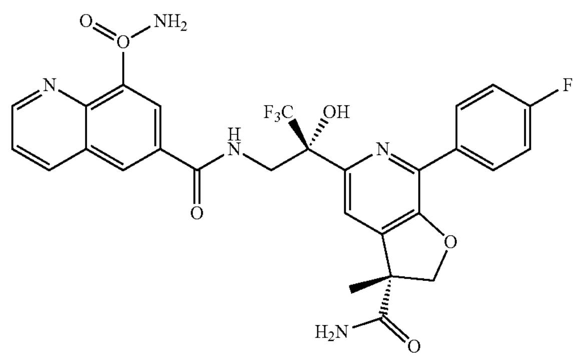 | 598.18 |
| 276 | 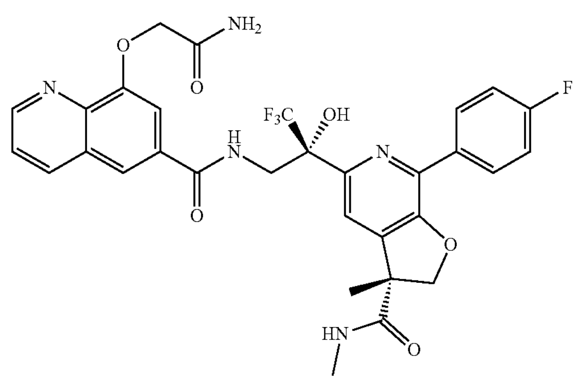 [SMILES: CNC(=O)[C@@]1(C)COc2c1cc([C@@](O)(CNC(=O)c1cc(OCC(N)=O)c3ncccc3c1)C(F)(F)F)nc2-c1ccc(F)cc1] | 642.19 |
| 277 | 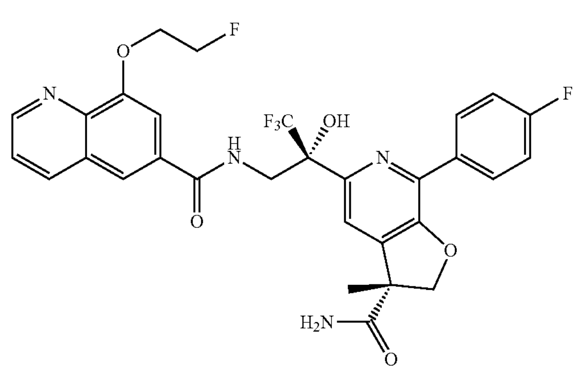 [SMILES: C[C@]1(C(N)=O)COc2c1cc([C@@](O)(CNC(=O)c1cc(OCCF)c3ncccc3c1)C(F)(F)F)nc2-c1ccc(F)cc1] | 617.20 |

TABLE 3-continued

| Example | Structure | MS+ m/z |
|---------|-----------|---------|
| 278 | 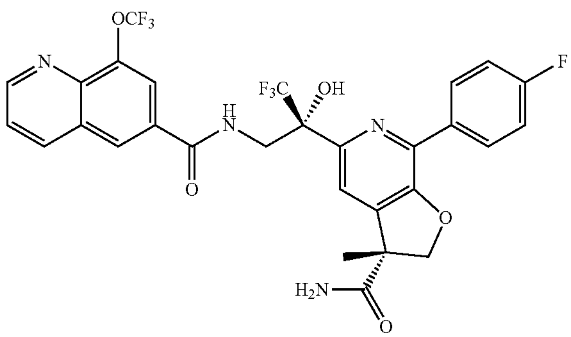 [SMILES: C[C@]1(C(N)=O)COc2c1cc([C@@](O)(CNC(=O)c1cc(OC(F)(F)F)c3ncccc3c1)C(F)(F)F)nc2-c1ccc(F)cc1] | 639.17 |
| 279 | 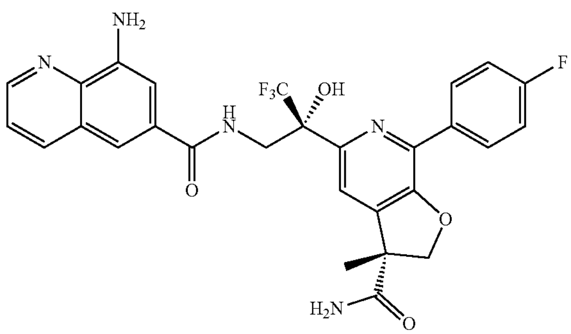 [SMILES: C[C@]1(C(N)=O)COc2c1cc([C@@](O)(CNC(=O)c1cc(N)c3ncccc3c1)C(F)(F)F)nc2-c1ccc(F)cc1] | 570.147 |
| 280 | 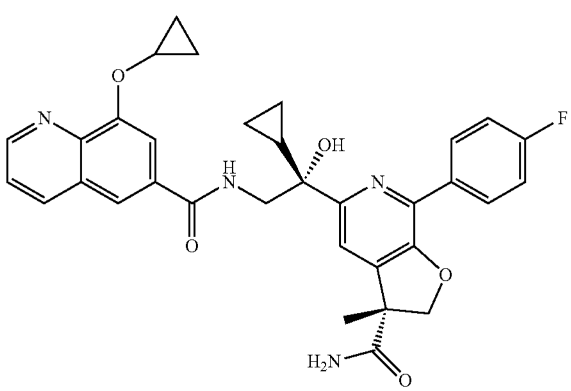 [SMILES: C[C@]1(C(N)=O)COc2c1cc([C@@](O)(CNC(=O)c1cc(OC3CC3)c3ncccc3c1)C1CC1)nc2-c1ccc(F)cc1] | 583.23 |
| 281 | 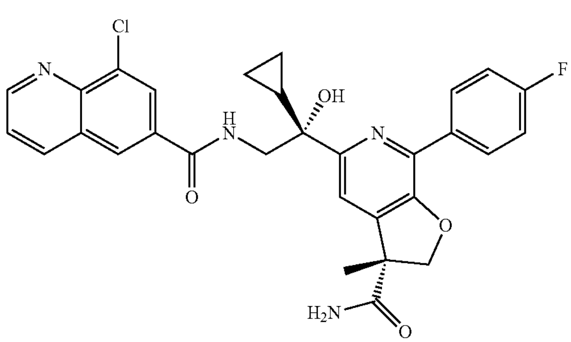 [SMILES: C[C@]1(C(N)=O)COc2c1cc([C@@](O)(CNC(=O)c1cc(Cl)c3ncccc3c1)C1CC1)nc2-c1ccc(F)cc1] | 561.17 |

TABLE 3-continued

| Example | Structure | MS+ m/z |
|---|---|---|
| 282 | 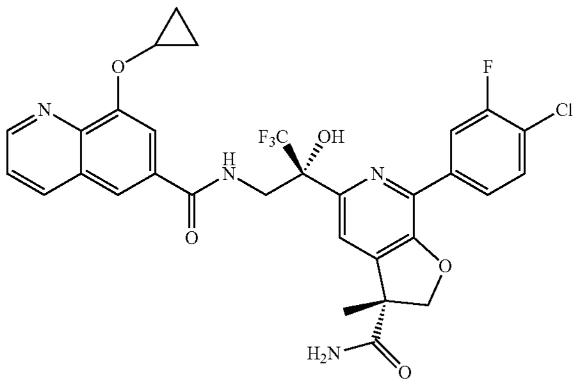 [SMILES: C[C@]1(C(N)=O)COc2c1cc([C@@](O)(CNC(=O)c1cc(OC3CC3)c3ncccc3c1)C(F)(F)F)nc2-c1ccc(Cl)c(F)c1] | 645.15 |
| 283 | 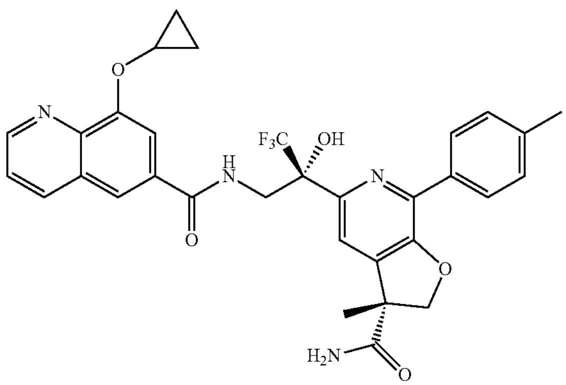 [SMILES: Cc1ccc(-c2nc([C@@](O)(CNC(=O)c3cc(OC4CC4)c4ncccc4c3)C(F)(F)F)cc3c2OC[C@]3(C)C(N)=O)cc1] | 607.22 |
| 284 | 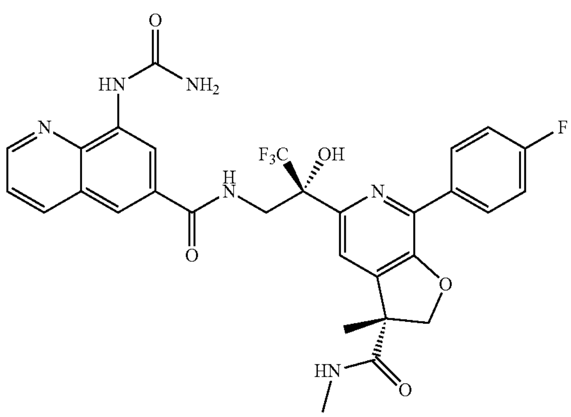 [SMILES: CNC(=O)[C@@]1(C)COc2c1cc([C@@](O)(CNC(=O)c1cc(NC(N)=O)c3ncccc3c1)C(F)(F)F)nc2-c1ccc(F)cc1] | 627.19 |
| 285 | 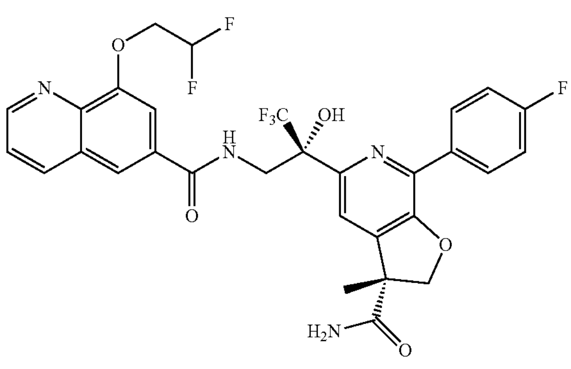 [SMILES: C[C@]1(C(N)=O)COc2c1cc([C@@](O)(CNC(=O)c1cc(OCC(F)F)c3ncccc3c1)C(F)(F)F)nc2-c1ccc(F)cc1] | 635.17 |

TABLE 3-continued

| Example | Structure | MS+ m/z |
|---|---|---|
| 286 | 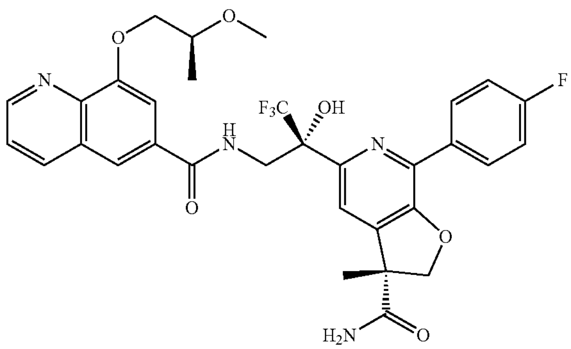 [SMILES: CO[C@@H](C)COc1cc(C(=O)NC[C@](O)(c2cc3c(c(-c4ccc(F)cc4)n2)OC[C@]3(C)C(N)=O)C(F)(F)F)cc2cccnc12] | 643.10 |
| 287 | 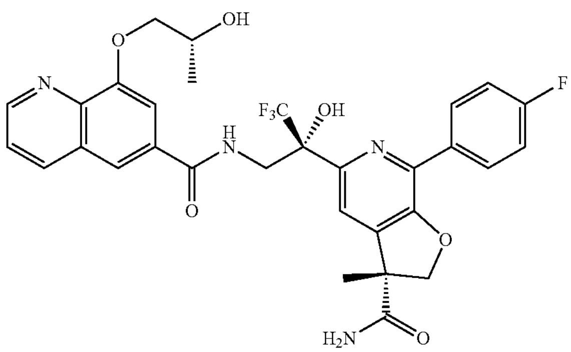 [SMILES: C[C@@H](O)COc1cc(C(=O)NC[C@](O)(c2cc3c(c(-c4ccc(F)cc4)n2)OC[C@]3(C)C(N)=O)C(F)(F)F)cc2cccnc12] | 629.20 |
| 288 | 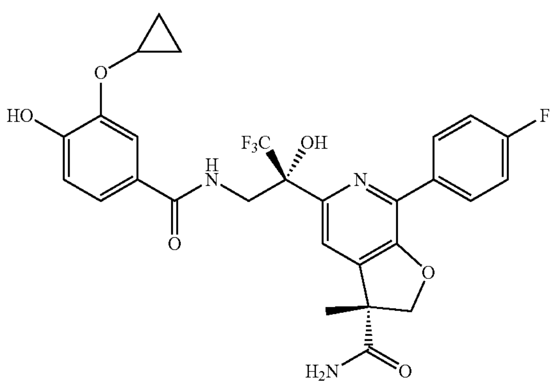 [SMILES: C[C@]1(C(N)=O)COc2c1cc([C@@](O)(CNC(=O)c1ccc(O)c(OC3CC3)c1)C(F)(F)F)nc2-c1ccc(F)cc1] | 572.20 |
| 289 | 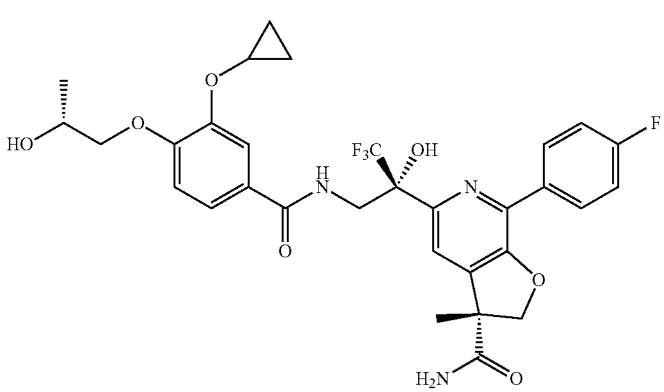 [SMILES: C[C@@H](O)COc1ccc(C(=O)NC[C@](O)(c2cc3c(c(-c4ccc(F)cc4)n2)OC[C@]3(C)C(N)=O)C(F)(F)F)cc1OC1CC1] | 634.05 |

TABLE 3-continued
| Example | Structure | MS+ m/z |
|---|---|---|
| 290 | 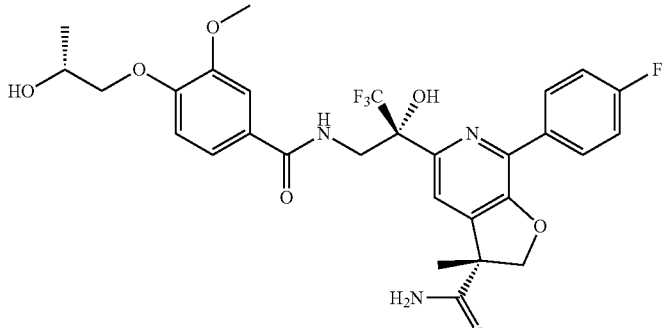 | 608.25 |
The following Table 4 contains examples that were prepared according to Method J (PyBOP or HATU) with commercially available aryl acid coupling partners. The majority of compounds were purified by Gilson prep-HPLC, and some were purified by automated column chromatography (silica gel).
TABLE 4
| Example | Structure | MS+ m/z |
|---|---|---|
| 291 | 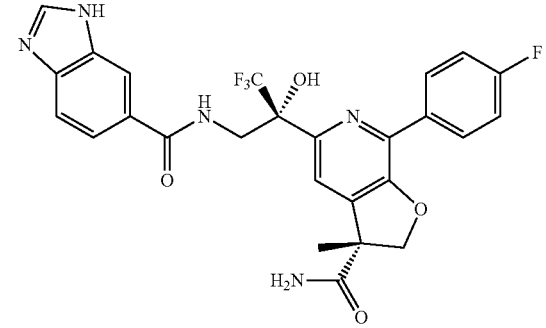 [SMILES: C[C@]1(C(N)=O)COc2c1cc([C@@](O)(CNC(=O)c1ccc3nc[nH]c3c1)C(F)(F)F)nc2-c1ccc(F)cc1] | 544.18 |
| 292 | 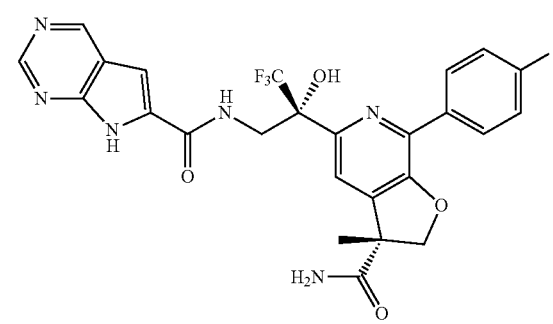 | 545.16 |
| 293 | 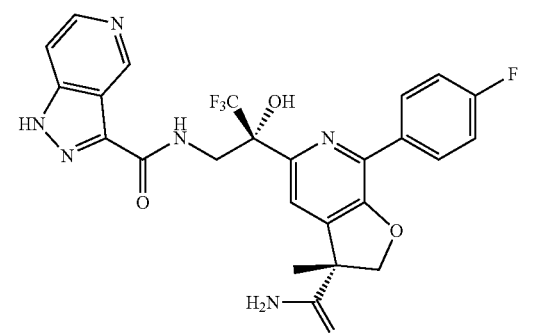 | 545.15 |

TABLE 4-continued

| Example | Structure | MS+ m/z |
|---|---|---|
| 294 | 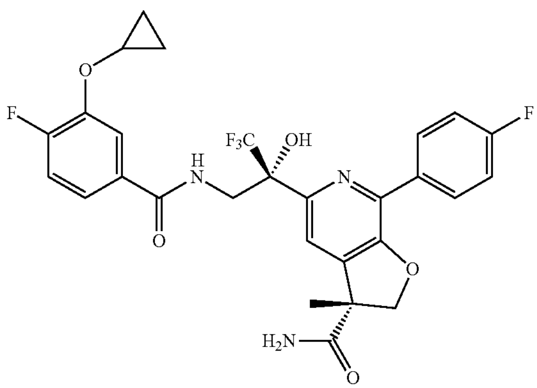 | 578.10 |
| 295 | 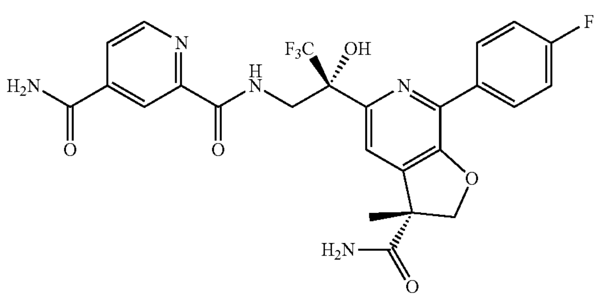 [SMILES: C[C@]1(C(N)=O)COc2c1cc([C@@](O)(CNC(=O)c1cc(C(N)=O)ccn1)C(F)(F)F)nc2-c1ccc(F)cc1] | 548.05 |
| 296 | 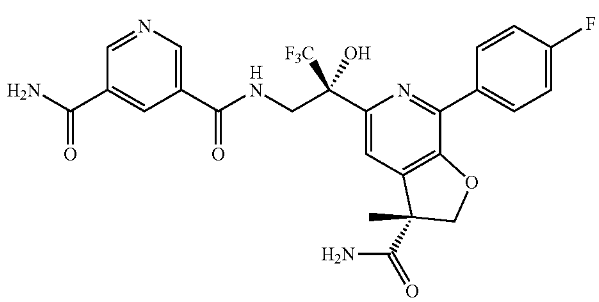 | 548.15 |
| 297 | 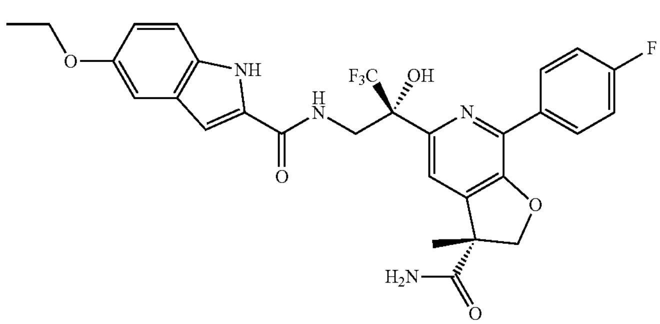 [SMILES: CCOc1ccc2[nH]c(C(=O)NC[C@](O)(c3cc4c(c(-c5ccc(F)cc5)n3)OC[C@]4(C)C(N)=O)C(F)(F)F)cc2c1] | 587.18 |

TABLE 4-continued

| Example | Structure | MS+ m/z |
|---|---|---|
| 298 | 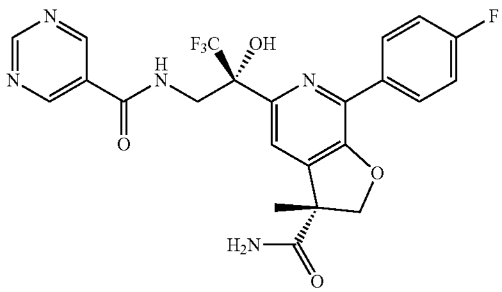 | 506.16 |
| 299 | 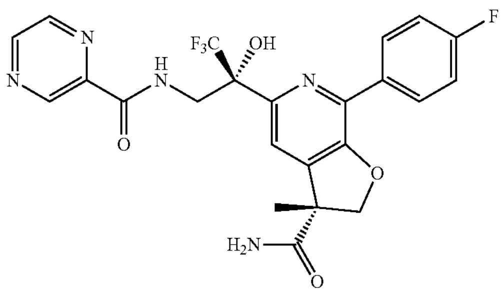 | 506.24 |
| 300 | 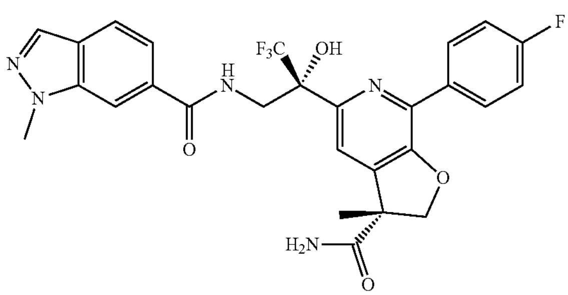 | 558.23 |
| 301 | 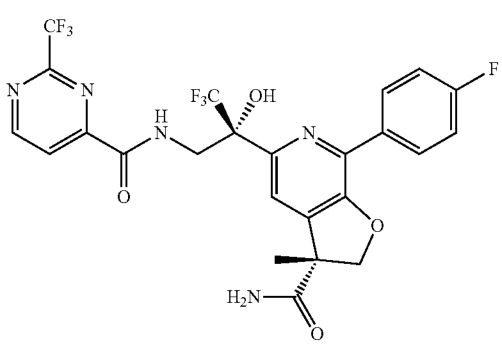 | 574.17 |
| 302 | 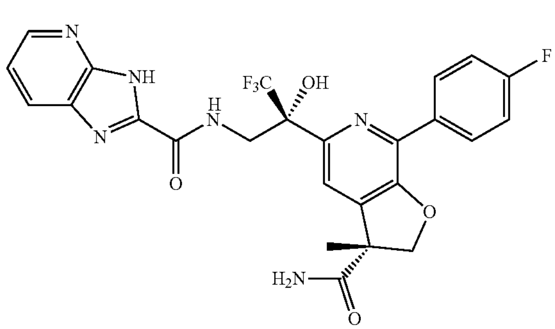 | 545.32 |

TABLE 4-continued

| Example | Structure | MS+ m/z |
|---|---|---|
| 303 | 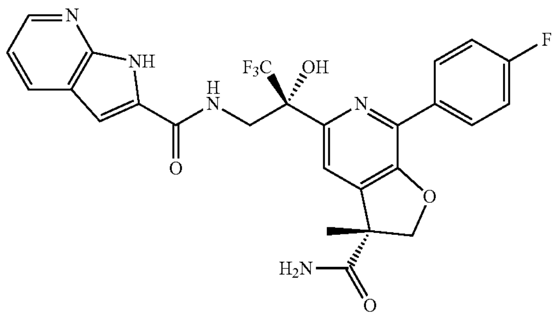 | 544.12 |
| 304 | 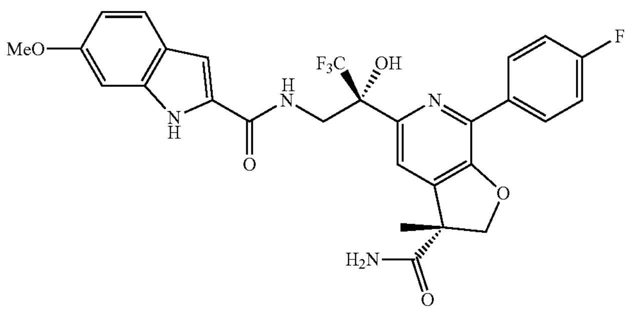 | 573.11 |
| 305 | 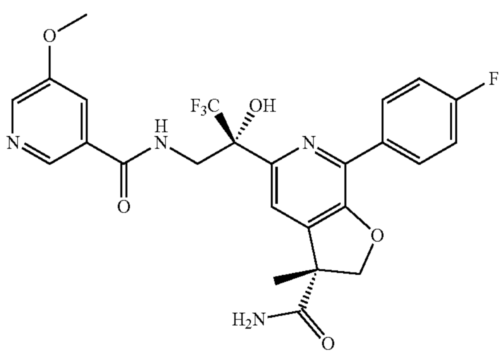 | 535.20 |
| 306 | 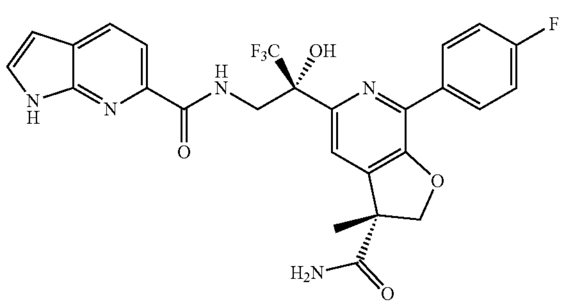 | 544.19 |
| 307 | 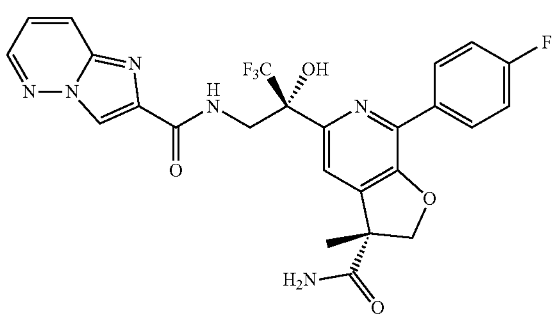 | 545.19 |

TABLE 4-continued

| Example | Structure | MS+ m/z |
|---|---|---|
| 308 | 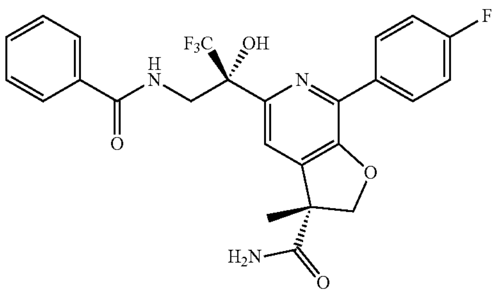 | 504.30 |
| 309 | 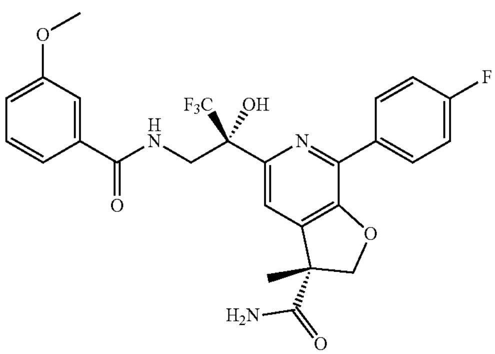 | 534.32 |
| 310 | 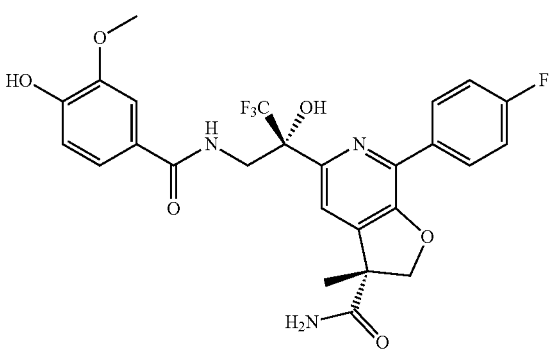 | 550.27 |
| 311 | 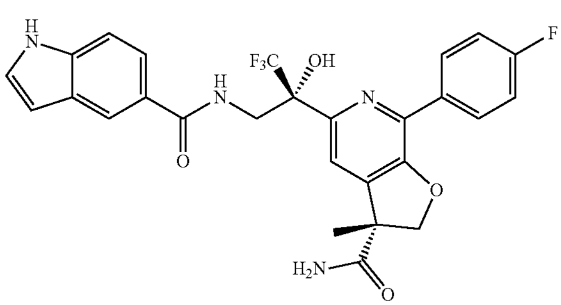 | 543.15 |

TABLE 4-continued

| Example | Structure | MS+ m/z |
|---------|-----------|---------|
| 312 | 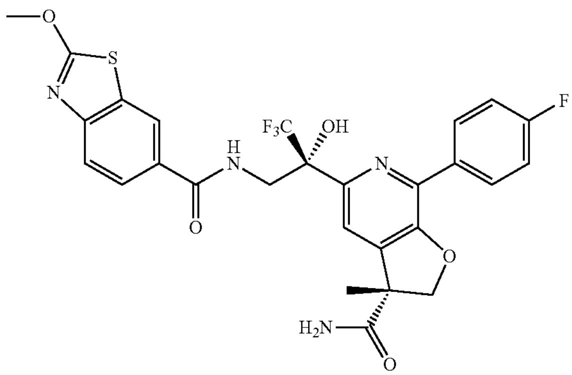 | 591.13 |
| 313 | 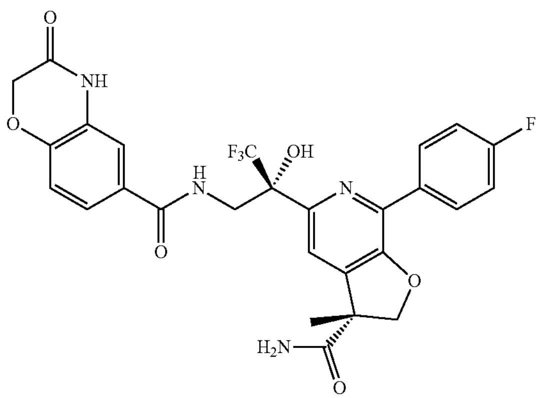 | 575.15 |
| 314 | 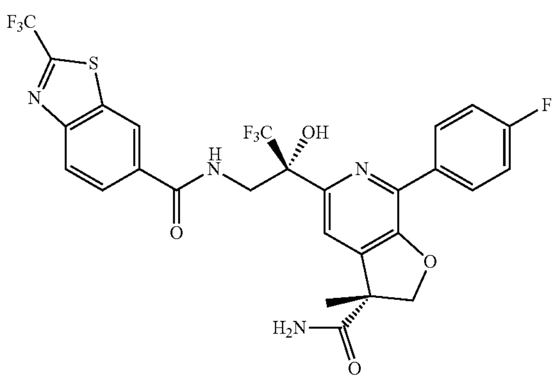 | 629.11 |
| 315 | 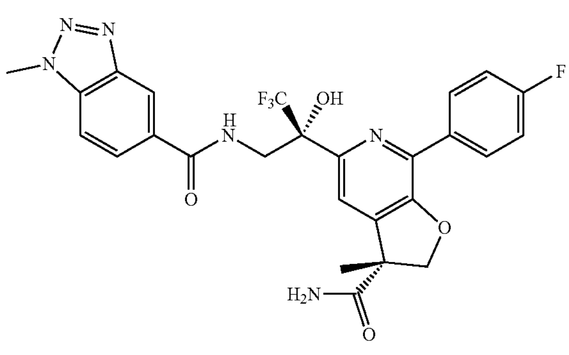 | 559.17 |

TABLE 4-continued

| Example | Structure | MS+ m/z |
|---|---|---|
| 316 | 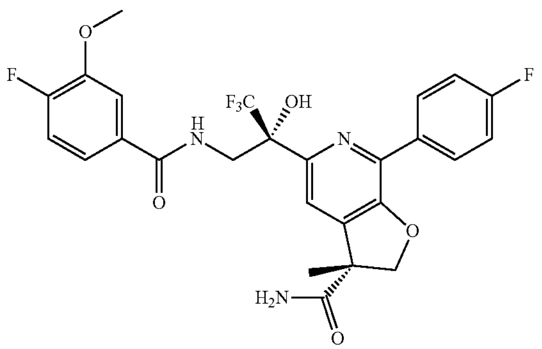 | 552.15 |
| 317 | 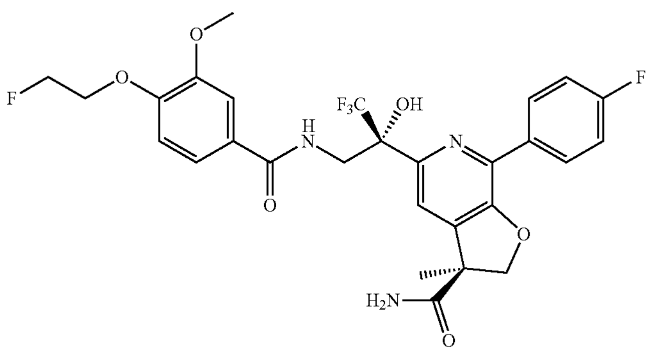 | 596.16 |
| 318 | 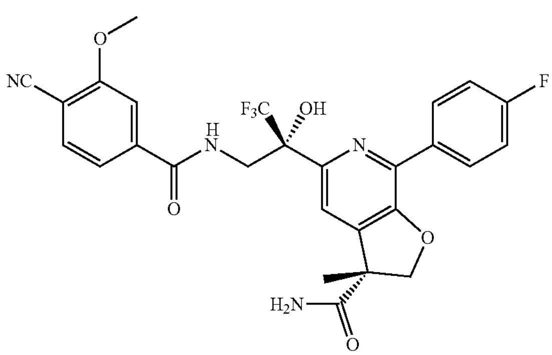 | 559.16 |
| 319 | 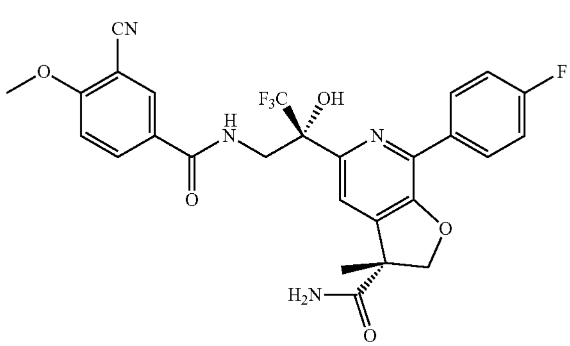 | 559.16 |

TABLE 4-continued
| Example | Structure | MS+ m/z |
|---|---|---|
| 320 | 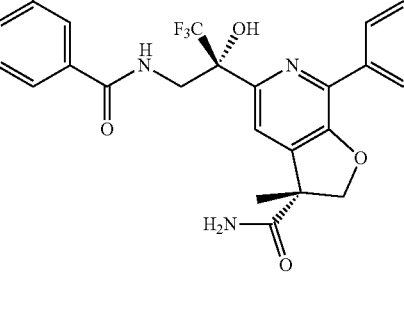 | 547.14 |
| 321 | 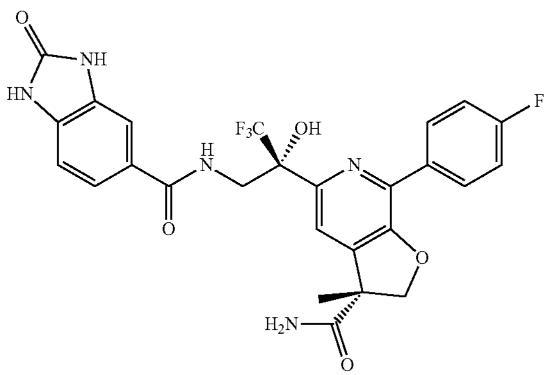 | 560.19 |
| 322 | 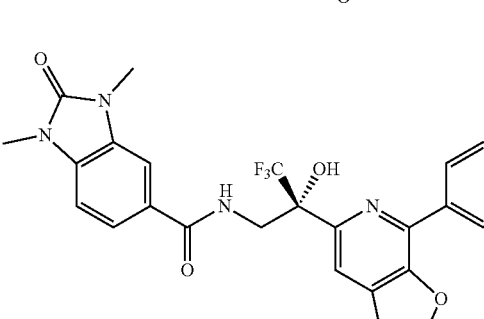 | 588.18 |
| 323 | 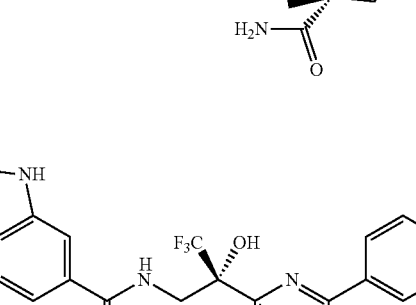 | 561.14 |

TABLE 4-continued

| Example | Structure | MS+ m/z |
|---|---|---|
| 324 | 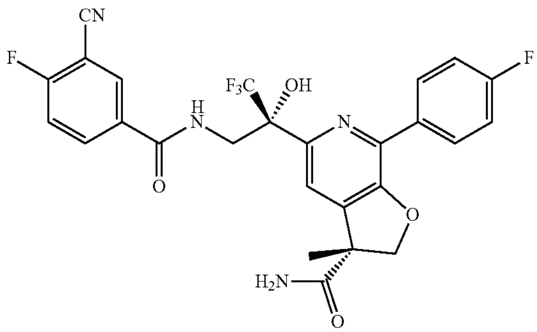 | 547.21 |
| 325 | 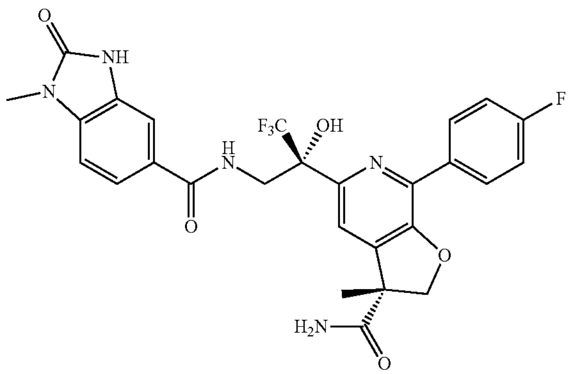 [SMILES: Cn1c(=O)[nH]c2cc(C(=O)NC[C@](O)(c3cc4c(c(-c5ccc(F)cc5)n3)OC[C@]4(C)C(N)=O)C(F)(F)F)ccc21] | 574.18 |
| 326 | 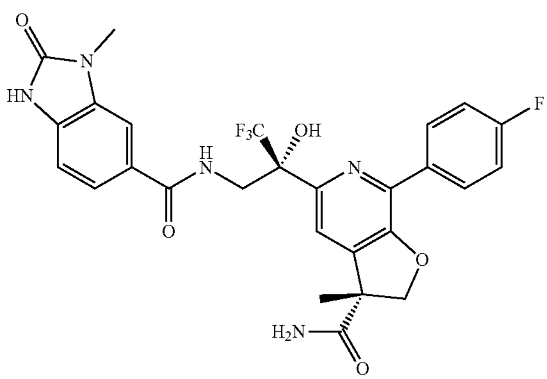 [SMILES: Cn1c(=O)[nH]c2ccc(C(=O)NC[C@](O)(c3cc4c(c(-c5ccc(F)cc5)n3)OC[C@]4(C)C(N)=O)C(F)(F)F)cc21] | 574.18 |
| 327 | 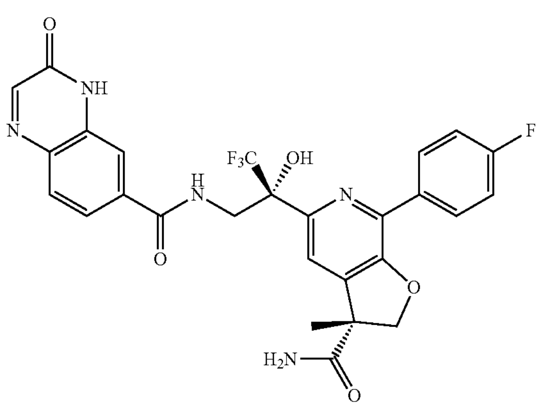 [SMILES: C[C@]1(C(N)=O)COc2c1cc([C@@](O)(CNC(=O)c1ccc3ncc(=O)[nH]c3c1)C(F)(F)F)nc2-c1ccc(F)cc1] | 572.27 |

TABLE 4-continued

| Example | Structure | MS+ m/z |
|---------|-----------|---------|
| 328 | 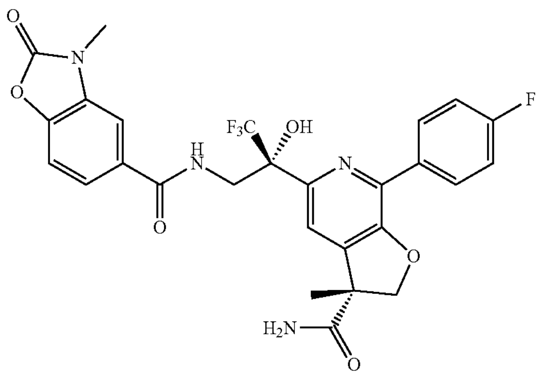 [SMILES: Cn1c(=O)oc2ccc(C(=O)NC[C@](O)(c3cc4c(c(-c5ccc(F)cc5)n3)OC[C@]4(C)C(N)=O)C(F)(F)F)cc21] | 575.24 |
| 329 | 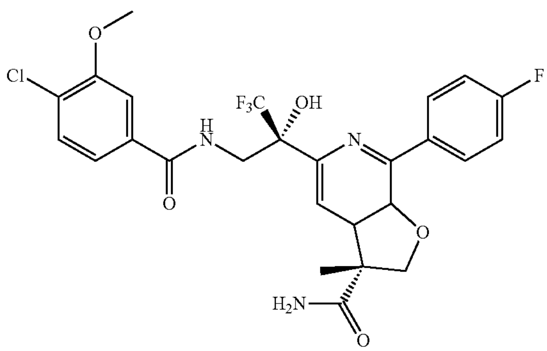 [SMILES: COc1cc(C(=O)NC[C@](O)(C2=CC3C(OC[C@]3(C)C(N)=O)C(c3ccc(F)cc3)=N2)C(F)(F)F)ccc1Cl] | 568.18 |
| 330 | 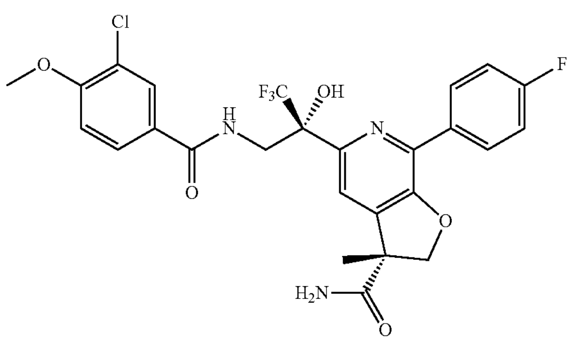 [SMILES: COc1ccc(C(=O)NC[C@](O)(c2cc3c(c(-c4ccc(F)cc4)n2)OC[C@]3(C)C(N)=O)C(F)(F)F)cc1Cl] | 568.18 |
| 331 | 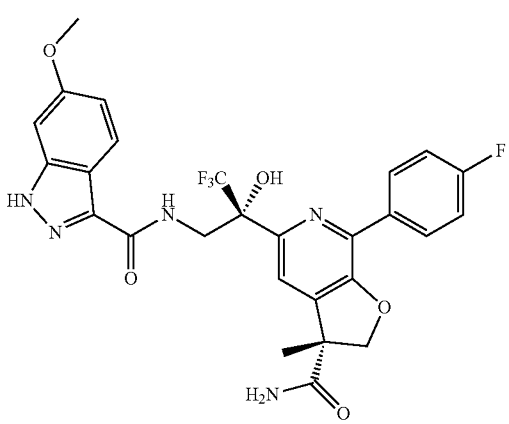 [SMILES: COc1ccc2c(C(=O)NC[C@](O)(c3cc4c(c(-c5ccc(F)cc5)n3)OC[C@]4(C)C(N)=O)C(F)(F)F)n[nH]c2c1] | 574.17 |

TABLE 4-continued
| Example | Structure | MS+ m/z |
|---|---|---|
| 332 | 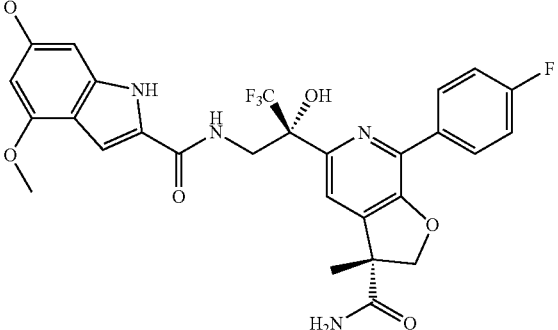 | 603.18 |
| 333 | 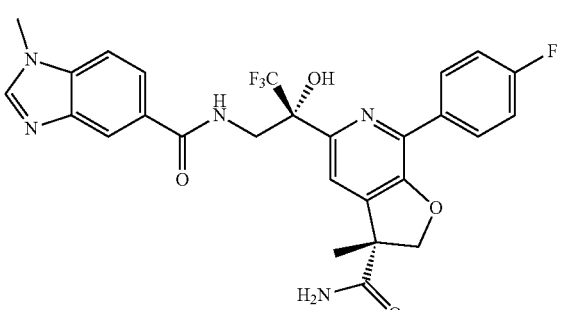 | 558.10 |
| 334 | 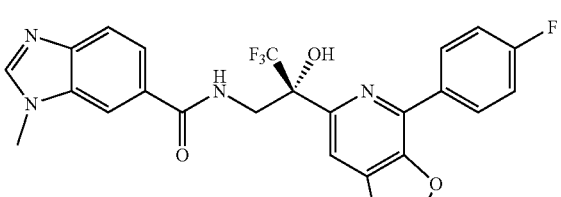 | 558.10 |
Method S
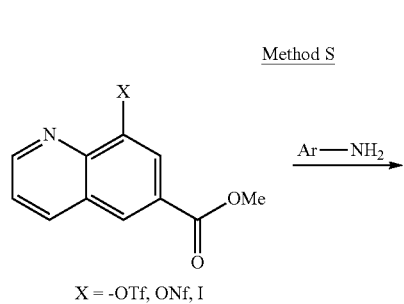
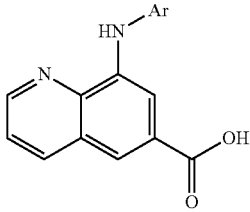
Example 335 Step a (Method S)
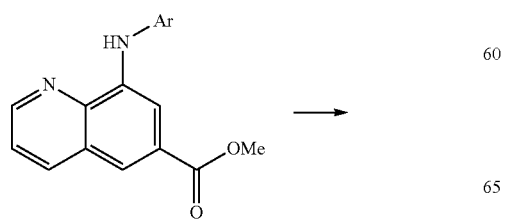

A suspension of methyl 8-hydroxyquinoline-6-carboxylate (3.00 g, 14.76 mmol) and Hunig's base (5.16 ml, 29.5 mmol) in DCM (59.1 ml) was cooled to 0° C. and treated with triflic anhydride (2.74 ml, 16.24 mmol). The suspension immediately became homogeneous and was warmed to room temperature and monitored by LC-MS. The reaction was quenched with sat'd aq. NaHCO$_3$ and extracted thrice with DCM. The combined organic extracts were dried over anhydrous MgSO$_4$, filtered, and concentrated. Purification by flash column chromatography on silica gel (0-100% EtOAc/hexanes) afforded the title compound (3.85 g, 78%). ESI-MS m/z: 336.1 [M+H]$^+$.

Example 335 Step b (Method S)

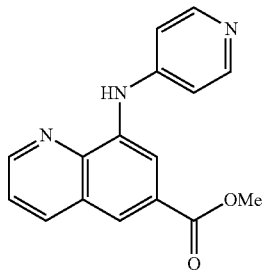 [SMILES: COC(=O)c1cc(Nc2ccncc2)c2ncccc2c1]

A mixture of pyridin-4-amine (0.047 g, 0.500 mmol), step a (0.168 g, 0.500 mmol), t-BuBrettPhos Pd G3 (0.021 g, 0.025 mmol), and potassium carbonate (0.097 g, 0.700 mmol) in t-BuOH (2.0 mL) was heated to 90° C. After stirring overnight, the reaction was cooled to room temperature, diluted with EtOAc, and washed with brine. The organic layer was dried over anhydrous magnesium sulfate, filtered, and concentrated. The crude residue was purified by flash column chromatography on silica gel, the material was used directly in the next step (yield nd). ESI-MS m/z: 280.1 [M+H]$^+$.

Note: For Method S additional amination conditions (X=I) that work well include Pd(OAc)$_2$ (cat), Xantphos (cat), Cs$_2$CO$_3$, toluene, 130° C., 2 hr.

Example 335 Step c (Method S)

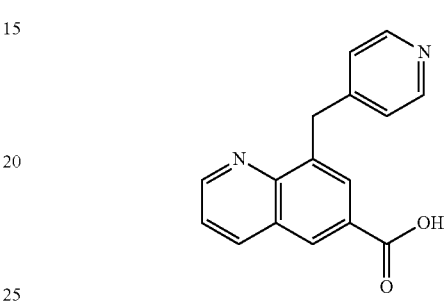

A solution of step b (0.140 g, 0.500 mmol) and potassium trimethylsilanolate (0.192 g, 1.500 mmol) in THF (5 mL) was stirred at room temperature overnight. The reaction was quenched with methanol, treated with silica gel, and concentrated. The resulting free-flowing admixture was directly purified by flash column chromatography on silica gel and used directly in the next step (19 mg, 14%). ESI-MS m/z: 265.9 [M+H]$^+$.

The following examples in Table 5 were prepared using Method J using HATU, and the crude material was purified by Gilson prep-HPLC (20-90%, MeCN/Water, 25 min) to afford the title compound. The aryl acid coupling partners were prepared in an analogous procedure to Method S.

TABLE 5

| Example | Structure | MS$^+$ m/z |
|---|---|---|
| 336 | 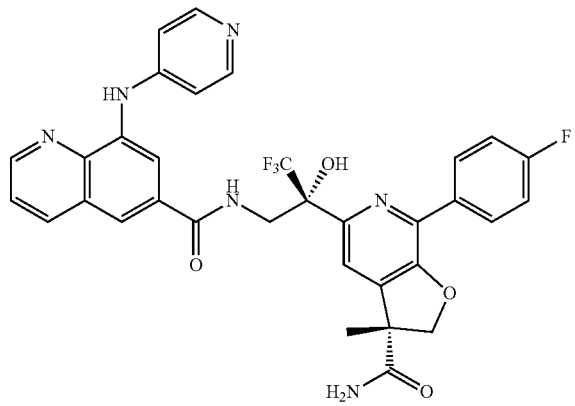 [SMILES: C[C@]1(C(N)=O)COc2c1cc([C@@](O)(CNC(=O)c1cc(Nc3ccncc3)c3ncccc3c1)C(F)(F)F)nc2-c1ccc(F)cc1] | 647.10 |

TABLE 5-continued

| Example | Structure | MS+ m/z |
|---------|-----------|---------|
| 337 | 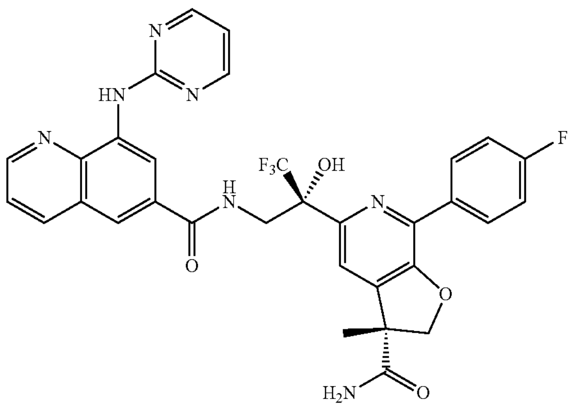 [SMILES: C[C@]1(C(N)=O)COc2c1cc([C@@](O)(CNC(=O)c1cc(Nc3ncccn3)c3ncccc3c1)C(F)(F)F)nc2-c1ccc(F)cc1] | 648.21 |
| 338 | 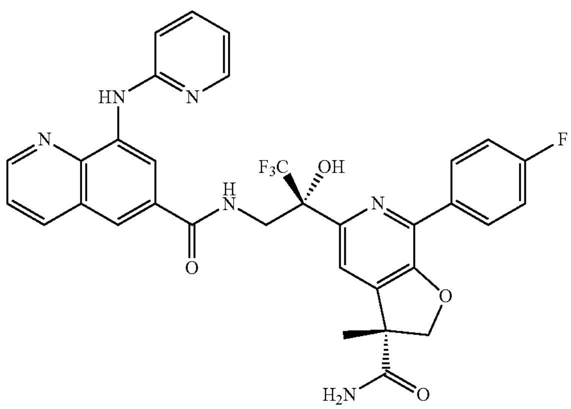 | 647.21 |
| 339 | 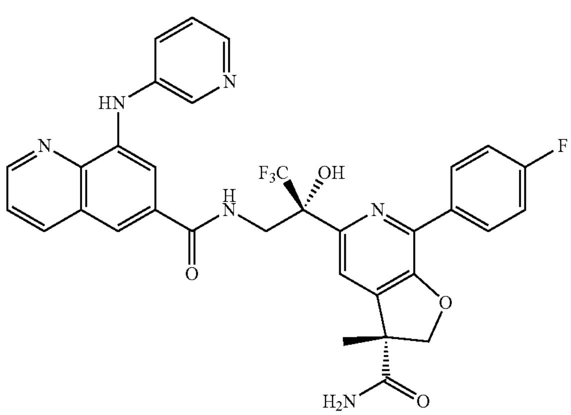 | 647.19 |

TABLE 5-continued
| Example | Structure | MS+ m/z |
|---|---|---|
| 340 | 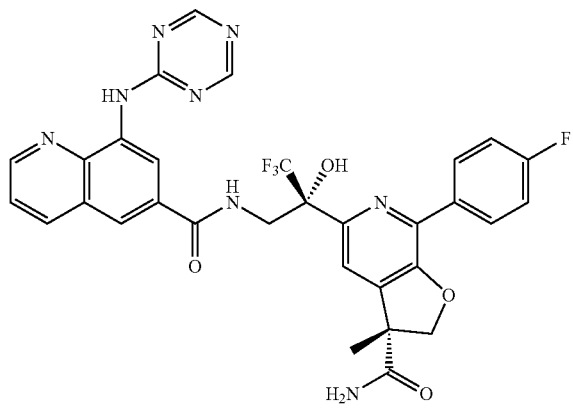 | 649.20 |
| 341 | 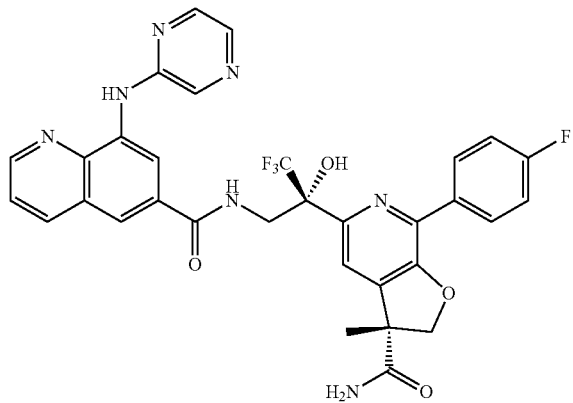 [SMILES: C[C@]1(C(N)=O)COc2c1cc([C@@](O)(CNC(=O)c1cc(Nc3cnccn3)c3ncccc3c1)C(F)(F)F)nc2-c1ccc(F)cc1] | 648.09 |
| 342 | 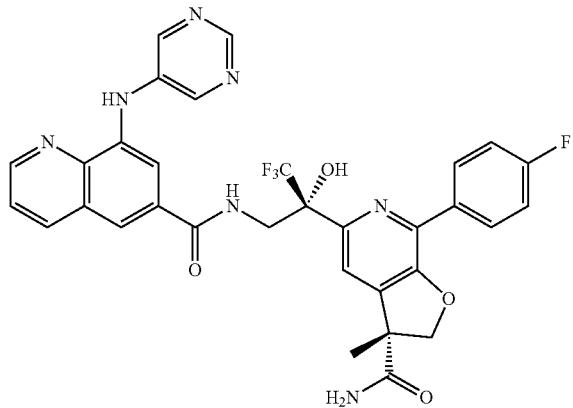 | 648.10 |

| Example | Structure | MS+ m/z |
|---|---|---|
| 343 | 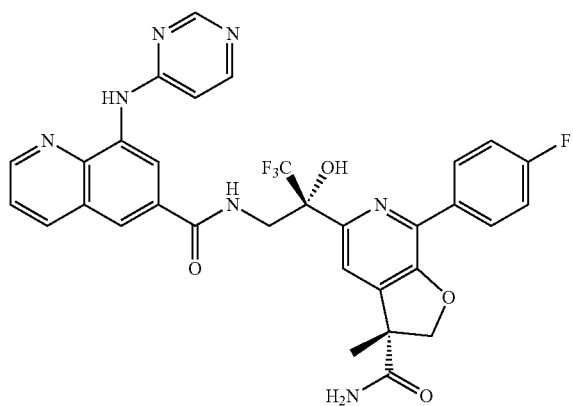 | 648.19 |
| 344 | 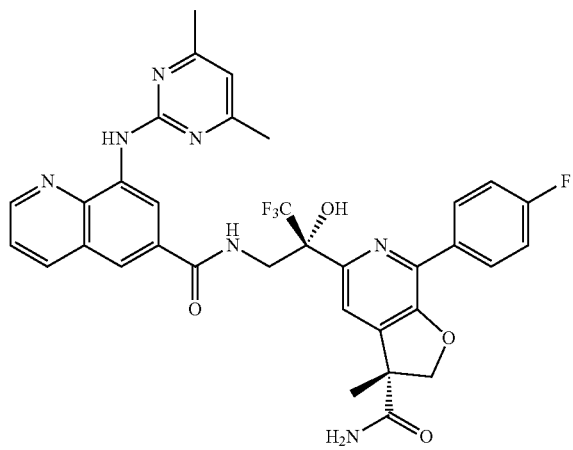 | 676.18 |
| 345 | 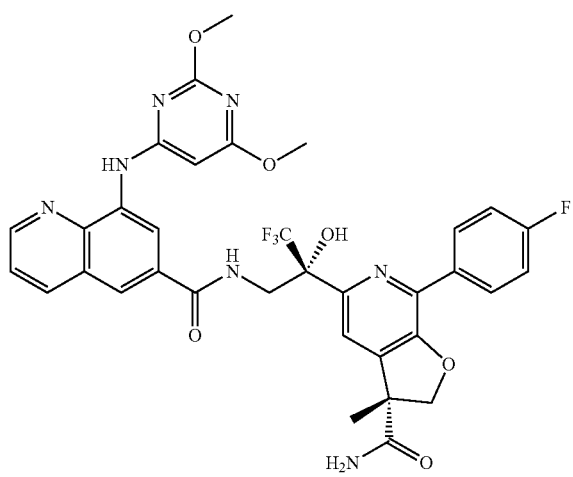 | 708.19 |

TABLE 5-continued
| Example | Structure | MS+ m/z |
|---|---|---|
| 346 | 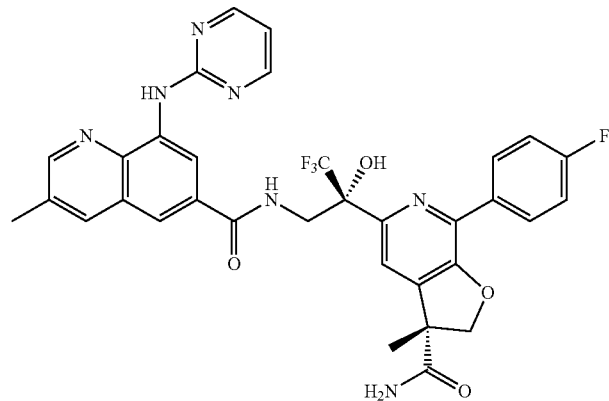 | 662.15 |
| 347 | 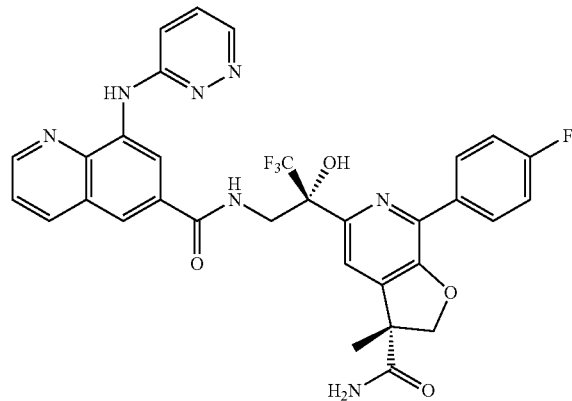 | 648.17 |
| 348 | 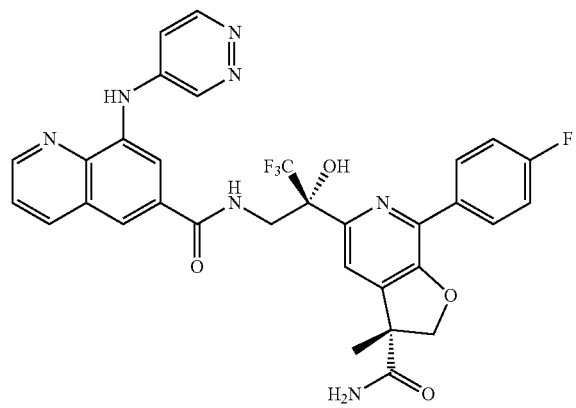 | 648.19 |

TABLE 5-continued

| Example | Structure | MS+ m/z |
|---|---|---|
| 349 | 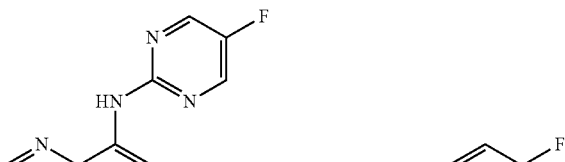 | 666.09 |

Example 350

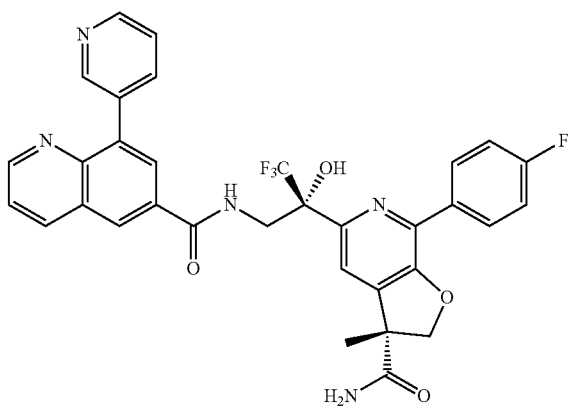 [SMILES: C[C@]1(C(N)=O)COc2c1cc([C@@](O)(CNC(=O)c1cc(-c3cccnc3)c3ncccc3c1)C(F)(F)F)nc2-c1ccc(F)cc1]

Example 350 Steps a and b

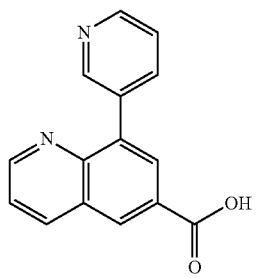 [SMILES: O=C(O)c1cc(-c2cccnc2)c2ncccc2c1]

A 20 mL vial was charged a magnetic stir-bar, pyridin-3-ylboronic acid (0.160 g, 1.300 mmol), Example 335 step a (Method S) (0.335 g, 1.00 mmol), and potassium carbonate (0.415 g, 3.00 mmol). THF (8 mL) and water (2 mL) were added and the reaction mixture was sparged with nitrogen and treated with bis(triphenylphosphine)palladium(II) chloride (0.070 g, 0.100 mmol). The reaction was heated to 70° C. and monitored by LC-MS (1 hr). The reaction was cooled to room temperature and poured into a separatory funnel, charged with EtOAc and brine. The organic phase was dried over anhydrous MgSO$_4$, filtered, and concentrated. Purification by flash column chromatography on silica gel afforded the title compound (260 mg, 98%) as a tan solid. ESI-MS m/z: 265.26 [M+H]+.

The methyl ester hydrolysis was carried out in an analogous fashion to Method S and was purified by automated column chromatography (silica gel, 0-30% MeOH/DCM) to afford the title compound (61 mg, 25%). ESI-MS m/z: 251.07 [M+H]+.

Example 350 Step c

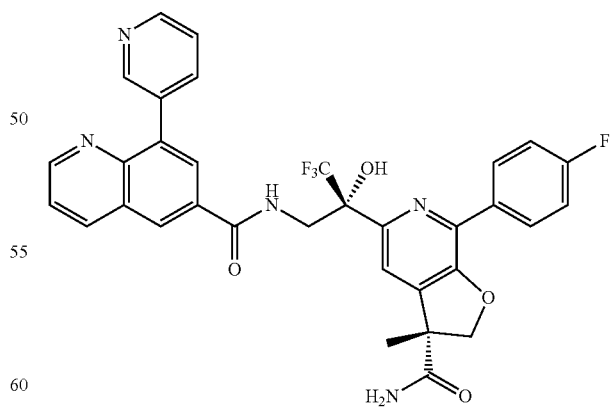

The following example was prepared using amine HCl salt (96 mg, 0.240 mmol) according to Method J (HATU). The crude material was purified by Gilson prep-HPLC (20-90%, MeCN/Water, 25 min) to afford the title compound (36 mg, 24%). ESI-MS m/z: 632.3 [M+H]+.

Example 351

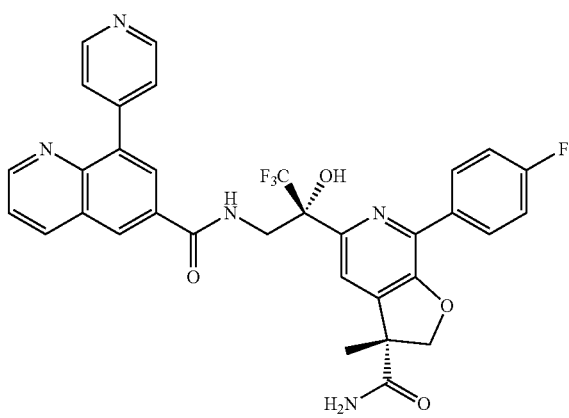 [SMILES: C[C@]1(C(N)=O)COc2c1cc([C@@](O)(CNC(=O)c1cc(-c3ccncc3)c3ncccc3c1)C(F)(F)F)nc2-c1ccc(F)cc1]

The following example was prepared in an analogous fashion to Example 350 using amine HCl salt (35 mg, 0.08 mmol), and the crude material was purified by Gilson prep-HPLC (20-90%, MeCN/Water, 25 min) to afford the title compound (24 mg, 48%). ESI-MS m/z: 632.3 [M+H]$^+$.

Example 352

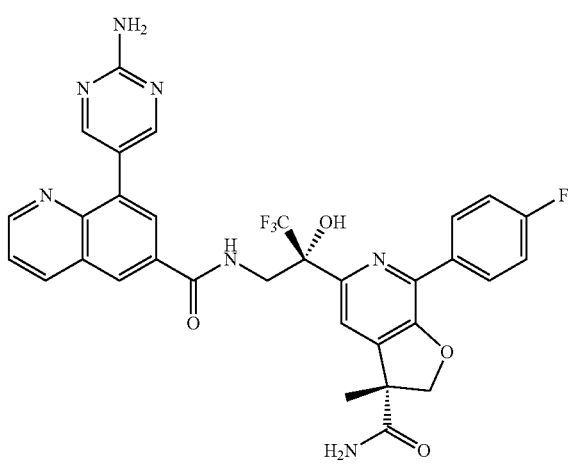 [SMILES: C[C@]1(C(N)=O)COc2c1cc([C@@](O)(CNC(=O)c1cc(-c3cnc(N)nc3)c3ncccc3c1)C(F)(F)F)nc2-c1ccc(F)cc1]

The following example was prepared in an analogous fashion to Example 350 using amine HCl salt (33 mg, 0.075 mmol), and the crude material was purified by Gilson prep-HPLC (20-90%, MeCN/Water, 25 min) to afford the title compound (0.5 mg, 1%). ESI-MS m/z: 648.3 [M+H]$^+$.

Example 353

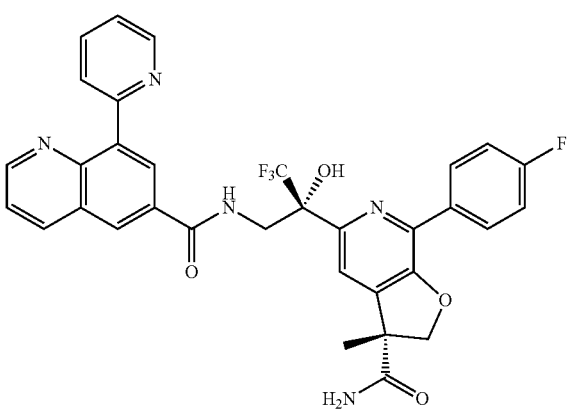 [SMILES: C[C@]1(C(N)=O)COc2c1cc([C@@](O)(CNC(=O)c1cc(-c3ccccn3)c3ncccc3c1)C(F)(F)F)nc2-c1ccc(F)cc1]

The following example was prepared in an analogous fashion to Example 350 using amine (52 mg, 0.120 mmol), and the crude material was purified by Gilson prep-HPLC (20-90%, MeCN/Water, 25 min) to afford the title compound (6.4 mg, 9%). ESI-MS m/z: 632.2 [M+H]$^+$.

Example 354

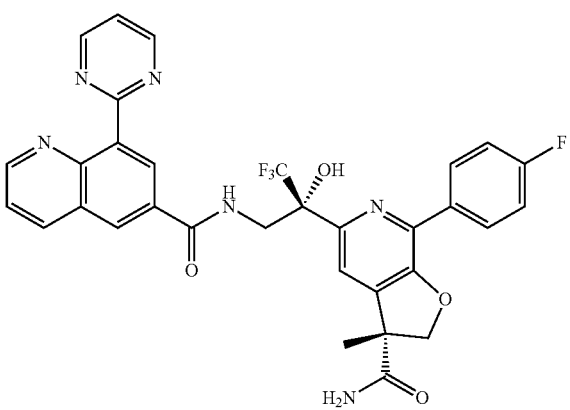

The following example was prepared in an analogous fashion to Example 350 using amine (78 mg, 0.179 mmol), and the crude material was purified by Gilson prep-HPLC (20-90%, MeCN/Water, 25 min) to afford the title compound (82 mg, 72%). ESI-MS m/z: 633.3 [M+H]$^+$.

Example 355

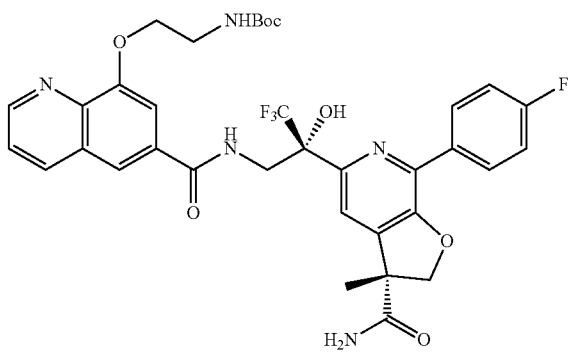 [SMILES: CC(C)(C)OC(=O)NCCOc1cc(C(=O)NC[C@](O)(c2cc3c(c(-c4ccc(F)cc4)n2)OC[C@]3(C)C(N)=O)C(F)(F)F)cc2cccnc12]

Example 355 Steps a and b

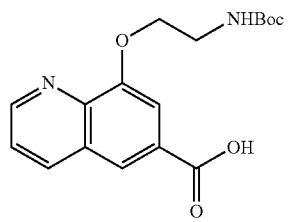 [SMILES: CC(C)(C)OC(=O)NCCOc1cc(C(=O)O)cc2cccnc12]

A mixture of methyl 8-hydroxyquinoline-6-carboxylate (1.00 g, 4.92 mmol), tert-butyl (2-iodoethyl)carbamate (2.00 g, 7.38 mmol), and cesium carbonate (3.21 g, 9.84 mmol) in DMF (20 mL) was stirred at room temperature for 24 hr. The reaction mixture was poured into brine and extracted thrice with EtOAc. The combined organic extracts were dried over anhydrous MgSO$_4$, filtered, and concentrated. Purification by flash column chromatography on silica gel (0-100% EtOAc/hexanes, then 0-30% MeOH/DCM) afforded an orange/brown oil. The product contained a lot of DMF but was otherwise pure. High-vacuum overnight afforded pure title compound (1.36 g, 80%). ESI-MS m/z: 347.21 [M+H]$^+$.

The methyl ester hydrolysis was carried out in an analogous fashion to Method S and was purified by automated column chromatography (silica gel, 0-30% MeOH/DCM) to afford the title compound (505 mg, 53%). ESI-MS m/z: 333.05 [M+H]$^+$.

Example 355 Step c

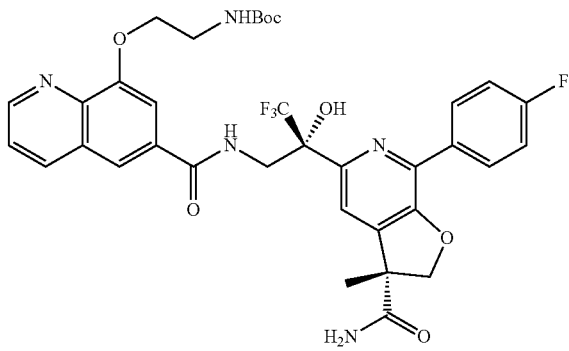 [SMILES: CC(C)(C)OC(=O)NCCOc1cc(C(=O)NC[C@](O)(c2cc3c(c(-c4ccc(F)cc4)n2)OC[C@]3(C)C(N)=O)C(F)(F)F)cc2cccnc12]

The following example was prepared according to Method J (HATU) with amine HCl salt (204 mg, 0.511 mmol), and the crude material was purified by automated column chromatography to afford the title compound (262 mg, 72%). ESI-MS m/z: 714.3 [M+H]$^+$.

Example 356

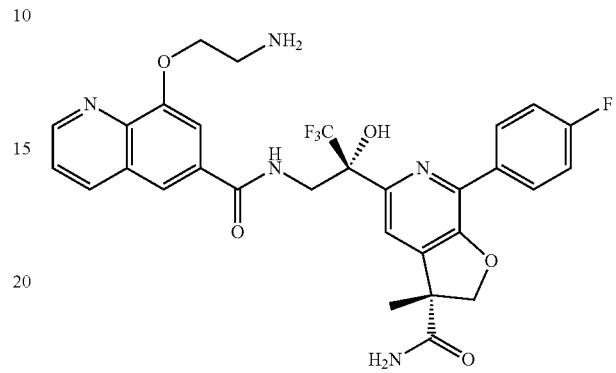

The following example was prepared according to Example 355 step b and Method J (HATU) with amine HCl salt (17 mg, 0.511 mmol) and Boc-acid (14 mg). The crude material was dissolved in ~1.5 mL DCM and treated with 0.25 mL TFA at room temperature. After 30 min, the reaction was concentrated and directly purified by Gilson prep-HPLC (20-90%, MeCN/Water, 25 min) to afford the title compound (2.8 mg, 11%). ESI-MS m/z: 614.1 [M+H]$^+$.

Example 357

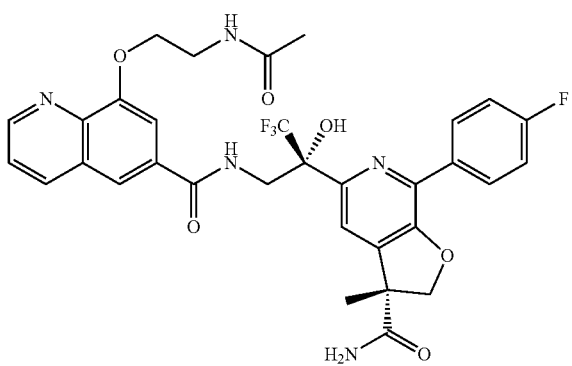 [SMILES: CC(=O)NCCOc1cc(C(=O)NC[C@](O)(c2cc3c(c(-c4ccc(F)cc4)n2)OC[C@]3(C)C(N)=O)C(F)(F)F)cc2cccnc12]

Example 357 Step a

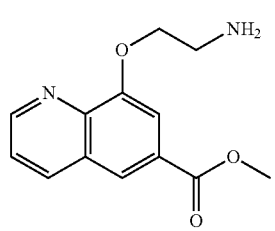 [SMILES: COC(=O)c1cc(OCCN)c2ncccc2c1]

A solution of Example 355 step a (1.00 g, 2.89 mmol) in DCM (9 mL) was treated with TFA (1.80 mL) at room temperature. Upon complete consumption of SM (14 hr, LCMS), the reaction was concentrated and partitioned between DCM/MeOH (9:1) and sat'd aq. NaHCO$_3$. The aqueous phase was extracted thrice with DCM/MeOH (9:1) and the combined organic extracts were dried over anhydrous magnesium sulfate, filtered, and concentrated to afford the title compound (0.7 g, 98%) as a light tan solid that was used without further purification. ESI-MS m/z: 247.1 [M+H]$^+$.

Example 357 Steps b and c

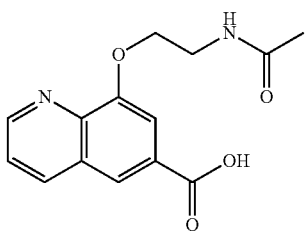 [SMILES: CC(=O)NCCOc1cc(C(=O)O)cc2cccnc12]

A solution step a (0.100 g, 0.406 mmol) and triethylamine (0.170 mL, 1.218 mmol) in DCM (5 mL) was treated with acetyl chloride (0.029 ml, 0.406 mmol) at room temperature and stirred overnight. The reaction was quenched with sat'd aq. NaHCO$_3$ and extracted with dichloromethane. The combined organic extracts were dried over anhydrous magnesium sulfate, filtered, and concentrated. The resulting crude material was used without further purification. ESI-MS m/z: 289.9 [M+H]$^+$.

The methyl ester hydrolysis was carried out in an analogous fashion to Method S and was purified by automated column chromatography (silica gel, 0-100% MeOH/DCM) to afford the title compound (109 mg, 98%). ESI-MS m/z: 275.06 [M+H]$^+$.

Example 357 Step d

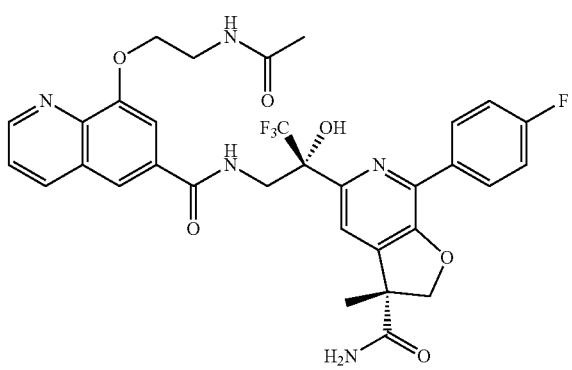 [SMILES: CC(=O)NCCOc1cc(C(=O)NC[C@](O)(c2cc3c(c(-c4ccc(F)cc4)n2)OC[C@]3(C)C(N)=O)C(F)(F)F)cc2cccnc12]

The following example was prepared according to Method J (HATU) with amine HCl salt (50 mg, 0.125 mmol). The crude material was purified by Gilson prep-HPLC (20-90%, MeCN/Water, 25 min) to afford the title compound (52 mg, 63%). ESI-MS m/z: 656.2 [M+H]$^+$.

Example 358

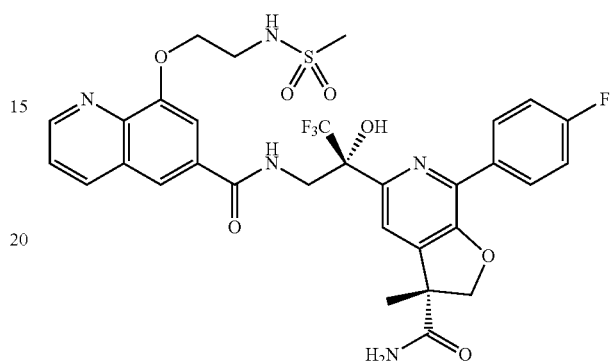

The aryl acid coupling partner was prepared using Example 357 step a (amine above) and mesyl-chloride over the same sequence to afford the title compound. ESI-MS m/z: 231.0 [M+H]$^+$. The following example was prepared according to Method J (HATU) with amine HCl salt (27 mg, 0.068 mmol) and the crude material was purified by Gilson prep-HPLC (20-90%, MeCN/Water, 25 min) to afford the title compound (30 mg, 64%). ESI-MS m/z: 692.1 [M+H]$^+$.

Example 359

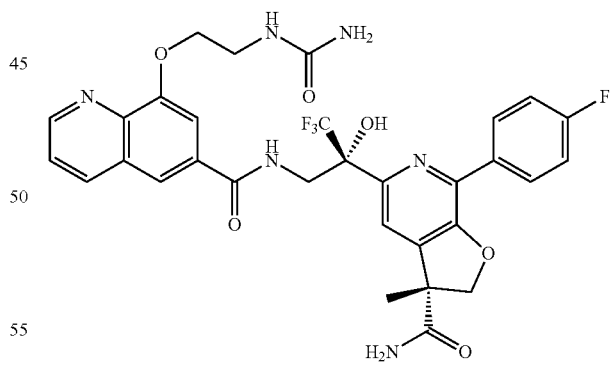

The aryl acid coupling partner was prepared using Example 357 step a (amine above) and potassium cyanate over the same sequence to afford the title compound (90 mg, 71%). ESI-MS m/z: 311.0 [M+H]$^+$. The following example was prepared according to Method J (HATU) with amine HCl salt (50 mg, 0.125 mmol) and the crude material was purified by Gilson prep-HPLC (20-90%, MeCN/Water, 25 min) afford the title compound (0.5 mg, 6%). ESI-MS m/z: 657.1 [M+H]$^+$.

Example 360

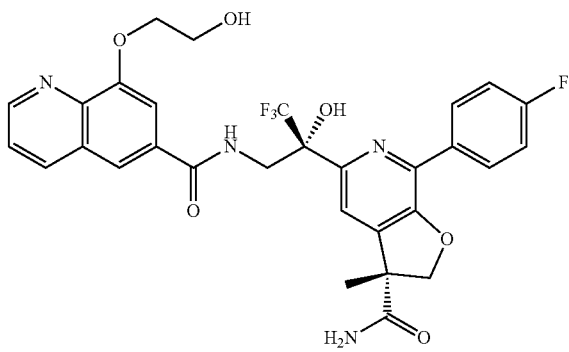 [SMILES: C[C@]1(C(N)=O)COc2c1cc([C@@](O)(CNC(=O)c1cc(OCCO)c3ncccc3c1)C(F)(F)F)nc2-c1ccc(F)cc1]

Example 360 Steps a and b

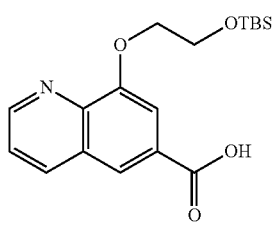 [SMILES: CC(C)(C)[Si](C)(C)OCCOc1cc(C(=O)O)cc2cccnc12]

A mixture of methyl 8-hydroxyquinoline-6-carboxylate (1.00 g, 4.92 mmol), tert-butyl(2-chloroethoxy)dimethylsilane (1.43 g, 7.38 mmol), and cesium carbonate (3.21 g, 9.84 mmol) in DMF (10 mL) was stirred at 50° C. for 24 hr. The reaction mixture was poured into brine and extracted thrice with EtOAc. The combined organic extracts were dried over anhydrous MgSO$_4$, filtered, and concentrated. Repeated purification by flash column chromatography on silica gel (0-50% EtOAc/hexanes) afforded the title compound (0.285 g, 16%) as a tan waxy solid. The methyl ester hydrolysis was carried out in an analogous fashion to Method S and was purified by automated column chromatography (silica gel, 0-100% acetone/cyclohexanes) to afford the title compound (74 mg, 27%). ESI-MS m/z: 348.16 [M+H]$^+$.

Example 360 Steps c and d

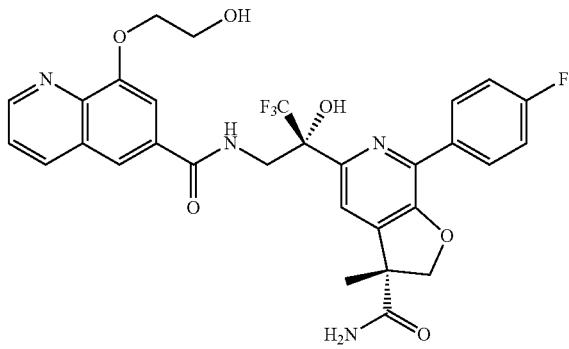 [SMILES: C[C@]1(C(N)=O)COc2c1cc([C@@](O)(CNC(=O)c1cc(OCCO)c3ncccc3c1)C(F)(F)F)nc2-c1ccc(F)cc1]

The following example was prepared according to Method J (HATU) with amine HCl salt (80 mg, 0.201 mmol). The crude material was dissolved in THF (2 mL), and treated with TBAF (1M in THF, 2.01 mL, 2.01 mmol). After full conversion, the reaction was concentrated and directly purified by Gilson prep-HPLC (20-90%, MeCN/Water, 25 min) afford the title compound (20 mg, 16%). ESI-MS m/z: 615.3 [M+H]$^+$.

Example 361

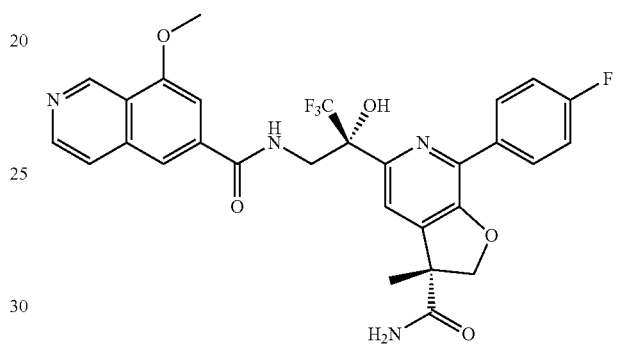

Example 361 Steps a and b

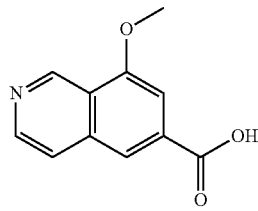

A solution of 6-bromo-8-methoxyisoquinoline (400 mg, 1.7 mmol), TEA (510 mg, 5.0 mmol) and Pd(dppf)Cl$_2$ (246 mg, 0.3 mmol) in MeOH (20 mL) was stirred for 3 h at 100° C. under a CO atmosphere (10 atm). The mixture was filtered, concentrated and purified by silica gel column chromatography (EtOAc/hexanes) to afford the desired compound as a light-yellow solid (300 mg, 82%). ESI-MS m/z: 218.05 [M+H]$^+$.

The methyl ester was hydrolyzed in a similar manner to Method O, and the material was purified by reverse phase prep-HPLC (MeCN/H$_2$O) to give the desired compound as a yellow solid (265 mg, 94%). ESI-MS m/z: 204.05 [M+H]$^+$.

Example 361 Step c

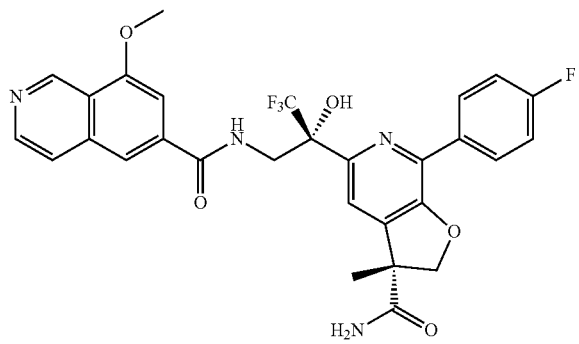 [SMILES: COc1cc(C(=O)NC[C@](O)(c2cc3c(c(-c4ccc(F)cc4)n2)OC[C@]3(C)C(N)=O)C(F)(F)F)cc2ccncc12]

The title compound was prepared in an analogous fashion using Method J with amine (30 mg, 0.075 mmol), and the material was purified by prep-HPLC (20-90%, MeCN/Water, 25 min) to afford the title compound (11 mg, 25%). ESI-MS m/z: 585.35 [M+H]$^+$.

Example 362

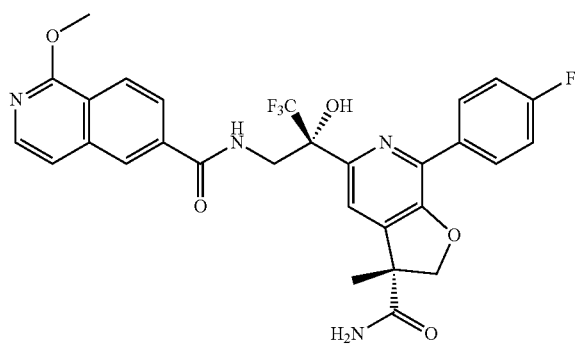 [SMILES: COc1nccc2cc(C(=O)NC[C@](O)(c3cc4c(c(-c5ccc(F)cc5)n3)OC[C@]4(C)C(N)=O)C(F)(F)F)ccc12]

Example 362 Step a

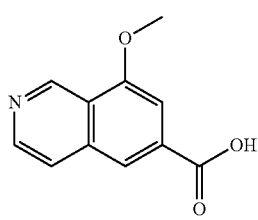

In a vial, 1-chloroisoquinoline-6-carboxylic acid (100 mg, 0.482 mmol) and sodium methoxide (771 μl, 3.37 mmol) (25% in MeOH) were stirred at reflux overnight. The reaction was concentrated, and water added. The aqueous layer acidified with 1M aq. HCl and washed with EtOAc. Combined organics dried over MgSO$_4$ and concentrated to give 1-methoxyisoquinoline-6-carboxylic acid (85 mg, 87%). ESI-MS m/z: 203.93 [M+H]$^+$.

Example 362 Step b

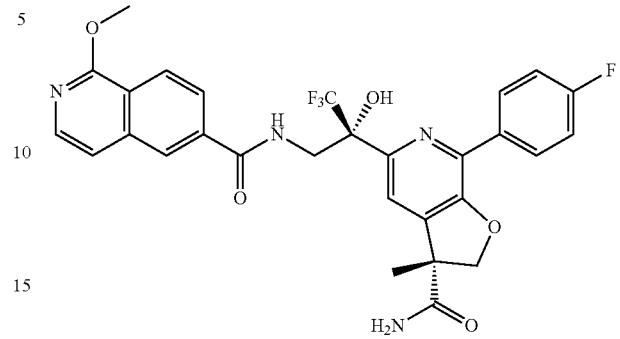

The title compound was prepared in an analogous fashion using Method J with amine (30 mg, 0.075 mmol), and the material was purified by prep-HPLC (20-90%, MeCN/Water, 25 min) to afford the title compound (13 mg, 30%). ESI-MS m/z: 585.10 [M+H]$^+$.

Example 363

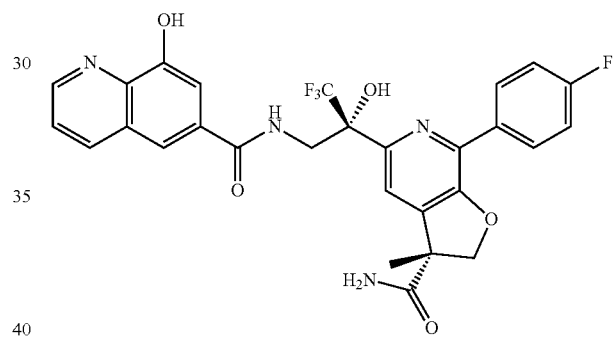

The following example was prepared using the same procedures as Method J (PyBOP) with the corresponding acid and amine HCl salt (200 mg) coupling partners, and purified by automated column chromatography (silica gel, 0-100% ethyl acetate in hexanes) to afford the title compound 195 mg (68%). ESI-MS m/z: 571.1 [M+H]$^+$.

Example 364

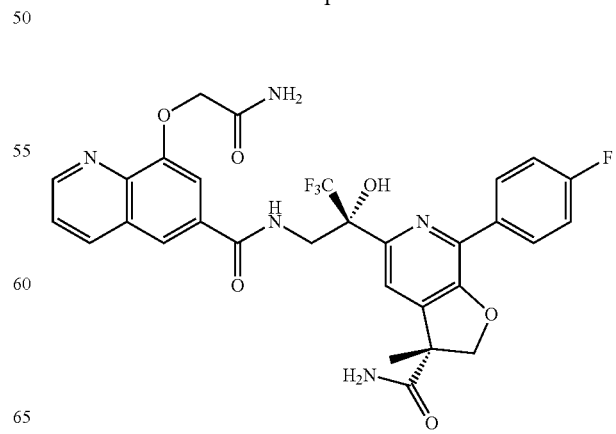

To a 2-dram vial containing a stir bar was added Example 363 (25 mg, 0.044 mmol), 2-bromoacetamide (7.25 mg, 0.053 mmol) and potassium carbonate (12.11 mg, 0.088 mmol). The solids were dissolved in DMF (0.15 M), the reaction stirred at room temperature and monitored by LCMS. Another equiv. of bromoacetamide was added after 2 hours to push conversion. The reaction was diluted with EtOAc and quenched with water. The aqueous was extracted with EtOAc, with a phase separator cartridge, and the combined organics were concentrated. The crude residue was purified by Gilson prep-HPLC (20-90%, MeCN/Water, 25 min) and lyophilized with ACN/H₂O to afford a white, fluffy solid (10.3 mg, 36%). ESI-MS m/z: 628.2.

Example 365

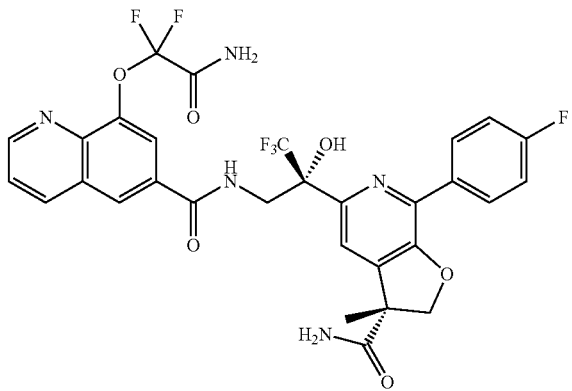 [SMILES: C[C@]1(C(N)=O)COc2c1cc([C@@](O)(CNC(=O)c1cc(OC(F)(F)C(N)=O)c3ncccc3c1)C(F)(F)F)nc2-c1ccc(F)cc1]

This example was prepared in an analogous fashion as Example 364 with 4 eq of 2-bromo-2,2-difluoroacetamide at 60° C. for 16 hrs. The material was purified by Gilson prep-HPLC (20-90%, MeCN/Water, 25 min) to afford the title compound (8.1 mg, 23%). ESI-MS m/z: 664.1 [M+H]⁺.

Example 366

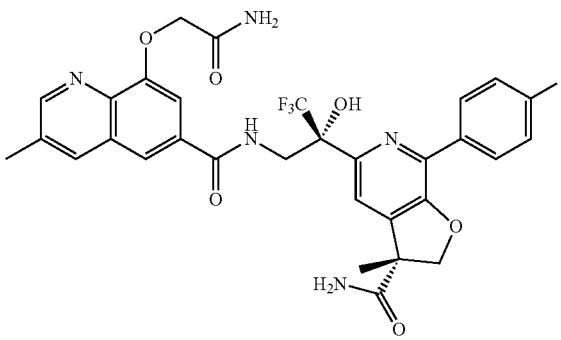

The starting material was prepared with Example 212 analogously to Example 363 to afford the hydroxyquinoline precursor (53 mg, 61%). ESI-MS m/z: 585.2 [M+H]⁺.

Example 366 was prepared in an analogous fashion as example 364 with 1.5 eq 2-bromoacetamide for 3 hr (added 1.2 eq more after 2 hr). The material was purified by Gilson prep-HPLC (20-90%, MeCN/Water, 25 min) to afford the title compound (25.0 mg, 43%). ESI-MS m/z: 642.1 [M+H]⁺.

Example 367

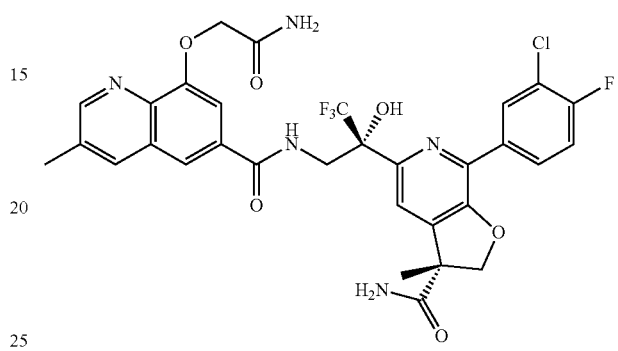

The starting material was prepared with Example 212 analogously to Example 363 to afford the hydroxyquinoline precursor (62 mg, 67%). ESI-MS m/z: 619.2 [M+H]⁺.

Example 367 was prepared in an analogous fashion as example 364. The material was purified by Gilson prep-HPLC (20-90%, MeCN/Water, 25 min) to afford the title compound (30.0 mg, 44%). ESI-MS m/z: 676.1 [M+H]⁺.

Example 368

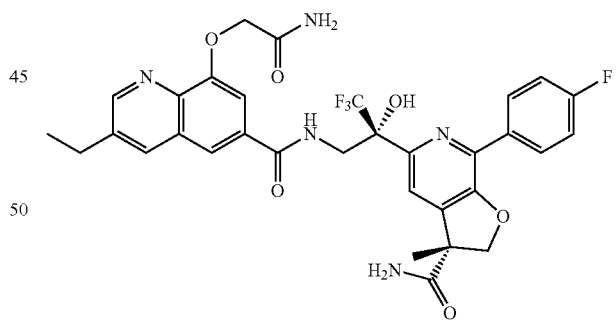

The starting material was prepared with Example 214 analogously to Example 363 to afford the hydroxyquinoline precursor (58 mg, 65%). ESI-MS m/z: 599.1 [M+H]⁺.

Example 368 was prepared in an analogous fashion as example 364 with 1.5 eq 2-bromoacetamide for 3 hr (added 1.2 eq more after 2 hr). The material was purified by Gilson prep-HPLC (20-90%, MeCN/Water, 25 min) to afford the title compound (31.5 mg, 50%). ESI-MS m/z: 656.2 [M+H]⁺.

Example 369

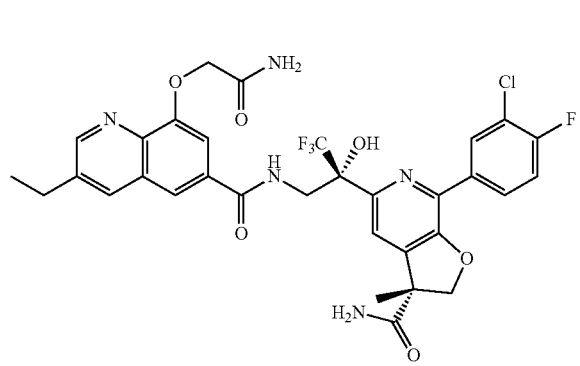 [SMILES: CCc1cnc2c(OCC(N)=O)cc(C(=O)NC[C@](O)(c3cc4c(c(-c5ccc(F)c(Cl)c5)n3)OC[C@]4(C)C(N)=O)C(F)(F)F)cc2c1]

The starting material was prepared with Example 214 analogously to Example 363 to afford the hydroxyquinoline precursor (63 mg, 66%). ESI-MS m/z: 635.3 [M+H]+.

Example 369 was prepared in an analogous fashion as Example 364. The material was purified by Gilson prep-HPLC (20-90%, MeCN/Water, 25 min) to afford the title compound (33.0 mg, 48%). ESI-MS m/z: 690.1 [M+H]+.

Method T

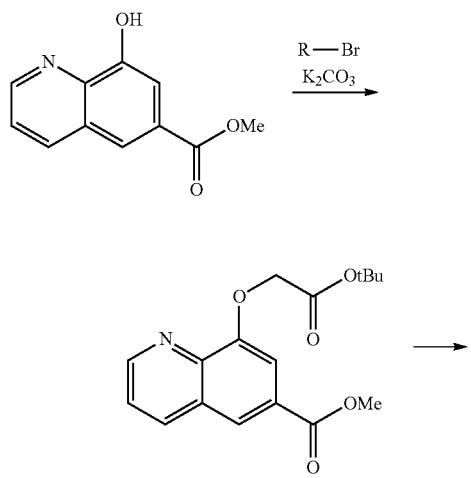

Example 370

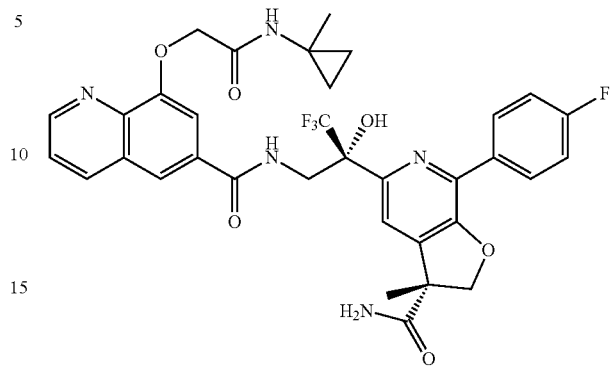

Example 370 Step a (Method T)

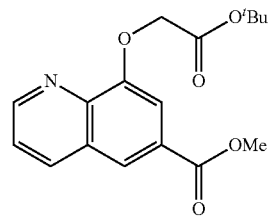 [SMILES: COC(=O)c1cc(OCC(=O)OC(C)(C)C)c2ncccc2c1]

To a 50 mL round-bottom flask equipped with a stir bar was added methyl 8-hydroxyquinoline-6-carboxylate (1.500 g, 7.38 mmol) and potassium carbonate (2.040 g, 14.76 mmol), and the solids were dissolved in DMF (0.5 M). tert-Butyl 2-bromoacetate (1.308 ml, 8.86 mmol) was then added, the reaction stirred at 40° C. and monitored by LCMS (2 hr). The reaction was cooled to r.t., diluted with EtOAc and quenched with water. Aqueous was extracted with EtOAc, and the combined organics dried, filtered, and concentrated. The residue was purified by automated column chromatography (silica gel, $R_f$=0.27 in 50% ethyl acetate in hexanes) to afford a white, solid (1.93 g, 82%). ESI-MS m/z: 262.0 [M+H]+.

Example 370 Step b (Method T)

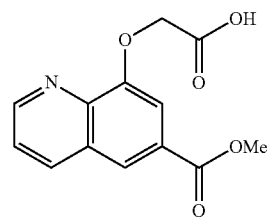 [SMILES: COC(=O)c1cc(OCC(=O)O)c2ncccc2c1]

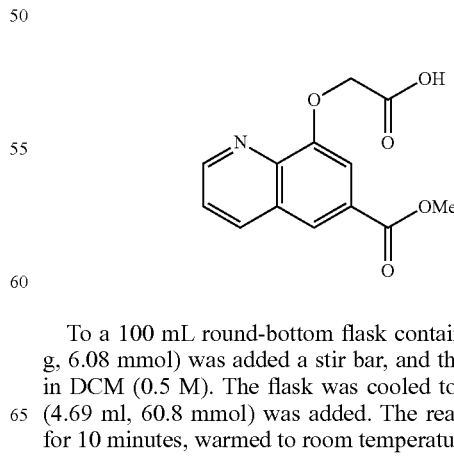

To a 100 mL round-bottom flask containing step a (1.93 g, 6.08 mmol) was added a stir bar, and the solid dissolved in DCM (0.5 M). The flask was cooled to 0° C., and TFA (4.69 ml, 60.8 mmol) was added. The reaction was stirred for 10 minutes, warmed to room temperature and monitored by LCMS (added 5.0 eq. more TFA after 3 hr, 5.5 hr total).

The mixture was quenched with water and diluted with DCM. Solid precipitates. Further diluted with DCM and stirred vigorously for 10 minutes. The solid was collected by filtration and washed multiple times with DCM and dried under high vacuum to afford a light brown, fluffy solid (2.21 g, 97%). ESI-MS m/z: 262.0 [M+H]⁺.

Example 370 Step c (Method T)

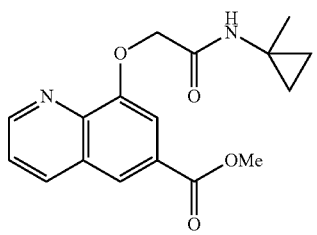 [SMILES: COC(=O)c1cc(OCC(=O)NC2(C)CC2)c2ncccc2c1]

To a 40 mL vial equipped with a stir bar was added step b (125 mg, 0.333 mmol). The solid was dissolved in DMF and cooled to 0° C. DIPEA (407 µl, 2.332 mmol) was added followed by 1-methylcyclopropan-1-amine hydrochloride (124 mg, 1.148 mmol). PyBOP (260 mg, 0.500 mmol) was then added in one portion, the reaction stirred for 10 minutes, warmed to room temperature and monitored by LCMS (1.5 hr). The reaction diluted was with EtOAc and quenched with water. The aqueous layer was extracted with EtOAc, with a phase separator cartridge, and the combined organics were concentrated. The residue was purified by automated column chromatography (silica gel, 0-20% methanol in dichloromethane) the title compound (98 mg, 82%). ESI-MS m/z: 216.0 [M+H]⁺.

Example 370 Step d (Method T)

General hydrolysis notes: In some cases, the reaction was heated to 45° C. to force material into solution and accelerate hydrolysis. After hydrolysis, the product was isolated by precipitation. If no precipitate, the product was either extracted, or the aqueous concentrated (material dried and used crude). The major MS⁺ m/z for all these compounds is C—C cleavage: ESI-MS m/z: 202.0 [M+H]⁺.

To a 20 mL vial containing Example 370 step c (9 mg, 0.312 mmol) was added a stir bar. The compound was dissolved in MeOH, THF and Water (0.2 M, 2:1:1). Lithium hydroxide hydrate (62 mg, 1.56 mmol) was added, the reaction stirred at room temperature and monitored by LCMS. The stir bar was removed, and the vial cooled to 0° C. The reaction was acidified with 2 M HCl, and the pH brought to around 4-5 (used 1M NaOH if too acidic). The product was extracted 3× with 10% MeOH/DCM with a phase separator and concentrated. Dried on high vacuum to afford the title compound (45 mg, 50%). ESI-MS m/z: 202.0 [M+H]⁺.

Example 370 Step e

The following example was prepared using the same procedures as Method J (PyBOP) with the corresponding acid from step d and amine HCl salt (25 mg) coupling partners. The residue was purified by Gilson prep-HPLC (20-90%, MeCN/Water, 25 min) to afford the title compound (8 mg, 20%) ESI-MS m/z: 682.2

Example 371

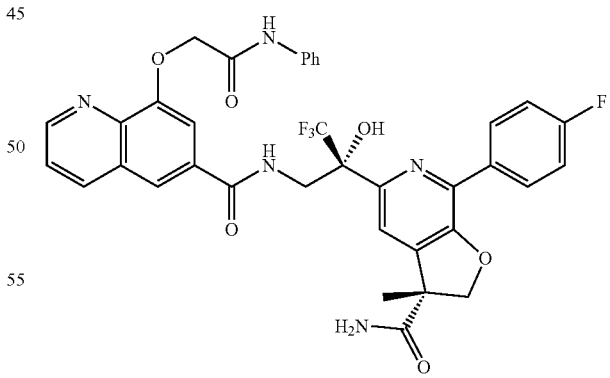

The following example was prepared using analogous procedures as Method J (PyBOP). The acid precursor was prepared according to Method T and isolated by extraction (32 mg, 50%). 20 mg amine HCl salt used for the final amide coupling. The residue was purified by Gilson prep-HPLC (20-90%, MeCN/Water, 25 min) to afford the title compound (13 mg, 40%) ESI-MS m/z: 704.2 [M+H]⁺.

Example 372

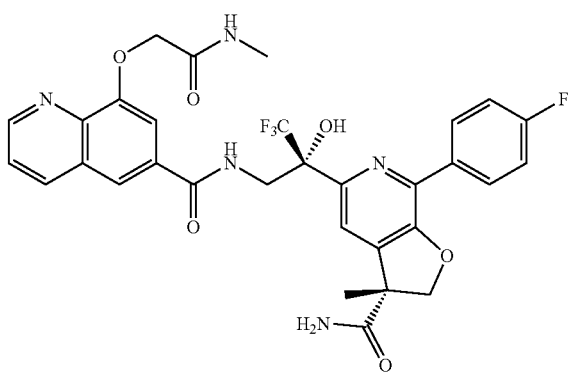 [SMILES: CNC(=O)COc1cc(C(=O)NC[C@](O)(c2cc3c(c(-c4ccc(F)cc4)n2)OC[C@]3(C)C(N)=O)C(F)(F)F)cc2cccnc12]

The following example was prepared using analogous procedures as Method J (PyBOP). The acid precursor was prepared according to Method T and isolated by extraction (14 mg, 40%), and 25 mg amine HCl salt used for the final amide coupling. The residue was purified by Gilson prep-HPLC (20-90%, MeCN/Water, 25 min) to afford the title compound (15 mg, 41%) ESI-MS m/z: 642.2 [M+H]$^+$.

Example 373

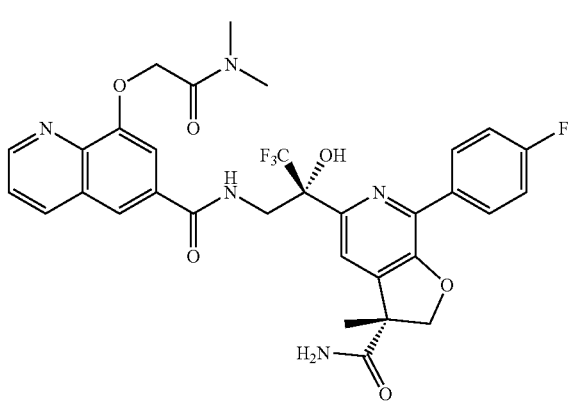 [SMILES: CN(C)C(=O)COc1cc(C(=O)NC[C@](O)(c2cc3c(c(-c4ccc(F)cc4)n2)OC[C@]3(C)C(N)=O)C(F)(F)F)cc2cccnc12]

The following example was prepared using analogous procedures as Method J (PyBOP). The acid precursor was prepared according to Method T and isolated by aqueous concentration (used crude), and 25 mg amine HCl salt used for the final amide coupling. The residue was purified by Gilson prep-HPLC (20-90%, MeCN/Water, 25 min) to afford the title compound (4.3 mg, 11%) ESI-MS m/z: 656.2 [M+H]$^+$.

Example 374

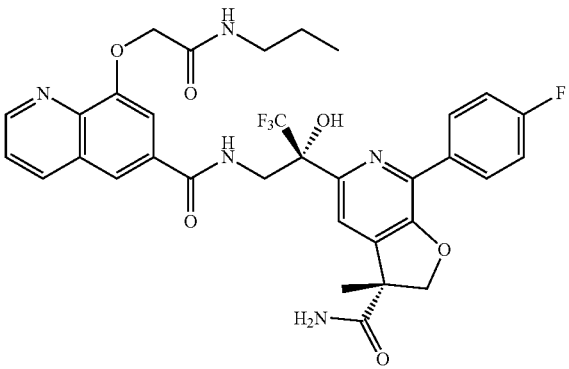 [SMILES: CCCNC(=O)COc1cc(C(=O)NC[C@](O)(c2cc3c(c(-c4ccc(F)cc4)n2)OC[C@]3(C)C(N)=O)C(F)(F)F)cc2cccnc12]

The following example was prepared using analogous procedures as Method J (PyBOP). The acid precursor was prepared according to Method T and isolated by extraction (41 mg, 69%), and 25 mg amine HCl salt used for the final amide coupling. The residue was purified by Gilson prep-HPLC (20-90%, MeCN/Water, 25 min) to afford the title compound (18.8 mg, 49%) ESI-MS m/z: 670.3 [M+H]$^+$.

Example 375

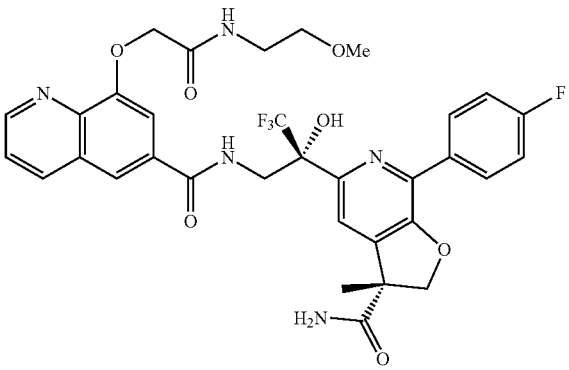 [SMILES: COCCNC(=O)COc1cc(C(=O)NC[C@](O)(c2cc3c(c(-c4ccc(F)cc4)n2)OC[C@]3(C)C(N)=O)C(F)(F)F)cc2cccnc12]

The following example was prepared using analogous procedures as Method J (PyBOP). The acid precursor was prepared according to Method T and isolated by precipitation (42 mg, 70%), and 25 mg amine HCl salt used for the final amide coupling. The residue was purified by Gilson prep-HPLC (20-90%, MeCN/Water, 25 min) to afford the title compound (13.4 mg, 35%) ESI-MS m/z: 686.3 [M+H]$^+$.

Example 376

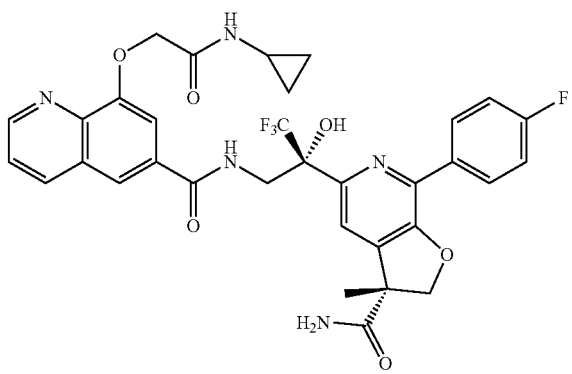 [SMILES: C[C@]1(C(N)=O)COc2c1cc([C@@](O)(CNC(=O)c1cc(OCC(=O)NC3CC3)c3ncccc3c1)C(F)(F)F)nc2-c1ccc(F)cc1]

The following example was prepared using analogous procedures as Method J (PyBOP). The acid precursor was prepared according to Method T and isolated by aqueous precipitation (used crude), and 25 mg amine HCl salt used for the final amide coupling. The residue was purified by Gilson prep-HPLC (20-90%, MeCN/Water, 25 min) to afford the title compound (13.0 mg, 34%) ESI-MS m/z: 668.2 [M+H]$^+$.

Example 377

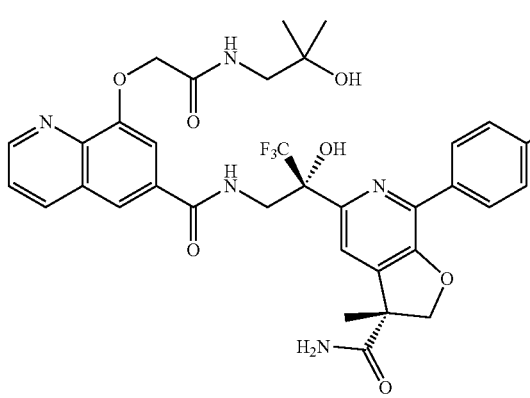

The following example was prepared using analogous procedures as Method J (PyBOP). The acid precursor was prepared according to Method T and isolated by Gilson HPLC purification (35 mg, 49%). 25 mg amine HCl salt used for the final amide coupling. The residue was purified by Gilson prep-HPLC (20-90%, MeCN/Water, 25 min) to afford the title compound (23.9 mg, 54%) ESI-MS m/z: 700.2 [M+H]$^+$.

Example 378

The following example was prepared using analogous procedures as Method J (PyBOP). The acid precursor was prepared according to Method T and isolated by aqueous concentration (used crude) and 25 mg amine HCl salt used for the final amide coupling. The residue was purified by Gilson prep-HPLC (20-90%, MeCN/Water, 25 min) to afford the title compound (8.0 mg, 29%) ESI-MS m/z: 702.2 [M+H]$^+$.

Example 379

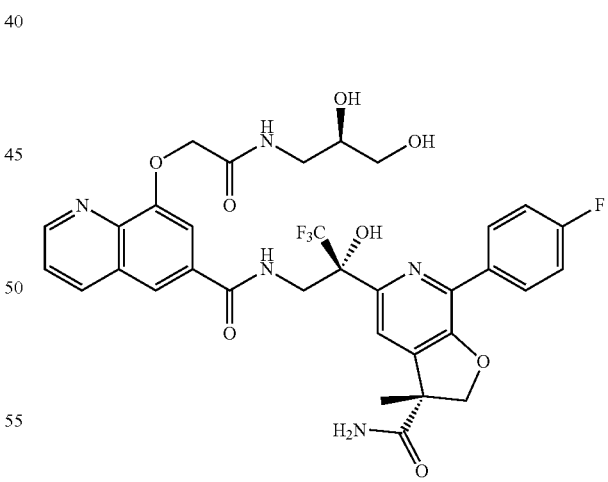

The following example was prepared using analogous procedures as according to Method J (PyBOP). The acid precursor was prepared according to Method T and isolated by aqueous concentration (used crude) and 25 mg amine HCl salt used for the final amide coupling. The residue was purified by Gilson prep-HPLC (20-90%, MeCN/Water, 25 min) to afford the title compound (6.0 mg, 15%) ESI-MS m/z: 702.2 [M+H]$^+$.

Example 380

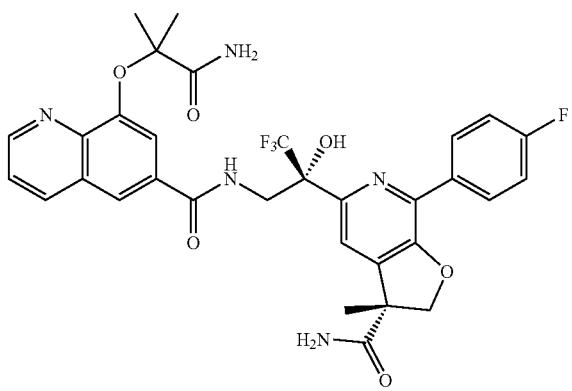 [SMILES: CC(C)(Oc1cc(C(=O)NC[C@](O)(c2cc3c(c(-c4ccc(F)cc4)n2)OC[C@]3(C)C(N)=O)C(F)(F)F)cc2cccnc12)C(N)=O]

Example 380 Steps a and b

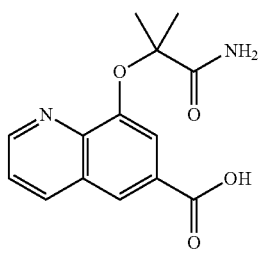 [SMILES: CC(C)(Oc1cc(C(=O)O)cc2cccnc12)C(N)=O]

The methyl ester was prepared using analogous procedures as Method R with 2.5 eq. K₂CO₃ and 1.5 eq. 2-bromo-2-methylpropionamide at 80° C. for 16 hrs. Residue was purified by automated column chromatography (silica gel, 0-100% EtOAc in hexanes) and then Gilson prep-HPLC (20-90%, MeCN/Water, 25 min) to afford the title compound (42.1 mg, 6%). ESI-MS m/z: 244.0 [M+H]⁺.

The acid precursor was prepared according to Method T and the material was isolated by aqueous concentration (used crude).

Example 380 Step c

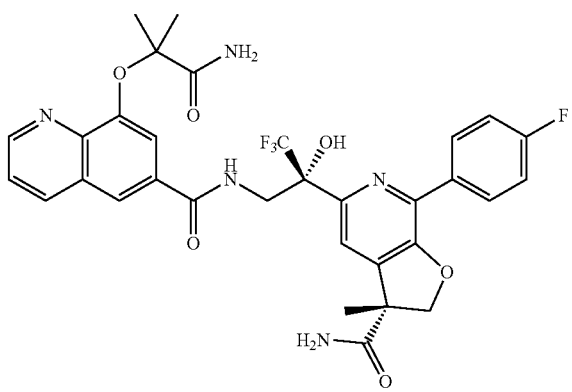 [SMILES: CC(C)(Oc1cc(C(=O)NC[C@](O)(c2cc3c(c(-c4ccc(F)cc4)n2)OC[C@]3(C)C(N)=O)C(F)(F)F)cc2cccnc12)C(N)=O]

The following example was prepared according to according to Method J (PyBOP) with 25 mg amine HCl salt used and 1.2 eq. acid for the final amide coupling. The residue was purified by Gilson prep-HPLC (20-90%, MeCN/Water, 25 min) to afford the title compound (17.6 mg, 46%) ESI-MS m/z: 656.2 [M+H]⁺.

Example 381

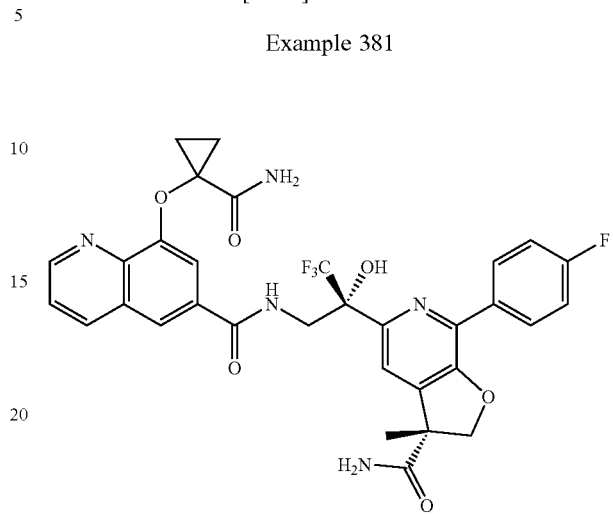

Example 381 Step a

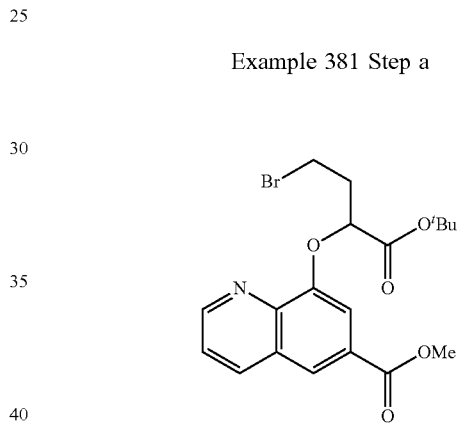

The following example was prepared according to Method T, step a with 2.5 eq. K₂CO₃ and 1.2 eq. tert-butyl 2,4-dibromobutanoate at 40° C. for 4 hr (Added 1.0 eq. more bromide after 3 hr). Material was purified by automated column chromatography (silica gel, 0-70% EtOAc in hexanes) to afford the title compound (1.23 g, 59%). ESI-MS m/z: 370.1 [M+H]⁺.

Example 381 Step b

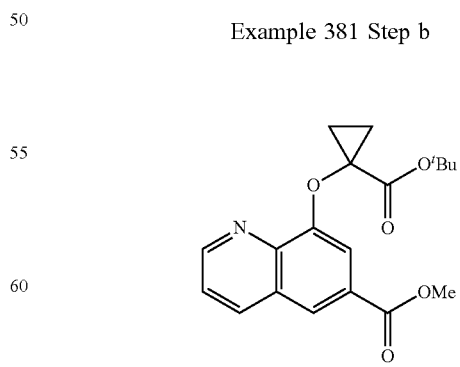

To a 100 mL round-bottom flask equipped with a stir bar was added step a (1.236 g, 2.91 mmol) as a solution of THF (0.1 M). The flask was cooled to 0° C., and potassium tert-butoxide (0.572 g, 5.10 mmol) was added in one portion. The flask was purged with nitrogen, stirred for 15 minutes, then allowed to warm to room temperature and monitored by LCMS (3.5 hr r.t, 1 hr at 40° C.). The reaction was cooled to r.t., diluted with EtOAc and quenched with water. Aqueous was extracted with EtOAc, and the combined organics dried, filtered, and concentrated. The material was purified by automated column chromatography (silica gel, 0-100% EtOAc in hexanes) to afford the title compound (82 mg, 8%). ESI-MS m/z: 344.2 [M+H]$^+$.

Example 381 Steps c, d, e

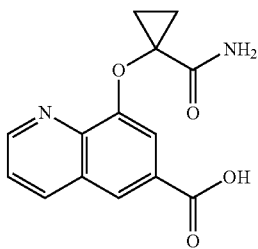 [SMILES: NC(=O)C1(Oc2cc(C(=O)O)cc3cccnc23)CC1]

The t-Bu ester deprotection was carried out analogously to Method T, step b (95 mg, 100%). ESI-MS m/z: 288.0 [M+H]. The primary amide formation was carried out with PyBOP (2 eq) and ammonium chloride (3 eq) according to Method J, and purified by automated column chromatography (silica gel, 0-100% EtOAc/hex to 0-10% DCM/MeOH) to afford the title compound (104 mg, 35% wt, 69%). ESI-MS m/z: 270.0 [M+H]. The methyl-ester hydrolysis was carried out according to Method T, step d, and was isolated by precipitation (17 mg, 50%). ESI-MS m/z: 256.0 [M+H].

Example 381 Step f

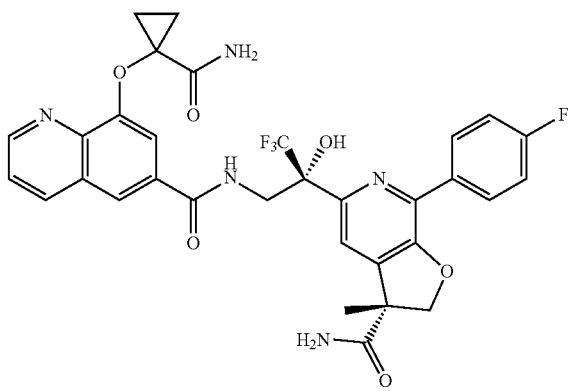 [SMILES: C[C@]1(C(N)=O)COc2c1cc([C@@](O)(CNC(=O)c1cc(OC3(C(N)=O)CC3)c3ncccc3c1)C(F)(F)F)nc2-c1ccc(F)cc1]

The following example was prepared with 25 mg amine HCl salt according to Method J (PyBOP) and the residue was purified by Gilson prep-HPLC (20-90%, MeCN/Water, 25 min) to afford the title compound (18 mg, 48%). ESI-MS m/z: 654.3 [M+H]$^+$.

Example 382

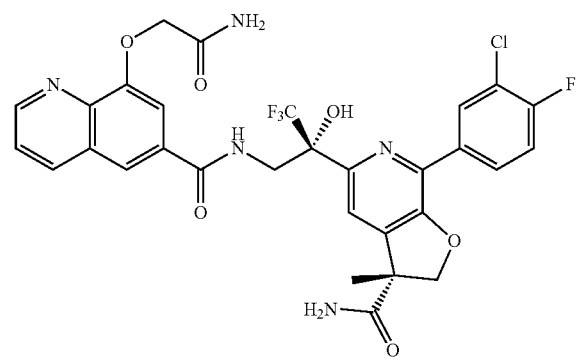 [SMILES: C[C@]1(C(N)=O)COc2c1cc([C@@](O)(CNC(=O)c1cc(OCC(N)=O)c3ncccc3c1)C(F)(F)F)nc2-c1ccc(F)c(Cl)c1]

The acid precursor was used from Method R and 20 mg of amine HCl salt precursor was used according to Method J (PyBOP), and the material was purified by Gilson prep-HPLC (20-90%, MeCN/Water, 25 min) to afford the title compound (12.4 mg, 41%). ESI-MS m/z: 662.1 [M+H]$^+$.

Example 383

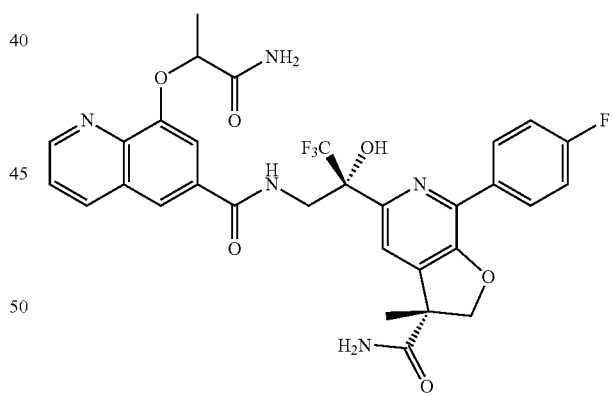

The methyl ester precursor was prepared in analogously to Method R with 1.5 eq. (±)-2-bromopropanamide at 40° C. for 16 hr (109 mg, 32%). ESI-MS m/z: 230.0 [M+H]$^+$. The methyl ester hydrolysis was carried out in an analogous fashion to Method R, and isolated by precipitation (50 mg, 48%). ESI-MS m/z: 260.9 [M+H]$^+$.

Example 383 was prepared with 60 mg of amine HCl salt precursor was according to Method J (PyBOP), and the material was purified by Gilson prep-HPLC (20-90%, MeCN/Water, 25 min) to afford the title compound as a mixture of diastereomers (34.3 mg, 38%). ESI-MS m/z: 642.1 [M+H]$^+$.

Example 384

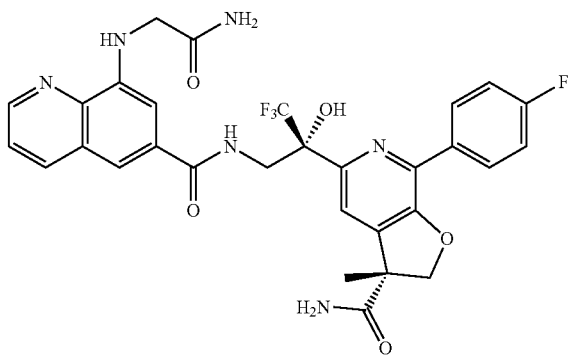 [SMILES: C[C@]1(C(N)=O)COc2c1cc([C@@](O)(CNC(=O)c1cc(NCC(N)=O)c3ncccc3c1)C(F)(F)F)nc2-c1ccc(F)cc1]

The methyl ester was prepared in an analogous fashion as Method R with methyl-8-aminoquinoline 6-carboxylate (200 mg), 4.0 eq. 2-bromoacetamide at 40° C. for 16 hr (78 mg, 30%). ESI-MS m/z: 215.0 [M+H]$^+$. The methyl ester hydrolysis was carried out in an analogous fashion to Method T, step d and isolated by precipitation (38 mg, 52%). ESI-MS m/z: 246.0 [M+H]$^+$.

Example 384 was prepared with 25 mg of amine HCl salt and the material was purified by Gilson prep-HPLC (20-90%, MeCN/Water, 25 min) to afford the title compound (14.0 mg, 39%). ESI-MS m/z: 627.2 [M+H]$^+$.

Example 385

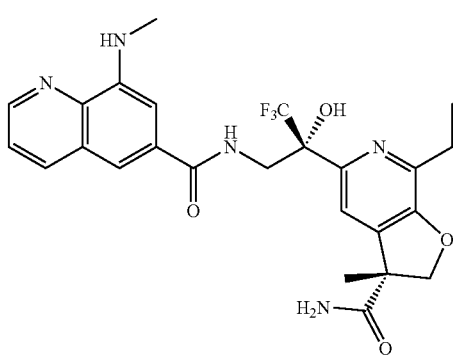

The methyl ester was prepared in an analogous fashion as Method R with methyl-8-aminoquinoline 6-carboxylate (300 mg), 1.2 eq. iodomethane at r.t. for 48 hrs (150 mg, 47%). ESI-MS m/z: 217.1 [M+H]$^+$. The methyl ester hydrolysis was carried out in an analogous fashion to Method T, step d, and isolated by precipitation (75 mg, 65%). ESI-MS m/z: 203.0 [M+H]$^+$.

Example 385 was prepared with 20 mg of amine HCl salt and the material was purified by Gilson prep-HPLC (20-90%, MeCN/Water, 25 min) to afford the title compound (19.6 mg, 72%). ESI-MS m/z: 585.2 [M+H]$^+$.

Example 386

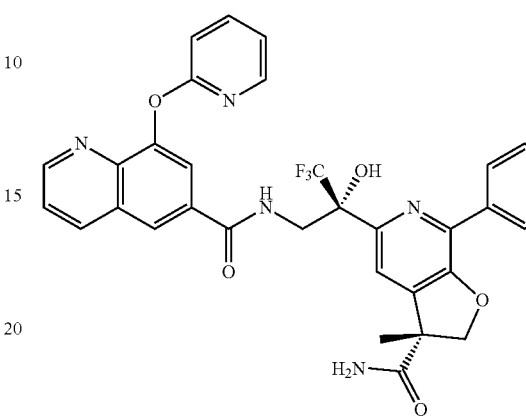

Example 386 Steps a and b

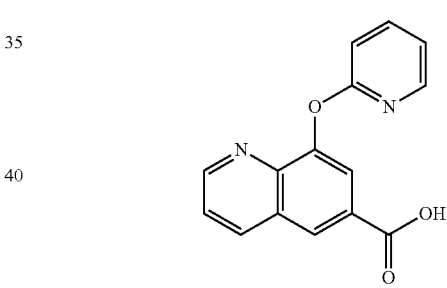

To a 20 mL vial equipped with a stir bar and pressure relief septa was added methyl 8-hydroxyquinoline-6-carboxylate (116 mg, 0.570 mmol), picolinic acid (11.69 mg, 0.095 mmol), potassium phosphate tribasic (202 mg, 0.949 mmol) and copper(I) iodide (9.04 mg, 0.047 mmol). The solids were dissolved in DMSO (0.33M), and 2-bromopyridine (45.3 µl, 0.475 mmol) was added. The flask was purged with N$_2$, and heated to 90° C. overnight for 14 hrs. The reaction was diluted with EtOAc and quenched with water. The copper salts were filtered away over celite, the aqueous extracted with 10% MeOH/DCM with a phase separator cartridge, and the combined organics concentrated. The residue was purified by automated column chromatography (silica gel, 0-100% EtOAc in hexanes) to afford the title compound (11 mg, 8%). ESI-MS m/z: 281.1 [M+H]$^+$. The methyl ester hydrolysis was carried out according to Method T, step d and isolated by aqueous concentration (used crude). ESI-MS m/z: 267.0 [M+H]$^+$.

Example 386 Step c

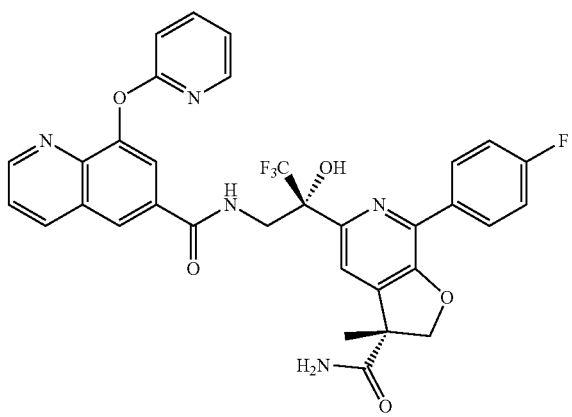 [SMILES: C[C@]1(C(N)=O)COc2c1cc([C@@](O)(CNC(=O)c1cc(Oc3ccccn3)c3ncccc3c1)C(F)(F)F)nc2-c1ccc(F)cc1]

This example was prepared according to Method J (PyBOP with 10 mg of amine HCl salt precursor. The material was purified by Gilson prep-HPLC (20-90%, MeCN/Water, 25 min) to afford the title compound (1.6 mg, 11%). ESI-MS m/z: 648.2 [M+H]$^+$.

Example 387

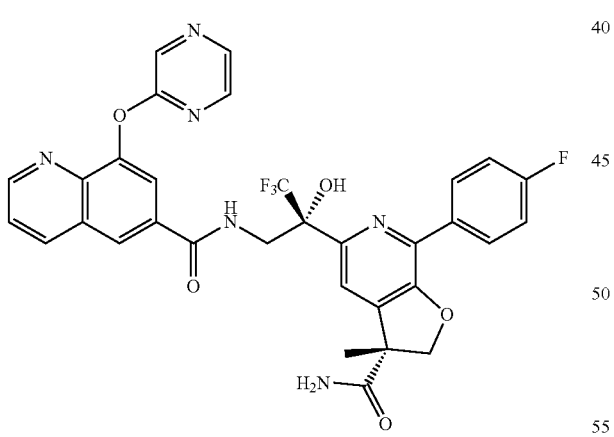

This example was prepared in an analogous sequence to Example 386. 2-bromopyrazine Ullman coupling (32 mg, 25%). ESI-MS m/z: 282.0 [M+H]$^+$. The acid hydrolysis was carried out according to Method T, step d and was isolated by aqueous extraction (15 mg, 50%). ESI-MS m/z: 268.0 [M+H]$^+$.

Example 387 was prepared with 25 mg of amine HCl salt precursor according to Method J (PyBOP) and the material purified by Gilson prep-HPLC (20-90%, MeCN/Water, 25 min) to afford the title compound (10.0 mg, 27%). ESI-MS m/z: 649.1 [M+H]$^+$.

Example 388

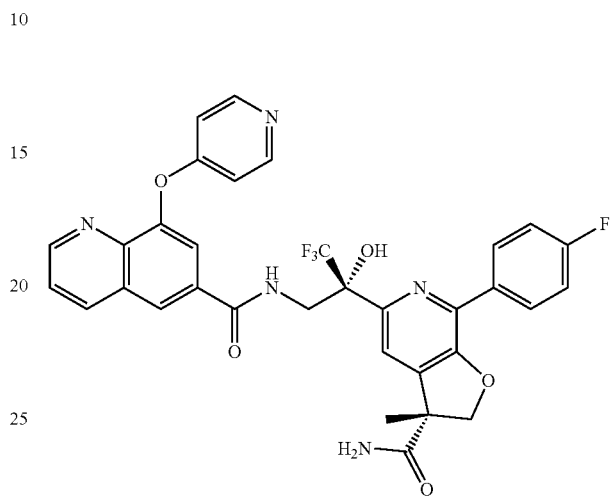

Example 388 Steps a and b

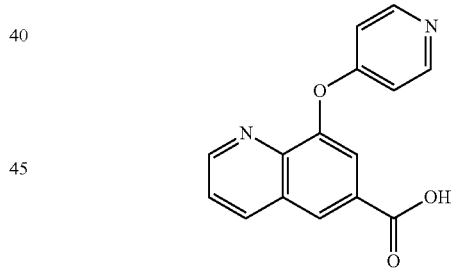

In a 20 mL vial equipped with a stir bar was added methyl 8-hydroxyquinoline-6-carboxylate (100 mg, 0.492 mmol), cesium carbonate (481 mg, 1.476 mmol) and 4-fluoropyridine HCl (526 mg, 3.94 mmol). The solids were dissolved in DMA (0.4 M), and DIPEA (688 µl, 3.94 mmol) was added. The reaction was stirred for 30 minutes at room temperature and heated to 100° C. for 22 hrs. The reaction was quenched with sat. ammonium chloride, the aqueous extracted with 10% MeOH/DCM with a phase separator cartridge, and concentrated. The material was purified by automated column chromatography (silica gel, 0-100% EtOAc in hexanes, then 0-20% MeOH in DCM) to afford the title compound (10 mg, 7%). ESI-MS m/z: 281.0 [M+H]$^+$. The methyl ester hydrolysis was carried out according to Method T, step d and isolated by aqueous concentration (used crude). ESI-MS m/z: 266.9 [M+H]$^+$.

Example 388 Step c

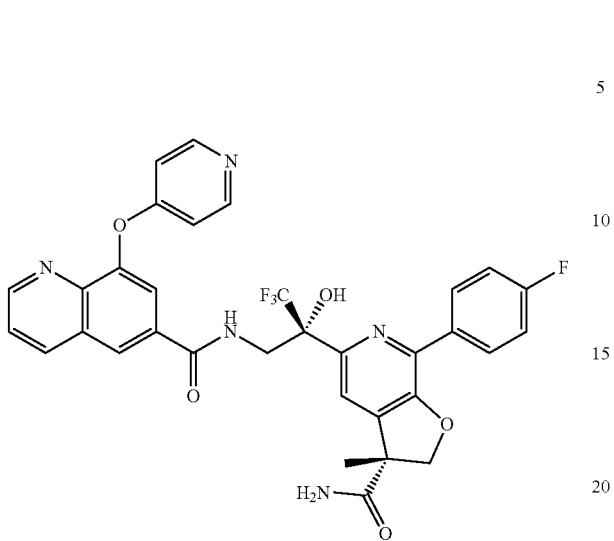

This example was prepared according to Method J (PyBOP) with 15 mg of amine HCl salt precursor, and the material purified by Gilson prep-HPLC (20-90%, MeCN/Water, 25 min) to afford the title compound (1.5 mg, 7%). ESI-MS m/z: 649.1 [M+H]$^+$.

Example 389

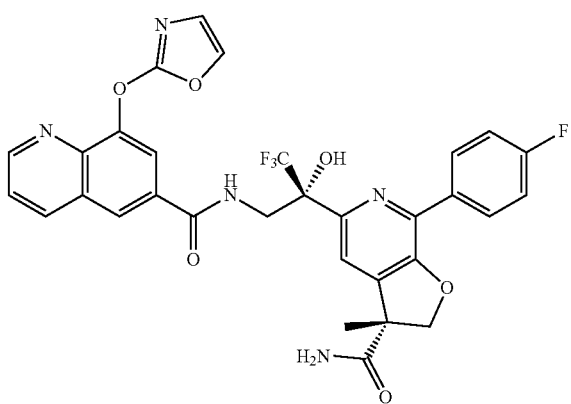 [SMILES: C[C@]1(C(N)=O)COc2c1cc([C@@](O)(CNC(=O)c1cc(Oc3ncco3)c3ncccc3c1)C(F)(F)F)nc2-c1ccc(F)cc1]

This example was prepared in an analogous sequence to Example 388. The SNA$_r$ was carried out with 3 eq of 2-bromooxazole in DMF (0.33 M) and no DIPEA at 60° C. (57 mg, 29%). ESI-MS m/z: 271.0 [M+H]$^+$. The acid precursor was prepared according to Method T and was isolated by precipitation (16 mg, 30%). ESI-MS m/z: 257.0 [M+H]$^+$.

Example 389 was prepared with 20 mg of amine HCl salt according to Method J (PyBOP), and the material purified by Gilson prep-HPLC (20-90%, MeCN/Water, 25 min) to afford the title compound (12 mg, 40%). ESI-MS m/z: 638.1 [M+H]$^+$.

Example 390

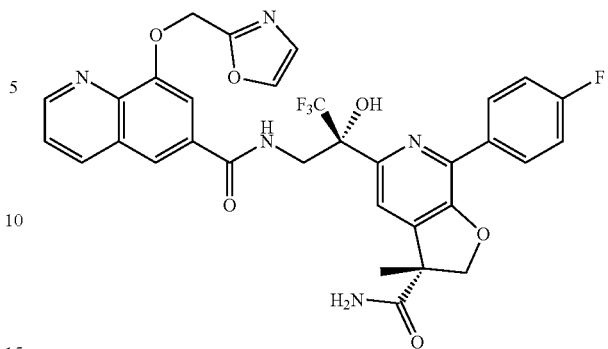

Example 390 Steps a and b

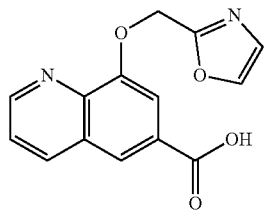 [SMILES: O=C(O)c1cc(OCc2ncco2)c2ncccc2c1]

To a 2-dram vial equipped with a stir bar was added oxazol-2-ylmethanol (58.5 mg, 0.591 mmol), and the oil was dissolved in THF. methyl 8-hydroxyquinoline-6-carboxylate (100 mg, 0.492 mmol) and 2-pyridyldiphenylphosphine (155 mg, 0.591 mmol) were then added, and the vial cooled to 0° C. DIAD (115 µl, 0.591 mmol) was added, the reaction stirred for 10 minutes, warmed to room temperature and monitored by LCMS (2 hrs). The reaction was quenched with MeOH, stir bar removed and reaction concentrated. The reaction was purified by automated column chromatography (silica gel, 0-100% EtOAc in hexanes, then 0-20% MeOH/DCM) to afford the title compound (140 mg, 99%). ESI-MS m/z: 285.0 [M+H]$^+$. The methyl ester hydrolysis was carried out according to Method T, step d and purified Gilson prep-HPLC (20-90%, MeCN/Water, 25 min) to afford the title compound (22 mg, 17%). ESI-MS m/z: 271.0 [M+H].

Example 390 Step c

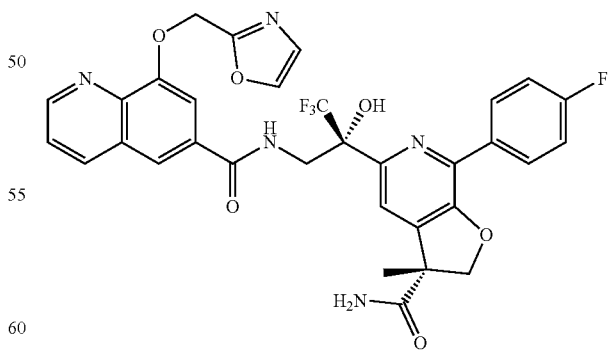

This example was prepared according to Method J (PyBOP) with 25 mg of amine HCl salt precursor. The material was purified by Gilson prep-HPLC (20-90%, MeCN/Water, 25 min) to afford the title compound (15.7 mg, 41%). ESI-MS m/z: 652.2 [M+H]$^+$.

Example 391

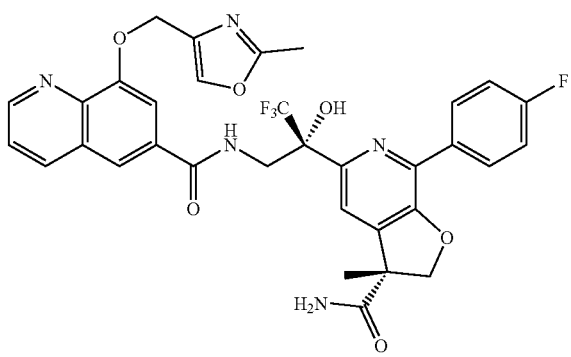 [SMILES: Cc1nc(COc2cc(C(=O)NC[C@](O)(c3cc4c(c(-c5ccc(F)cc5)n3)OC[C@]4(C)C(N)=O)C(F)(F)F)cc3cccnc23)co1]

This example was prepared in an analogous sequence to Example 390. Mitsunobu reaction (162 mg, 110%, impure). ESI-MS m/z: 299.1 [M+H]+. Ester hydrolysis prepared according to Method T, step d and isolated by precipitation (17 mg, 12%). ESI-MS m/z: 285.0 [M+H]+.

Example 391 was prepared with 25 mg of amine HCl salt precursor was used according to Method J (PyBOP), and the material purified by Gilson prep-HPLC (20-90%, MeCN/Water, 25 min) to afford the title compound (13.8 mg, 36%). ESI-MS m/z: 666.2 [M+H]+.

Example 392

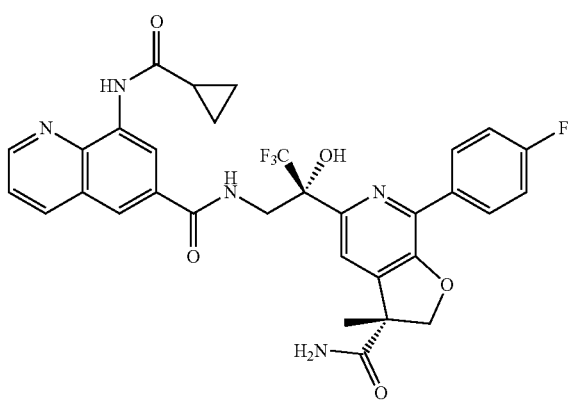 [SMILES: C[C@]1(C(N)=O)COc2c1cc([C@@](O)(CNC(=O)c1cc(NC(=O)C3CC3)c3ncccc3c1)C(F)(F)F)nc2-c1ccc(F)cc1]

Example 392 Steps a and b

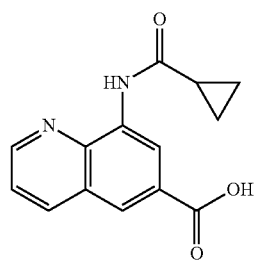 [SMILES: O=C(O)c1cc(NC(=O)C2CC2)c2ncccc2c1]

To a 40 mL vial equipped with a stir bar was added methyl 8-aminoquinoline-6-carboxylate (100 mg, 0.495 mmol). The solid was dissolved in DCM (0.2 M) and cooled to 0C. DIPEA (216 µl, 1.236 mmol) was added followed by cyclopropanecarbonyl chloride (49.4 µl, 0.544 mmol). The reaction was allowed to warm naturally to room temperature and monitored by LCMS (1 hr). The reaction was diluted with DCM and quenched with water and sat. sodium bicarbonate. Aqueous was extracted with 10% MeOH/DCM with a phase separator cartridge and concentrated. The material was purified by automated column chromatography (silica gel, 0-100% EtOAc in hexanes) to afford the title compound (120 mg, 89%). ESI-MS m/z: 271.2 [M+H]+. The methyl ester hydrolysis was carried out according to Method T, step d and isolated by precipitation (73 mg, 64%). ESI-MS m/z: 257.0 [M+H]+.

Example 392 Step c

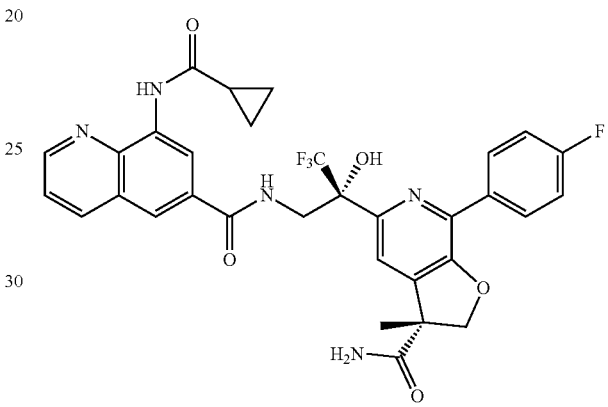

This example was prepared according to Method J (PyBOP) with 25 mg of amine HCl salt precursor, and the material purified by Gilson prep-HPLC (20-90%, MeCN/Water, 25 min) to afford the title compound (22.2 mg, 60%). ESI-MS m/z: 628.2 [M+H]+.

Example 393

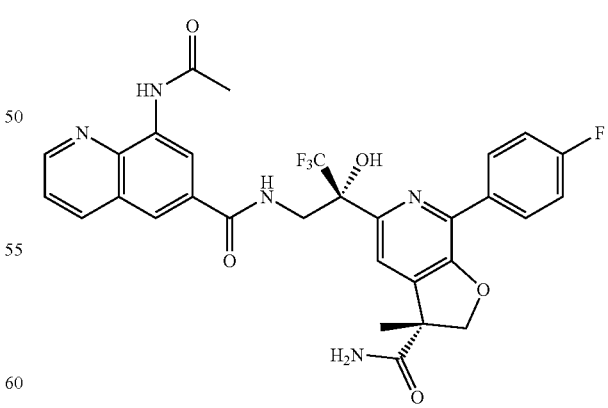

This example was prepared in an analogous sequence to Example 392. Aminoquinoline acylation (99 mg, 82%). ESI-MS m/z: 245.1 [M+H]+. The acid precursor was heated to 55° C. to hydrolyze (Method T, step d) and isolated by precipitation (69 mg, 74%). ESI-MS m/z: 230.9 [M+H]+.

25 mg of amine HCl salt precursor used according to Method J (PyBOP), and the material purified by Gilson prep-HPLC (20-90%, MeCN/Water, 25 min) to afford the title compound (19 mg, 53%). ESI-MS m/z: 612.1 [M+H]⁺.

Example 394

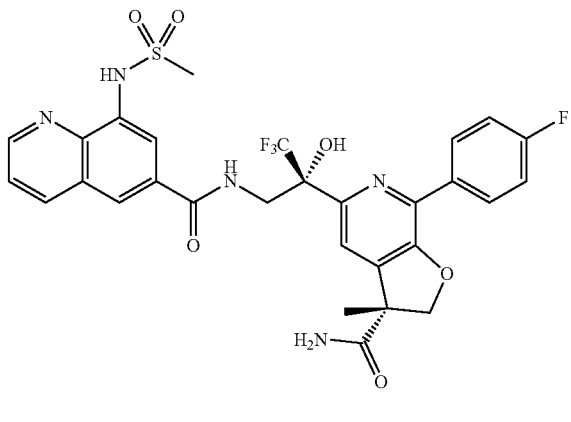 [SMILES: C[C@]1(C(N)=O)COc2c1cc([C@@](O)(CNC(=O)c1cc(NS(C)(=O)=O)c3ncccc3c1)C(F)(F)F)nc2-c1ccc(F)cc1]

This example was prepared in an analogous sequence to Example 392. Aminoquinoline mesylation (98 mg, 71%). ESI-MS m/z: 281.2 [M+H]⁺. The acid precursor was prepared according to Method T, step d and isolated by precipitation (51 mg, 55%). ESI-MS m/z: 266.8 [M+H]⁺.

25 mg of amine HCl salt precursor used according to Method J (PyBOP), and the material purified by Gilson prep-HPLC (20-90%, MeCN/Water, 25 min) to afford the title compound (25.2 mg, 67%). ESI-MS m/z: 648.1 [M+H]⁺.

Example 395

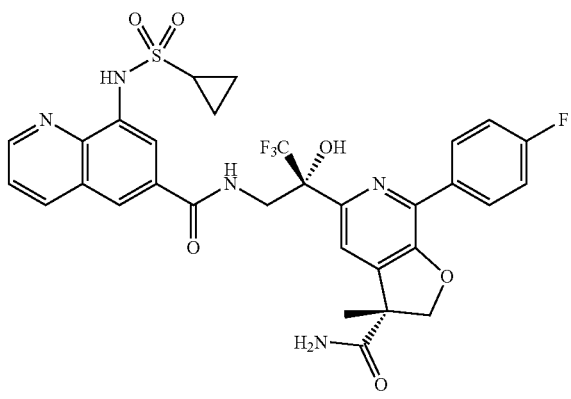 [SMILES: C[C@]1(C(N)=O)COc2c1cc([C@@](O)(CNC(=O)c1cc(NS(=O)(=O)C3CC3)c3ncccc3c1)C(F)(F)F)nc2-c1ccc(F)cc1]

This example was prepared in an analogous sequence to Example 392. Aminoquinoline sulfonylation required adding 10 eq. more sulfonyl chloride and 16 hrs (36 mg, 24%). ESI-MS m/z: 307.3 [M+H]⁺. The acid precursor was prepared according to Method T, step d and isolated by precipitation (16 mg, 47%). ESI-MS m/z: 292.9 [M+H]⁺.

25 mg of amine HCl salt precursor used according to Method J (PyBOP), and the material purified by Gilson prep-HPLC (20-90%, MeCN/Water, 25 min) to afford the title compound (12.0 mg, 30%). ESI-MS m/z: 674.1 [M+H]⁺.

Method U

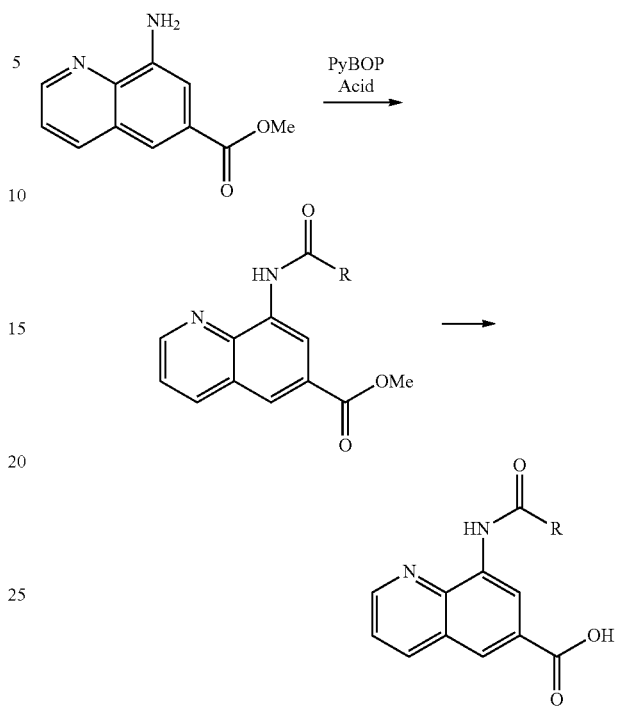

Example 396

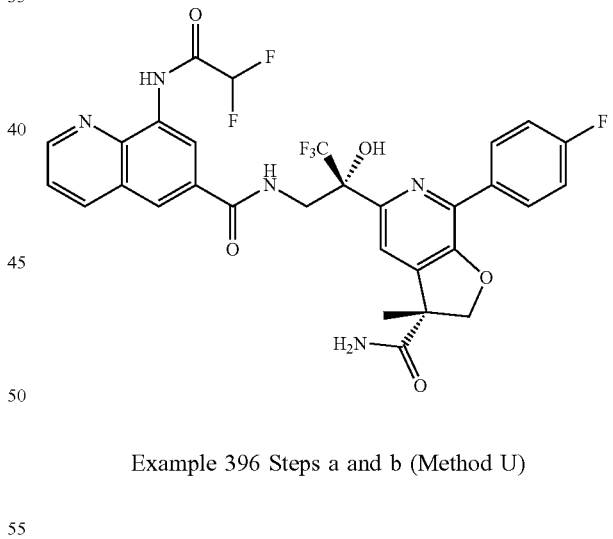

Example 396 Steps a and b (Method U)

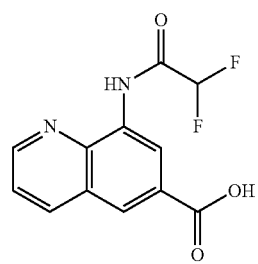 [SMILES: O=C(O)c1cc(NC(=O)C(F)F)c2ncccc2c1]

To a 20 mL vial equipped with a stir bar was added methyl 8-aminoquinoline-6-carboxylate (75 mg, 0.371 mmol), DIPEA (486 μl, 2.78 mmol), and the material dissolved in DMF (0.2 M). 2,2-difluoroacetic acid (46.7 μl, 0.742 mmol) was then added after to be buffered, and the vial was cooled to 0° C. PyBOP (290 mg, 0.556 mmol) was then added, the reaction stirred for 10 minutes, warmed to room temperature and monitored by LCMS (16 hr). The reaction was diluted with DCM and quenched with water and sat. sodium bicarbonate. Aqueous was extracted with 10% MeOH/DCM with a phase separator cartridge and concentrated. The material was purified by automated column chromatography (silica gel, 0-50% EtOAc in hexanes) to afford the title compound (37 mg, 36%). ESI-MS m/z: 263.0 [M+H]⁺. The methyl ester hydrolysis was carried out according to Method T, step d with 2.5 eq of LiOH (acetamide hydrolysis occurs) and isolated by precipitation (12 mg, 50%). ESI-MS m/z: 265.0 [M−H]⁻.

Example 396 Step c (19 mg, 17%). ESI-MS m/z: 312.0 [M+H]⁺. The methyl ester was hydrolyzed according to Method t, step d (heated to 45° C.) and isolated by aqueous concentration (used crude). ESI-MS m/z: 298.0 [M+H]⁺.

20 mg of amine HCl salt precursor was used according to Method J (PyBOP), and the material purified by Gilson prep-HPLC (20-90%, MeCN/Water, 25 min) to afford the title compound (14.7 mg, 47%). ESI-MS m/z: 679.1 [M+H]⁺.

Method V

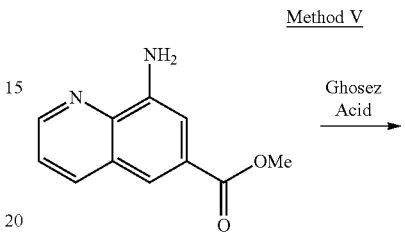

This example was prepared according to Method J (PyBOP) with 25 mg of amine HCl salt precursor, and the material purified by Gilson prep-HPLC (20-90%, MeCN/Water, 25 min) to afford the title compound (5.0 mg, 13%). ESI-MS m/z: 648.1 [M+H]⁺.

Example 397

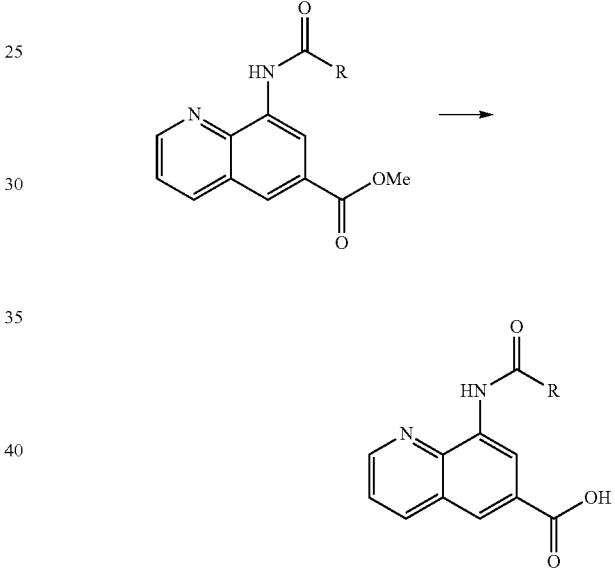

Example 398

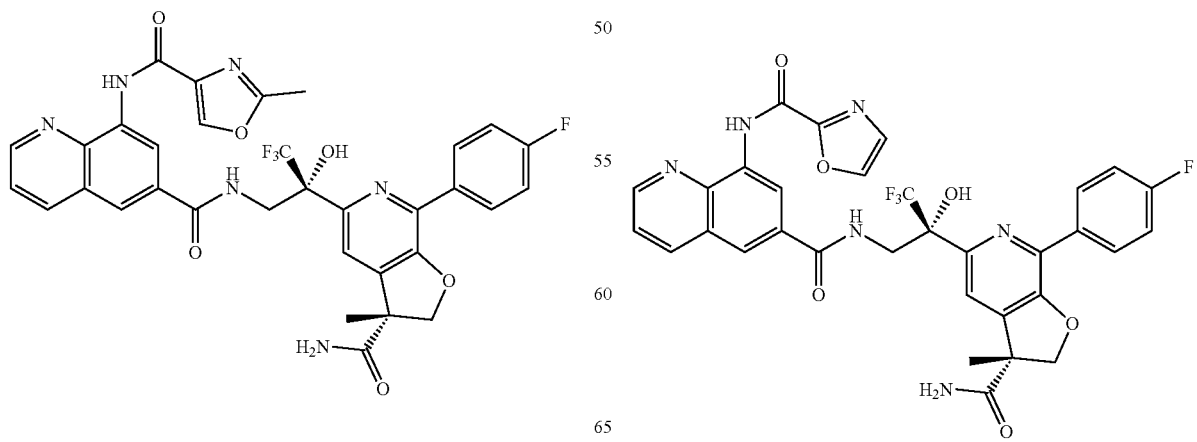

The acid precursor was prepared in an analogous sequence to Method U. Aminoquinoline amide formation

Example 398 Steps a and b (Method V)

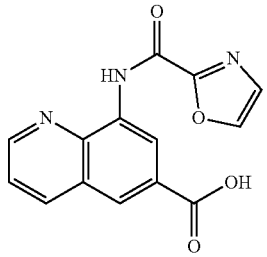 [SMILES: O=C(O)c1cc(NC(=O)c2ncco2)c2ncccc2c1]

To a 20 ml vial containing a stir bar was added oxazole-2-carboxylic acid (41.9 mg, 0.371 mmol). The solid was suspended in DCM and the vial cooled to 0° C. 1-chloro-N,N,2-trimethylprop-1-en-1-amine (58.9 µl, 0.445 mmol) was added, the reaction stirred at 0° C. for 15 min, and warmed to room temperature (solid went into solution after 1.5 hr). The reaction was cooled to 0° C., and pyridine (225 µL, 2.78 mmol) was added followed by methyl 8-aminoquinoline-6-carboxylate (75 mg, 0.371 mmol) in one portion. The reaction was allowed to warm naturally to room temperature and monitored by LCMS (2 hr longer). The reaction was diluted with DCM and quenched with water and sat. sodium bicarbonate. Aqueous was extracted with 10% MeOH/DCM with a phase separator cartridge and concentrated. The material was purified by automated column chromatography (silica gel, 0-100% EtOAc in hexanes) to afford the title compound (63 mg, 57%). ESI-MS m/z: 298.0 [M+H]$^+$.

The methyl ester hydrolysis was carried out according to Method T, step d and isolated by precipitation (17 mg, 80% wt, 23%). ESI-MS m/z: 214.8 [M+H]$^+$.

Example 398 Step c

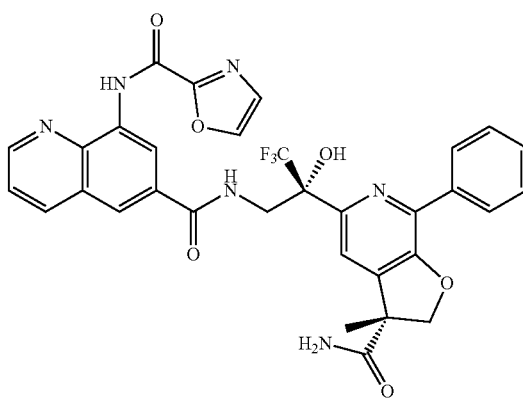

This example was prepared according to Method J (PyBOP) with 20 mg of amine HCl salt precursor, and the material purified by Gilson prep-HPLC (20-90%, MeCN/Water, 25 min) to afford the title compound (12.0 mg, 35%). ESI-MS m/z: 665.1 [M+H]$^+$.

Example 399

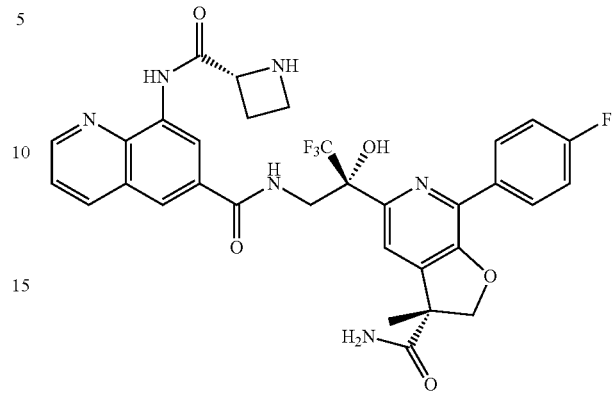

Example 399 Steps a and b

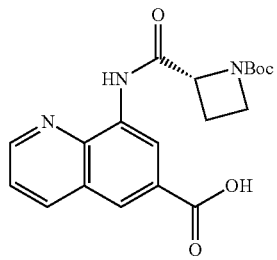 [SMILES: CC(C)(C)OC(=O)N1CC[C@@H]1C(=O)Nc1cc(C(=O)O)cc2cccnc12]

The acid intermediate was prepared according to Method V. Ghosez coupling carried out for 14 hrs (134 mg, 94%). ESI-MS m/z: 330.0 [M+H]$^+$. Methyl ester hydrolysis according to Method T, step d and was isolated by aqueous extraction (115 mg, 89%). ESI-MS m/z: 316.0 [M+H]$^+$.

Example 399 Steps c and d

Amide formation was carried out according to Method J (PyBOP) with step b and 40 mg of amine HCl salt precursor. The material was purified by automated column chromatography (silica gel, 0-100% EtOAc in hexanes) to afford the title compound (65 mg, 94%). ESI-MS m/z: 753.2 [M+H]$^+$.

To a 20 mL vial containing example 399 step c (65 mg, 0.086 mmol) was added a stir bar and the material was dissolved in DCM. The reaction was cooled to 0° C., and TFA (66.5 µl, 0.864 mmol) was added. The reaction was stirred for 10 minutes, warmed to room temperature and monitored by LCMS (3 hr). The reaction was diluted with DCM and quenched with water and sat. sodium bicarbonate. The pH was adjusted to about pH=9, extracted with DCM/MeOH with a phase separator cartridge, and concentrated. The material was purified by Gilson prep-HPLC (20-90%, MeCN/Water, 25 min) to afford the title compound (13.0 mg, 23%). ESI-MS m/z: 653.2 [M+H]⁺.

Example 400

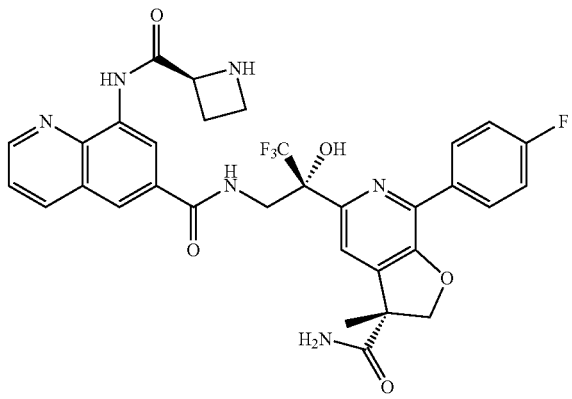 [SMILES: C[C@]1(C(N)=O)COc2c1cc([C@@](O)(CNC(=O)c1cc(NC(=O)[C@@H]3CCN3)c3ncccc3c1)C(F)(F)F)nc2-c1ccc(F)cc1]

The following example was prepared in an analogous sequence to Example 399. Boc-azetidine Ghosez coupling, Method V (131 mg, 92%). ESI-MS m/z: 330.0 [M+H]⁺. Methyl ester hydrolysis according to Method T, step d and was isolated by aqueous extraction (120 mg, 95%). ESI-MS m/z: 316.0 [M+H]⁺.

Quinoline acid amide formation with 40 mg amine HCl salt precursor according to Method J (PyBOP) (65 mg, 94%). ESI-MS m/z: 753.2 [M+H]⁺. TFA deprotection and the material was purified by Gilson prep-HPLC (20-90%, MeCN/Water, 25 min) to afford the title compound (21.0 mg, 37%). ESI-MS m/z: 653.2 [M+H]⁺.

Example 401

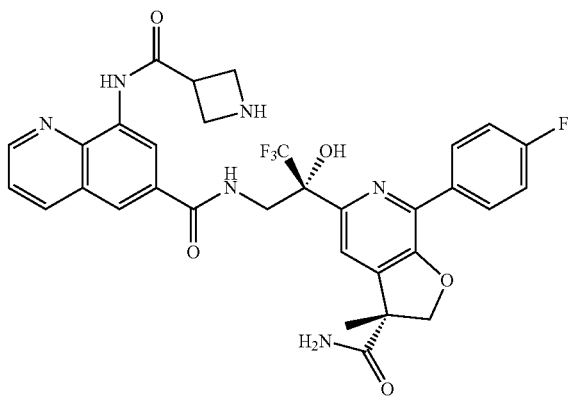 [SMILES: C[C@]1(C(N)=O)COc2c1cc([C@@](O)(CNC(=O)c1cc(NC(=O)C3CNC3)c3ncccc3c1)C(F)(F)F)nc2-c1ccc(F)cc1]

The following example was prepared in an analogous sequence to Example 399. Boc-azetidine Ghosez coupling Method V (119 mg, 83%). ESI-MS m/z: 330.0 [M+H]⁺. Methyl ester hydrolysis according to Method T, step d and was isolated by aqueous extraction (80 mg, 70%). ESI-MS m/z: 316.0 [M+H]⁺. Method J (PyBOP) amide formation with 40 mg amine HCl salt precursor and TFA deprotection done in one-pot: the material was purified by Gilson prep-HPLC (20-90%, MeCN/Water, 25 min) to afford the title compound (3.6 mg, 8%). ESI-MS m/z: 653.2 [M+H]⁺.

Example 402

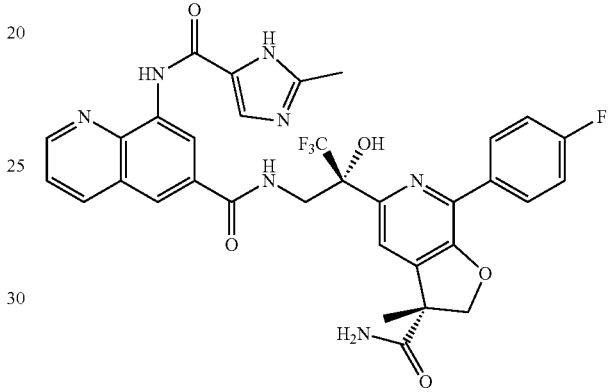

Example 402 Steps a and b

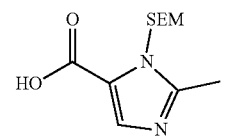

To a 40 mL vial equipped with a stir bar was added ethyl 2-methyl-1H-imidazole-4-carboxylate (500 mg, 3.24 mmol), and the material was dissolved in DMF. The vial was cooled to 0C, and NaH (136 mg, 5.68 mmol) was added in one portion. The reaction was allowed to stir for 30 minutes at r.t. The vial was then cooled to 0° C., and (2-(chloromethoxy)ethyl)trimethylsilane (861 µl, 4.86 mmol) was slowly added. The reaction was allowed to warm naturally to room temperature for 16 hrs. The reaction was diluted with EtOAc and quenched with water and sat. ammonium chloride. Aqueous was extracted with EtOAc with a phase separator cartridge and concentrated. The material was purified by automated column chromatography (silica gel, 0-100% EtOAc in hexanes) to afford the title compound (500 mg, 56% wt, 35%). ESI-MS m/z: 285.1 [M+H]⁺. Ethyl ester hydrolysis was carried out according to Method T, step d and isolated by precipitation (233 mg, 80%). ESI-MS m/z: 199.0 [M+H]⁺.

Example 402 Steps c and d

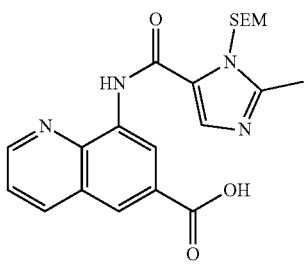 [SMILES: Cc1ncc(C(=O)Nc2cc(C(=O)O)cc3cccnc23)n1COCC[Si](C)(C)C]

The following example was prepared according to Method V: SEM-imidazole aminoquinoline Ghosez coupling (81 mg, 50%). ESI-MS m/z: 441.1 [M+H]$^+$.

Methyl ester hydrolysis according to Method T, step d was isolated by precipitation (25 mg, 31%). ESI-MS m/z: 427.1 [M+H]$^+$.

Example 402 Steps e and f

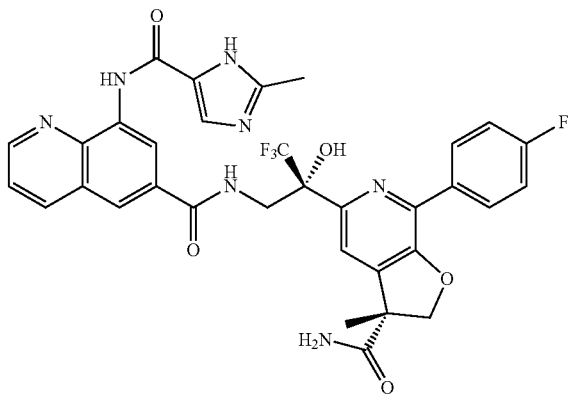 [SMILES: Cc1ncc(C(=O)Nc2cc(C(=O)NC[C@](O)(c3cc4c(c(-c5ccc(F)cc5)n3)OC[C@]4(C)C(N)=O)C(F)(F)F)cc3cccnc23)[nH]1]

SEM-imidazole amide formation with according to Method J (PyBOP) with 25 mg amine HCl salt precursor, purified by automated column chromatography (silica gel, 0-100% EtOAc/hexanes) to afford the title compound (50 mg, 100%). ESI-MS m/z: 808.2 [M+H]$^+$. TFA deprotection done with 60 eq TFA (20 eq each over 3 hr): the material was purified by Gilson prep-HPLC (20-90%, MeCN/Water, 25 min) to afford the title compound (15 mg, 35%). ESI-MS m/z: 678.1 [M+H]$^+$.

Example 403

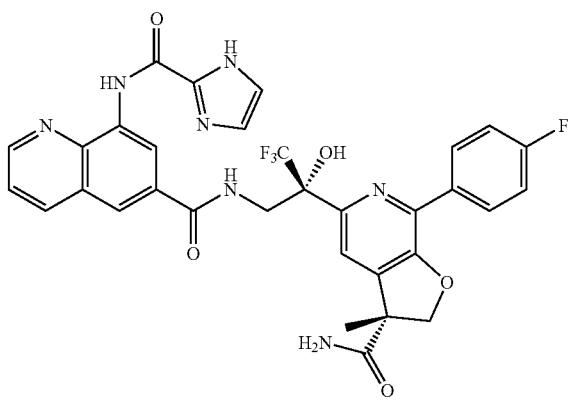 [SMILES: C[C@]1(C(N)=O)COc2c1cc([C@@](O)(CNC(=O)c1cc(NC(=O)c3ncc[nH]3)c3ncccc3c1)C(F)(F)F)nc2-c1ccc(F)cc1]

The following example was prepared in an analogous sequence to Example 402. Ethyl imidazole carboxylate SEM-protection (872 mg, 90%). ESI-MS m/z: 199.0 [M+H]$^+$. SEM-ethyl imidazole carboxylate hydrolysis (Method T, step d) isolated by extraction (320 mg, 89%). ESI-MS m/z: 185.0 [M+H]$^+$. Aminoquinoline and SEM-imidazole carboxylic acid amide according to Method U (158 mg, 60% wt, 45%). ESI-MS m/z: 427.0 [M+H]$^+$. Quinoline methyl ester hydrolysis according to Method T, step d (at 45° C.) and isolated by precipitation (86 mg, 61%). ESI-MS m/z: 265.0 [M+H]$^+$.

Amide formation according to Method J (PyBOP) with 30 mg amine HCl salt precursor, purified by automated column chromatography (silica gel, 0-100% EtOAc/hexanes) to afford the title compound (50 mg, 100%). ESI-MS m/z: 894.2 [M+H]$^+$. TFA deprotection done with 60 eq TFA (20 eq each over 3 hr): the material was purified by Gilson prep-HPLC (20-90%, MeCN/Water, 25 min) to afford the title compound (17.4 mg, 37%). ESI-MS m/z: 664.1 [M+H]$^+$.

Example 404

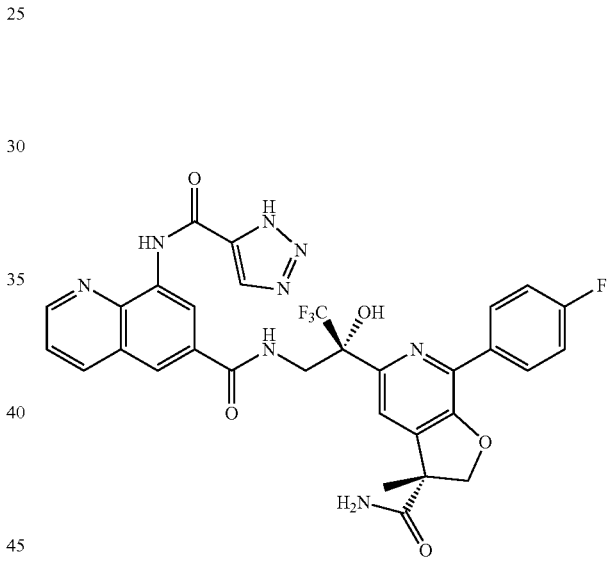

The following example was prepared in an analogous sequence to Example 402. Ethyl triazole carboxylate SEM-protection (800 mg, 83%). ESI-MS m/z: 272.2 [M+H]$^+$. SEM-ethyl triazole carboxylate hydrolysis (Method T, step d) isolated by extraction (310 mg, 86%). ESI-MS m/z: 186.0 [M+H]$^+$. Aminoquinoline and SEM-triazole carboxylic acid amide formation Method U (150 mg, 40% wt, 28%). ESI-MS m/z: 428.1 [M+H]$^+$. Methyl ester hydrolysis according to Method T, step d isolated by extraction (82 mg, 57%). ESI-MS m/z: 414.1 [M+H]$^+$.

Method J (PyBOP) amide formation with 40 mg amine HCl salt precursor, purified by automated column chromatography (silica gel, 0-100% EtOAc/hexanes) to afford the title compound (64 mg, 88%). ESI-MS m/z: 795.2 [M+H]$^+$. TFA deprotection done with 40 eq TFA (20 eq each over 2 hr): the material was purified by Gilson prep-HPLC (20-90%, MeCN/Water, 25 min) to afford the title compound (19.0 mg, 35%). ESI-MS m/z: 665.1 [M+H]$^+$.

Example 405

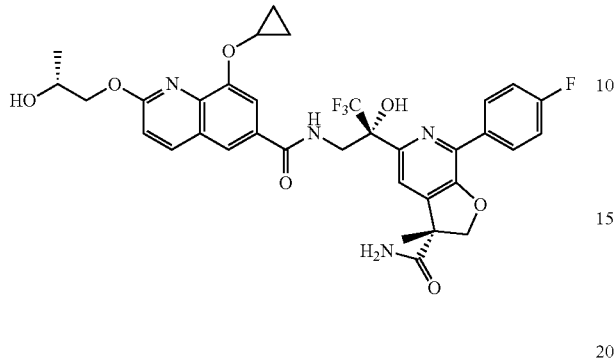

Example 405 Steps a and b

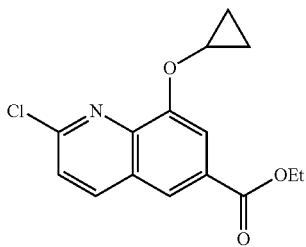 [SMILES: CCOC(=O)c1cc(OC2CC2)c2nc(Cl)ccc2c1]

To a 50 mL round-bottom flask equipped with a stir bar was added ethyl 8-cyclopropoxyquinoline-6-carboxylate (10.29 g, 40.0 mmol), and the solid was dissolved in CHCl₃ (0.33 M). The flask was cooled to 0° C. and mCPBA (19.72 g, 80 mmol) was added portionwise over 5-10 minutes (monitoring internal temperature at 3° C.). The reaction was stirred for 10 minutes and warmed to room temperature over 20 minutes. The reaction was then warmed to 45° C. (with internal temperature monitoring) and monitored by LCMS (2 hr) The reaction was diluted with DCM and quenched with water and sat. sodium thiosulfate. The aqueous was extracted with DCM, dried, filtered and concentrated. The material was purified by automated column chromatography (silica gel, 0-100% EtOAc/hexanes then 0-20% MeOH/DCM) to afford the title compound (4.14 g, 38%). ESI-MS m/z: 274.1 [M+H]⁺.

To a 50 mL vial containing a stir bar was added ethyl 2-chloro-8-cyclopropoxyquinoline-6-carboxylate (2.8 g, 9.60 mmol, 63%), and the solid was dissolved in DCM. POCl₃ (2.83 ml, 30.3 mmol) was added, the flask equipped with a condenser and the reaction heated to 45° C. The reaction was monitored by LCMS and complete after 2 hrs. The reaction was cooled to 0° C., diluted with EtOAc and quenched with water slowly. Allowed to quench for 30 minutes, slowly adding more water and sat. sodium bicarbonate. The aqueous was extracted with DCM, dried, filtered and concentrated. The material was purified by automated column chromatography (silica gel, 0-50% EtOAc/hexanes) to afford the title compound (2.80 g, 63%). ESI-MS m/z: 292.0 [M+H]⁺.

Example 405 Steps c and d

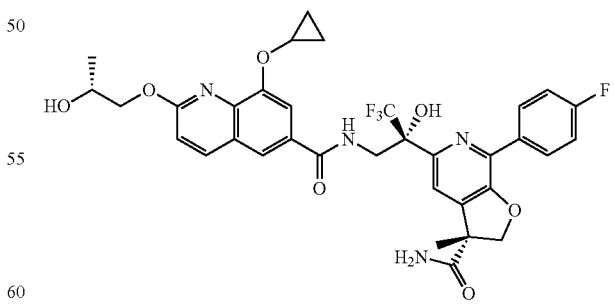

To a 20 mL vial equipped with a stir bar was added (R)-2-((tert-butyldimethylsilyl)oxy)propan-1-ol (362 mg, 1.902 mmol) and the oil was dissolved in DMF. The vial was cooled to 0° C., and NaH (116 mg, 2.66 mmol) was added. The reaction was warmed to room temperature and stirred for 30 minutes. ethyl 2-chloro-8-cyclopropoxyquinoline-6-carboxylate (111 mg, 0.380 mmol) was then added, and the reaction stirred for 1 hr at room temperature. The reaction was diluted with EtOAc and quenched with water and 2 M HCl. Aqueous was extracted with EtOAc with a phase separator cartridge and concentrated. The material was purified by automated column chromatography (silica gel, 0-100% EtOAc in hexanes) to afford the title compound (50 mg, 32%) ESI-MS m/z: 418.2 [M+H]⁺. (Note: methyl ester hydrolyzed while quenching with HCl). The TBS group was removed with TBAF over 1 hr and purified by automated column chromatography (silica gel, 0-100% EtOAc/hexanes then 0-20% MeOH/DCM) to afford the title compound (15 mg, 42%). ESI-MS m/z: 304.1 [M+H]⁺.

Example 405 Step e

This example was prepared according to Method J (PyBOP) with 20 mg of amine HCl salt precursor, and the material purified by Gilson prep-HPLC (20-90%, MeCN/Water, 25 min) to afford the title compound (12.0 mg, 37%). ESI-MS m/z: 685.2 [M+H]⁺.

Example 406

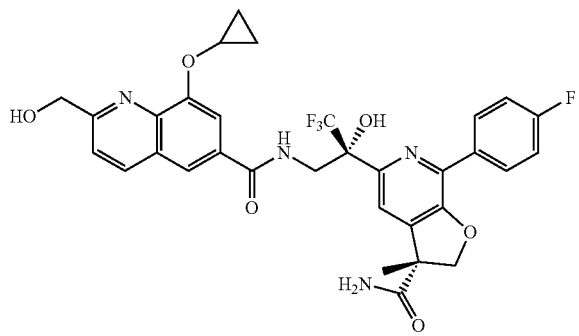 [SMILES: C[C@]1(C(N)=O)COc2c1cc([C@@](O)(CNC(=O)c1cc(OC3CC3)c3nc(CO)ccc3c1)C(F)(F)F)nc2-c1ccc(F)cc1]

Example 406 Step a

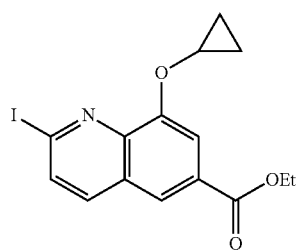 [SMILES: CCOC(=O)c1cc(OC2CC2)c2nc(I)ccc2c1]

To a 50 mL round-bottom flask equipped with bar was added ethyl 2-chloro-8-cyclopropoxyquinoline-6-carboxylate (300 mg, 1.028 mmol), and the solid was dissolved in ACN (0.5 M). Sodium iodide (231 mg, 1.543 mmol) was added followed by acetyl chloride (146 µl, 2.057 mmol). The reaction was stirred for 5 minutes (turn cloudy and orange), heated to 100° C. and monitored by LCMS (4 hrs, 80% conv). The flask was cooled to r.t. and diluted with EtOAc. The reaction was quenched with 5 mL of 10% K2CO3 solution and 5 mL of sat. sodium thiosulfate. The aqueous was extracted with EtOAc and with 2×DCM/MeOH with a phase separator cartridge, and concentrated. The material was purified by automated column chromatography (silica gel, 0-30% EtOAc/hexanes) to afford the title compound (341 mg, 78%). ESI-MS m/z: 384.1 [M+H]⁺.

Example 406 Steps b, c, d

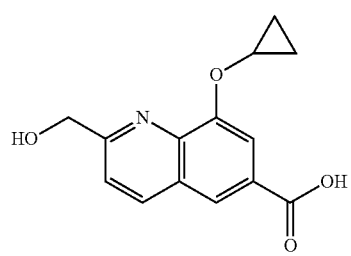 [SMILES: O=C(O)c1cc(OC2CC2)c2nc(CO)ccc2c1]

Aldehyde intermediate: To a 20 mL vial equipped with a stir bar was added step a (100 mg, 0.261 mmol), and the solid was dissolved in THF (0.33 M). The vial was cooled to −15° C., and isopropylmagnesium chloride (261 µl, 0.522 mmol) was added. The reaction was stirred for 30 minutes, then N,N-dimethylformamide (404 µl, 5.22 mmol) was added. The reaction was allowed to warm to 0° C. and stirred for 1 hr longer. The reaction was diluted with EtOAc and quenched with water and sat. ammonium chloride. Aqueous was extracted with EtOAc with a phase separator cartridge and concentrated. The material was purified by automated column chromatography (silica gel, 0-100% EtOAc in hexanes) to afford the title compound (26 mg, 35%) ESI-MS m/z: 286.1 [M+H]⁺.

Alcohol: To a 20 mL vial containing ethyl 8-cyclopropoxy-2-formylquinoline-6-carboxylate, step b (26 mg, 0.091 mmol) was added a stir bar and the solid was dissolved in EtOH (0.2 M). The reaction was cooled to 0° C., and NaBH4 (5.17 mg, 0.137 mmol) was added. The reaction was kept at 0° C. for 1 hr, diluted with EtOAc and quenched with water and sat. ammonium chloride. Aqueous was extracted with EtOAc with a phase separator cartridge and concentrated (25 mg, 95%).

The quinoline ethyl ester hydrolysis according to Method T, step d and was isolated by aqueous concentration (used crude) ESI-MS m/z: 260.0 [M+H]⁺.

Example 406 Step e

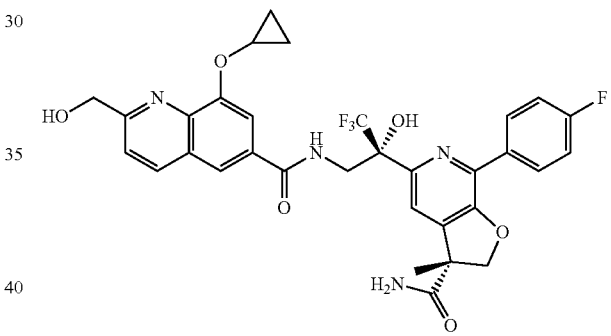

This example was prepared according to Method J (PyBOP) with step d and 30 mg of amine HCl salt precursor, and the material purified by Gilson prep-HPLC (20-90%, MeCN/Water, 25 min) to afford the title compound. (15.0 mg, 33%). ESI-MS m/z: 641.2 [M+H]⁺.

Example 407

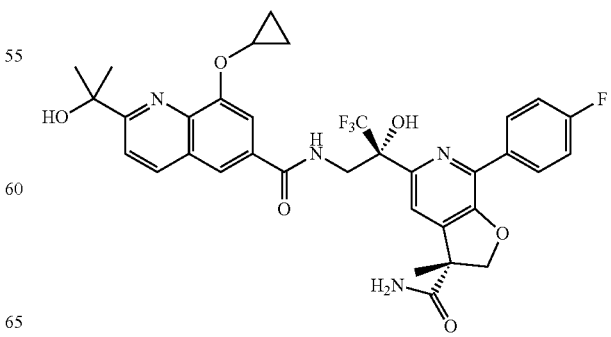

The following example was prepared analogously to Example 406 steps b and d (Grignard exchange and addition). Grignard quench was carried out with acetone (20 eq) and allowed to go for 16 hr (14 mg, 11%). ESI-MS m/z: 316.1 [M+H]+.

The quinoline ethyl ester hydrolysis according to Method T, step d was isolated by aqueous concentration (used crude) ESI-MS m/z: 288.1 [M+H]+.

Method J (PyBOP) amide coupling was carried out with 20 mg of amine HCl salt precursor: the material was purified by Gilson prep-HPLC (20-90%, MeCN/Water, 25 min) to afford the title compound (3 mg, 61%). ESI-MS m/z: 669.2 [M+H]+.

Method W

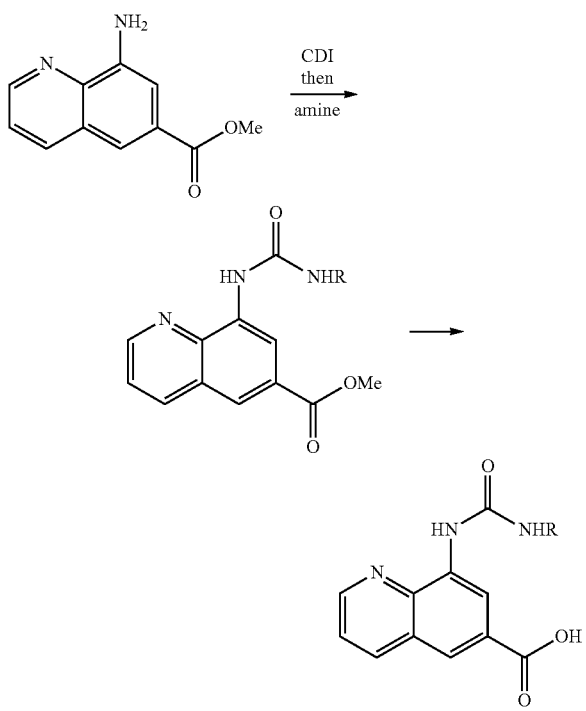

Example 408

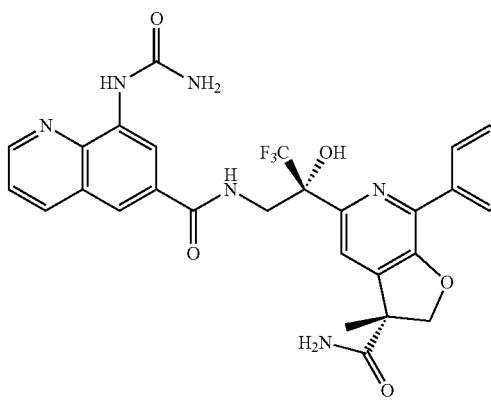

Example 408 Steps a and b (Method W)

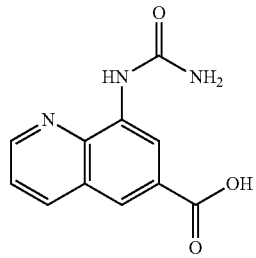 [SMILES: NC(=O)Nc1cc(C(=O)O)cc2cccnc12]

To a 20 mL vial equipped with a stir bar was added methyl 8-aminoquinoline-6-carboxylate (300 mg, 1.484 mmol) and CDI (289 mg, 1.780 mmol). The solids were dissolved in DCM (0.5 M) and DIPEA (518 µl, 2.97 mmol) was added. The reaction was stirred at room temperature for 1.5 hr (CDI intermediate precipitates). Ammonia (1060 µl, 7.42 mmol) was added and the reaction monitored by LCMS (1.5 hr). The reaction was quenched with water, and further diluted with DCM (product precipitates). The vial was vortexed to induce precipitation, the solid was collected by vacuum filtration, and dried on high vacuum to afford the desired product (220 mg, 61%). ESI-MS m/z: 245.9 [M+H]+.

The methyl ester hydrolysis was carried out according to Method T, step d at 45° C. for 1 hr, and isolated by precipitation (184 mg, 89%).

Example 408 Step c

This example was prepared according to Method J (PyBOP) with 25 mg of amine HCl salt precursor, and the material purified by Gilson prep-HPLC (20-90%, MeCN/Water, 25 min) to afford the title compound (21.8 mg, 61%). ESI-MS m/z: 613.1 [M+H]+.

Example 409

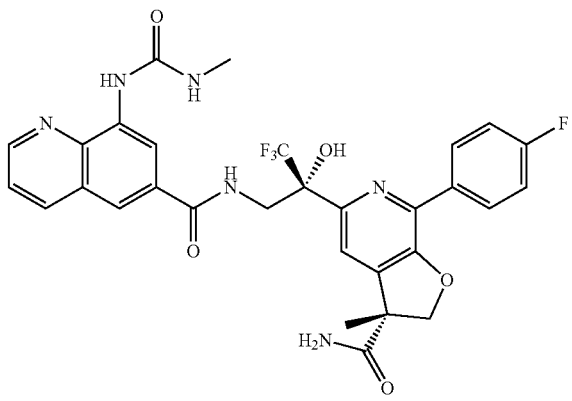 [SMILES: CNC(=O)Nc1cc(C(=O)NC[C@](O)(c2cc3c(c(-c4ccc(F)cc4)n2)OC[C@]3(C)C(N)=O)C(F)(F)F)cc2cccnc12]

The acid precursor was prepared following example was prepared according to Method W. Methyl urea formation extracted, and purified by automated column chromatography (silica gel, 0-100% EtOAc in hexanes) to afford the title compound (17 mg, 13%). ESI-MS m/z: 260.2. [M+H]⁺. The methyl ester hydrolysis was carried out according to Method T, step d at 45° C. for 1 hr, and isolated by aqueous concentration (used crude). ESI-MS m/z: 245.9 [M+H]⁺. 25 mg of amine HCl salt precursor used according to Method J (PyBOP), and the material purified by Gilson prep-HPLC (20-90%, MeCN/Water, 25 min) to afford the title compound (12 mg, 33%). ESI-MS m/z: 627.2 [M+H]⁺.

Example 410

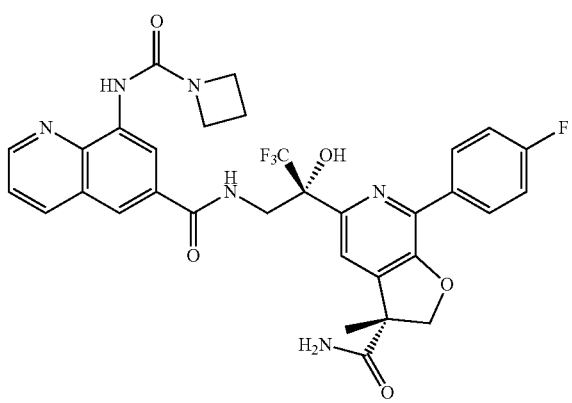 [SMILES: C[C@]1(C(N)=O)COc2c1cc([C@@](O)(CNC(=O)c1cc(NC(=O)N3CCC3)c3ncccc3c1)C(F)(F)F)nc2-c1ccc(F)cc1]

The acid precursor was prepared following example was prepared according to Method W. Urea formation extracted and used crude (91 mg, 100%). ESI-MS m/z: 286.0. [M+H]⁺. The methyl ester hydrolysis was carried out according to Method T, step d and isolated by precipitation (60 mg, 69%). ESI-MS m/z: 271.9 [M+H]⁺.

20 mg of amine HCl salt precursor used according to Method J (PyBOP), and the material purified by Gilson prep-HPLC (20-90%, MeCN/Water, 25 min) to afford the title compound (20.0 mg, 65%). ESI-MS m/z: 653.2 [M+H]⁺.

Example 411

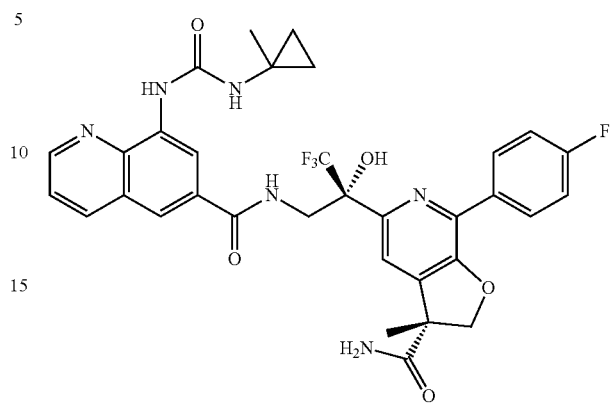

The acid precursor was prepared following example was prepared according to Method W. Urea formation (40 mg, 36%). ESI-MS m/z: 258.1 [M+H]⁺. The methyl ester hydrolysis was carried out according to Method T, step d at 45° C. and isolated by precipitation (23 mg, 60%). ESI-MS m/z: 189.0 [M+H]⁺.

20 mg of amine HCl salt precursor used according to Method J (PyBOP), and the material purified by Gilson prep-HPLC (20-90%, MeCN/Water, 25 min) to afford the title compound. (15.7 mg, 50%). ESI-MS m/z: 667.2 [M+H]⁺.

Example 412

The acid precursor was prepared following example was prepared according to Method W. Urea formation (86 mg, 73%). ESI-MS m/z: 318.1 [M+H]⁺. The methyl ester hydrolysis was carried out according to Method T, step d at 45° C. and isolated by precipitation (59 mg, 70%). ESI-MS m/z: 304.1 [M+H]⁺.

25 mg of amine HCl salt precursor used according to Method J (PyBOP), and the material purified by Gilson prep-HPLC (20-90%, MeCN/Water, 25 min) to afford the title compound (20.7 mg, 52%). ESI-MS m/z: 685.2 [M+H]⁺.

Example 413

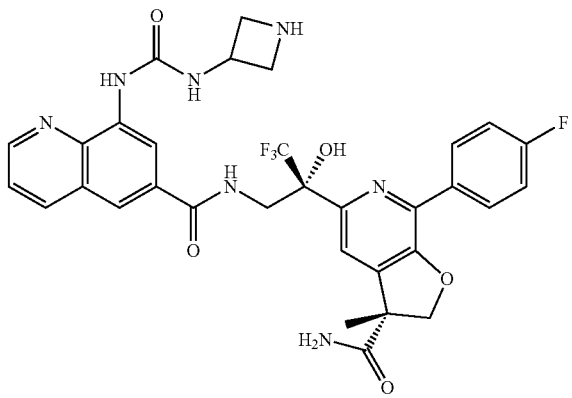 [SMILES: C[C@]1(C(N)=O)COc2c1cc([C@@](O)(CNC(=O)c1cc(NC(=O)NC3CNC3)c3ncccc3c1)C(F)(F)F)nc2-c1ccc(F)cc1]

The acid precursor was prepared following example was prepared according to Method W with additional Boc-deprotection at end. Urea formation extracted and purified (127 mg, 86%). ESI-MS m/z: 401.1 [M+H]$^+$. The methyl ester hydrolysis was carried out according to Method T, step d at 45° C. and isolated by precipitation (97 mg, 79%). ESI-MS m/z: 331.1 [M+H]$^+$. 35 mg of amine HCl salt precursor used according to Method J (PyBOP) and the material was purified by automated column chromatography (silica gel, 0-100% EtOAc/hexanes) to afford title compound (60 mg, 97%). Boc-deprotection with TFA and the material purified by Gilson prep-HPLC (20-90%, MeCN/Water, 25 min) to afford the title compound (20.0 mg, 37%). ESI-MS m/z: 668.2 [M+H]$^+$.

Example 414

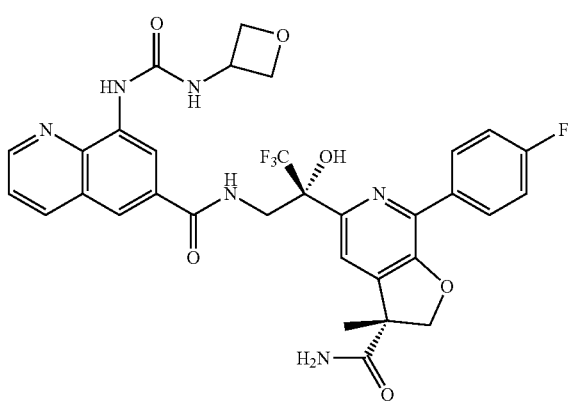 [SMILES: C[C@]1(C(N)=O)COc2c1cc([C@@](O)(CNC(=O)c1cc(NC(=O)NC3COC3)c3ncccc3c1)C(F)(F)F)nc2-c1ccc(F)cc1]

The acid precursor was prepared following example was prepared according to Method W. Urea formation (56 mg, 50%). ESI-MS m/z: 302.0 [M+H]$^+$. The methyl ester hydrolysis was carried out according to Method T, step d at 45° C. and isolated by precipitation (26 mg, 50%). ESI-MS m/z: 288.0 [M+H]$^+$.

25 mg of amine HCl salt precursor used according to Method J (PyBOP), and the material purified by Gilson prep-HPLC (20-90%, MeCN/Water, 25 min) to afford the title compound (15.0 mg, 38%). ESI-MS m/z: 669.2 [M+H]$^+$.

Example 415

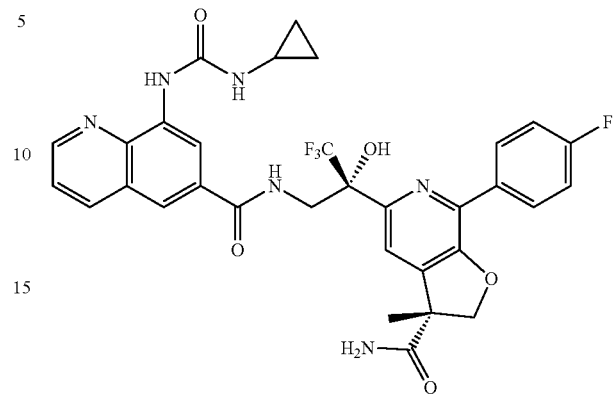

The acid precursor was prepared following example was prepared according to Method W. Urea formation extracted and used crude (106 mg, 100%). ESI-MS m/z: 286.0 [M+H]$^+$. The methyl ester hydrolysis was carried out according to Method T, step d at 45° C. and isolated by precipitation (26 mg, 26%). ESI-MS m/z: 271.8 [M+H]$^+$.

25 mg of amine HCl salt precursor used according to Method J (PyBOP), and the material purified by Gilson prep-HPLC (20-90%, MeCN/Water, 25 min) to afford the title compound (20.0 mg, 52%). ESI-MS m/z: 653.2 [M+H]$^+$.

Example 416

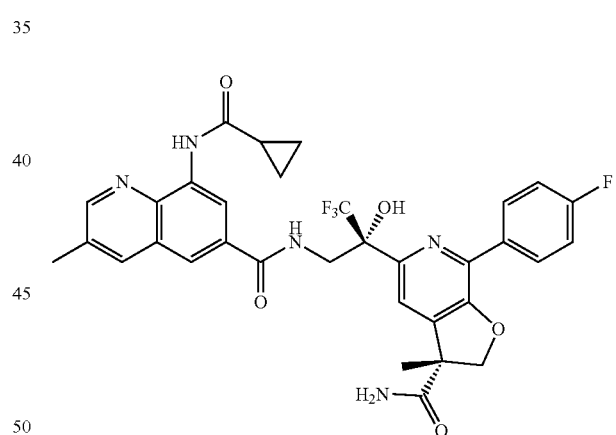

Example 416 Step a

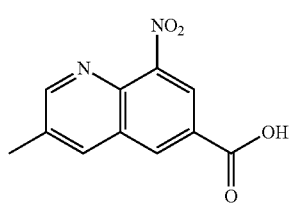 [SMILES: Cc1cnc2c([N+](=O)[O-])cc(C(=O)O)cc2c1]

A 50 mL round-bottom flask was charged with 4-amino-3-nitrobenzoic acid (3.26 g, 17.90 mmol) then 30 mL conc.

HCl followed by methacrylaldehyde (2.95 ml, 35.8 mmol). The mixture was heated to 100° C. for 5 h, then cooled to room temperature. The mixture was filtered through celite. The aqueous layer was concentrated to afford a brown mass, which was stirred with MeOH for 1 h. The solids were collected by filtration and found to be mostly desired product (349.4 mg, 8%). ESI-MS m/z: 233.1 [M+H]⁺.

Example 416 Steps b and c

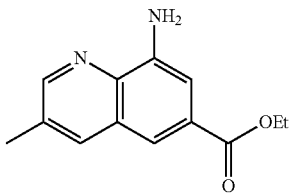 [SMILES: CCOC(=O)c1cc(N)c2ncc(C)cc2c1]

To a 20 mL vial containing 3-methyl-8-nitroquinoline-6-carboxylic acid (357 mg, 1.538 mmol) was added a stir bar and the solid was dissolved in DMF. Potassium carbonate (531 mg, 3.84 mmol) was added followed by iodoethane (373 µl, 4.61 mmol). The reaction was stirred for 14 hr at room temperature. The reaction was diluted with EtOAC and quenched with water and sat. sodium ammonium chloride. The aqueous was extracted with EtOAc and DCM/MeOH with a phase separator cartridge, and concentrated (168 mg, 42%). ESI-MS m/z: 261.0 [M+H]⁺. The crude material from step b (168 mg, 0.646 mmol in a 40 mL was added a stir bar, and the solids were dissolved in EtOH and Water (2:1, 0.15 M). Iron (180 mg, 3.23 mmol) and ammonium chloride (345 mg, 6.46 mmol) were added, and the reaction heated to 80° C. for 2 hr. The reaction was cooled, and diluted with EtOAc. The mixture was filtered through celite, and rinsed with EtOAc and MeOH. The organics were concentrated. EtOAc was then added, and the aqueous basified with sat. sodium bicarbonate. EtOAc and DCM/MeOH extractions, combined, dried, and concentrated (115 mg, 77%). ESI-MS m/z: 231.1 [M+H]⁺.

Example 416 Steps d, e and f

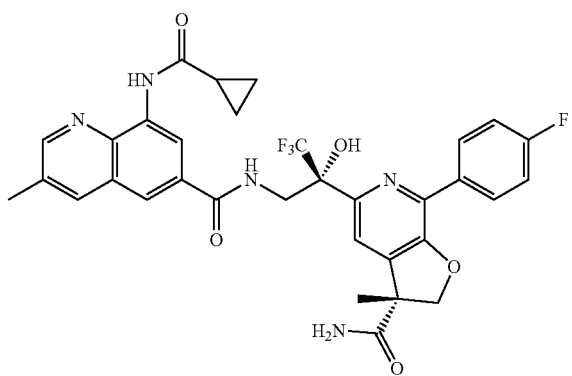 [SMILES: Cc1cnc2c(NC(=O)C3CC3)cc(C(=O)NC[C@](O)(c3cc4c(c(-c5ccc(F)cc5)n3)OC[C@]4(C)C(N)=O)C(F)(F)F)cc2c1]

The acid precursor was prepared in an analogous fashion to Example 392 with step c above. Methylaminoquinoline acylation extracted and used crude (39 mg, 100%). ESI-MS m/z: 299.1 [M+H]⁺. The ethyl ester hydrolysis was carried out according to Method T, step d at 45° C. and isolated by precipitation (26 mg, 68%). ESI-MS m/z: 271.0 [M+H]⁺.

25 mg of amine HCl salt precursor used according to Method J (PyBOP), and the material purified by Gilson prep-HPLC (20-90%, MeCN/Water, 25 min) to afford the title compound (21.0 mg, 55%). ESI-MS m/z: 652.2 [M+H]⁺.

Example 417

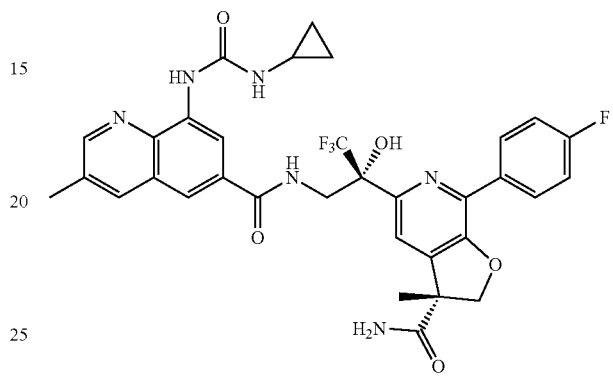

The acid precursor was prepared following example was prepared according to Method W with 3-methylquinoline analog from Example 416 step c. Urea formation extracted and used crude (54 mg, 99%). ESI-MS m/z: 314.0 [M+H]⁺. The ethyl ester hydrolysis was carried out according to Method T, step d at 45° C. and isolated by precipitation (26 mg, 53%). ESI-MS m/z: 285.8 [M+H]⁺.

25 mg of amine HCl salt precursor used according to Method J (PyBOP), and the material purified by Gilson prep-HPLC (20-90%, MeCN/Water, 25 min) to afford the title compound. (15.0 mg, 38%). ESI-MS m/z: 667.2 [M+H]⁺.

Example 418

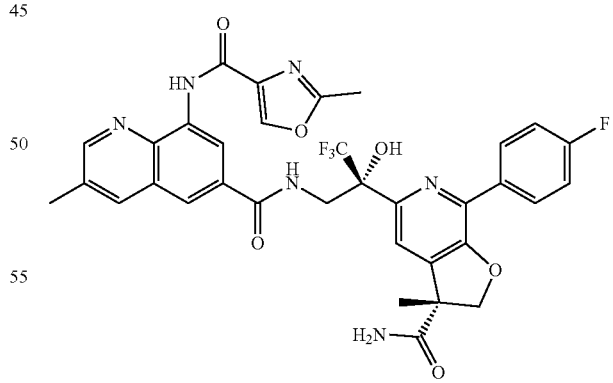

The following acid precursor was prepared according to Method V with 3-methylquinoline analog from Example 416 step c. Amide Ghosez coupling purified by automated column chromatography (silica gel, 0-100% EtOAc/hexanes) to afford the title compound (58 mg, 99%). ESI-MS m/z: 340.1 [M+H]⁺. The ethyl ester hydrolysis was carried out according to Method T, step d at 45° C. and isolated by precipitation (25 mg, 47%). ESI-MS m/z: 312.2 [M+H]+. 25 mg of amine HCl salt precursor used according to Method J (PyBOP), and the material purified by Gilson prep-HPLC (20-90%, MeCN/Water, 25 min) to afford the title compound (10.0 mg, 24%). ESI-MS m/z: 693.2 [M+H]+.

Example 419 Steps a and b

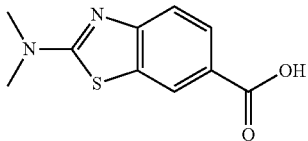

In a vial, ethyl 2-chlorobenzo[d]thiazole-6-carboxylate (250 mg, 1.034 mmol) and dimethylamine hydrochloride (101 mg, 1.241 mmol) were dissolved in DMF (2.96 ml). Triethylamine (721 µl, 5.17 mmol) was added and the reaction was allowed to stir overnight at room temperature. The reaction was diluted with water and the aqueous layer was washed with EtOAc. The combined organic layer was washed with brine before drying over MgSO4 and concentrating under reduced pressure. The crude reaction mixture was purified by silica gel column chromatography (0-60% EtOAc/Hexanes) to furnish the title compound (250 mg, 97%). In a vial, compound from step a (250 mg, 0.999 mmol) and lithium hydroxide (239 mg, 10 equiv) were dissolved in THF (2.335 ml), MeOH (0.259 ml), and Water (0.259 ml). The reaction was heated to 40° C. for 4 hours. The reaction was diluted with water and the pH adjusted to 3-4 with 1M aq. HCl. The aqueous layer washed with DCM and 9:1 DCM/MeOH, combined organics dried over MgSO4 and concentrated under reduced pressure to furnish the title compound (220 mg, 99% yield). ESI-MS m/z: 223.16 [M+H]+.

Example 420

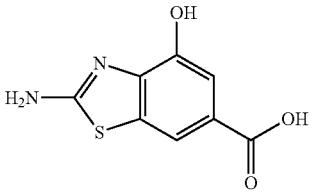 [SMILES: Nc1nc2c(O)cc(C(=O)O)cc2s1]

To a suspension of 4-amino-3-hydroxybenzoic acid (500 mg, 3.27 mmol) in acetic acid (6 ml, 105 mmol) was added potassium thiocyanate (1586 mg, 16.33 mmol). The mixture was chilled and a solution of bromine (0.336 ml, 6.53 mmol) in acetic acid (6 ml, 3.27 mmol) was added drop-wise keeping the temperature below 10° C. The mixture was allowed to warm to room temperature and stir for 1 h. The reaction was quenched with water, boiled for 15 min, and filtered while it was still hot. The filtrate was cooled in an ice bath and the crystalized solid removed by filtration. The pH of the water was adjusted to 4 and the solid precipitated was collected by filtration. The solid was rinsed with water and dried under vacuum to give the title compound (125 mg, 0.595 mmol, 18%). ESI-MS m/z: 210.83 [M+H]+.

Example 421 Steps a and b

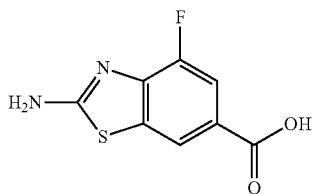 [SMILES: Nc1nc2c(F)cc(C(=O)O)cc2s1]

To methyl 4-amino-3-fluorobenzoate (45 g, 266 mmol) and sodium thiocyanate (86 g, 1064 mmol) in acetic acid (350 ml) at 0° C. was added bromine (13.57 ml, 263 mmol) in AcOH (100 ml) via additional funnel over 1 h, and the mixture was warmed up to RT and stirred for 2 days. The mixture was filtered, and the precipitate was washed with water and dried under vacuum to the title compound and taken forward as a crude mixture.

A slurry of the product of step a (0.8 g, 3.54 mmol) in THF:EtOH (1:1, 12 mL) was mixed with a solution of potassium hydroxide (2.98 g, 53.0 mmol) in water (6 mL). The reaction mixture was heated to 60° C. and stirred for 4 hr, cooled to RT, and then concentrated under reduced pressure. The pH was adjusted to 5 with 3M HCl and 3% citric acid. The pale-yellow solid was precipitated and collected by filtration, washed with water, dried. The aqueous layer was extracted with ethyl acetate and the combined organic layers were dried over Na2SO4 and concentrated to give the title compound (250 mg, 33%) as a pale-yellow solid.

Example 422 Steps a and b

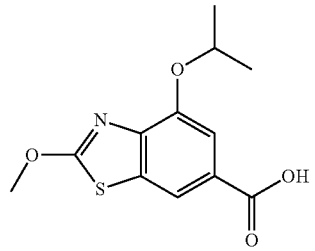 [SMILES: COc1nc2c(OC(C)C)cc(C(=O)O)cc2s1]

In a vial, methyl 2-bromo-4-isopropoxybenzo[d]thiazole-6-carboxylate (500 mg, 1.514 mmol) was dissolved in MeOH (1.514 mL). Sodium methoxide (1039 µl, 4.54 mmol) (25% in MeOH) was added and the reaction was heated to 65° C. After 5 h, the reaction was cooled to room temperature and water added. The precipitate was filtered and dried under vacuum to give the title compound (400 mg, 94%). ESI-MS m/z: 282.15 [M+H]+.

In a vial, the compound from step a (100 mg, 0.355 mmol) and lithium hydroxide (85 mg, 3.55 mmol) were dissolved in THF (2.91 ml), Water (0.323 ml), and MeOH (0.323 ml). The reaction was allowed to stir at room temperature overnight. Water was added and the reaction acidified to pH 2-3 with 1M aq. HCl. The aqueous layer was extracted with EtOAc and the combined organics were dried over MgSO4 and concentrated to give the title compound (90 mg, 95%). ESI-MS m/z: 267.92 [M+H]+.

Example 423 Step a

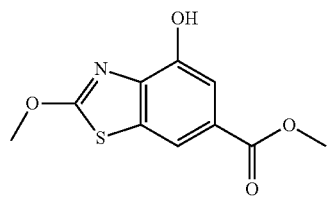

In a vial, methyl 4-isopropoxy-2-methoxybenzo[d]thiazole-6-carboxylate (180 mg, 0.640 mmol) was dissolved in DCM (8 mL) and the solution was cooled to 0° C. Boron trichloride (2559 µl, 2.56 mmol) was added slowly and the reaction was allowed to warm to RT and stir for 2 hr. The reaction was quenched upon addition of 1N HCl. The aqueous layer washed with DCM and combined organic layer dried over MgSO$_4$ and concentrated. Crude mixture purified by silica gel column chromatography eluting with (0-50% EtOAc/Hexanes) to the title compound (150 mg, 98%). ESI-MS m/z: 240.07 [M+H]$^+$.

Example 423 Steps b and c

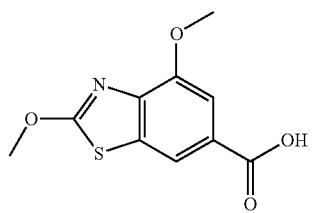 [SMILES: COc1nc2c(OC)cc(C(=O)O)cc2s1]

In a vial, step a (150 mg, 0.627 mmol) was dissolved in THF (4.18 mL) and MeOH (2.090 mL). The solution was cooled to 0° C. and trimethylsilyldiazomethane (940 µl, 1.881 mmol) was added slowly and the reaction was allowed to warm to room temperature. After 4 hr, trimethylsilyldiazomethane (940 µl, 1.881 mmol) was added and the reaction allowed to stir an additional 12 hr. Water was added and the aqueous layer extracted with EtOAc. Combined organic layer dried over MgSO$_4$ and concentrated. Crude mixture purified by silica gel column chromatography (0-50% EtOAc/Hexanes) to afford the title compound (105 mg, 66%). In a vial, the compound from step b (50 mg, 0.197 mmol) and lithium hydroxide (47.3 mg, 1.974 mmol) were dissolved in THF (1.615 ml), MeOH (0.179 ml), and Water (0.179 ml). The reaction was allowed to stir 4 hr. Water was then added and the pH adjusted to 2-3 upon addition of 4M aq. HCl. The aqueous layer was washed with DCM and the combined organic layer was dried over MgSO$_4$ and concentrated under reduced pressure to give the title compound (47 mg, 100%). ESI-MS m/z: 239.87 [M+H]$^+$.

The following examples in Table 6 were prepared using the corresponding intermediates from Examples 205-207 and derivatives thereof. The compounds were made according to Method J with PyBOP, and in some cases HATU. The compounds were purified by Gilson prep-HPLC (20-90%, MeCN/Water, 25 min) in most cases. The aryl acids were prepared according to Examples 419-423 if not commercially available. If not specifically listed, the acids were synthesized in an analogous fashion to the aforementioned examples.

TABLE 6

| Example | Structure | MS$^+$ m/z |
|---|---|---|
| 424 | 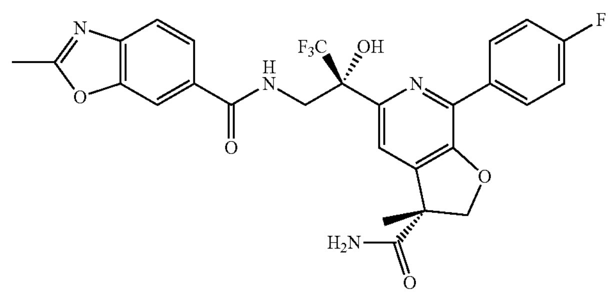 | 559.16 |
| 425 | 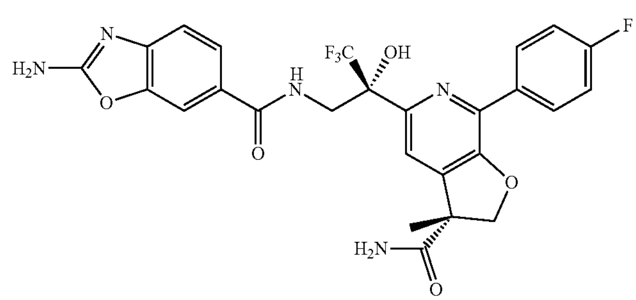 | 560.15 |

TABLE 6-continued
| Example | Structure | MS+ m/z |
|---|---|---|
| 426 | 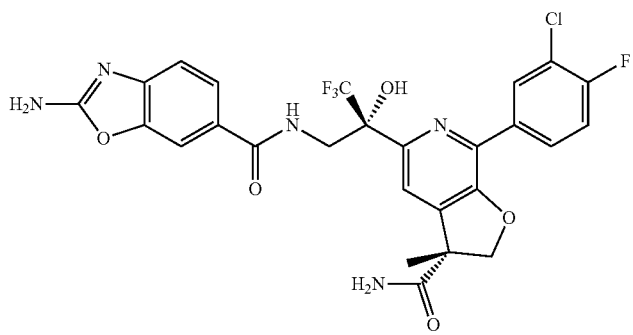 | 594.12 |
| 427 | 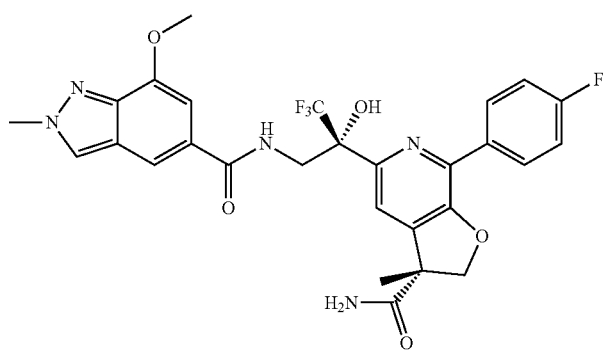 | 588.19 |
| 428 | 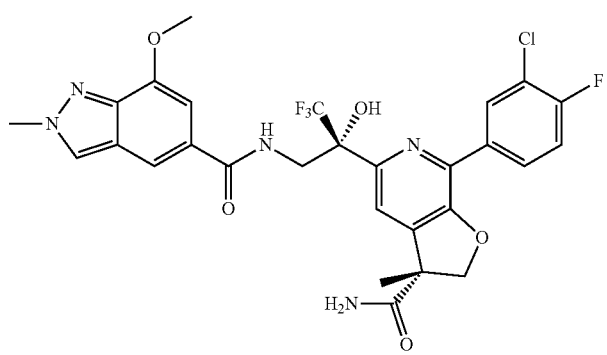 | 622.15 |
| 429 | 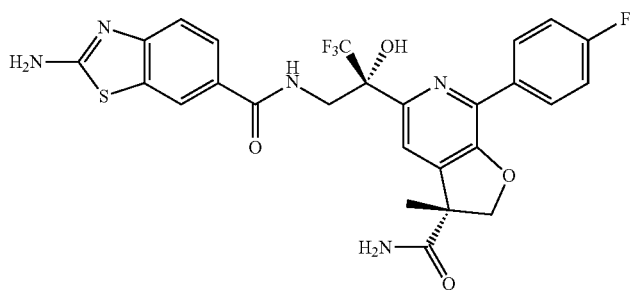 [SMILES: C[C@]1(C(N)=O)COc2c1cc([C@@](O)(CNC(=O)c1ccc3nc(N)sc3c1)C(F)(F)F)nc2-c1ccc(F)cc1] | 576.07 |

TABLE 6-continued
| Example | Structure | MS+ m/z |
|---------|-----------|---------|
| 430 | 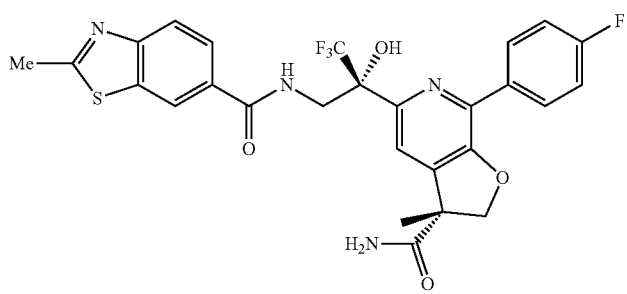 | 575.25 |
| 431 | 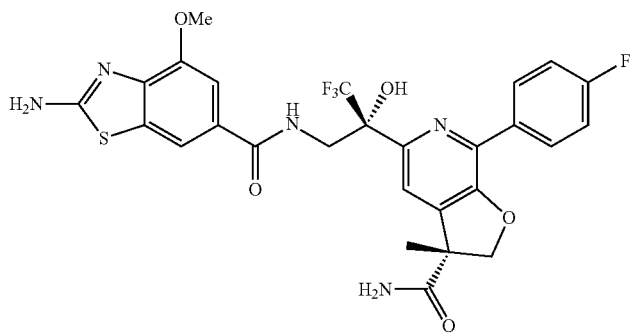 [SMILES: COc1cc(C(=O)NC[C@](O)(c2cc3c(c(-c4ccc(F)cc4)n2)OC[C@]3(C)C(N)=O)C(F)(F)F)cc2sc(N)nc12] | 606.06 |
| 432 | 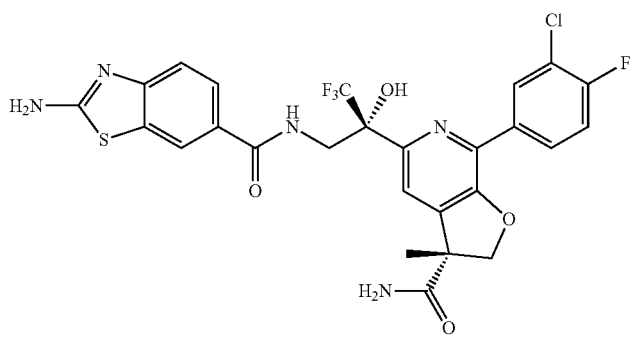 [SMILES: C[C@]1(C(N)=O)COc2c1cc([C@@](O)(CNC(=O)c1ccc3nc(N)sc3c1)C(F)(F)F)nc2-c1ccc(F)c(Cl)c1] | 609.97 |
| 433 | 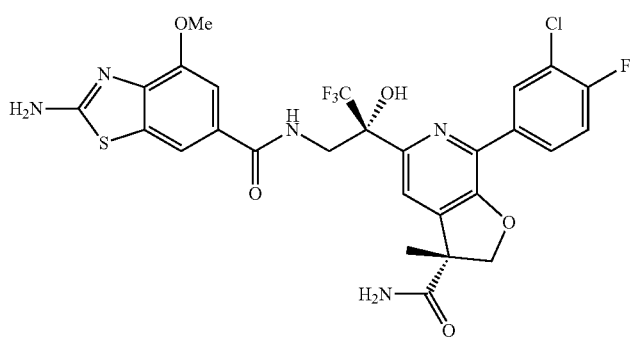 [SMILES: COc1cc(C(=O)NC[C@](O)(c2cc3c(c(-c4ccc(F)c(Cl)c4)n2)OC[C@]3(C)C(N)=O)C(F)(F)F)cc2sc(N)nc12] | 640.15 |

TABLE 6-continued

| Example | Structure | MS+ m/z |
|---------|-----------|---------|
| 434 | 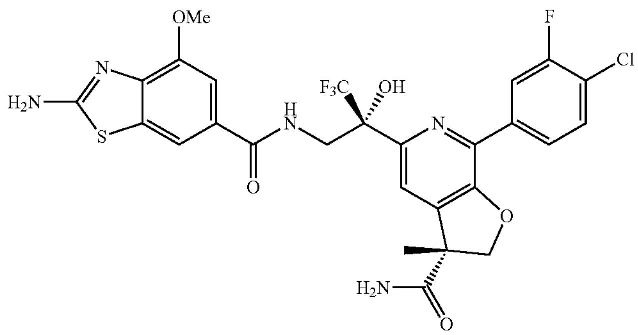 [SMILES: COc1cc(C(=O)NC[C@](O)(c2cc3c(c(-c4ccc(Cl)c(F)c4)n2)OC[C@]3(C)C(N)=O)C(F)(F)F)cc2sc(N)nc12] | 640.03 |
| 435 | 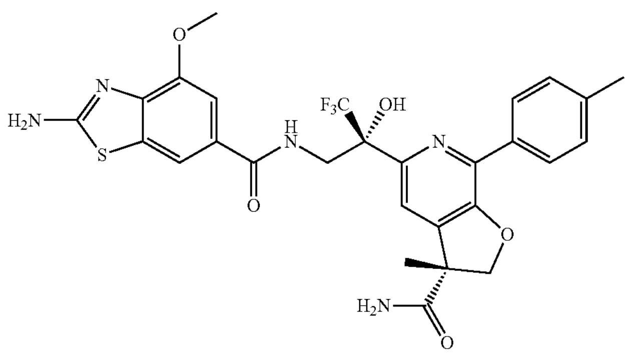 [SMILES: COc1cc(C(=O)NC[C@](O)(c2cc3c(c(-c4ccc(C)cc4)n2)OC[C@]3(C)C(N)=O)C(F)(F)F)cc2sc(N)nc12] | 602.20 |
| 436 | 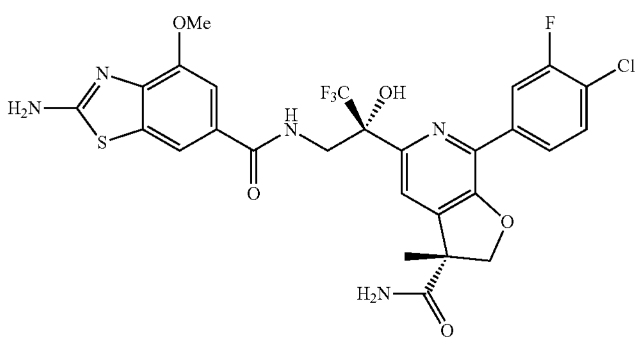 [SMILES: COc1cc(C(=O)NC[C@](O)(c2cc3c(c(-c4ccc(Cl)c(F)c4)n2)OC[C@]3(C)C(N)=O)C(F)(F)F)cc2sc(N)nc12] | 610.17 |
| 437 | 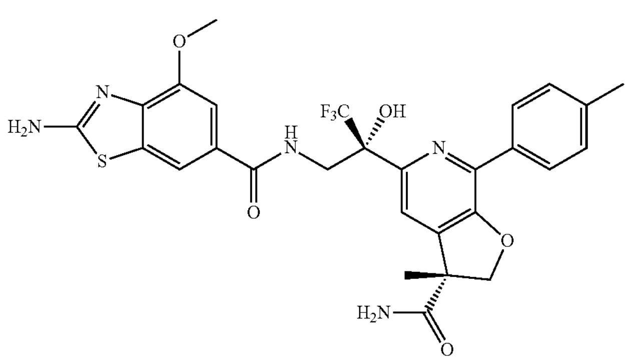 [SMILES: COc1cc(C(=O)NC[C@](O)(c2cc3c(c(-c4ccc(C)cc4)n2)OC[C@]3(C)C(N)=O)C(F)(F)F)cc2sc(N)nc12] | 572.42 |

TABLE 6-continued

| Example | Structure | MS+ m/z |
|---|---|---|
| 438 | 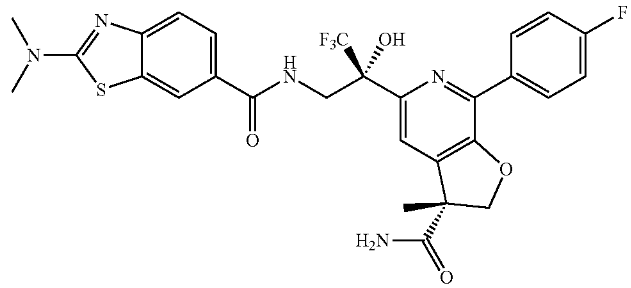 [SMILES: CN(C)c1nc2ccc(C(=O)NC[C@](O)(c3cc4c(c(-c5ccc(F)cc5)n3)OC[C@]4(C)C(N)=O)C(F)(F)F)cc2s1] | 604.38 |
| 439 | 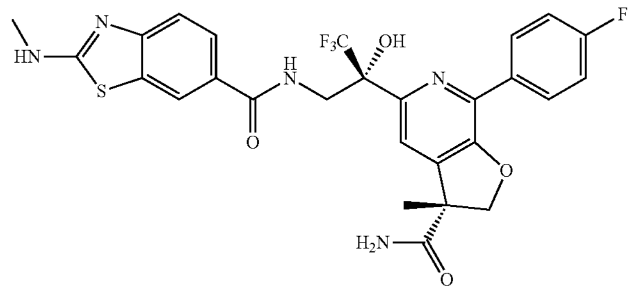 [SMILES: CNc1nc2ccc(C(=O)NC[C@](O)(c3cc4c(c(-c5ccc(F)cc5)n3)OC[C@]4(C)C(N)=O)C(F)(F)F)cc2s1] | 590.38 |
| 440 | 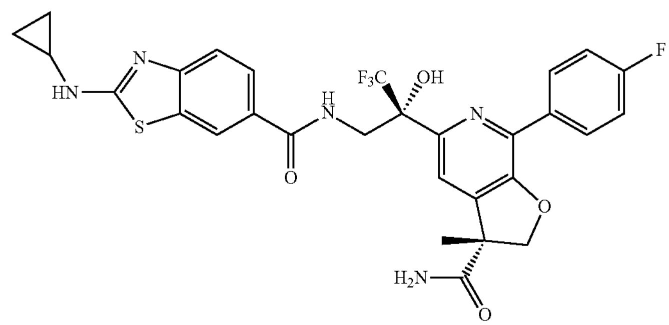 [SMILES: C[C@]1(C(N)=O)COc2c1cc([C@@](O)(CNC(=O)c1ccc3nc(NC4CC4)sc3c1)C(F)(F)F)nc2-c1ccc(F)cc1] | 616.41 |
| 441 | 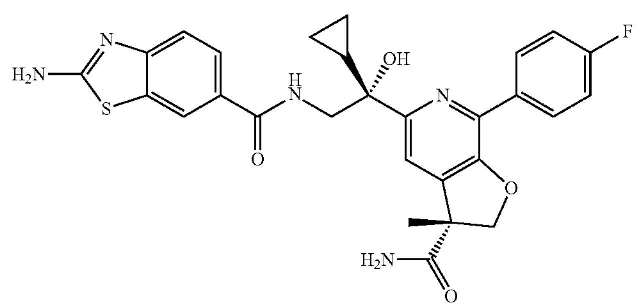 [SMILES: C[C@]1(C(N)=O)COc2c1cc([C@@](O)(CNC(=O)c1ccc3nc(N)sc3c1)C1CC1)nc2-c1ccc(F)cc1] | 548.21 |
| 442 | 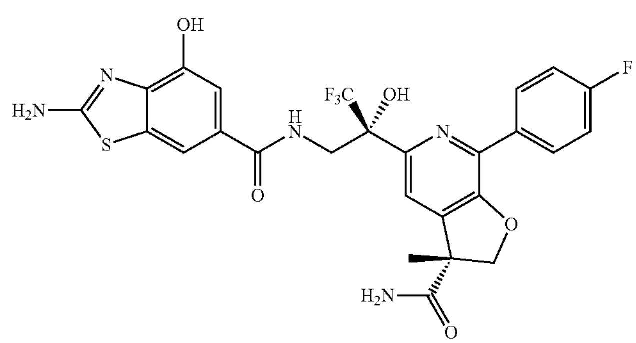 [SMILES: C[C@]1(C(N)=O)COc2c1cc([C@@](O)(CNC(=O)c1cc(O)c3nc(N)sc3c1)C(F)(F)F)nc2-c1ccc(F)cc1] | 592.30 |

TABLE 6-continued

| Example | Structure | MS+ m/z |
|---|---|---|
| 443 | 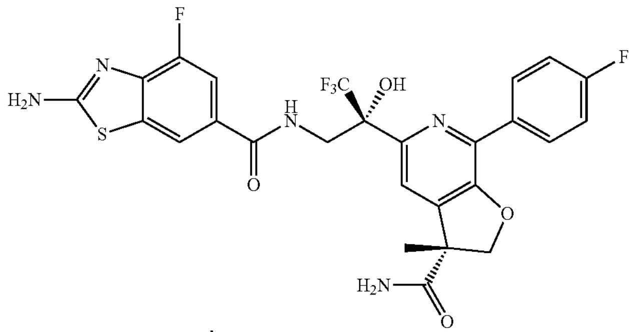 | 593.96 |
| 444 | 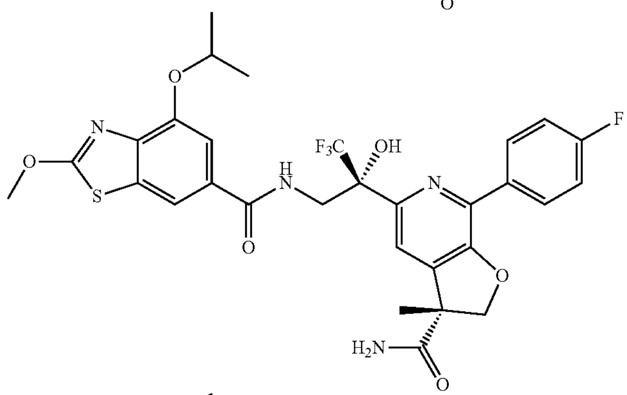 | 649.26 |
| 445 | 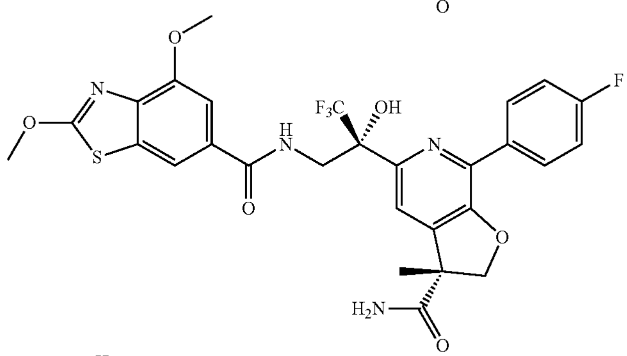 | 621.13 |
| 446 | 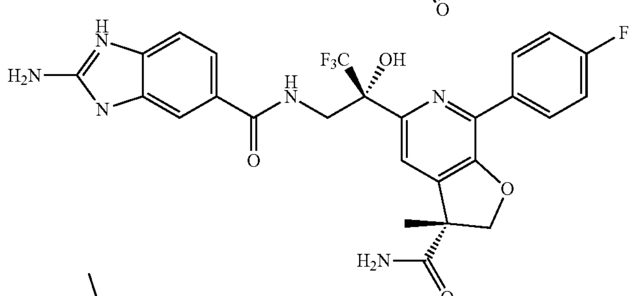 | 559.19 |
| 447 | 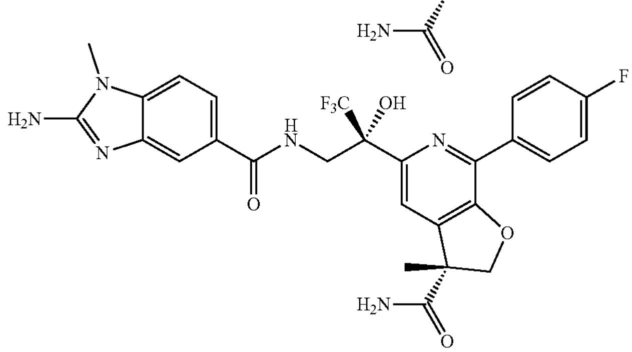 | 573.25 |

TABLE 6-continued

| Example | Structure | MS+ m/z |
|---|---|---|
| 448 | 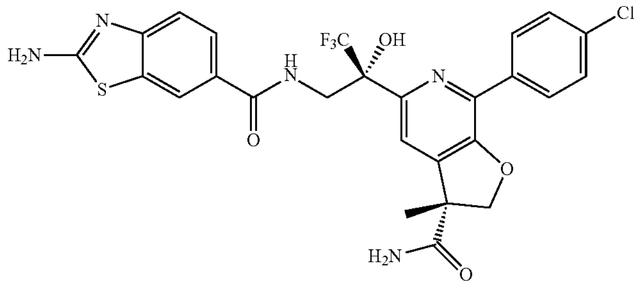 [SMILES: C[C@]1(C(N)=O)COc2c1cc([C@@](O)(CNC(=O)c1ccc3nc(N)sc3c1)C(F)(F)F)nc2-c1ccc(Cl)cc1] | 592.10 |

Example 449

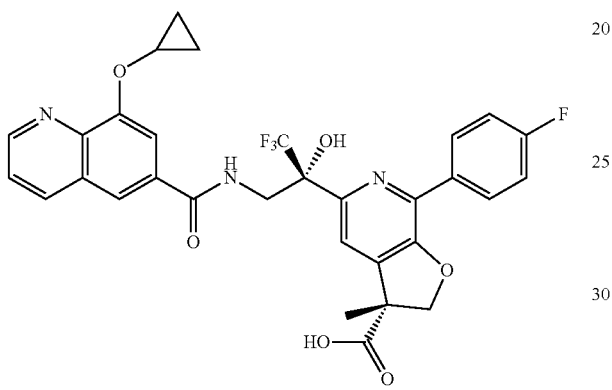

The Example 449 was prepared diastereomerically pure using the methods described in Example 206 (with CF₃ olefin and TBS-alcohol). The TBS-alcohol was converted into the acid according to Methods A, B and F. (1.34 g, 58%). ESI-MS m/z: 612.17 [M+H]⁺.

The following Table 7 contains examples that were synthesized using Example 449 (or methoxy analog) and Method J (PyBOP). The compounds were either purified by automated column chromatography or Gilson prep-HPLC (20-90%, MeCN/Water, 25 min).

TABLE 7

| Example | Structure | MS+ m/z |
|---|---|---|
| 450 | 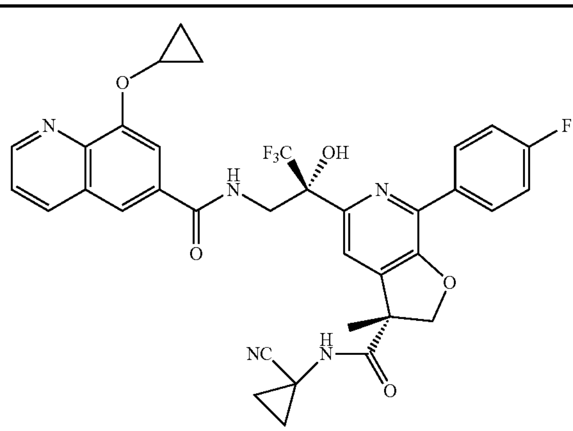 | 676.23 |

TABLE 7-continued

| Example | Structure | MS+ m/z |
|---|---|---|
| 451 | 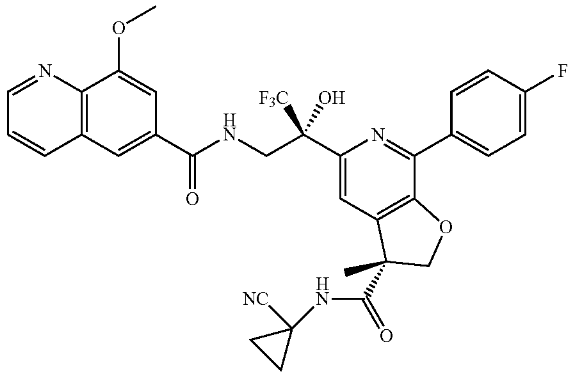 [SMILES: COc1cc(C(=O)NC[C@](O)(c2cc3c(c(-c4ccc(F)cc4)n2)OC[C@]3(C)C(=O)NC2(C#N)CC2)C(F)(F)F)cc2cccnc12] | 650.21 |
| 452 | 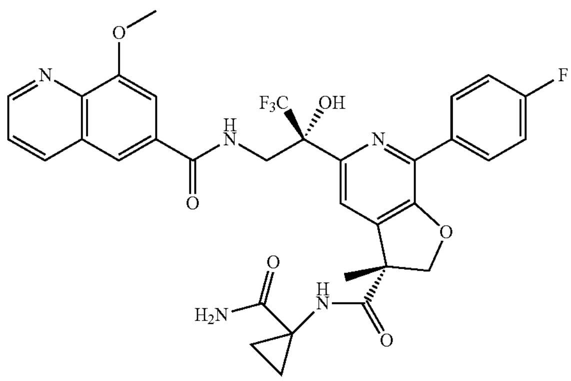 [SMILES: COc1cc(C(=O)NC[C@](O)(c2cc3c(c(-c4ccc(F)cc4)n2)OC[C@]3(C)C(=O)NC2(C(N)=O)CC2)C(F)(F)F)cc2cccnc12] | 645.10 |
| 453 | 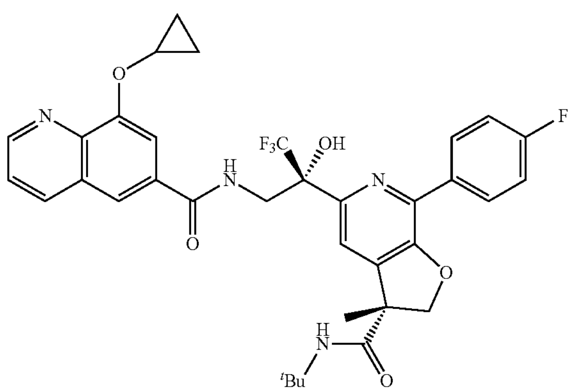 [SMILES: CC(C)(C)NC(=O)[C@@]1(C)COc2c1cc([C@@](O)(CNC(=O)c1cc(OC3CC3)c3ncccc3c1)C(F)(F)F)nc2-c1ccc(F)cc1] | 667.26 |
| 454 | 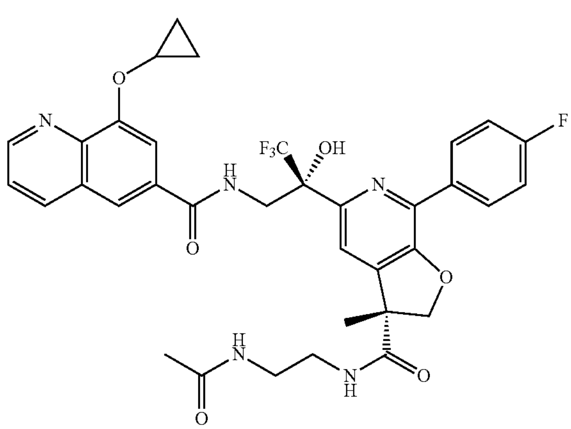 [SMILES: CC(=O)NCCNC(=O)[C@@]1(C)COc2c1cc([C@@](O)(CNC(=O)c1cc(OC3CC3)c3ncccc3c1)C(F)(F)F)nc2-c1ccc(F)cc1] | 696.26 |

TABLE 7-continued
| Example | Structure | MS+ m/z |
|---|---|---|
| 455 | 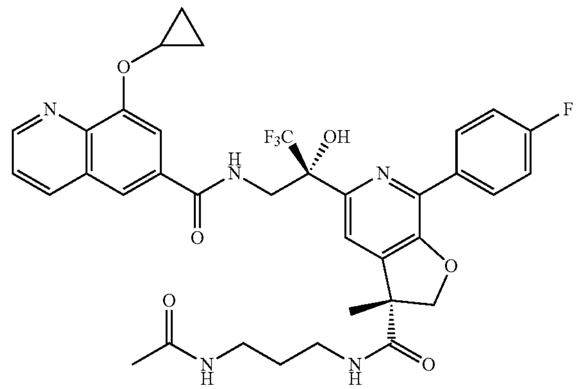 [SMILES: CC(=O)NCCCNC(=O)[C@@]1(C)COc2c1cc([C@@](O)(CNC(=O)c1cc(OC3CC3)c3ncccc3c1)C(F)(F)F)nc2-c1ccc(F)cc1] | 710.26 |
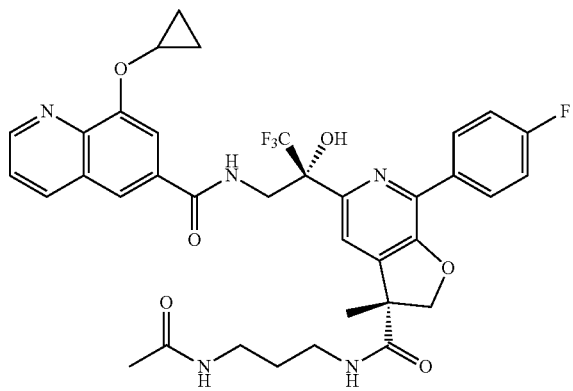
| | | |
|---|---|---|
| 456 | | 653.24 |
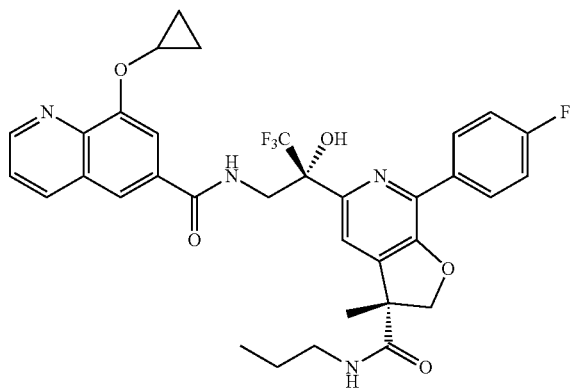 [SMILES: CCCNC(=O)[C@@]1(C)COc2c1cc([C@@](O)(CNC(=O)c1cc(OC3CC3)c3ncccc3c1)C(F)(F)F)nc2-c1ccc(F)cc1]
| | | |
|---|---|---|
| 457 | | 712.24 |
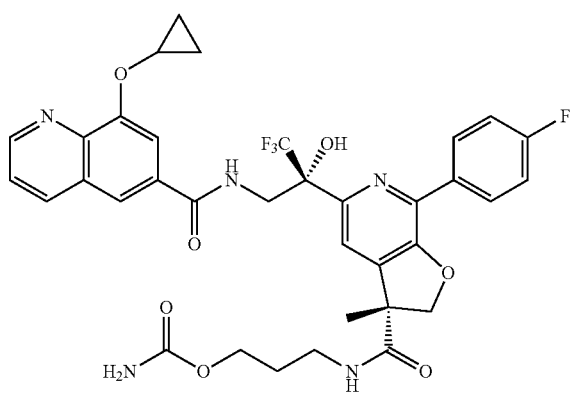 [SMILES: C[C@]1(C(=O)NCCCOC(N)=O)COc2c1cc([C@@](O)(CNC(=O)c1cc(OC3CC3)c3ncccc3c1)C(F)(F)F)nc2-c1ccc(F)cc1]

TABLE 7-continued
| Example | Structure | MS+ m/z |
|---|---|---|
| 458 | 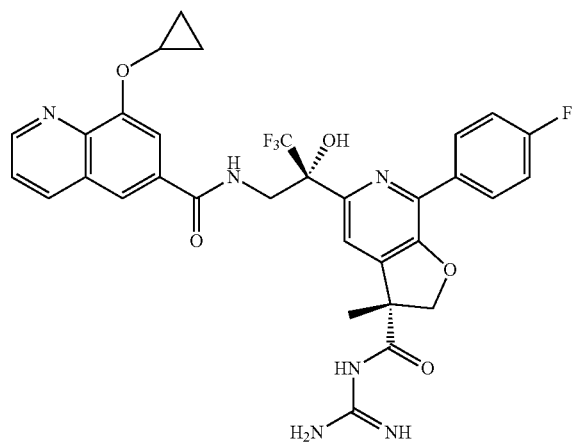 [SMILES: C[C@]1(C(=O)NC(=N)N)COc2c1cc([C@@](O)(CNC(=O)c1cc(OC3CC3)c3ncccc3c1)C(F)(F)F)nc2-c1ccc(F)cc1] | 653.21 |
| 459 | 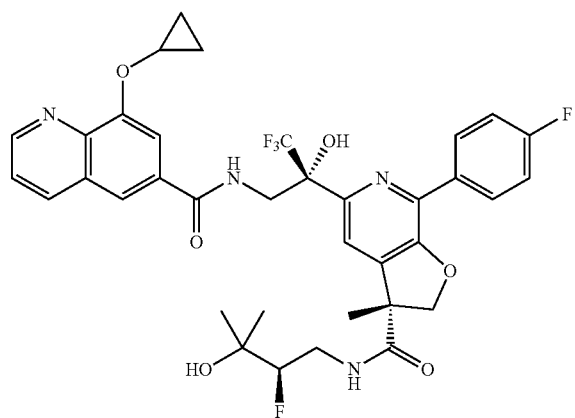 [SMILES: CC(C)(O)[C@H](F)CNC(=O)[C@@]1(C)COc2c1cc([C@@](O)(CNC(=O)c1cc(OC3CC3)c3ncccc3c1)C(F)(F)F)nc2-c1ccc(F)cc1] | 715.26 |
| 460 | 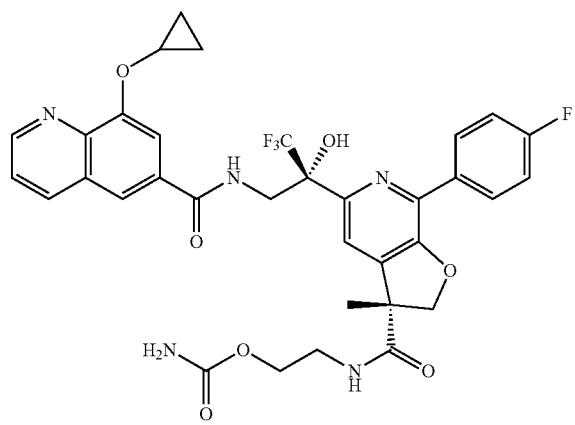 [SMILES: C[C@]1(C(=O)NCCOC(N)=O)COc2c1cc([C@@](O)(CNC(=O)c1cc(OC3CC3)c3ncccc3c1)C(F)(F)F)nc2-c1ccc(F)cc1] | 698.23 |

TABLE 7-continued
| Example | Structure | MS+ m/z |
|---------|-----------|---------|
| 461 | 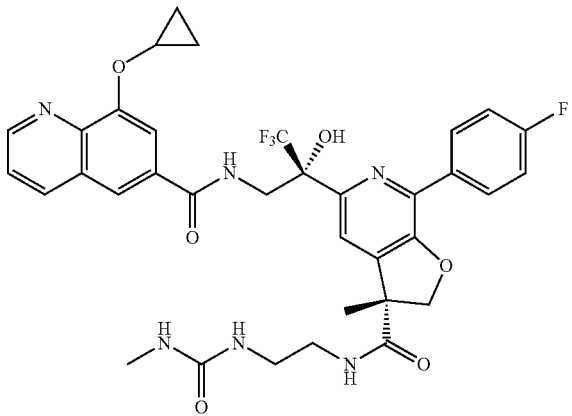 [SMILES: CNC(=O)NCCNC(=O)[C@@]1(C)COc2c1cc([C@@](O)(CNC(=O)c1cc(OC3CC3)c3ncccc3c1)C(F)(F)F)nc2-c1ccc(F)cc1] | 711.25 |
| 462 | 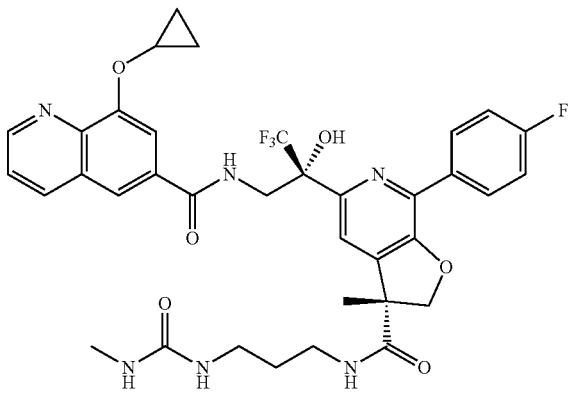 [SMILES: CNC(=O)NCCCNC(=O)[C@@]1(C)COc2c1cc([C@@](O)(CNC(=O)c1cc(OC3CC3)c3ncccc3c1)C(F)(F)F)nc2-c1ccc(F)cc1] | 724.27 |
| 463 | 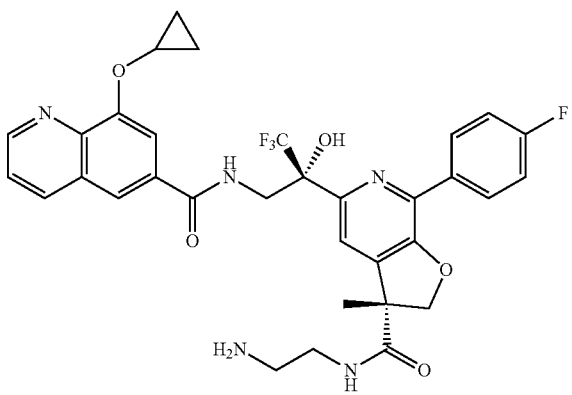 [SMILES: C[C@]1(C(=O)NCCN)COc2c1cc([C@@](O)(CNC(=O)c1cc(OC3CC3)c3ncccc3c1)C(F)(F)F)nc2-c1ccc(F)cc1] | 654.23 |

TABLE 7-continued

| Example | Structure | MS+ m/z |
|---|---|---|
| 464 | 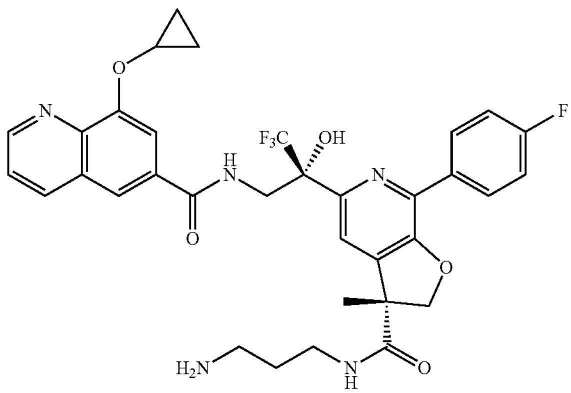 [SMILES: C[C@]1(C(=O)NCCCN)COc2c1cc([C@@](O)(CNC(=O)c1cc(OC3CC3)c3ncccc3c1)C(F)(F)F)nc2-c1ccc(F)cc1] | 668.25 |
| 465 | 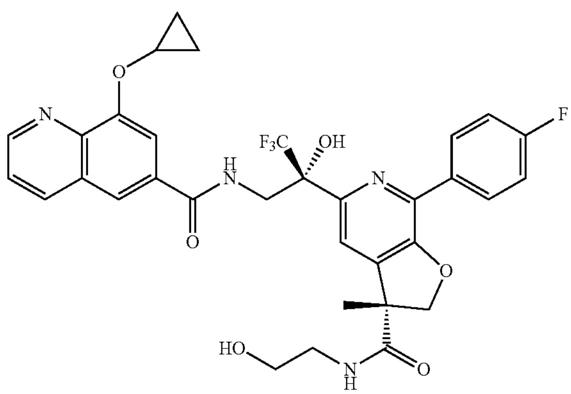 [SMILES: C[C@]1(C(=O)NCCO)COc2c1cc([C@@](O)(CNC(=O)c1cc(OC3CC3)c3ncccc3c1)C(F)(F)F)nc2-c1ccc(F)cc1] | 655.22 |
| 466 | 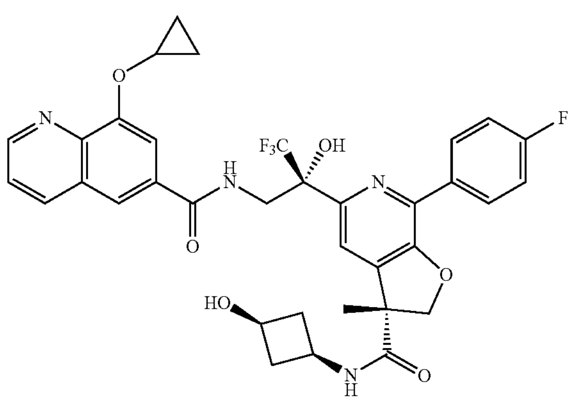 [SMILES: C[C@]1(C(=O)N[C@H]2C[C@@H](O)C2)COc2c1cc([C@@](O)(CNC(=O)c1cc(OC3CC3)c3ncccc3c1)C(F)(F)F)nc2-c1ccc(F)cc1] | 681.23 |
| 467 | 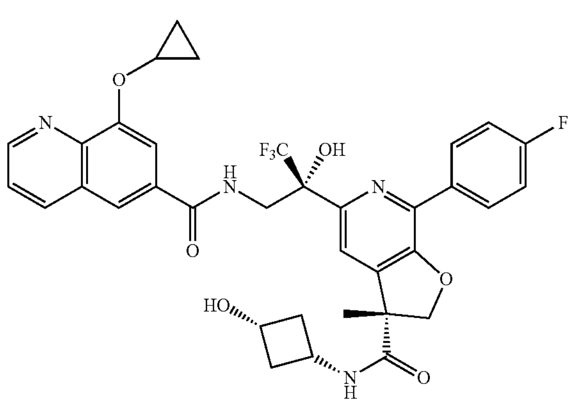 | 681.24 |

TABLE 7-continued
| Example | Structure | MS+ m/z |
|---|---|---|
| 468 | 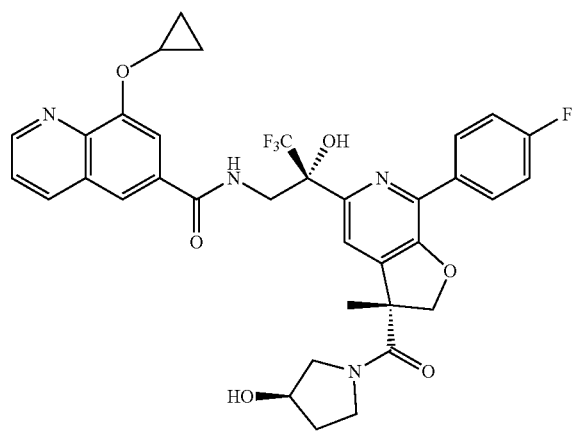 [SMILES: C[C@]1(C(=O)N2CC[C@@H](O)C2)COc2c1cc([C@@](O)(CNC(=O)c1cc(OC3CC3)c3ncccc3c1)C(F)(F)F)nc2-c1ccc(F)cc1] | 681.23 |
| 469 | 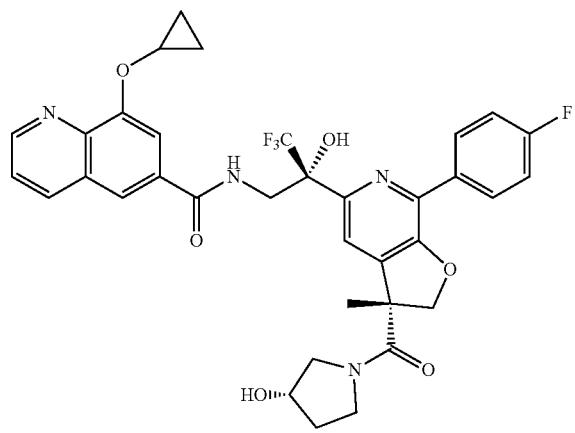 [SMILES: C[C@]1(C(=O)N2CC[C@H](O)C2)COc2c1cc([C@@](O)(CNC(=O)c1cc(OC3CC3)c3ncccc3c1)C(F)(F)F)nc2-c1ccc(F)cc1] | 681.23 |
| 470 | 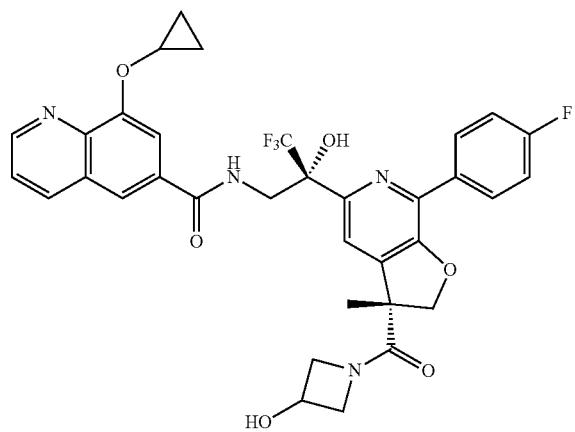 [SMILES: C[C@]1(C(=O)N2CC(O)C2)COc2c1cc([C@@](O)(CNC(=O)c1cc(OC3CC3)c3ncccc3c1)C(F)(F)F)nc2-c1ccc(F)cc1] | 667.22 |

TABLE 7-continued
| Example | Structure | MS+ m/z |
|---|---|---|
| 471 | 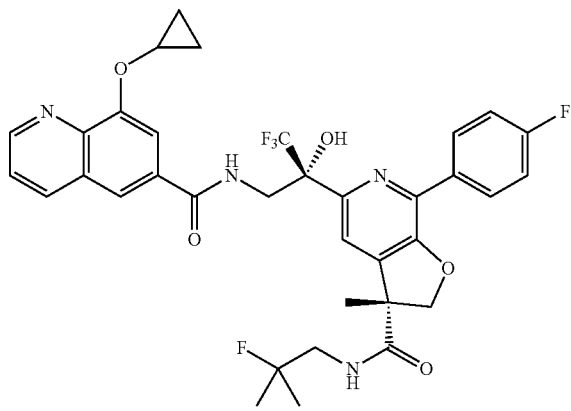 [SMILES: CC(C)(F)CNC(=O)[C@@]1(C)COc2c1cc([C@@](O)(CNC(=O)c1cc(OC3CC3)c3ncccc3c1)C(F)(F)F)nc2-c1ccc(F)cc1] | 699.26 |
| 472 | 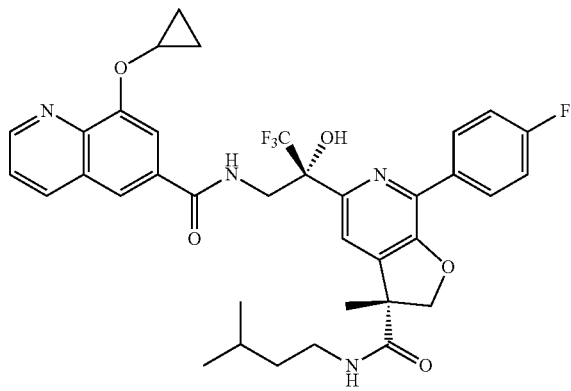 [SMILES: CC(C)CCNC(=O)[C@@]1(C)COc2c1cc([C@@](O)(CNC(=O)c1cc(OC3CC3)c3ncccc3c1)C(F)(F)F)nc2-c1ccc(F)cc1] | 681.27 |
| 473 | 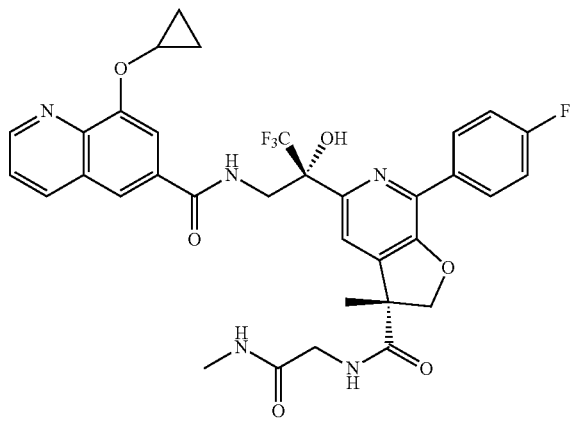 [SMILES: CNC(=O)CNC(=O)[C@@]1(C)COc2c1cc([C@@](O)(CNC(=O)c1cc(OC3CC3)c3ncccc3c1)C(F)(F)F)nc2-c1ccc(F)cc1] | 682.23 |

TABLE 7-continued
| Example | Structure | MS+ m/z |
|---|---|---|
| 474 | 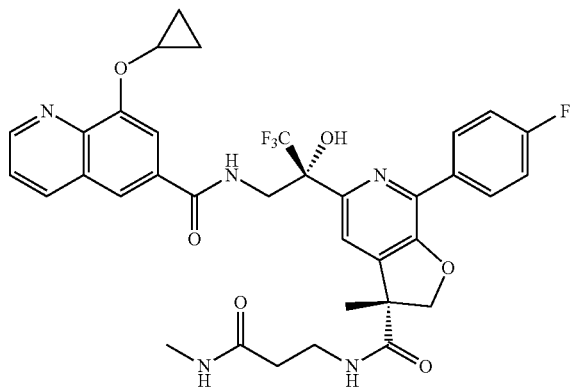 [SMILES: CNC(=O)CCNC(=O)[C@@]1(C)COc2c1cc([C@@](O)(CNC(=O)c1cc(OC3CC3)c3ncccc3c1)C(F)(F)F)nc2-c1ccc(F)cc1] | 696.25 |
| 475 | 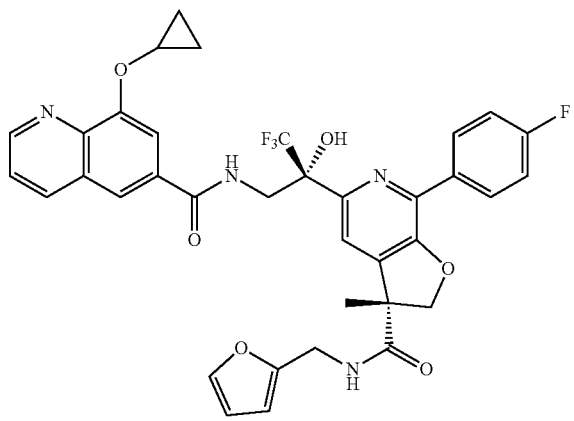 [SMILES: C[C@]1(C(=O)NCc2ccco2)COc2c1cc([C@@](O)(CNC(=O)c1cc(OC3CC3)c3ncccc3c1)C(F)(F)F)nc2-c1ccc(F)cc1] | 691.22 |
| 476 | 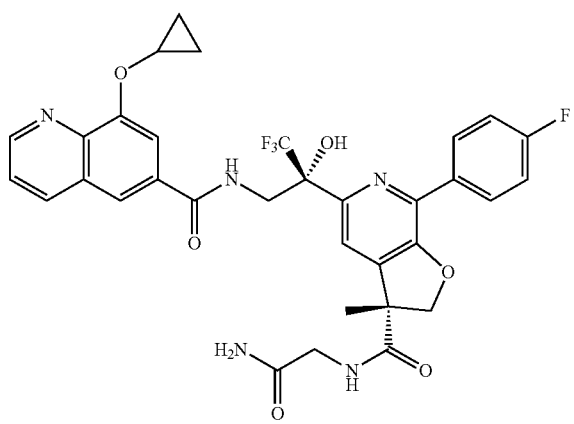 [SMILES: C[C@]1(C(=O)NCC(N)=O)COc2c1cc([C@@](O)(CNC(=O)c1cc(OC3CC3)c3ncccc3c1)C(F)(F)F)nc2-c1ccc(F)cc1] | 668.21 |

TABLE 7-continued
| Example | Structure | MS+ m/z |
|---------|-----------|---------|
| 477 | 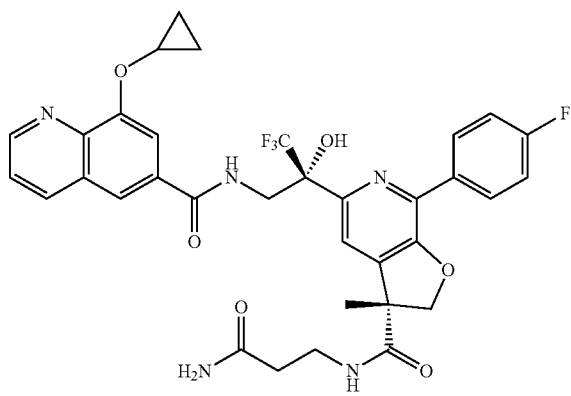 [SMILES: C[C@]1(C(=O)NCCC(N)=O)COc2c1cc([C@@](O)(CNC(=O)c1cc(OC3CC3)c3ncccc3c1)C(F)(F)F)nc2-c1ccc(F)cc1] | 682.23 |
| 478 | 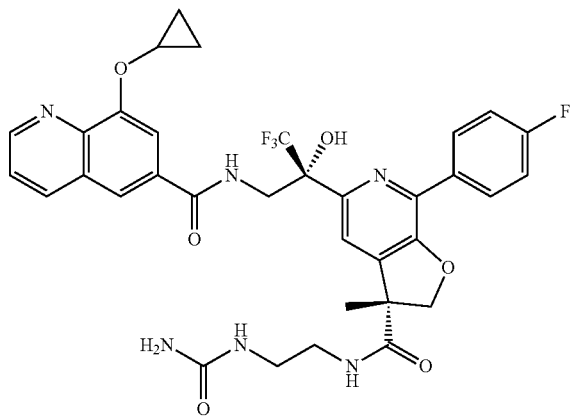 [SMILES: C[C@]1(C(=O)NCCNC(N)=O)COc2c1cc([C@@](O)(CNC(=O)c1cc(OC3CC3)c3ncccc3c1)C(F)(F)F)nc2-c1ccc(F)cc1] | 697.24 |
| 479 | 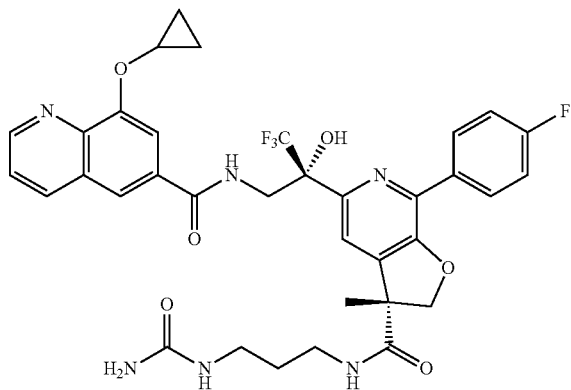 [SMILES: C[C@]1(C(=O)NCCCNC(N)=O)COc2c1cc([C@@](O)(CNC(=O)c1cc(OC3CC3)c3ncccc3c1)C(F)(F)F)nc2-c1ccc(F)cc1] | 711.26 |

TABLE 7-continued
| Example | Structure | MS+ m/z |
|---------|-----------|---------|
| 480 | 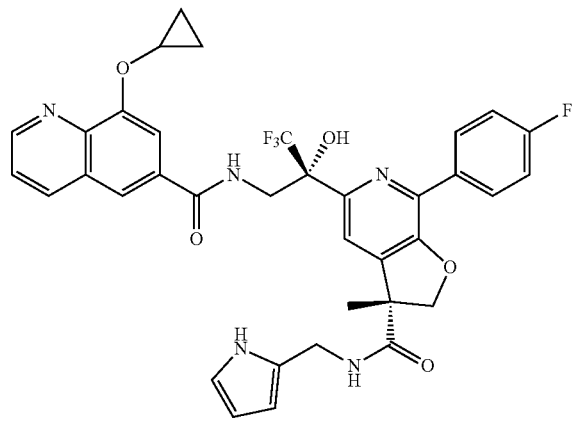 [SMILES: C[C@]1(C(=O)NCc2ccc[nH]2)COc2c1cc([C@@](O)(CNC(=O)c1cc(OC3CC3)c3ncccc3c1)C(F)(F)F)nc2-c1ccc(F)cc1] | 690.23 |
| 481 | 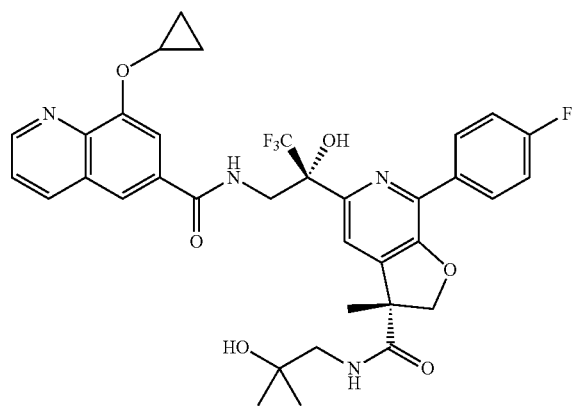 [SMILES: CC(C)(O)CNC(=O)[C@@]1(C)COc2c1cc([C@@](O)(CNC(=O)c1cc(OC3CC3)c3ncccc3c1)C(F)(F)F)nc2-c1ccc(F)cc1] | 697.26 |
| 482 | 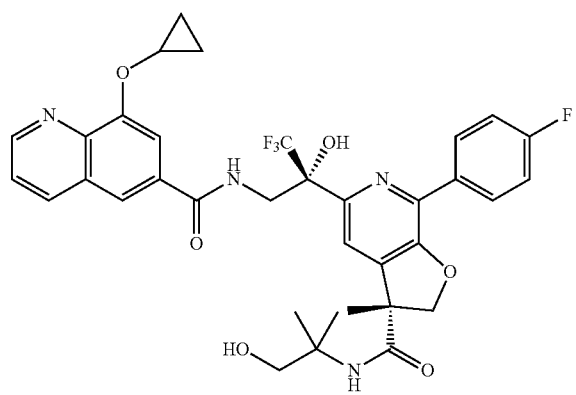 [SMILES: CC(C)(CO)NC(=O)[C@@]1(C)COc2c1cc([C@@](O)(CNC(=O)c1cc(OC3CC3)c3ncccc3c1)C(F)(F)F)nc2-c1ccc(F)cc1] | 683.25 |

TABLE 7-continued

| Example | Structure | MS+ m/z |
|---|---|---|
| 483 | 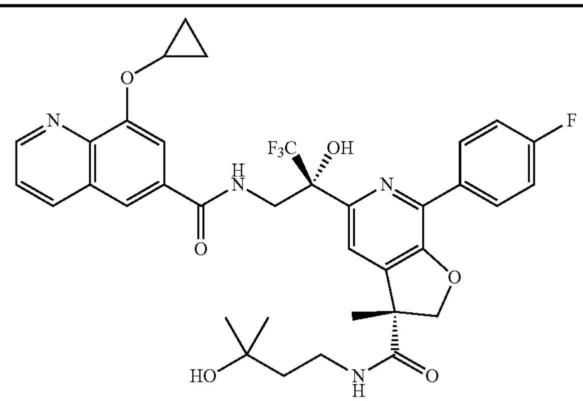 | 697.27 |
| 484 | 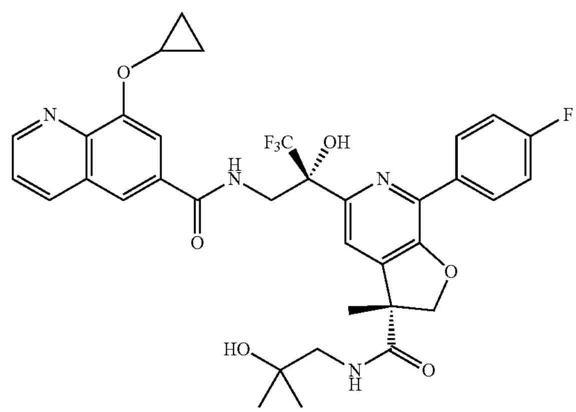 [SMILES: CC(C)(O)CNC(=O)[C@@]1(C)COc2c1cc([C@@](O)(CNC(=O)c1cc(OC3CC3)c3ncccc3c1)C(F)(F)F)nc2-c1ccc(F)cc1] | 683.25 |
| 485 | 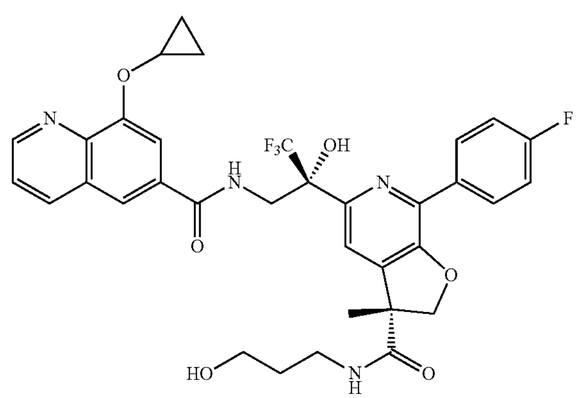 [SMILES: C[C@]1(C(=O)NCCCO)COc2c1cc([C@@](O)(CNC(=O)c1cc(OC3CC3)c3ncccc3c1)C(F)(F)F)nc2-c1ccc(F)cc1] | 669.24 |
| 486 | 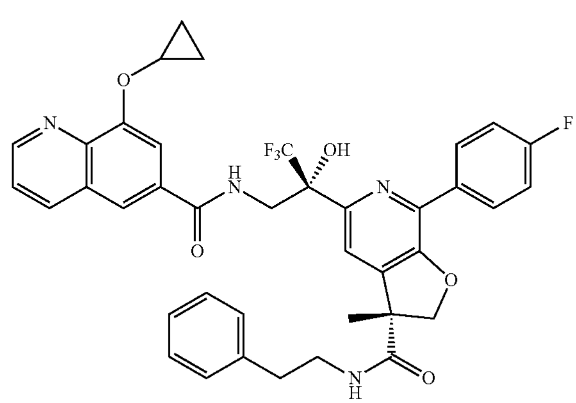 [SMILES: C[C@]1(C(=O)NCCc2ccccc2)COc2c1cc([C@@](O)(CNC(=O)c1cc(OC3CC3)c3ncccc3c1)C(F)(F)F)nc2-c1ccc(F)cc1] | 715.26 |

TABLE 7-continued
| Example | Structure | MS+ m/z |
|---------|-----------|---------|
| 487 | 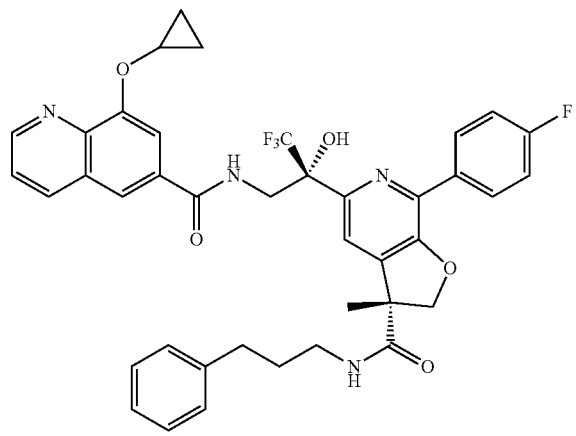 [SMILES: C[C@]1(C(=O)NCCCc2ccccc2)COc2c1cc([C@@](O)(CNC(=O)c1cc(OC3CC3)c3ncccc3c1)C(F)(F)F)nc2-c1ccc(F)cc1] | 729.27 |
| 488 | 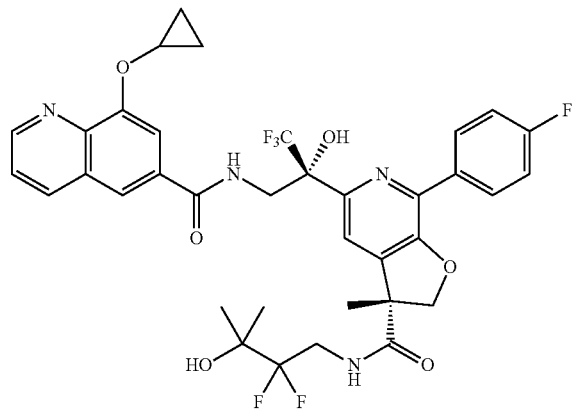 [SMILES: CC(C)(O)C(F)(F)CNC(=O)[C@@]1(C)COc2c1cc([C@@](O)(CNC(=O)c1cc(OC3CC3)c3ncccc3c1)C(F)(F)F)nc2-c1ccc(F)cc1] | 733.25 |
| 489 | 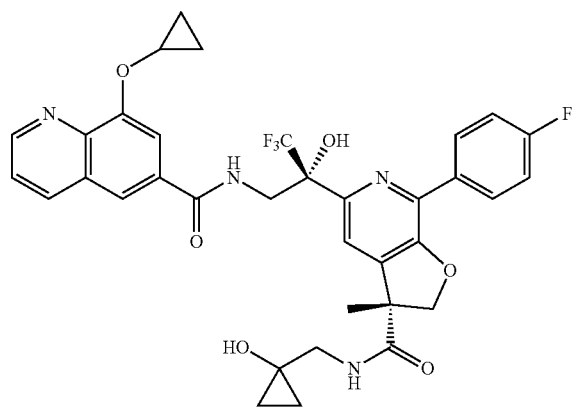 [SMILES: C[C@]1(C(=O)NCC2(O)CC2)COc2c1cc([C@@](O)(CNC(=O)c1cc(OC3CC3)c3ncccc3c1)C(F)(F)F)nc2-c1ccc(F)cc1] | 681.23 |

TABLE 7-continued
| Example | Structure | MS+ m/z |
|---|---|---|
| 490 | 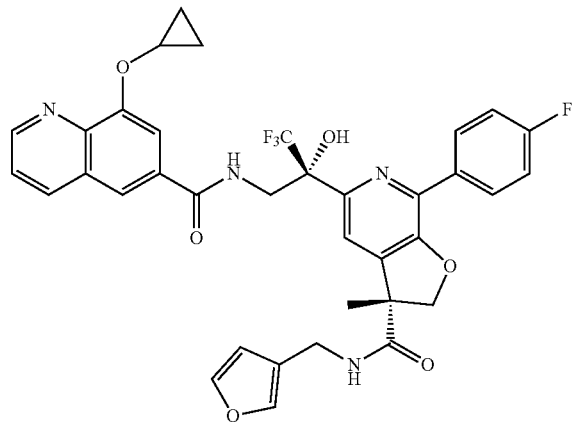 [SMILES: C[C@]1(C(=O)NCc2ccoc2)COc2c1cc([C@@](O)(CNC(=O)c1cc(OC3CC3)c3ncccc3c1)C(F)(F)F)nc2-c1ccc(F)cc1] | 691.22 |
| 491 | 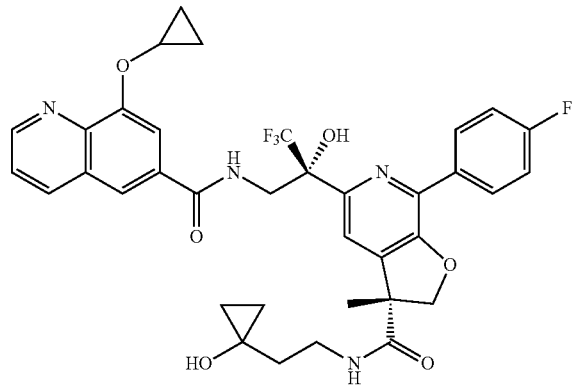 [SMILES: C[C@]1(C(=O)NCCC2(O)CC2)COc2c1cc([C@@](O)(CNC(=O)c1cc(OC3CC3)c3ncccc3c1)C(F)(F)F)nc2-c1ccc(F)cc1] | 695.25 |
| 492 | 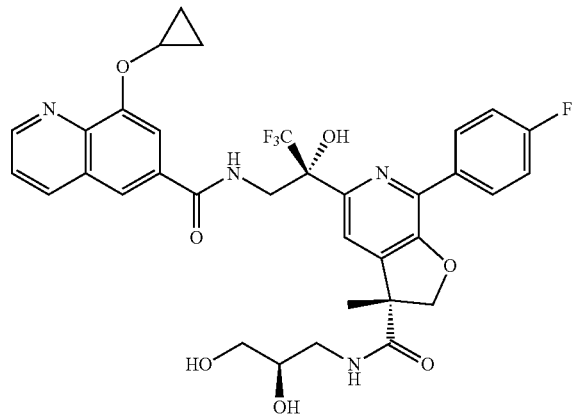 [SMILES: C[C@]1(C(=O)NC[C@@H](O)CO)COc2c1cc([C@@](O)(CNC(=O)c1cc(OC3CC3)c3ncccc3c1)C(F)(F)F)nc2-c1ccc(F)cc1] | 685.23 |

TABLE 7-continued

| Example | Structure | MS+ m/z |
|---|---|---|
| 493 | 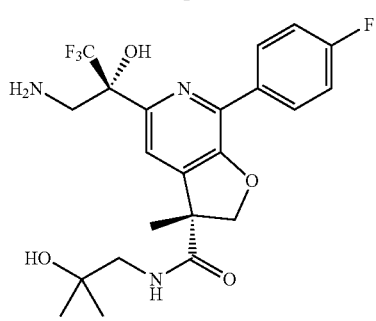 | 685.23 |
| 494 | 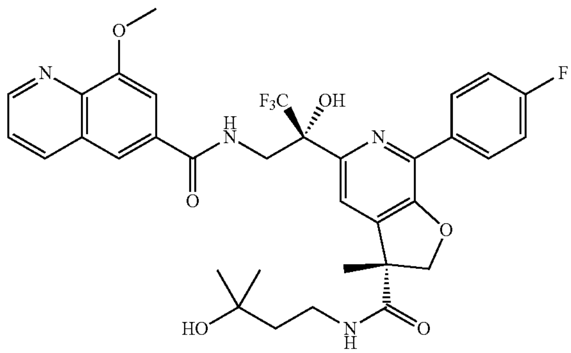 [SMILES: COc1cc(C(=O)NC[C@](O)(c2cc3c(c(-c4ccc(F)cc4)n2)OC[C@]3(C)C(=O)NCCC(C)(C)O)C(F)(F)F)cc2cccnc12] | 671.25 |

Example 495

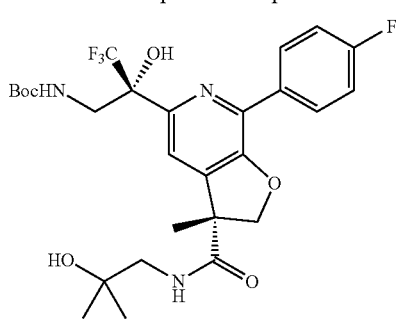

Example 495 Step a

Compound from Example 59 step a (400 mg, 0.80 mmol) and 1-amino-2-methylpropan-2-ol (142 mg, 1.60 mmol) were dissolved in DMF (2 mL) in a round bottom flask, cooled down to 0° C., then Hunig's base (698 µl, 4.00 mmol) was slowly added. After 5 min, PyBOP (832 mg, 1.60 mmol) was slowly added. The resulting solution was stirred for 2 hrs at rt. The reaction was then quenched by the addition of water (10 mL), extracted with ethyl acetate (50 mL×2). The organic layer was washed with brine (50 mL×2) and dried over Na$_2$SO$_4$. The residue was purified by automated column chromatography (eluting with 0-70% EtOAc/hexanes) to afford the desired compound (380 mg, 83% yield). ESI-MS m/z=572.20 [M+H]$^+$.

Example 495 Step b

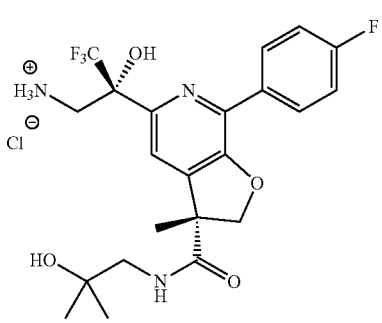 [SMILES: [Cl-] ; CC(C)(O)CNC(=O)[C@@]1(C)COc2c1cc([C@@](O)(C[NH3+])C(F)(F)F)nc2-c1ccc(F)cc1]

389

Compound from step a (360 mg, 0.63 mmol) was dissolved in DCM (2 mL), then 4N HCl in 1,4-dioxane (2 mL) was slowly added. After stirred at rt for 2 hrs, reaction was completed. After evaporated the solvent and dried in vacuo, the desired compound (310 mg, 970%) was obtained as a HCl salt. ESI-MS m/z=472.20 [M+H]⁺.

390

The following Table 8 contains examples that were synthesized according to Method J (PyBOP). The majority of compounds were purified by Gilson prep-HPLC, and some were purified by automated column chromatography (silica gel).

TABLE 8

| Example | Structure | MS⁺ m/z |
|---------|-----------|---------|
| 496 | 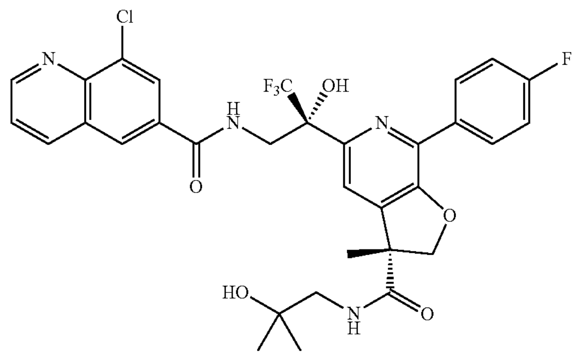 [SMILES: CC(C)(O)CNC(=O)[C@@]1(C)COc2c1cc([C@@](O)(CNC(=O)c1cc(Cl)c3ncccc3c1)C(F)(F)F)nc2-c1ccc(F)cc1] | 661.18 |
| 497 | 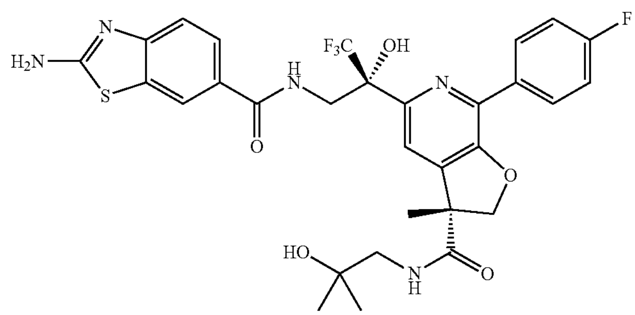 [SMILES: CC(C)(O)CNC(=O)[C@@]1(C)COc2c1cc([C@@](O)(CNC(=O)c1ccc3nc(N)sc3c1)C(F)(F)F)nc2-c1ccc(F)cc1] | 648.19 |
| 498 | 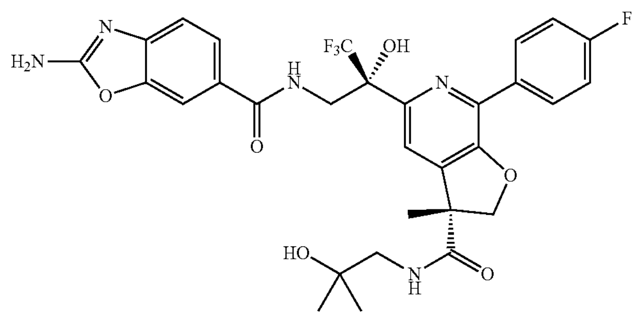 | 632.21 |
| 499 | 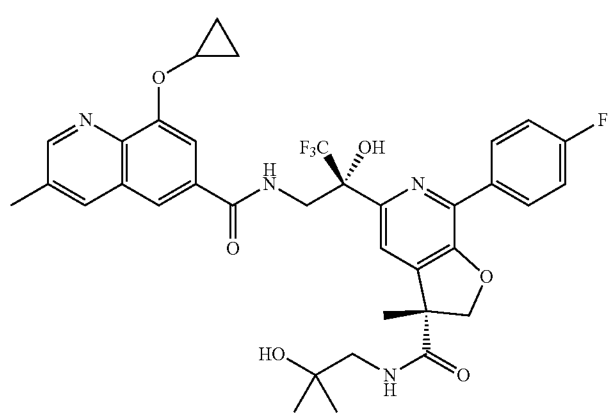 [SMILES: Cc1cnc2c(OC3CC3)cc(C(=O)NC[C@](O)(c3cc4c(c(-c5ccc(F)cc5)n3)OC[C@]4(C)C(=O)NCC(C)(C)O)C(F)(F)F)cc2c1] | 697.27 |

TABLE 8-continued

| Example | Structure | MS+ m/z |
|---|---|---|
| 500 | 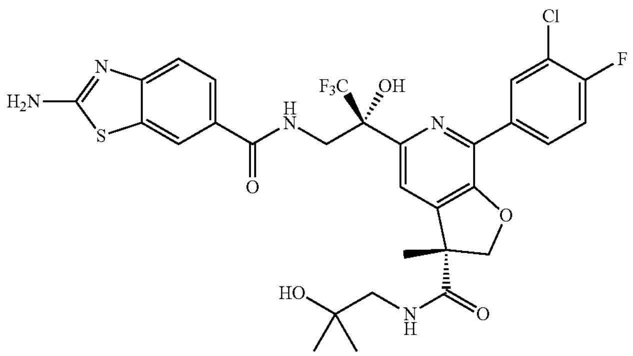 [SMILES: CC(C)(O)CNC(=O)[C@@]1(C)COc2c1cc([C@@](O)(CNC(=O)c1ccc3nc(N)sc3c1)C(F)(F)F)nc2-c1ccc(F)c(Cl)c1] | 682.15 |
| 501 | 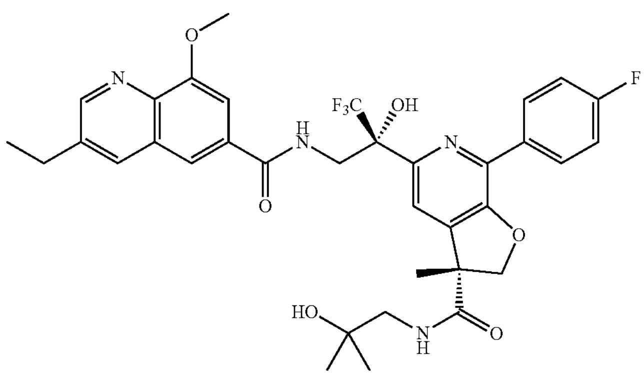 [SMILES: CCc1cnc2c(OC)cc(C(=O)NC[C@](O)(c3cc4c(c(-c5ccc(F)cc5)n3)OC[C@]4(C)C(=O)NCC(C)(C)O)C(F)(F)F)cc2c1] | 719.23 |
| 502 | 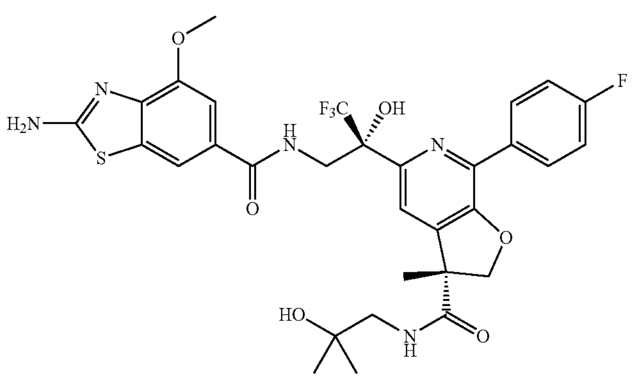 [SMILES: COc1cc(C(=O)NC[C@](O)(c2cc3c(c(-c4ccc(F)cc4)n2)OC[C@]3(C)C(=O)NCC(C)(C)O)C(F)(F)F)cc2sc(N)nc12] | 678.25 |
| 503 | 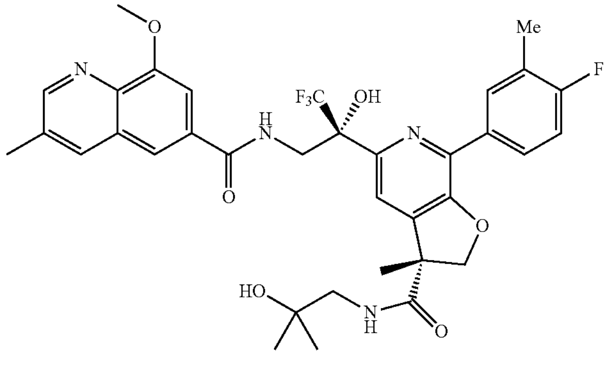 [SMILES: COc1cc(C(=O)NC[C@](O)(c2cc3c(c(-c4ccc(F)c(C)c4)n2)OC[C@]3(C)C(=O)NCC(C)(C)O)C(F)(F)F)cc2cc(C)cnc12] | 685.39 |

TABLE 8-continued

| Example | Structure | MS+ m/z |
|---|---|---|
| 504 | 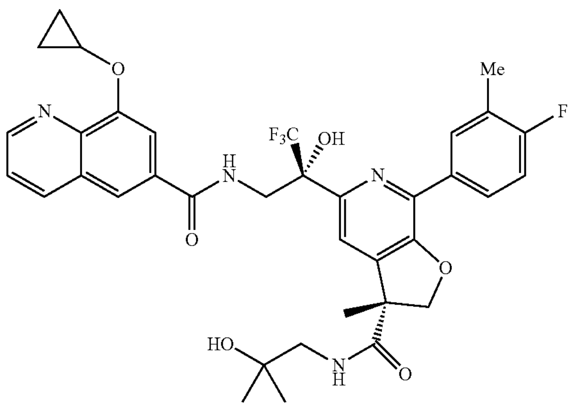 [SMILES: Cc1cc(-c2nc([C@@](O)(CNC(=O)c3cc(OC4CC4)c4ncccc4c3)C(F)(F)F)cc3c2OC[C@]3(C)C(=O)NCC(C)(C)O)ccc1F] | 697.30 |
| 505 | 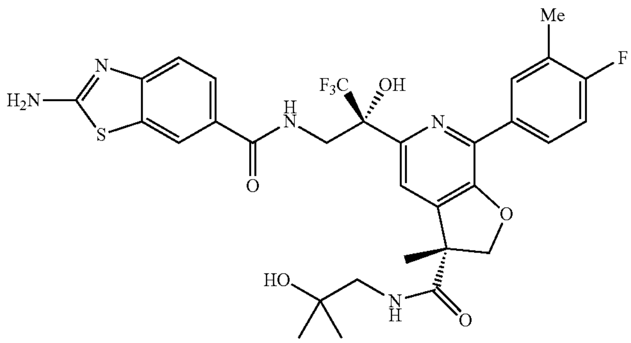 [SMILES: Cc1cc(-c2nc([C@@](O)(CNC(=O)c3ccc4nc(N)sc4c3)C(F)(F)F)cc3c2OC[C@]3(C)C(=O)NCC(C)(C)O)ccc1F] | 662.18 |
| 506 | 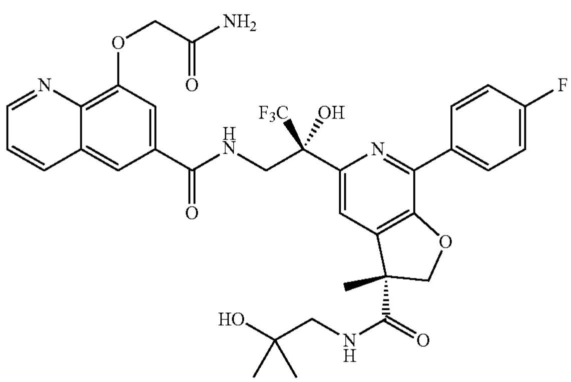 [SMILES: CC(C)(O)CNC(=O)[C@@]1(C)COc2c1cc([C@@](O)(CNC(=O)c1cc(OCC(N)=O)c3ncccc3c1)C(F)(F)F)nc2-c1ccc(F)cc1] | 700.24 |
| 507 | 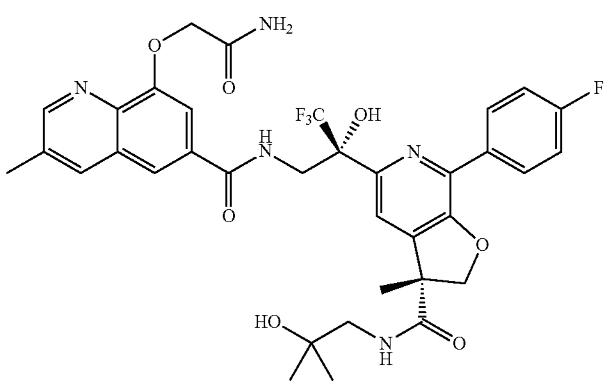 [SMILES: Cc1cnc2c(OCC(N)=O)cc(C(=O)NC[C@](O)(c3cc4c(c(-c5ccc(F)cc5)n3)OC[C@]4(C)C(=O)NCC(C)(C)O)C(F)(F)F)cc2c1] | 714.25 |

Example 508

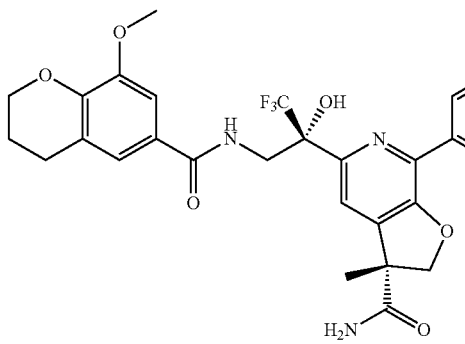

Example 508 Step a

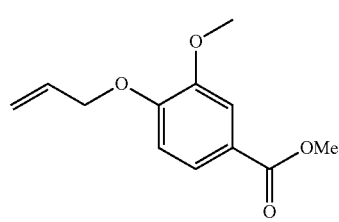 [SMILES: C=CCOc1ccc(C(=O)OC)cc1OC]

A solution of methyl 4-hydroxy-3-methoxybenzoate (2.0 g, 10.98 mmol), allyl bromide (1.58 g, 13.18 mmol) and K$_2$CO$_3$ (3.10 g, 22.50 mmol) in DMF (20 mL), was stirred for 2 hr at 40° C. The resulting mixture was concentrated under vacuum. The crude product was purified by reverse phase chromatography (MeCN/H$_2$O, 0% to 100%, 30 min) to give the desired compound as a yellow oil (2.3 g, 95%). ESI-MS m/z: 223.10 [M+H]$^+$.

Example 508 Step b

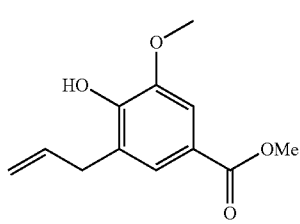 [SMILES: C=CCc1cc(C(=O)OC)cc(OC)c1O]

A solution of the compound from step a (2.3 g, 10.08 mmol) in NMP (10 mL), was stirred for 16 hrs at 200° C. The crude product was purified by reverse phase chromatography (MeCN/H$_2$O, 0% to 100%, 30 min) to give the desired compound as a yellow oil (2.0 g, 87%). ESI-MS m/z: 223.10 [M+H]$^+$.

Example 508 Step c

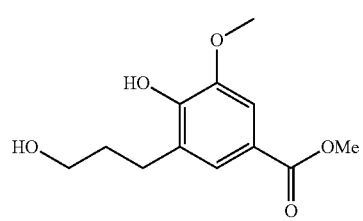 [SMILES: COC(=O)c1cc(CCCO)c(O)c(OC)c1]

To a stirred solution of the compound step b (2.0 g, 9 mmol) in THF (20 mL) were added H$_2$O$_2$ (30%) (2.00 mL) and BH$_3$.THF (1 N) (1.7 mL, 18 mmol) in portions at 0° C. under nitrogen atmosphere and the reaction was stirred for 1 hr. The reaction was quenched by the addition of NaOH (0.02 M) and warmed to room temperature. The resulting mixture was extracted with DCM and the combined organics washed with brine, dried and concentrated. The crude product mixture was used in the next step directly without further purification. ESI-MS m/z: 241.10 [M+H]$^+$.

Example 508 Steps d and e

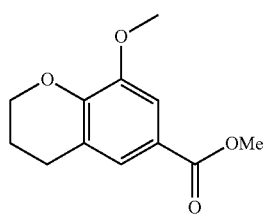 [SMILES: COC(=O)c1cc2c(c(OC)c1)OCCC2]

To a stirred mixture of the compound step c (1.8 g, 7.3 mmol) and PPh$_3$ (2.9 g, 11 mmol) in THF (30 mL) was added DIAD (2.95 g, 15 mmol) in portions at 0° C. The resulting mixture was stirred 16 hr at room temperature. The reaction was quenched with water/ice at 0° C. and extracted with DCM. The combined organic layers were washed with brine, dried and concentrated under reduced pressure. The material was purified by reverse phase column chromatography to afford the desired product as a white solid (1.4 g, 86%). ESI-MS m/z: 223.09 [M+H]$^+$.

The methyl ester was hydrolyzed in a similar manner to Method O, and the material was purified by reverse phase prep-HPLC (MeCN/H$_2$O) to afford the title compound (720 mg, 55%) as a white solid. ESI-MS m/z: 248.25 [M+H]$^+$.

Example 508 Step f

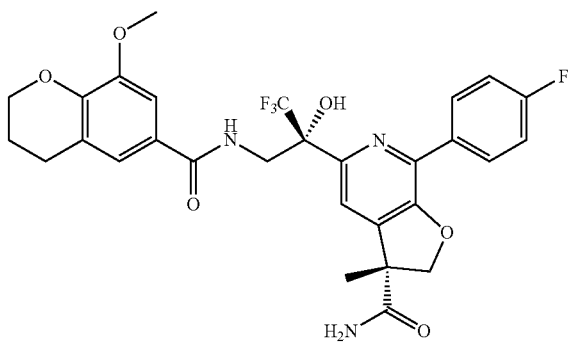 [SMILES: COc1cc(C(=O)NC[C@](O)(c2cc3c(c(-c4ccc(F)cc4)n2)OC[C@]3(C)C(N)=O)C(F)(F)F)cc2c1OCCC2]

The title compound was prepared in an analogous fashion to Method J with amine (30 mg, 0.075 mmol), and the material was purified by prep-HPLC (20-90%, 25 min) to afford the title compound (23.4 mg, 53%). ESI-MS m/z: 590.40 [M+H]$^+$.

Example 509

Example 509 Step a

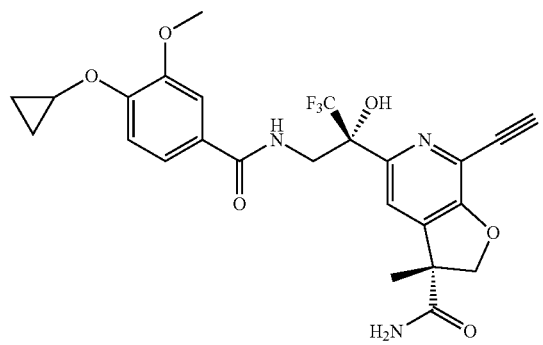 [SMILES: C#Cc1nc([C@@](O)(CNC(=O)c2ccc(OC3CC3)c(OC)c2)C(F)(F)F)cc2c1OC[C@]2(C)C(N)=O]

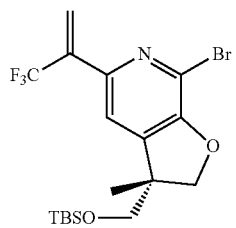 [SMILES: C=C(c1cc2c(c(Br)n1)OC[C@]2(C)CO[Si](C)(C)C(C)(C)C)C(F)(F)F]

This example was prepared in an analogous procedure to Example 205, with the TBS-alcohol precursor used instead. The material was prepared using 3.05 g of (R)-7-bromo-3-(((tert-butyldimethylsilyl)oxy)methyl)-5-iodo-3-methyl-2,3-dihydrofuro[2,3-c]pyridine for the cross-coupling to afford the title compound as a clear, yellow oil. (2.37 g, 83%). ESI-MS m/z: 452.0/454.0 [M+H]$^+$.

Example 509 Step b

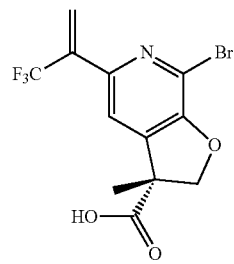 [SMILES: C=C(c1cc2c(c(Br)n1)OC[C@]2(C)C(=O)O)C(F)(F)F]

A solution of step a (4.75 g, 10.50 mmol) in acetone (105 ml) was cooled to 0° C. and treated with Jones reagent (2M in aq H$_2$SO$_4$, 13.12 ml, 26.2 mmol). The reaction was allowed to slowly warm to room temperature and stirred overnight. Upon completion, the reaction was quenched with isopropanol and the majority of acetone was removed by rotary evaporation. The remaining material was taken up in water and extracted with EtOAc. The combined organic extracts were washed with brine, dried, filtered, and concentrated. Purification by flash column chromatography (silica gel) afforded the title compound (3.024 g, 82%) as a sticky syrup. ESI-MS m/z: 351.8/353.8 [M+H]$^+$.

Example 509 Step c

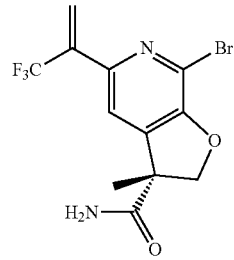 [SMILES: C=C(c1cc2c(c(Br)n1)OC[C@]2(C)C(N)=O)C(F)(F)F]

This example was prepared according to the procedure of Example 97 step b (New route) with step b (3.024 g) and the material was purified by automated column chromatography (silica gel, 0-100% EtOAc) to afford the title compound as a clear yellow oil (2.97 g, 98%). ESI-MS m/z: 352.8 [M+H]$^+$.

Example 509 Step d

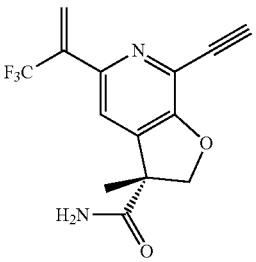 [SMILES: C#Cc1nc(C(=C)C(F)(F)F)cc2c1OC[C@]2(C)C(N)=O]

A 500 mL round-bottom flask charged with step c (2.87 g, 8.17 mmol) was added a magnetic stir-bar, bis(triphenylphosphine)palladium(II) chloride (0.287 g, 0.409 mmol), and copper(I) iodide (0.078 g, 0.409 mmol). The flask was evacuated and backfilled with nitrogen 3 times and dry diisopropylamine (40.9 ml) was added by syringe. The resulting mixture was treated with ethynyltrimethylsilane (2.83 ml, 20.43 mmol) at room temperature. After 6 hr, the reaction was concentrated under reduced pressure.

The resulting crude material was taken up in MeOH (50 mL) and treated with potassium carbonate (1.130 g, 8.17 mmol) at room temperature. The reaction was stirred for 2 hr at room temperature and filtered over a short pad of silica gel and concentrated. Purification by flash column chromatography on silica gel afforded the title compound (1.3 g, 53%) as a light brown foam. ESI-MS m/z: 297.2 [M+H]$^+$.

Example 509 Step e

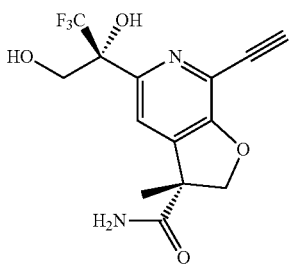 [SMILES: C#Cc1nc([C@@](O)(CO)C(F)(F)F)cc2c1OC[C@]2(C)C(N)=O]

The above compound was prepared according to the procedure in Example 205 step e with step d (1.3 g). The reaction was allowed to go for 53 hr and the crude material was purified by automated column chromatography (silica gel, 0-100% EtOAc) to afford the title compound (0.643 g, 44%). ESI-MS m/z: 331.0 [M+H]$^+$.

Example 509 Step f

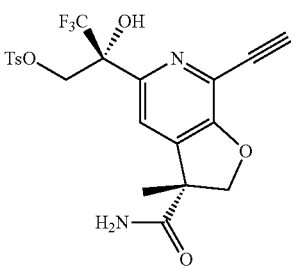 [SMILES: C#Cc1nc([C@@](O)(COS(=O)(=O)c2ccc(C)cc2)C(F)(F)F)cc2c1OC[C@]2(C)C(N)=O]

The above compound was prepared according to the procedure in Example 205 step f with step e (0.643 g). The reaction was allowed to go for 53 hr and the crude material was purified by automated column chromatography (silica gel, 0-100% EtOAc) to afford the title compound (0.712 g, 76%) as a white foam. ESI-MS m/z: 485.1 [M+H]$^+$.

Example 509 Step g

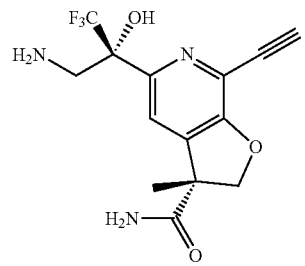 [SMILES: C#Cc1nc([C@@](O)(CN)C(F)(F)F)cc2c1OC[C@]2(C)C(N)=O]

The above compound was prepared according to the procedure in Example 205 step g with step f (0.712 g). The crude material was dissolved in EtOAc and washed with sat. sodium bicarbonate three times to afford the title compound white foam which was used without further purification. ESI-MS m/z: 330.1 [M+H]$^+$.

Example 509 Step h

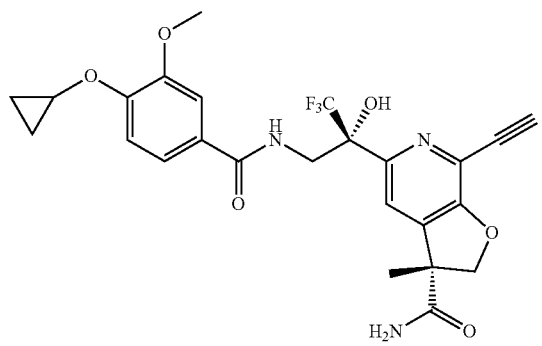 [SMILES: C#Cc1nc([C@@](O)(CNC(=O)c2ccc(OC3CC3)c(OC)c2)C(F)(F)F)cc2c1OC[C@]2(C)C(N)=O]

The Example 509 was prepared according to Method J with step g (0.494 g) and HATU. The crude material was purified by automated column chromatography to afford the title compound as a white solid (0.150 g, 19%) as a white solid. ESI-MS m/z: 520.3 [M+H]$^+$.

Example 510

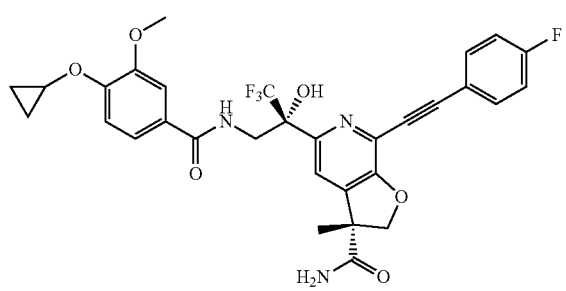 [SMILES: COc1cc(C(=O)NC[C@](O)(c2cc3c(c(C#Cc4ccc(F)cc4)n2)OC[C@]3(C)C(N)=O)C(F)(F)F)ccc1OC1CC1]

401

A 1-dram vial was charged a stir-bar, Example 509 step h (0.025 g, 0.048 mmol), 1-fluoro-4-iodobenzene (0.014 ml, 0.120 mmol), bis(triphenylphosphine)palladium(II) chloride (6.76 mg, 9.63 µmol), and copper(I) iodide (1.833 mg, 9.63 µmol). The vial was purged with nitrogen and 1 mL dry diisopropylamine was added. The yellow suspension was vigorously stirred at room temperature and monitored by LC-MS. The reaction was transferred to a 20 mL scintillation vial with EtOAc and concentrated. The resulting crude material was directly purified by flash column chromatography on silica gel to afford the title compound (20 mg, 67%) as a light-yellow solid. ESI-MS m/z: 614.2 [M+H]$^+$.

Example 511

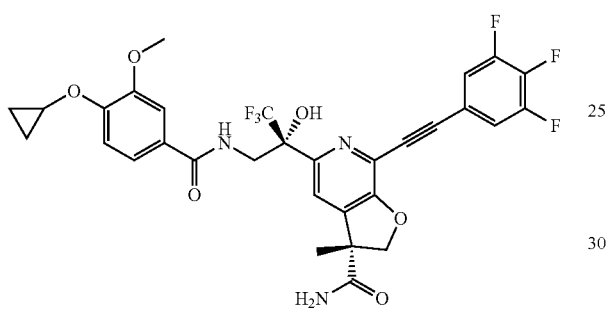

The Example 511 was prepared according to the procedure in Example 510. The crude material was purified by flash column chromatography on silica gel and further purified by prep-HPLC (20-90%, MeCN/Water, 25 min) to afford the title compound (3 mg, 23%) as a white solid. ESI-MS m/z: 650.1 [M+H]$^+$.

Example 512

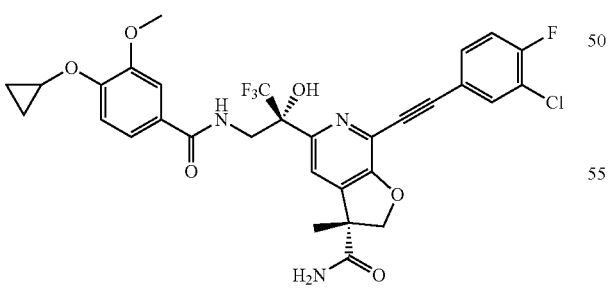

Example 512 was prepared according to the procedure in Example 510. The crude material was purified by flash column chromatography on silica gel and further purified by prep-HPLC (20-90%, MeCN/Water, 25 min) to afford the title compound (3 mg, 10%) as a white solid. ESI-MS m/z: 648.2 [M+H]$^+$.

402

Example 513

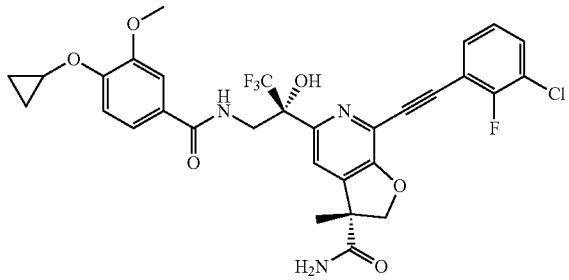 [SMILES: COc1cc(C(=O)NC[C@](O)(c2cc3c(c(C#Cc4cccc(Cl)c4F)n2)OC[C@]3(C)C(N)=O)C(F)(F)F)ccc1OC1CC1]

The Example 513 was prepared according to the procedure in Example 510. The crude material was purified by flash column chromatography on silica gel and further purified by prep-HPLC (20-90%, MeCN/Water, 25 min) to afford the title compound (3 mg, 10%) as a white solid. ESI-MS m/z: 648.2 [M+H]$^+$.

Example 514

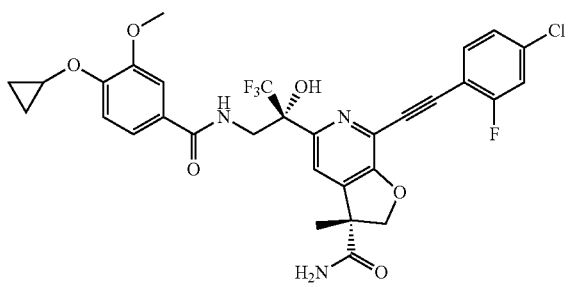 [SMILES: COc1cc(C(=O)NC[C@](O)(c2cc3c(c(C#Cc4ccc(Cl)cc4F)n2)OC[C@]3(C)C(N)=O)C(F)(F)F)ccc1OC1CC1]

The Example 514 was prepared according to the procedure in Example 510. The crude material was purified by flash column chromatography on silica gel and further purified by prep-HPLC (20-90%, MeCN/Water, 25 min) to afford the title compound (3 mg, 10%) as a white solid. ESI-MS m/z: 648.2 [M+H]$^+$.

Example 515

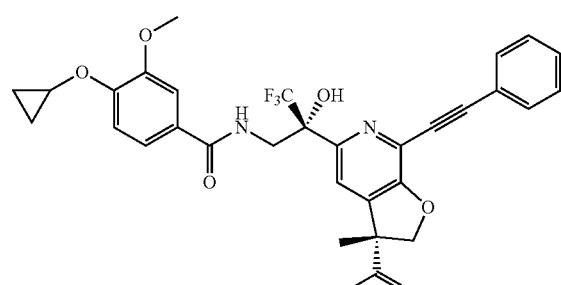

The Example 515 was prepared according to the procedure in Example 510. The crude material was purified by flash column chromatography on silica gel and further purified by prep-HPLC (20-90%, MeCN/Water, 25 min) to afford the title compound (6 mg, 21%) as a white solid. ESI-MS m/z: 596.2 [M+H]$^+$.

Example 516

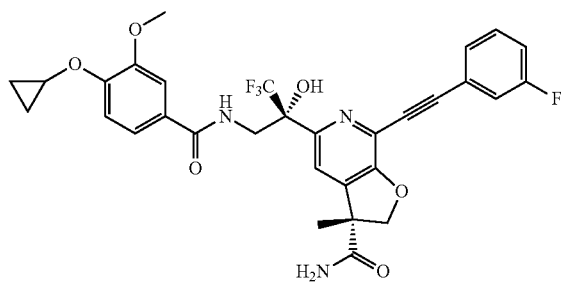 [SMILES: COc1cc(C(=O)NC[C@](O)(c2cc3c(c(C#Cc4cccc(F)c4)n2)OC[C@]3(C)C(N)=O)C(F)(F)F)ccc1OC1CC1]

The Example 516 was prepared according to the procedure in Example 510. The crude material was purified by flash column chromatography on silica gel and further purified by prep-HPLC (20-90%, MeCN/Water, 25 min) to afford the title compound (2 mg, 7%) as a white solid. ESI-MS m/z: 613.5 [M+H]$^+$.

Example 517

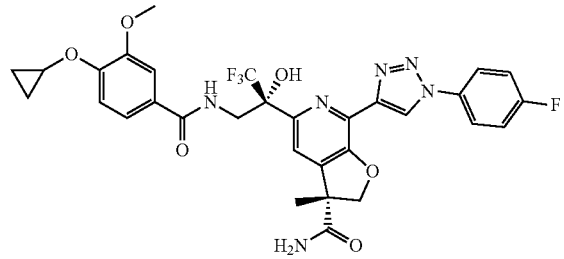 [SMILES: COc1cc(C(=O)NC[C@](O)(c2cc3c(c(-c4cn(-c5ccc(F)cc5)nn4)n2)OC[C@]3(C)C(N)=O)C(F)(F)F)ccc1OC1CC1]

A solution of Example 510 (0.050 g, 0.096 mmol) and 1-azido-4-fluorobenzene (0.193 ml, 0.096 mmol) in t-BuOH-H$_2$O (1:1, 1 mL) was treated with sodium ascorbate (1.907 mg, 9.63 μmol) and copper(II) sulfate (0.154 mg, 0.963 μmol). The reaction was monitored by LC-MS; after 2 h an additional portion of 1-azido-4-fluorobenzene (0.193 ml, 0.096 mmol) was added and the reaction was stirred at room temperature overnight. Organic solvent was removed under reduced pressure and 3 mL DMF was added which provided a slightly more homogeneous reaction mixture. The reaction was then heated to 50° C. for 4 days. The reaction was poured into brine and extracted with EtOAc. The organic extract was dried over anhydrous MgSO$_4$, filtered, and concentrated. The crude residue was purified by prep-HPLC (20-90%, MeCN/Water, 25 min) to afford the title compound (9 mg, 140%) as a white solid. ESI-MS m/z: 657.2 [M+H]$^+$.

The following Table 9 contains examples that were synthesized using the methods previously described (See general methods for starting material synthesis after Table 9). The compounds were either purified by automated column chromatography or Gilson prep-HPLC (20-90%, MeCN/Water, 25 min). The synthesis of Examples 545 and 546 is described after Table 9.

TABLE 9

| Example | Structure | MS$^+$ m/z |
|---|---|---|
| 518 | 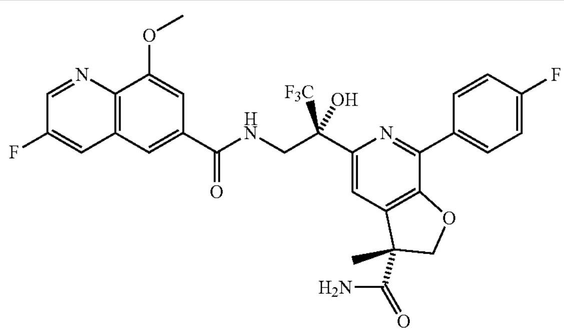 [SMILES: COc1cc(C(=O)NC[C@](O)(c2cc3c(c(-c4ccc(F)cc4)n2)OC[C@]3(C)C(N)=O)C(F)(F)F)cc2cc(F)cnc12] | 603.10 |
| 519 | 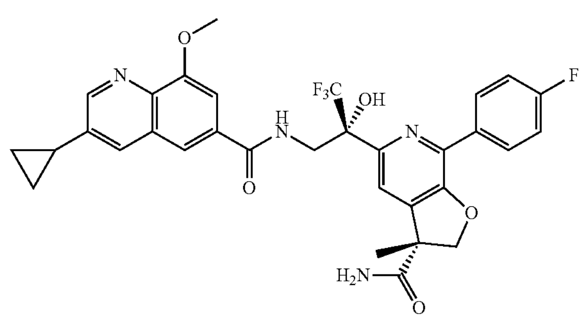 [SMILES: COc1cc(C(=O)NC[C@](O)(c2cc3c(c(-c4ccc(F)cc4)n2)OC[C@]3(C)C(N)=O)C(F)(F)F)cc2cc(C3CC3)cnc12] | 625.30 |

TABLE 9-continued

| Example | Structure | MS+ m/z |
|---|---|---|
| 520 | 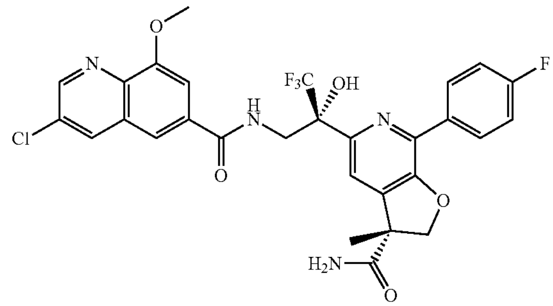 [SMILES: COc1cc(C(=O)NC[C@](O)(c2cc3c(c(-c4ccc(F)cc4)n2)OC[C@]3(C)C(N)=O)C(F)(F)F)cc2cc(Cl)cnc12] | 619.10 |
| 521 | 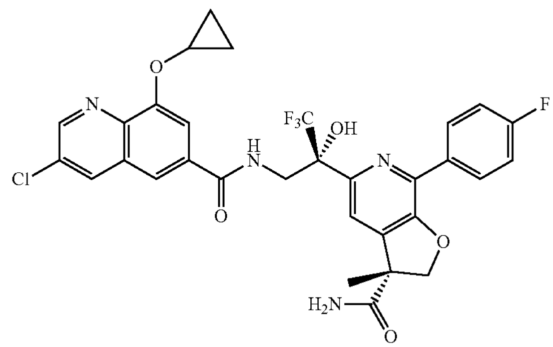 [SMILES: C[C@]1(C(N)=O)COc2c1cc([C@@](O)(CNC(=O)c1cc(OC3CC3)c3ncc(Cl)cc3c1)C(F)(F)F)nc2-c1ccc(F)cc1] | 645.10 |
| 522 | 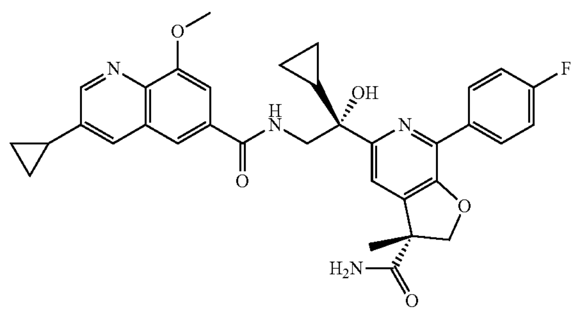 [SMILES: COc1cc(C(=O)NC[C@](O)(c2cc3c(c(-c4ccc(F)cc4)n2)OC[C@]3(C)C(N)=O)C2CC2)cc2cc(C3CC3)cnc12] | 597.35 |
| 523 | 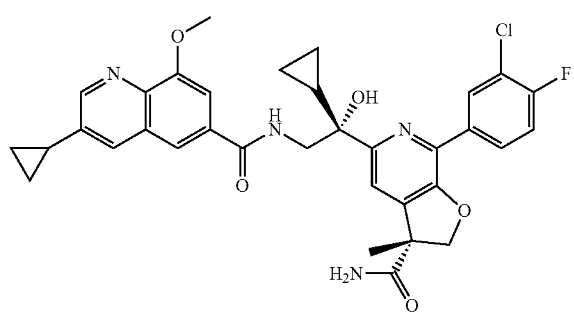 [SMILES: COc1cc(C(=O)NC[C@](O)(c2cc3c(c(-c4ccc(F)c(Cl)c4)n2)OC[C@]3(C)C(N)=O)C2CC2)cc2cc(C3CC3)cnc12] | 631.30 |
| 524 | 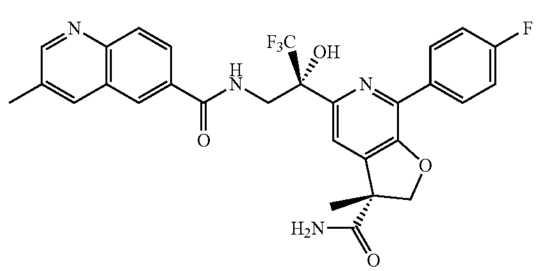 [SMILES: Cc1cnc2ccc(C(=O)NC[C@](O)(c3cc4c(c(-c5ccc(F)cc5)n3)OC[C@]4(C)C(N)=O)C(F)(F)F)cc2c1] | 569.25 |

TABLE 9-continued

| Example | Structure | MS+ m/z |
|---|---|---|
| 525 | 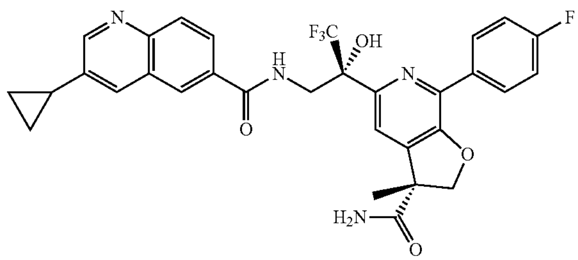 [SMILES: C[C@]1(C(N)=O)COc2c1cc([C@@](O)(CNC(=O)c1ccc3ncc(C4CC4)cc3c1)C(F)(F)F)nc2-c1ccc(F)cc1] | 595.25 |
| 526 | 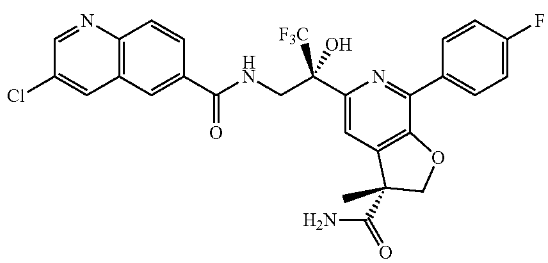 [SMILES: C[C@]1(C(N)=O)COc2c1cc([C@@](O)(CNC(=O)c1ccc3ncc(Cl)cc3c1)C(F)(F)F)nc2-c1ccc(F)cc1] | 589.20 |
| 527 | 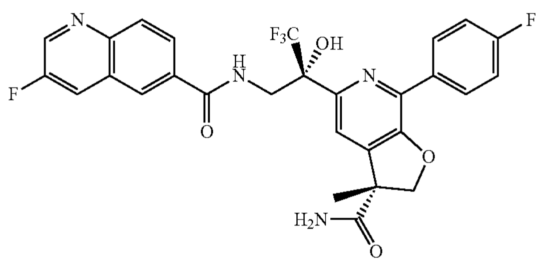 [SMILES: C[C@]1(C(N)=O)COc2c1cc([C@@](O)(CNC(=O)c1ccc3ncc(F)cc3c1)C(F)(F)F)nc2-c1ccc(F)cc1] | 573.10 |
| 528 | 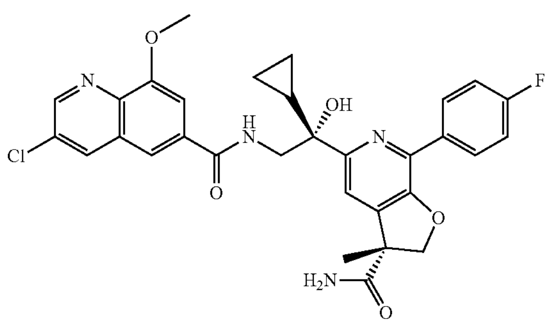 [SMILES: COc1cc(C(=O)NC[C@](O)(c2cc3c(c(-c4ccc(F)cc4)n2)OC[C@]3(C)C(N)=O)C2CC2)cc2cc(Cl)cnc12] | 591.10 |
| 529 | 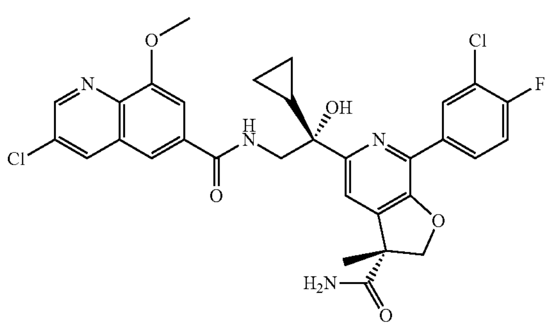 [SMILES: COc1cc(C(=O)NC[C@](O)(c2cc3c(c(-c4ccc(F)c(Cl)c4)n2)OC[C@]3(C)C(N)=O)C2CC2)cc2cc(Cl)cnc12] | 625.10 |

TABLE 9-continued

| Example | Structure | MS+ m/z |
|---------|-----------|---------|
| 530 | 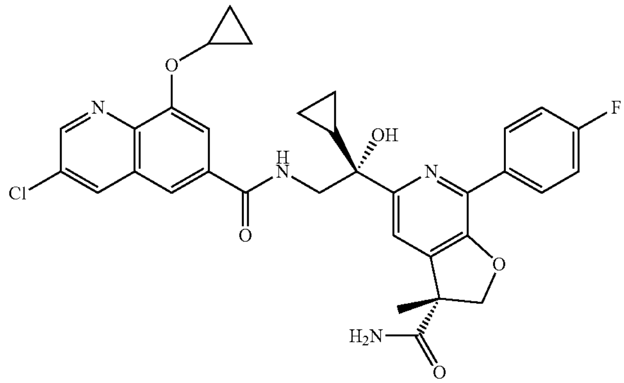 [SMILES: C[C@]1(C(N)=O)COc2c1cc([C@@](O)(CNC(=O)c1cc(OC3CC3)c3ncc(Cl)cc3c1)C1CC1)nc2-c1ccc(F)cc1] | 617.15 |
| 531 | 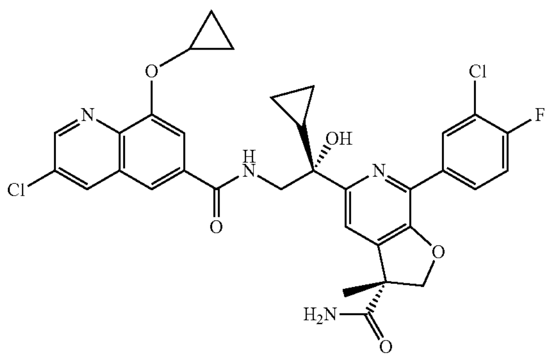 [SMILES: C[C@]1(C(N)=O)COc2c1cc([C@@](O)(CNC(=O)c1cc(OC3CC3)c3ncc(Cl)cc3c1)C1CC1)nc2-c1ccc(F)c(Cl)c1] | 651.15 |
| 532 | 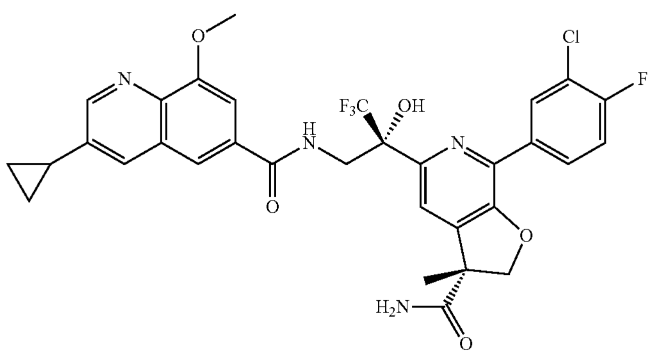 [SMILES: COc1cc(C(=O)NC[C@](O)(c2cc3c(c(-c4ccc(F)c(Cl)c4)n2)OC[C@]3(C)C(N)=O)C(F)(F)F)cc2cc(C3CC3)cnc12] | 659.05 |
| 533 | 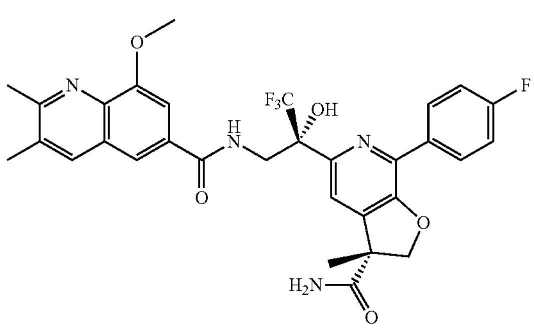 [SMILES: COc1cc(C(=O)NC[C@](O)(c2cc3c(c(-c4ccc(F)cc4)n2)OC[C@]3(C)C(N)=O)C(F)(F)F)cc2cc(C)c(C)nc12] | 613.15 |

TABLE 9-continued

| Example | Structure | MS+ m/z |
| --- | --- | --- |
| 534 | 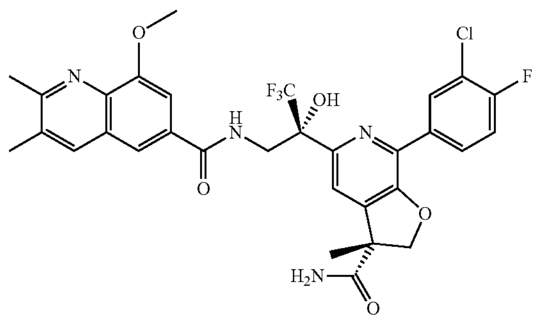 | 647.10 |
| 535 | 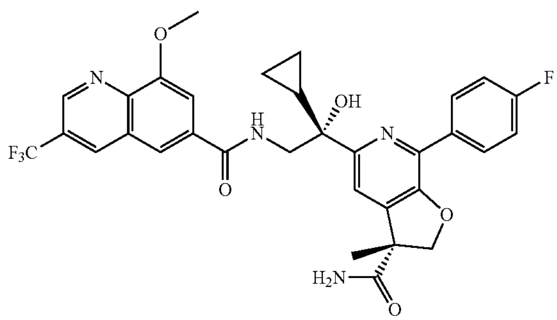 [SMILES: COc1cc(C(=O)NC[C@](O)(c2cc3c(c(-c4ccc(F)cc4)n2)OC[C@]3(C)C(N)=O)C2CC2)cc2cc(C(F)(F)F)cnc12] | 625.10 |
| 536 | 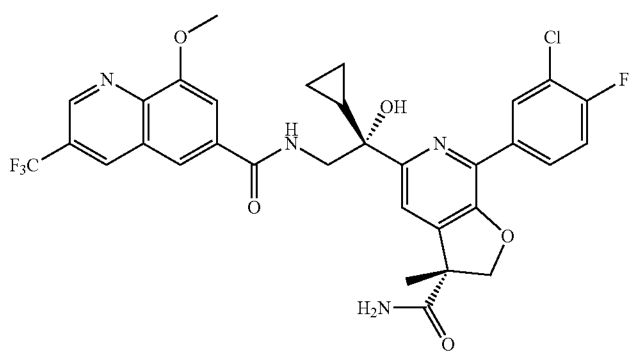 [SMILES: COc1cc(C(=O)NC[C@](O)(c2cc3c(c(-c4ccc(F)c(Cl)c4)n2)OC[C@]3(C)C(N)=O)C2CC2)cc2cc(C(F)(F)F)cnc12] | 659.05 |
| 537 | 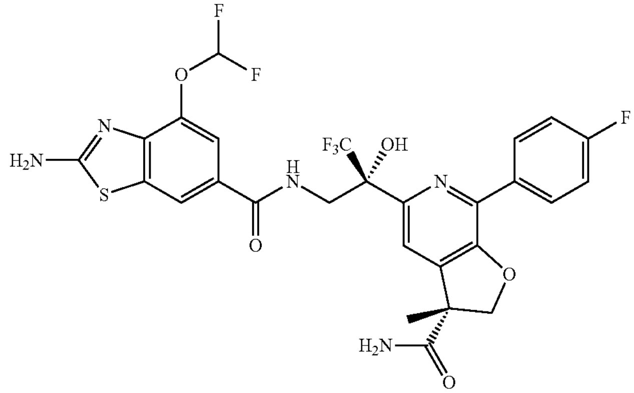 [SMILES: C[C@]1(C(N)=O)COc2c1cc([C@@](O)(CNC(=O)c1cc(OC(F)F)c3nc(N)sc3c1)C(F)(F)F)nc2-c1ccc(F)cc1] | 642.05 |

TABLE 9-continued
| Example | Structure | MS+ m/z |
|---|---|---|
| 538 | 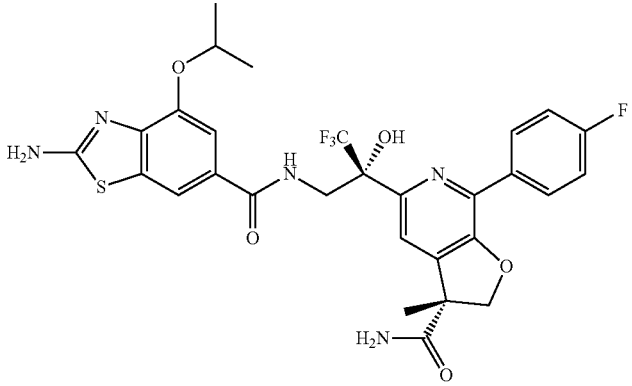 [SMILES: CC(C)Oc1cc(C(=O)NC[C@](O)(c2cc3c(c(-c4ccc(F)cc4)n2)OC[C@]3(C)C(N)=O)C(F)(F)F)cc2sc(N)nc12] | 634.10 |
| 539 | 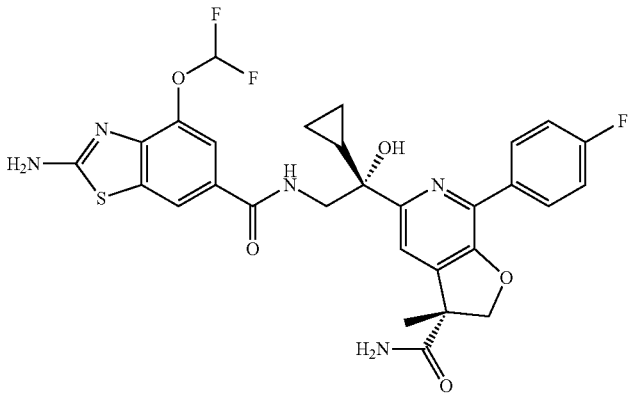 [SMILES: C[C@]1(C(N)=O)COc2c1cc([C@@](O)(CNC(=O)c1cc(OC(F)F)c3nc(N)sc3c1)C1CC1)nc2-c1ccc(F)cc1] | 614.05 |
| 540 | 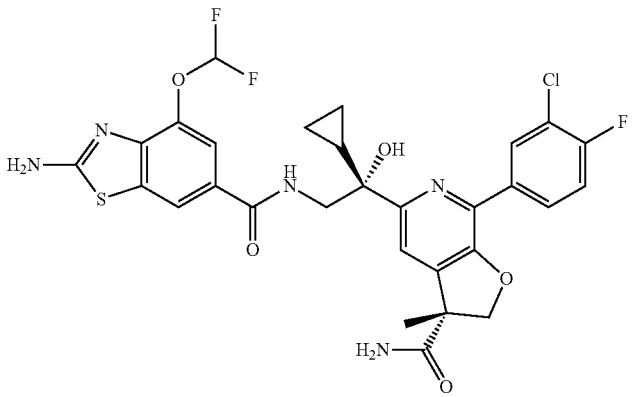 [SMILES: C[C@]1(C(N)=O)COc2c1cc([C@@](O)(CNC(=O)c1cc(OC(F)F)c3nc(N)sc3c1)C1CC1)nc2-c1ccc(F)c(Cl)c1] | 648.05 |
| 541 | 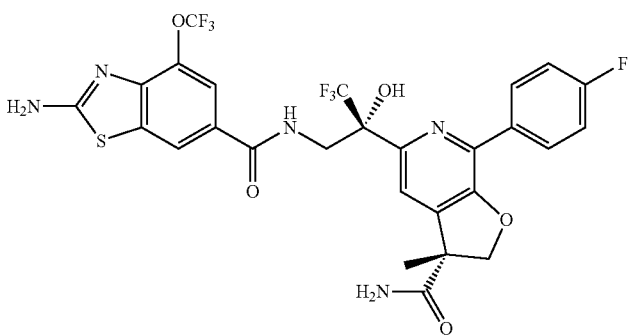 [SMILES: C[C@]1(C(N)=O)COc2c1cc([C@@](O)(CNC(=O)c1cc(OC(F)(F)F)c3nc(N)sc3c1)C(F)(F)F)nc2-c1ccc(F)cc1] | 660.05 |

TABLE 9-continued

| Example | Structure | MS+ m/z |
|---|---|---|
| 542 | 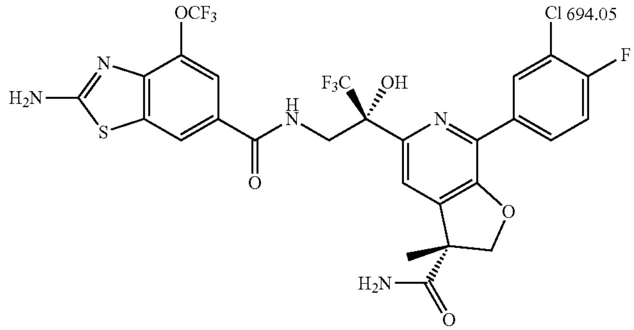 | Cl 694.05 |
| 543 | 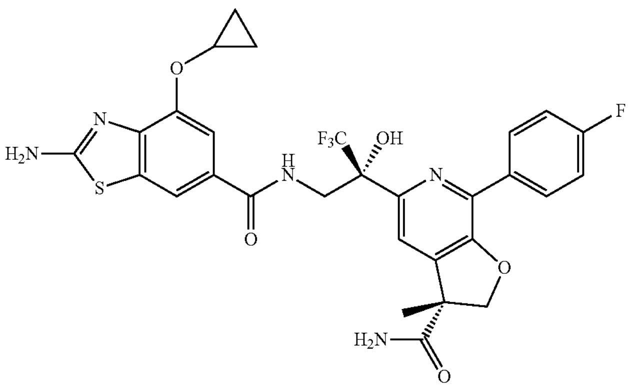 [SMILES: C[C@]1(C(N)=O)COc2c1cc([C@@](O)(CNC(=O)c1cc(OC3CC3)c3nc(N)sc3c1)C(F)(F)F)nc2-c1ccc(F)cc1] | 632.10 |
| 544 | 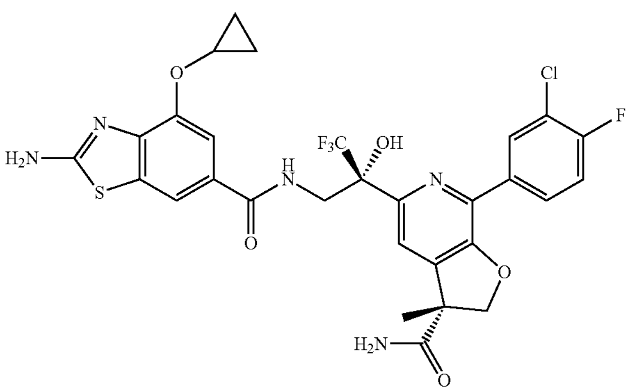 [SMILES: C[C@]1(C(N)=O)COc2c1cc([C@@](O)(CNC(=O)c1cc(OC3CC3)c3nc(N)sc3c1)C(F)(F)F)nc2-c1ccc(F)c(Cl)c1] | 666.10 |
| 545 | 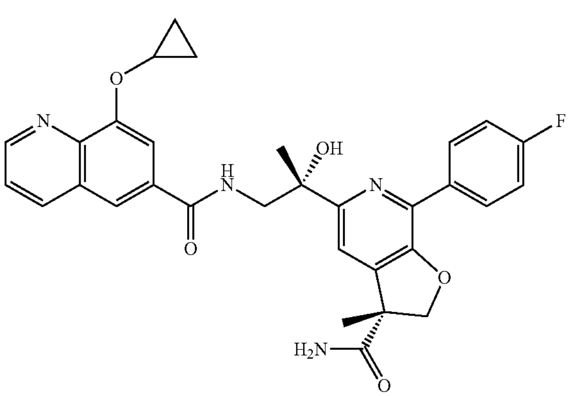 [SMILES: C[C@](O)(CNC(=O)c1cc(OC2CC2)c2ncccc2c1)c1cc2c(c(-c3ccc(F)cc3)n1)OC[C@]2(C)C(N)=O] | 559.30 |

TABLE 9-continued

| Example | Structure | MS+ m/z |
|---|---|---|
| 546 | 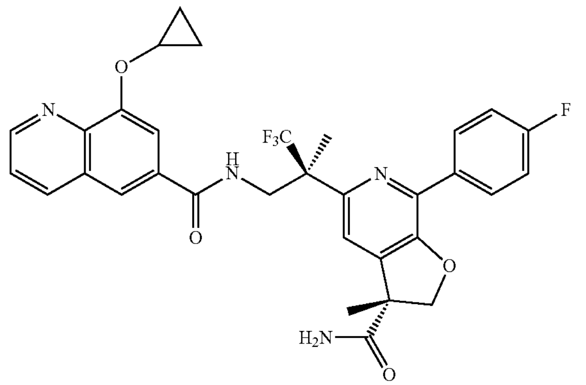 | 559.15 |
| 547 | 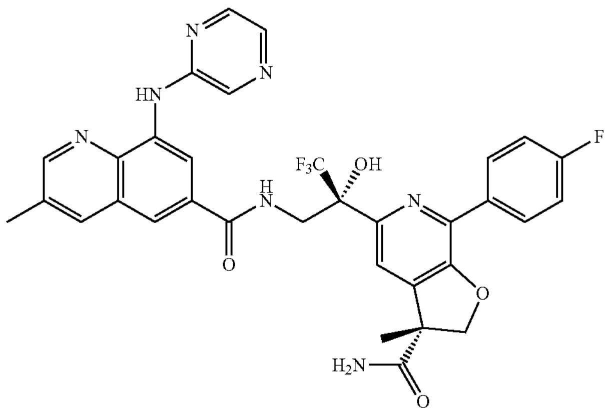 [SMILES: Cc1cnc2c(Nc3cnccn3)cc(C(=O)NC[C@](O)(c3cc4c(c(-c5ccc(F)cc5)n3)OC[C@]4(C)C(N)=O)C(F)(F)F)cc2c1] | 662.15 |
| 548 | 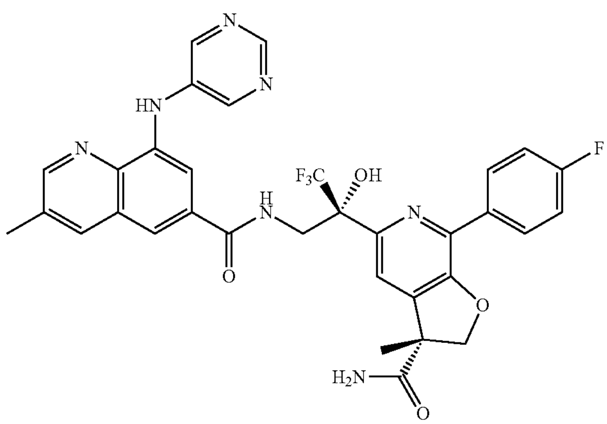 [SMILES: Cc1cnc2c(Nc3cncnc3)cc(C(=O)NC[C@](O)(c3cc4c(c(-c5ccc(F)cc5)n3)OC[C@]4(C)C(N)=O)C(F)(F)F)cc2c1] | 662.15 |
| 549 | 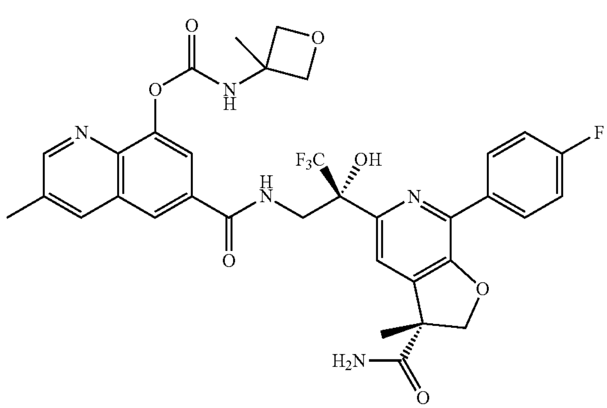 [SMILES: Cc1cnc2c(OC(=O)NC3(C)COC3)cc(C(=O)NC[C@](O)(c3cc4c(c(-c5ccc(F)cc5)n3)OC[C@]4(C)C(N)=O)C(F)(F)F)cc2c1] | 697.30 |

TABLE 9-continued
| Example | Structure | MS⁺ m/z |
|---|---|---|
| 550 | 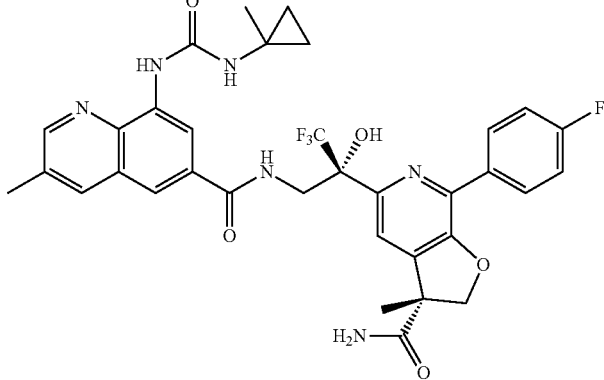 | 681.15 |
| 551 | 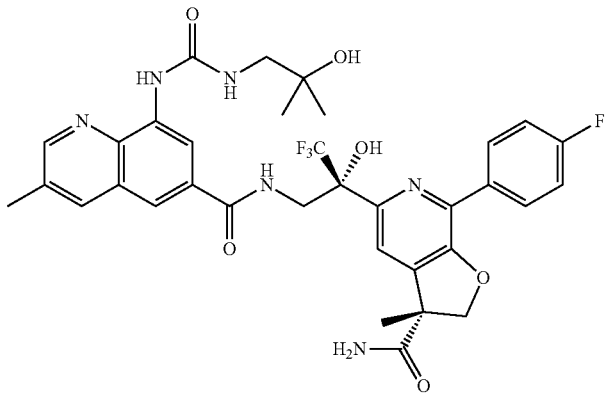 [SMILES: Cc1cnc2c(NC(=O)NCC(C)(C)O)cc(C(=O)NC[C@](O)(c3cc4c(c(-c5ccc(F)cc5)n3)OC[C@]4(C)C(N)=O)C(F)(F)F)cc2c1] | 699.15 |
| 552 | 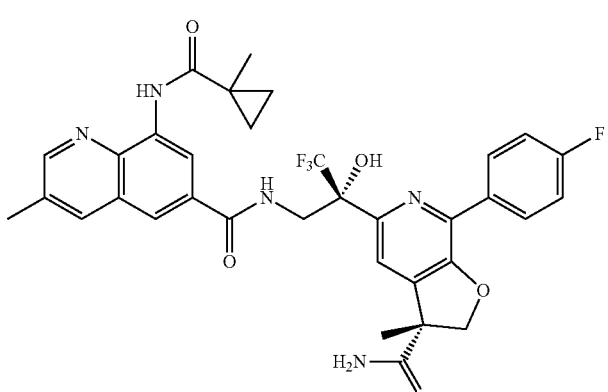 | 666.15 |
| 553 | 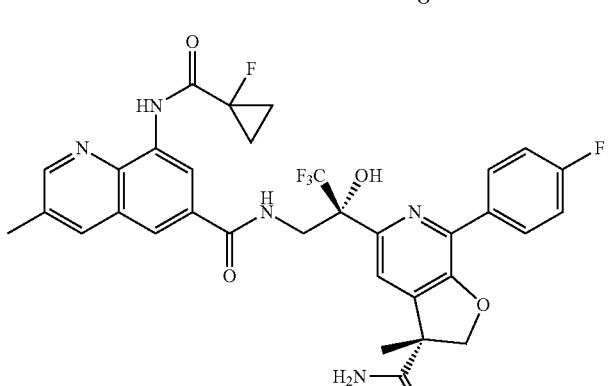 | 670.15 |

TABLE 9-continued
| Example | Structure | MS+ m/z |
|---------|-----------|---------|
| 554 | 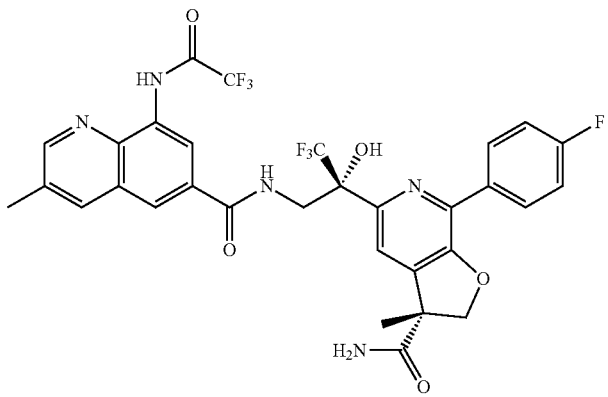 [SMILES: Cc1cnc2c(NC(=O)C(F)(F)F)cc(C(=O)NC[C@](O)(c3cc4c(c(-c5ccc(F)cc5)n3)OC[C@]4(C)C(N)=O)C(F)(F)F)cc2c1] | 680.10 |
| 555 | 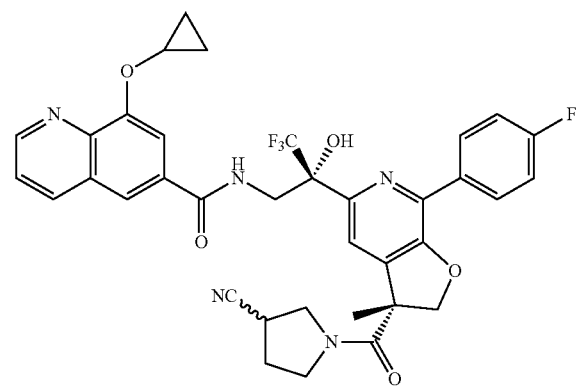 [SMILES: C[C@]1(C(=O)N2CCC(C#N)C2)COc2c1cc([C@@](O)(CNC(=O)c1cc(OC3CC3)c3ncccc3c1)C(F)(F)F)nc2-c1ccc(F)cc1] | 690.25 |
| 556 | 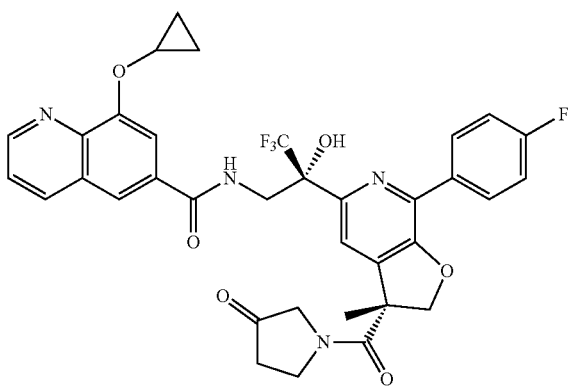 [SMILES: C[C@]1(C(=O)N2CCC(=O)C2)COc2c1cc([C@@](O)(CNC(=O)c1cc(OC3CC3)c3ncccc3c1)C(F)(F)F)nc2-c1ccc(F)cc1] | 679.23 |
| 557 | 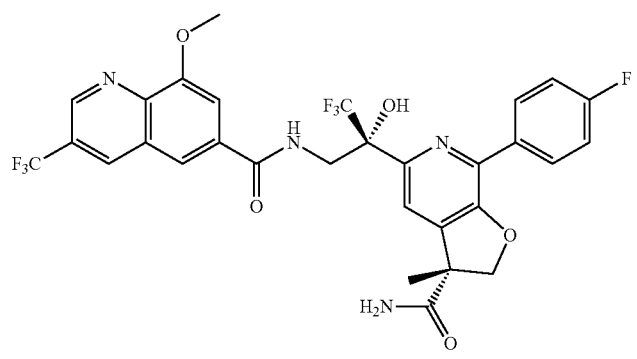 [SMILES: COc1cc(C(=O)NC[C@](O)(c2cc3c(c(-c4ccc(F)cc4)n2)OC[C@]3(C)C(N)=O)C(F)(F)F)cc2cc(C(F)(F)F)cnc12] | 653.05 |

TABLE 9-continued

| Example | Structure | MS+ m/z |
|---|---|---|
| 558 | 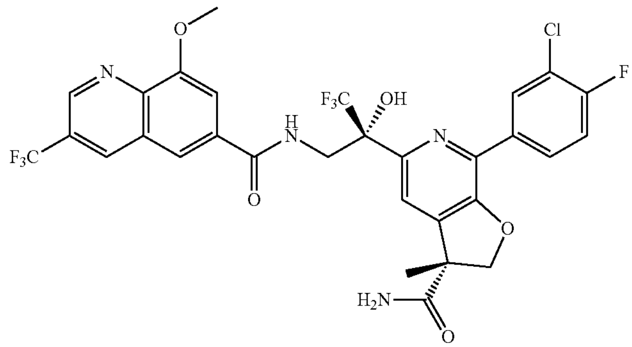 [SMILES: COc1cc(C(=O)NC[C@](O)(c2cc3c(c(-c4ccc(F)c(Cl)c4)n2)OC[C@]3(C)C(N)=O)C(F)(F)F)cc2cc(C(F)(F)F)cnc12] | 687.00 |
| 559 | 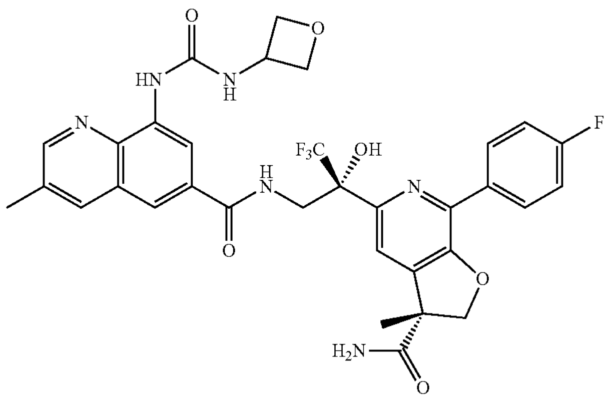 [SMILES: Cc1cnc2c(NC(=O)NC3COC3)cc(C(=O)NC[C@](O)(c3cc4c(c(-c5ccc(F)cc5)n3)OC[C@]4(C)C(N)=O)C(F)(F)F)cc2c1] | 683.15 |
| 560 | 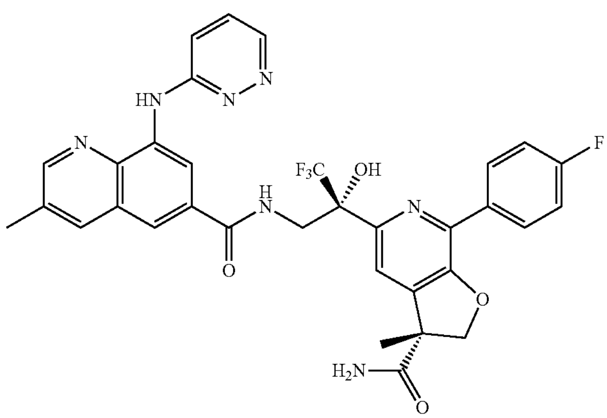 [SMILES: Cc1cnc2c(Nc3cccnn3)cc(C(=O)NC[C@](O)(c3cc4c(c(-c5ccc(F)cc5)n3)OC[C@]4(C)C(N)=O)C(F)(F)F)cc2c1] | 662.05 |
| 561 | 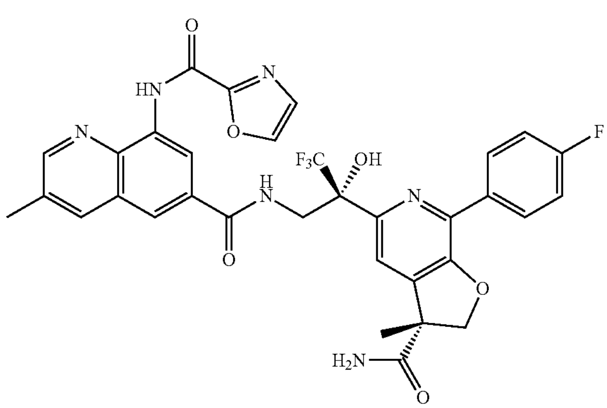 [SMILES: Cc1cnc2c(NC(=O)c3ncco3)cc(C(=O)NC[C@](O)(c3cc4c(c(-c5ccc(F)cc5)n3)OC[C@]4(C)C(N)=O)C(F)(F)F)cc2c1] | 679.10 |

TABLE 9-continued

| Example | Structure | MS⁺ m/z |
|---|---|---|
| 562 | 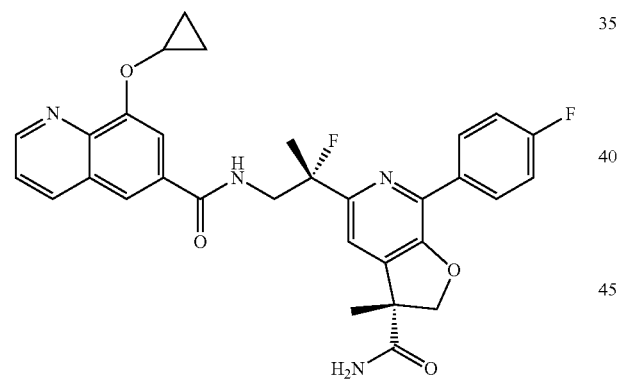 | 605.20 |
| 563 | 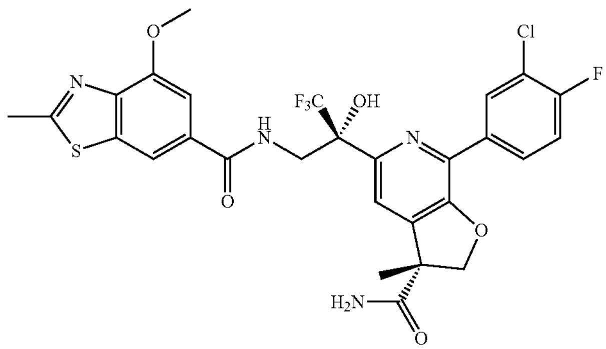 [SMILES: COc1cc(C(=O)NC[C@](O)(c2cc3c(c(-c4ccc(F)cc4)n2)OC[C@]3(C)C(N)=O)C(F)(F)F)cc2sc(C)nc12] | 653.05 |

Example 545 (in Table)

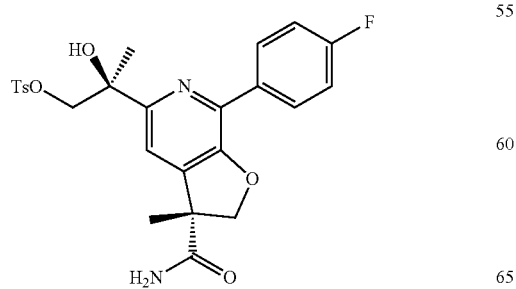

Example 545 Step a

The title compound was prepared in an analogous sequence to Example 205. The residue was concentrated under reduced pressure to afford the crude product as a brown solid. ESI-MS m/z: 501.15 [M+H]⁺.

Example 545 Step b

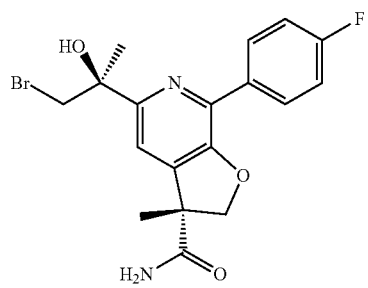 [SMILES: C[C@@](O)(CBr)c1cc2c(c(-c3ccc(F)cc3)n1)OC[C@]2(C)C(N)=O]

A mixture of the compound from step a (1.30 g, 2.59 mmol) and LiBr (676 mg) in acetone (50 mL) was stirred for 3 days at 60° C. The resulting mixture was concentrated under reduced pressure. The residue was purified by reverse flash chromatography to afford the desired product (630 mg, 59%) as a brown solid. ESI-MS m/z: 409.00 [M+H]⁺.

Example 545 Step c

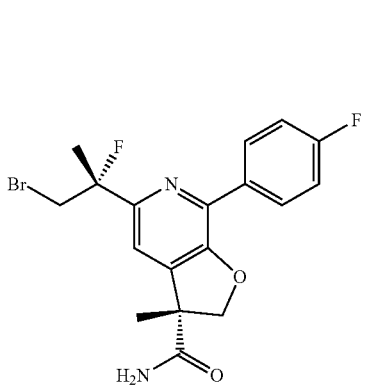 [SMILES: C[C@](F)(CBr)c1cc2c(c(-c3ccc(F)cc3)n1)OC[C@]2(C)C(N)=O]

Into a 100 mL round-bottom flask were added the compound from step b (620 mg, 1.51 mmol) and DCM (15 mL) at room temperature. The mixture was cooled to 0° C., DAST (488 mg, 3.03 mmol) was added and the reaction stirred for 30 min at the same temperature. The reaction was allowed to stirred for 5 min at room temperature and quenched with a cold aq. NaHCO₃ solution. The aqueous layer was extracted with CH₂Cl₂, dried over anhydrous Na₂SO₄. After filtration, the filtrate was concentrated under reduced pressure. The residue was purified by prep-TLC (EtOAc/hexanes, 1:1) to afford the crude product as a yellow solid. ESI-MS m/z: 411.10 [M+H]⁺.

Example 545 Step d

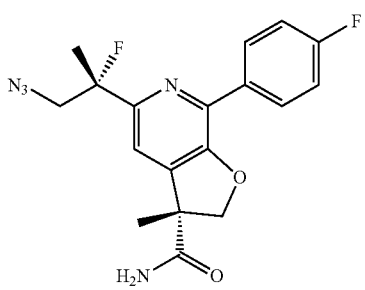 [SMILES: C[C@](F)(CN=[N+]=[N-])c1cc2c(c(-c3ccc(F)cc3)n1)OC[C@]2(C)C(N)=O]

A mixture of the compound from step c (545 mg, 1.32 mmol), NaN₃ (1.39 g, 21.38 mmol) and TBAI (244 mg, 0.66 mmol) in DMSO (25 mL) was stirred for 4 h at 100° C. The mixture was allowed to cool down to room temperature, poured into water and extracted with EtOAc. The combined organic layers were washed with brine, dried over anhydrous Na₂SO₄. After filtration, the filtrate was concentrated under reduced pressure. The residue was purified by reverse flash chromatography to afford the crude product (370 mg) as a yellow solid. ESI-MS m/z: 374.15 [M+H]⁺.

Example 545 Step e

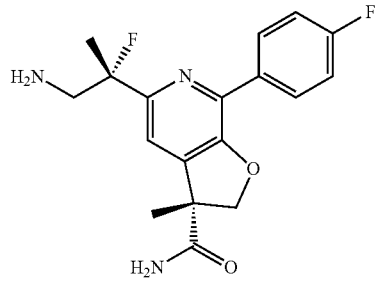 [SMILES: C[C@](F)(CN)c1cc2c(c(-c3ccc(F)cc3)n1)OC[C@]2(C)C(N)=O]

A mixture of the compound from step d (370 mg, 0.99 mmol), PPh₃ (2.60 g, 9.91 mmol), THF (20 mL) and H₂O (2 mL) was stirred for 1 h at 70° C. under nitrogen atmosphere. The mixture was purified by prep-TLC (CH₂Cl₂/7 N NH₃ in MeOH, 15:1) to afford the desired product (200 mg, 58%) as a white solid. ESI-MS m/z: 348.15 [M+H]⁺.

Example 545 Step f

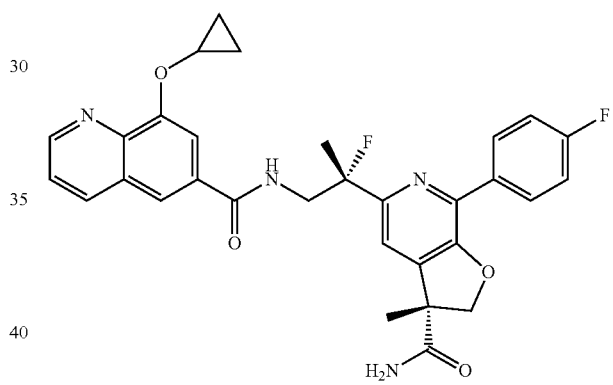

The title compound was synthesized according to Method J. The mixture was purified by prep-HPLC to afford the desired product (32.5 mg, 80%) as a white solid. ESI-MS m/z: 559.30 [M+H]⁺.

Example 564

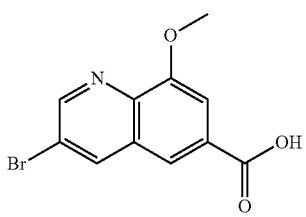

The title compound was prepared in a similar fashion to Example 210 with 2-bromoacrolein. 2-bromoacrolein was prepared according to the literature (di-bromination of acrolein followed by TEA promoted elimination). The crude compound was purified by reverse flash chromatography with C18 silica gel (MeOH/H$_2$O) to afford the title compound as a red solid (240 mg, 14%). ESI-MS m/z: 282.10 [M+H]$^+$.

Example 565 Step a

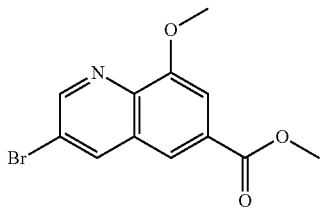 [SMILES: COC(=O)c1cc(OC)c2ncc(Br)cc2c1]

A solution of Example 564 (1.30 g, 4.61 mmol) in H$_2$SO$_4$ (2 mL) and MeOH (20 mL) was stirred for 2 hr at 80° C. The resulting mixture was diluted with water and was extracted with EtOAc. The combined organic layers were dried over anhydrous Na$_2$SO$_4$, filtered, and the filtrate was concentrated under reduced pressure to afford desired product (1.2 g, 88%) as a brown solid. ESI-MS m/z: 296.05 [M+H]$^+$.

Example 565 Step b

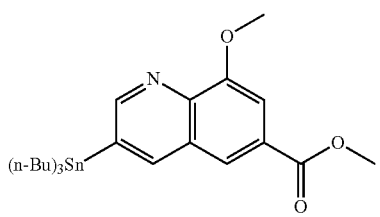

A solution of the compound from step a (1.00 g, 3.38 mmol), Pd(PPh$_3$)$_4$ (585 mg, 0.51 mmol) and Sn$_2$(nBu)$_6$ (3.92 g, 6.76 mmol) in dioxane (20.00 mL) was stirred for 8 hr at 100° C. under nitrogen atmosphere. The resulting mixture was concentrated under vacuum. The residue was purified by silica gel column chromatography (eluted with 20% ethyl acetate in hexanes) to afford desired product (910 mg, 53%) as a yellow solid. ESI-MS m/z: 508.15 [M+H]$^+$.

Example 565 Steps c and d

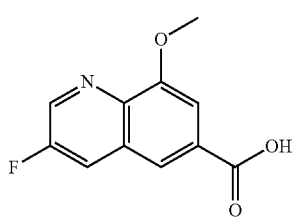 [SMILES: COc1cc(C(=O)O)cc2cc(F)cnc12]

A solution of the compound from step b (850 mg, 1.68 mmol), Ag$_2$O (155 mg, 0.67 mmol), F-TEDA-BF$_4$ (892 mg, 2.52 mmol), MeOH (269 mg, 8.40 mmol) and NaHCO$_3$ (282 mg, 3.36 mmol) in acetone (20 mL) was stirred for 48 h at 65° C. under nitrogen atmosphere. The resulting mixture was concentrated under vacuum. The residue was purified by silica gel column chromatography (eluted with 50% ethyl acetate in hexanes) to afford desired product (110 mg, 28%) as a yellow solid. ESI-MS m/z: 236.06 [M+H]$^+$.

The ester hydrolysis was carried out in a similar manner to Method T (step d) to afford the desired acid product. ESI-MS m/z: 222.05 [M+H]$^+$.

Example 566 Steps a and b

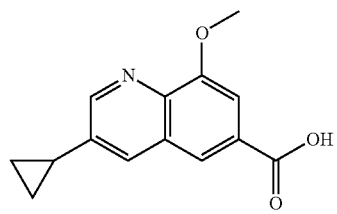 [SMILES: COc1cc(C(=O)O)cc2cc(C3CC3)cnc12]

A solution of Example 565 step a (300 mg, 1.01 mmol), cyclopropylboronic acid (261 mg, 3.04 mmol), PCy$_3$ (284 mg, 1.01 mmol), tricyclohexylphosphine (9 mg, 0.03 mmol) and K$_3$PO$_4$ (645 mg, 3.04 mmol) in Toluene/H$_2$O (6 mL, 5:1) was stirred for 2 hours at 100° C. under nitrogen atmosphere. The resulting solution was diluted with water, extracted with EtOAc, and the organic layer dried and concentrated. The resulting solution was purified by reverse phase C18 column chromatography (CH$_3$CN/H$_2$O) to afford desired product as a yellow solid. ESI-MS m/z: 258.00 [M+H]$^+$.

The ester hydrolysis was carried out in a similar manner to Method T (step d). The resulting solution was purified by reverse phase C18 column chromatography (MeOH/0.1% FA in H$_2$O) to afford desired product (120 mg) as a light yellow solid. ESI-MS m/z: 244.05 [M+H]$^+$.

Example 567

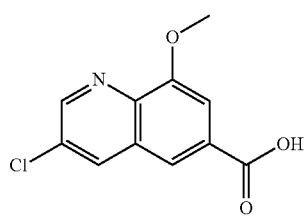 [SMILES: COc1cc(C(=O)O)cc2cc(Cl)cnc12]

The title compound was prepared in a similar fashion to Example 210 with 2-chloroacrolein. 2-chloroacrolein was prepared according to the literature (Eur. J. Org. Chem. 2018, 45, 6256) in two steps from 2,3-dichloropropene. The resulting solution was purified by reverse phase C18 column chromatography (CH$_3$CN/H$_2$O) to afford desired product (300 mg, 23%) as a yellow solid. ESI-MS m/z: 238.15 [M+H]$^+$.

Example 568

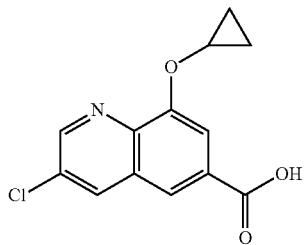 [SMILES: O=C(O)c1cc(OC2CC2)c2ncc(Cl)cc2c1]

The title compound was prepared in a similar fashion to Example 567 to afford the desired product (350 mg, 27%) as a white solid. ESI-MS m/z: 264.00 [M+H]$^+$.

Example 569 Steps a and b

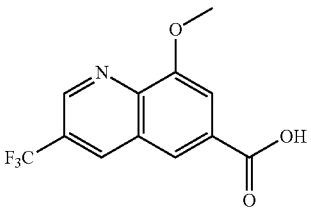 [SMILES: COc1cc(C(=O)O)cc2cc(C(F)(F)F)cnc12]

A solution of methyl 3-iodo-8-methoxyquinoline-6-carboxylate (400 mg, 1.16 mmol), CuI (444 mg, 2.33 mmol), KF (135 mg, 2.33 mmol), and methyl 2,2-difluoro-2-sulfoacetate (1.1 g, 5.83 mmol) in NMP (3 mL) was stirred for 4 hours at 120° C. under nitrogen atmosphere. The resulting solution was diluted with water, extracted with EtOAc and the organic layer was dried and concentrated. The resulting solution was purified by reverse phase C18 column chromatography (CH$_3$CN/H$_2$O) to afford desired product (200 mg, 60%) as a light yellow solid. ESI-MS m/z: 286.00 [M+H]$^+$.

The ester hydrolysis was carried out in a similar manner to Method T (step d). The resulting solution was purified by reverse phase C18 column chromatography (CH$_3$CN/H$_2$O) to afford desired product (120 mg crude) as a light yellow solid. ESI-MS m/z: 271.95 [M+H]$^+$.

Example 570

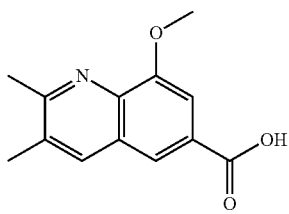 [SMILES: COc1cc(C(=O)O)cc2cc(C)c(C)nc12]

The title compound was prepared in a similar fashion to Example 210 and Method P with 2-methyl-2-butenal (commercially available). ESI-MS m/z: 232.10 [M+H]$^+$.

Example 571

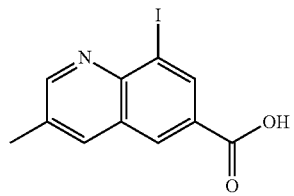

The title compound was prepared in a similar fashion to Example 210 and Method P with methacrolein and methyl 4-amino-3-iodobenzoate. The crude product was re-crystallized from EA/H$_2$O to afford the desired product (7 g, 62%) as a yellow solid. ESI-MS m/z: 313.85 [M+H]$^+$.

Example 572 Step a

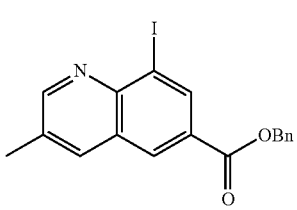 [SMILES: Cc1cnc2c(I)cc(C(=O)OCc3ccccc3)cc2c1]

A solution of the crude from Example 571 above, benzyl bromide (6.56 g, 38.35 mmol) and DIEA (0.50 mg, 2.87 mmol) in DMSO (20 mL) was stirred for 6 hours at room temperature. The residue was purified by silica gel column chromatography (ethyl acetate in hexanes) to afford the desired product (20 g) as a yellow solid. ESI-MS m/z: 404.00 [M+H]$^+$.

Example 572 Steps b and c

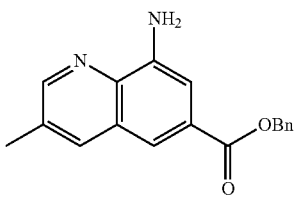 [SMILES: Cc1cnc2c(N)cc(C(=O)OCc3ccccc3)cc2c1]

A solution of compound from step a (9 g, 22.32 mmol), BocNH$_2$ (3.66 g, 31.24 mmol), Pd(OAc)$_2$ (100 mg, 0.45 mmol), BINAP (417 mg, 0.67 mmol) and Cs$_2$CO$_3$ (10 g, 31.24 mmol) in toluene was stirred for 2 hours at 100° C. under N$_2$ atmosphere. The crude product was purified by reverse phase flash to afford the desired product (6 g, 68%) as a yellow solid. ESI-MS m/z: 393.05 [M+H]$^+$.

A solution of compound from step b (8 g, 20.39 mmol,) in HCl (8 mL) and EtOAc (50 mL) was stirred for 2 hours at room temperature. The residue was purified by silica gel column chromatography to afford the desired product (3 g, 50%) as a yellow solid. ESI-MS m/z: 293.05 [M+H]$^+$.

Example 573

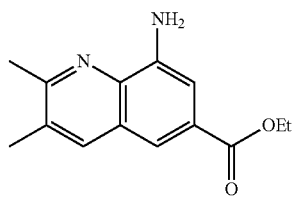 [SMILES: CCOC(=O)c1cc(N)c2nc(C)c(C)cc2c1]

The title compound was prepared in a similar fashion to Examples 571 and 572. The residue was purified by reverse flash chromatography (10-50% MeOH/H₂O) to afford the desired product as off-white solid (1.62 g, 67%). ESI-MS m/z: 245.12 [M+H]⁺.

Example 574

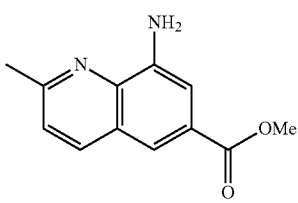 [SMILES: COC(=O)c1cc(N)c2nc(C)ccc2c1]

The title compound was prepared in a similar fashion to Examples 571 and 572. The crude product was purified by reverse phase flash chromatography to afford the desired product (1.2 g) as a yellow solid. ESI-MS m/z: 217.05 [M+H]⁺.

Example 575 Step a

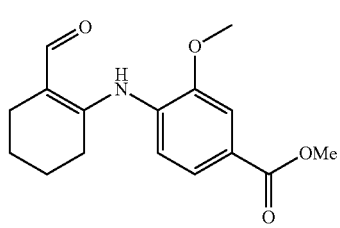 [SMILES: COC(=O)c1ccc(NC2=C(C=O)CCCC2)c(OC)c1]

A solution of methyl 4-amino-3-methoxybenzoate (2.00 g, 11.1 mmol) and 2-chlorocyclohex-1-enecarbaldehyde (4.32 g, 0.1 mmol) in toluene were added BINAP (1.37 g, 2.2 mmol), Pd(OAc)₂ (495 mg, 2.2 mmol) and Cs₂CO₃ (10.79 g, 33.1 mmol) dropwise at 90° C. under nitrogen atmosphere for 3 hrs. The resulting solution was extracted with EtOAc, the organic layer was dried and concentrated. The crude product was purified by silica gel column chromatography (ethyl acetate in hexanes) to afford the desired product (2.6 g, 86%). ESI-MS m/z: 290.05 [M+H]⁺.

Example 575 Steps b and c

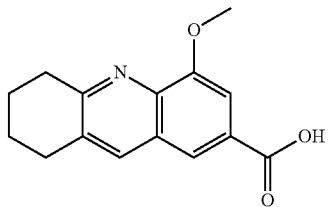 [SMILES: COc1cc(C(=O)O)cc2cc3c(nc12)CCCC3]

A solution of step a (2.6 g, 8.9 mmol) in TFA (10 mL) was stirred for 12 h at 80° C. under N₂ atmosphere. The resulting solution was extracted with EtOAc, the organic layer was dried and concentrated to afford the desired product (300 mg) as a yellow oil. ESI-MS m/z: 272.05 [M+H]⁺.

The ester hydrolysis was carried out in a similar manner to Method T (step d). The resulting solution was purified by reverse phase C18 column chromatography (CH₃CN/H₂O) to afford desired product (106 mg, 40%) as a yellow solid. ESI-MS m/z: 258.05 [M+H]⁺.

Example 576 Step a

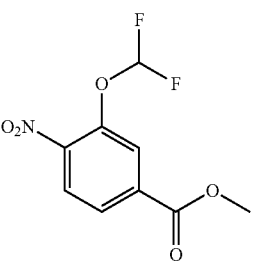 [SMILES: COC(=O)c1ccc([N+](=O)[O-])c(OC(F)F)c1]

Into a 100 mL round-bottom flask were added methyl 4-amino-3-hydroxybenzoate (5 g, 30 mmol), methyl 2-chloro-2,2-difluoroacetate (6.5 g, 45 mmol), K₂CO₃ (8.3 g, 60 mmol) and DMF (30 mL) at room temperature. The resulting mixture was stirred for 2 hr at 60° C. under nitrogen atmosphere. The reaction was monitored by TLC. The reaction was diluted with water and the aqueous layer was extracted with CH₂Cl₂. The resulting mixture was concentrated under reduced pressure and the residue was purified by silica gel column chromatography (0-20% EtOAc in hexanes) to give the desired compound (4.2 g, 65%) as an off-white solid. ESI-MS m/z: 248.05 [M+H]⁺.

Example 576 Step b

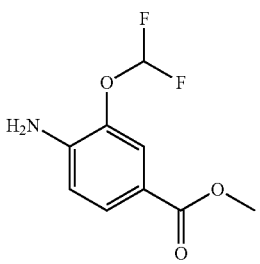

Into a 250 mL round-bottom flask were added the compound from step a (1.7 g, 6.9 mmol), Fe (3.07 g, 55.03 mmol), NH$_4$Cl (2.94 g, 55.03 mmol), EtOH (30 mL) and H$_2$O (30 mL) at room temperature. The resulting mixture was stirred overnight at 80° C. under nitrogen atmosphere. The resulting mixture was filtered, the filter cake was washed with EtOH and the filtrate was concentrated under reduced pressure. The residue was purified by silica gel column chromatography (0-33% EtOAc in hexanes) to give the desired compound (1.2 g, 80%) as an off-white solid. ESI-MS m/z: 218.00 [M+H]$^+$.

Example 576 Steps c and d

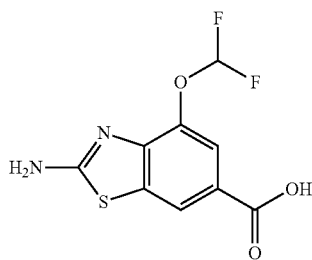 [SMILES: Nc1nc2c(OC(F)F)cc(C(=O)O)cc2s1]

The title compound was synthesized in a similar manner to Example 421. The ester hydrolysis was carried out in a similar manner to Method T (step d). The residue was purified by reverse flash chromatography (0-50% MeOH/H$_2$O, 25 min) to give the desired compound (105 mg, 55%). ESI-MS m/z: 260.95 [M+H]$^+$.

Example 577 Step a

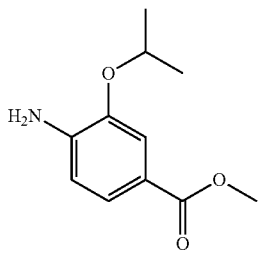

Into a 100 mL round-bottom flask were added methyl 4-amino-3-hydroxybenzoate (2 g, 11.96 mmol), 2-iodopropane (3.05 g, 17.95 mmol), Cs$_2$CO$_3$ (7.8 g, 23.93 mmol) and acetone (20 mL) at room temperature. The resulting mixture was stirred for 2 hr at 60° C. under nitrogen atmosphere. The aqueous layer was extracted with CH$_2$Cl$_2$ and concentrated under reduced pressure. The residue was purified by silica gel column chromatography (0-20% EtOAc in hexanes) to give the desired compound (2.54 g, 100%). ESI-MS m/z: 210.15 [M+H]$^+$.

Example 577 Steps b and c

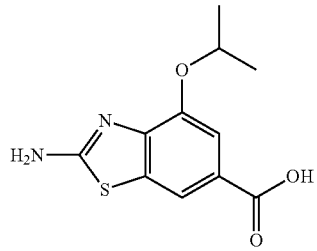 [SMILES: CC(C)Oc1cc(C(=O)O)cc2sc(N)nc12]

The title compound was synthesized in a similar manner to Example 421. The ester hydrolysis was carried out in a similar manner to Method T (step d). The residue was purified by reverse flash chromatography (0-50% MeOH/H$_2$O, 25 min) to afford the title compound (850 mg, 60%) as an off-white solid. ESI-MS m/z: 252.95 [M+H]$^+$.

Example 578 Step a

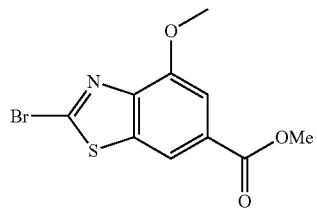

A solution methyl 2-amino-4-methoxybenzo[d]thiazole-6-carboxylate (2 g), CuBr$_2$ (3.7 g, 16.78 mmol) and t-BuNO$_2$ (1.7 g, 16.77 mmol) in CH$_3$CN was stirred for 16 hours at room temperature under N$_2$ atmosphere. The resulting solution was diluted with water, extracted with EtOAc and the organic layer was dried, concentrated. The resulting solution was purified by silica gel column chromatography (EtOAc in hexanes) to afford desired product (1.6 g, 63%) as orange solid. ESI-MS m/z: 301.90 [M+H]$^+$.

Example 578 Steps b and c

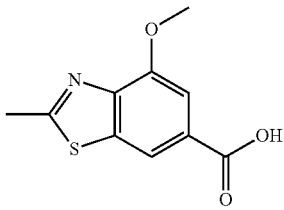

A solution of the compound from step a (1.6 g), Pd(dppf)Cl$_2$.CH$_2$Cl$_2$ (0.9 g, 1.06 mmol), Na$_2$CO$_3$ (1.7 g, 23.50 mmol), H$_2$O (1 mL) and methylboronic acid (0.48 g, 7.94 mmol) in dioxane (30 mL) was stirred for 3 hours at 100° C. under N$_2$ atmosphere. The resulting solution was diluted with water, extracted with EtOAc and the organic layer was dried, concentrated. The resulting solution was purified by silica gel column chromatography (ethyl acetate in hexanes)

to afford desired product (700 mg, 56%) as orange solid. ESI-MS m/z: 237.95 [M+H]⁺.

The ester hydrolysis was carried out in a similar manner to Method T (step d). The residue was purified by reverse flash chromatography (MeCN/H₂O) to afford the title compound (350 mg) as a white solid ESI-MS m/z: 223.90 [M+H]⁺.

Example 579 Steps a and b

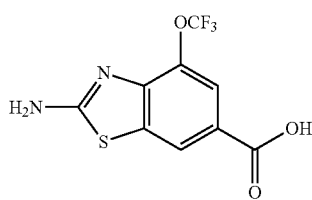 [SMILES: Nc1nc2c(OC(F)(F)F)cc(C(=O)O)cc2s1]

The title compound was synthesized in a similar manner to Example 421 using methyl 4-amino-3-(trifluoromethoxy) benzoate (1.50 g, 6.4 mmol). The ester hydrolysis was carried out in a similar manner to Method T (step d). The title compound was isolated by precipitation, and the solids were washed with MeCN to afford the desired product (370 mg, 74.74%) as a white solid. ESI-MS m/z: 279.05 [M+H]⁺.

Example 580 Steps a and b

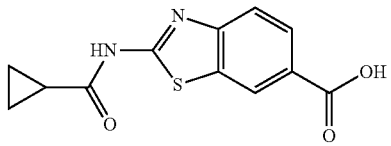 [SMILES: O=C(O)c1ccc2nc(NC(=O)C3CC3)sc2c1]

In a vial, methyl 2-aminobenzo[d]thiazole-6-carboxylate (350 mg, 1.681 mmol) was dissolved in DCM (8.40 ml). Cyclopropanecarbonyl chloride (183 μl, 2.017 mmol) was added followed by pyridine (408 μl, 5.04 mmol). The reaction was allowed to stir overnight. Water was added and the aqueous layer was washed with DCM. Combined organic layer dried over MgSO₄ and concentrated under reduced pressure. Crude reaction mixture purified by silica gel chromatography eluting with 0-60% EtOAc/Hexanes to give the title compound as a yellow solid (120 mg, 0.434 mmol, 25%). ESI-MS m/z: 276.81 [M+H]⁺.

The ester hydrolysis was carried out in a similar manner to Method T (step d). The title compound was isolated by DCM extraction and concentrated (65 mg, 0.248 mmol, 90%).

Example 581 Step a

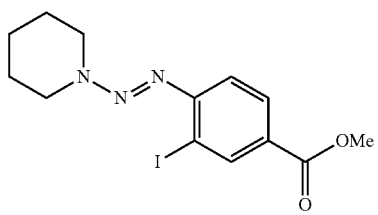 [SMILES: COC(=O)c1ccc(/N=N/N2CCCCC2)c(I)c1]

To a stirred solution of methyl 4-amino-3-iodobenzoate (2.7 g, 10 mmol) in HCl (6 mL) were added NaNO₂ (0.7 g in 5 mL water) dropwise at 5° C. for 1 hr. To the above mixture was added piperidine (1 mL) dropwise at 5° C. The resulting mixture was stirred for additional 1 hr at room temperature. The resulting mixture was extracted with EA and the combined organic layers were washed with water, dried over anhydrous Na₂SO₄. The residue purified by silica gel column chromatography (EtOAc in hexanes) to afford the desired product (2.7 g) as a yellow solid. ESI-MS m/z: 374.00 [M+H]⁺.

Example 581 Step b

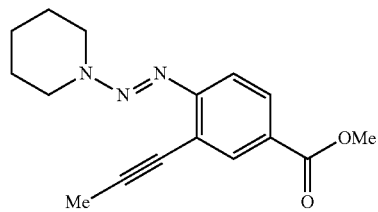 [SMILES: CC#Cc1cc(C(=O)OC)ccc1/N=N/N1CCCCC1]

To a dry and N₂-flushed 50 mL Schlenk tube, equipped with a magnetic stirrer and a septum, was added bromo (prop-1-yn-1-yl)magnesium (4.3 g, 29.94 mmol). The solution was cooled to −30° C. and ZnBr2 (5.08 g, 22.56 mmol) was added dropwise to the reaction mixture. The reaction mixture was warmed to room temperature for 30 minutes. The compound from step a (2 g, 5.36 mmol) was added followed by (PPh₃)₄ (309 mg, 0.27 mmol). The reaction mixture was stirred at room temperature for 2 hr and quenched by saturated aqueous NH₄Cl. The aqueous was extracted with EtOAc, dried, and concentrated under reduced pressure. The residue was purified by silica gel column chromatography (EtOAc in hexanes) to afford the desired product (2 g, 97%) as a yellow solid. ESI-MS m/z: 286.00 [M+H]⁺.

Example 581 Step c

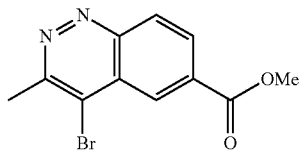 [SMILES: COC(=O)c1ccc2nnc(C)c(Br)c2c1]

A solution of the compound from step b (1.5 g, 5.26 mmol,) and HBr in water (850 mg, 10.51 mmol) in acetone (10 mL) was stirred for 2 hr at room temperature. The resulting mixture was extracted with EtOAc and the combined organic layers were washed with water and dried over anhydrous Na₂SO₄. The residue was purified by silica gel column chromatography (EtOAc in hexanes) to afford the desired product (900 mg, 61%) as a yellow solid. ESI-MS m/z: 281.00 [M+H]⁺.

Example 581 Step d

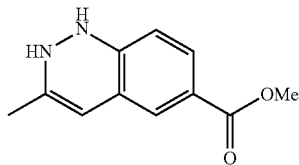

A solution of the compound from step c (900 mg, 3.2 mmol) and Pd/C (681 mg, 6.40 mmol) in MeOH (20 mL) was stirred for 2 hr at room temperature under H$_2$ atmosphere. The resulting mixture was filtered and the solution was concentrated to use directly for next step. ESI-MS m/z: 205.00 [M+H]$^+$.

Example 581 Steps e and f

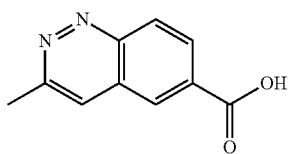

A solution of compound from step d and MnO$_2$ (1.5 g, 17.67 mmol) in THF (20 mL) was stirred for 2 hr at room temperature. The crude product was purified by reverse phase flash to afford the desired product (253 mg, 51%) as a yellow solid. ESI-MS m/z: 203.00 [M+H]$^+$.

In a vial, compound from step e (100 mg, 0.495 mmol) and lithium hydroxide (118 mg, 4.95 mmol) were dissolved in THF (2.2 ml), MeOH (2.2 ml), and Water (0.55 ml). The reaction was allowed to stir at room temperature for 4 hours. Reaction diluted with water and the pH adjusted to 3-4 with 1M aq. HCl. Aqueous layer washed with DCM and 9:1 DCM/MeOH. Combined organic layer dried over MgSO$_4$ and concentrated under reduced pressure to furnish the title compound (45 mg, 48%). ESI-MS m/z: 188.68 [M+H]$^+$.

Example 582 Steps a and b

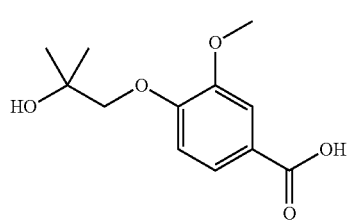 [SMILES: COc1cc(C(=O)O)ccc1OCC(C)(C)O]

A solution of methyl vanillate (3 g, 16.47 mmol), 1-chloro-2-methyl-2-propanol (3.58 g, 32.97 mmol) and Cs$_2$CO$_3$ (6.81 g, 20.90 mmol) in MeOH (10 mL) was stirred for 4 hr at 80° C. The crude product was purified by reverse phase flash to afford the desired product (3.2 g, 76%) as a yellow solid.

The ester hydrolysis was carried out in a similar manner to Method T (step d). The crude product was purified by reverse phase flash to afford the desired product (3 g) as a white solid. ESI-MS m/z: 241.10 [M+H]$^+$.

Example 583

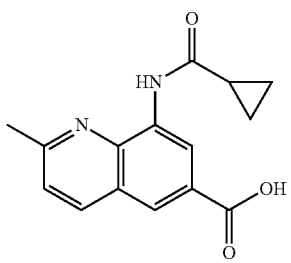 [SMILES: Cc1ccc2cc(C(=O)O)cc(NC(=O)C3CC3)c2n1]

The title compound was prepared in an analogous procedure to Example 392 steps a and b. The compound was isolated by precipitation to afford the desired compound (19 mg, 47%). ESI-MS m/z: 270.95 [M+H]$^+$.

Example 584

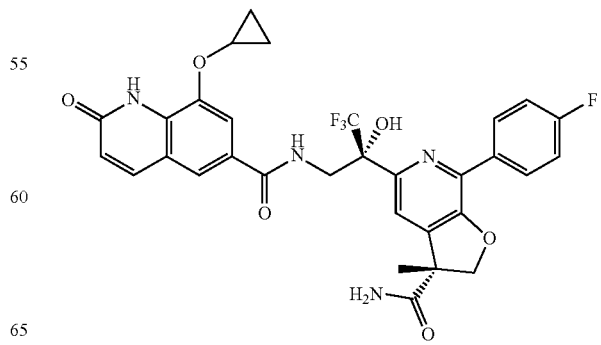

441

Example 584 Steps a and b

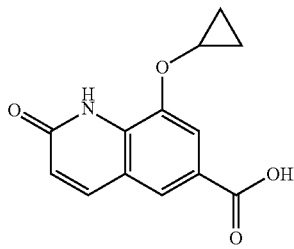 [SMILES: O=C(O)c1cc(OC2CC2)c2[nH]c(=O)ccc2c1]

To a vial containing N-oxide Example 405 step a (100 mg) was added Water (3.7 mL, 0.1 M), and Ms-Cl (0.057 mL, 0.732 mmol) was slowly added. The reaction was stirred at room temperature and monitored by LCMS. The reaction was diluted with DCM and quenched with sat. sodium bicarbonate. The aqueous was extracted with DCM/ MeOH with a phase separator cartridge. The crude residue was purified by automated column chromatography (eluted in 75% EtOAc in hexanes) to afford the title compound (62 mg, 62%). ESI-MS m/z: 273.86 [M+H]$^+$.

The ester hydrolysis was carried out in a similar manner to Method T (step d). The title compound was isolated by acid precipitation (40 mg, 72%). ESI-MS m/z: 246.07 [M+H]$^+$.

442

Example 584 Step c

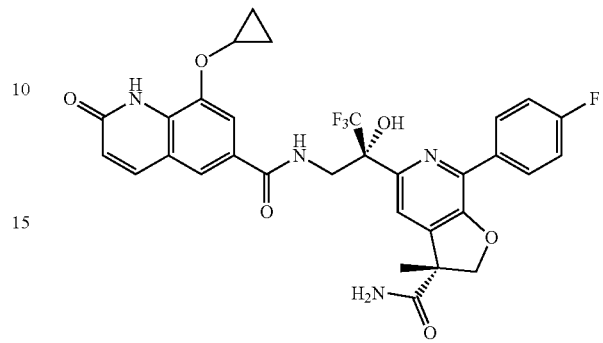

The title compound was prepared according to Method J and the title compound was purified by Gilson prep-HPLC (20-90%, 25 min) to afford the desired product (23 mg, 460%). ESI-MS m/z: 627.20 [M+H]$^+$. The following Table 10 contains examples that were prepared according to Method J (PyBOP or HATU) with commercially available aryl acid coupling partners. The majority of compounds were purified by Gilson prep-HPLC, and some were purified by automated column chromatography (silica gel).

TABLE 10

| Example | Structure | MS$^+$ m/z |
|---------|-----------|------------|
| 585 | 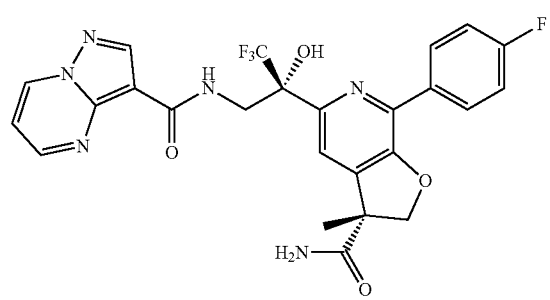 [SMILES: C[C@]1(C(N)=O)COc2c1cc([C@@](O)(CNC(=O)c1cnn3cccnc13)C(F)(F)F)nc2-c1ccc(F)cc1] | 544.10 |
| 586 | 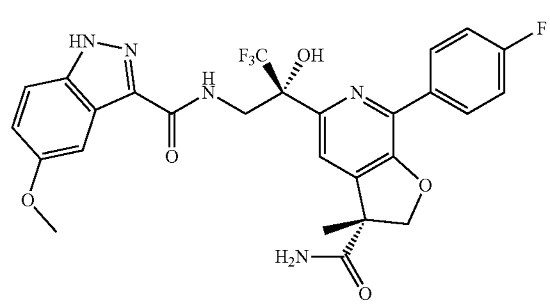 [SMILES: COc1ccc2[nH]nc(C(=O)NC[C@](O)(c3cc4c(c(-c5ccc(F)cc5)n3)OC[C@]4(C)C(N)=O)C(F)(F)F)c2c1] | 574.00 |

TABLE 10-continued

| Example | Structure | MS⁺ m/z |
|---------|-----------|---------|
| 587 | 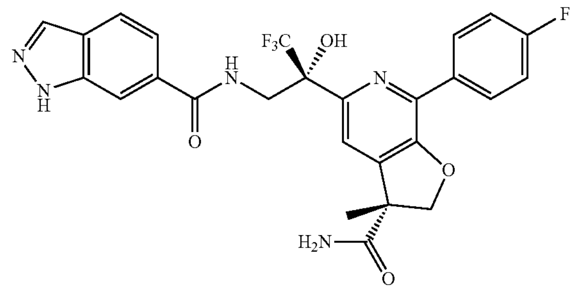 [SMILES: C[C@]1(C(N)=O)COc2c1cc([C@@](O)(CNC(=O)c1ccc3cn[nH]c3c1)C(F)(F)F)nc2-c1ccc(F)cc1] | 543.90 |
| 588 | 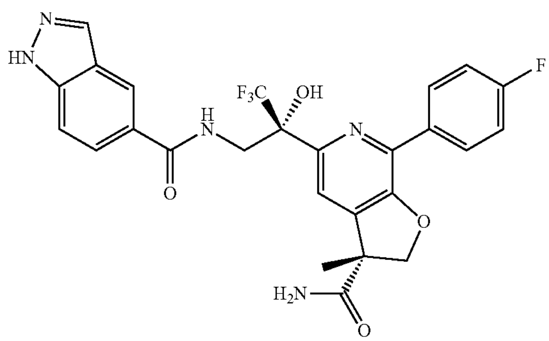 [SMILES: C[C@]1(C(N)=O)COc2c1cc([C@@](O)(CNC(=O)c1ccc3[nH]ncc3c1)C(F)(F)F)nc2-c1ccc(F)cc1] | 544.0 |
| 589 | 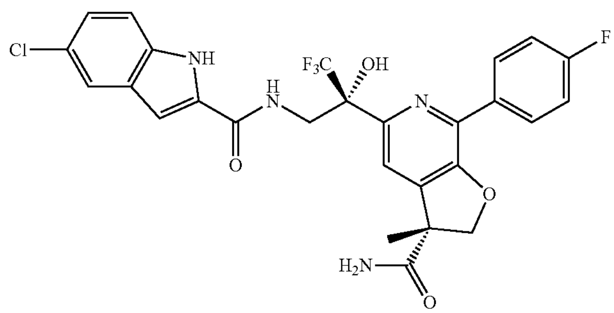 [SMILES: C[C@]1(C(N)=O)COc2c1cc([C@@](O)(CNC(=O)c1cc3cc(Cl)ccc3[nH]1)C(F)(F)F)nc2-c1ccc(F)cc1] | 576.8 |
| 590 | 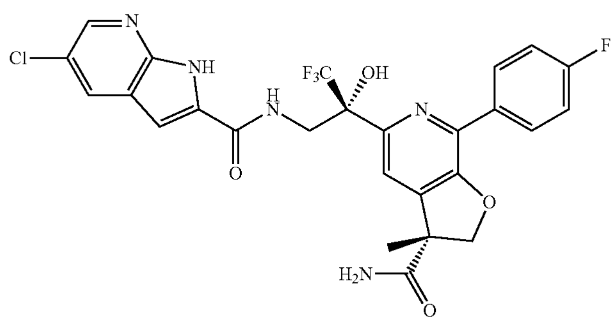 [SMILES: C[C@]1(C(N)=O)COc2c1cc([C@@](O)(CNC(=O)c1cc3cc(Cl)cnc3[nH]1)C(F)(F)F)nc2-c1ccc(F)cc1] | 648.2 |
| 591 | 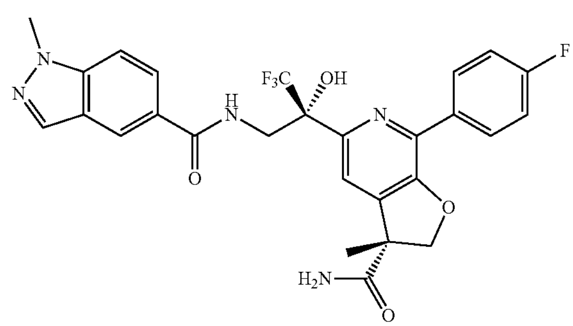 [SMILES: Cn1ncc2cc(C(=O)NC[C@](O)(c3cc4c(c(-c5ccc(F)cc5)n3)OC[C@]4(C)C(N)=O)C(F)(F)F)ccc21] | 558.1 |

TABLE 10-continued

| Example | Structure | MS+ m/z |
|---------|-----------|---------|
| 592 | 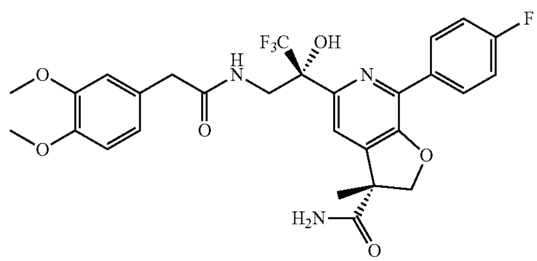 [SMILES: COc1ccc(CC(=O)NC[C@](O)(c2cc3c(c(-c4ccc(F)cc4)n2)OC[C@]3(C)C(N)=O)C(F)(F)F)cc1OC] | 578.19 |
| 593 | 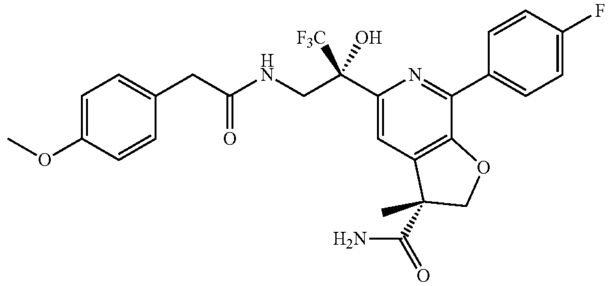 [SMILES: COc1ccc(CC(=O)NC[C@](O)(c2cc3c(c(-c4ccc(F)cc4)n2)OC[C@]3(C)C(N)=O)C(F)(F)F)cc1] | 548.19 |
| 594 | 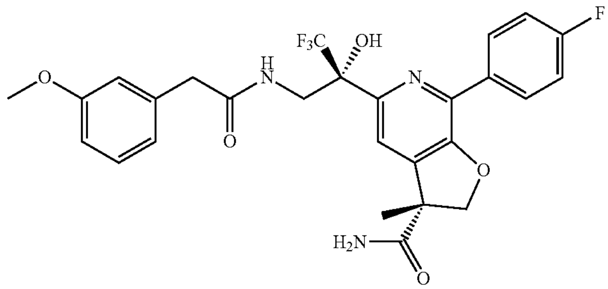 [SMILES: COc1cccc(CC(=O)NC[C@](O)(c2cc3c(c(-c4ccc(F)cc4)n2)OC[C@]3(C)C(N)=O)C(F)(F)F)c1] | 548.19 |
| 595 | 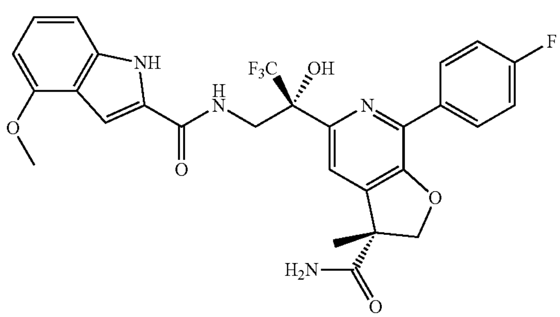 [SMILES: COc1cccc2[nH]c(C(=O)NC[C@](O)(c3cc4c(c(-c5ccc(F)cc5)n3)OC[C@]4(C)C(N)=O)C(F)(F)F)cc12] | 573.18 |
| 596 | 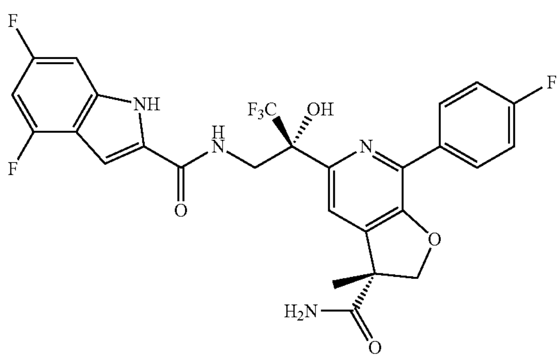 [SMILES: C[C@]1(C(N)=O)COc2c1cc([C@@](O)(CNC(=O)c1cc3c(F)cc(F)cc3[nH]1)C(F)(F)F)nc2-c1ccc(F)cc1] | 579.15 |

TABLE 10-continued
| Example | Structure | MS+ m/z |
|---|---|---|
| 597 | 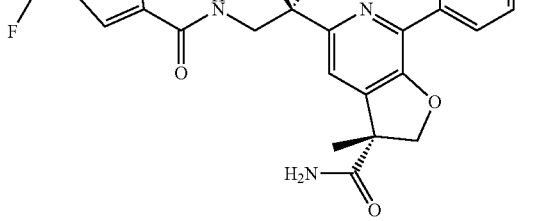 | 595.12 |
| 598 | 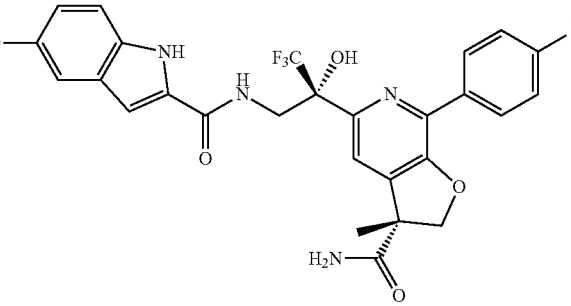 | 573.18 |
| 599 | 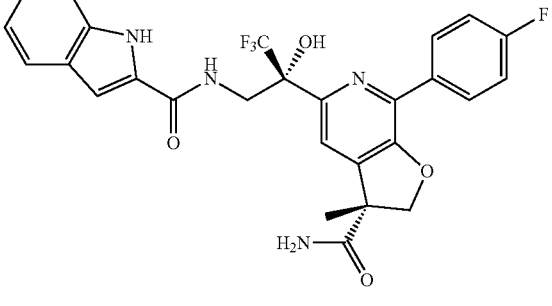 | 543.17 |
| 600 | 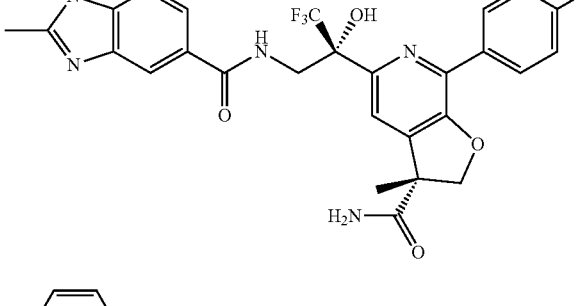 | 558.18 |
| 601 | 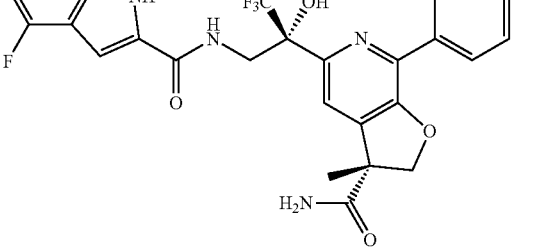 | 561.15 |

TABLE 10-continued

| Example | Structure | MS⁺ m/z |
|---------|-----------|---------|
| 602 | 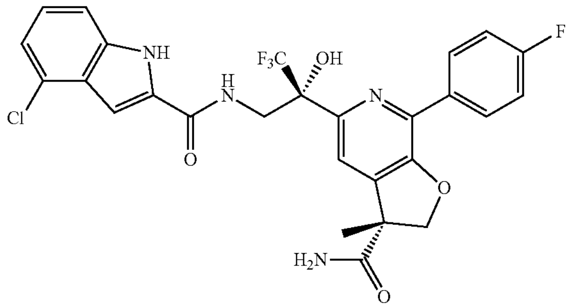 [SMILES: C[C@]1(C(N)=O)COc2c1cc([C@@](O)(CNC(=O)c1cc3c(Cl)cccc3[nH]1)C(F)(F)F)nc2-c1ccc(F)cc1] | 577.12 |
| 603 | 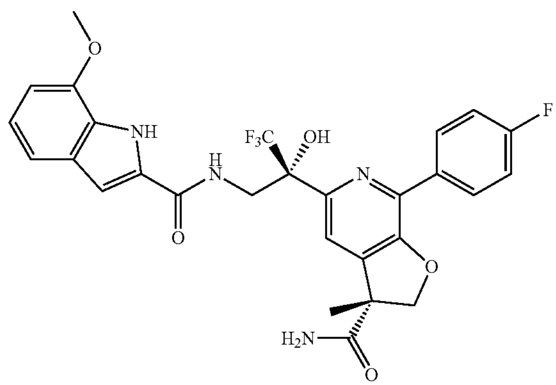 [SMILES: COc1cccc2cc(C(=O)NC[C@](O)(c3cc4c(c(-c5ccc(F)cc5)n3)OC[C@]4(C)C(N)=O)C(F)(F)F)[nH]c12] | 573.17 |
| 604 | 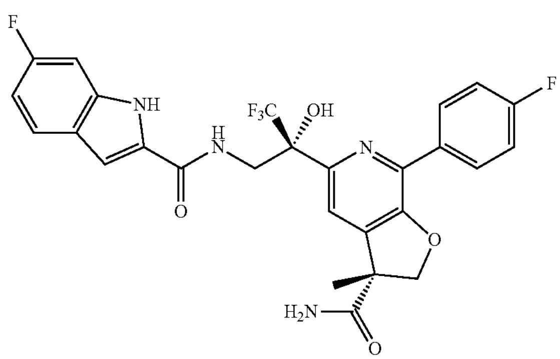 [SMILES: C[C@]1(C(N)=O)COc2c1cc([C@@](O)(CNC(=O)c1cc3ccc(F)cc3[nH]1)C(F)(F)F)nc2-c1ccc(F)cc1] | 561.16 |
| 605 | 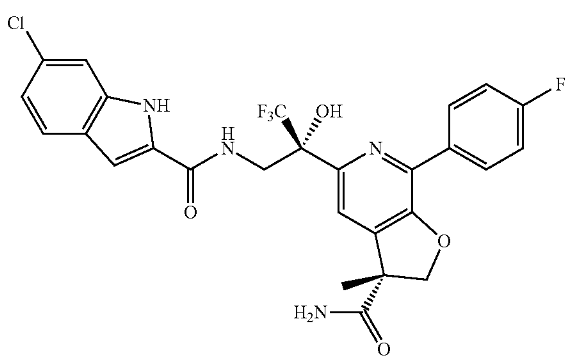 [SMILES: C[C@]1(C(N)=O)COc2c1cc([C@@](O)(CNC(=O)c1cc3ccc(Cl)cc3[nH]1)C(F)(F)F)nc2-c1ccc(F)cc1] | 577.12 |

TABLE 10-continued

| Example | Structure | MS+ m/z |
|---|---|---|
| 606 | 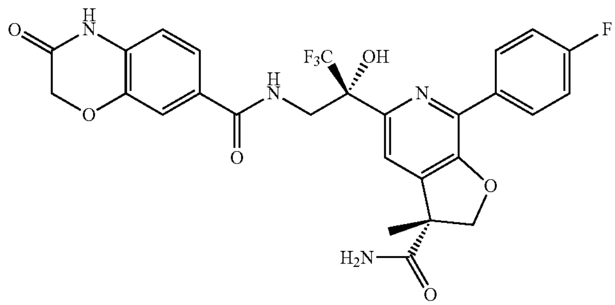 [SMILES: C[C@]1(C(N)=O)COc2c1cc([C@@](O)(CNC(=O)c1ccc3c(c1)OCC(=O)N3)C(F)(F)F)nc2-c1ccc(F)cc1] | 575.16 |
| 607 | 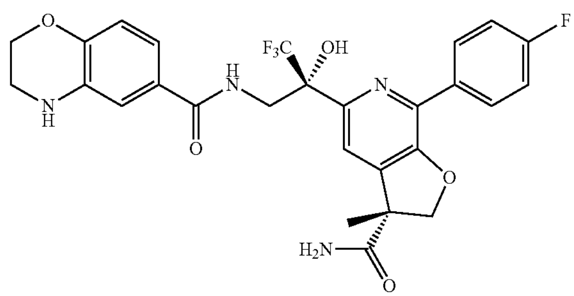 [SMILES: C[C@]1(C(N)=O)COc2c1cc([C@@](O)(CNC(=O)c1ccc3c(c1)NCCO3)C(F)(F)F)nc2-c1ccc(F)cc1] | 561.18 |
| 608 | 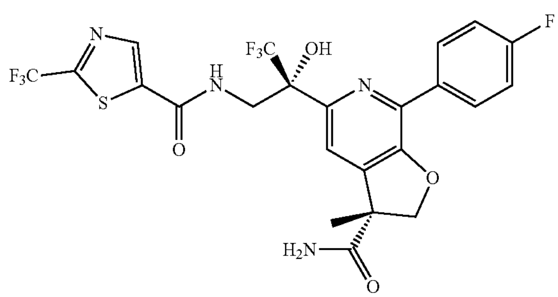 [SMILES: C[C@]1(C(N)=O)COc2c1cc([C@@](O)(CNC(=O)c1cnc(C(F)(F)F)s1)C(F)(F)F)nc2-c1ccc(F)cc1] | 579.10 |
| 609 | 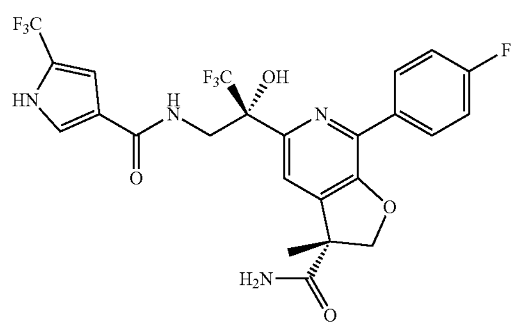 [SMILES: C[C@]1(C(N)=O)COc2c1cc([C@@](O)(CNC(=O)c1c[nH]c(C(F)(F)F)c1)C(F)(F)F)nc2-c1ccc(F)cc1] | 561.13 |
| 610 | 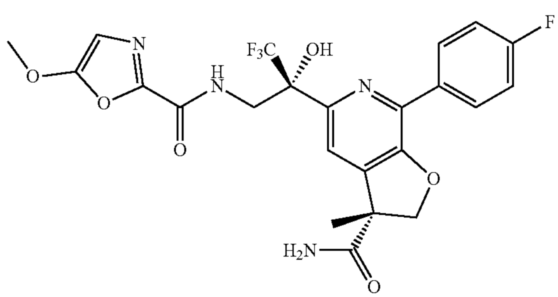 [SMILES: COc1cnc(C(=O)NC[C@](O)(c2cc3c(c(-c4ccc(F)cc4)n2)OC[C@]3(C)C(N)=O)C(F)(F)F)o1] | 525.14 |

The following Table 11 contains examples that were prepared according to Method J (PyBOP or HATU). The majority of compounds were purified by Gilson prep-HPLC, and some were purified by automated column chromatography (silica gel). The aryl acid coupling partners were prepared according to Methods S, U, V, W or previously described methods.

TABLE 11

| Example | Structure | MS+ m/z |
|---|---|---|
| 611 | 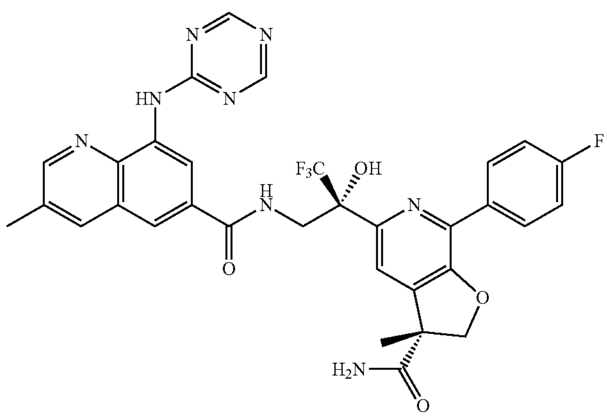 [SMILES: Cc1cnc2c(Nc3ncncn3)cc(C(=O)NC[C@](O)(c3cc4c(c(-c5ccc(F)cc5)n3)OC[C@]4(C)C(N)=O)C(F)(F)F)cc2c1] | 663.05 |
| 612 | 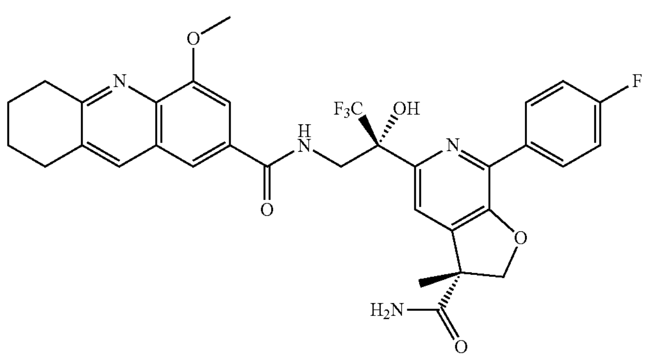 [SMILES: COc1cc(C(=O)NC[C@](O)(c2cc3c(c(-c4ccc(F)cc4)n2)OC[C@]3(C)C(N)=O)C(F)(F)F)cc2cc3c(nc12)CCCC3] | 639.15 |
| 613 | 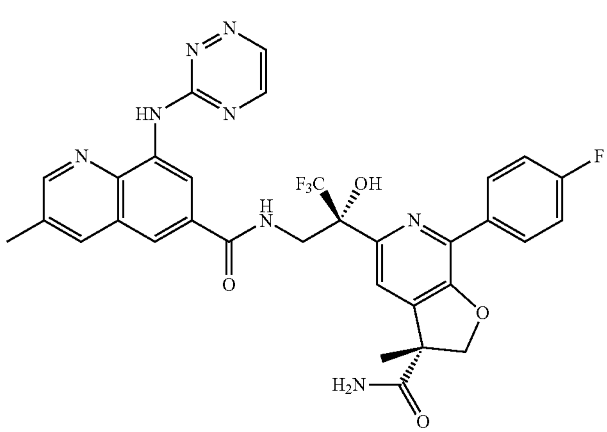 [SMILES: Cc1cnc2c(Nc3nccnn3)cc(C(=O)NC[C@](O)(c3cc4c(c(-c5ccc(F)cc5)n3)OC[C@]4(C)C(N)=O)C(F)(F)F)cc2c1] | 663.10 |

TABLE 11-continued
| Example | Structure | MS+ m/z |
|---|---|---|
| 614 | 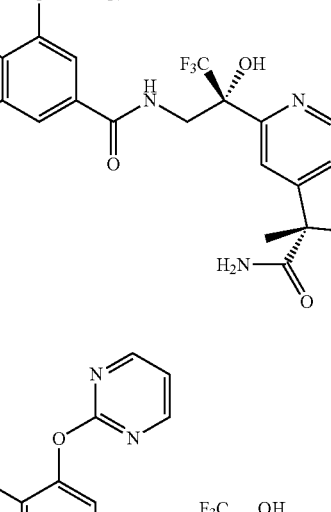 | 648.90 |
| 615 | 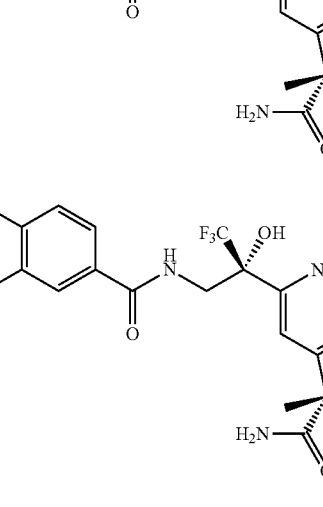 | 663.10 |
| 616 | 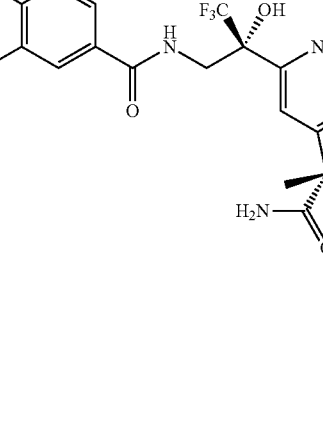 | 570.06 |
| 617 | 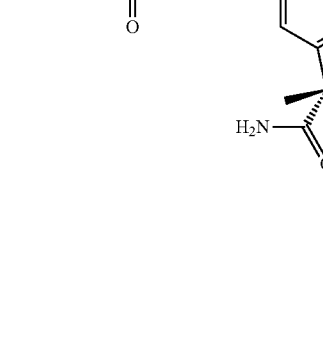 | 603.96 |

TABLE 11-continued
| Example | Structure | MS+ m/z |
|---|---|---|
| 618 | 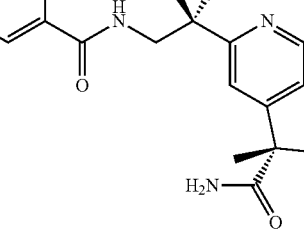 | 664.80 |
| 619 | 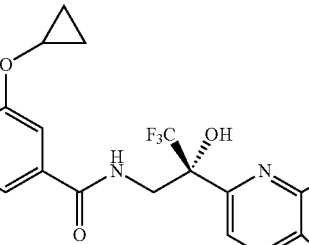 | 669.31 |
| 620 | 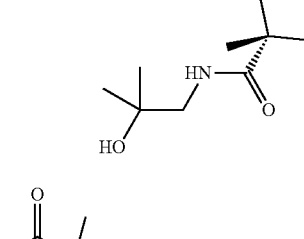 | 682.23 |
| 621 | 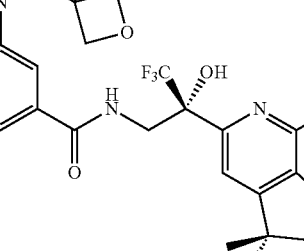 | 679.19 |

TABLE 11-continued

| Example | Structure | MS+ m/z |
|---|---|---|
| 622 | 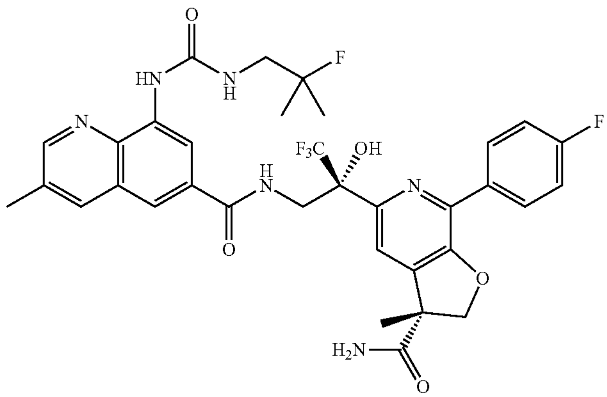 [SMILES: Cc1cnc2c(NC(=O)NCC(C)(C)F)cc(C(=O)NC[C@](O)(c3cc4c(c(-c5ccc(F)cc5)n3)OC[C@]4(C)C(N)=O)C(F)(F)F)cc2c1] | 701.25 |
| 623 | 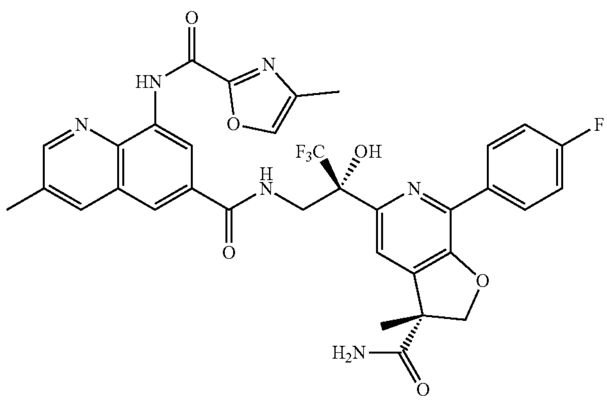 [SMILES: Cc1cnc2c(NC(=O)c3nc(C)co3)cc(C(=O)NC[C@](O)(c3cc4c(c(-c5ccc(F)cc5)n3)OC[C@]4(C)C(N)=O)C(F)(F)F)cc2c1] | 693.21 |
| 624 | 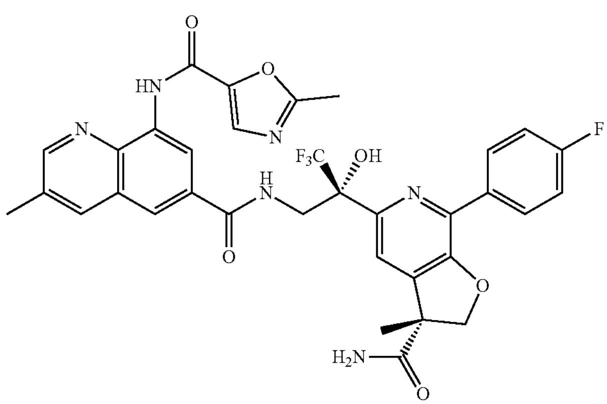 [SMILES: Cc1cnc2c(NC(=O)c3cnc(C)o3)cc(C(=O)NC[C@](O)(c3cc4c(c(-c5ccc(F)cc5)n3)OC[C@]4(C)C(N)=O)C(F)(F)F)cc2c1] | 693.21 |
| 625 | 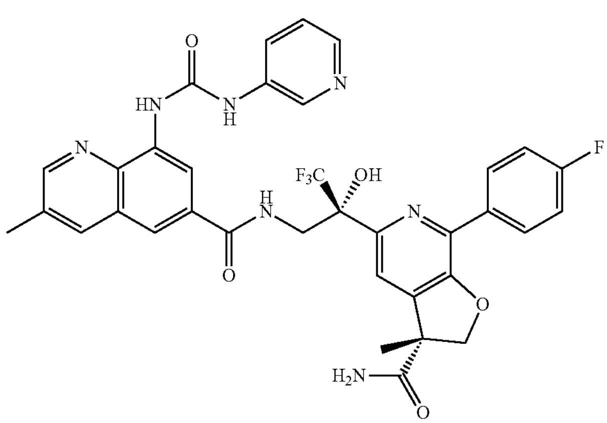 [SMILES: Cc1cnc2c(NC(=O)Nc3cccnc3)cc(C(=O)NC[C@](O)(c3cc4c(c(-c5ccc(F)cc5)n3)OC[C@]4(C)C(N)=O)C(F)(F)F)cc2c1] | 704.29 |

TABLE 11-continued

| Example | Structure | MS+ m/z |
|---|---|---|
| 626 | 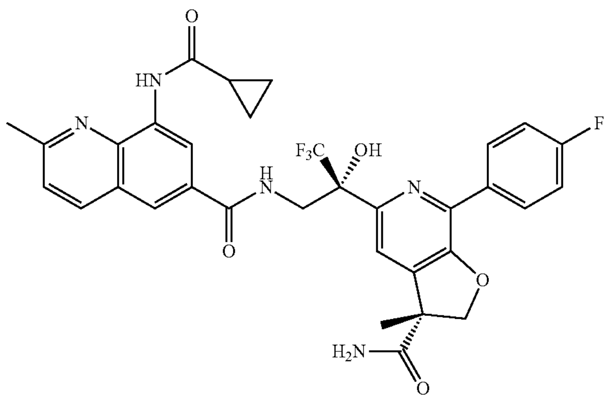 [SMILES: Cc1ccc2cc(C(=O)NC[C@](O)(c3cc4c(c(-c5ccc(F)cc5)n3)OC[C@]4(C)C(N)=O)C(F)(F)F)cc(NC(=O)C3CC3)c2n1] | 652.22 |
| 627 | 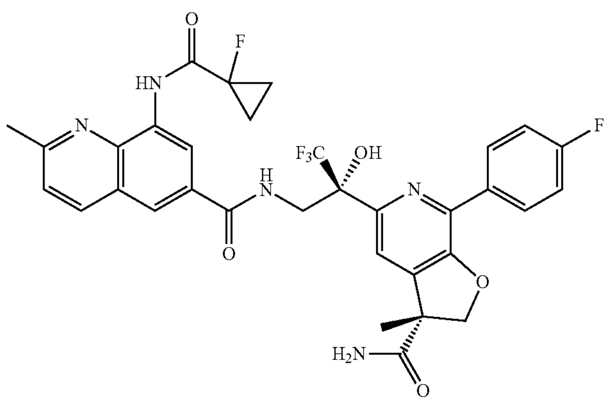 [SMILES: Cc1ccc2cc(C(=O)NC[C@](O)(c3cc4c(c(-c5ccc(F)cc5)n3)OC[C@]4(C)C(N)=O)C(F)(F)F)cc(NC(=O)C3(F)CC3)c2n1] | 670.21 |
| 628 | 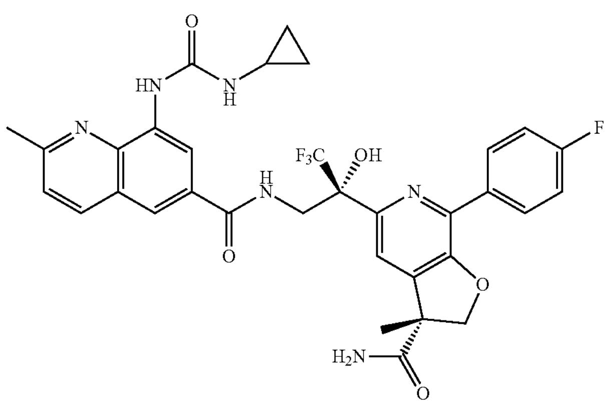 [SMILES: Cc1ccc2cc(C(=O)NC[C@](O)(c3cc4c(c(-c5ccc(F)cc5)n3)OC[C@]4(C)C(N)=O)C(F)(F)F)cc(NC(=O)NC3CC3)c2n1] | 667.23 |
| 629 | 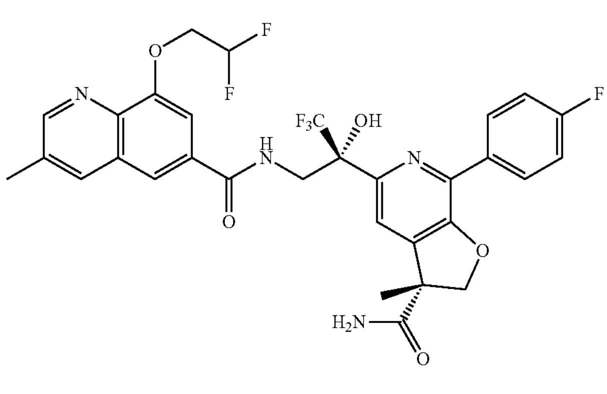 [SMILES: Cc1cnc2c(OCC(F)F)cc(C(=O)NC[C@](O)(c3cc4c(c(-c5ccc(F)cc5)n3)OC[C@]4(C)C(N)=O)C(F)(F)F)cc2c1] | 649.20 |

TABLE 11-continued

| Example | Structure | MS+ m/z |
|---------|-----------|---------|
| 630 | 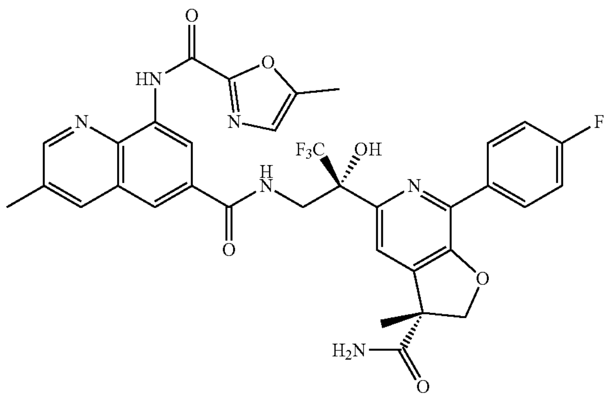 [SMILES: Cc1cnc2c(NC(=O)c3ncc(C)o3)cc(C(=O)NC[C@](O)(c3cc4c(c(-c5ccc(F)cc5)n3)OC[C@]4(C)C(N)=O)C(F)(F)F)cc2c1] | 693.21 |
| 631 | 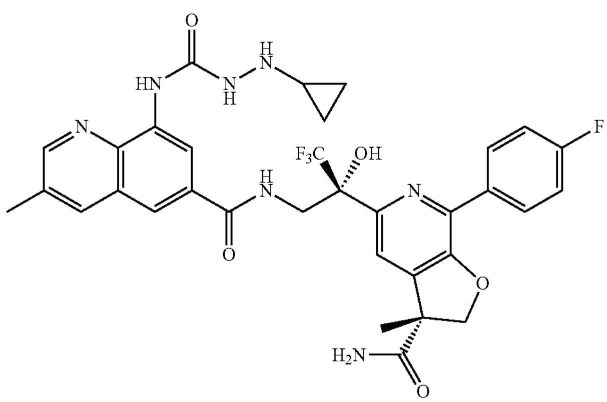 [SMILES: Cc1cnc2c(NC(=O)NNC3CC3)cc(C(=O)NC[C@](O)(c3cc4c(c(-c5ccc(F)cc5)n3)OC[C@]4(C)C(N)=O)C(F)(F)F)cc2c1] | 682.24 |
| 632 | 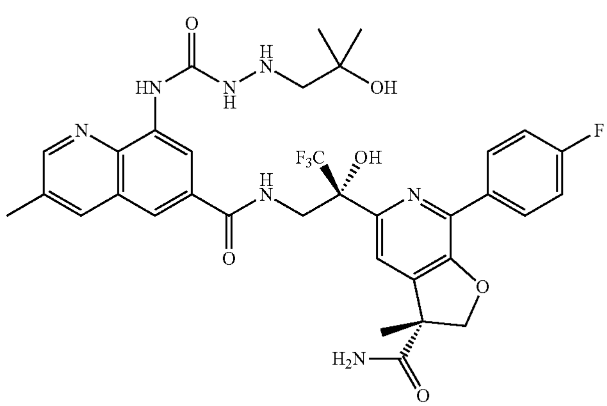 [SMILES: Cc1cnc2c(NC(=O)NNCC(C)(C)O)cc(C(=O)NC[C@](O)(c3cc4c(c(-c5ccc(F)cc5)n3)OC[C@]4(C)C(N)=O)C(F)(F)F)cc2c1] | 714.27 |

The following Table 12 contains examples that were prepared according to Method J (PyBOP or HATU). The majority of compounds were purified by Gilson prep-HPLC, and some were purified by automated column chromatography (silica gel). The aryl acid coupling partners were prepared according the previously described procedures.

TABLE 12

| Example | Structure | MS⁺ m/z |
|---|---|---|
| 633 | 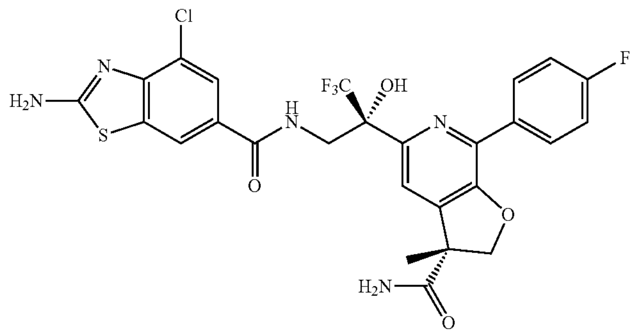 [SMILES: C[C@]1(C(N)=O)COc2c1cc([C@@](O)(CNC(=O)c1cc(Cl)c3nc(N)sc3c1)C(F)(F)F)nc2-c1ccc(F)cc1] | 609.89 |
| 634 | 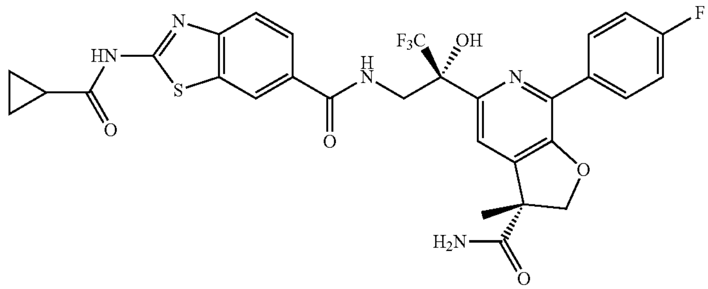 [SMILES: C[C@]1(C(N)=O)COc2c1cc([C@@](O)(CNC(=O)c1ccc3nc(NC(=O)C4CC4)sc3c1)C(F)(F)F)nc2-c1ccc(F)cc1] | 644.04 |
| 635 | 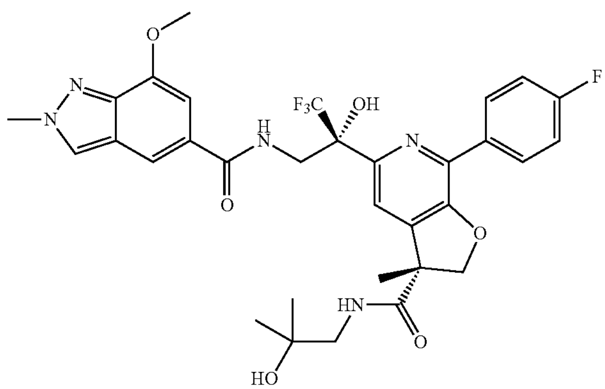 [SMILES: COc1cc(C(=O)NC[C@](O)(c2cc3c(c(-c4ccc(F)cc4)n2)OC[C@]3(C)C(=O)NCC(C)(C)O)C(F)(F)F)cc2cn(C)nc12] | 660.25 |
| 636 | 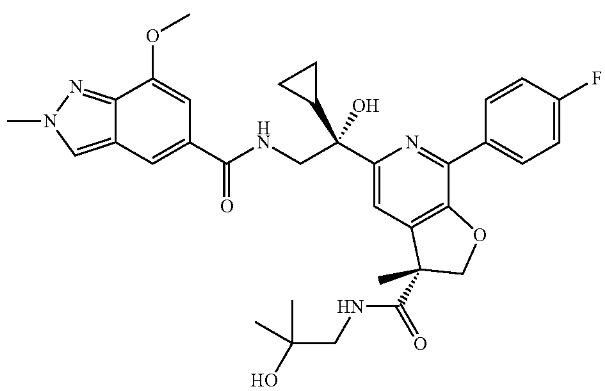 [SMILES: COc1cc(C(=O)NC[C@](O)(c2cc3c(c(-c4ccc(F)cc4)n2)OC[C@]3(C)C(=O)NCC(C)(C)O)C2CC2)cc2cn(C)nc12] | 560.23 |

TABLE 12-continued

| Example | Structure | MS+ m/z |
|---|---|---|
| 637 | 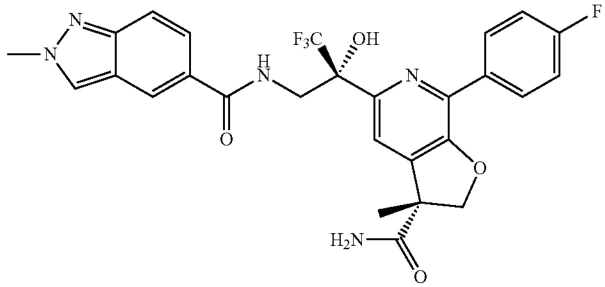 [SMILES: Cn1cc2cc(C(=O)NC[C@](O)(c3cc4c(c(-c5ccc(F)cc5)n3)OC[C@]4(C)C(N)=O)C(F)(F)F)ccc2n1] | 558.17 |
| 638 | 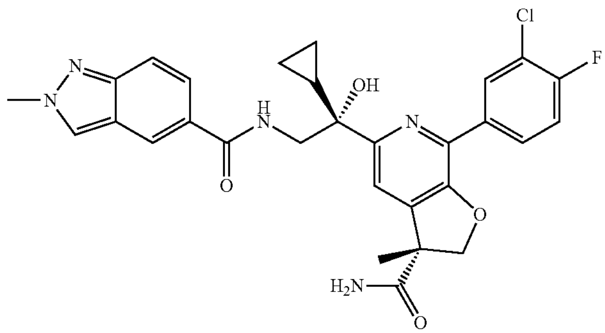 [SMILES: Cn1cc2cc(C(=O)NC[C@](O)(c3cc4c(c(-c5ccc(F)c(Cl)c5)n3)OC[C@]4(C)C(N)=O)C3CC3)ccc2n1] | 564.18 |
| 639 | 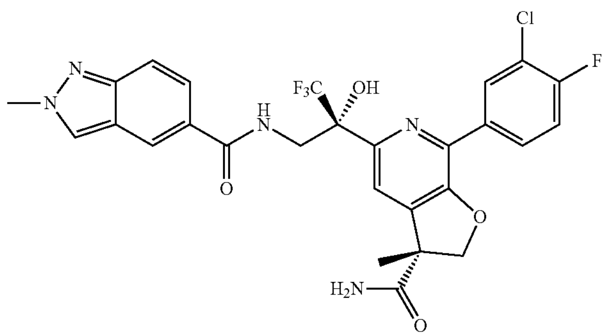 [SMILES: Cn1cc2cc(C(=O)NC[C@](O)(c3cc4c(c(-c5ccc(F)c(Cl)c5)n3)OC[C@]4(C)C(N)=O)C(F)(F)F)ccc2n1] | 592.14 |
| 640 | 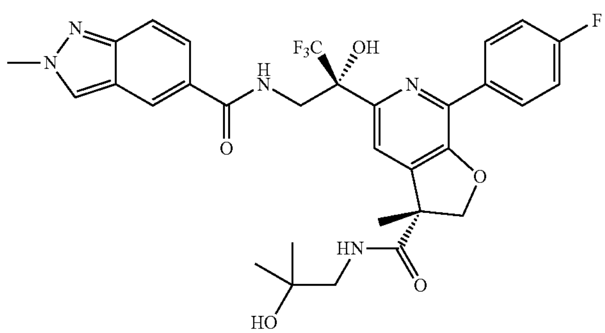 [SMILES: Cn1cc2cc(C(=O)NC[C@](O)(c3cc4c(c(-c5ccc(F)cc5)n3)OC[C@]4(C)C(=O)NCC(C)(C)O)C(F)(F)F)ccc2n1] | 630.24 |
| 641 | 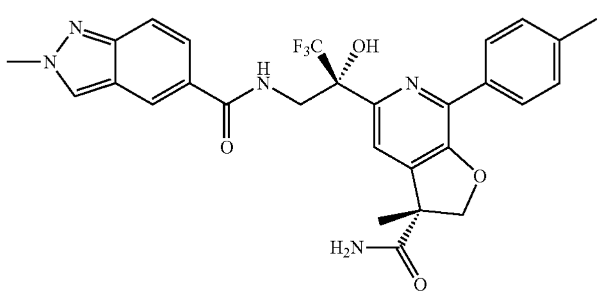 | 554.20 |

TABLE 12-continued

| Example | Structure | MS⁺ m/z |
|---|---|---|
| 642 | 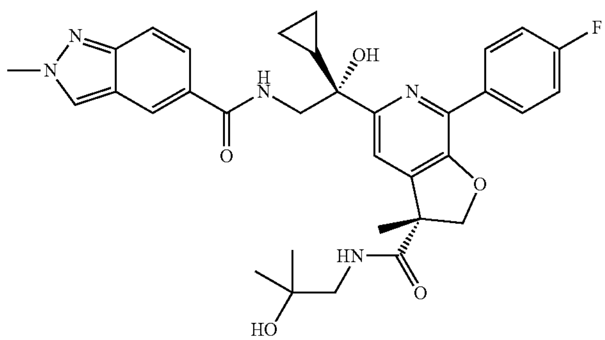 [SMILES: Cn1cc2cc(C(=O)NC[C@](O)(c3cc4c(c(-c5ccc(F)cc5)n3)OC[C@]4(C)C(=O)NCC(C)(C)O)C3CC3)ccc2n1] | 602.28 |
| 643 | 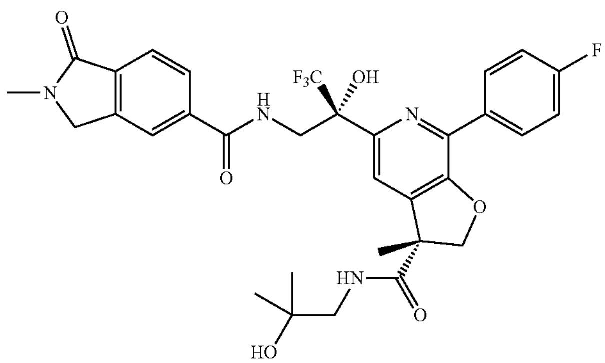 [SMILES: CN1Cc2cc(C(=O)NC[C@](O)(c3cc4c(c(-c5ccc(F)cc5)n3)OC[C@]4(C)C(=O)NCC(C)(C)O)C(F)(F)F)ccc2C1=O] | 645.23 |
| 644 | 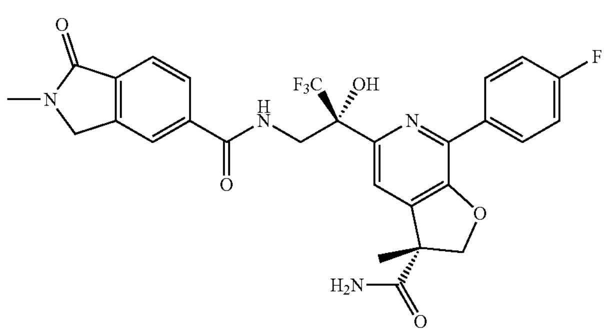 [SMILES: CN1Cc2cc(C(=O)NC[C@](O)(c3cc4c(c(-c5ccc(F)cc5)n3)OC[C@]4(C)C(N)=O)C(F)(F)F)ccc2C1=O] | 573.18 |
| 645 | 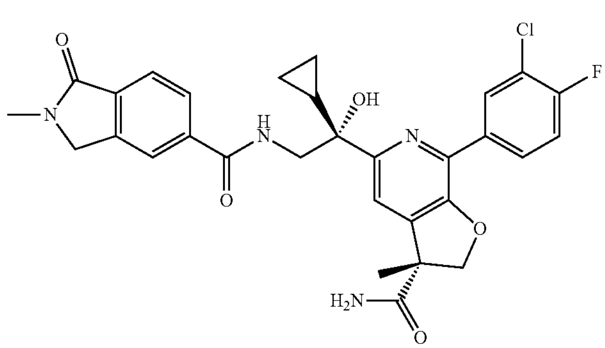 [SMILES: CN1Cc2cc(C(=O)NC[C@](O)(c3cc4c(c(-c5ccc(F)c(Cl)c5)n3)OC[C@]4(C)C(N)=O)C3CC3)ccc2C1=O] | 579.18 |

TABLE 12-continued

| Example | Structure | MS⁺ m/z |
|---|---|---|
| 646 | 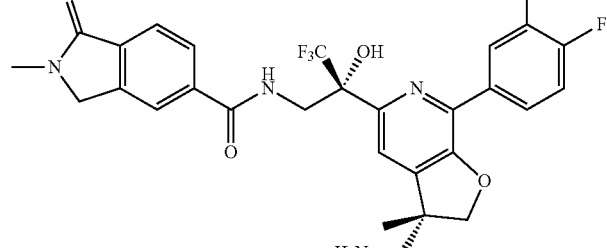 | 607.14 |
| 647 | 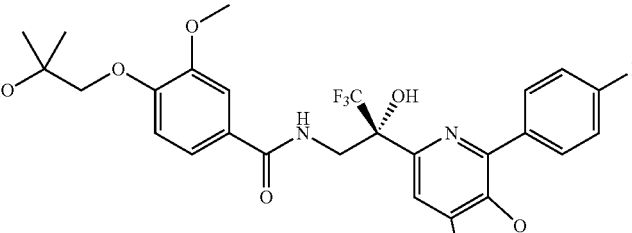 | 622.10 |

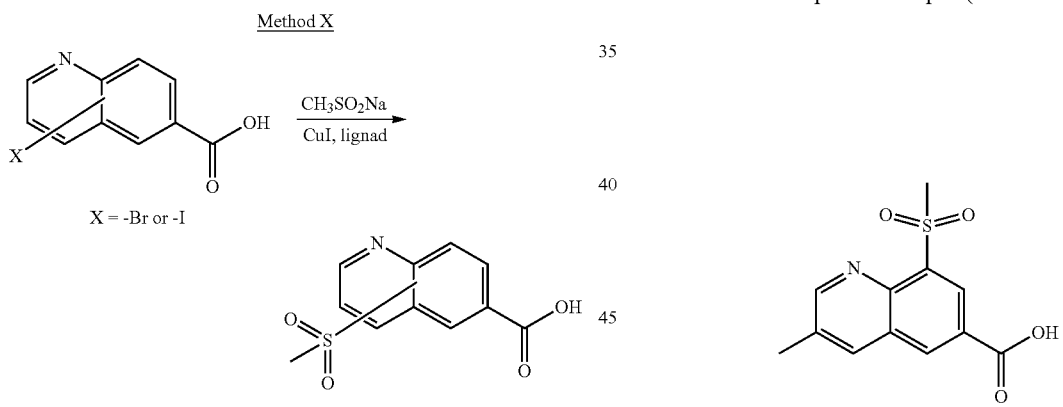

Example 648

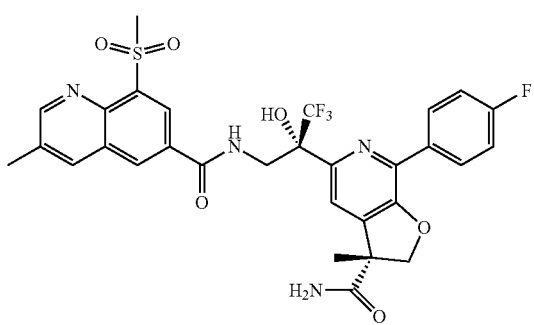 [SMILES: Cc1cnc2c(S(C)(=O)=O)cc(C(=O)NC[C@](O)(c3cc4c(c(-c5ccc(F)cc5)n3)OC[C@]4(C)C(N)=O)C(F)(F)F)cc2c1]

Example 648 Step a (Method X)

To a 4 mL vial equipped with a stir bar was added a 4 mL vial was charged with 8-iodo-3-methylquinoline-6-carboxylic acid (196.0 mg, 0.626 mmol), (2S,4R)—N-(2,6-dimethylphenyl)-4-hydroxypyrrolidine-2-carboxamide (58.7 mg, 0.250 mmol), CuI, potassium phosphate (133 mg, 0.626 mmol) sodium methanesulfinate (77 mg, 0.751 mmol), the solids were dissolved in DMSO (1.6 M) and the mixture was stirred at 100° C. for 16 h. The reaction mixture was then diluted with EtOAc, filtered through celite and concentrated. The residue was purified by automated column chromatography (silica gel $R_f$=0.20 in ethyl acetate) to afford a brown solid (53 mg, 32%). ESI-MS m/z: 265.7 [M+H]⁺.

Example 648 Step b

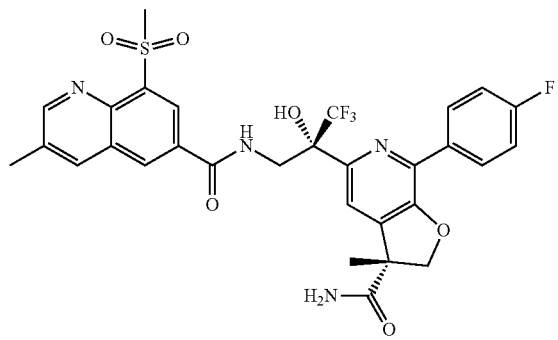 [SMILES: Cc1cnc2c(S(C)(=O)=O)cc(C(=O)NC[C@](O)(c3cc4c(c(-c5ccc(F)cc5)n3)OC[C@]4(C)C(N)=O)C(F)(F)F)cc2c1]

The title compound was prepared according to Method J with step a (25 mg) and PyBOP. The crude material was purified by Shimadzu prep-HPLC (20-95%, MeCN/Water, 0.1% formic acid, 25 min) to afford the title compound as a white solid (23 mg, 38%) as a white solid. ESI-MS m/z: 647.2 [M+H]$^+$.

Example 649 Step a (Method X)

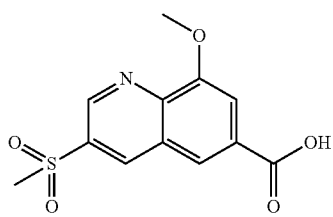 [SMILES: COc1cc(C(=O)O)cc2cc(S(C)(=O)=O)cnc12]

The compound was prepared according to Method X, and the resulting residue was purified by automated column chromatography (silica gel R$_f$=0.20 in ethyl acetate) to afford a brown solid (32 mg, 32%). ESI-MS m/z: 281.7, 283.6 [M+H]$^+$.

Example 649 Step b

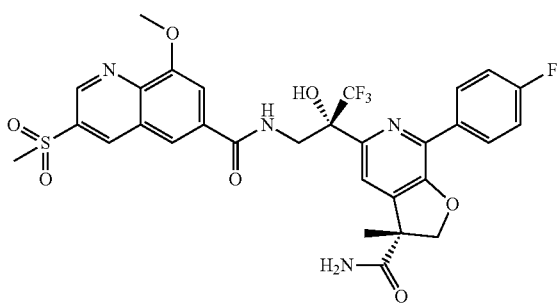 [SMILES: COc1cc(C(=O)NC[C@](O)(c2cc3c(c(-c4ccc(F)cc4)n2)OC[C@]3(C)C(N)=O)C(F)(F)F)cc2cc(S(C)(=O)=O)cnc12]

The title compound was prepared according to Method J with step a (16 mg) and PyBOP. The crude material was purified by Shimadzu prep-HPLC (20-95%, MeCN/Water, 0.1% formic acid 25 min) to afford the title compound as a white solid (7 mg, 20%) as a white solid. ESI-MS m/z: 663.1 [M+H]$^+$.

Example 650

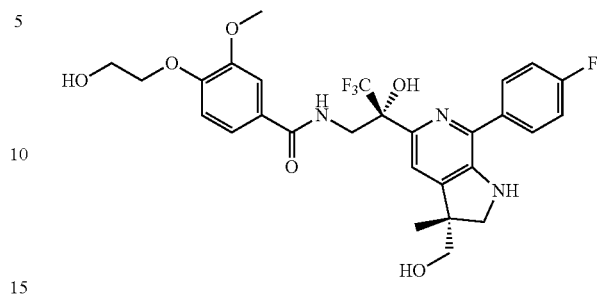

Example 650 Step a

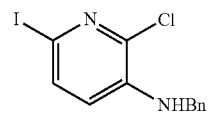

To a 50-mL round bottom flask equipped with a stir bar was charged 2,6-dichloropyridin-3-amine (0.489 g, 3 mmol) and benzaldehyde (0.350 g, 3.30 mmol) followed by ethyl acetate (6 mL). Then trifluoroacetic acid (0.462 ml, 6.00 mmol) was added dropwise at room temperature. After stirred for 5 min, sodium triacetoxyborohydride (0.763 g, 3.60 mmol) was added as a solid over 1 min, accompanied by an increase in temperature to ~ 40° C. After 30 min stirring, the mixture was homogeneous and LC-MS analysis indicated complete consumption of the arylamine. The reaction was added aqueous NaOH solution (20%) to adjust the pH to 8-9 and then extracted with EtOAc. The combined organic layer was dried over MgSO$_4$, filtered and concentrated. The crude residue was purified by automated column chromatography (silica gel, R$_f$=0.75 in 50% ethyl acetate in hexanes) and dried under high vacuum to give the title compound as a yellow oil (0.54 g, 71%). ESI-MS m/z: 254.0 [M+H]$^+$.

Example 650 Step b

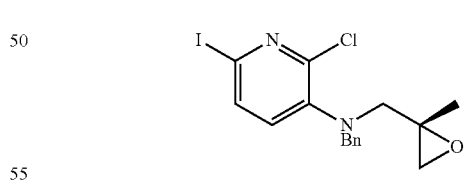

To a 50-mL round bottom flask containing the compound from step a (3600 mg, 10.45 mmol in DMF (10 mL) was added a stir bar. The flask was cooled to 0° C. and added sodium hydride (627 mg, 15.67 mmol) in 2 min. The reaction was stirred for 15 min at 0° C. and (R)-(2-methyloxiran-2-yl)methyl 4-methylbenzenesulfonate (2531 mg, 10.45 mmol) was added (as 30 mL solution in DMF). The reaction was stirred at room temperature for 12 hours. The reaction was then quenched with NaHCO$_3$ (aq) and extracted with EtOAc. The combined organic layer was washed by water, dried over MgSO$_4$, filtered and concen-

Example 650 Step c

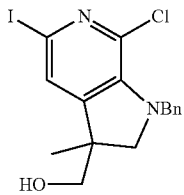

To a 100-mL round bottom flask containing the compound from step b (1130 mg, 2.73 mmol) in THF (27.3 ml) was added a stir bar, and the flask was purged with nitrogen. The flask was cooled at 0° C. and added LDA (1998 µl, 3.00 mmol) dropwise. The reaction was stirred at 0° C. for 5 min then stirred at 35° C. for 4 hr. The reaction was quenched with EtOAc/water and extracted with EtOAc. The combined organic layer was washed by water, dried over MgSO$_4$, filtered and concentrated. The crude residue was purified by automated column chromatography (silica gel, R$_f$=0.5 in 60% ethyl acetate in hexanes) and dried under high vacuum to give the title compound as a yellow oil (360 mg, 32%, e.r.=2:1). ESI-MS m/z: 414.6/415.6 [M+H]$^+$.

Example 650 Step d

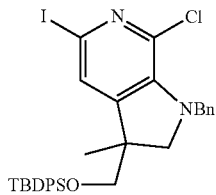

To a 250-mL round bottom flask containing the compound from step c (1780 mg, 4.29 mmol) was added a stir bar. The residue was dissolved in DMF (10.73 ml) and then added 1H-imidazole (701 mg, 10.30 mmol) followed by tert-butylchlorodiphenylsilane (1416 mg, 5.15 mmol). The reaction was stirred overnight. The reaction was then quenched with NaHCO$_3$ (aq) and extracted with EtOAc. The combined organic layer was washed with water, dried over MgSO$_4$, filtered and concentrated. The crude residue was purified by automated column chromatography (silica gel, R$_f$=0.5 in 20% ethyl acetate in hexanes) and dried under high vacuum to give the title compound as a yellow oil (1.70 g, 61%, e.r.=2:1). ESI-MS m/z: 653.1 [M+H]$^+$.

Example 650 Step e

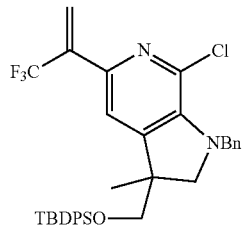

To a 30 mL microwave vial containing the compound from step d (817 mg, 1.25 mmol) was added a stir bar. The residue was dissolved in DME/water (12.5 mL, 4:1), and cesium carbonate (812 mg, 2.50 mmol), PdCl$_2$(dppf) (92 mg, 0.125 mmol) were added followed by 2-(4-fluorophenyl)-4,4,5,5-tetramethyl-1,3,2-dioxaborolane (557 mg, 2.50 mmol). The reaction mixture was purged with nitrogen and heated at 90° C. for 40 min under microwave irradiation. The reaction was then diluted with water/EtOAc and extracted with EtOAc. The combined organic layer was dried over MgSO$_4$, filtered and concentrated. The crude residue was purified by automated column chromatography (silica gel, R$_f$=0.5 in 20% ethyl acetate in hexanes) and dried under high vacuum to give the title compound as a colorless oil (735 mg, 90%, e.r.=2:1). ESI-MS m/z: 622.0 [M+H]$^+$.

Example 650 Step f

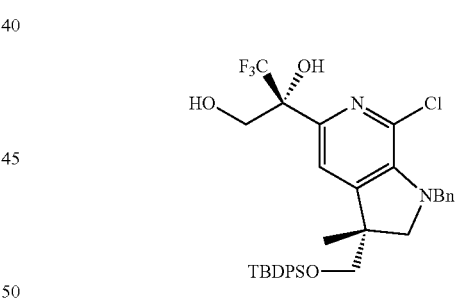

To a 50-mL round bottom flask containing the compound from step e (400 mg, 0.644 mmol) was added a stir bar. The residue was dissolved in t-Butanol (5.37 ml) and Water (5.37 ml) at room temperature. Methanesulfonamide (61.2 mg, 0.644 mmol) was added followed AD-mix beta (1003 mg, 1.288 mmol). The mixture was stirred at room temperature for 48 hours (LC-MS showed >50% conversion). The reaction was quenched with sat. aqueous Na$_2$SO$_3$ solution and extracted with EtOAc. The combined organic layer was dried over MgSO$_4$, filtered and concentrated. The crude residue was purified by automated column chromatography (silica gel, R$_f$=0.5 in 50% ethyl acetate in hexanes) and dried under high vacuum to give the title compound as a white foam (100 mg, 24%). ESI-MS m/z: 656.1 [M+H]$^+$.

--- trated. The crude residue was purified by automated column chromatography (silica gel, R$_f$=0.5 in 40% ethyl acetate in hexanes) and dried under high vacuum to give the title compound as a yellow oil (2.80 g, 65%). ESI-MS m/z: 414.6/415.6 [M+H]$^+$.

Example 650 Step g

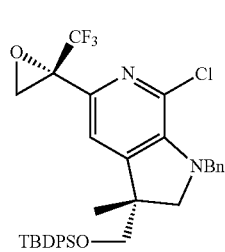

To a 25-mL round bottom flask containing the compound from step f (400 mg, 0.610 mmol) was added a stir bar. The residue was dissolved in THF (6.10 ml) and the flask was cooled to 0° C. Sodium hydride (61.0 mg, 1.526 mmol) was added to the reaction (gas evolution) and the reaction was allowed to stir for 1 hour at 0° C. before 4-methylbenzenesulfonyl chloride (140 mg, 0.733 mmol) was added. The reaction was stirred for 1 hour then warmed to room temperature and stirred for another 1 hour. The reaction was quenched with water and extracted with EtOAc. The combined organic layer was dried over MgSO$_4$, filtered and concentrated. The crude residue was purified by automated column chromatography (silica gel, R$_f$=0.5 in 30% ethyl acetate in hexanes) and dried under high vacuum to give the title compound as a white foam (330 mg, 85%). ESI-MS m/z: 638.1 [M+H]$^+$.

Example 650 Step h

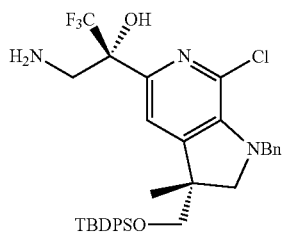

To a 25-mL round bottom flask containing the compound from step g (330 mg, 0.518 mmol) was added a stir bar. The residue was dissolved in DMF (8.63 ml) at room temperature. Ammonium hydroxide (626 μl, 5.18 mmol) was added and the reaction was stirred overnight. The reaction was quenched with water and extracted with DCM. The combined organic layer was washed with DCM, dried over MgSO$_4$, filtered and concentrated. The crude residue (300 mg) was taken to the next reaction without further purification. ESI-MS m/z: 655.1 [M+H]$^+$.

Example 650 Step i

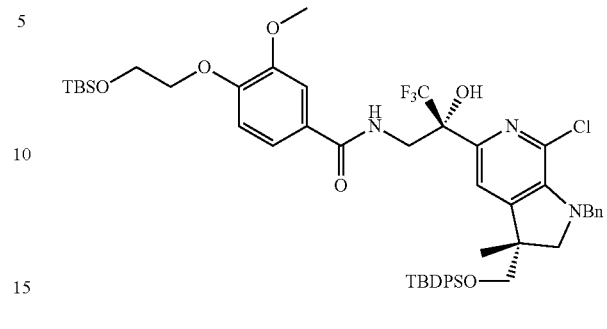

The title compound was synthesized using step h (300 mg, 0.459 mmol) according to Method J. The crude residue was purified by automated column chromatography (silica gel, R$_f$=0.5 in 50% ethyl acetate in hexanes) and dried under high vacuum to give the title compound as a white foam (250 mg, 57%). ESI-MS m/z: 963.4 [M+H]$^+$.

Example 650 Step j

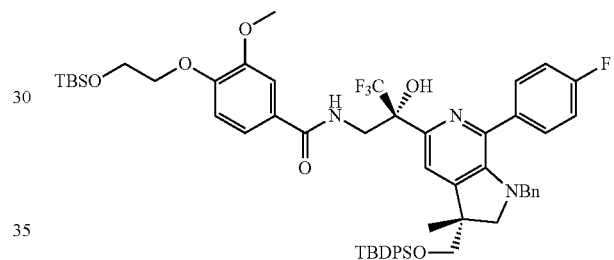

To a 5-mL microwave vial containing the compound from step i (57 mg, 0.059 mmol) was added a stir bar. The residue was dissolved in 1,4-dioxane/water (9:1, 0.8 mL) and the vial was added (4-fluorophenyl)boronic acid (41 mg, 0.390 mmol), cesium carbonate (39 mg, 0.156 mmol) followed by PdCl$_2$(dppf) (6 mg, 0.01 mmol). The mixture was degassed for 5 min using nitrogen. The vial was then sealed and heated at 130° C. for 2 hours. The reaction was diluted with water and extracted with EtOAc. The combined organic layer was dried over MgSO$_4$, filtered and concentrated. The crude residue was purified by automated column chromatography (silica gel, R$_f$=0.5 in 50% ethyl acetate in hexanes) and dried under high vacuum to give the title compound as a white foam (30 mg, 50%). ESI-MS m/z: 1023.0 [M+H]$^+$.

Example 650 Step k

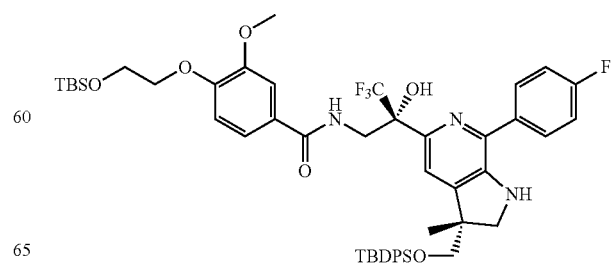

To a 10-mL round bottom flask containing the compound from step j (30 mg, 0.029 mmol) was added a stir bar. The residue was dissolved in MeOH/EtOH (1:1, 2.0 mL) and the flask was added palladium hydroxide (4 mg, 0.003 mmol). The reaction was stirred under a hydrogen balloon (1 atm) for 12 hr. The reaction was diluted with EtOAc and filtered. The filtrate was concentrated to give the crude residue, which was carried to the next step without purification. ESI-MS m/z: 818.3 [M+H]$^+$.

Example 650 Step 1

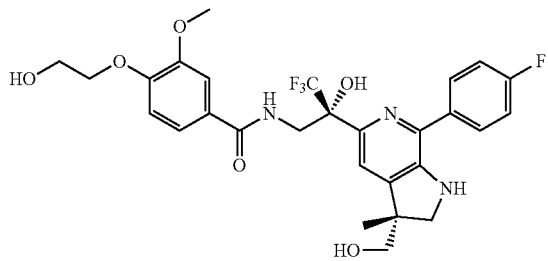 [SMILES: COc1cc(C(=O)NC[C@](O)(c2cc3c(c(-c4ccc(F)cc4)n2)NC[C@]3(C)CO)C(F)(F)F)ccc1OCCO]

To a 4-mL vial containing the compound from step k (25 mg, 0.030 mmol) was added a stir bar. The residue was added TBAF (1.0 M in THF solution, 0.3 mL, 0.3 mmol) at 0° C. The reaction was stirred at room temperature for 6 hours. The reaction was quenched with aqueous ammonium chloride solution and extracted with EtOAc. The combined organic layer was dried over MgSO$_4$, filtered and concentrated. The crude residue was purified by automated column chromatography (silica gel, R$_f$=0.8 in 10% MeOH in CH$_2$C$_2$) and dried under high vacuum to give the title compound as a white foam (7.0 mg, 40% for 2 steps). ESI-MS m/z: 580.1[M+H]$^+$.

The following Table 13 contains examples that were prepared according to Method J (PyBOP or HATU). The majority of compounds were purified by Gilson prep-HPLC, and some were purified by automated column chromatography (silica gel). The aryl acid coupling partners were prepared according to Methods S, U, V, W or previously described methods.

TABLE 13

| Example | Structure | MS$^+$ m/z |
|---|---|---|
| 651 | 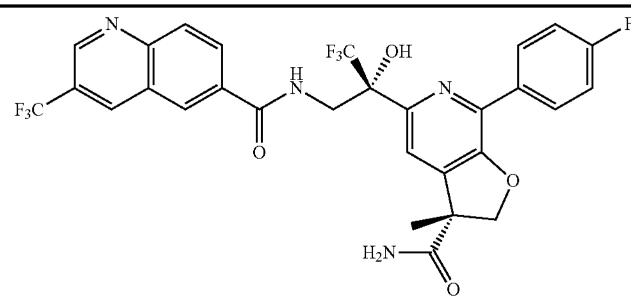 | 623.05 |
| 652 | 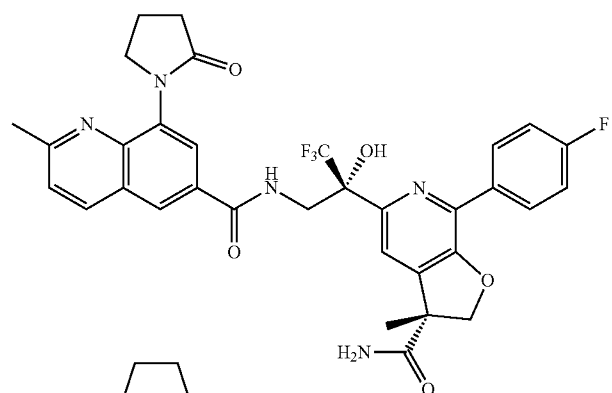 [SMILES: Cc1ccc2cc(C(=O)NC[C@](O)(c3cc4c(c(-c5ccc(F)cc5)n3)OC[C@]4(C)C(N)=O)C(F)(F)F)cc(N3CCCC3=O)c2n1] | 652.22 |
| 653 | 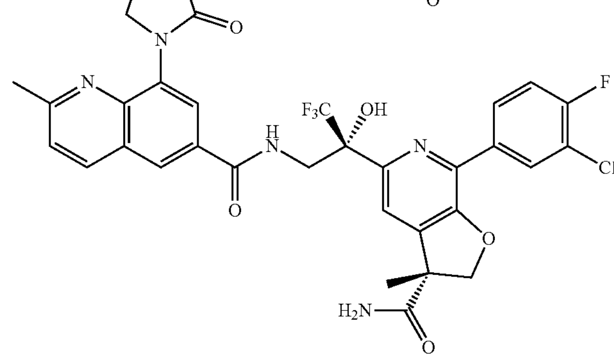 | 686.18 |

TABLE 13-continued

| Example | Structure | MS+ m/z |
|---|---|---|
| 654 | 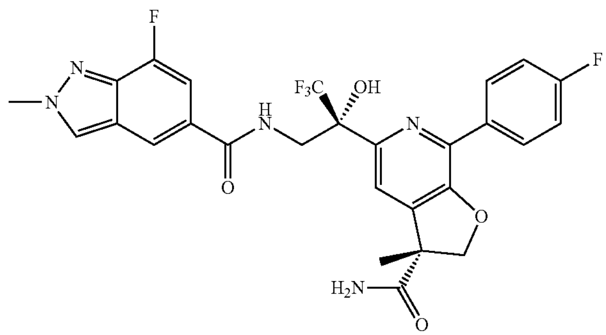 [SMILES: Cn1cc2cc(C(=O)NC[C@](O)(c3cc4c(c(-c5ccc(F)cc5)n3)OC[C@]4(C)C(N)=O)C(F)(F)F)cc(F)c2n1] | 576.16 |
| 655 | 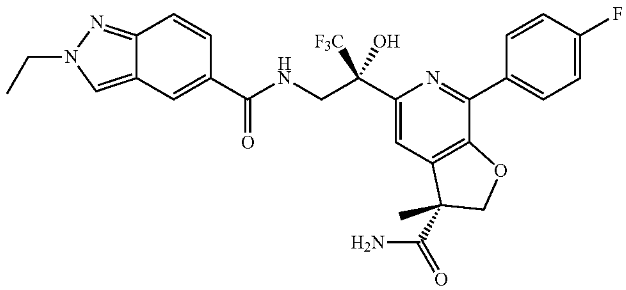 [SMILES: CCn1cc2cc(C(=O)NC[C@](O)(c3cc4c(c(-c5ccc(F)cc5)n3)OC[C@]4(C)C(N)=O)C(F)(F)F)ccc2n1] | 572.19 |
| 656 | 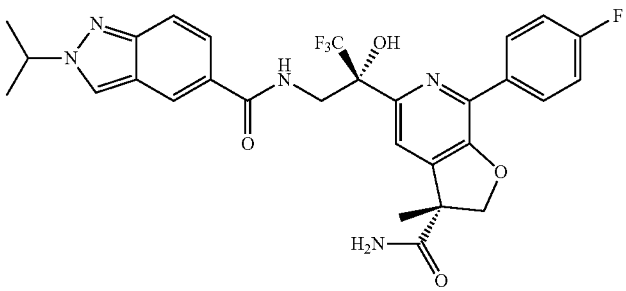 [SMILES: CC(C)n1cc2cc(C(=O)NC[C@](O)(c3cc4c(c(-c5ccc(F)cc5)n3)OC[C@]4(C)C(N)=O)C(F)(F)F)ccc2n1] | 582.21 |
| 657 | 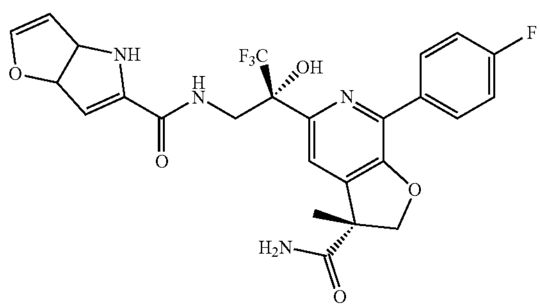 [SMILES: C[C@]1(C(N)=O)COc2c1cc([C@@](O)(CNC(=O)C1=CC3OC=CC3N1)C(F)(F)F)nc2-c1ccc(F)cc1] | 533.10 |
| 658 | 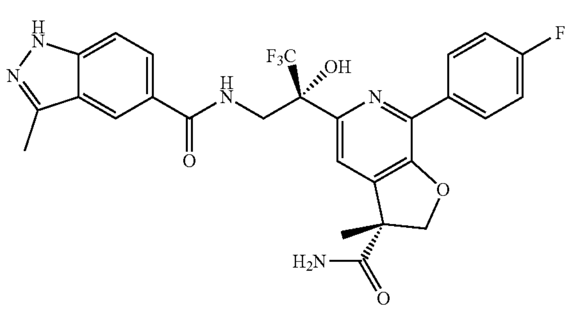 [SMILES: Cc1n[nH]c2ccc(C(=O)NC[C@](O)(c3cc4c(c(-c5ccc(F)cc5)n3)OC[C@]4(C)C(N)=O)C(F)(F)F)cc12] | 558.21 |

TABLE 13-continued
| Example | Structure | MS+ m/z |
|---|---|---|
| 659 | 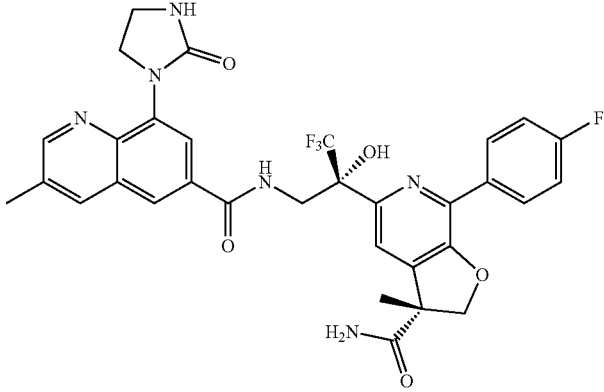 [SMILES: Cc1cnc2c(N3CCNC3=O)cc(C(=O)NC[C@](O)(c3cc4c(c(-c5ccc(F)cc5)n3)OC[C@]4(C)C(N)=O)C(F)(F)F)cc2c1] | 653.32 |
| 660 | 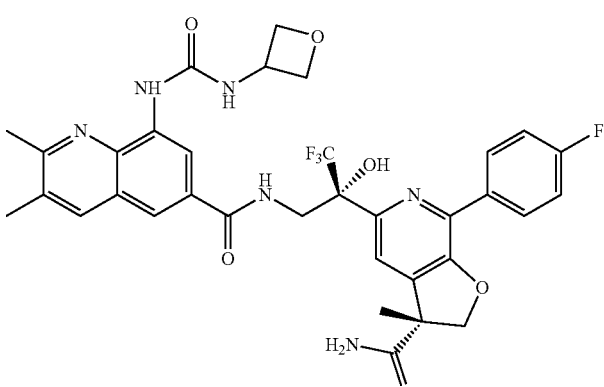 | 697.24 |
| 661 | 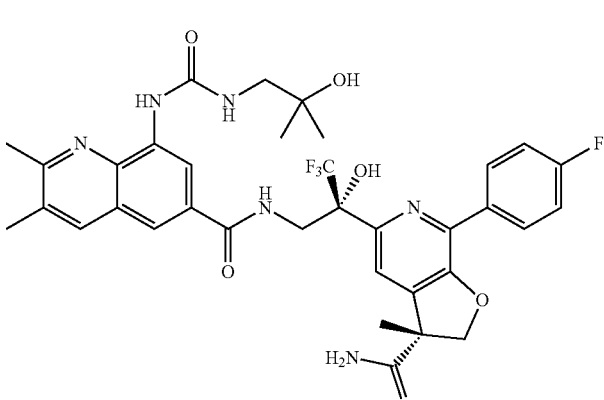 | 713.28 |
| 662 | 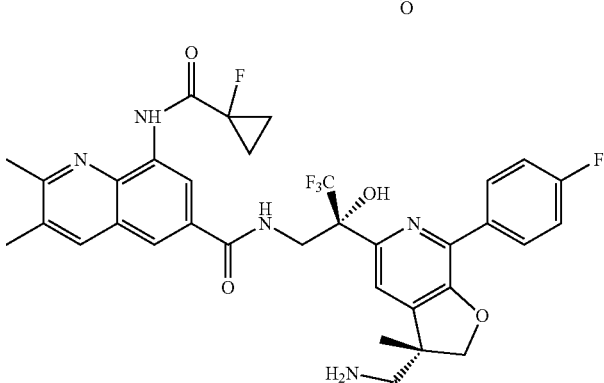 | 684.22 |

The following examples in Table 14 are prepared by using procedures similar to those described above:
TABLE 14
| Entry | Compound |
|---|---|
| P-1 | 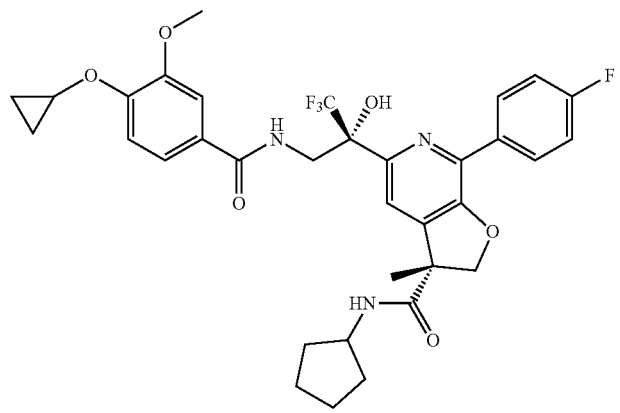 |
| P-2 | 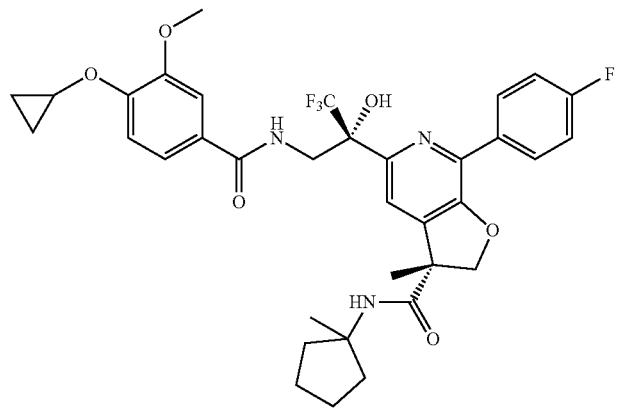 |
| P-3 | 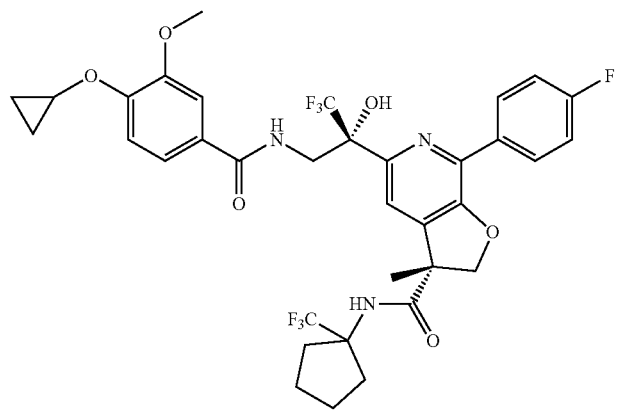 |

TABLE 14-continued

| Entry | Compound |
|---|---|
| P-4 | |
| P-5 | |
| P-6 | |
| P-7 | |

TABLE 14-continued
| Entry | Compound |
|---|---|
| P-8 | 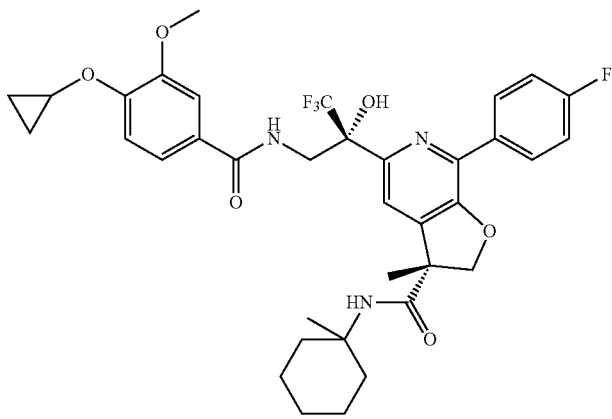 |
| P-9 | 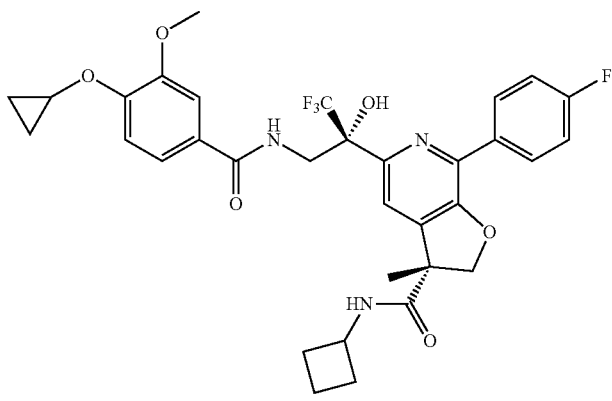 |
| P-10 | 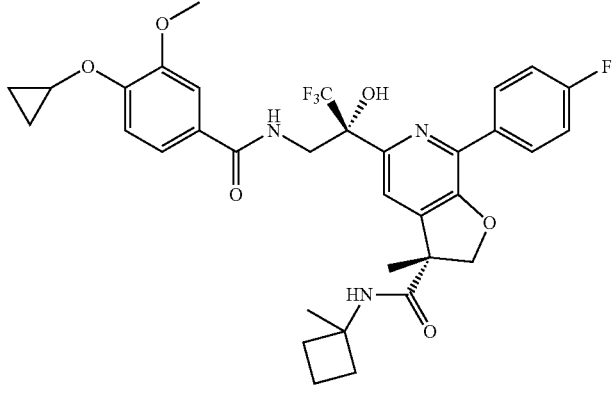 |
| P-11 | 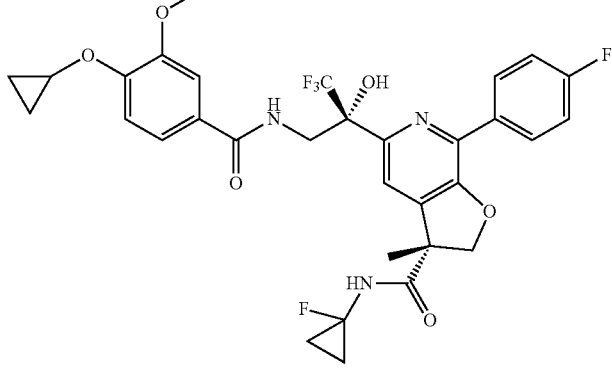 |

TABLE 14-continued

| Entry | Compound |
|---|---|
| P-12 | |
| P-13 | |
| P14 | |
| P-15 | |

TABLE 14-continued

| Entry | Compound |
|---|---|
| P-16 | |
| P-17 | |
| P-18 | |
| P-19 | |

TABLE 14-continued

| Entry | Compound |
|---|---|
| P-20 | |
| P-23 | |
| P-24 | |
| P-25 | |

TABLE 14-continued

| Entry | Compound |
|---|---|
| P-26 | |

Example 663

Example 663 Step a

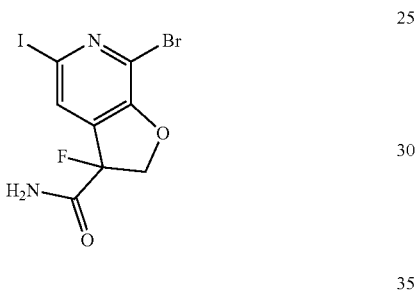

To a 20 mL vial equipped with a stir bar was added N-fluoro-N-(phenylsulfonyl) benzenesulfonamide (963 mg, 3.05 mmol) and methyl 7-bromo-5-iodo-2,3-dihydrofuro[2,3-c]pyridine-3-carboxylate (586 mg, 1.526 mmol), and the solids were dissolved in THF (0.25M). The vial was cooled to −78° C., and LDA (916 µl, 1.831 mmol) was slowly added. The reaction was stirred at −78° C. for 1 hr. After 1 hr at −78° C., reaction gelled up. The reaction was warmed to rt and stirred and monitored by LCMS. The reaction was diluted with EtOAc and quenched with water and sat. ammonium chloride. EtOAc and DCM/MeOH 1× each extraction with a phase separator cartridge. Concentrated. The material was purified by automated column chromatography (0-1900% EtOAc/cHex) to afford the title compound (483 mg, 71%). ESI-MS m/z: 401.86/403.86 [M+H]⁺.

Example 663 Step b

To a 20 mL vial containing step a (483 mg, 1.081 mmol) was added and stir bar, and the material was dissolved in THF/MeOH, and Water (1:1:1, 0.25 M). Lithium hydroxide hydrate (113 mg, 2.70 mmol) was added, the reaction stirred at room temperature and monitored by LCMS. The reaction was diluted with EtOAc and acidified to pH=2 with 2M HCl. EtOAc and DCM/MeOH extraction with a phase separator cartridge. The material was tritterated with DCM/hexanes to afford an orange solid. (455 mg, 92%) ESI-MS m/z: 387.82/387.82 [M+H]⁺.

Example 663 Step c

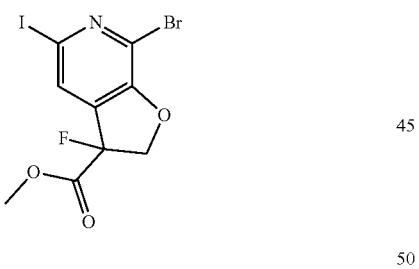

The above compound was prepared in an analogous fashion to Intermediate 36 step b. The crude material was purified by automated column chromatography (silica gel, 0-100% EtOAc/cHex) to afford the title compound as an orange oil (243 mg, 43%) ESI-MS m/z: 386.33 [M+H]⁺.

Example 664

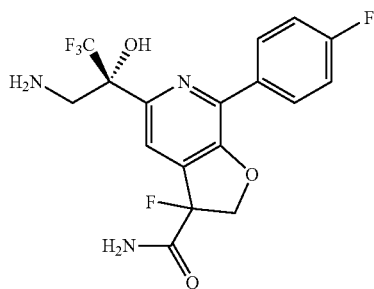 [SMILES: NC[C@](O)(c1cc2c(c(-c3ccc(F)cc3)n1)OCC2(F)C(N)=O)C(F)(F)F]

The above example was prepared in an analogous sequence to Intermediate 36 as a mixture of diastereomers to afford the desired amino alcohol (42 mg). ESI-MS m/z: 404.09 [M+H]$^+$.

The following Table 15 contains examples that were prepared with the similar method to Method J (PyBOP or HATU). The amine coupling partners were prepared as a mixture of diastereomers. The majority of compounds were purified by Gilson prep-HPLC. If depicted as a single diasteromer, the diastereomers were separated on Gilson prep-HPLC.

TABLE 15

| Example | Structure | MS$^+$ m/z |
|---|---|---|
| 665 | 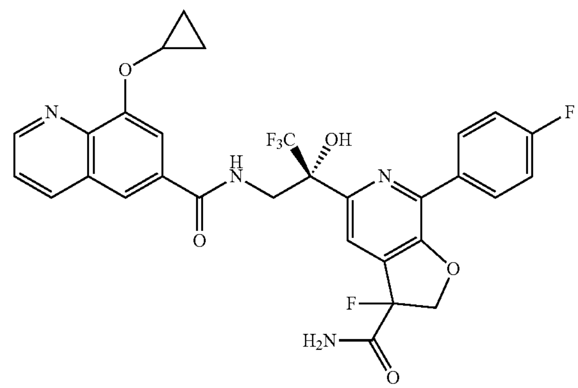 [SMILES: NC(=O)C1(F)COc2c1cc([C@@](O)(CNC(=O)c1cc(OC3CC3)c3ncccc3c1)C(F)(F)F)nc2-c1ccc(F)cc1] | 615.16 |
| 666 | 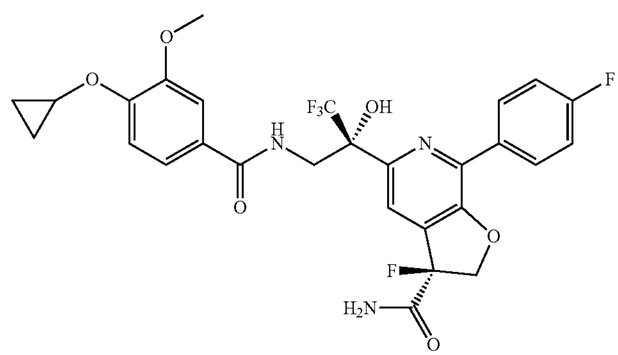 [SMILES: COc1cc(C(=O)NC[C@](O)(c2cc3c(c(-c4ccc(F)cc4)n2)OC[C@]3(F)C(N)=O)C(F)(F)F)ccc1OC1CC1] | 594.15 |
| 667 | 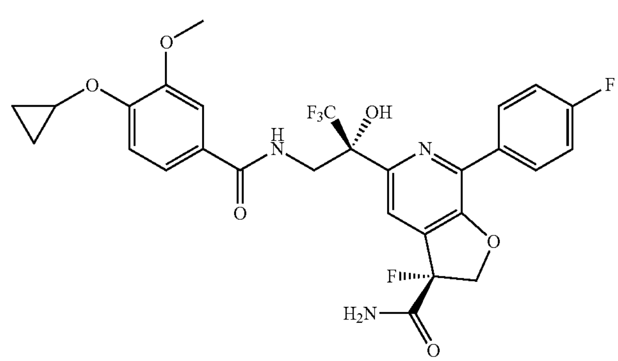 [SMILES: COc1cc(C(=O)NC[C@](O)(c2cc3c(c(-c4ccc(F)cc4)n2)OC[C@@]3(F)C(N)=O)C(F)(F)F)ccc1OC1CC1] | 594.15 |

TABLE 15-continued

| Example | Structure | MS+ m/z |
|---------|-----------|---------|
| 668 | 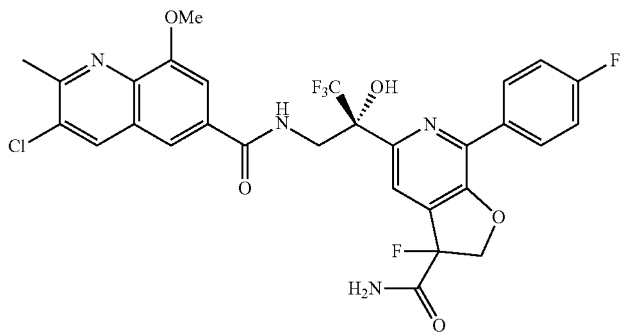 [SMILES: COc1cc(C(=O)NC[C@](O)(c2cc3c(c(-c4ccc(F)cc4)n2)OCC3(F)C(N)=O)C(F)(F)F)cc2cc(Cl)c(C)nc12] | 636.98 |
| 669 | 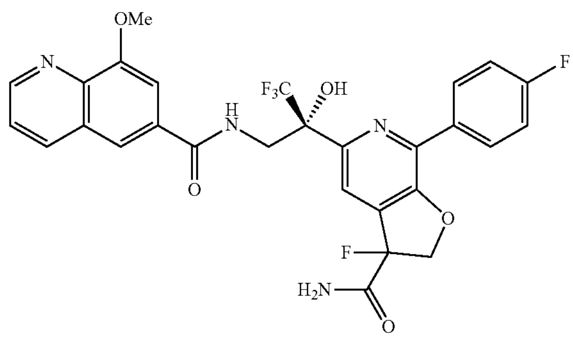 [SMILES: COc1cc(C(=O)NC[C@](O)(c2cc3c(c(-c4ccc(F)cc4)n2)OCC3(F)C(N)=O)C(F)(F)F)cc2cccnc12] | 589.04 |
| 670 | 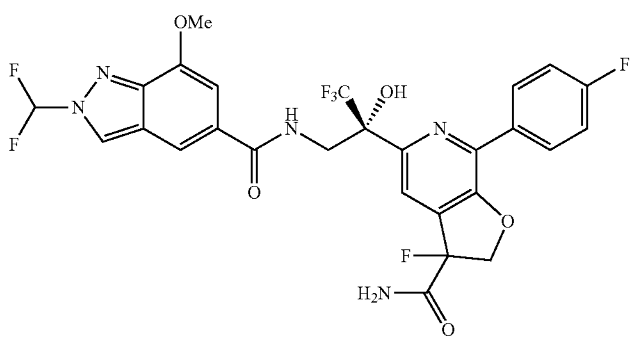 [SMILES: COc1cc(C(=O)NC[C@](O)(c2cc3c(c(-c4ccc(F)cc4)n2)OCC3(F)C(N)=O)C(F)(F)F)cc2cn(C(F)F)nc12] | 627.82 |
| 671 | 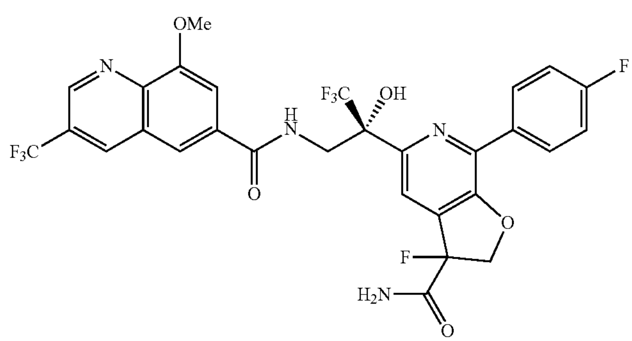 [SMILES: COc1cc(C(=O)NC[C@](O)(c2cc3c(c(-c4ccc(F)cc4)n2)OCC3(F)C(N)=O)C(F)(F)F)cc2cc(C(F)(F)F)cnc12] | 656.92 |

TABLE 15-continued

| Example | Structure | MS+ m/z |
|---|---|---|
| 672 | 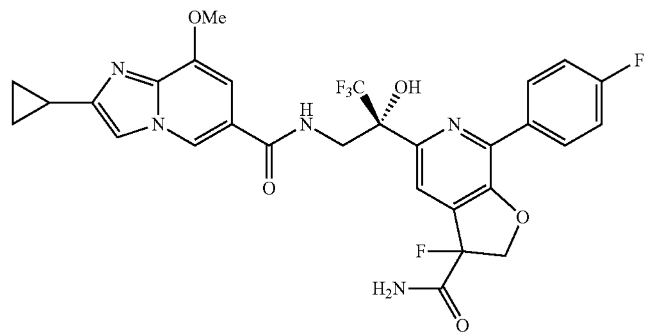 [SMILES: COc1cc(C(=O)NC[C@](O)(c2cc3c(c(-c4ccc(F)cc4)n2)OCC3(F)C(N)=O)C(F)(F)F)cn2cc(C3CC3)nc12] | 618.11 |
| 673 | 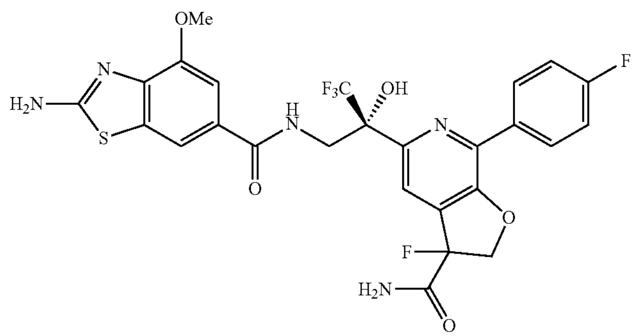 [SMILES: COc1cc(C(=O)NC[C@](O)(c2cc3c(c(-c4ccc(F)cc4)n2)OCC3(F)C(N)=O)C(F)(F)F)cc2sc(N)nc12] | 597.91 |
| 674 | 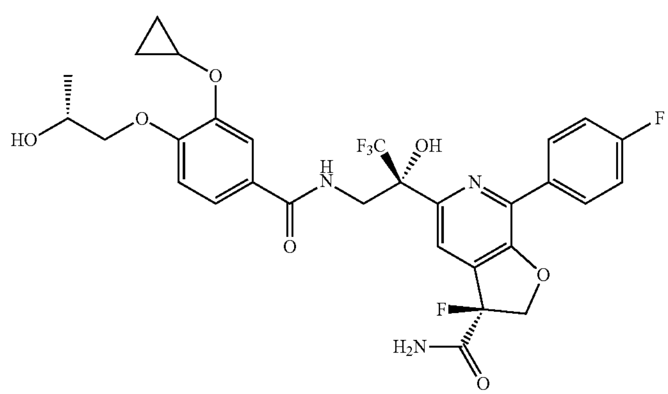 [SMILES: C[C@@H](O)COc1ccc(C(=O)NC[C@](O)(c2cc3c(c(-c4ccc(F)cc4)n2)OC[C@]3(F)C(N)=O)C(F)(F)F)cc1OC1CC1] | 637.96 |
| 675 | 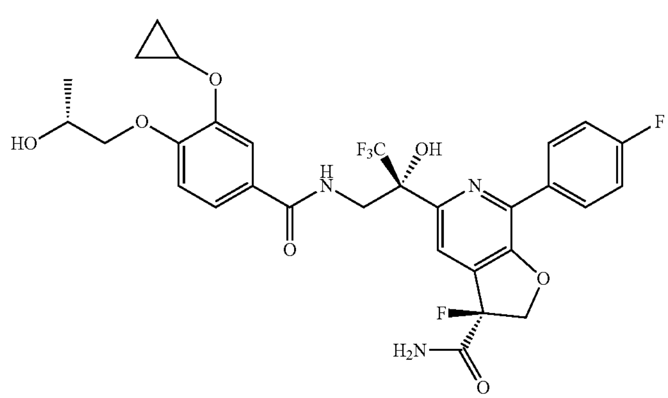 [SMILES: C[C@@H](O)COc1ccc(C(=O)NC[C@](O)(c2cc3c(c(-c4ccc(F)cc4)n2)OC[C@]3(F)C(N)=O)C(F)(F)F)cc1OC1CC1] | 638.01 |

TABLE 15-continued

| Example | Structure | MS⁺ m/z |
|---|---|---|
| 676 | (structure) | 617.90 |

The following examples in Table 16 are prepared by using procedures similar to those described above:

TABLE 16

| Entry | Compound |
|---|---|
| P-25 | (structure) |
| P-26 | (structure) |
| P-27 | (structure) |

TABLE 16-continued

| Entry | Compound |
|---|---|
| P-28 | |
| P-29 | |
| P-30 | |
| P-31 | |

TABLE 16-continued

| Entry | Compound |
|---|---|
| P-32 | |
| P-33 | |
| P-34 | |
| P-35 | |

TABLE 16-continued
| Entry | Compound |
|---|---|
| P-36 | 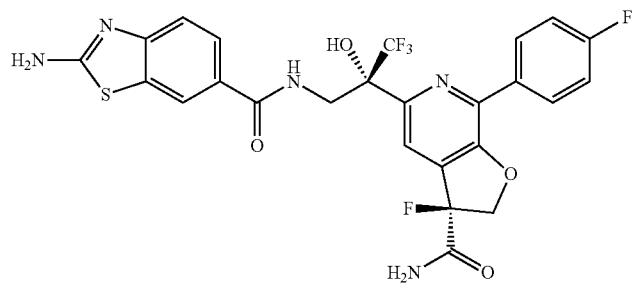 |
| P-37 | 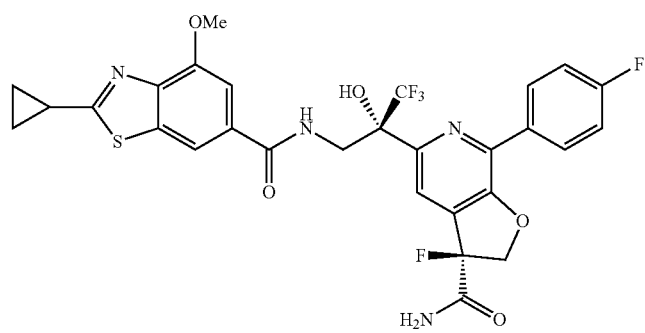 [SMILES: COc1cc(C(=O)NC[C@](O)(c2cc3c(c(-c4ccc(F)cc4)n2)OC[C@]3(F)C(N)=O)C(F)(F)F)cc2sc(C3CC3)nc12] |
| P-38 | 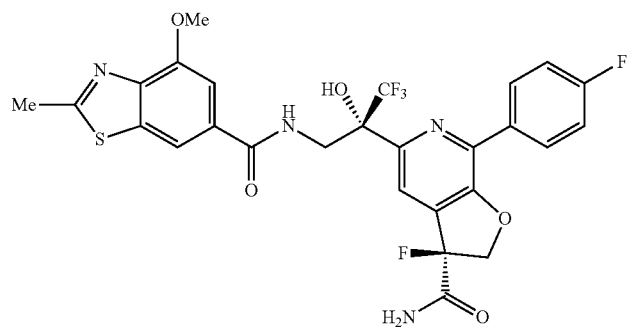 [SMILES: COc1cc(C(=O)NC[C@](O)(c2cc3c(c(-c4ccc(F)cc4)n2)OC[C@]3(F)C(N)=O)C(F)(F)F)cc2sc(C)nc12] |
| P-39 | 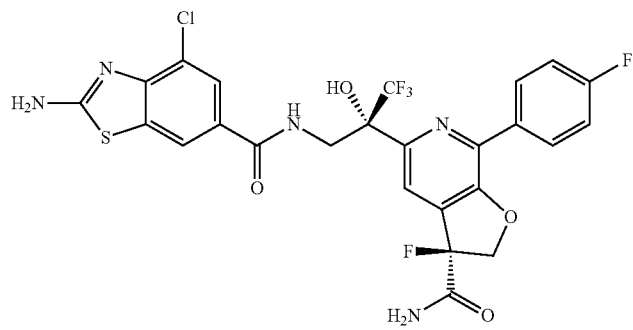 [SMILES: NC(=O)[C@@]1(F)COc2c1cc([C@@](O)(CNC(=O)c1cc(Cl)c3nc(N)sc3c1)C(F)(F)F)nc2-c1ccc(F)cc1] |

TABLE 16-continued
| Entry | Compound |
|---|---|
| P-40 | 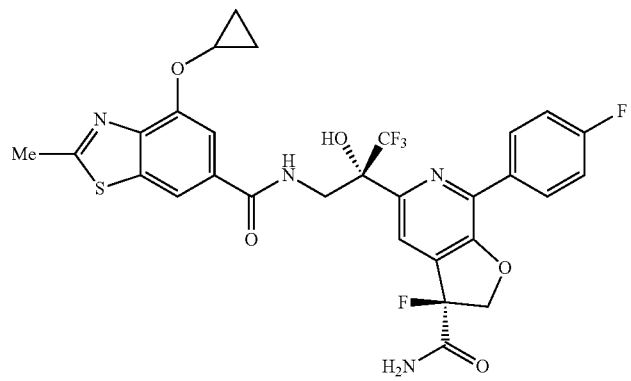 [SMILES: Cc1nc2c(OC3CC3)cc(C(=O)NC[C@](O)(c3cc4c(c(-c5ccc(F)cc5)n3)OC[C@]4(F)C(N)=O)C(F)(F)F)cc2s1] |
| P-41 | 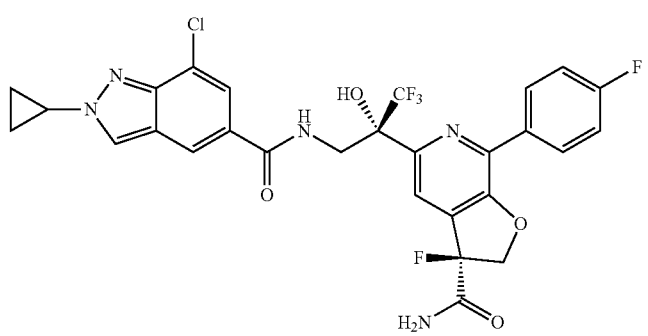 [SMILES: NC(=O)[C@@]1(F)COc2c1cc([C@@](O)(CNC(=O)c1cc(Cl)c3nn(C4CC4)cc3c1)C(F)(F)F)nc2-c1ccc(F)cc1] |
| P-42 | |
| P-43 | 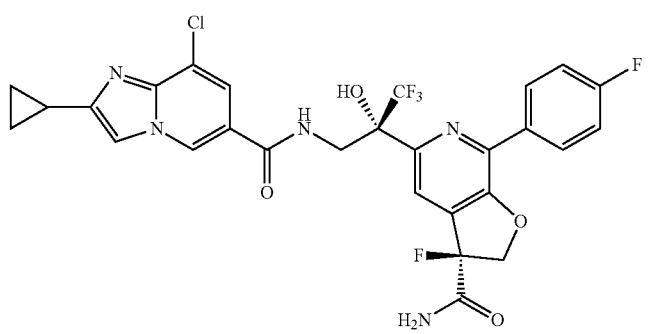 [SMILES: NC(=O)[C@@]1(F)COc2c1cc([C@@](O)(CNC(=O)c1cc(Cl)c3nc(C4CC4)cn3c1)C(F)(F)F)nc2-c1ccc(F)cc1] |

TABLE 16-continued
| Entry | Compound |
|---|---|
| P-44 | 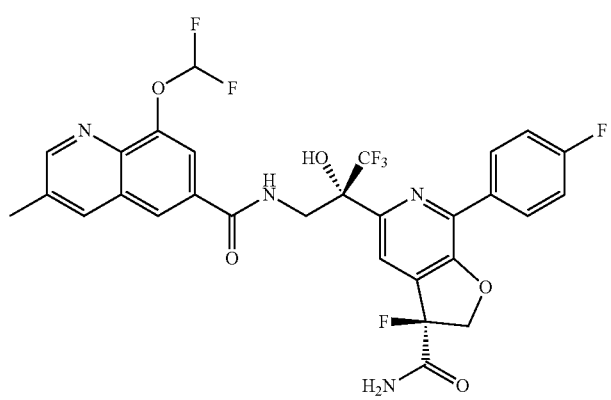 [SMILES: Cc1cnc2c(OC(F)F)cc(C(=O)NC[C@](O)(c3cc4c(c(-c5ccc(F)cc5)n3)OC[C@]4(F)C(N)=O)C(F)(F)F)cc2c1] |
| P-45 | 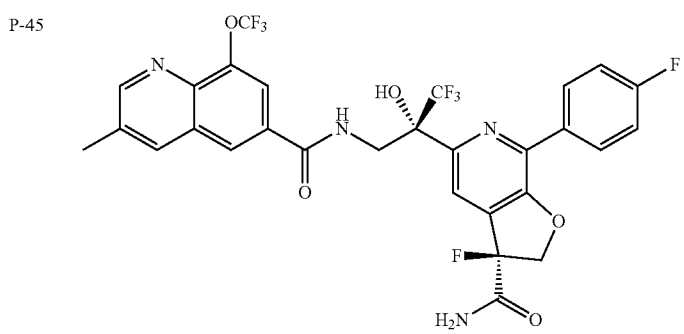 |
| P-46 | 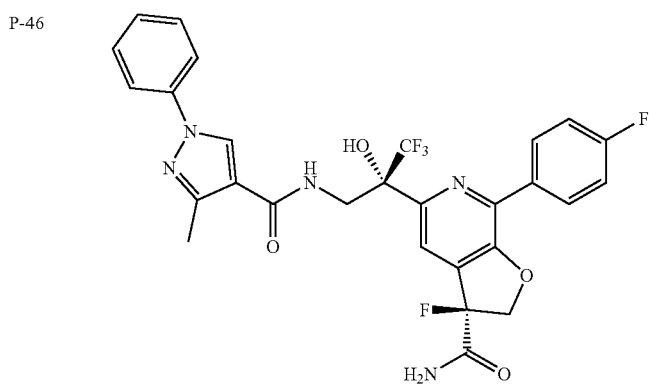 |
| P-47 | 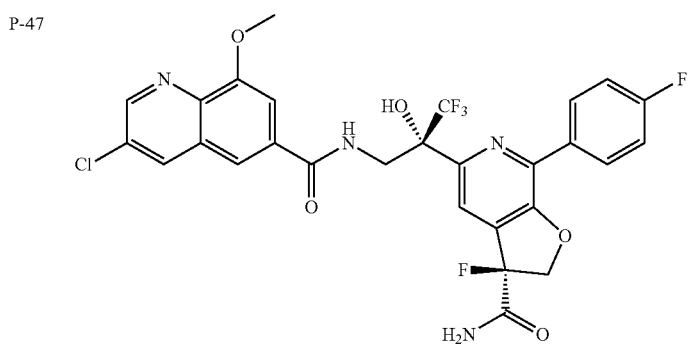 |

TABLE 16-continued

| Entry | Compound |
|---|---|
| P-48 | (2-methylbenzoxazole-6-carboxamide linked to a chiral 2-hydroxy-3,3,3-trifluoropropyl group attached to a pyridine bearing a 4-fluorophenyl substituent and fused to a fluorinated dihydrofuran bearing a primary carboxamide) |

Assays

Methods for RSV-A Assay

Hep-2 cells, (originally derived from tumors grown in irradiated-cortisonised weanling rats that had been injected with epidermoid carcinoma tissue from a 56 year old male's larynx, but later found to be indistinguishable from HeLa cells by PCR DNA analysis), were used for the culturing of genotype A, "Long" strain RSV. Flasks were inoculated with RSV and viral stocks were collected once cytopathic effect (CPE) was greater than 9000. Viral stocks in 2500 sucrose media were snap frozen using liquid nitrogen to increase viral stability. Viral stock titers were quantified by tissue culture infectious dose 50% ($TCID_{50}$) using 8,000 cells per well and 3-fold viral dilutions across a 96-well plate, cultured for 4 days. Viral stock titers were also quantified by a plaque forming unit assay, as described elsewhere.

Following extensive parameter testing, the final assay is run as follows: Hep-2 cells are seeded into the inner 60 wells of a 96-well plate at 8,000 cells per well in a volume of 50 µL using Growth Media (DMEM without phenol red, 1% L-Glut, 1% Penn/Strep, 1% nonessential amino acids, 10% heat-inactivated FBS). 2-fold serial dilutions of control and test compounds are added to the wells in duplicate in a total volume of 25 µL. Viral stock is then added to the wells at a multiplicity of infection (MOI) of 0.1 in a volume of 25 µL, bringing the total volume of each well to 100 µL. The MOI is calculated using the PFU/mL, or $TCID_{50}$ if unavailable. Each 96-well plate has a control column of 6 wells with cells and virus but no compound (negative control, max CPE), a column with cells but no compound or virus (positive control, minimum CPE), and a column with no cells or virus or compound (background plate/reagent control). The control wells with cells but no virus are given an additional 25 µL of growth media containing an equal quantity of sucrose as those wells receiving the viral stock in order to keep consistent in media and volume conditions. The outer wells of the plate are filled with 125 µL of moat media (DMEM, 1% Penn/Strep) to act as a thermal and evaporative moat around the test wells. Following a 5-day incubation period, the plates are read using ATPlite (50 uL added per well), which quantifies the amount of ATP (a measure of cell health) present in each well. Assay plates are read using the Envision luminometer. These data are used to calculate the $EC_{50}$ each compound (Table 17). $EC_{50}$ ranges are as follows: A<0.2 µM; B>0.2 µM.

TABLE 17

Summary of Activities for RSV-A

| Compound | Human RSV-A ("Long" strain) $EC_{50}$ | Compound | HumanRSV-A ("Long" strain) $EC_{50}$ |
|---|---|---|---|
| 3 | A | 4 | A |
| 5 | B | 6 | B |
| 7 | B | 8 | B |
| 9 | A | 10 | A |
| 11 | A | 12 | B |
| 13 | B | 17

TABLE 17-continued

Summary of Activities for RSV-A

| Compound | Human RSV-A ("Long" strain) $EC_{50}$ | Compound | HumanRSV-A ("Long" strain) $EC_{50}$ |
|---|---|---|---|
| 124 | A | 125 | A |
| 126 | A | 127 | A |
| 128 | A | 129 | A |
| 130 | B | 131 | A |
| 132 | B | 133 | A |
| 134 | B | 135 | A |
| 136 | A | 137 | A |
| 138 | A | 139 | B |
| 141 | A | 142 | B |
| 143 | B | 144 | B |
| 145 | B | 146 | B |
| 147 | B | 148 | B |
| 149 | B | 150 | A |
| 151 | A | 152 | B |
| 153 | B | 154 | B |
| 155 | B | 156 | B |
| 157 | B | 158 | B |
| 159 | A | 160 | B |
| 161 | B | 162 | B |
| 163 | B | 164 | B |
| 165 | B | 166 | A |
| 167 | B | 168 | A |
| 169 | B | 170 | B |
| 171 | A | 172 | B |
| 173 | B | 174 | B |
| 175 | A | 176 | B |
| 177 | B | 178 | B |
| 179 | A | 180 | A |
| 181 | A | 182 | A |
| 183 | A | 184 | A |
| 185 | A | 186 | A |
| 187 | A | 188 | B |
| 189 | B | 190 | B |
| 191 | B | 192 | B |
| 193 | B | 196 | B |
| 197 | B | 198 | A |
| 199 | A | 200 | A |
| 201 | A | 203 | B |
| 204 | B | 219 | A |
| 220 | A | 221 | A |
| 222 | A | 223 | A |
| 224 | B | 225 | B |
| 226 | A | 227 | B |
| 228 | A | 229 | B |
| 230 | A | 231 | B |
| 232 | A | 233 | B |
| 234 | B | 235 | B |
| 236 | B | 237 | B |
| 238 | B | 239 | A |
| 240 | B | 241 | B |
| 242 | B | 243 | B |
| 244 | B | 247 | A |
| 248 | A | 249 | A |
| 250 | B | 251 | B |
| 252 | A | 253 | A |
| 254 | A | 255 | A |
| 256 | A | 257 | A |
| 258 | A | 259 | A |
| 260 | A | 261 | A |
| 262 | A | 263 | A |
| 264 | A | 265 | A |
| 266 | A | 267 | A |
| 268 | A | 269 | A |
| 270 | B | 271 | B |
| 272 | B | 273 | A |
| 274 | A | 275 | A |
| 276 | A | 277 | A |
| 278 | A | 279 | A |
| 280 | A | 281 | A |
| 282 | A | 283 | A |
| 284 | A | 285 | A |
| 286 | B | 287 | B |
| 288 | A | 289 | A |
| 290 | A | 291 | A |
| 292 | B | 293 | B |
| 294 | A | 295 | B |
| 296 | B | 297 | B |
| 298 | B | 299 | B |
| 300 | A | 301 | B |
| 302 | B | 303 | A |
| 304 | A | 305 | B |
| 306 | B | 307 | B |
| 308 | B | 309 | B |
| 310 | A | 311 | A |
| 312 | A | 313 | B |
| 314 | A | 315 | B |
| 316 | B | 317 | B |
| 318 | B | 319 | A |
| 320 | B | 321 | B |
| 322 | B | 323 | B |
| 324 | B | 325 | B |
| 326 | B | 327 | B |
| 328 | B | 329 | A |
| 330 | A | 331 | B |
| 332 | A | 333 | B |
| 334 | B | 336 | A |
| 337 | A | 338 | A |
| 339 | A | 340 | A |
| 341 | A | 342 | A |
| 343 | A | 344 | A |
| 345 | B | 346 | A |
| 347 | A | 348 | A |
| 349 | A | 350 | A |
| 351 | A | 352 | A |
| 353 | A | 354 | B |
| 355 | B | 356 | B |
| 357 | B | 358 | B |
| 359 | B | 360 | B |
| 361 | A | 362 | B |
| 363 | A | 364 | A |
| 365 | A | 366 | A |
| 367 | A | 368 | A |
| 369 | A | 370 | B |
| 371 | A | 372 | A |
| 373 | A | 374 | A |
| 375 | B | 376 | B |
| 377 | B | 378 | B |
| 379 | B | 380 | A |
| 381 | B | 382 | A |
| 383 | B | 384 | A |
| 385 | A | 386 | B |
| 387 | A | 388 | A |
| 389 | A | 390 | A |
| 391 | B | 392 | A |
| 393 | A | 394 | B |
| 395 | B | 396 | A |
| 397 | A | 398 | A |
| 399 | B | 400 | B |
| 401 | B | 402 | A |
| 403 | A | 404 | B |
| 405 | B | 406 | A |
| 407 | B | 408 | A |
| 409 | A | 410 | A |
| 411 | A | 412 | A |
| 413 | B | 414 | A |
| 415 | A | 416 | A |
| 417 | A | 418 | A |
| 424 | A | 425 | A |
| 426 | A | 427 | A |
| 428 | A | 429 | A |
| 430 | A | 431 | A |
| 432 | A | 433 | A |
| 434 | A | 435 | A |
| 436 | A | 437 | A |
| 438 | A | 439 | A |
| 440 | A | 441 | A |
| 442 | A | 443 | A |
| 444 | A | 445 | A |
| 446 | A | 447 | B |
| 448 | A | 450 | A |

TABLE 17-continued

Summary of Activities for RSV-A

| Compound | Human RSV-A ("Long" strain) EC$_{50}$ | Compound | HumanRSV-A ("Long" strain) EC$_{50}$ |
|---|---|---|---|
| 451 | A | 452 | A |
| 453 | A | 454 | B |
| 455 | A | 456 | A |
| 457 | A | 458 | B |
| 459 | A | 460 | A |
| 461 | B | 462 | B |
| 463 | B | 464 | A |
| 465 | A | 466 | A |
| 467 | A | 468 | B |
| 469 | B | 470 | B |
| 471 | A | 472 | B |
| 473 | A | 474 | A |
| 475 | A | 476 | A |
| 477 | A | 478 | B |
| 479 | A | 480 | A |
| 481 | A | 482 | A |
| 483 | A | 484 | A |
| 485 | A | 486 | B |
| 487 | B | 488 | A |
| 489 | A | 490 | A |
| 491 | A | 492 | A |
| 493 | A | 494 | A |
| 496 | A | 497 | A |
| 498 | A | 499 | A |
| 500 | A | 501 | A |
| 502 | A | 503 | A |
| 504 | B | 505 | A |
| 506 | A | 507 | A |
| 508 | B | 509 | B |
| 510 | B | 511 | B |
| 512 | B | 513 | B |
| 514 | B | 515 | B |
| 516 | B | 517 | B |
| 518 | A | 519 | A |
| 520 | A | 521 | A |
| 522 | A | 523 | A |
| 524 | A | 525 | A |
| 526 | A | 527 | A |
| 528 | A | 529 | A |
| 530 | A | 531 | A |
| 532 | A | 533 | A |
| 534 | A | 535 | A |
| 536 | A | 537 | A |
| 538 | A | 539 | A |
| 540 | A | 541 | A |
| 542 | A | 543 | A |
| 544 | A | 545 | B |
| 546 | A | 547 | A |
| 548 | A | 549 | A |
| 550 | A | 551 | A |
| 552 | A | 553 | A |
| 554 | A | 555 | A |
| 556 | A | 557 | A |
| 558 | A | 559 | A |
| 560 | A | 561 | A |
| 562 | A | 563 | A |
| 584 | A | 585 | B |
| 586 | B | 587 | B |
| 588 | A | 589 | B |
| 590 | B | 591 | A |
| 592 | B | 593 | B |
| 594 | B | 595 | A |
| 596 | A | 597 | A |
| 598 | A | 599 | B |
| 600 | A | 601 | B |
| 602 | B | 603 | B |
| 604 | A | 605 | A |
| 606 | B | 607 | A |
| 611 | A | 612 | A |
| 613 | A | 614 | B |
| 615 | A | 616 | A |
| 617 | A | 618 | A |
| 619 | A | 620 | A |
| 621 | A | 622 | A |
| 623 | A | 624 | A |
| 625 | A | 626 | A |
| 627 | A | 628 | B |
| 629 | A | 630 | A |
| 631 | A | 632 | A |
| 633 | A | 635 | A |
| 636 | A | 637 | A |
| 638 | A | 639 | A |
| 640 | A | 641 | A |
| 642 | A | 643 | A |
| 644 | A | 645 | A |
| 646 | A | 647 | A |
| 648 | A | 649 | B |
| 650 | A | 651 | A |
| 652 | B | 653 | B |
| 654 | A | 655 | A |
| 656 | A | 657 | B |
| 658 | A | 659 | A |
| 660 | A | 661 | A |
| 662 | A | 665 | B |
| 666 | A | 667 | B |
| 668 | A | 669 | A |
| 670 | A | 671 | A |
| 672 | A | 673 | A |
| 674 | B | 675 | B |
| 676 | A | | |

Methods for HMPV Antiviral Assay

HMPV antiviral activity was evaluated using a recombinant version of HMPV CAN97-83 engineered to contain the coding sequence for enhanced green fluorescence protein (eGFP) in the 3' end of the virus genome (MPV-GFP1, ViraTree). Vero E6 cells (ATCC #CCL-7) were seeded at a density of 12,000 cells/100 µL/well into 96-well cell plates one day prior to the assay. On the day of screening, the cell culture medium was aspirated from the wells and cells were washed twice with serum-free Eagle's Modified Essential Medium (EMEM, ATCC #) containing 1% penicillin-streptomycin (Invitrogen) (SF-EMEM). Cell washes were performed by dispensing 100 µL SF-EMEM per well and immediately aspirating the wash medium from the well. Following the second wash step, serum-free OptiMEM (Invitrogen, Cat No.) (SF-OptiMEM) containing 0.5 µg/mL TPCK-Trypsin (VENDOR) and 1% penicillin-streptomycin was added to the cells at 50 µL/well. Compounds were added into the 96-well plates using a JANUS automated liquid handling system (VENDOR). Compounds were initially diluted 1:50 into an intermediate 96-well plate containing SF-OptiMEM prior to transfer to the assay plate (25 µL/well). Each of the test compounds were tested in duplicate wells at final concentrations starting from 8 µM or 2 µM using ½ stepwise dilutions for a total of 8 points. Virus infection was performed by preparing a working stock of MPV-GFP1 at a multiplicity of infection (MOI) equal to 0.05/25 µL and aliquoting 25 µL of virus inoculum to the compound and positive control wells. SF-OptiMEM was added (25 µL/well) to the appropriate wells to serve as a virus-free negative control for the assay. The final DMSO concentration of all wells is 0.5%. Plates were incubated at 32° C., 5% CO$_2$ for 5 days.

After 5 days incubation, eGFP fluorescence intensity was measured at (X) nM wavelength using a Spectramax i3X plate reader (VENDOR). Percent viral inhibition was calculated using the following equation:

$$y = [100 - (X_Q/X_P)] \times 100$$

Where $X_Q$ is the fluorescence intensity measured in a well containing recombinant MPV-GFP1-infected, compound-treated cells and $X_P$ is the average fluorescence intensity measured in the wells containing untreated cells infected with recombinant virus. $EC_{50}$ values were then calculated by non-linear regression using a four parameter curve logistic equation. The curve fit model employed was XLFit Dose Response One Site Model 200:

$$y=(A+(B/(1+((x/C)\hat{}D))))$$

Where A is the minimum y value, B is the maximum y value, C is the log $EC_{50}$ value, and D is the slope factor. These data are used to calculate the $EC_{50}$ each compound (Table 18). $EC_{50}$ ranges are as follows: A<0.5 µM; B>0.5 µM.

TABLE 18

Summary of Activities for HMPV

| Compound | HMPV $EC_{50}$ | Compound | HMPV $EC_{50}$ |
|---|---|---|---|
| 27 | A | 34 | B |
| 35 | B | 36 | B |
| 37 | B | 44 | B |
| 45 | B | 46 | A |
| 49 | B | 52 | A |
| 53 | B | 56 | A |
| 61 | A | 62 | A |
| 69 | B | 73 | A |
| 74 | A | 75 | B |
| 79 | A | 80 | A |
| 81 | A | 82 | B |
| 83 | B | 84 | B |
| 85 | A | 86 | A |
| 87 | B | 88 | A |
| 89 | A | 90 | A |
| 91 | A | 92 | A |
| 93 | B | 94 | A |
| 95 | B | 96 | A |
| 103 | B | 104 | B |
| 110 | B | 114 | B |
| 116 | B | 123 | B |
| 124 | B | 126 | B |
| 127 | B | 136 | B |
| 137 | A | 179 | B |
| 180 | B | 183 | B |
| 196 | B | 219 | B |
| 221 | A | 222 | A |
| 223 | A | 228 | B |
| 230 | B | 232 | B |
| 252 | B | 255 | A |
| 256 | A | 257 | A |
| 262 | B | 265 | A |
| 266 | B | 269 | A |
| 280 | A | 281 | A |
| 287 | B | 289 | B |
| 290 | A | 336 | B |
| 337 | B | 339 | B |
| 340 | B | 341 | B |
| 342 | B | 350 | B |
| 361 | B | 363 | A |
| 364 | B | 366 | B |
| 373 | B | 374 | A |
| 380 | B | 384 | B |
| 387 | B | 388 | B |
| 390 | B | 393 | A |
| 397 | B | 398 | A |
| 406 | B | 408 | B |
| 411 | A | 416 | B |
| 417 | A | 418 | A |
| 424 | A | 429 | B |
| 430 | A | 431 | A |
| 433 | A | 444 | B |
| 445 | A | 451 | A |
| 459 | B | 460 | B |
| 464 | B | 465 | A |
| 466 | A | 467 | A |
| 473 | B | 475 | A |

TABLE 18-continued

Summary of Activities for HMPV

| Compound | HMPV $EC_{50}$ | Compound | HMPV $EC_{50}$ |
|---|---|---|---|
| 477 | B | 479 | B |
| 482 | B | 484 | A |
| 485 | A | 492 | B |
| 493 | B | 497 | B |
| 508 | A | 518 | B |
| 519 | A | 520 | A |
| 521 | A | 522 | A |
| 523 | A | 524 | A |
| 526 | A | 527 | B |
| 528 | A | 529 | A |
| 530 | A | 531 | A |
| 532 | A | 533 | A |
| 534 | A | 535 | A |
| 536 | A | 537 | B |
| 538 | B | 539 | A |
| 540 | A | 541 | B |
| 542 | A | 543 | A |
| 544 | A | 546 | B |
| 547 | B | 548 | B |
| 549 | B | 550 | A |
| 551 | B | 552 | A |
| 553 | A | 557 | A |
| 558 | A | 560 | A |
| 561 | A | 562 | A |
| 588 | B | 595 | A |
| 600 | B | 611 | B |
| 613 | A | 615 | B |
| 616 | A | 617 | A |
| 619 | A | 621 | B |
| 622 | A | 623 | B |
| 624 | A | 626 | B |
| 627 | B | 633 | A |
| 635 | A | 636 | A |
| 638 | A | 640 | B |
| 641 | B | 642 | B |
| 668 | A | 669 | B |
| 670 | A | 676 | A |

While this invention has been particularly shown and described with reference to preferred embodiments thereof, it will be understood by those skilled in the art that various changes in form and details may be made therein without departing from the scope of the invention encompassed by the appended claims.

What is claimed:
1. A compound represented by Formula (I):

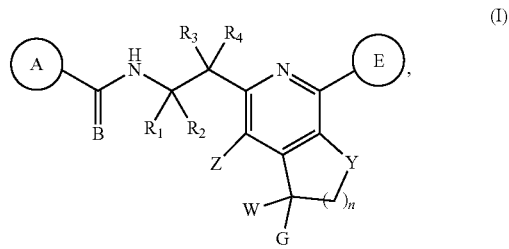

or a pharmaceutically acceptable salt thereof, wherein:
A is selected from the group consisting of:
 1) optionally substituted aryl; and
 2) optionally substituted heteroaryl;
B is O or S;
$R_1$ and $R_2$ are each independently selected from the group consisting of:
 1) hydrogen;
 2) fluorine; and
 3) optionally substituted —$C_1$-$C_6$ alkyl;

alternatively, $R_1$ and $R_2$ are taken together with the carbon atom to which they are attached to form an optionally substituted 3- to 6-membered cyclic ring;

Z is selected from the group consisting of:
1) hydrogen;
2) halogen;
3) hydroxy;
4) cyano;
5) nitro;
6) optionally substituted —$C_1$-$C_6$ alkoxy; and
7) optionally substituted —$C_1$-$C_6$ alkyl;

W is halogen;

G is selected from the group consisting of:
1) —C(O)O$R_{12}$;
2) —C(O)N$R_{11}R_{12}$;
3) optionally substituted —$C_1$-$C_6$ alkyl-CN;
4) optionally substituted —$C_1$-$C_6$ alkyl-C(O)N$R_{11}R_{12}$;
5) optionally substituted —$C_1$-$C_6$ alkyl-C(O)N$R_{11}$S(O)$_2R_{12}$;
6) optionally substituted —$C_1$-$C_6$ alkyl-OC(O)N$R_{11}R_{12}$;
7) optionally substituted —$C_1$-$C_6$ alkyl-NH$R_{13}$;
8) optionally substituted —$C_1$-$C_6$ alkyl-NHC(O)$R_{13}$; and
9) —C(O)N$R_{11}$S(O)$_2R_{12}$;

n is 1, 2 or 3;

Y is O, S, S(O)$_2$, or N$R_{14}$;

E is selected from the group consisting of:
1) optionally substituted aryl;
2) optionally substituted heteroaryl;
3) optionally substituted 3- to 8-membered heterocyclic, and
4) optionally substituted alkynyl;

$R_3$ is hydroxy or fluorine;

$R_4$ is selected from the group consisting of:
1) hydrogen;
2) optionally substituted —$C_1$-$C_6$ alkyl;
3) optionally substituted —$C_3$-$C_8$ cycloalkyl; and
4) optionally substituted 3- to 8-membered heterocyclic;

$R_{11}$ at each occurrence is independently selected from the group consisting of:
1) hydrogen;
2) optionally substituted —$C_1$-$C_8$-alkyl;
3) optionally substituted —$C_3$-$C_8$-cycloalkyl;
4) optionally substituted 3- to 8-membered heterocyclic;
5) optionally substituted aryl;
6) optionally substituted arylalkyl;
7) optionally substituted heteroaryl; and
8) optionally substituted heteroarylalkyl;

$R_{12}$ at each occurrence is independently selected from the group consisting of:
1) hydrogen;
2) optionally substituted —$C_1$-$C_8$-alkyl;
3) optionally substituted —$C_3$-$C_8$-cycloalkyl;
4) optionally substituted 3- to 8-membered heterocyclic;
5) optionally substituted aryl;
6) optionally substituted arylalkyl;
7) optionally substituted heteroaryl; and
8) optionally substituted heteroarylalkyl;

alternatively, $R_{11}$ and $R_{12}$ are taken together with the nitrogen atom to which they are attached to form a 3- to 12-membered heterocyclic ring; $R_{13}$ at each occurrence is independently selected from the group consisting of:

1) Optionally substituted —$C_1$-$C_8$ alkyl;
2) Optionally substituted —$C_3$-$C_8$ cycloalkyl;
3) Optionally substituted 3- to 8-membered heterocyclic;
4) Optionally substituted aryl;
5) Optionally substituted arylalkyl;
6) Optionally substituted heteroaryl; and
7) Optionally substituted heteroarylalkyl; and $R_{14}$ is selected from:
1) hydrogen;
2) optionally substituted —$C_1$-$C_8$-alkyl; and
3) optionally substituted —$C_3$-$C_8$-cycloalkyl.

2. The compound of claim 1, wherein G is —C(O)N$R_{11}R_{12}$, —CH$_2$C(O)N$R_{11}R_{12}$, —CH$_2$NHC(O)$R_{13}$, —CH$_2$NH$R_{13}$, —CH$_2$OC(O)N$R_{11}R_{12}$, —CH$_2$CN, or —C(O)N$R_{11}$S(O)$_2R_{12}$, wherein $R_{11}$, $R_{12}$, and $R_{13}$ are as defined in claim 1.

3. The compound of claim 1, wherein E is selected from the group consisting of

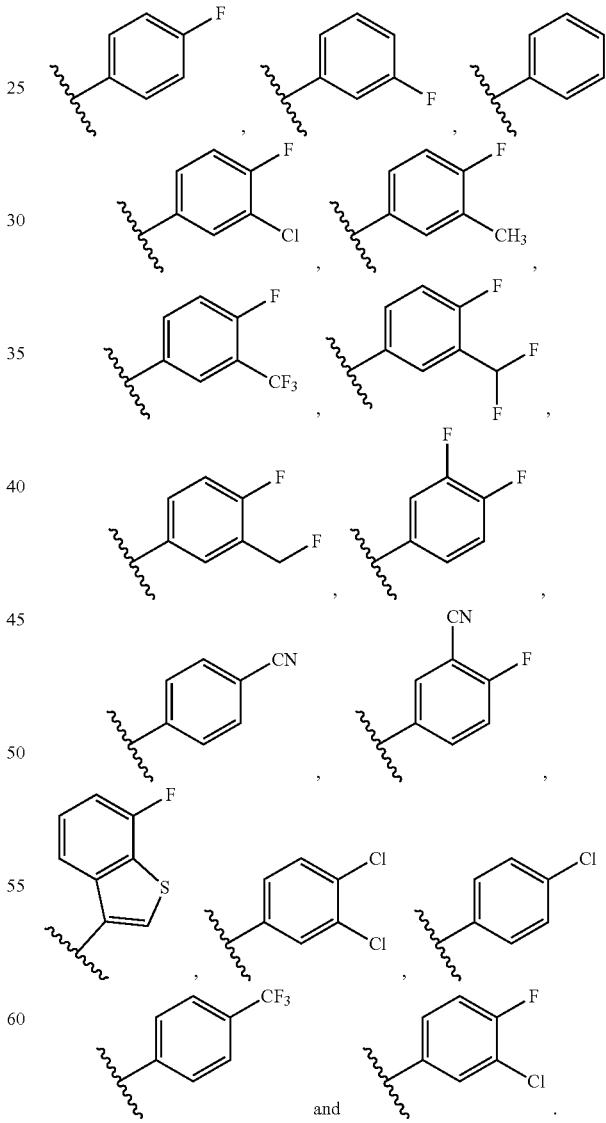

4. The compound of claim 1, wherein A is selected from the groups set forth below by removal of a hydrogen atom:

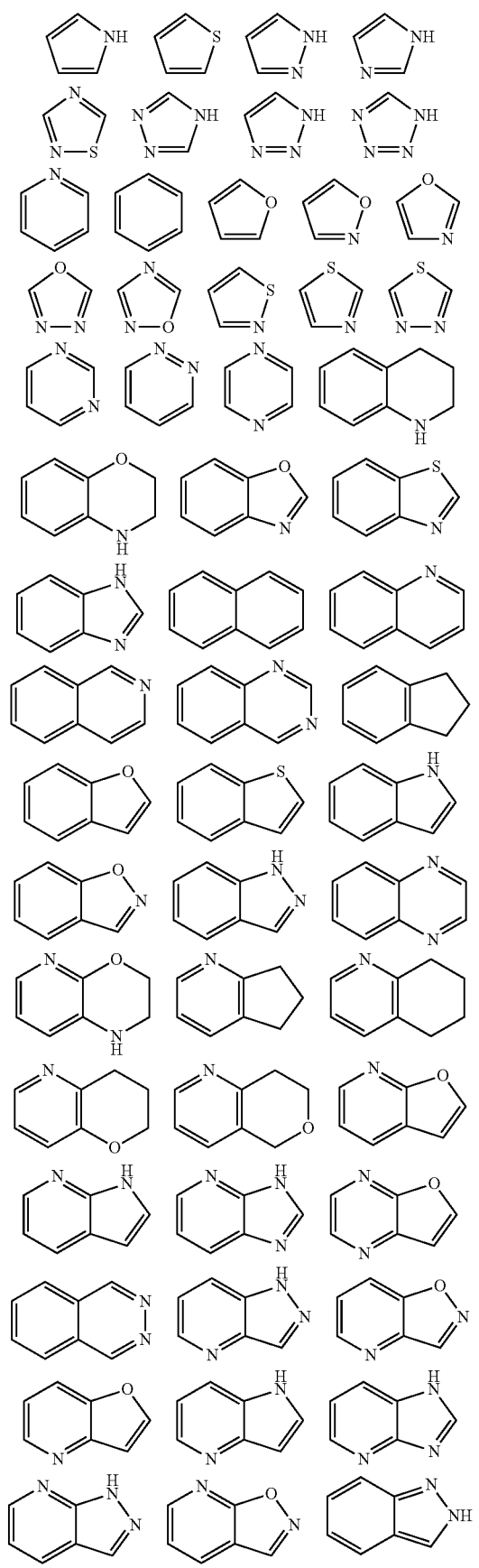
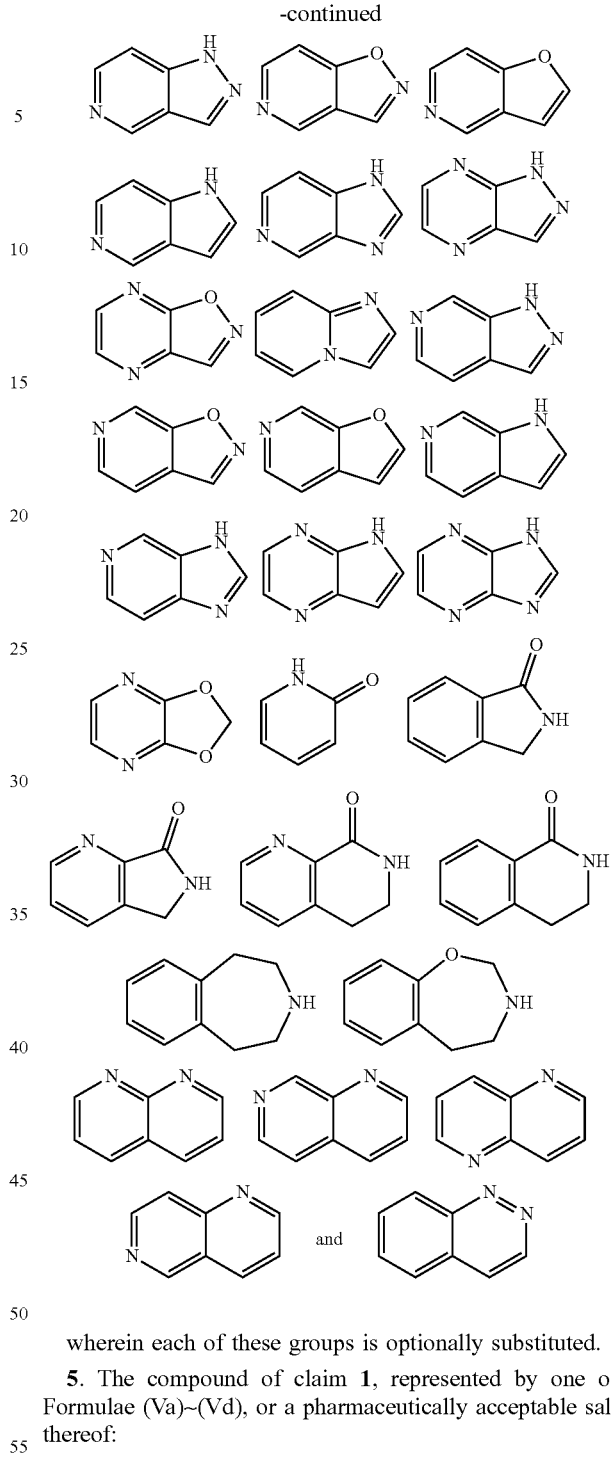
wherein each of these groups is optionally substituted.
5. The compound of claim 1, represented by one of Formulae (Va)~(Vd), or a pharmaceutically acceptable salt thereof:
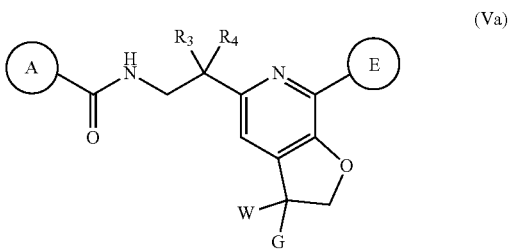

(Vb)
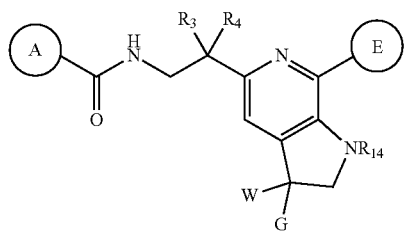

(Vc)
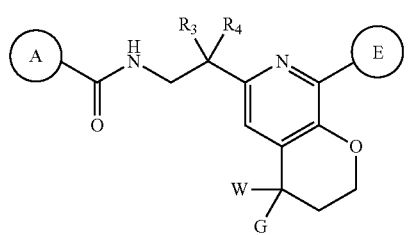

(Vd)
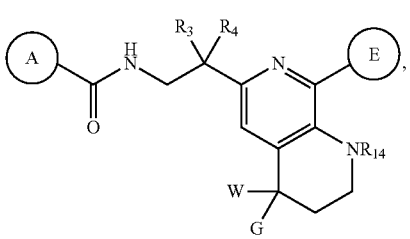

wherein A, W, G, E, $R_{14}$, $R_3$, and $R_4$ are as defined in claim 1.

6. The compound of claim 1, represented by one of Formulae (VIIIa)~(VIIId), or a pharmaceutically acceptable salt thereof:

(VIIIa)
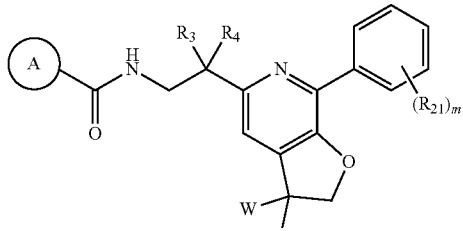

(VIIIb)
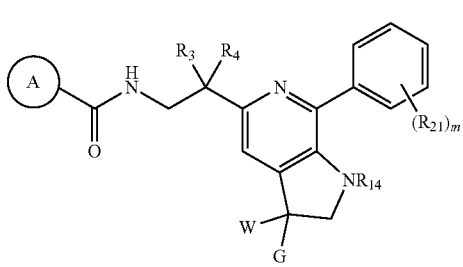

(VIIIc)
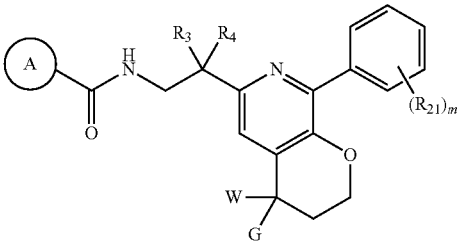

(VIIId)
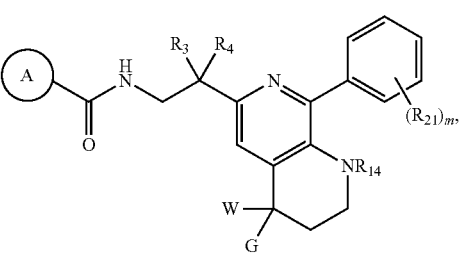

wherein each $R_{21}$ is independently hydrogen, optionally substituted methyl, halo, CN, $OR_{11}$, or $NR_{11}R_{12}$; m is 1, 2, 3, 4 or 5; and A, W, G, $R_3$, $R_4$, $R_{11}$, $R_{12}$, and $R_{14}$ are as defined in claim 1.

7. The compound of claim 1, represented by one of Formulae (IXa)~(IXd), or a pharmaceutically acceptable salt thereof:

(IXa)
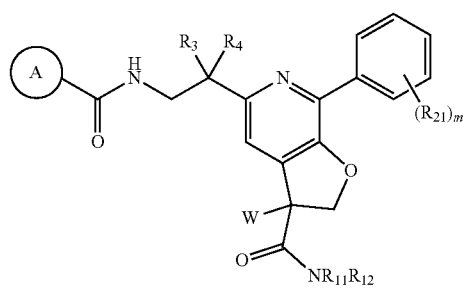

(IXb)
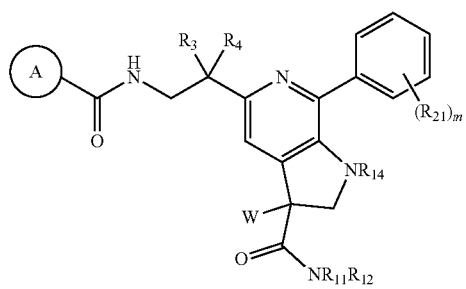

(IXc)
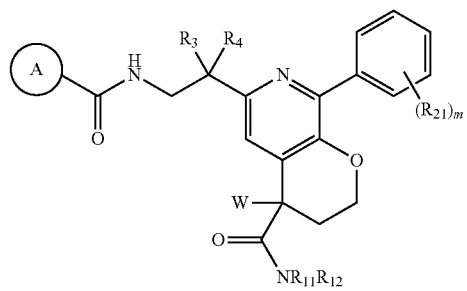

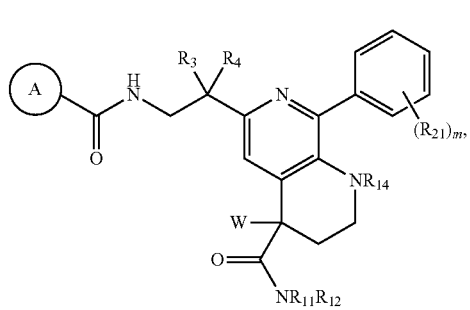

(IXd)

wherein $R_{21}$ is optionally substituted methyl, halo, CN, $OR_{11}$, or $NR_{11}R_{12}$; m is 0, 1, 2, 3, 4 or 5; and A, W, $R_3$, $R_4$, $R_{11}$, $R_{12}$, and $R_{14}$ are as defined in claim 1.

8. The compound of claim 1, represented by one of Formulae (X-1)~(X-6), or a pharmaceutically acceptable salt thereof:

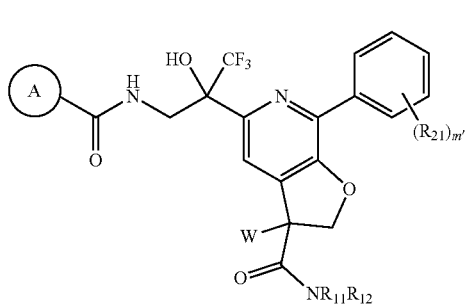

(X-1)

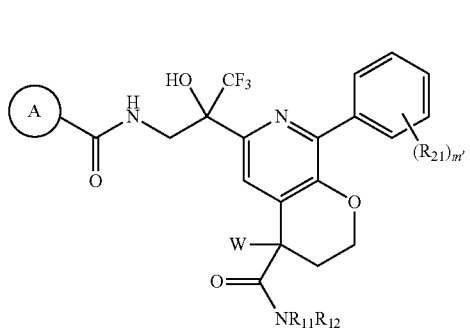

(X-2)

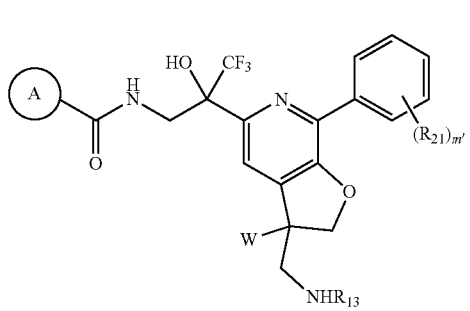

(X-3)

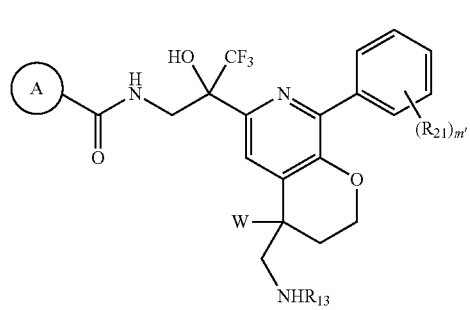

(X-4)

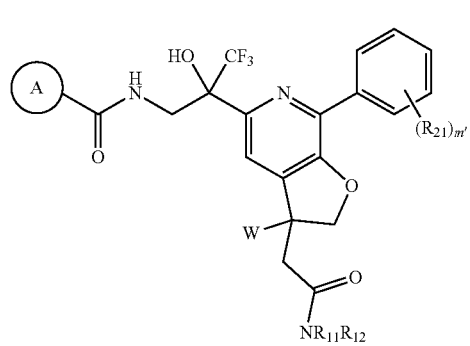

(X-5)

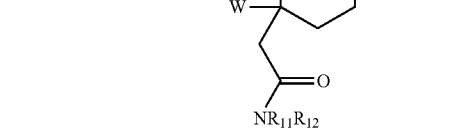

(X-6)

wherein $R_{12}$ is optionally substituted methyl, halo, CN, $OR_{11}$, or $NR_{11}R_{12}$; m' is 0, 1 or 2; and A, W, $R_{11}$, $R_{12}$, and $R_{14}$ are as defined in claim 1.

9. The compound of claim 1, represented by one of Formulae (X-1a)~(X-6a), or a pharmaceutically acceptable salt thereof:

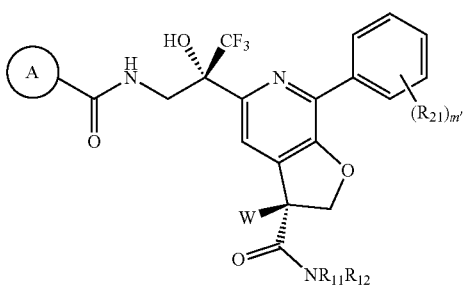

(X-1a)

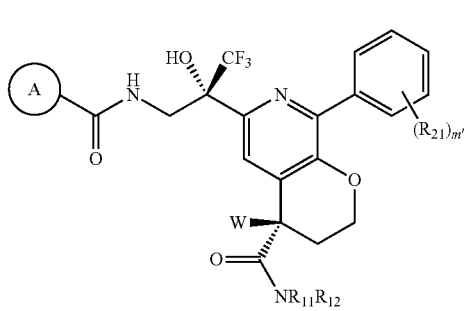 (X-2a)
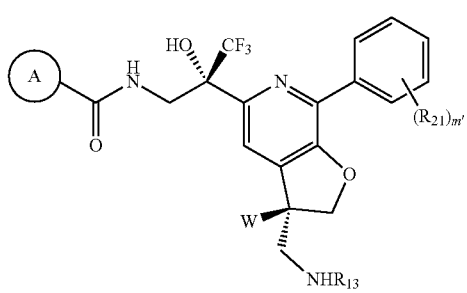 (X-3a)
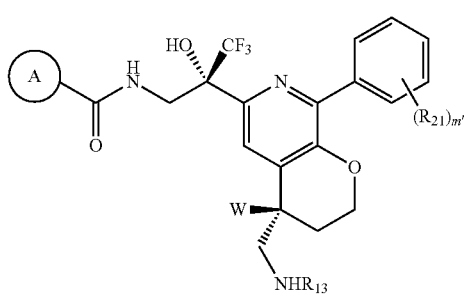 (X-4a)
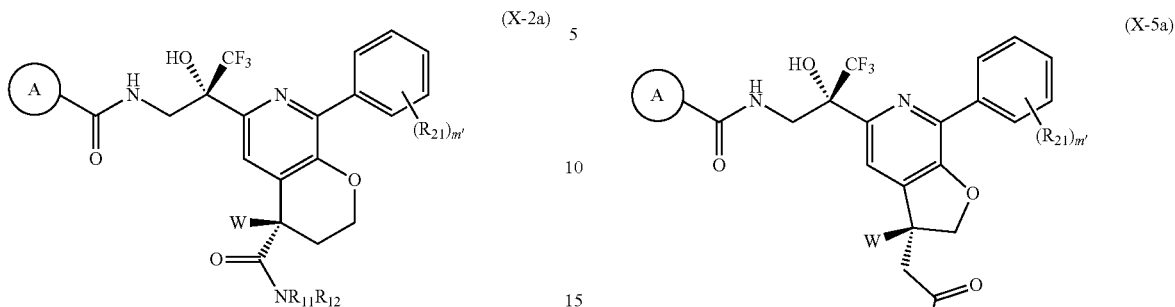 (X-5a)
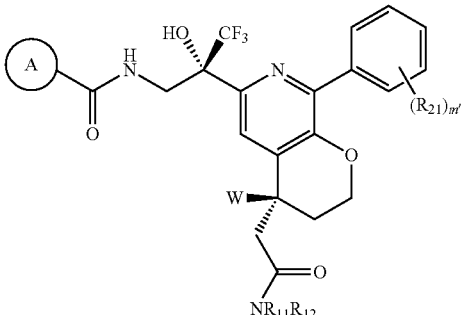 (X-6a)
wherein $R_{21}$ is optionally substituted methyl, halo, CN, $OR_{11}$, or $NR_{11}R_{12}$; m' is 0, 1 or 2; and A, W, $R_{11}$, $R_{12}$, and $R_{13}$ are as defined in claim 1.
10. The compound of claim 1, selected from the compounds set forth below, or a pharmaceutically acceptable salt thereof.
| Compound | Structure |
|---|---|
| 665 | 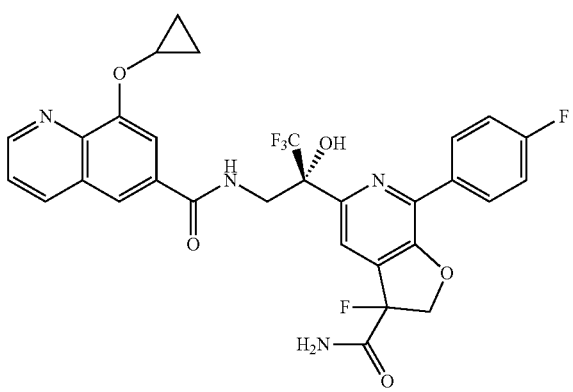 [SMILES: NC(=O)C1(F)COc2c1cc([C@@](O)(CNC(=O)c1cc(OC3CC3)c3ncccc3c1)C(F)(F)F)nc2-c1ccc(F)cc1] |

-continued
| Compound | Structure |
|---|---|
| 666 | 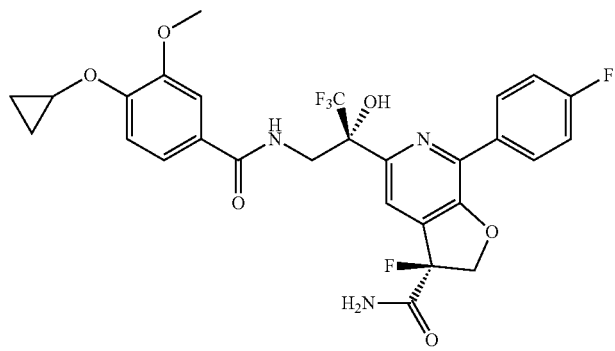 [SMILES: COc1cc(C(=O)NC[C@](O)(c2cc3c(c(-c4ccc(F)cc4)n2)OC[C@]3(F)C(N)=O)C(F)(F)F)ccc1OC1CC1] |
| 667 | 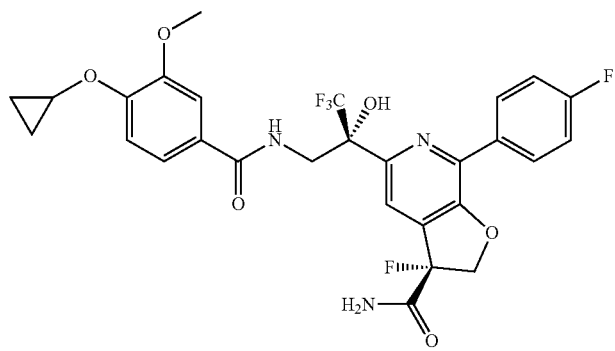 [SMILES: COc1cc(C(=O)NC[C@](O)(c2cc3c(c(-c4ccc(F)cc4)n2)OC[C@@]3(F)C(N)=O)C(F)(F)F)ccc1OC1CC1] |
| 668 | 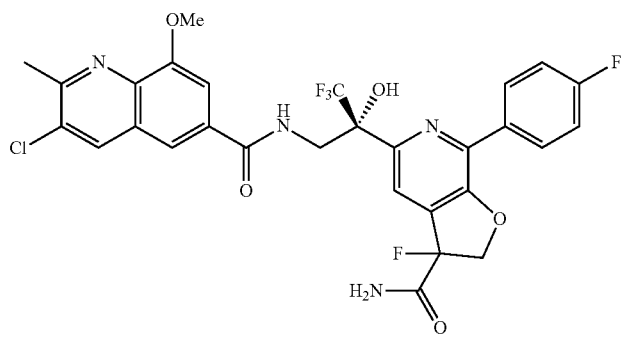 [SMILES: COc1cc(C(=O)NC[C@](O)(c2cc3c(c(-c4ccc(F)cc4)n2)OCC3(F)C(N)=O)C(F)(F)F)cc2cc(Cl)c(C)nc12] |
| 669 | 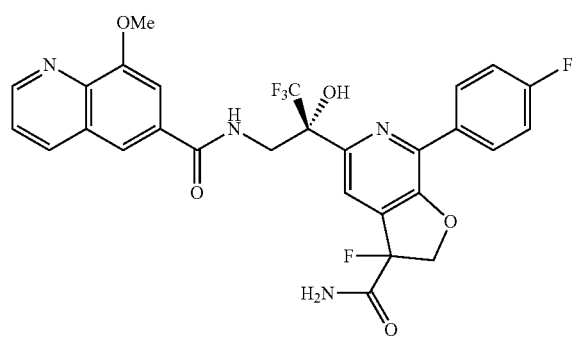 [SMILES: COc1cc(C(=O)NC[C@](O)(c2cc3c(c(-c4ccc(F)cc4)n2)OCC3(F)C(N)=O)C(F)(F)F)cc2cccnc12] |

US 11,505,558 B1
537
-continued
538
| Compound | Structure |
|---|---|
| 670 | 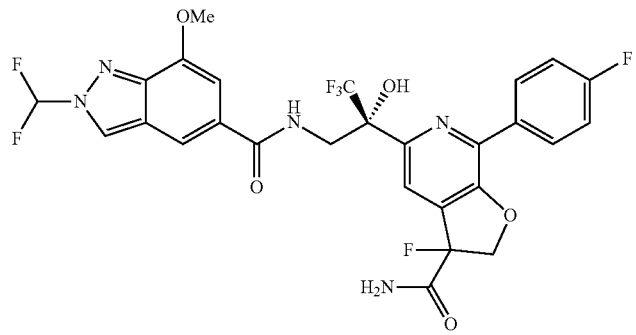 [SMILES: COc1cc(C(=O)NC[C@](O)(c2cc3c(c(-c4ccc(F)cc4)n2)OCC3(F)C(N)=O)C(F)(F)F)cc2cn(C(F)F)nc12] |
| 671 | 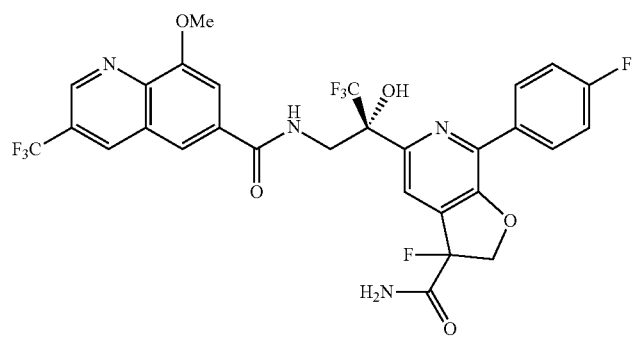 [SMILES: COc1cc(C(=O)NC[C@](O)(c2cc3c(c(-c4ccc(F)cc4)n2)OCC3(F)C(N)=O)C(F)(F)F)cc2cc(C(F)(F)F)cnc12] |
| 672 | 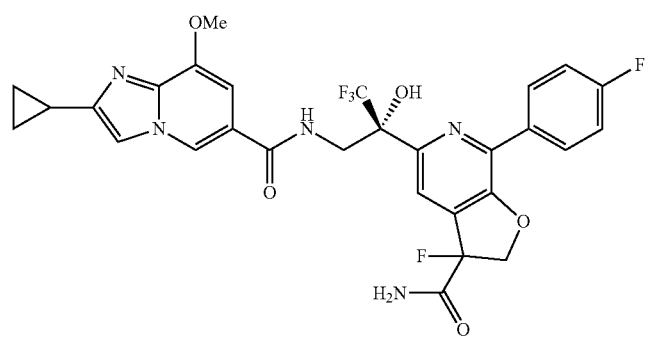 [SMILES: COc1cc(C(=O)NC[C@](O)(c2cc3c(c(-c4ccc(F)cc4)n2)OCC3(F)C(N)=O)C(F)(F)F)cn2cc(C3CC3)nc12] |
| 673 | 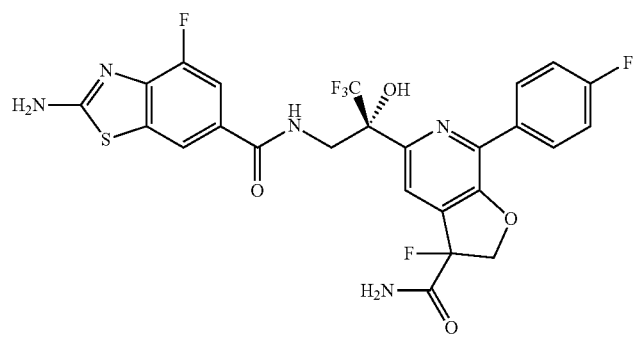 [SMILES: NC(=O)C1(F)COc2c1cc([C@@](O)(CNC(=O)c1cc(F)c3nc(N)sc3c1)C(F)(F)F)nc2-c1ccc(F)cc1] |

-continued
| Compound | Structure |
|---|---|
| 674 | 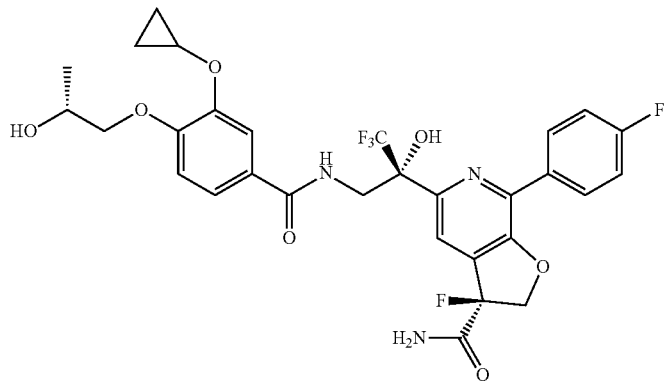 [SMILES: C[C@@H](O)COc1ccc(C(=O)NC[C@](O)(c2cc3c(c(-c4ccc(F)cc4)n2)OC[C@]3(F)C(N)=O)C(F)(F)F)cc1OC1CC1] |
| 675 | 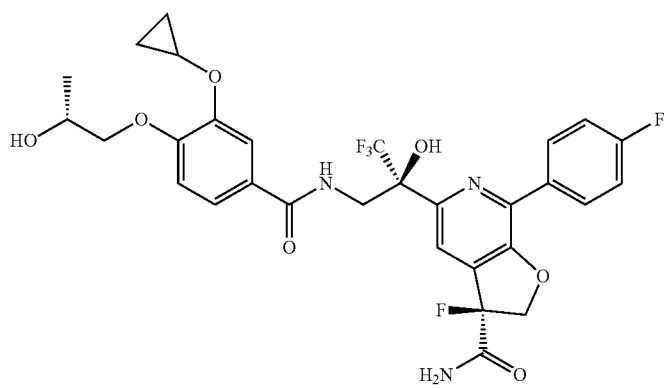 [SMILES: C[C@@H](O)COc1ccc(C(=O)NC[C@@](O)(c2cc3c(c(-c4ccc(F)cc4)n2)OC[C@]3(F)C(N)=O)C(F)(F)F)cc1OC1CC1] |
| 676 | 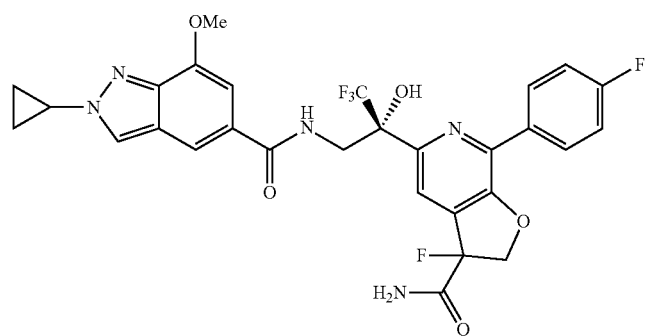 [SMILES: COc1cc(C(=O)NC[C@](O)(c2cc3c(c(-c4ccc(F)cc4)n2)OCC3(F)C(N)=O)C(F)(F)F)cc2cn(C3CC3)nc12] |
| P-25 | 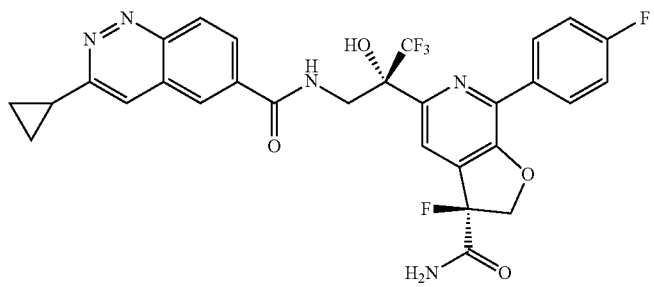 [SMILES: NC(=O)[C@@]1(F)COc2c1cc([C@@](O)(CNC(=O)c1ccc3nnc(C4CC4)cc3c1)C(F)(F)F)nc2-c1ccc(F)cc1] |

| Compound | Structure |
|---|---|
| P-26 | 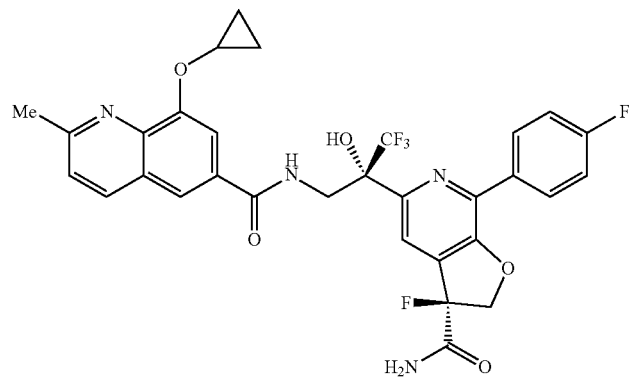 [SMILES: Cc1ccc2cc(C(=O)NC[C@](O)(c3cc4c(c(-c5ccc(F)cc5)n3)OC[C@]4(F)C(N)=O)C(F)(F)F)cc(OC3CC3)c2n1] |
| P-27 | 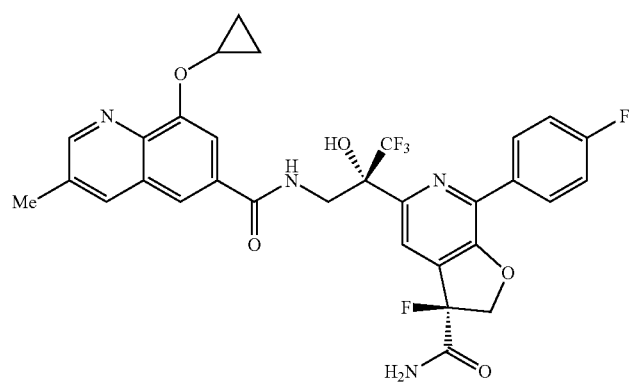 [SMILES: Cc1cnc2c(OC3CC3)cc(C(=O)NC[C@](O)(c3cc4c(c(-c5ccc(F)cc5)n3)OC[C@]4(F)C(N)=O)C(F)(F)F)cc2c1] |
| P-28 | 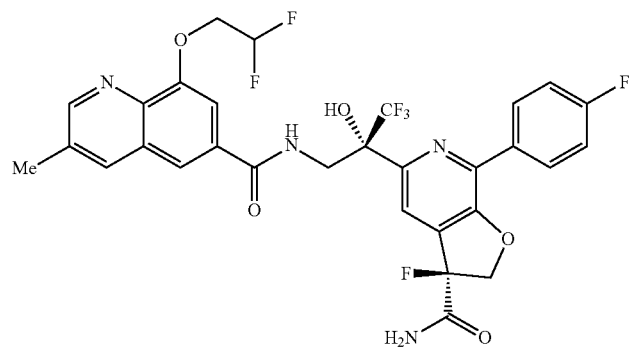 [SMILES: Cc1cnc2c(OCC(F)F)cc(C(=O)NC[C@](O)(c3cc4c(c(-c5ccc(F)cc5)n3)OC[C@]4(F)C(N)=O)C(F)(F)F)cc2c1] |
| P-29 | 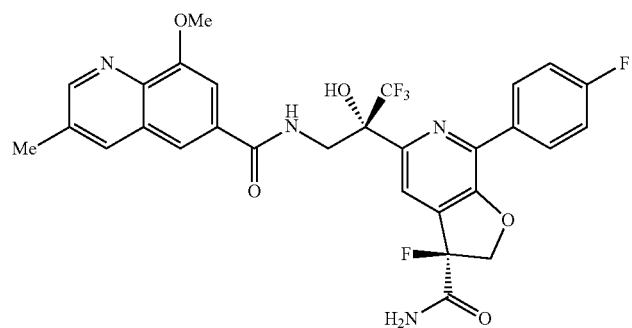 [SMILES: COc1cc(C(=O)NC[C@](O)(c2cc3c(c(-c4ccc(F)cc4)n2)OC[C@]3(F)C(N)=O)C(F)(F)F)cc2cc(C)cnc12] |

-continued

| Compound | Structure |
|---|---|
| P-30 | 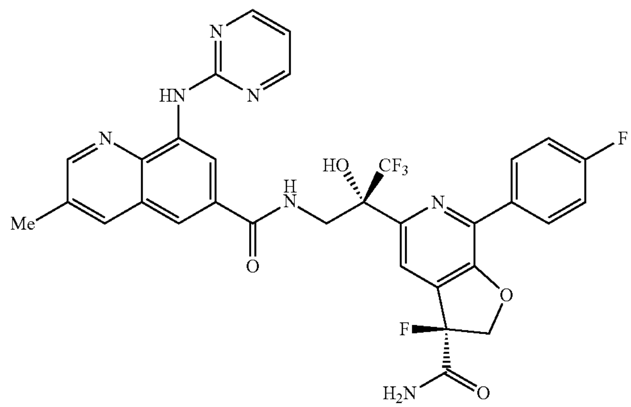 [SMILES: Cc1cnc2c(Nc3ncccn3)cc(C(=O)NC[C@](O)(c3cc4c(c(-c5ccc(F)cc5)n3)OC[C@]4(F)C(N)=O)C(F)(F)F)cc2c1] |
| P-31 | 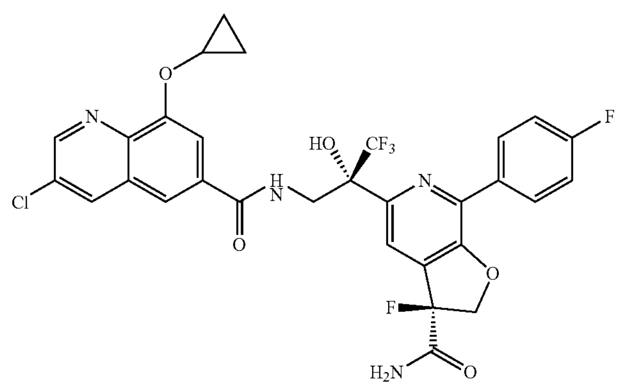 [SMILES: NC(=O)[C@@]1(F)COc2c1cc([C@@](O)(CNC(=O)c1cc(OC3CC3)c3ncc(Cl)cc3c1)C(F)(F)F)nc2-c1ccc(F)cc1] |
| P-32 | 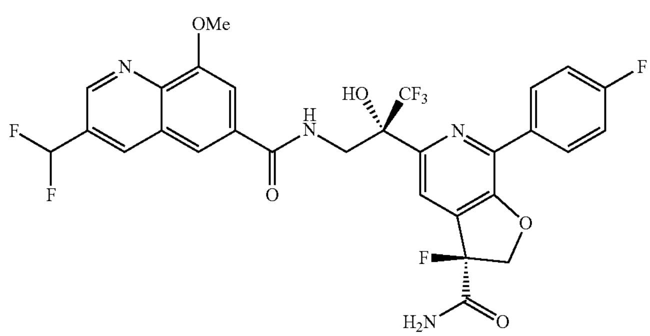 [SMILES: COc1cc(C(=O)NC[C@](O)(c2cc3c(c(-c4ccc(F)cc4)n2)OC[C@]3(F)C(N)=O)C(F)(F)F)cc2cc(C(F)F)cnc12] |
| P-33 | 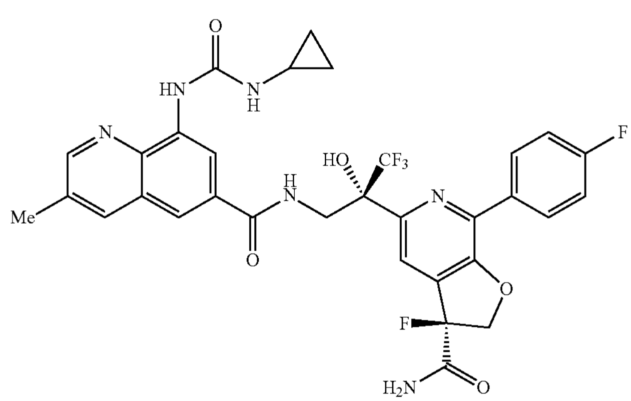 [SMILES: Cc1cnc2c(NC(=O)NC3CC3)cc(C(=O)NC[C@](O)(c3cc4c(c(-c5ccc(F)cc5)n3)OC[C@]4(F)C(N)=O)C(F)(F)F)cc2c1] |

-continued
| Compound | Structure |
|---|---|
| P-34 | 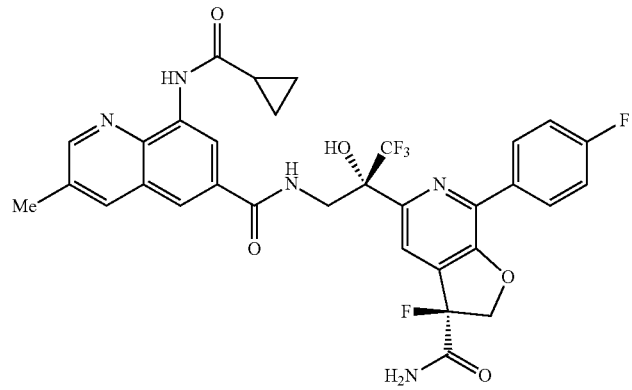 [SMILES: Cc1cnc2c(NC(=O)C3CC3)cc(C(=O)NC[C@](O)(c3cc4c(c(-c5ccc(F)cc5)n3)OC[C@]4(F)C(N)=O)C(F)(F)F)cc2c1] |
| P-35 | 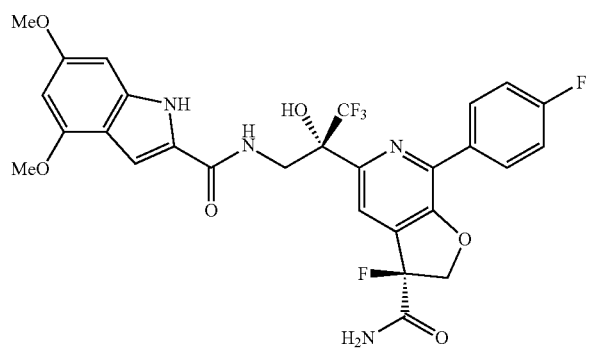 [SMILES: COc1cc(OC)c2cc(C(=O)NC[C@](O)(c3cc4c(c(-c5ccc(F)cc5)n3)OC[C@]4(F)C(N)=O)C(F)(F)F)[nH]c2c1] |
| P-36 | 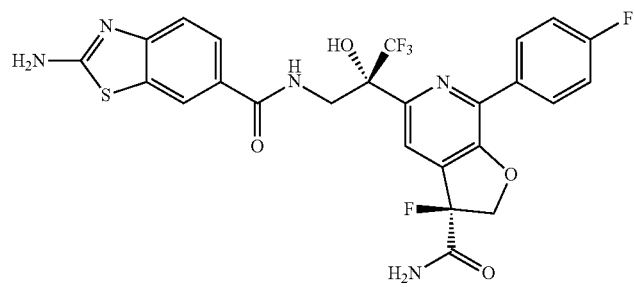 [SMILES: NC(=O)[C@@]1(F)COc2c1cc([C@@](O)(CNC(=O)c1ccc3nc(N)sc3c1)C(F)(F)F)nc2-c1ccc(F)cc1] |
| P-37 | 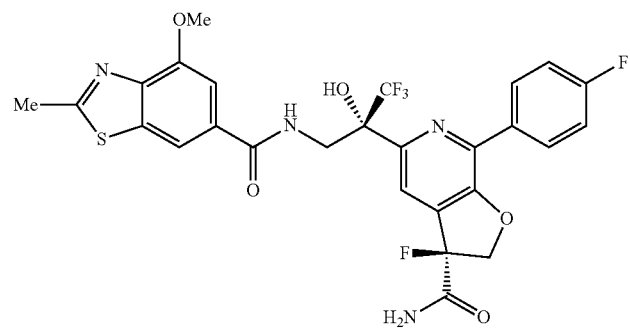 [SMILES: COc1cc(C(=O)NC[C@](O)(c2cc3c(c(-c4ccc(F)cc4)n2)OC[C@]3(F)C(N)=O)C(F)(F)F)cc2sc(C)nc12] |

-continued
| Compound | Structure |
|---|---|
| P-38 | 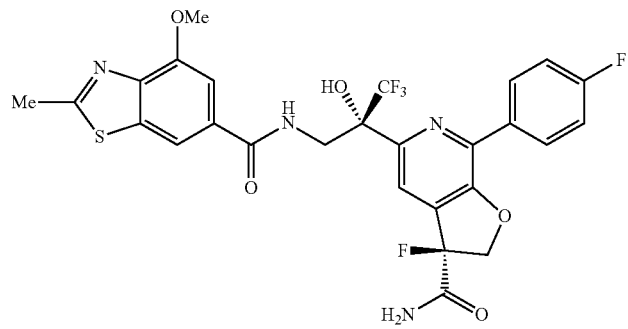 [SMILES: COc1cc(C(=O)NC[C@](O)(c2cc3c(c(-c4ccc(F)cc4)n2)OC[C@]3(F)C(N)=O)C(F)(F)F)cc2sc(C)nc12] |
| P-39 | 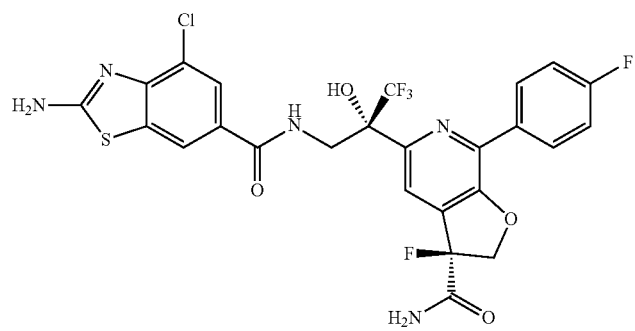 [SMILES: NC(=O)[C@@]1(F)COc2c1cc([C@@](O)(CNC(=O)c1cc(Cl)c3nc(N)sc3c1)C(F)(F)F)nc2-c1ccc(F)cc1] |
| P-40 | 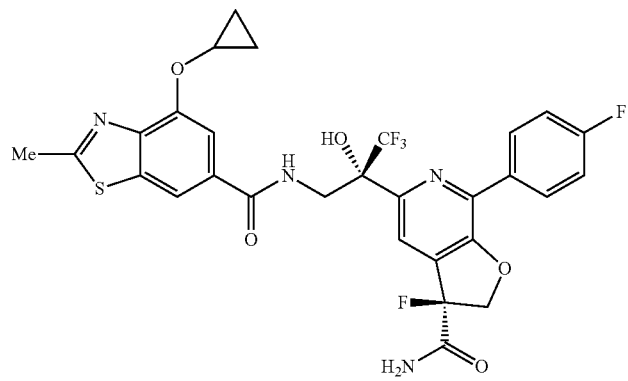 [SMILES: Cc1nc2c(OC3CC3)cc(C(=O)NC[C@](O)(c3cc4c(c(-c5ccc(F)cc5)n3)OC[C@]4(F)C(N)=O)C(F)(F)F)cc2s1] |
| P-41 | 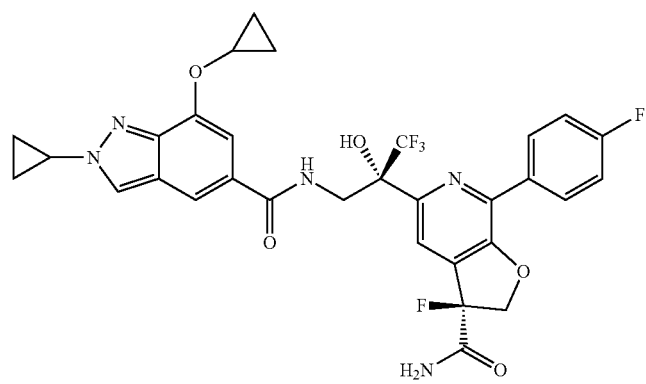 [SMILES: NC(=O)[C@@]1(F)COc2c1cc([C@@](O)(CNC(=O)c1cc(OC3CC3)c3nn(C4CC4)cc3c1)C(F)(F)F)nc2-c1ccc(F)cc1] |

| Compound | Structure |
|---|---|
| P-42 | 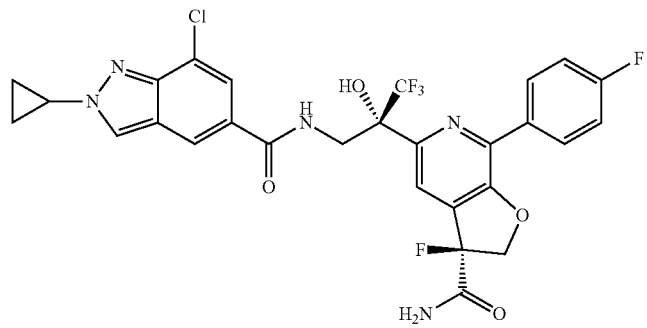 [SMILES: NC(=O)[C@@]1(F)COc2c1cc([C@@](O)(CNC(=O)c1cc(Cl)c3nn(C4CC4)cc3c1)C(F)(F)F)nc2-c1ccc(F)cc1] |
| P-43 | 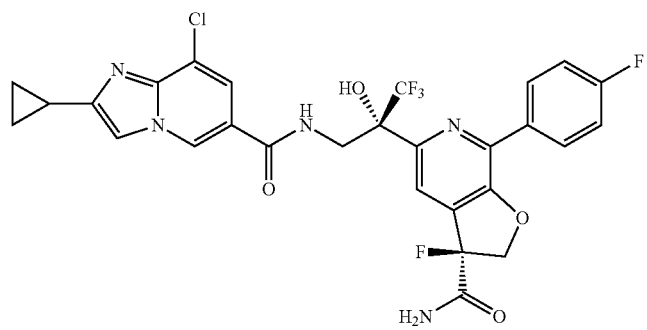 [SMILES: NC(=O)[C@@]1(F)COc2c1cc([C@@](O)(CNC(=O)c1cc(Cl)c3nc(C4CC4)cn3c1)C(F)(F)F)nc2-c1ccc(F)cc1] |
| P-44 | 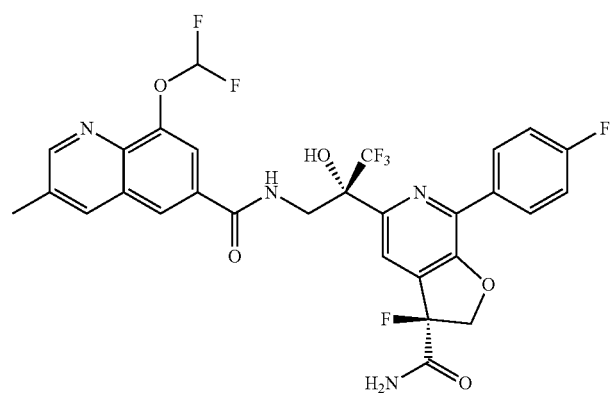 [SMILES: Cc1cnc2c(OC(F)F)cc(C(=O)NC[C@](O)(c3cc4c(c(-c5ccc(F)cc5)n3)OC[C@]4(F)C(N)=O)C(F)(F)F)cc2c1] |
| P-45 | 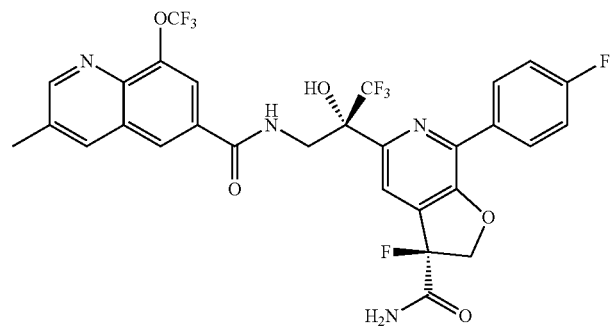 [SMILES: Cc1cnc2c(OC(F)(F)F)cc(C(=O)NC[C@](O)(c3cc4c(c(-c5ccc(F)cc5)n3)OC[C@]4(F)C(N)=O)C(F)(F)F)cc2c1] |

| Compound | Structure |
|---|---|
| P-46 | 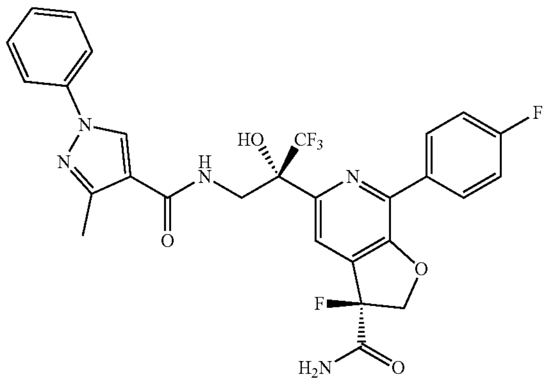 [SMILES: Cc1nn(-c2ccccc2)cc1C(=O)NC[C@](O)(c1cc2c(c(-c3ccc(F)cc3)n1)OC[C@]2(F)C(N)=O)C(F)(F)F] |
| P-47 | and |
| P-48 | 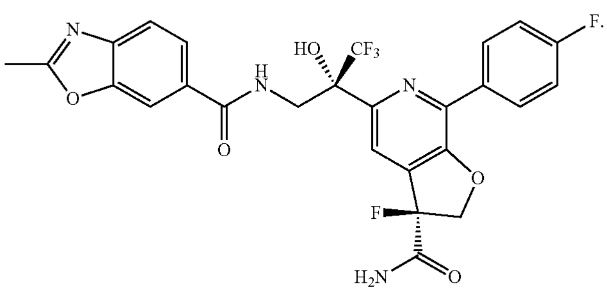 [SMILES: Cc1nc2ccc(C(=O)NC[C@](O)(c3cc4c(c(-c5ccc(F)cc5)n3)OC[C@]4(F)C(N)=O)C(F)(F)F)cc2o1] |

11. A pharmaceutical composition comprising a compound according to claim 1, or a pharmaceutically acceptable salt thereof, and a pharmaceutically acceptable carrier, diluent or excipient.

12. A method of treating an RSV infection in a subject in need thereof, comprising administering to the subject a therapeutically effective amount of a compound of claim 1 or a pharmaceutically acceptable salt thereof.

13. The method of claim 12, further comprising the step of administering to the subject an anti-RSV agent.

14. The method of claim 12, further comprising administering to the subject a steroid anti-inflammatory compound.

15. A method of treating RSV and influenza in a subject in need thereof, comprising administering to the subject a therapeutically effective amount of a compound of claim 1, or a pharmaceutically acceptable salt thereof, and a therapeutically effective amount of an anti-influenza agent.

16. The method of claim 13, wherein the compound and the anti-RSV agent are co-formulated.

17. The method of claim 13, wherein the compound and the anti-RSV agent are co-administered.

18. A method of treating an HMPV infection in a subject in need thereof, comprising administering to the subject a therapeutically effective amount of a compound of claim 1 or a pharmaceutically acceptable salt thereof.

19. The method of claim 18, further comprising the step of administering to the subject an anti-HMPV agent.

20. The method of claim 19, wherein the compound and the anti-HMPV agent are co-formulated.

21. The method of claim 19, wherein the compound and the anti-HMPV agent are co-administered.

* * * * *

UNITED STATES PATENT AND TRADEMARK OFFICE
CERTIFICATE OF CORRECTION

PATENT NO. : 11,505,558 B1
APPLICATION NO. : 17/220300
DATED : November 22, 2022
INVENTOR(S) : Adam Szymaniak et al.

Page 1 of 2

It is certified that error appears in the above-identified patent and that said Letters Patent is hereby corrected as shown below:

In the Claims

At Column 527

In Claim 4, Line 65 delete " " and insert -- --.
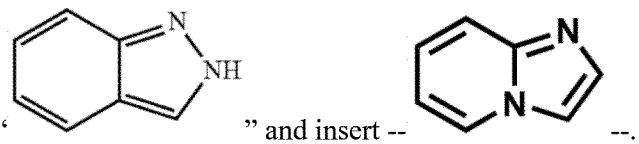

At Column 528

In Claim 4, Line 15 after delete " ".
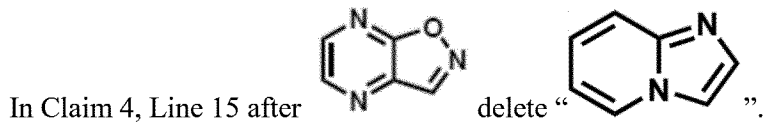

At Column 532
In Claim 8, Line 47 delete "$R_{12}$" and insert -- $R_{21}$ --; and
In Claim 8, Line 49 delete "$R_{14}$" and insert -- $R_{13}$ --.

At Column 545

In Claim 10, delete structure P-37 " " and insert
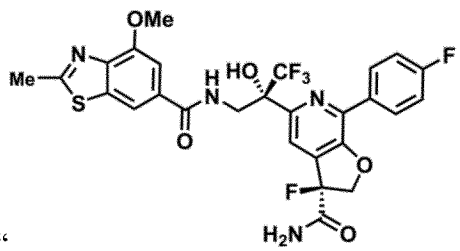

Signed and Sealed this
Twenty-first Day of March, 2023

*Katherine Kelly Vidal*

Katherine Kelly Vidal
*Director of the United States Patent and Trademark Office*

CERTIFICATE OF CORRECTION (continued)
U.S. Pat. No. 11,505,558 B1

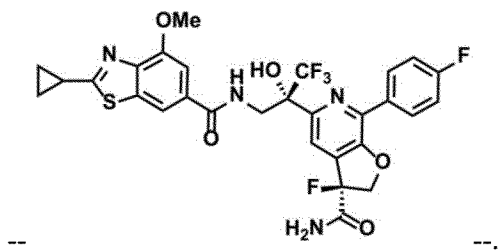

--          --.